(12) United States Patent
Skaaksrud et al.

(10) Patent No.: US 9,402,242 B2
(45) Date of Patent: *Jul. 26, 2016

(54) ASSOCIATION MANAGEMENT IN A WIRELESS NODE NETWORK

(71) Applicant: FedEx Corporate Services, Inc., Collierville, TN (US)

(72) Inventors: Ole-Petter Skaaksrud, Germantown, TN (US); Terence Hollahan, Collierville, TN (US); Steven Benton, Cordova, TN (US)

(73) Assignee: FEDEX CORPORATE SERVICES, INC., Collierville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/611,362

(22) Filed: Feb. 2, 2015

(65) Prior Publication Data

US 2016/0037478 A1 Feb. 4, 2016

Related U.S. Application Data

(63) Continuation of application No. 14/445,523, filed on Jul. 29, 2014, now Pat. No. 8,989,053.

(60) Provisional application No. 61/910,202, filed on Nov. 29, 2013, provisional application No. 62/003,566, filed on May 28, 2014.

(51) Int. Cl.
*H04L 12/24* (2006.01)
*H04L 12/751* (2013.01)
(Continued)

(52) U.S. Cl.
CPC ....... *H04W 64/003* (2013.01); *G06Q 10/08355* (2013.01); *H04W 4/008* (2013.01); *H04W 4/023* (2013.01); *H04W 12/08* (2013.01)

(58) Field of Classification Search
CPC ................................ H04L 41/12; H04L 45/02
USPC .................................................. 370/254, 255
See application file for complete search history.

(56) References Cited

U.S. PATENT DOCUMENTS 5,223,844 A 6/1993 Mansell et al.
5,400,020 A 3/1995 Jones et al.
(Continued)

FOREIGN PATENT DOCUMENTS

EP 0936794 8/1999
WO 0128274 4/2001
(Continued)

OTHER PUBLICATIONS

M. Hachman, "Bluetooth 4.1 Prepares Headsets and More to Connect to the 'Net", online publication dated Dec. 4, 2013 (http://www.techhive.com/category/holiday/.
(Continued)

*Primary Examiner* — Ronald B Abelson
(74) *Attorney, Agent, or Firm* — Withers & Keys, LLC

(57) ABSTRACT

Methods and systems for association management within a wireless node network of nodes and a server are described. A method may identify a first node as a potential for associating with a second node based, for example, upon status information about the nodes. An association request is transmitted by the second node to the server. The server may determine the locations of the nodes, determine if associating the nodes is desired based on the locations, and record new association data if association should occur. Upon receiving a permissive response from the server, which may include one or more authorization credentials, the first node and second node may be associated. Then with authorization credentials, the first and second nodes may securely connect and share data. And once associated, responsibility for a task previously done by the first node may be shifted to the second node after the nodes are associated.

20 Claims, 124 Drawing Sheets

(51) Int. Cl.
| | |
|---|---|
| H04W 64/00 | (2009.01) |
| H04W 4/02 | (2009.01) |
| H04W 12/08 | (2009.01) |
| H04W 4/00 | (2009.01) |
| G06Q 10/08 | (2012.01) |

(56) References Cited

U.S. PATENT DOCUMENTS

| | | | |
|---|---|---|---|
| 5,414,432 | A | 5/1995 | Penny, Jr. et al. |
| 5,691,980 | A | 11/1997 | Welles, II et al. |
| 5,884,216 | A | 3/1999 | Shah |
| 5,917,632 | A | 6/1999 | Lesesky |
| 5,953,650 | A | 9/1999 | Villevieille |
| 5,959,577 | A | 9/1999 | Fan et al. |
| 5,969,673 | A | 10/1999 | Bickley et al. |
| 6,011,510 | A | 1/2000 | Yee et al. |
| 6,052,597 | A | 4/2000 | Ekstrom |
| 6,085,090 | A | 7/2000 | Yee et al. |
| 6,240,365 | B1 | 5/2001 | Bunn |
| 6,255,989 | B1 | 7/2001 | Munson et al. |
| 6,311,069 | B1 | 10/2001 | Havinis et al. |
| 6,360,102 | B1 | 3/2002 | Havinis et al. |
| 6,466,788 | B1 | 10/2002 | Carlsson |
| 6,505,048 | B1 | 1/2003 | Moles et al. |
| 6,526,335 | B1 | 2/2003 | Treyz et al. |
| 6,577,484 | B1 | 6/2003 | Stanley et al. |
| 6,674,860 | B1 | 1/2004 | Pirila |
| 6,711,399 | B1 | 3/2004 | Granier |
| 6,748,318 | B1 | 6/2004 | Jones |
| 6,748,320 | B2 | 6/2004 | Jones |
| 6,853,911 | B1 | 2/2005 | Sakarya |
| 6,904,359 | B2 | 6/2005 | Jones |
| 7,085,629 | B1 | 8/2006 | Gotou et al. |
| 7,212,829 | B1 | 5/2007 | Lau et al. |
| 7,242,926 | B1 | 7/2007 | Murakami et al. |
| 7,370,079 | B2 | 5/2008 | Murata et al. |
| 7,623,033 | B2 | 11/2009 | Ainsworth et al. |
| 7,876,239 | B2 | 1/2011 | Horstemeyer |
| 8,239,169 | B2 | 8/2012 | Gregory et al. |
| 8,299,920 | B2 | 10/2012 | Hamm et al. |
| 8,447,882 | B2 | 5/2013 | Twitchell, Jr. |
| 8,560,274 | B2 | 10/2013 | Gregory et al. |
| 8,725,165 | B2 | 5/2014 | Lau et al. |
| 8,755,823 | B2 | 6/2014 | Proietti et al. |
| 8,766,797 | B2 | 7/2014 | Hamm et al. |
| 2001/0022615 | A1 | 9/2001 | Fernandez et al. |
| 2002/0000916 | A1 | 1/2002 | Richards |
| 2004/0253923 | A1 | 12/2004 | Braley et al. |
| 2006/0018274 | A1 | 1/2006 | Twitchell, Jr. |
| 2006/0200560 | A1 | 9/2006 | Waugh et al. |
| 2008/0004994 | A1 | 1/2008 | Ainsworth et al. |
| 2009/0201850 | A1 | 8/2009 | Davis et al. |
| 2010/0267375 | A1 | 10/2010 | Lemmon et al. |
| 2011/0022533 | A1 | 1/2011 | Lau et al. |
| 2011/0078089 | A1 | 3/2011 | Hamm et al. |
| 2012/0036198 | A1 | 2/2012 | Marzencki et al. |
| 2013/0106893 | A1 | 5/2013 | Davis et al. |
| 2013/0273938 | A1 | 10/2013 | Ng et al. |
| 2014/0025746 | A1 | 1/2014 | Rhee et al. |
| 2014/0211691 | A1 | 7/2014 | Emadzadeh et al. |

FOREIGN PATENT DOCUMENTS

| | | |
|---|---|---|
| WO | 0146649 | 6/2001 |
| WO | 0160038 | 8/2001 |
| WO | 0163318 | 8/2001 |

OTHER PUBLICATIONS

M. Schuster, "The Biggest iPhone 5S Feature Nobody's Talking About", online publication dated Sep. 18, 2013 (http://www.minyanville.com/sectors/technology/articles/The-Biggest-iPhone-5S-Feature-Nobodys/Sep. 18, 2013/id/51810#ixzz2fHNaHphq).

E. Betters, "Apple's iBeacons Explained: What It Is and Why It Matters", online publication dated Sep. 18, 2013 (http://www.pocket-lint.com/news/123730-apple-s-ibeacons-explained-what-it-is-and-why-it-matters).
P. Pachal, "Bluetooth Devices Are About to Get a Lot Smarter", online publication dated Dec. 5, 2013 (http://mashable.com/Dec. 5, 2013/bluetooth-4-1/).
X. Luo et al., "Comparative Evaluation of Received Signal-Strength Index (RSSI) Based Indoor Localization Techniques for Construction Jobsites", Adv. Eng. Informat. (2010), doi:10.1016/j.aei.Sep. 3, 2010.
B. Amutha et al., "Location Update Accuracy in Human Tracking System Using Zigbee Modules", International Journal of Computer Science and Information Security, vol. 6, No. 2, 2009.
"Bluetooth 4.1 Quick Reference Guide", Bluetooth SIG 2013, Nov. 2013.
"Intelligent Transportation System—Wikipedia, the free encyclopedia", online publication dated Oct. 21, 2013 (http://en.wikipedia.org/wiki/Intelligent_transportion_system).
J. Johnson et al., "Ultra-Wideband Aiding of GPS for Quick Deployment of Anchors in a GPS-denied Ad-hoc Sensor Tracking and Communication System", presented at ION GNSS (Portland, or Sep. 10-23, 2011).
C. Liu et al., "Location Tracking by ZigBee", online publication undated (http://ir.csu.edu.tw/dspace/bitstream/987654321/1288/1/496.pdf).
R. Horblyuk et al., "Out of Control: Little-Used Clinical Assets Are Draining Healthcare Budgets", Healthcare Financial Management, Jul. 2012 issue, p. 68-72.
"P410 UWB OEM Modules for Ranging and Communications | Time Domain", online publication dated Apr. 24, 2014 (http://www.timedomain.com/p400.php).
J. Terry et al., "Patient Flow and Access. Unlocking the Capacity of Acute Care Hospitals and Our National Healthcare Infrastructure", undated publication from GE Healthcare.
D. Long et al., "Wasting Away: The Quality, Safety, and Financial Case for Clinical Asset Optimization", undated publication from GE Healthcare.
"Awarepoint Real-time Awareness Solutions", online publication dated Oct. 1, 2013 (http://www.awarepoint.com/solutions).
M. Gheza et al., "Real Time Location System—Case Study: ZigBee System-on-Chip Solution", online publication dated Aug. 22, 2013 (www.slideshare.net/mihaigheza/real-time-location-system-with-zigbee).
Product Brochure for Time Domain's PulsON 410 (P410) Ultra Wideband (UWB) Ranging and Communication Module, undated.
"AutonoNav Scalable Autonomous Navigation System", online publication dated Oct. 21, 2013 (www.torcrobotics.com/products/autononav).
"Locating ZigBee Nodes Using Ti's CC2431 Location Engine and Daintree's SNA", Daintree Networks Application Note AN016, Copyright 2008 (http://www.daintree.net_downloads_appnotes_appnote_016_sna_ti_locationing.pdf).
"Wireless ZigBee Networks for Real-Time Location Systems", online publication undated (www.ece.gatech.edu_academic_courses_ece4007_11spring_EDE4007L04_da2_ECE4007TRP_Sheng.pdf).
O. Hernandez et al., "Position Location Monitoring Using IEEE 802.15.4/ZigBee Technology", online publication undated (http://www.freescale.com_files_microcontrollers_doc_broachure_PositionLocationMonitoring.pdf).
"Estimote for Retail", online publication undated (http://www.estimote.com/estimote-for-retail.html).
Online Estimote App for Managing Estimote Beacons, online publication dated Aug. 18, 2014 (https://itunes.apple.com/us/app/estimote-virtual-beacon/id686915066).
"Environmental Cyberinfrastructure Needs for Distributed Sensor Networks", A Report from a National Science Foundation Sponsored Workshop, Scripps Inst. Oceanography, Aug. 12-13, 2003, pp. 1-66.
"A Standard Smart Transducer Interface", IEEE 1451. Sensors Expo, Philadelphia, Oct. 2, 2011, pp. 1-27.

(56) References Cited

OTHER PUBLICATIONS

Wolfe, "Electronic Cargo Seals: Context, Technologies and Marketplace", http://ops.fhwa.dot.gov/freight/E-Seal%20WP%final%20Jul%2012.htm. Jul. 12, 2002, pp. 1-47.

Maestas et al., "Demonstration of the Radio Frequency Identification Transportation Security and Safety System", Applied Sci. Laboratory, Oct. 15, 2003. pp. 1-11.

Remote Sensing for Transportation: Report of a Conference. Washington D.C., Dec. 4-5, 2000, pp. 1-59.

Ho et al., "In-Situ Chemiresistor Sensor Package for Real-Time Detection of Volatile Organic Compounds in Soil and Groundwater", Sensors vol. 2, 2002, pp. 23-34.

"System Planning Corp. Helps Evaluate Seamless Container-Security System", Jrnl. Commerce, May 30, 2005.

Wiczer Ph.D., "Connectivity: Smart Sensors or Smart Interfaces". ISA 2001 Emerging Technologies Conference. Sep. 2001, pp. 1-9.

Natalia Marmasse, "comMotion: A Context-Aware Communication System" Item: Masters Thesis submitted to MIT Libraries, Date: Oct. 1, 1999 the document: http://dspace.mit.edu/bitstrea/handle/1721.1/61841/44869691.pdf?sequence=1.

Marmasse, et al., "Location-Aware Information Delivery with comMotion", HUC 2000 Proceedings, pp. 1-15.

Katz, "E-Mail, Anywhere, in the Palm of Your Hand", Technology Cypertimes, http://partners.nytimes.com/week/091497email.html, Sep. 14, 1997.

• Location of ID Node C determined through triangulation across ID Node B and Master Nodes M1 and M2

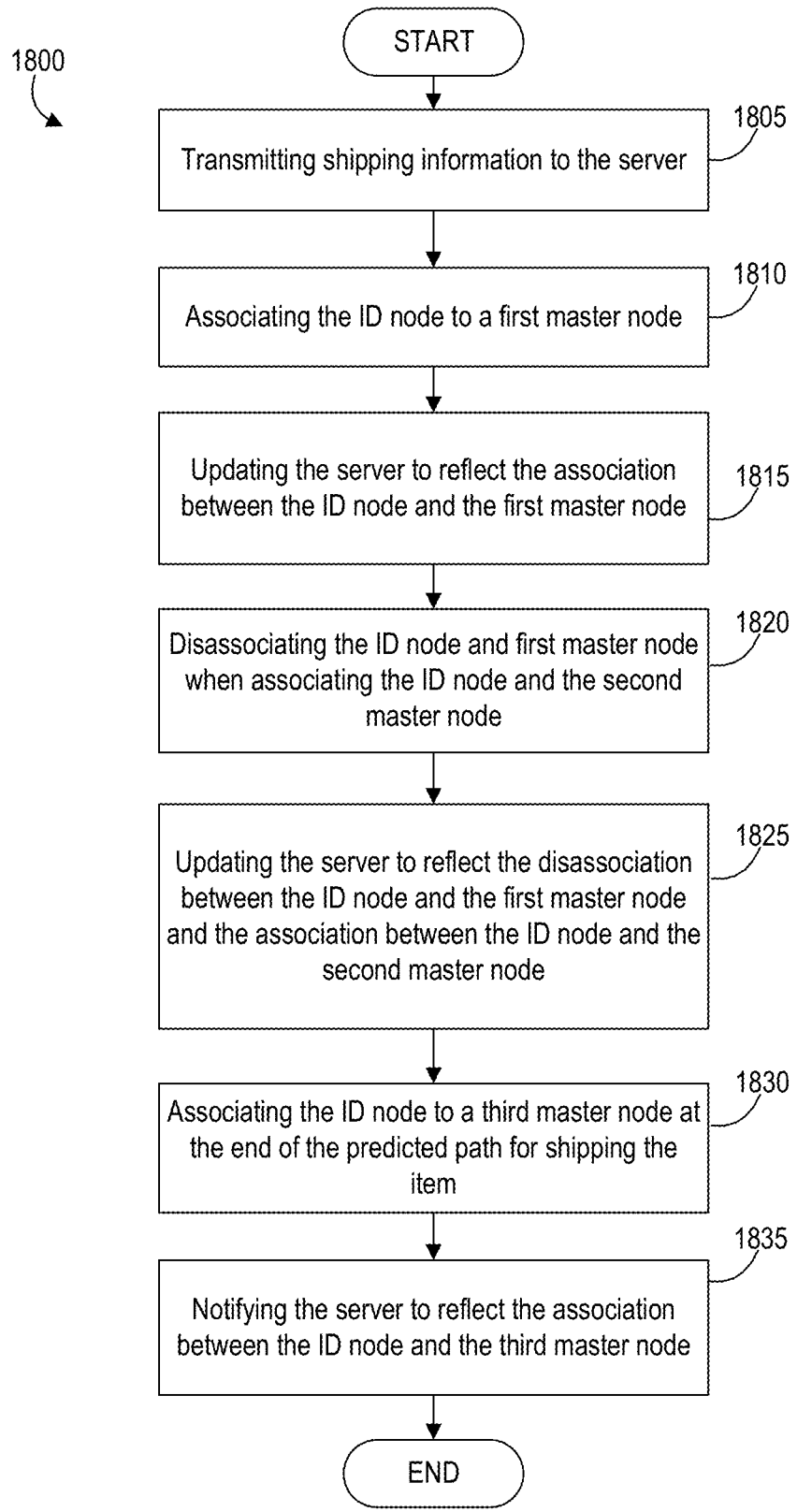

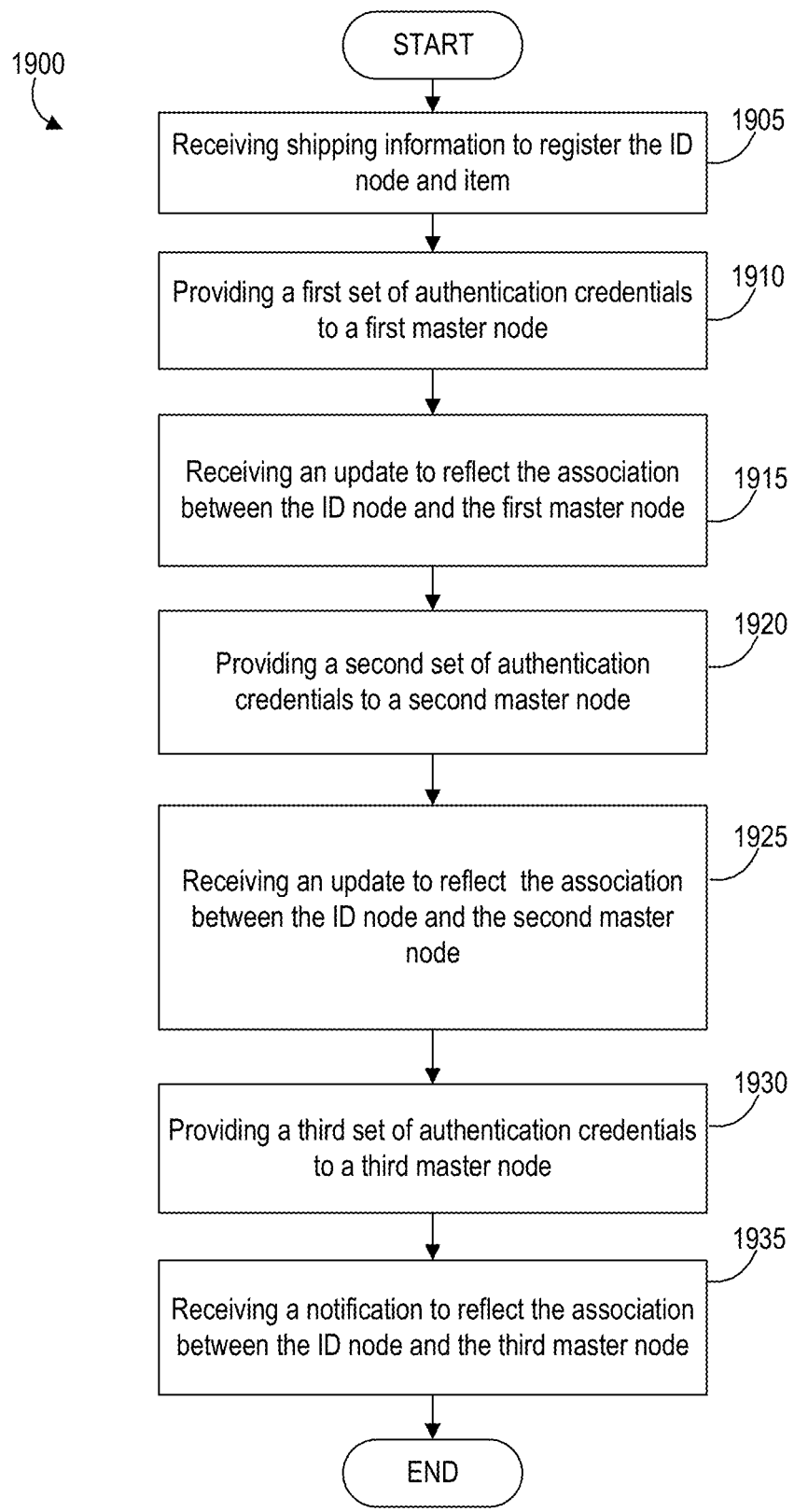

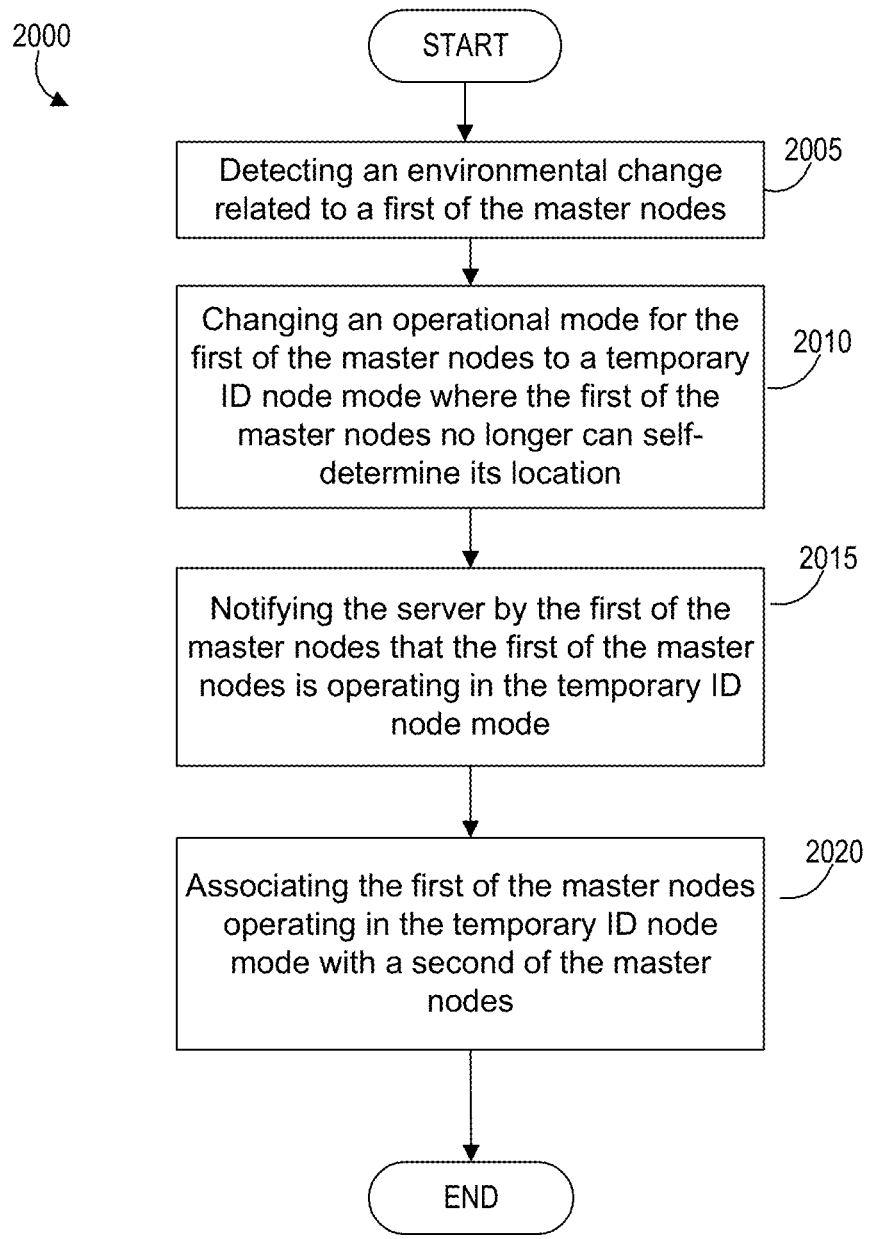

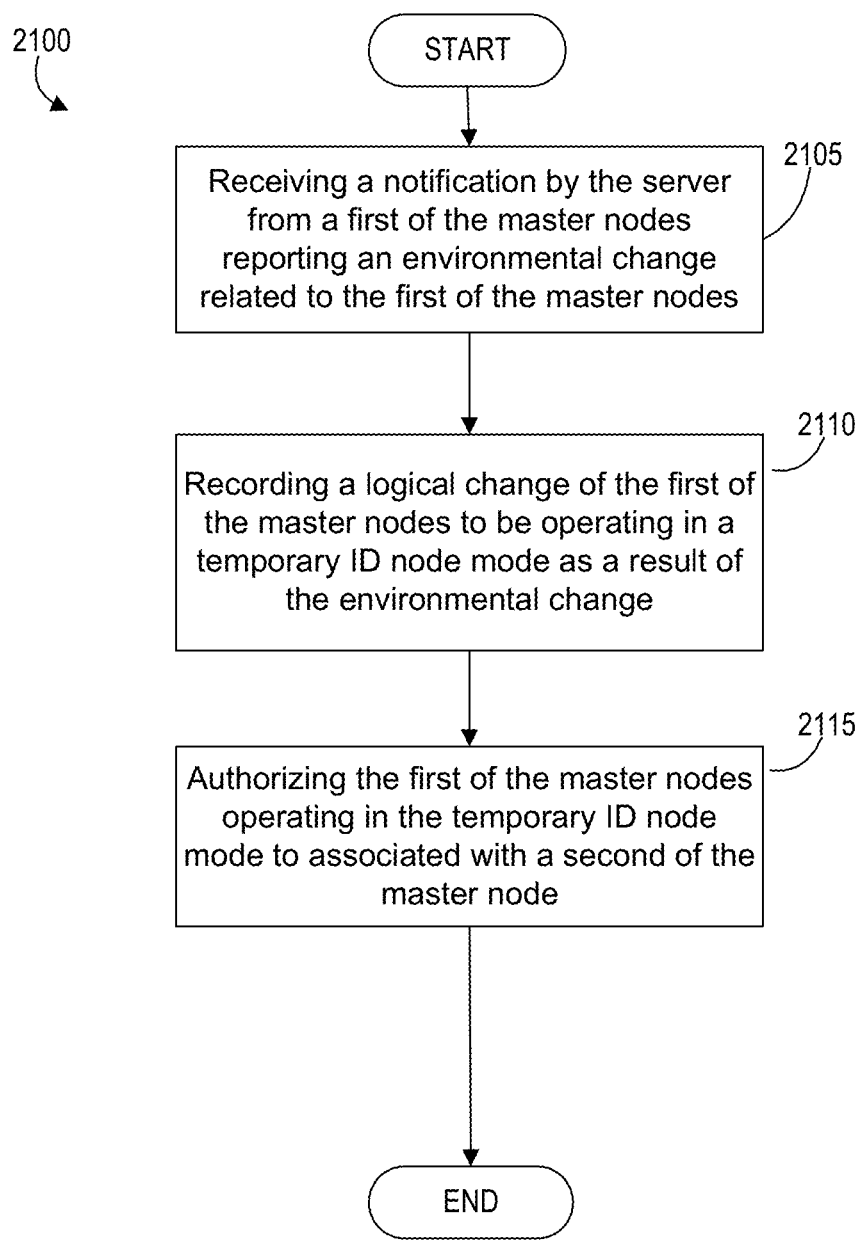

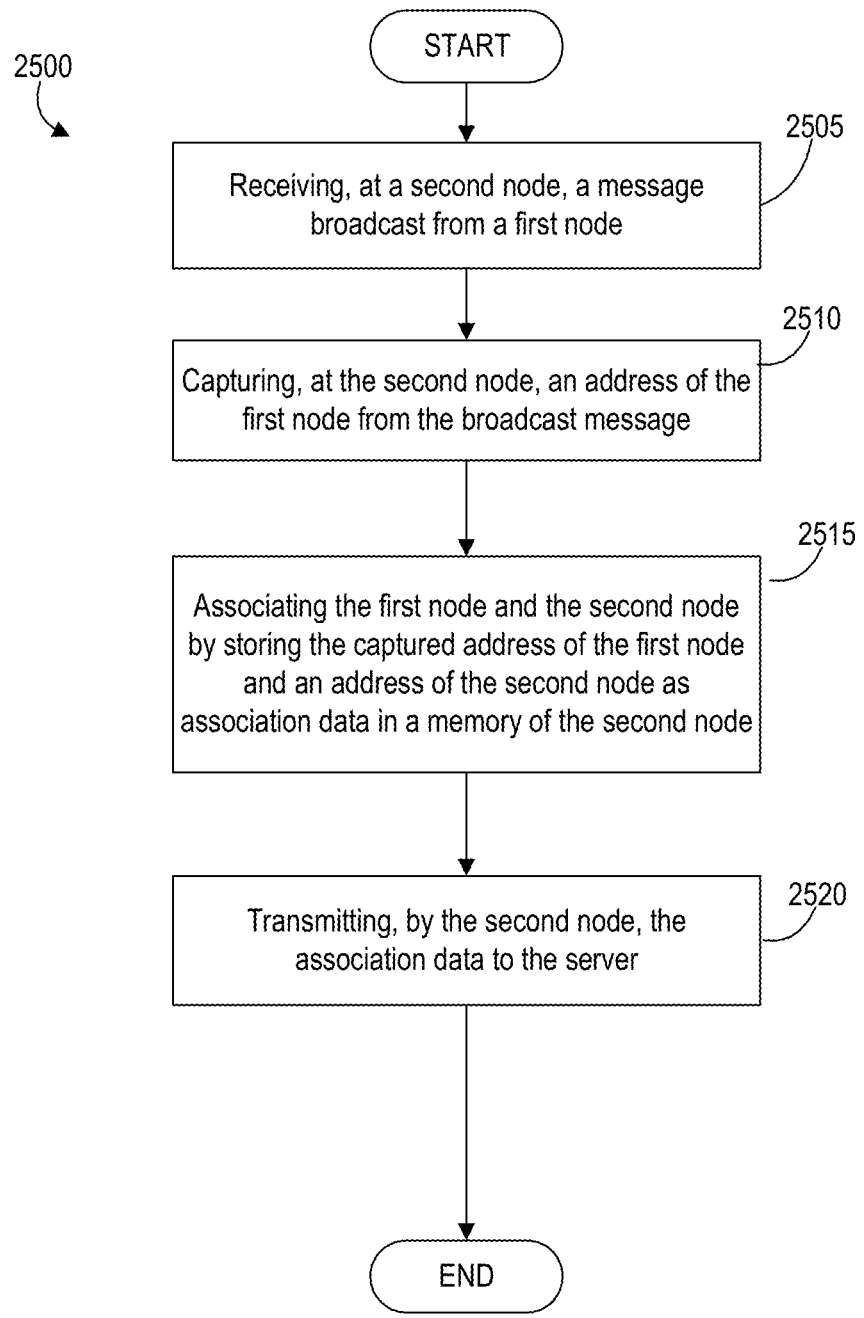

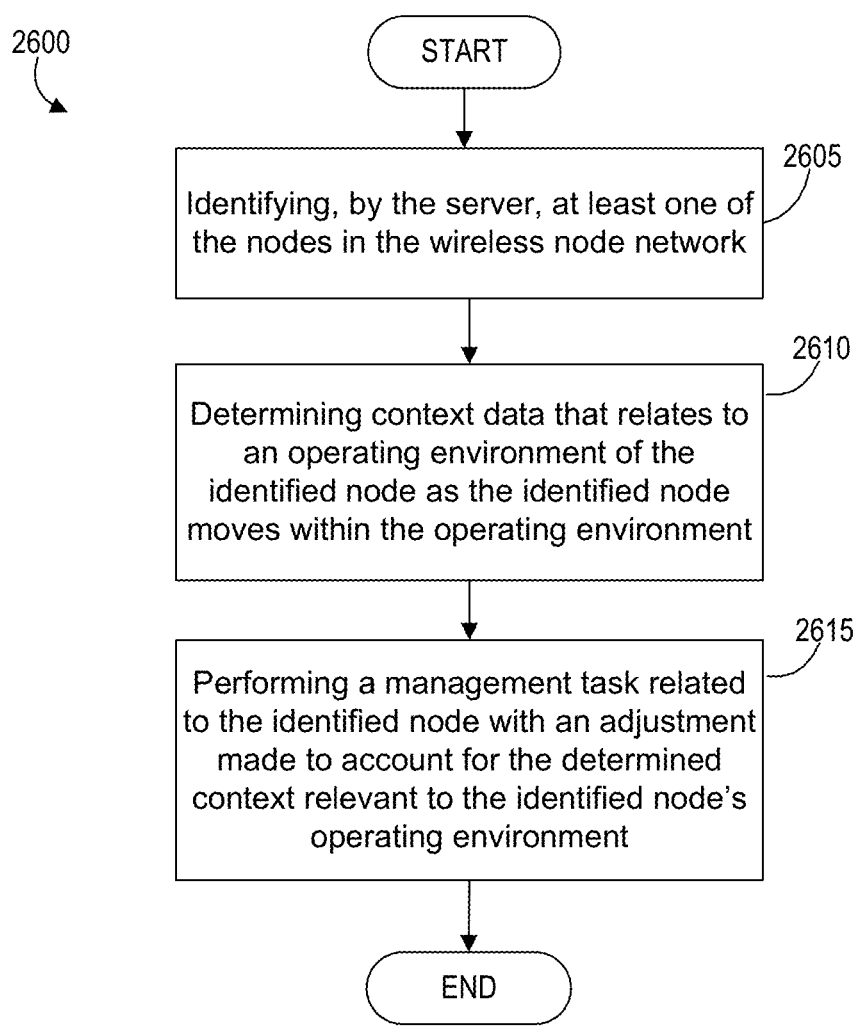

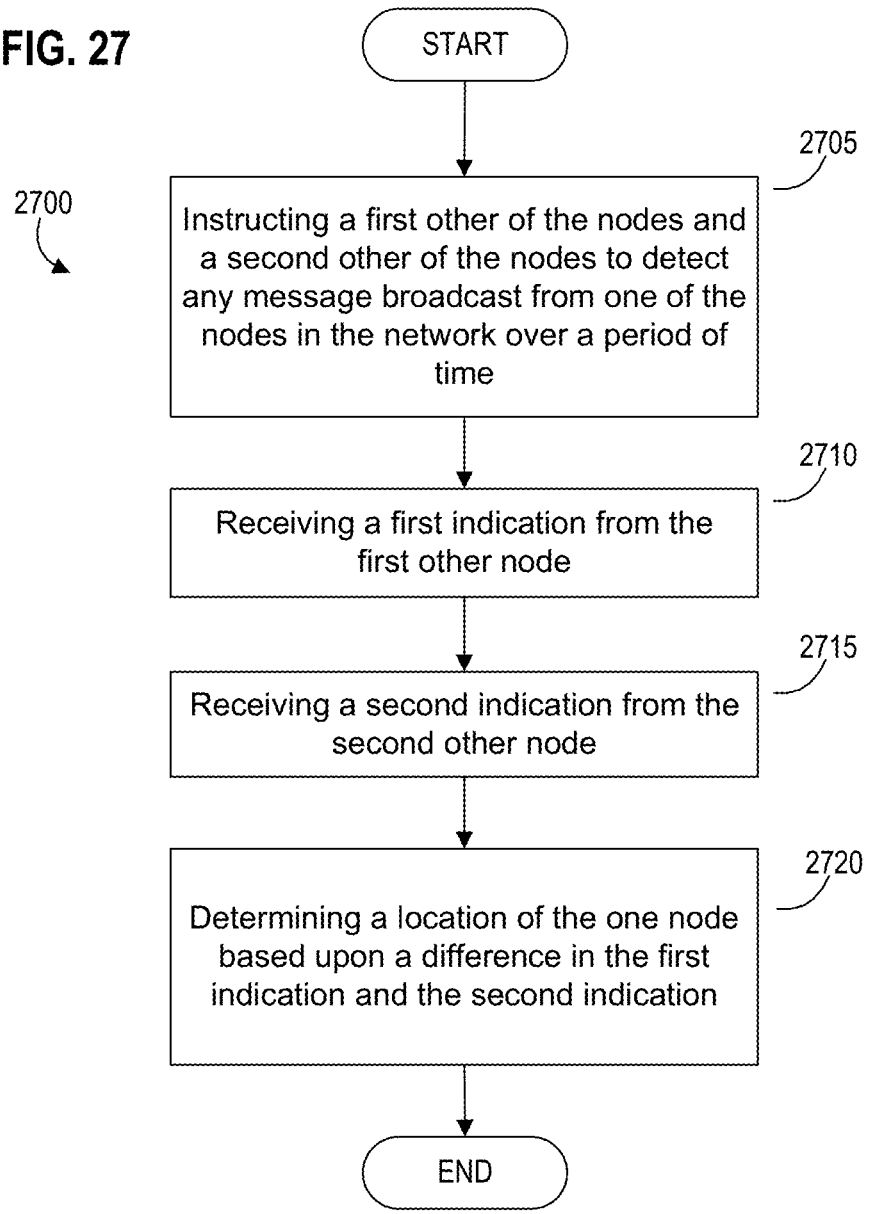

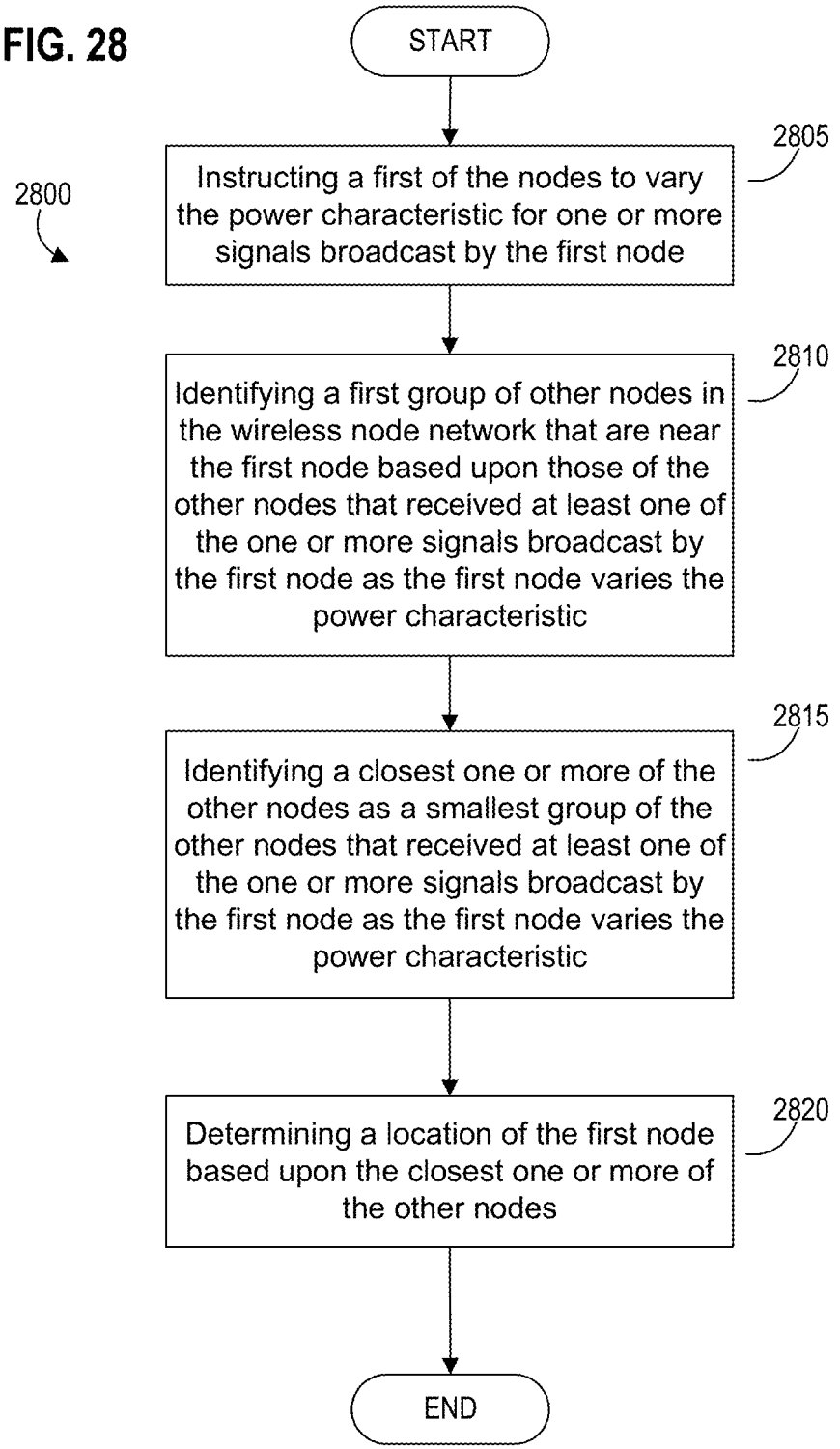

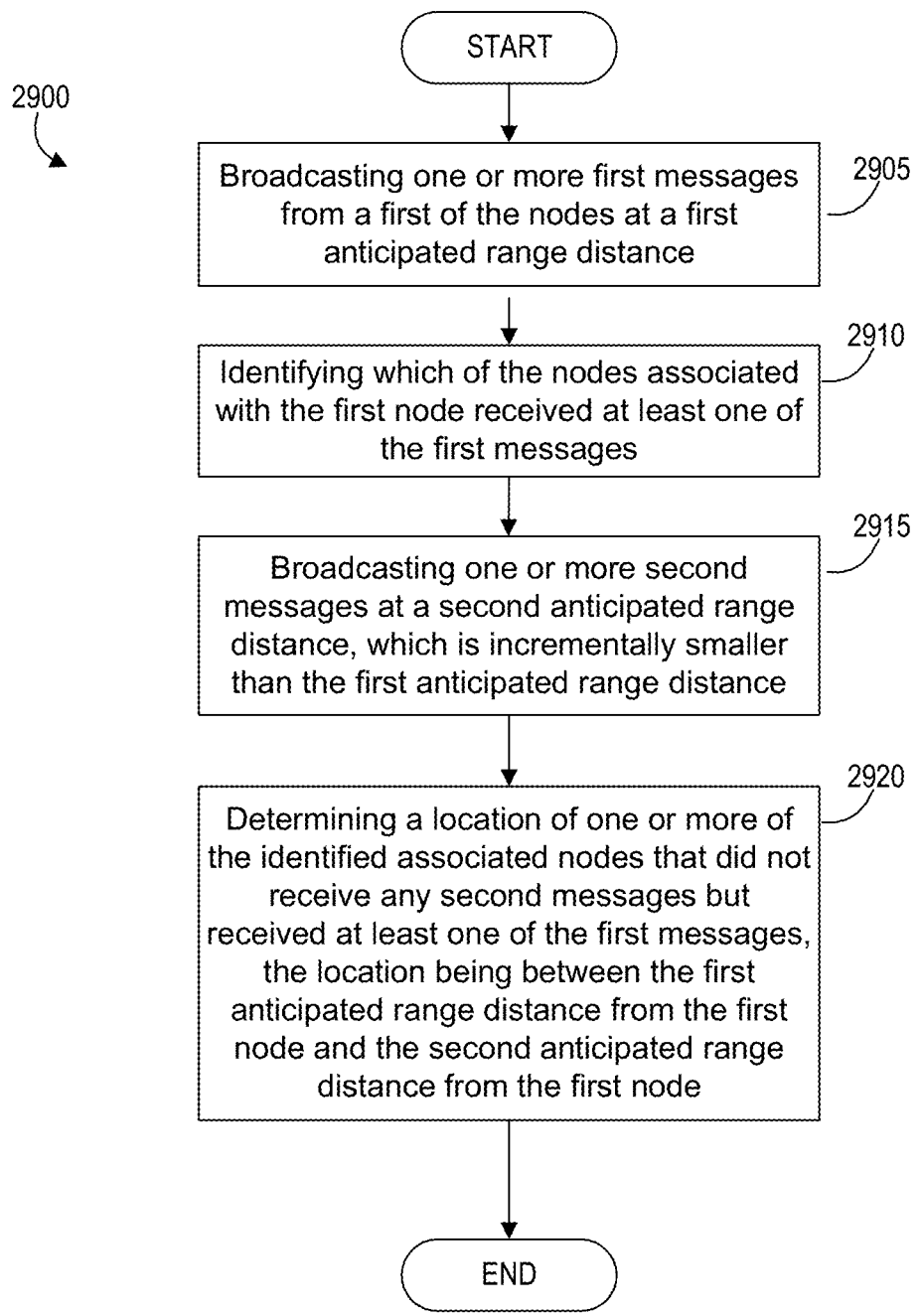

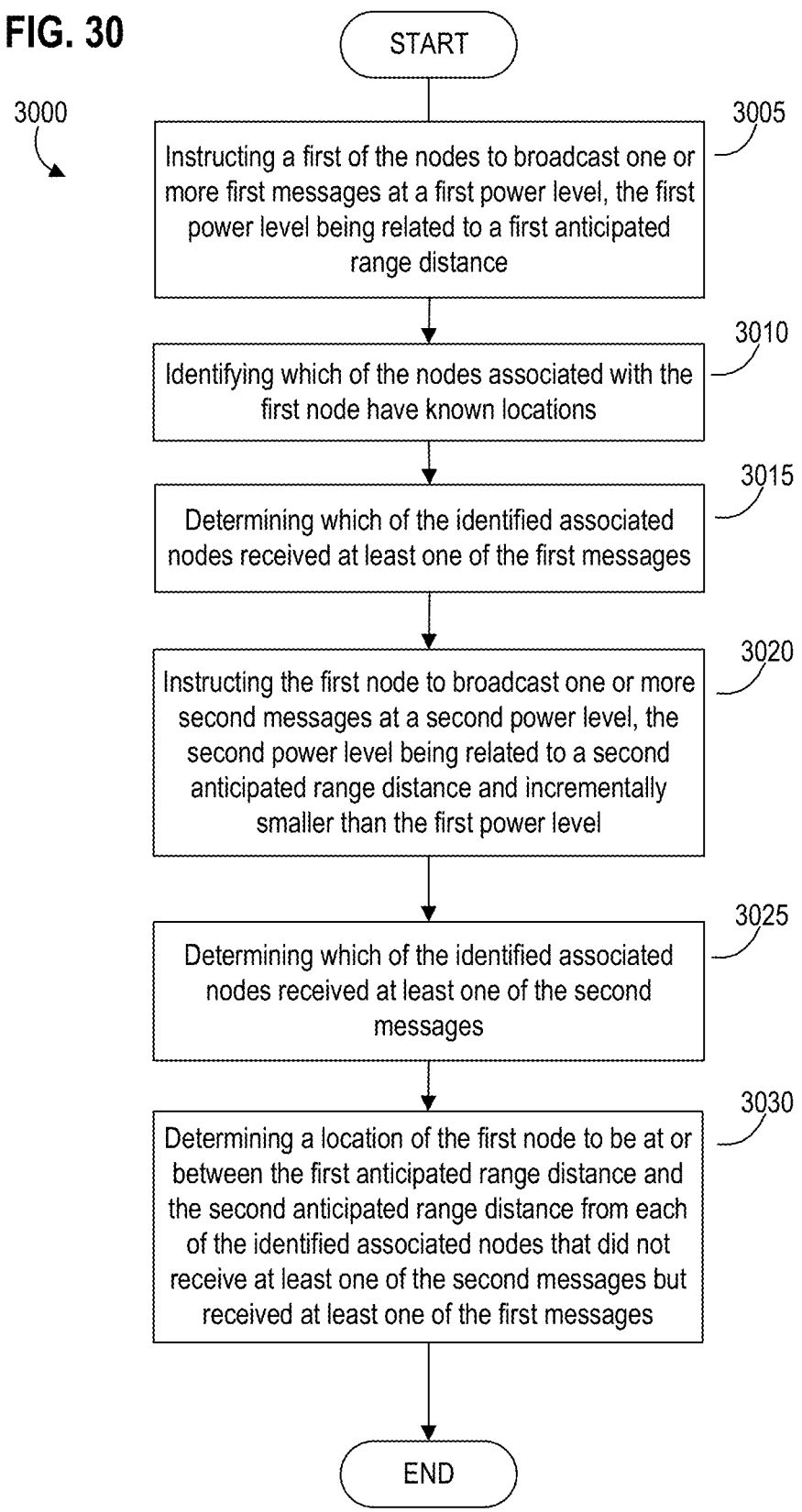

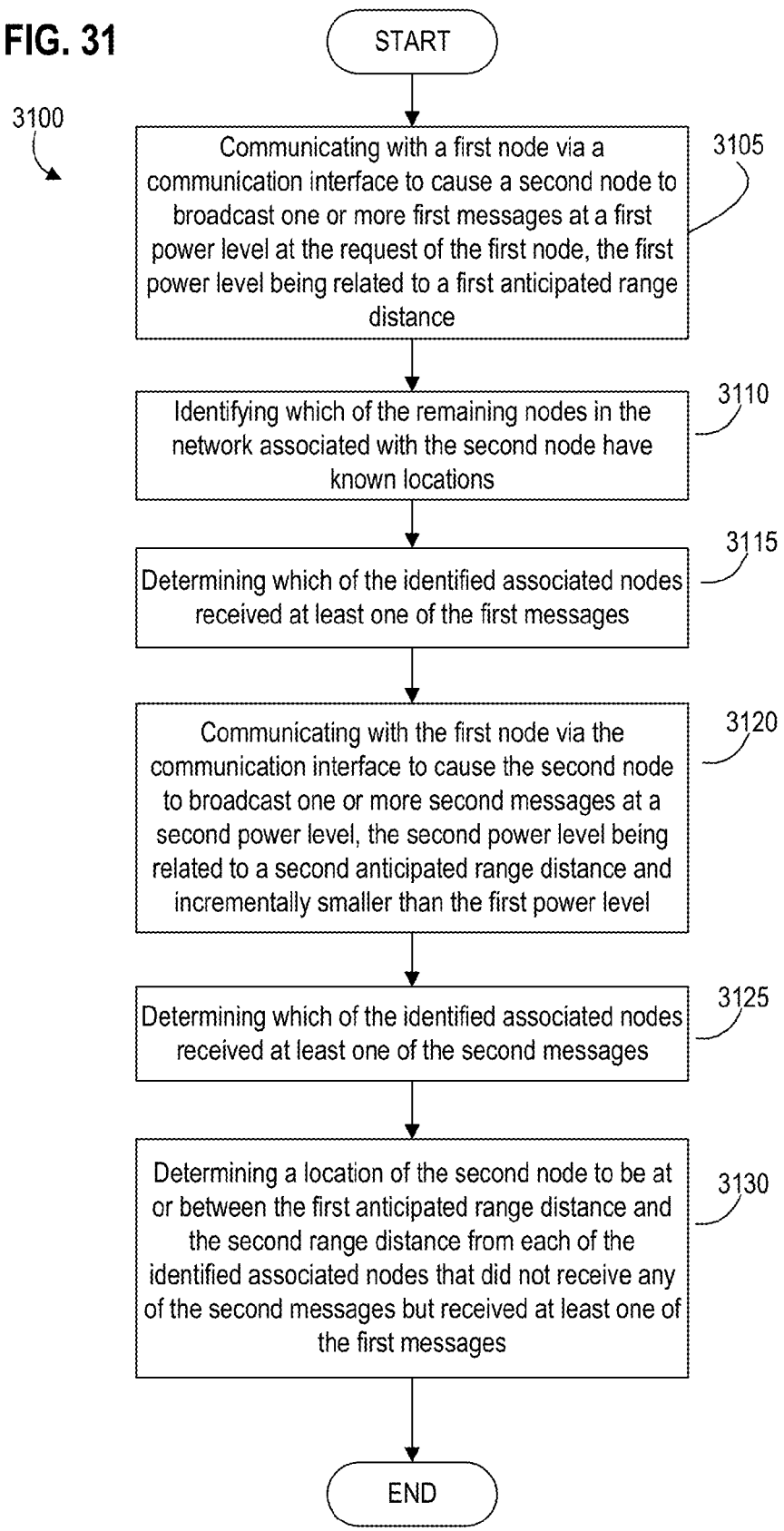

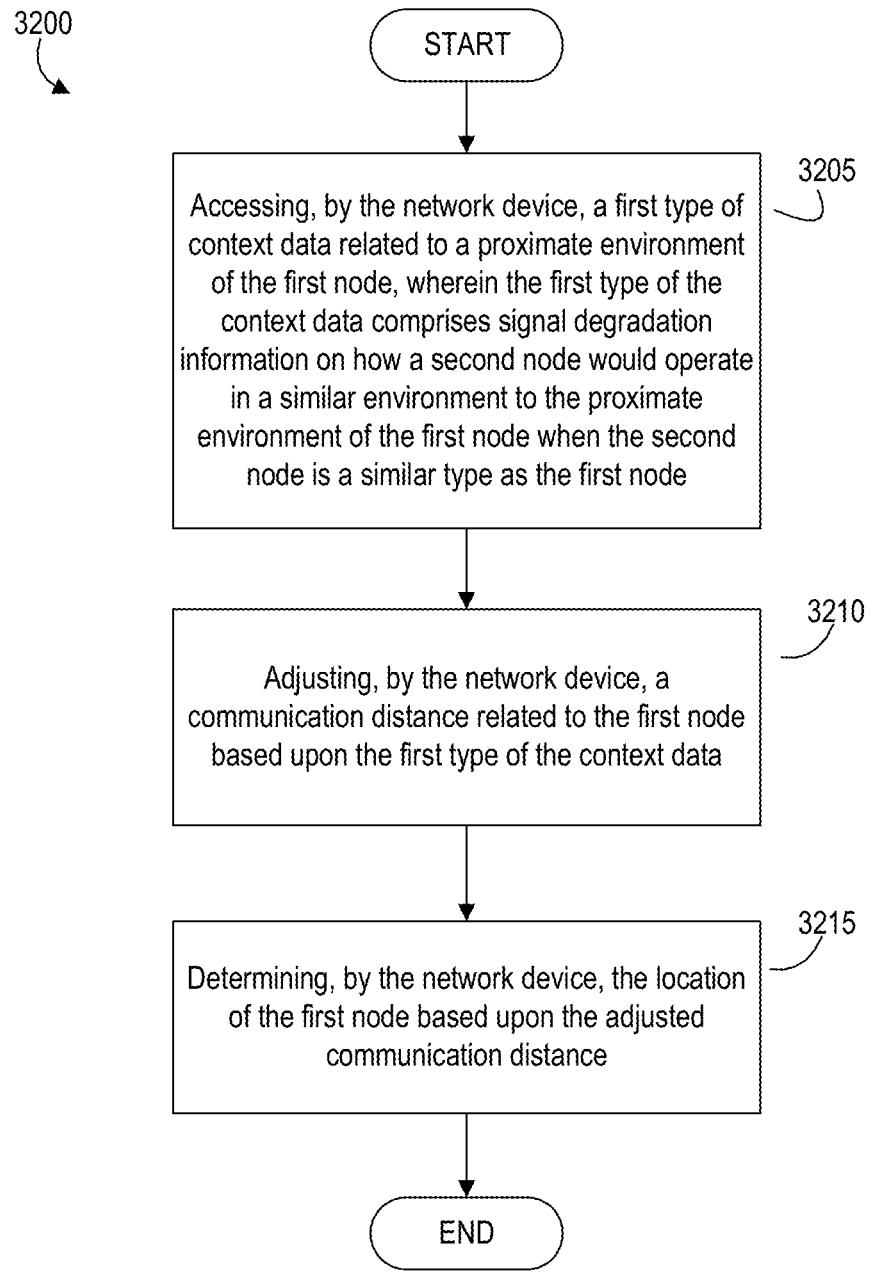

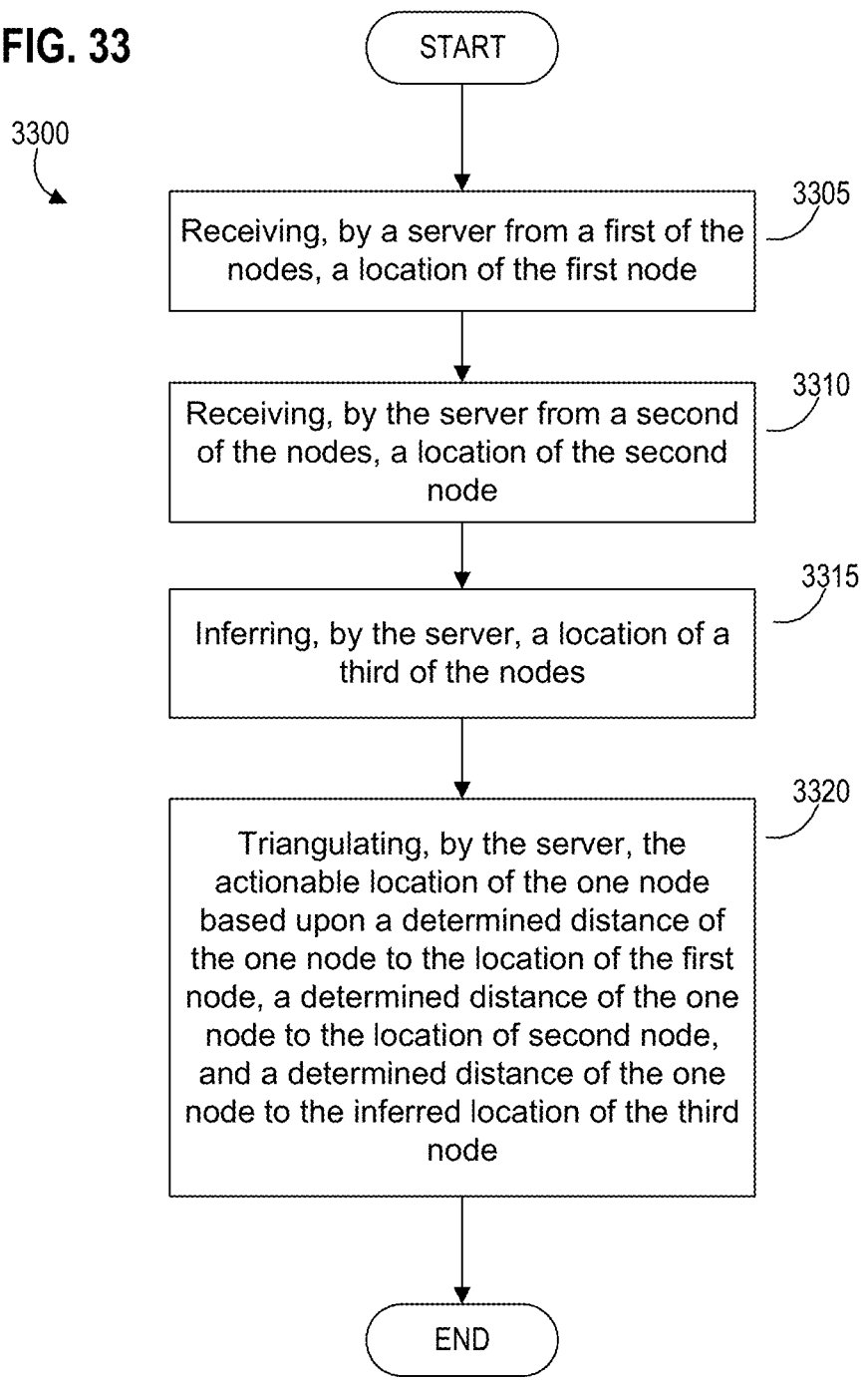

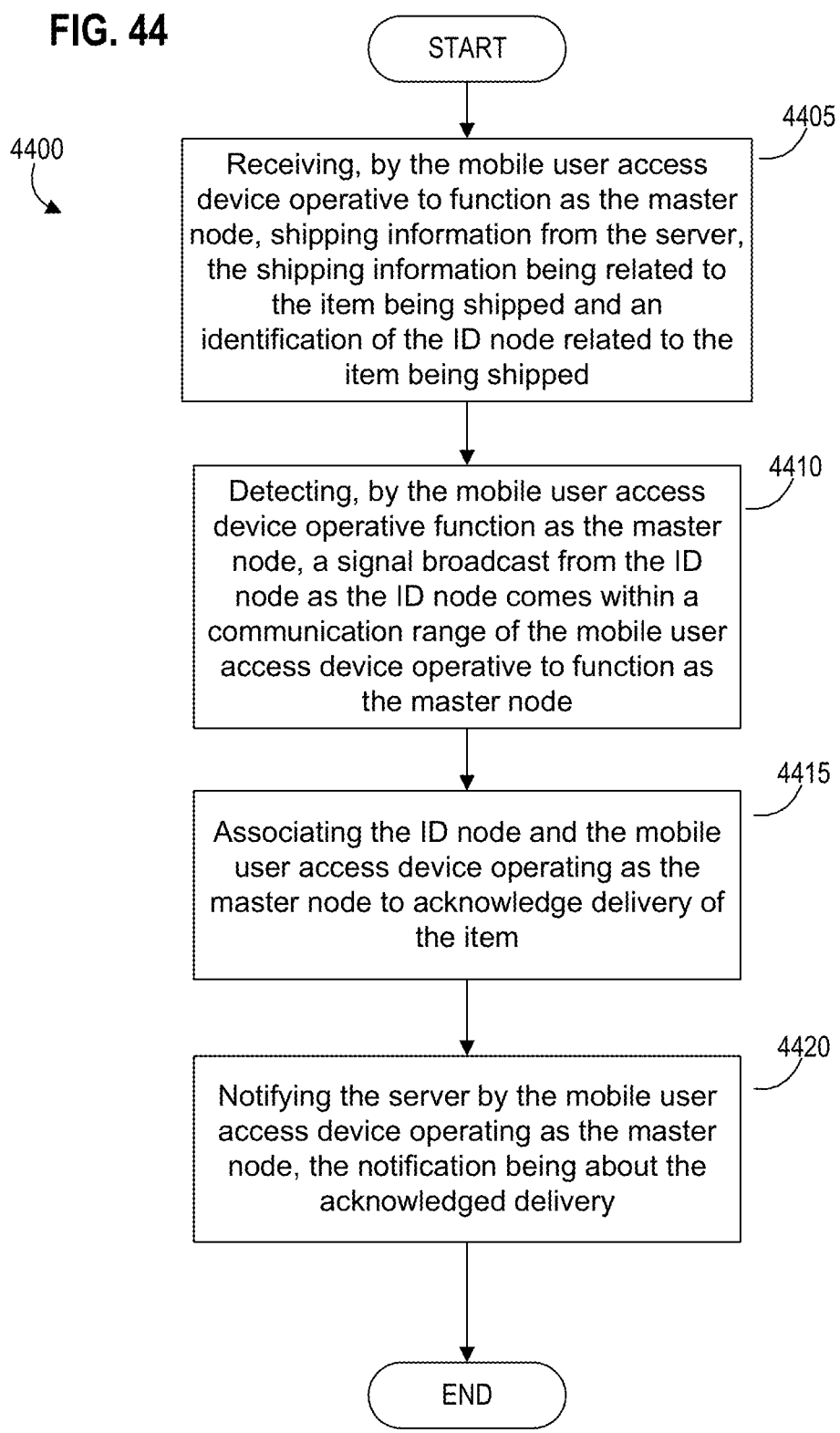

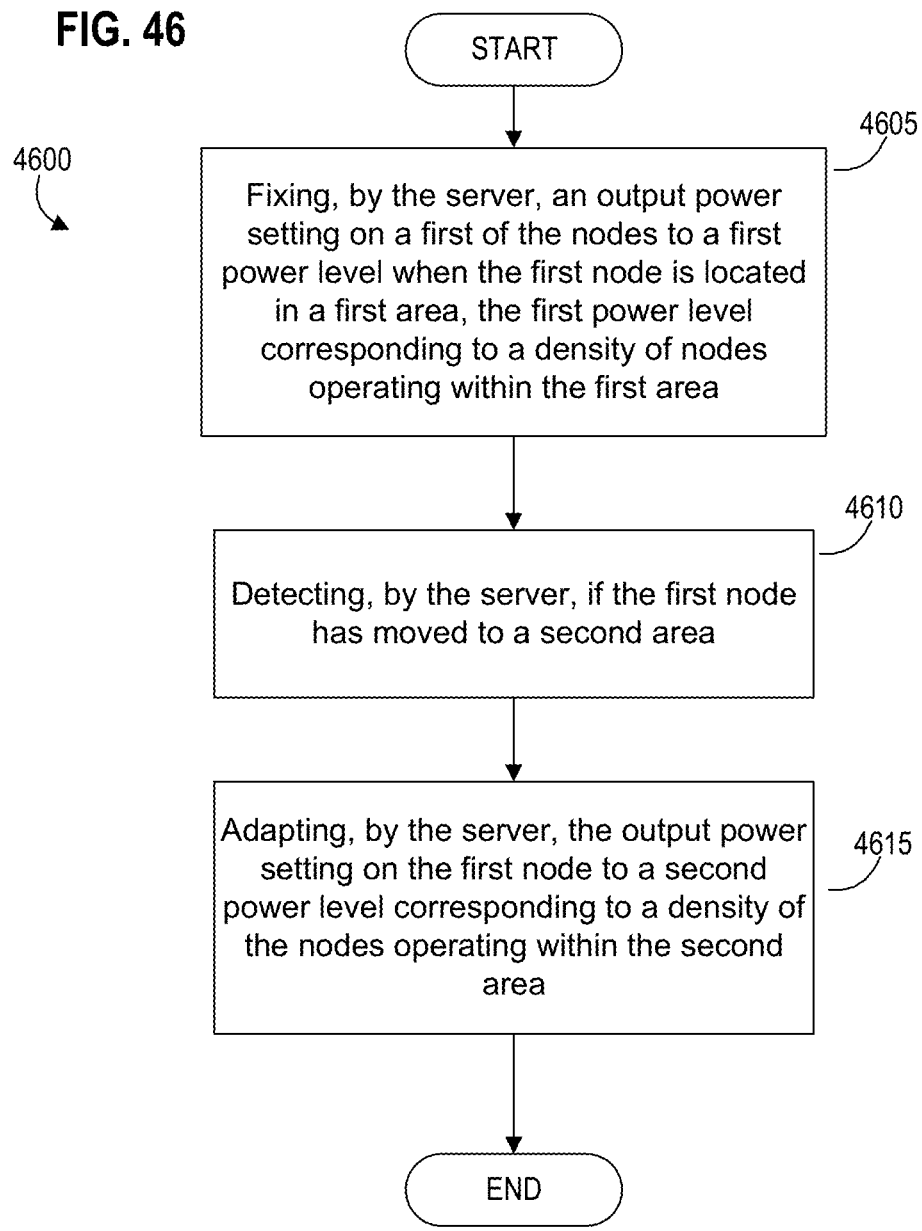

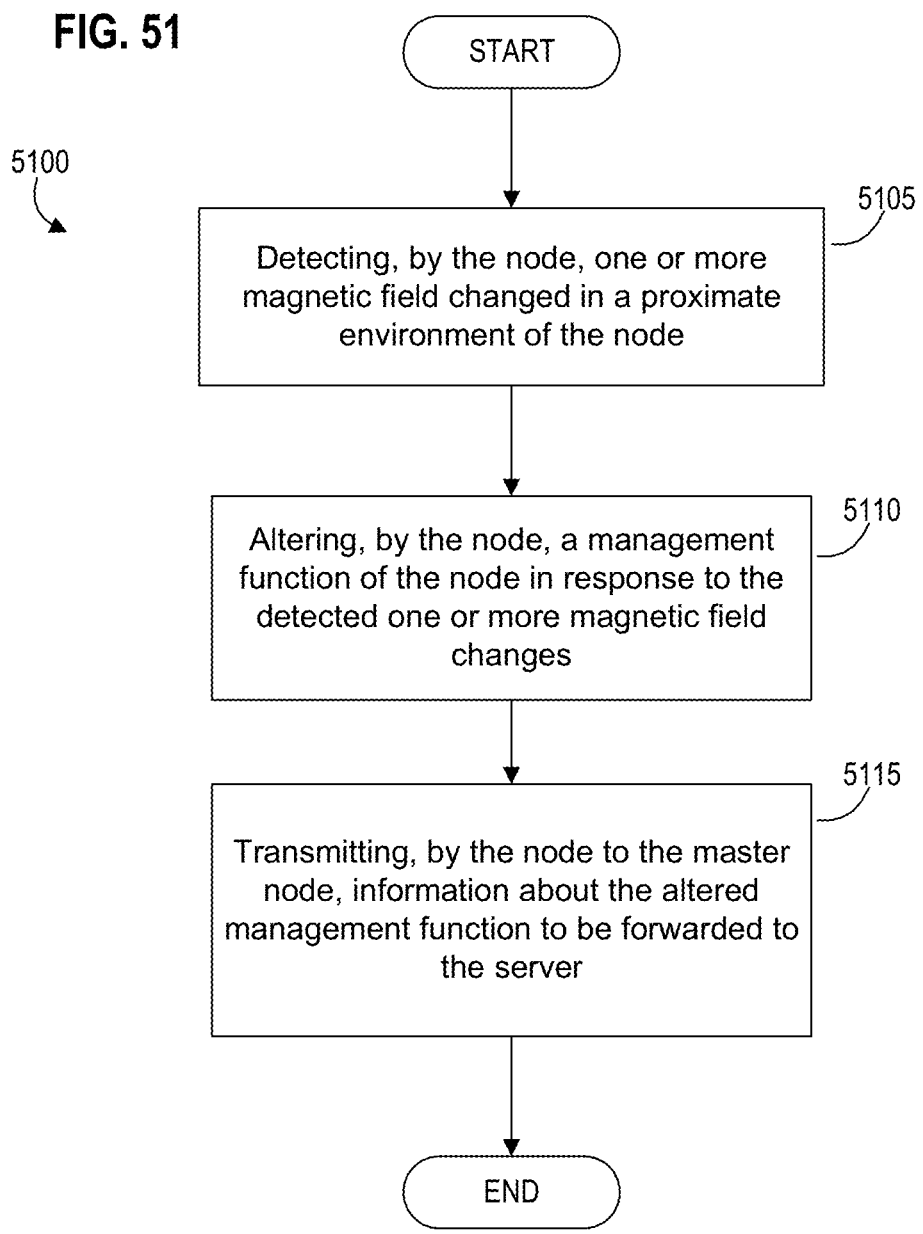

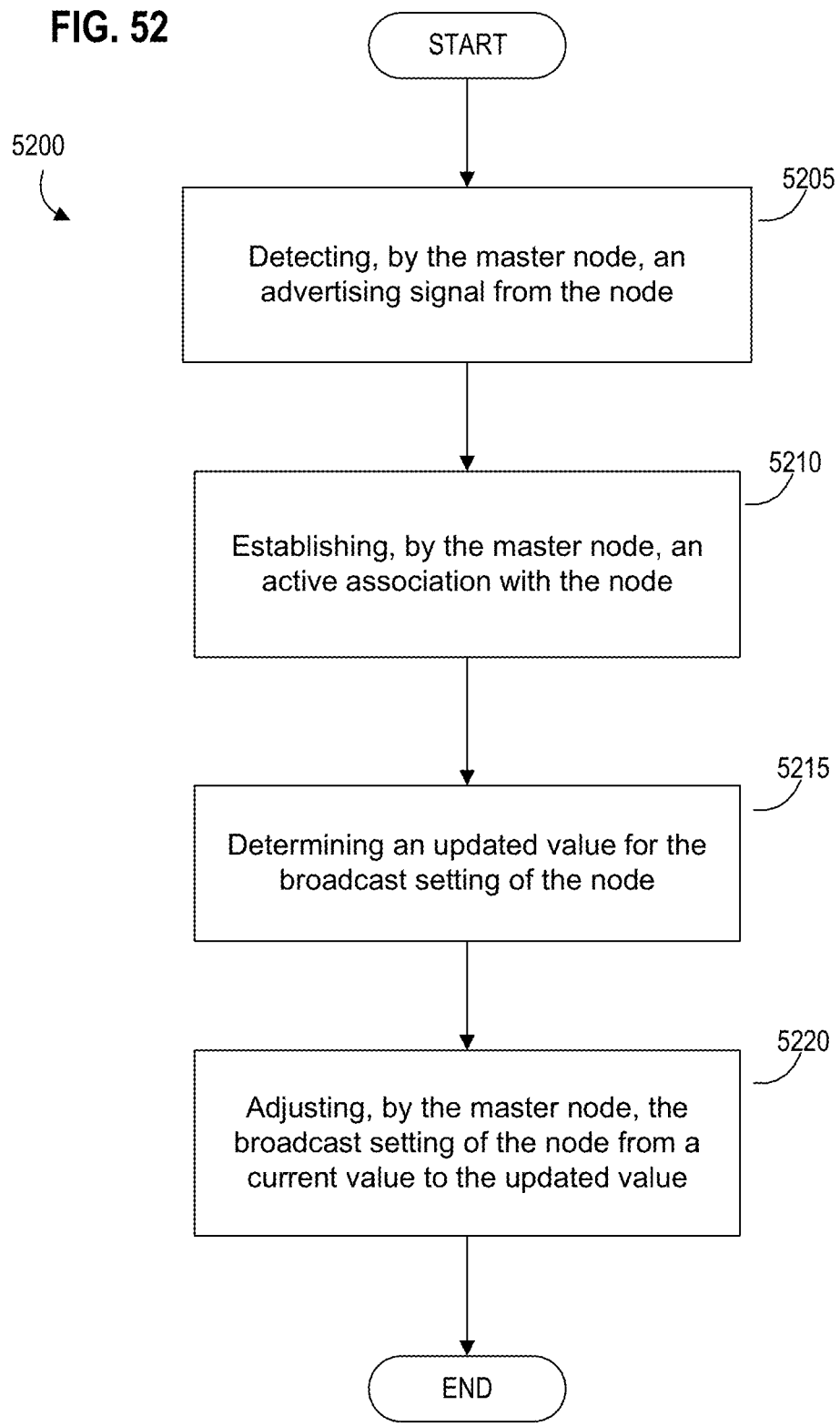

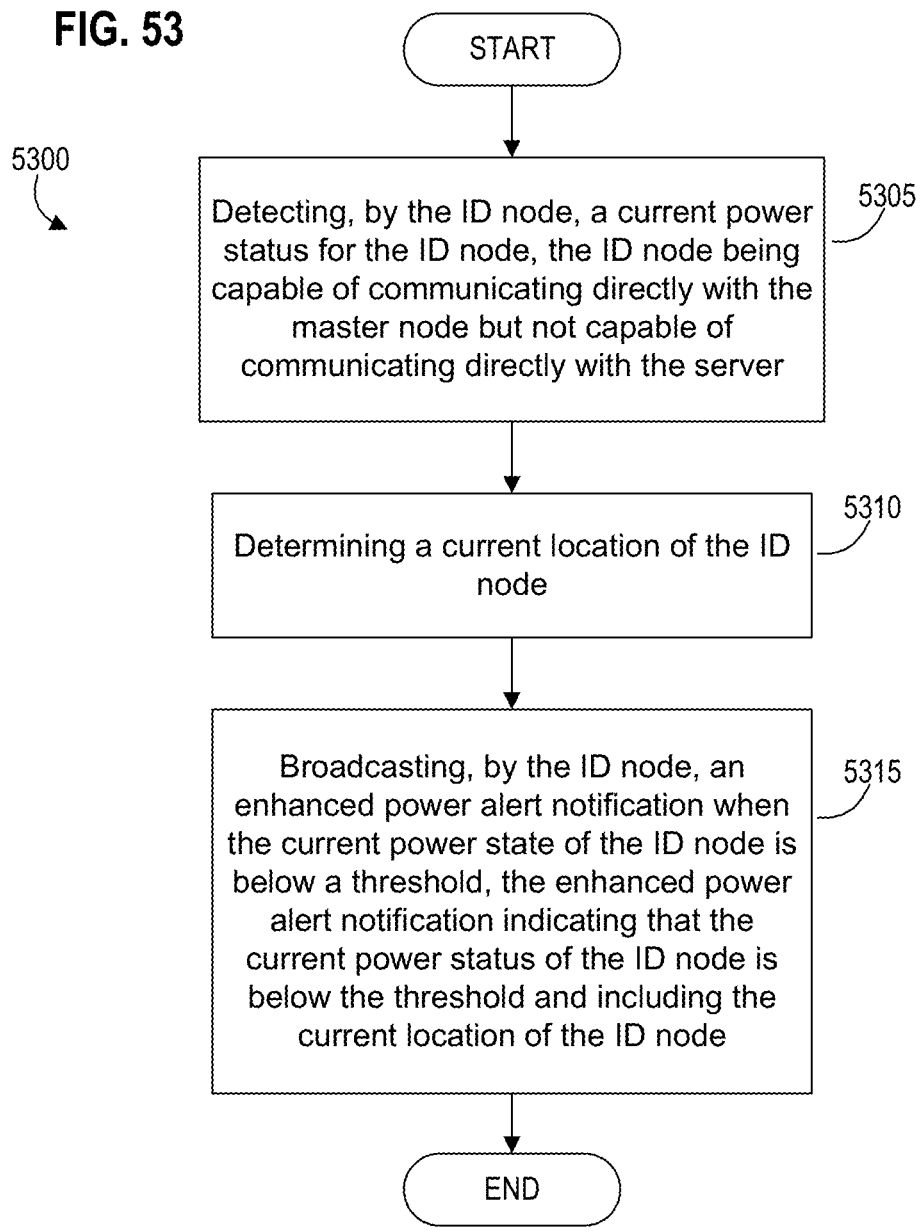

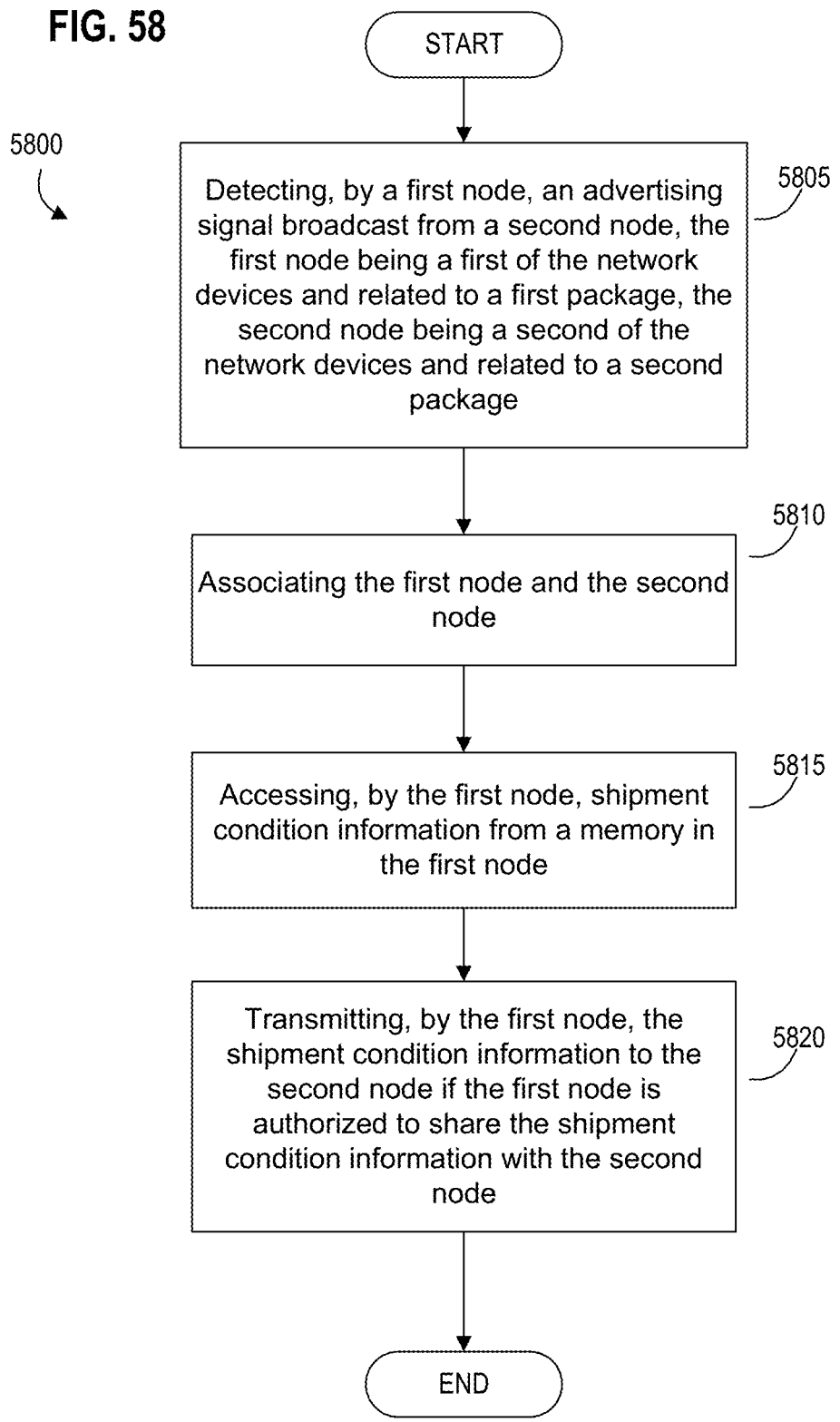

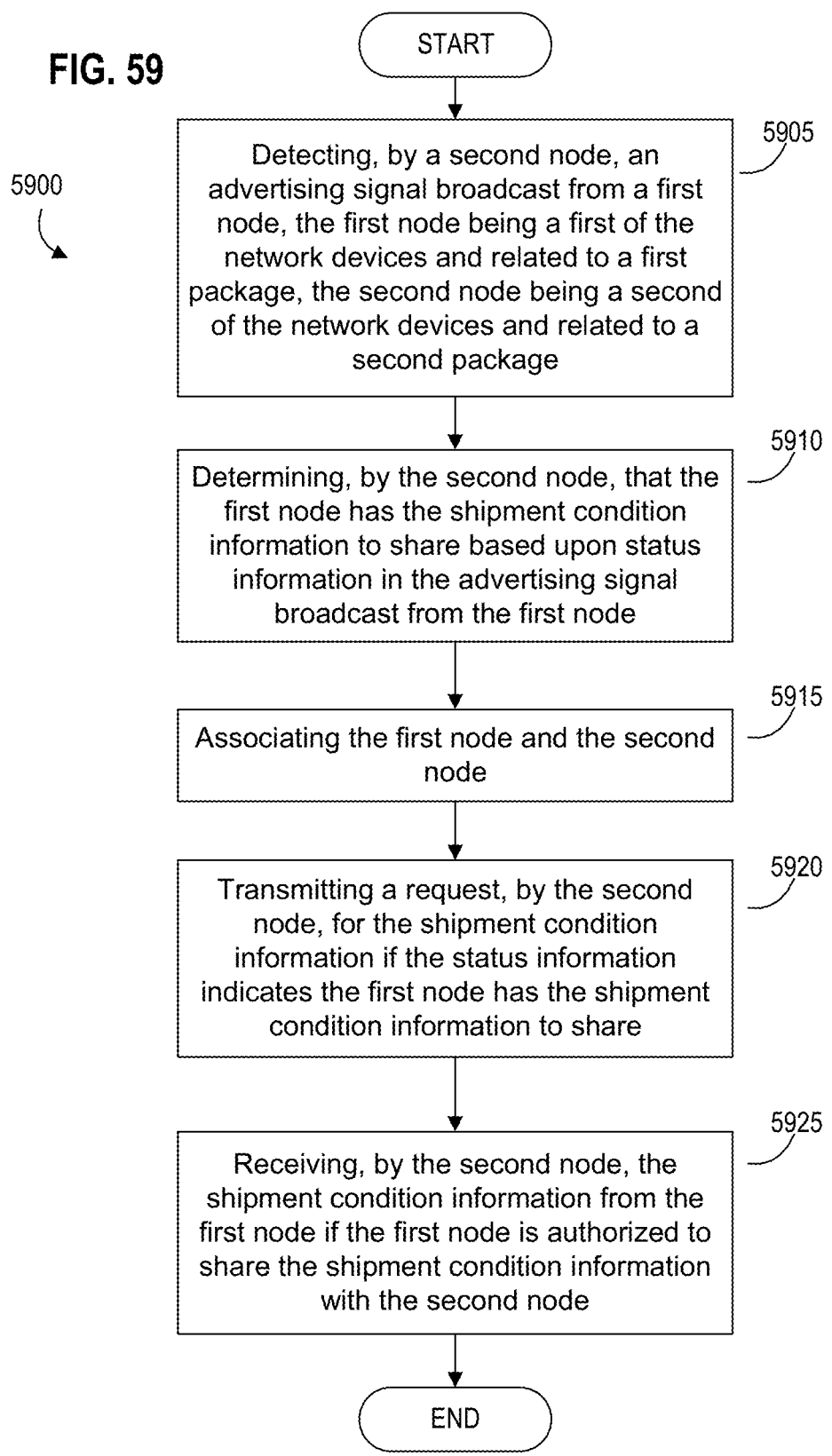

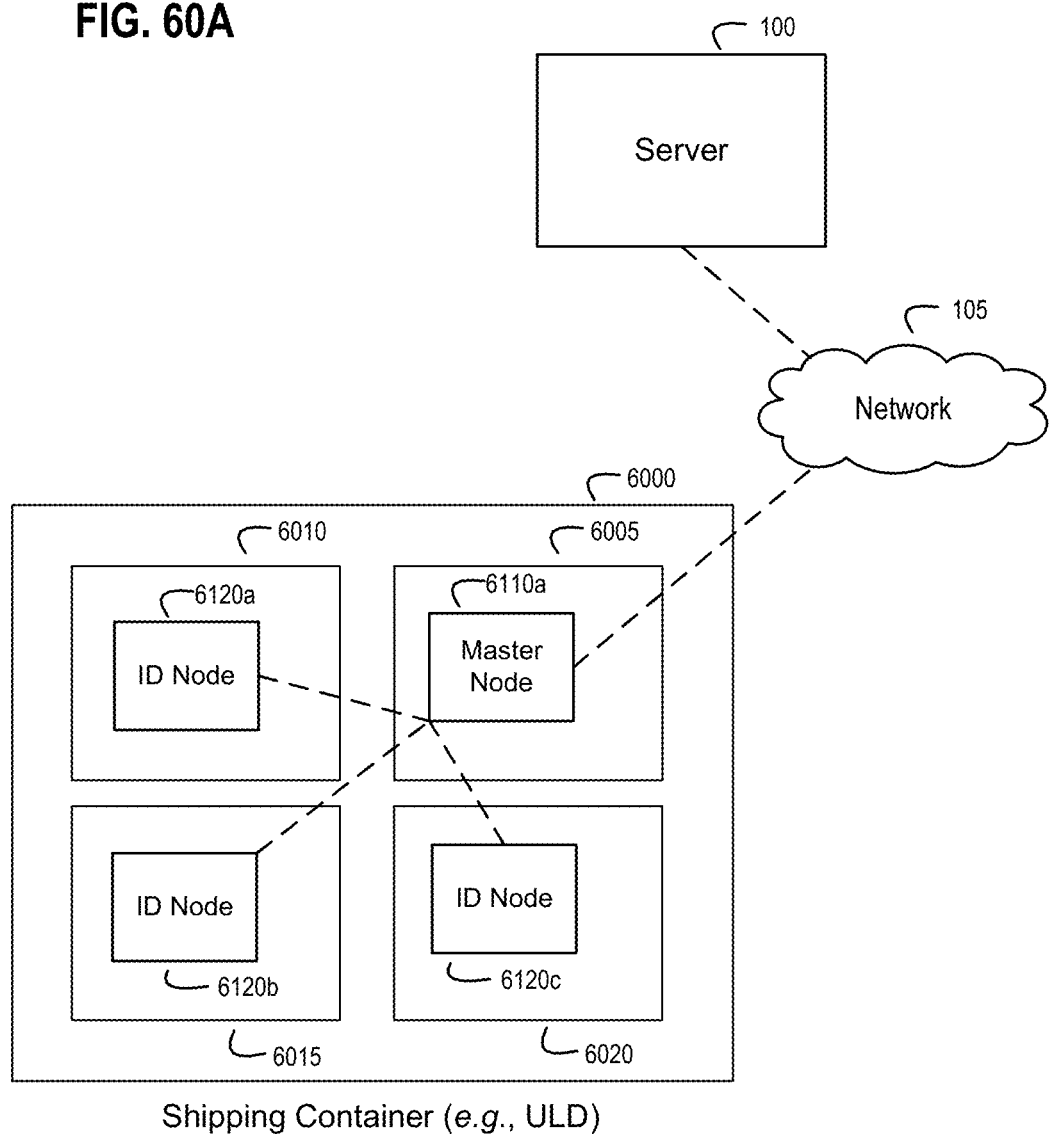

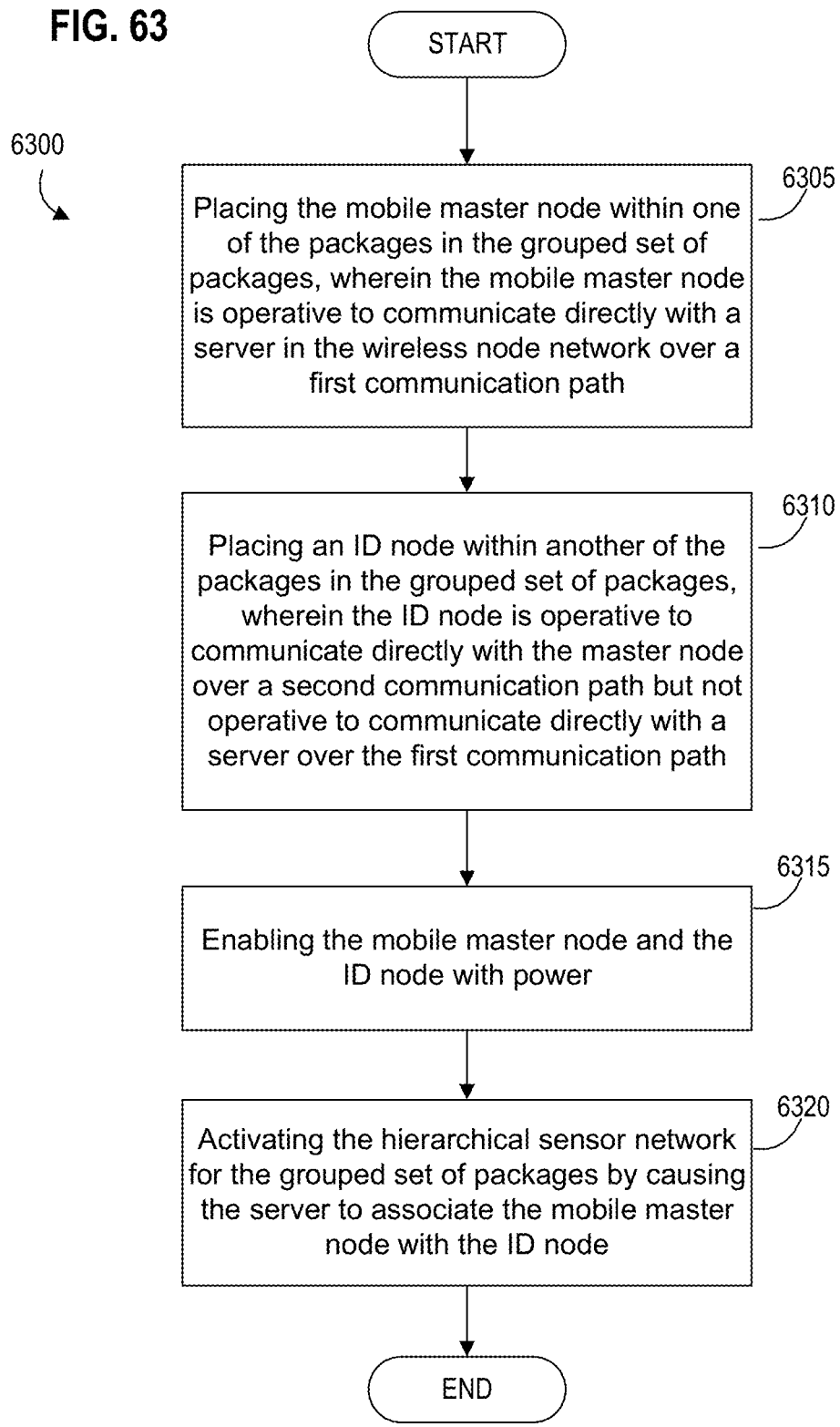

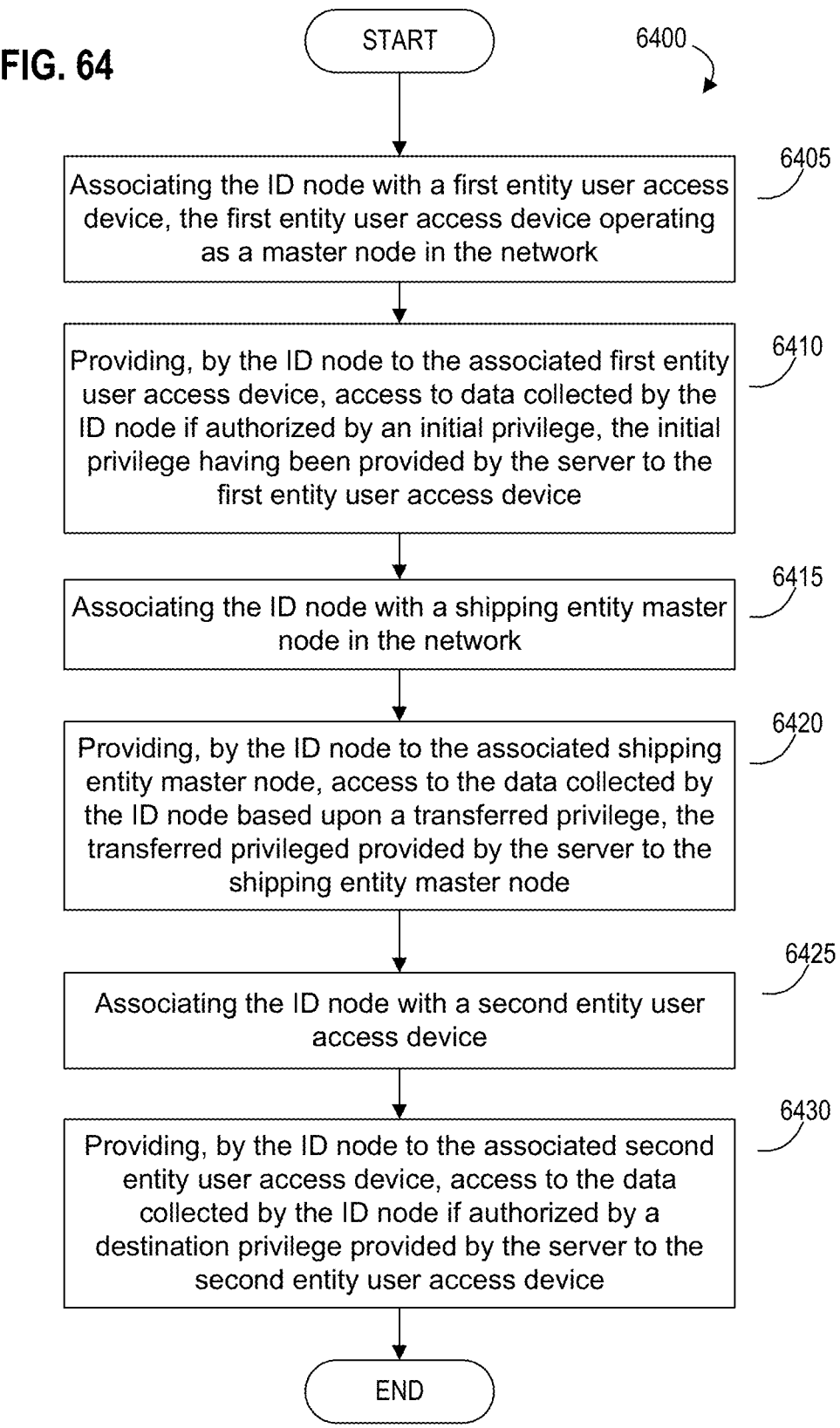

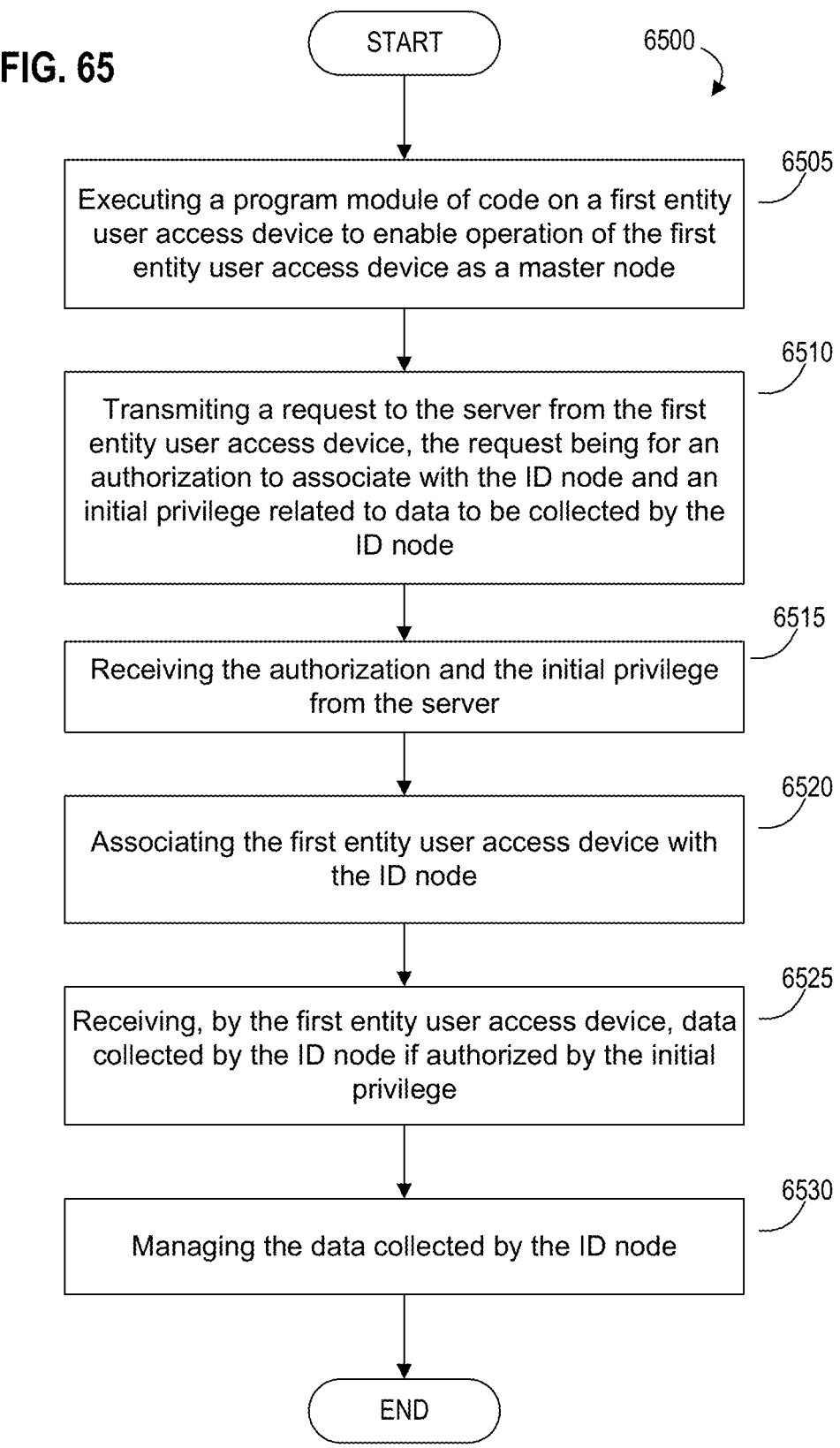

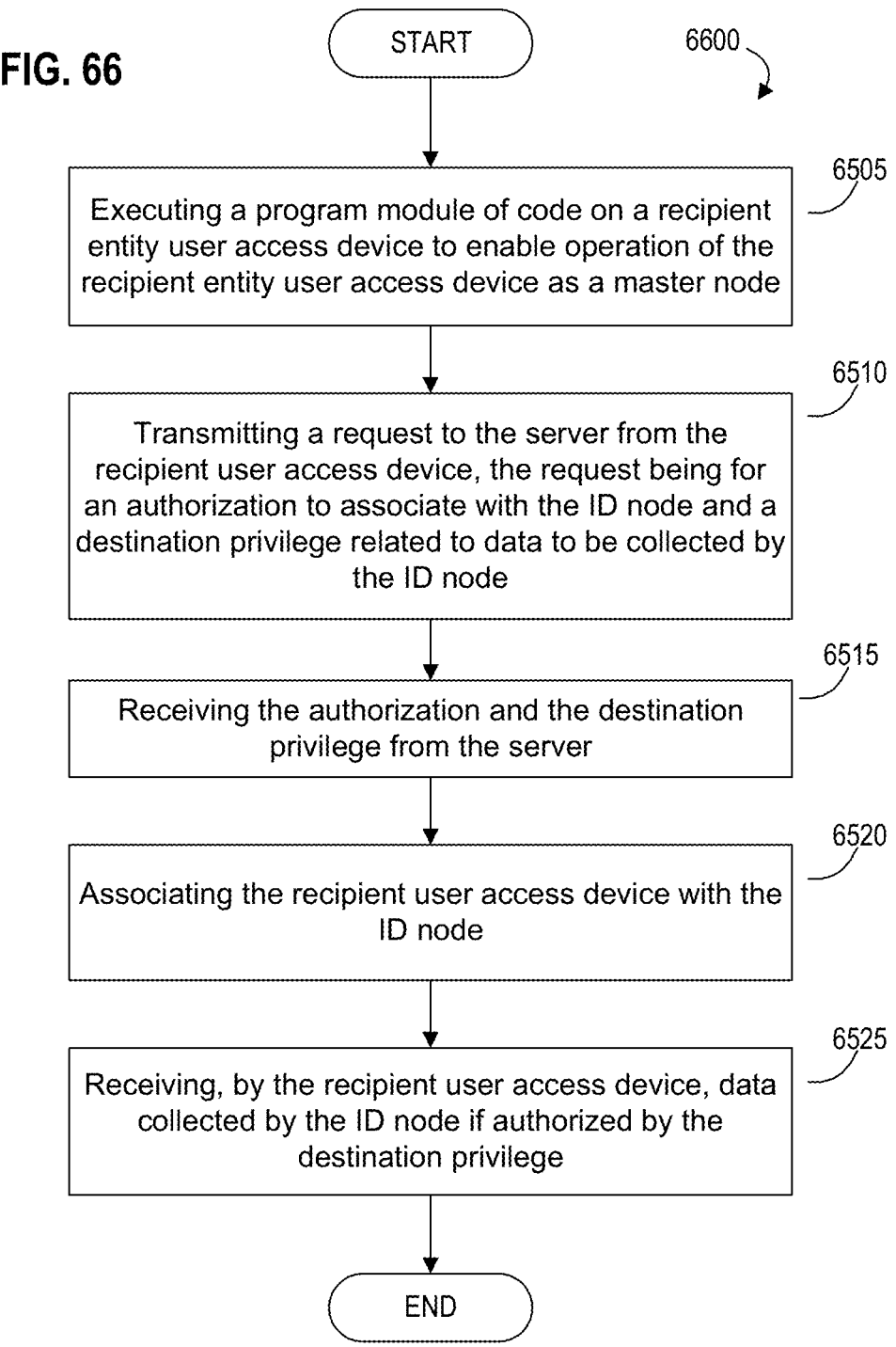

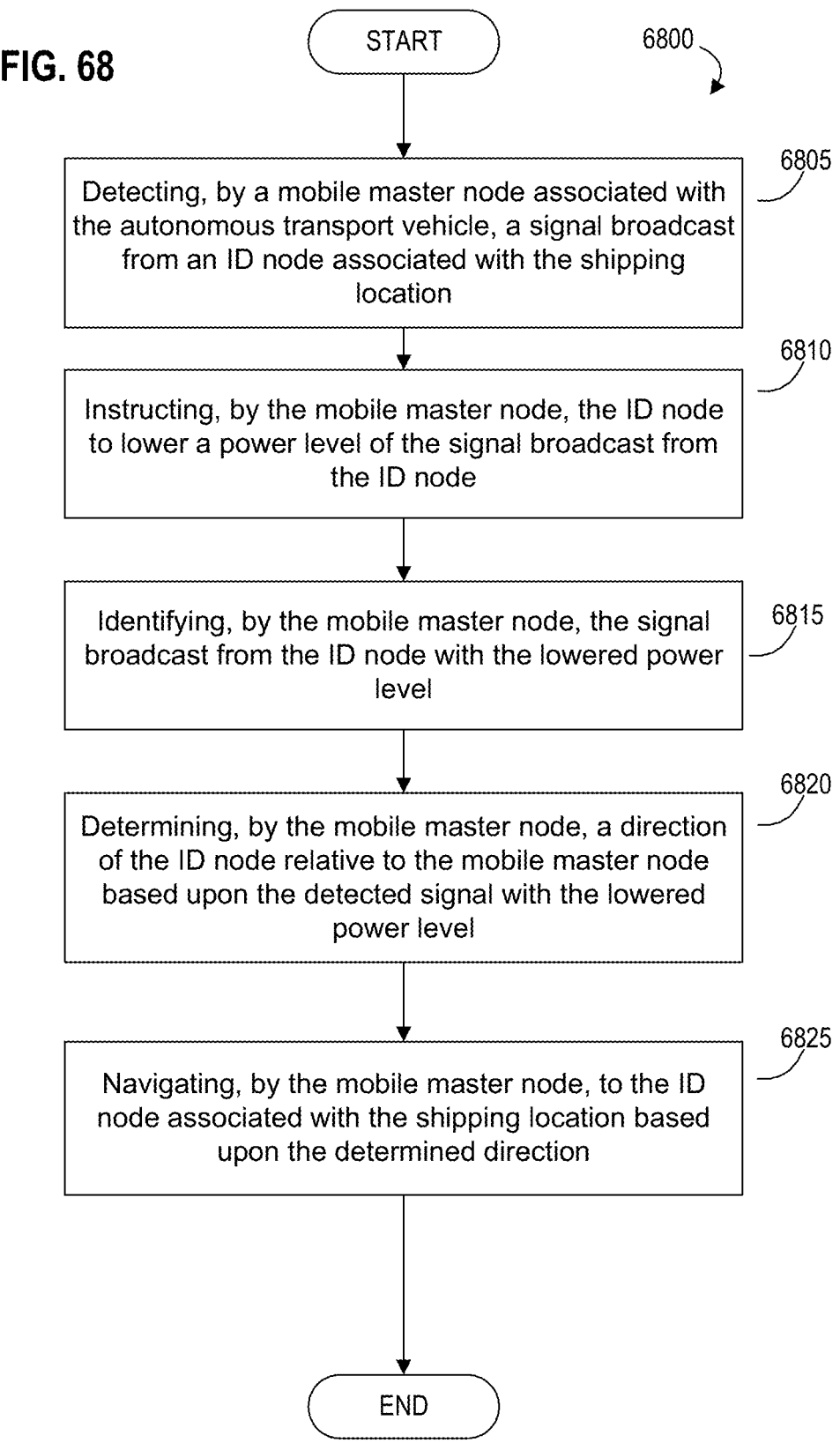

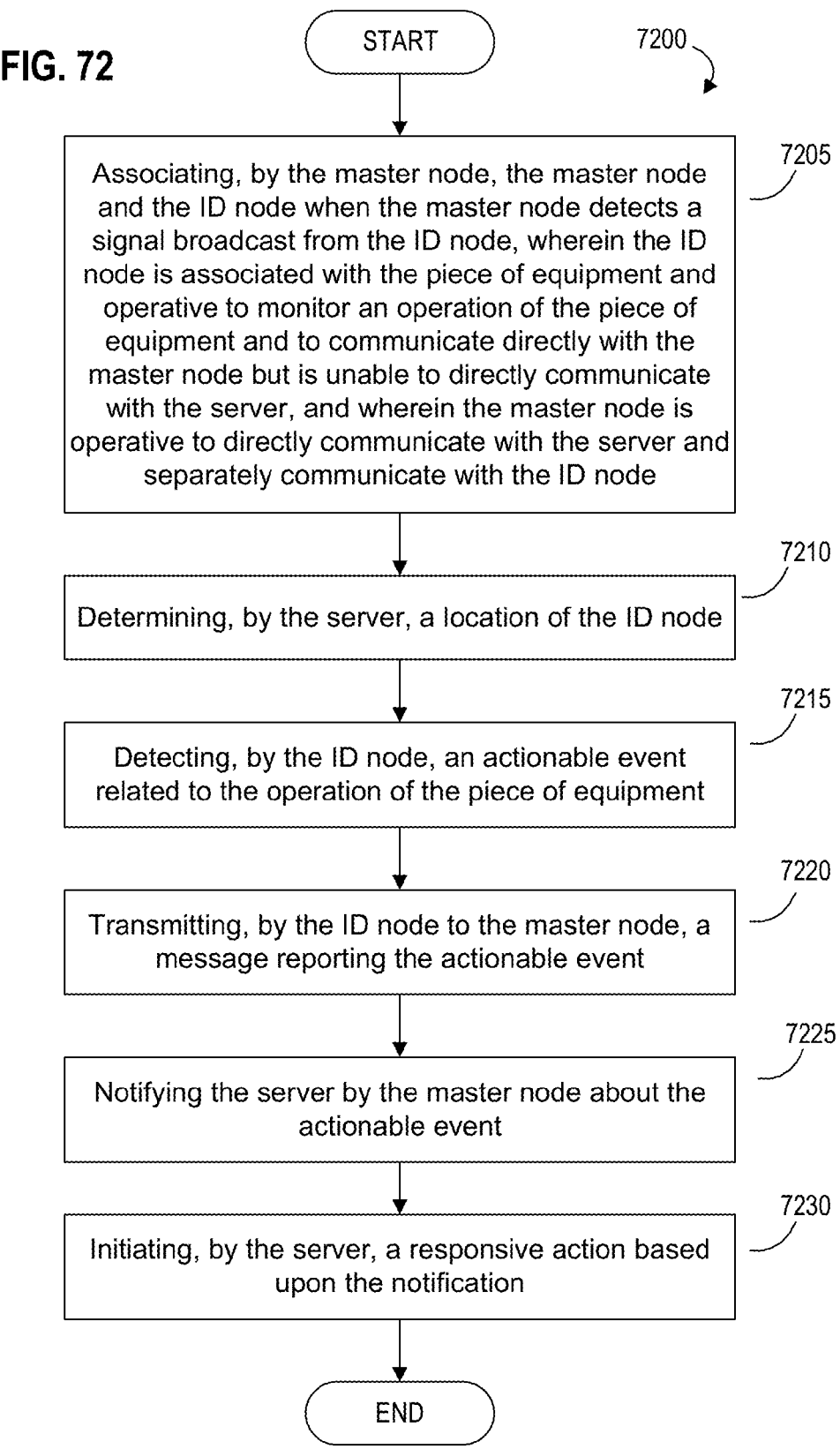

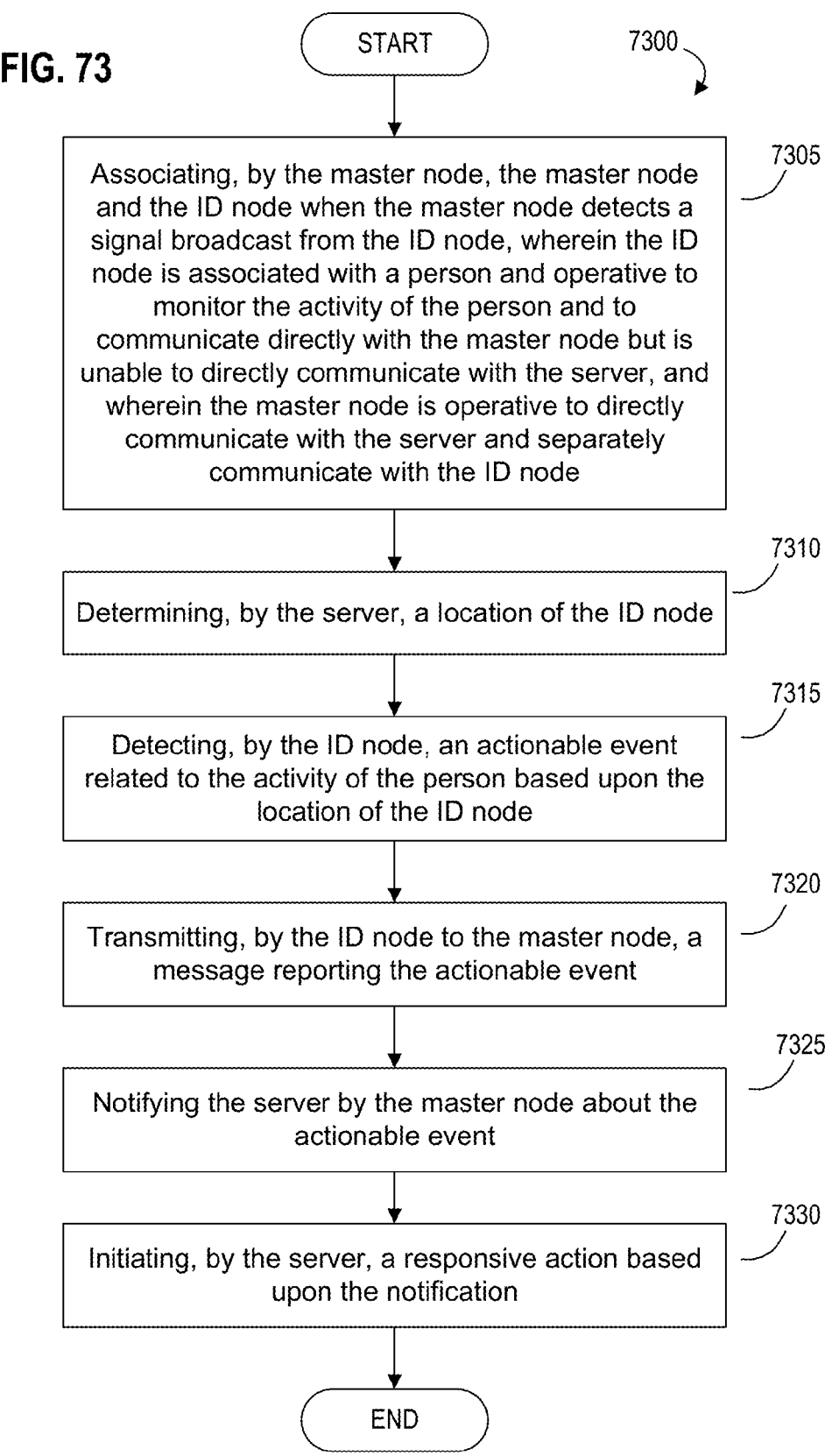

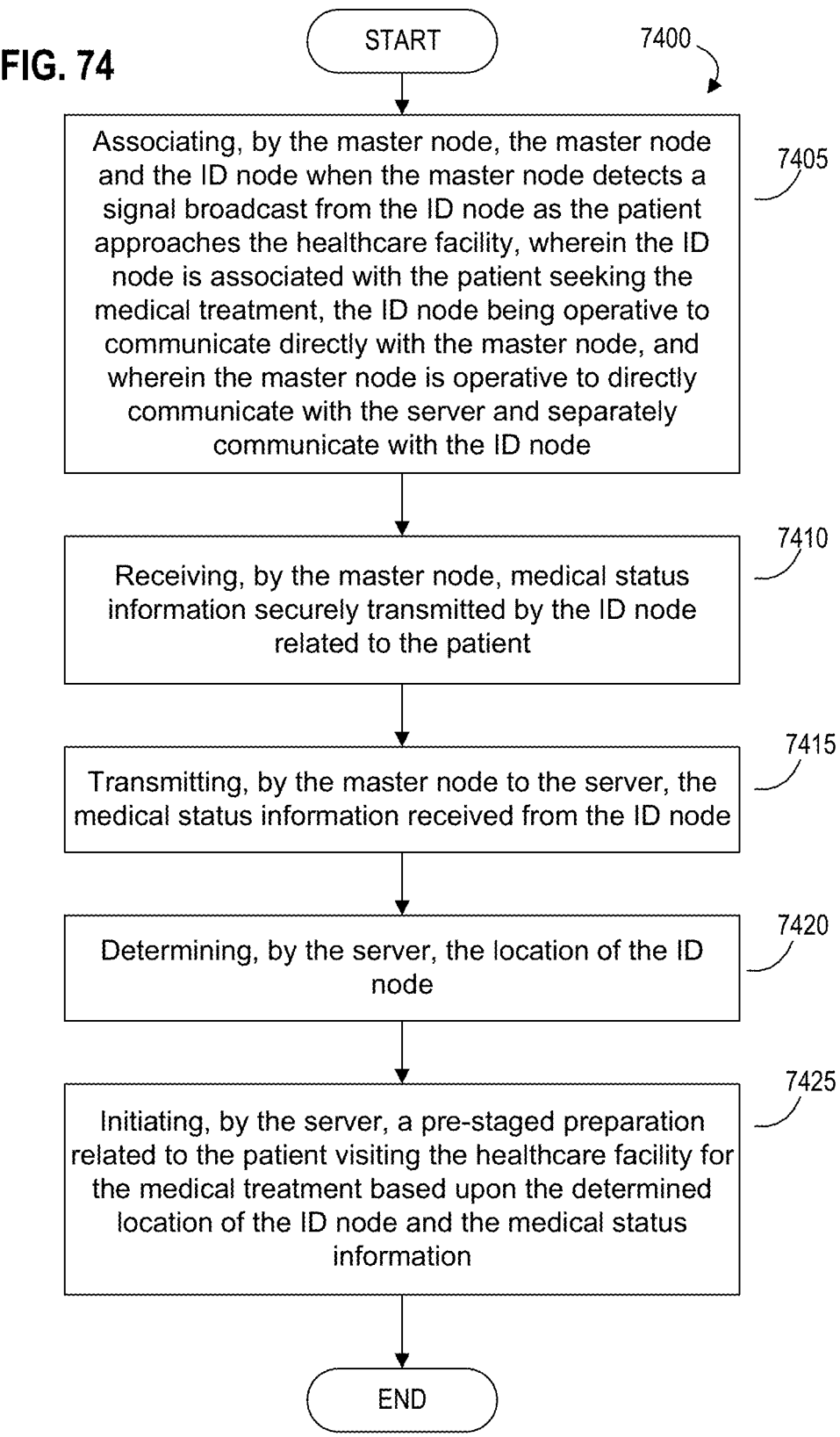

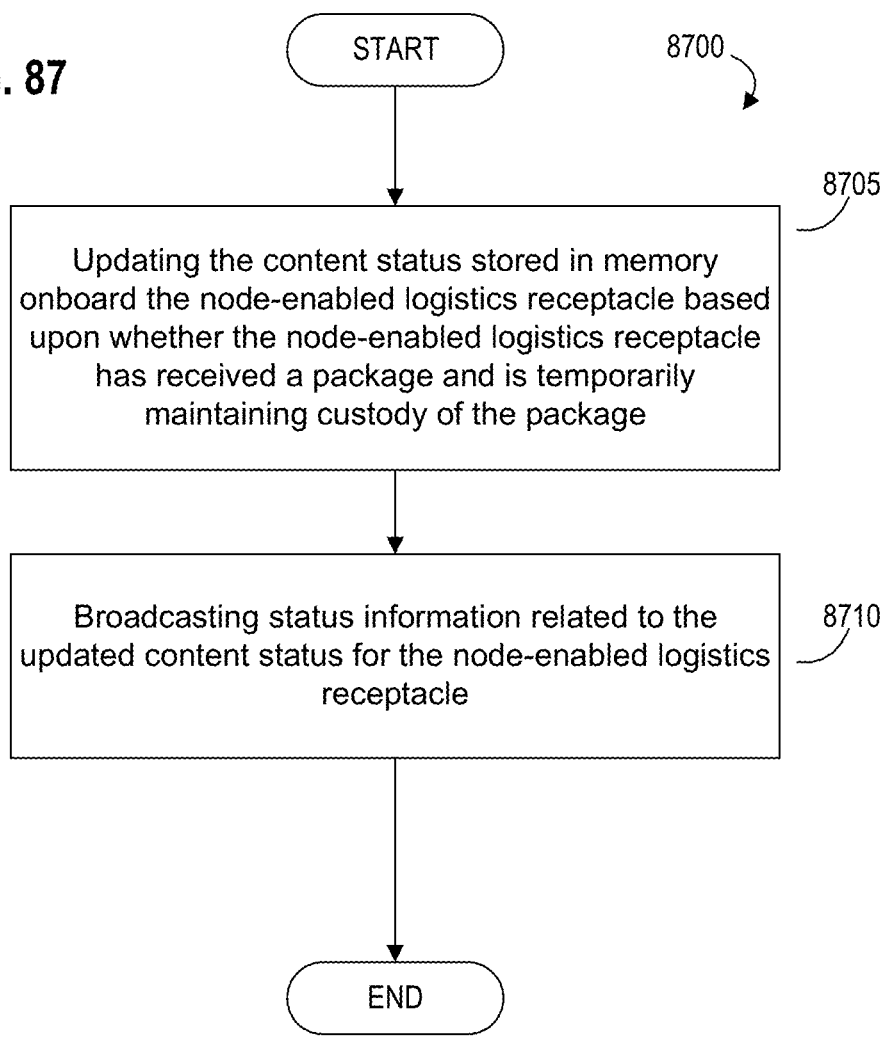

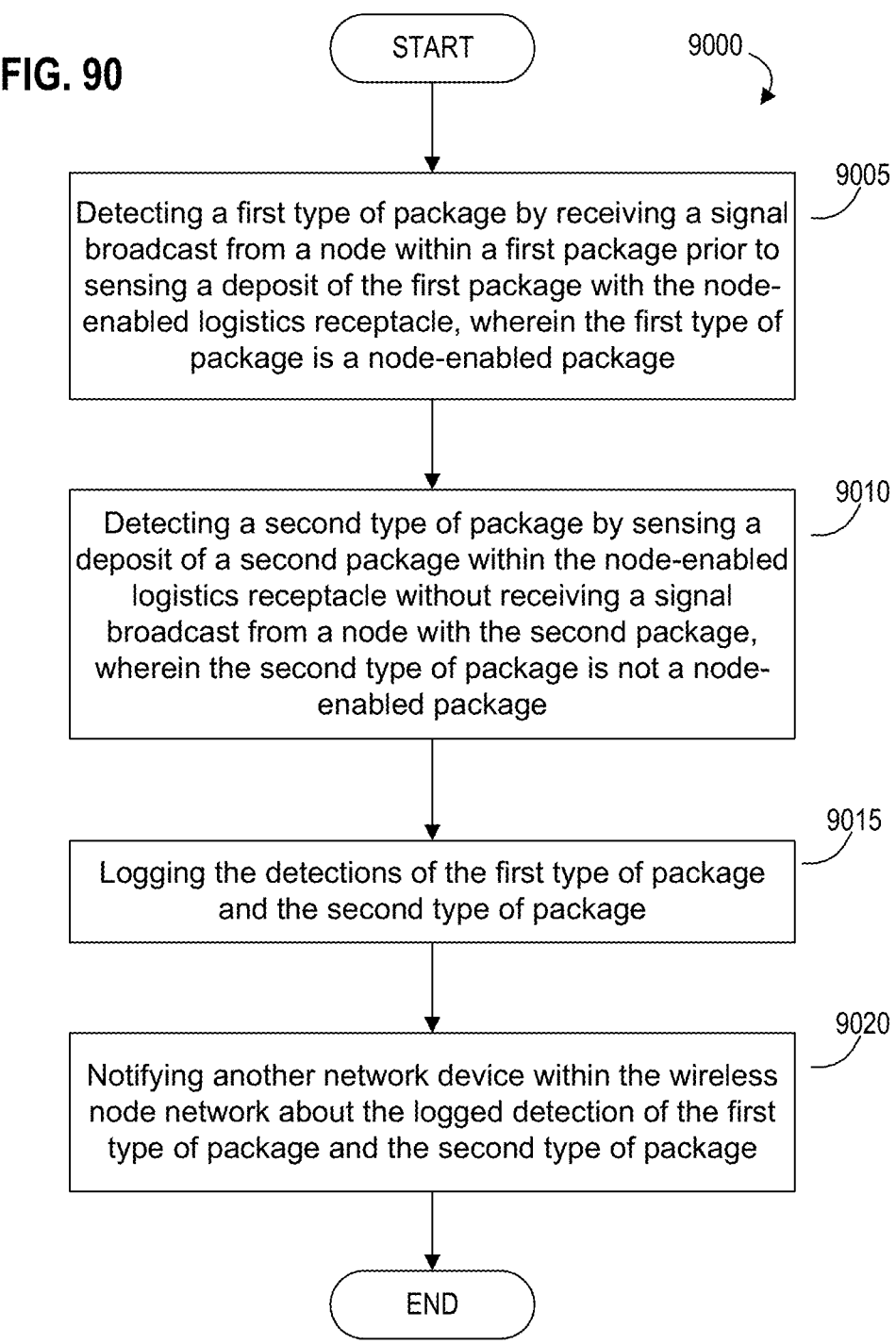

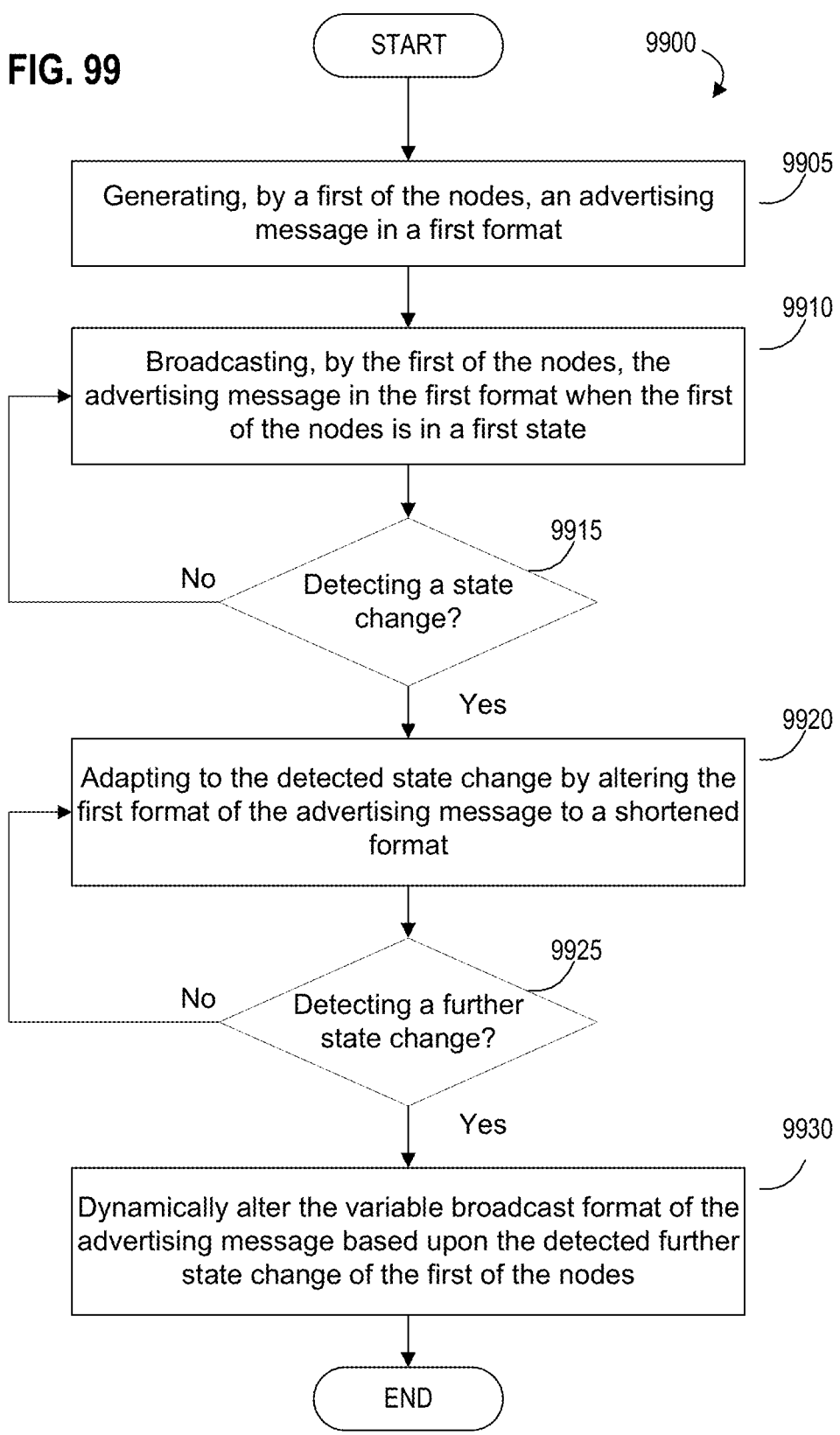

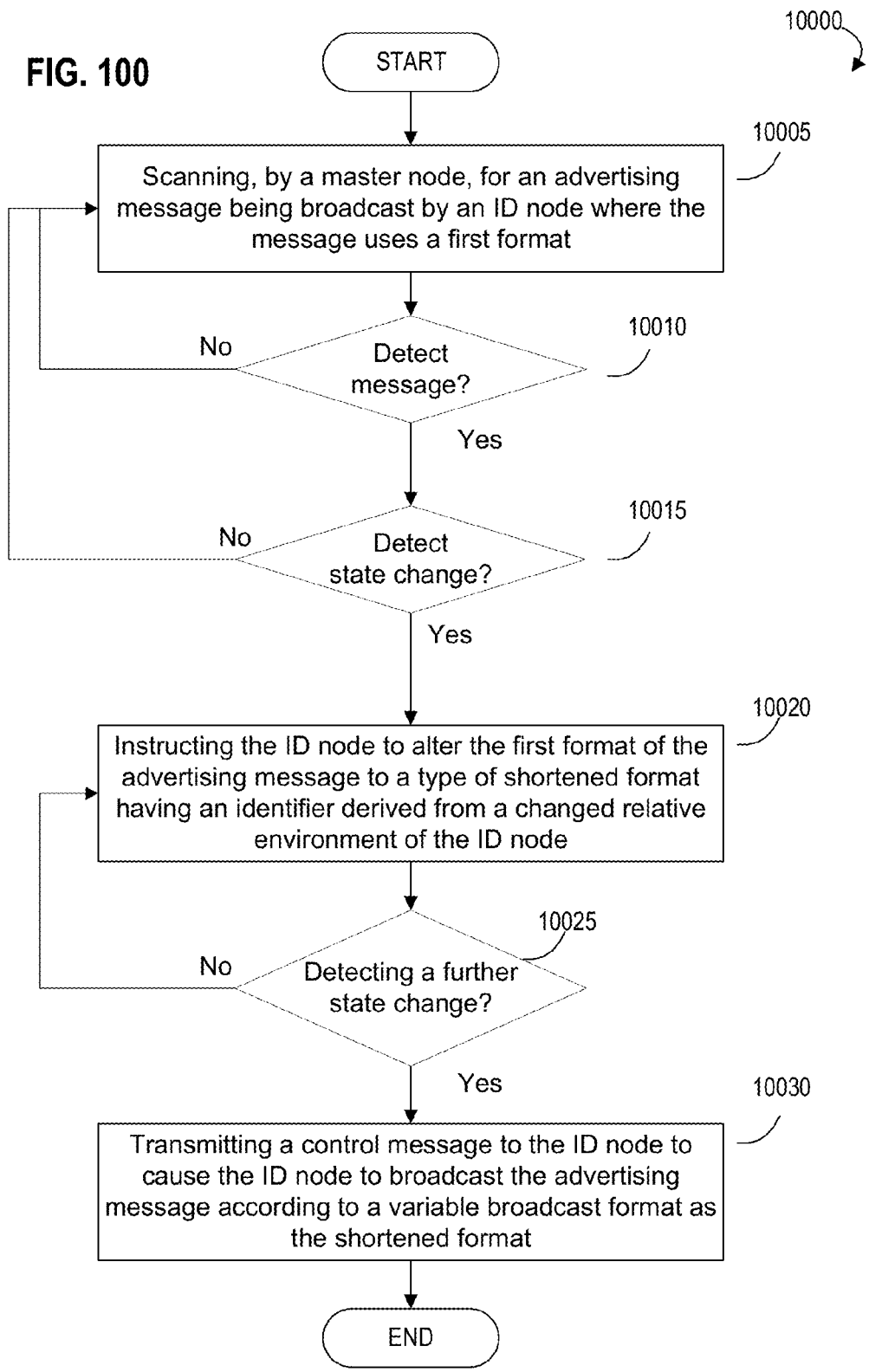

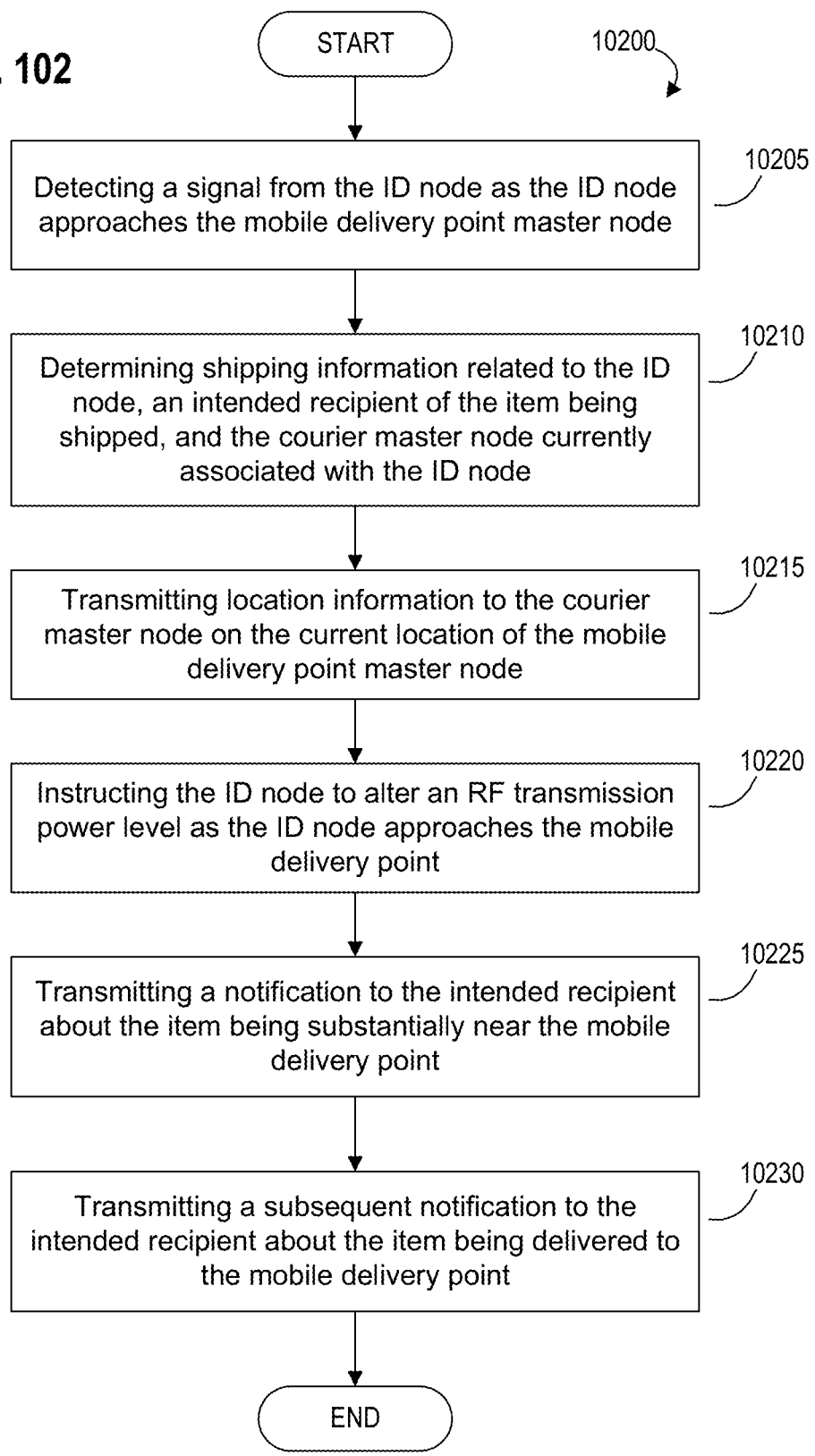

ASSOCIATION MANAGEMENT IN A WIRELESS NODE NETWORK

CROSS-REFERENCE TO RELATED APPLICATIONS

This patent application claims the benefit of priority to U.S. Provisional Patent Application Ser. No. 61/910,202 filed on Nov. 29, 2013 and U.S. Provisional Patent Application Ser. No. 62/003,566 filed on May 28, 2014.

FIELD OF THE DISCLOSURE

The present disclosure generally relates to systems, apparatus and methods in the field of tracking items (e.g., an object, a package, a person, a piece of equipment) and, more particularly, to various aspects involving systems, apparatus and methods for improved asset identification, location services, and node management using an adaptive, context-aware wireless node network.

BACKGROUND

Asset management has always been an important part of commerce, and the ability to identify an item and locate its whereabouts may be considered core to companies that ship items from one location to another. For example, tracking packages is important to organizations of all kinds, whether it be a company keeping track of inventory to be sold in its stores, or a package delivery provider keeping track of packages being transported through its delivery network. To provide quality service, an organization typically creates and maintains a highly organized network for tracking its items—packages, people, objects, etc. Effective management of such networks allows lower cost, reduced delivery time, and enhanced customer service. And efficient deployment of the network helps manage costs.

In addition to tracking packages, parties that ship and receive packages may also need information regarding the conditions of the packages, such as the temperature and humidity of the package. For example, a customer that has ordered a box of wine may want to monitor the temperature of the contents of the box to determine if the temperature and/or humidity goes above or below a set range. Likewise, the party that ships the package may also want to monitor the conditions of the package to ensure that the content arrives in the proper condition.

Conventionally, this tracking function may be provided by a variety of known mechanisms and systems. Machine-readable barcodes are one way organizations keep track of items. A retailer, for example, may use bar codes on items in its inventory. For example, items to be sold in a retailer's store may each be labeled with a different machine-readable bar code. In order to keep track of inventory, the retailer typically scans or otherwise captures an image of the bar code on each item so that a back-end part of the retailer's operation can keep track of what is coming in and leaving their possession from suppliers. In addition, when an item is sold to a consumer, the bar code for that item is scanned or captured to track sales and inventory levels.

Similarly, a package delivery provider may utilize machine-readable bar codes by associating a bar code with packages to be delivered to a recipient. For example, a package may have a bar code corresponding to a tracking number for that package. Each time the package goes through a transit checkpoint (e.g., the courier taking initial control of the package, the package being temporarily placed in a storage facility while being moved from a pickup point to a delivery location, and the package being delivered to the recipient, etc.), the package's bar code may be scanned. Bar codes, however, have the disadvantage that personnel must manually scan each bar code on each item in order to effectively track the items.

Radio-frequency identification (RFID) tags are another known mechanism for tracking items. In contrast to barcodes, RFID tags do not usually require manual scanning. For example, in a retail context, an RFID tag on an inventory item may be able to communicate with an electronic reader that detects items in a shopping cart and adds the cost of each item to a bill for the consumer. The RFID tag usually transfers a coded number when queried or prompted by the reader. RFID tags have also been used to track items such as livestock, railroad cars, trucks, and even airline baggage. These tags typically only allow for basic tracking, but do not provide a way to improve asset management using information about the environment in which the items are tracked.

Sensor-based tracking systems are also known which can provide more information than RFID systems. Shippers, carriers, recipients, and other parties often wish to know the location, condition, and integrity of shipments before, during, and after transport to satisfy quality control goals, meet regulatory requirements, and optimize business processes. However, such systems are typically expensive given the complexity of the sensors, and may provide extraneous and redundant item information.

To address these requirements, a system is needed that may monitor data regarding objects (such as shipped items, personnel, or equipment) and efficiently extend visibility of such objects. Thus, there remains a need for an improved system that may provide more extensive and robust identification, tracking, and management of objects and do so in a cost effective manner.

SUMMARY

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

One aspect of the disclosure relates to a method for association management within a wireless node network having at least a plurality of nodes and a server. The method begins with a second node identifying a first node as a potential for associating with the second node. Next, an association request is transmitted to the server by the second node. The second node receives a permissive response from the server related to the association request, and the method associates the first node and the second node.

In another aspect of the disclosure, a method is disclosed for association management of a wireless node network having at least a plurality of nodes and a server. The method begins by receiving an association request by the server sent from a second of the nodes. The association request asks for permission to associate a first of the nodes to the second node. Next, the server determines a location of the first node and second node, and then determines if associating the first node to the second node is desired based at least upon the location of the first node and the location of the second node. The method then has the server recording new association data in the server's memory if it is desired to associate the first node with the second node. And then the method has the server transmitting a response to the second node granting the permission to associate the first node to the second node.

In another aspect of the disclosure, a non-transitory computer-readable medium is disclosed that contains instructions, which when executed on a processor, performs the each of the above described methods for association management of a wireless node network having at least a plurality of nodes and a server.

In another aspect of the disclosure, a system is disclosed for association management of a wireless node network. The system generally comprises a first node, a second node, and a server. The second node includes a node processing unit, a node volatile memory coupled to the node processing unit, a first communication interface coupled to the node processing unit, and a second communication interface coupled to the node processing unit. As part of the second node, the first communication interface provides a short-range communication path between the first node and the second node.

The server includes a server processing unit, a server volatile memory, and a third communication interface that provides a longer range communication path between the server and the second communication interface of the second node.

During operation of the system, when the second node's node processing unit is executing at least a first program code section resident in the node volatile memory, the second node is operative to identify the first node as a potential for associating with the second node, transmit an association request over the second communication interface to the server, receive an association response (that includes at least authorization information generated by the server) over the second communication interface from the server, provide the authorization information to the first node, and associate the first node and the second node.

During operation of the system, when the server processing unit is executing at least a second program code section resident in the server volatile memory, the server is operative to determine a location of the first node and second node, determine if associating the first node to the second node is desired based at least upon the location of the first node and the location of the second node, store new association data (reflecting the associated status of the first and the second node) in the server volatile memory if it is desired to associate the first node with the second node, and transmit the authorization response to the second node granting the permission to associate the first node to the second node.

In another aspect of the disclosure, yet another method is disclosed for association management of a wireless node network having at least a plurality of nodes and a server. The method begins with a second of the nodes receiving a message broadcast from a first of the nodes. The second node captures an address of the first node from the message. The method then associates the first node and the second node by storing the captured address of the first node and an address of the second node as association data in a memory of the second node. Finally, the method has the second node transmit the association data to the server.

And in still another aspect of the disclosure, a managing node is disclosed in a wireless node network having at least another node and a server. The managing node comprises at least a processing unit and a first and second communication interface coupled to the processing unit. The first communication interface provides a first communication path to the other node and operates to receive a message broadcast from the other node and provide the message to the processing unit. The second communication interface provides a second communication path to the server. The managing node also comprises a volatile memory coupled to the processing unit and memory storage coupled to the processing unit. The memory storage maintains at least a node association manager module. When the processing unit executes instructions of the node association manager module, the processing unit is operative to receive the message from the first communication interface, capture an address of the other node from the message, store the captured address of the other node and an address of the managing node as part of association data in the memory storage (where the association data reflects an association between the managing node and the other node), and transmit the association data to the server through the second communication interface.

Each of these aspects respectively effect improvements to the technology of how different wireless nodes are managed by network elements within a wireless node network having one or more nodes and a server. Additional advantages of this and other aspects of the disclosed embodiments and examples will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments according to one or more principles of the invention and together with the description, serve to explain one or more principles of the invention. In the drawings.

FIG. 18 is a flow diagram illustrating an example method for managing shipment of an item using a wireless node network in accordance with an embodiment of the invention;

FIG. 19 is a flow diagram illustrating another example method for managing shipment of an item using a wireless node network in accordance with an embodiment of the invention;

FIG. 20 is a flow diagram illustrating an example method for dynamically changing an operational mode of node operations in a wireless node network in accordance with an embodiment of the invention;

FIG. 21 is a flow diagram illustrating an example method for managing a dynamically changing operational mode of node operations in a wireless node network in accordance with an embodiment of the invention;

FIG. 25 is a flow diagram illustrating yet another example method for association management of a wireless node network in accordance with an embodiment of the invention;

FIG. 26 is a flow diagram illustrating an exemplary method for context management of a wireless node network in accordance with an embodiment of the invention;

FIG. 27 is a flow diagram illustrating an exemplary method for locating a node in a wireless node network based upon observed signal patterns and characteristic indications over a period of time in accordance with an embodiment of the invention;

FIG. 28 is a flow diagram illustrating an exemplary method for location determination by varying a power characteristic of nodes in a wireless node network in accordance with an embodiment of the invention;

FIG. 29 is a flow diagram illustrating an exemplary method for location determination using one or more associations of nodes in a wireless node network in accordance with an embodiment of the invention;

FIG. 30 is a flow diagram illustrating another exemplary method for location determination using one or more associations of nodes in a wireless node network in accordance with an embodiment of the invention;

FIG. 31 is a flow diagram illustrating yet another exemplary method for location determination using one or more associations of nodes in a wireless node network in accordance with an embodiment of the invention;

FIG. 32 is a flow diagram illustrating an exemplary method for location determination of a first node in a wireless node network based on context data in accordance with an embodiment of the invention;

FIG. 33 is a flow diagram illustrating an exemplary method for determining a location using chaining triangulation for one of a plurality of nodes in a wireless node network having a server in accordance with an embodiment of the invention;

FIG. 44 is a flow diagram illustrating an exemplary method for managing a delivery of an item being shipped using a wireless node network in accordance with an embodiment of the invention;

FIG. 46 is a flow diagram illustrating an exemplary method for adaptive adjustment of node power level in a wireless node network depending upon operating node densities when a node moves to a new area in accordance with an embodiment of the invention;

FIG. 51 is a flow diagram illustrating an exemplary method for magnetically altering an operation of a node in a wireless node network having a master node and a server in accordance with an embodiment of the invention;

FIG. 52 is a flow diagram illustrating an exemplary method for adjusting a broadcast setting of a node in a wireless node network having a master node and a server in accordance with an embodiment of the invention;

FIG. 53 is a flow diagram illustrating an exemplary method for enhanced power notification from an ID node in a wireless node network having a master node and a server in accordance with an embodiment of the invention;

FIG. 58 is a flow diagram illustrating an exemplary method for sharing shipment condition information in a wireless node network having a plurality of network devices and a server in accordance with an embodiment of the invention;

FIG. 59 is a flow diagram illustrating an exemplary method for requesting shared shipment condition information in a wireless node network having a plurality of network devices and a server in accordance with an embodiment of the invention;

FIG. 60A is a diagram illustrating an exemplary group of nodes associated with a multi-piece shipment in an exemplary shipping container in accordance with an embodiment of the invention;

FIG. 63 is a flow diagram illustrating an exemplary method of creating a hierarchical sensor network for a grouped set of packages being shipped in accordance with an embodiment of the invention;

FIG. 64 is a flow diagram illustrating an exemplary method for multi-entity management of an ID node in a wireless node network in accordance with an embodiment of the invention;

FIG. 65 is a flow diagram illustrating an exemplary method for multi-entity management of an ID node in a wireless node network from the perspective of a shipping customer entity in accordance with an embodiment of the invention;

FIG. 66 is a flow diagram illustrating an exemplary method for multi-entity management of an ID node in a wireless node network from the perspective of recipient entity in accordance with an embodiment of the invention;

FIG. 68 is a flow diagram illustrating an exemplary method for navigating to a shipping location by an autonomous transport vehicle using a plurality of nodes in a wireless node network in accordance with an embodiment of the invention;

FIG. 72 is a flow diagram illustrating an exemplary method for monitoring a piece of equipment using a hierarchical node network having at least an ID node, a master node, and a server in accordance with an embodiment of the invention;

FIG. 73 is a flow diagram illustrating an exemplary method for monitoring a person's activity using a hierarchical node network having at least an ID node, a master node, and a server in accordance with an embodiment of the invention;

FIG. 74 is a flow diagram illustrating an exemplary method for initiating a pre-staged preparation related to medical treatment to be provided to a patient at a healthcare facility using a hierarchical node network in accordance with an embodiment of the invention;

FIG. 87 is a flow diagram illustrating an exemplary method for proactively reporting a content status of a node-enabled logistics receptacle in a wireless node network in accordance with an embodiment of the invention;

FIG. 90 is a flow diagram illustrating an exemplary method for detecting a plurality of package types within a node-enabled logistics receptacle in a wireless node network in accordance with an embodiment of the invention;

FIG. 99 is a flow diagram illustrating an exemplary method for adaptive node communication within a wireless node network having a plurality of nodes in accordance with an embodiment of the invention;

FIG. 100 is a flow diagram illustrating an exemplary method for adaptive node communication within a wireless node network having at least a master node and an ID node in accordance with an embodiment of the invention;

FIG. 102 is a flow diagram illustrating an exemplary method for delivery to a mobile delivery point and notification of an intended recipient in accordance with an embodiment of the invention.

DESCRIPTION OF THE EMBODIMENTS

Figure 1:
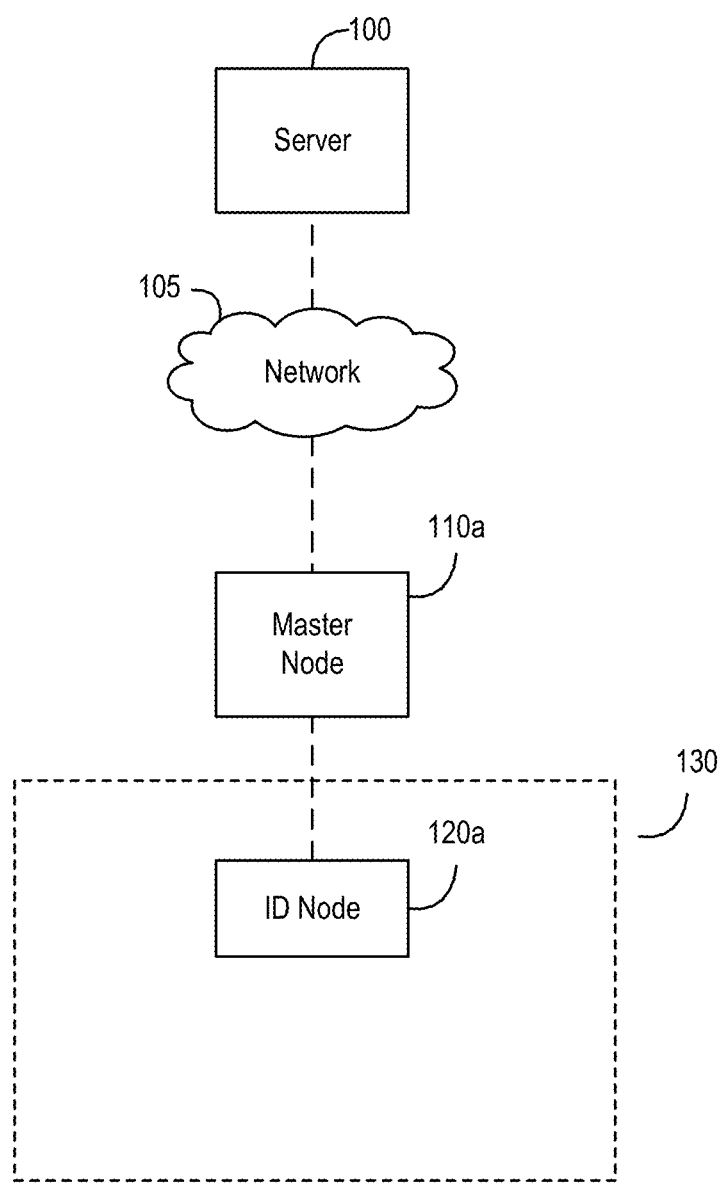
FIG. 1 is a diagram of an exemplary wireless node network in accordance with an embodiment of the invention.

Reference will now be made in detail to exemplary embodiments. Wherever possible, the same reference numbers are used in the drawings and the description to refer to the same or like parts.

In general, the following describes various embodiments of a contextually aware hierarchical wireless node network that may be managed, operated, and applied by principles as set forth herein. In general, embodiments of the wireless node network may include one or more lower level devices or nodes (e.g., an ID node) that rely on shorter-range communication with a higher level device or node (e.g., a master node), which is operative to communicate with a server over a different communication interface while the lower level node is unable to communicate directly with the server. Those skilled in the art will appreciate that such a hierarchy of different functional communicating network components (generally referred to as network devices) may be characterized as a network of nodes. Those skilled in the art will appreciate that in some embodiments, the wireless node network may include the server as well as different wireless nodes despite the fact that the server may not be a dedicated wireless component. In other embodiments, the network may include similar types of wireless nodes or different types of wireless nodes.

Further, those skilled in the art will appreciate that each embodiment described herein effects improvements to particular technologies, such as asset identification and monitoring, location services, logistics operations & infrastructure, and node operation and management using an adaptive, context-aware wireless node network. Each embodiment describes a specific technological application of one or more nodes that operate in such a wireless node network where the specific technological application improves or otherwise enhances such technical fields as explained and supported by the disclosure that follows.

Those skilled in the art will understand through the following detailed description that the nodes may be associated with items (e.g., an object, a package, a person, a piece of equipment) and may be used to identify and locate the items while being dynamically programmed during operation of the network and while the items move along an anticipated path (e.g., a transit path from an origin point to a destination point). The following further describes various embodiments of a wireless node network, exemplary ways to manage components of a wireless node network, exemplary ways to better determine the location of components of a wireless node network, and applications of a wireless node network to enhance logistics operations that rely upon a wireless node network.

Wireless Node Networks

FIG. 1 illustrates a basic diagram of an exemplary wireless node network in accordance with an embodiment of the invention. The exemplary network shown in FIG. 1 comprises a server 100 connected to a network 105, which is also operatively connected to different network components, such as a master node 110a and indirectly to an ID node 120a through master node 110a. Master node 110a is typically connected to an ID node 120a via short-range wireless communications (e.g., Bluetooth® formatted communications). Master node 110a is typically connected to server 100 through network 105 via longer-range wireless communication (e.g., cellular) and/or medium range wireless communication (e.g., wireless local area data networks or Wi-Fi). ID node 120a is typically a low cost device that may be easily placed into a package, be integrated as part of packaging, or otherwise associated with an item to be tracked and located, such as package 130, a person, or object (e.g., vehicle, etc.). Generally, an ID node is capable of communicating directly with a master node but incapable of communicating directly with the server, while a master node is capable of communicating directly with the server and separately and directly communicating with other nodes (such as an ID node or another master node). The ability to deploy a hierarchy of nodes within an exemplary wireless node network to distribute tasks and functions at the different levels in an efficient and economical manner helps to facilitate a wide variety of adaptive locating, tracking, managing, and reporting applications using such a network of nodes as discussed in more detail below.

In general, the lower cost, lower complexity ID node 120a is managed by the higher complexity master node 110a and server 100 as part of keeping track of the location of ID node 120a (and the associated item), thereby providing intelligent, robust, and broad visibility about the location and status of ID node 120a. In a typical embodiment, ID node 120a is first associated with an item (e.g., package 130, a person, or object). As ID node 120a moves with the item, the ID node 120a becomes associated with the master node 110a, and the server 100 is updated with such information. Further movement of the ID node 120a and item may cause the ID node 120a to disassociate with master node 110a and be handed off to become associated another master node (not shown), after which the server 100 is again updated. As such, the server 100 generally operates to coordinate and manage information related to the ID node 120a as the item physically moves from one location to another. Further details of the architecture and functionality of an embodiment of an exemplary ID node and master node as described below in more detail with respect to FIGS. 3 and 4, while exemplary server 100 is described below in more detail with respect to FIG. 5.

While server 100 is shown connecting through network 105, those skilled in the art will appreciate that server 100 may have a more direct or dedicated connections to other components illustrated in FIG. 1, such as master node 110a, depending upon implementation details and desired communication paths. Furthermore, those skilled in the art will appreciate that an exemplary server may contain a collection of information in a database (not shown in FIG. 1), while multiple databases maintained on multiple server platforms or network storage servers may be used in other embodiments to maintain such a collection of information. Furthermore, those skilled in the art will appreciate that a database may be implemented with cloud technology that essentially provides networked storage of collections of information that may be directly accessible to devices, such as master node 110a.

Network 105 may be a general data communication network involving a variety of communication networks or paths. Those skilled in the art will appreciate that such exemplary networks or paths may be implemented with hard wired structures (e.g., LAN, WAN, telecommunication lines, telecommunication support structures and telecommunication processing equipment, etc.), wireless structures (e.g., antennas, receivers, modems, routers, repeaters, etc.) and/or a combination of both depending upon the desired implementation of a network that interconnects server 100 and other components shown in FIG. 1 in an embodiment of the present invention.

Master node 110*a* and ID node 120*a* are types of nodes. A node is generally an apparatus or device used to perform one or more tasks as part of a network of components. An embodiment of a node may have a unique identifier, such as a Media Access Control (MAC) address or an address assigned to a hardware radio like an Internet Protocol 6 (IPv6) identifier. In some embodiments, the node's unique identifier may be correlated to a shipment identifier (e.g., a shipment tracking number in one example), or may itself be a shipment's tracking reference.

An ID node, such as ID node 120*a*, is generally a low cost active wireless device. In one embodiment, an exemplary ID node is a transceiver-based processing or logic unit having a short-range radio with variable RF characteristics (e.g., programmable RF output power range, programmable receiver sensitivity), memory accessible by the processing unit, a timer operatively coupled to the processing unit, and a power source (e.g., a battery) that provides power for the circuitry of the ID node. For example, the physical implementation of an exemplary ID node may be small, and, thus, amenable to integration into a package, label, container, or other type of object. In some implementations of an ID node, the node is rechargeable while other implementations do not permit recharging the power source for the ID node. In other implementations, the ID node is environmentally self-contained or sealed so as to enable robust and reliable operations in a variety of environmentally harsh conditions.

A master node, such as master node 110*a*, generally serves as an intelligent bridge between the ID node 120*a* and the server 100. Accordingly, a master node is generally more sophisticated than an ID node. In one example embodiment, an exemplary master node is a device having a processing or logic unit, a short-range radio (with may have variable RF characteristics) used for communicating with other nodes (ID nodes and other master nodes), a medium and/or long-range radio for communication with the server 100, memory accessible by the processing unit, a timer operatively coupled to the processing unit, and a power source (e.g., a battery or a wired power supply connection) that provides power for the circuitry of the master node. The exemplary master node, such as master node 110*a*, may be positioned in a known fixed location or, alternatively, be a mobile unit having dedicated location positioning circuitry (e.g., GPS circuitry) to allow the master node to determine its location by itself.

Figure 2:
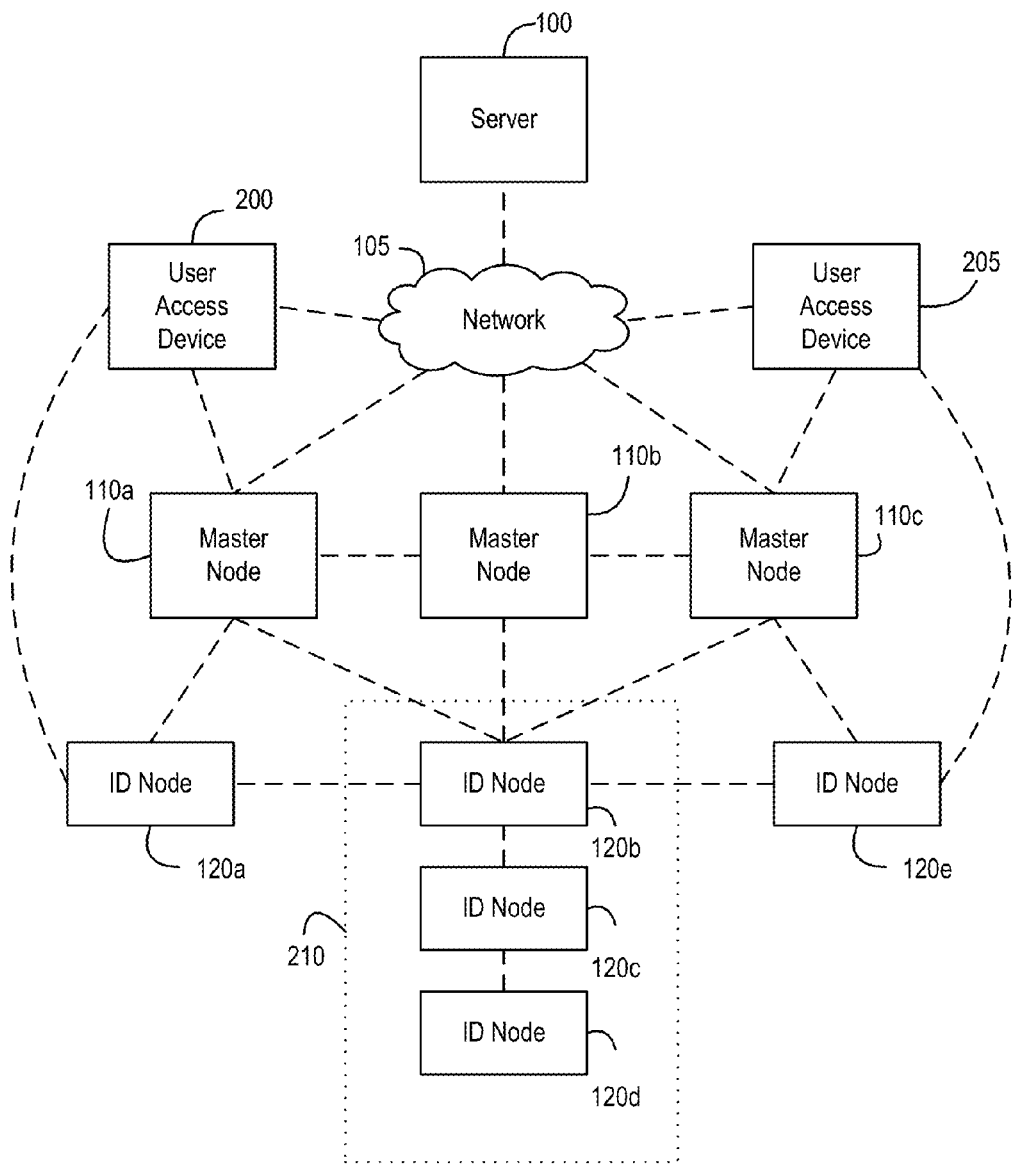
FIG. 2 is a more detailed diagram of an exemplary wireless node network in accordance with an embodiment of the invention.

While the embodiment illustrated in FIG. 1 shows only a single master node and a single ID node, those skilled in the art will appreciate that a wireless network consistent with an embodiment of the invention may include a wide array of similar or different master nodes that each communicate with the server 100 and/or other master nodes, and a wide variety of similar or different ID nodes. Thus, the exemplary network shown in FIG. 1 is a basic embodiment, while the exemplary network shown in FIG. 2 is a more detailed exemplary wireless node network in accordance with another embodiment of the invention Referring now to FIG. 2, another exemplary wireless node network is shown including server 100 and network 105. Here, master nodes 110*a*, 110*b*, 110*c* are deployed and connected to network 105 (and by virtue of those respective connections, to server 100) as well as to each other. ID nodes 120*a*, 120*b*, 120*e* are shown as connectable or operative to communicate via different paths to various master nodes. However, ID nodes 120*c* and 120*d* are shown in FIG. 2 connected to ID node 120*b* but not to any of the master nodes.

This may be the case if, for example, ID nodes 120*b*, 120*c*, 120*d* are associated with different items (e.g., packages) within a larger container 210 (or grouped together on a pallet). In such an example, only ID node 120*b* may remain within the wireless communication range of any master node. This may, for example, be because of the positions of the different ID nodes within the container relative to the closest master node, adverse RF shielding caused by the container, adverse RF shielding caused by packaging of the item, or adverse RF shielding caused by other proximate material that interferes with radio transmissions (e.g., several packages of metal items between the ID node and any master node outside the container). Thus, in the illustrated configuration of the exemplary network shown in FIG. 2, ID nodes 120*c* and 120*d* may be out of range from the master nodes, yet still have an operative communication path to a master node through ID node 120*b*.

Indeed, in one example, prior to placement within container 210, ID node 120*b* may actually be a master node but the changed RF environment when placing it in container 210 may interfere with the master node's ability to locate itself via location signals (e.g., GPS signals) and cause the master node to temporarily operate as an ID node while still providing communications and data sharing with other ID nodes in container 210.

User access devices 200, 205 are also illustrated in FIG. 2 as being able to connect to network 105, master nodes, and ID nodes. Generally, user access devices 200 and 205 allow a user to interact with one or more components of the exemplary wireless node network. In various embodiments, user access devices 200, 205, may be implemented using a desktop computer, a laptop computer, a tablet (such as an Apple iPad® touchscreen tablet), a personal area network device (such as a Bluetooth® device), a smartphone (such as an Apple iPhone®), a smart wearable device (such as a Samsung Galaxy Gear™ smartwatch device, or a Google Glass™ wearable smart optics) or other such devices capable of communicating over network 105 with server 100, over a wired or wireless communication path to master node and ID nodes.

As shown in FIG. 2, user access devices 200, 205 are coupled and in communication with network 105, but each of them may also be in communication with each other or other network components in a more direct manner (e.g., via near field communication (NFC), over a Bluetooth® wireless connection, over a WiFi network, dedicated wired connection, or other communication path).

In one example, a user access device, such as device 200 or 205, may facilitate associating an ID node (such as ID node 120*a*) with the tracking number of a package at the start of a shipment process, coordinating with the server 100 to check on the status and/or location of the package and associated ID node during transit, and possibly retrieving data from a master node or ID node related to the shipped package. Thus, those skilled in the art will appreciate that a user access device, such as devices 200, 205, are essentially interactive communication platforms by which a user may initiate shipment of an item, track an item, determine the status and location of an item, and retrieve information about an item.

An exemplary user access device, such as device 200 or 205, may include sufficient hardware and code (e.g., an app or other program code section or sections) to operate as a master node or an ID node in various embodiments as discussed in more detail below. For example, device 200 may be implemented as a mobile smartphone and functionally may operate as an exemplary ID node that broadcasts advertising packet messages to other ID nodes or master nodes for association and sharing data with such nodes. In another example, device 200 is implemented as a mobile smartphone and may operate as an exemplary master node that communicates and associates with ID nodes and other master nodes, as described herein, and communicates with the server 100. Thus, those skilled in the art will appreciate an exemplary ID node in FIG. 3 and an exemplary master node in FIG. 4, and their respective parts, code and program modules, may be implemented with an appropriately programmed user access device, such as device 200 or 205. Thus, the following description of an exemplary ID node in FIG. 3 and an exemplary master node in FIG. 4 will be applicable to a user access device operating as an ID node or a master node, respectively.

ID Node

Figure 3:
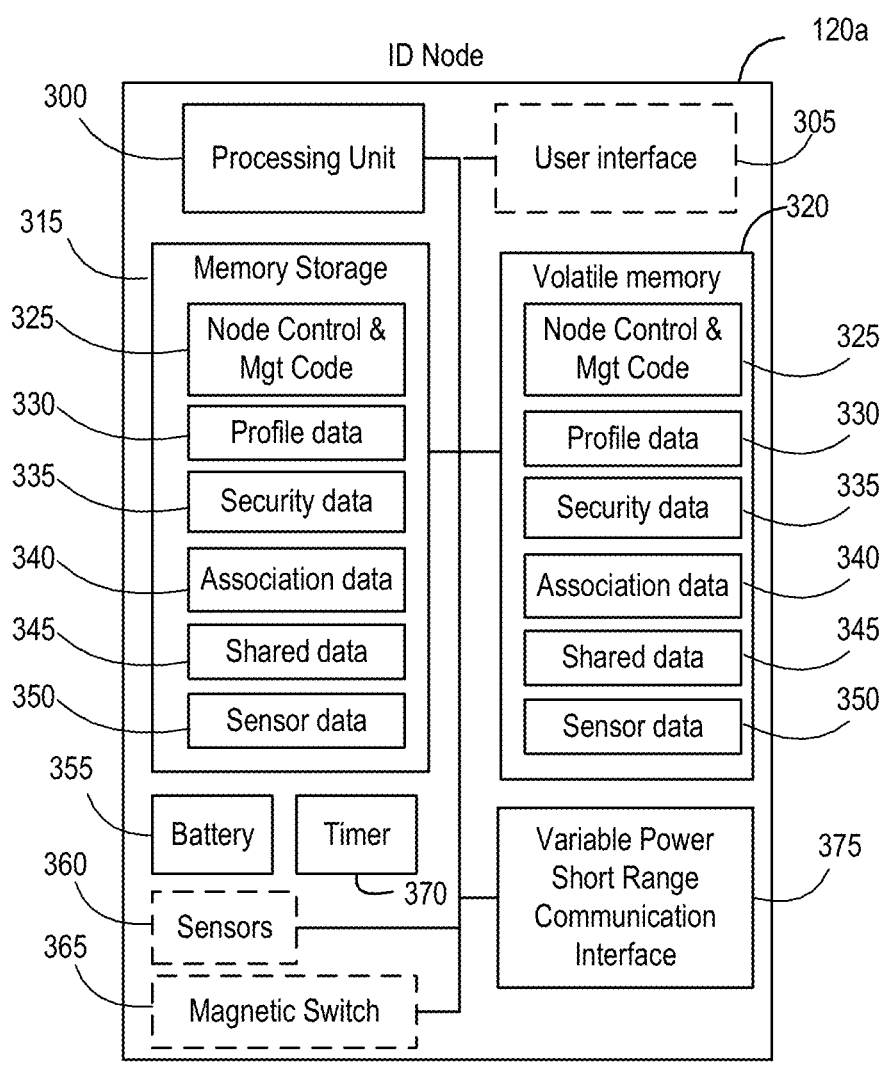
FIG. 3 is a more detailed diagram of an exemplary ID node device in accordance with an embodiment of the invention.

FIG. 3 is a more detailed diagram of an exemplary ID node device in accordance with an embodiment of the invention. As previously described, one embodiment of an ID node includes a transceiver-based processing or logic unit having a short-range radio with variable RF characteristics (e.g., programmable RF output power range, programmable receiver sensitivity), memory accessible by the processing unit, a timer operatively coupled to the processing unit, and a power source (e.g., a battery) that provides power for the circuitry of the ID node. Referring now to the more detailed embodiment of FIG. 3, exemplary ID node 120a is shown to comprise a processing or logic unit 300 coupled to a variable power short-range communication interface 375, memory storage 315, volatile memory 320, timer 370, and battery 355. Those skilled in the art will appreciate that processing unit 300 is logic, such as a low power consumption microcontroller, that generally performs computations on data and executes operational and application program code and other program modules or sections thereof within the ID node 120a. As such, exemplary processing unit 300 operates as a transceiver-based processing core of ID node 120a.

Those skilled in the art will also appreciate that exemplary ID node 120a is a hardware-based component that may be implemented with a single processor or logic unit, such as unit 300. In one embodiment, processing unit 300 may be implemented with an Intel® 8051 CPU Core and associated peripheral circuitry as dictated by the needs of the particular application. Less complex microcontrollers or discrete circuitry may be used to implement processing unit 300 as well as more complex and sophisticated microprocessors. Additionally, exemplary processing unit 300 may be integrated into a single chip transceiver used as a core of ID node 120a.

The variable power short-range communication interface 375 of ID node 120a is generally a programmable radio and an omni-directional antenna coupled to the processing unit 300. In other embodiments, interface 375 may use an antenna with a different antenna profile when directionality may be desired. Examples of variable power short-range communication interface 375 may include other interfacing hardware (not shown) for operatively coupling the device to a specific short-range communication path (e.g., a Bluetooth® Low Energy (BLE) connection path communicating at 2.4 GHz).

In one embodiment, various RF characteristics of the radio's transceiver, such as the RF output power and/or the RF receiver sensitivity may be dynamically and programmatically varied under control of processing unit 300. In other embodiments, further RF characteristics of the radio's transceiver may be programmatically varied, such as frequency, duty cycle, timing, modulation schemes, spread spectrum frequency hopping aspects, etc., as needed to flexibly adjust the RF output signal depending upon a desired implementation and anticipated use of ID node 120a. As will be explained in more detail below, some embodiments may use Broadcast Profile having parameters that may be programmatically altered or adjusted. In other words, embodiments of ID node 120a (or any other ID node) may have programmatically adjustable RF characteristics (such as an adjustable RF output signal power, an adjustable RF receiver sensitivity, the ability to switch to a different frequency or frequency band, etc.).

The battery 355 for ID node 120a is a type of power source that generally powers the circuitry implementing ID node 120a. In one embodiment, battery 355 may be a rechargeable power source. In other embodiments, battery 355 may be a non-rechargeable power source intended to be disposed of after use. In some embodiments of an ID node, the power source may involve alternative energy generation, such as a solar cell.

The timer 370 for ID node 120a generally provides one or more timing circuits used in, for example, time delay, pulse generation, and oscillator applications. In an embodiment where ID node 120a conserves power by entering a sleep or dormant state for a predetermined time period as part of overall power conservation techniques, timer 370 assists processing unit 300 in managing timing operations. Additionally, an embodiment may allow an ID node to share data to synchronize different nodes with respect to timer 370 and a common timing reference between nodes and the server.

An embodiment may implement ID node 120a to optionally include a basic user interface (UI) 305 indicating status and allowing basic interaction like start/stop. In one embodiment, the UI 305 may be implemented with status lights, such as multi-mode LEDs. Different colors of the lights may indicate a different status or mode for the ID node 120a (e.g., an advertising mode (broadcasting), a scanning mode (listening), a current power status, a battery level status, an association status, an error, as sensed condition (e.g., exceeding a temperature threshold, exceeding a moisture threshold, and the like)). Other embodiments of an ID node may implement U! 305 in a more sophisticated manner with a graphics display or the like where such status or mode information may be displayed as well as one or more prompts.

In a further embodiment, an exemplary status light used as part of the UI 305 of an ID node may also indicate a shipment state. In more detail, an exemplary shipment state may include a status of the shipped item or a status of the item's current shipment journey from an origin to a destination.

An embodiment may also implement ID node 120a to optionally include one or more sensors 360. In some embodiments, an ID node implemented with one or more sensors 360 may be referred to as a Sensor node. Examples of sensor 360 may include one or more environmental sensors (e.g., pressure, movement, light, temperature, humidity, magnetic field, altitude, attitude, orientation, acceleration, etc.) and dedicated location sensors (e.g., GPS sensor, IR sensor, proximity sensor, etc.). Those skilled in the art will understand that additional types of sensors that measure other characteristics are contemplated for use as sensor 360. Additionally, those skilled in the art will understand that a Sensor node may include additional program features to manage the collection, storage, sharing, and publication of the captured sensor data.

An embodiment may further implement ID node 120a to optionally include one or more magnetic switches 365. A magnetic switch 365, such as a reed switch, generally operates to close or open an electrical path or connection in response to an applied magnetic field. In other words, magnetic switch 365 is actuated by the presence of a magnetic field or the removal of a magnetic field. Various applications, as discussed in embodiments described in more detail below, may involve the operation of ID node 120a having magnetic switch 365.

Consistent with the embodiment shown in FIG. 3, exemplary ID node 120a may be implemented based upon a Texas Instruments CC2540 Bluetooth® Low Energy (BLE) System-on-Chip, which includes various peripherals (e.g., timer circuitry, USB, USART, general-purpose I/O pins, IR interface circuitry, DMA circuitry) to operate as an ID node and, if necessary, to interface with different possible sensors and other circuitry (e.g., additional logic chips, relays, magnetic switches) that make up the ID node.

In additional embodiments, one skilled in the art will appreciate that similar functionality in an ID node may be implemented in other types of hardware. For example, ID node 110a may be implemented with specially optimized hardware (e.g., a particular application specific integrated circuit (ASIC) having the same operational control and functionality as node control and management code, as described below, discrete logic, or a combination of hardware and firmware depending upon requirements of the ID node, such as power, processing speed, level of adjustability for the RF characteristics, number of memory storage units coupled to the processor(s), cost, space, etc.

As noted above, ID node 120a includes memory accessible by the processing unit 300. Memory storage 315 and volatile memory 320 are each operatively coupled to processing unit 300. Both memory components provide programming and data elements used by processing unit 300. In the embodiment shown in FIG. 3, memory storage 315 maintains a variety of program code (e.g., node control and management code 325) and other data elements (e.g., profile data 330, security data 335, association data 340, shared data 345, sensor data 350, and the like). Memory storage 315 is a tangible, non-transient computer readable medium on which information (e.g., executable code/modules, node data, sensor measurements, etc.) may be kept in a non-volatile and non-transitory manner. Examples of such memory storage 315 may include a hard disk drive, ROM, flash memory, or other media structure that allows long term, non-volatile storage of information. In contrast, volatile memory 320 is typically a random access memory (RAM) structure used by processing unit 300 during operation of the ID node 120a. Upon power up of ID node 120a, volatile memory 320 may be populated with an operational program (such as node control and management code 325) or specific program modules that help facilitate particular operations of ID node 120a. And during operation of ID node 120a, volatile memory 320 may also include certain data (e.g., profile data 330, security data 335, association data 340, shared data 345, sensor data 350, and the like) generated as the ID node 120a executes instructions as programmed or loaded from memory storage 315. However, those skilled in the art will appreciate that not all data elements illustrated in FIG. 3 must appear in memory storage 315 and volatile memory 320 at the same time.

Node Control & Management Code

Generally, an embodiment of node control and management code 325 is a collection of software features implemented as programmatic functions or program modules that generally control the behavior of a node, such as ID node 120a. In an embodiment, the functionality of code 325 may be generally similar as implemented in different types of nodes, such as a master node, an ID node, and a sensor node. However, those skilled in the art will appreciate that while some principles of operation are similar between such nodes, other embodiments may implement the functionality with some degree of specialization or in a different manner depending on the desired application and use of the node.

In a general embodiment, exemplary node control and management code 325 may generally comprise several programmatic functions or program modules including (1) a node advertise and query (scan) logic manager (also referred to herein as a node communications manager), which manages how and when a node communicates; (2) an information control and exchange manager, which manages whether and how information may be exchanged between nodes; (3) a node power manager, which manages power consumption and aspects of RF output signal power and/or receiver sensitivity for variable short-range communications; and (4) an association manager focusing on how the node associates with other nodes. What follows is description of various embodiments of these basic program modules used by nodes.

Node Communications Manager—Advertising & Scanning

In an exemplary embodiment, the node advertise and query (scan) logic manager governs how and when a node should advertise (transmit) its address or query (scan) for the address of neighboring nodes. Advertising is generally done with a message, which may have different information in various parts (e.g., headers, fields, flags, etc.). The message may be a single or multiple packets.

In the exemplary embodiment, the "advertise" mode (as opposed to "query" or "scan" mode) is a default mode for an ID Node and has the node broadcasting or transmitting a message with its address and related metadata regarding the node. For example, in one embodiment, exemplary metadata may include information such as the RF output power level, a reference number, a status flag, a battery level, and a manufacturer name for the node.

Figure 6:
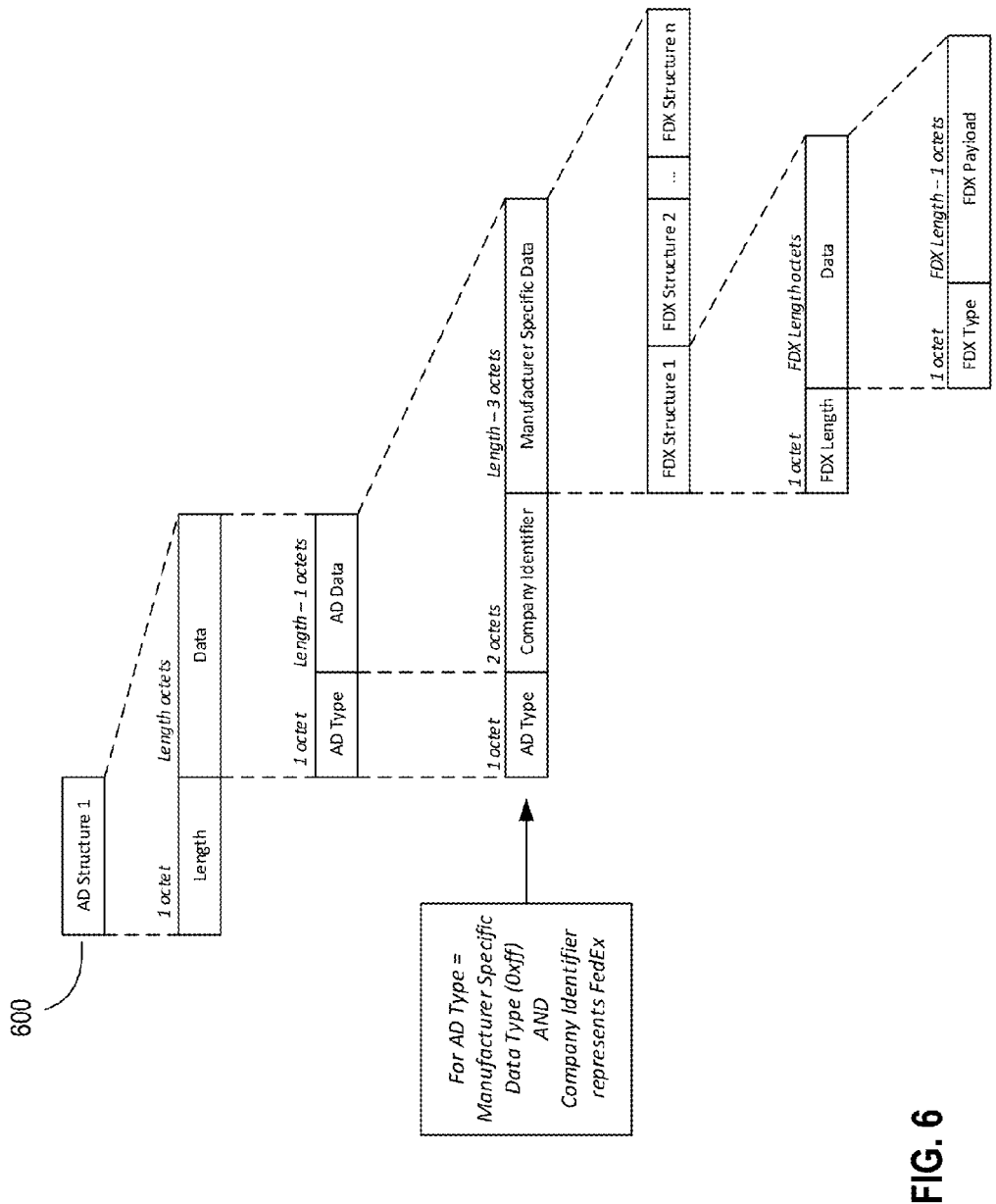
FIG. 6 is a diagram illustrating the structure or format of an exemplary advertisement data packet in accordance with an embodiment of the invention.

FIG. 6 is a diagram illustrating the structure or format of an exemplary advertisement data packet in accordance with a general embodiment of the invention. Referring now to FIG. 6, the structure of an exemplary advertisement data packet 600 broadcast as a signal or message from an ID node, such as ID node 120a, is shown. Packet 600 appears with an increasing level of detail showing exemplary metadata and a format that separately maintains distinct types of metadata in different parts of the packet. Different embodiments may include different types of metadata depending on the deployed application of the ID node.

Figure 7:
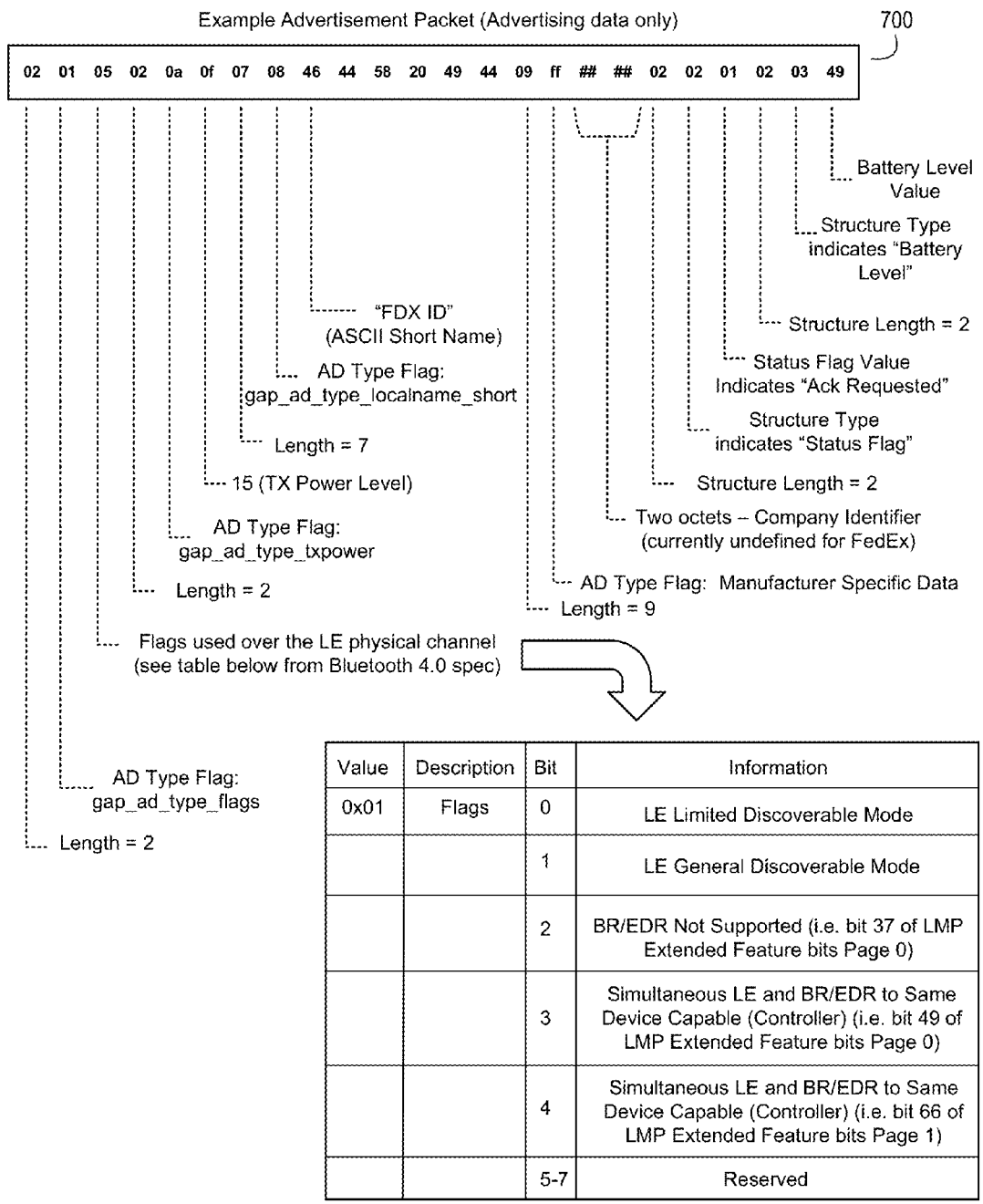
FIG. 7 is a diagram illustrating sample content for an exemplary advertisement data packet in accordance with an embodiment of the invention.

FIG. 7 is a diagram illustrating sample content for an exemplary advertisement data packet in accordance with an embodiment of the invention. Referring now to FIG. 7, an exemplary advertisement data packet 700 is illustrated with exemplary metadata including showing sample information such as the RF Output Power level (e.g., "TX Power Level"), a reference number (e.g., "'FDX ID' (ASCII Short Name)", a status flag (e.g., "Status Flag Value (indicates 'Ack Requested')"), a battery level (e.g., "Battery Level Value (Indicates 73% charge)", and a manufacturer name for the node (e.g., "Company Identifier (currently undefined for FedEx)"). In one embodiment, those skilled in the art will appreciate that the reference number may be omitted or obfuscated for security purposes.

In one embodiment, an exemplary advertising data packet may include the RF Output power level, as noted above in FIG. 7, to enable one way to help identify the type of node doing the broadcasting and the location of the broadcasting node. However, if the broadcast RF output power level is fixed and known by the node type, only the node type need be identifiable from an exemplary advertising data packet, such as packet 700.

Regarding how a node communicates, an exemplary node may be in one of several different communication modes. A node in an advertising (or transmit or broadcast) mode is visible to any other node set in a query (or scan or listen) mode. In an embodiment, the frequency and length of advertising may be application and power dependent. For example, in normal operations, an exemplary node will generally advertise in a periodic manner and expect to make an active connection to another node at certain intervals, which may be dictated by conditions set by server 100. In an embodiment, such conditions may be set individually for a node by the server or a higher level node in the network.

If an exemplary node has not received acknowledgement for an advertising packet within a particular period, it may enter one or more alert stages. For example, if an exemplary node has not received acknowledgement from another node for an advertising packet broadcast by the exemplary node within a particular time period (also generally referred to as an Alert Interval), the exemplary node will enter an Alert Stage 1 status. This prompts the exemplary node to issue a follow-up advertising packet having one or more parts of it altered to indicate the Alert Stage 1 status. In more detail, this exemplary follow-up advertising packet may have a different advertising alert header instructing nearby nodes to send a SCAN_REQ message upon receiving an advertisement packet.

If an exemplary node has not received acknowledgement from a master node for an advertising packet broadcast by the exemplary node within another time period (e.g., a request from the master node to actively connect and a success connection made), it will enter another alert stage, such as an Alert Stage 2 status. This prompts the exemplary node to issue a follow-up advertising packet having one or more parts of it altered to indicate the Alert Stage 2 status. In more detail, this exemplary follow-up advertising packet may have a different advertising alert header instructing nearby master nodes to send a SCAN_REQ message upon receiving an advertisement packet.

If an exemplary node has data to upload to the backend, it may also enter another type of alert stage. In one embodiment, for example, if an exemplary node has sensor data collected by the exemplary node (or received from one or more other nodes that have communicated with the exemplary node), and the data needs to be uploaded to server 100, the exemplary node may enter an update alert stage, such as an Alert Stage 3. This prompts the exemplary node to issue a follow-up advertising packet having one or more parts of it altered to indicate the Alert Stage 3 status. In more detail, this exemplary follow-up advertising packet may have a different advertising alert header instructing nearby master nodes to make a connection with the exemplary node so that the data (e.g., sensor data 350) may be transmitted from the exemplary node (e.g., ID node 120*a*) to a nearby master node (e.g., master node 110*a*). The transmitted data may then be stored by the nearby master node as sensor data 450 in either or both of the master node's volatile memory 420 and memory storage 415. Subsequent to that storage operation, the nearby master node will transfer the data (e.g., sensor data 450) to server 100.

As illustrated in FIG. 7 and explained in the above description of alert level stages, a status flag in a header of an exemplary advertising data packet is a field used in the association logic in one or more embodiments. For example, in one embodiment, the existence of a status flag in the advertising data packet allows a first node to communicate its status to a second node, and for the second node to report that status to the backend server, such as server 100, without an active direct connection from the first node to the server. In other words, the status flag helps facilitate passive interactions between nodes (such as passive associations).

In a more detailed embodiment, several exemplary status types are established with respect to communications with other nodes. For example, the exemplary status types may comprise the following:

Alert Level 0—no issue, operating normal;
Alert Level 1—The advertising node is requesting that any available node acknowledge the receipt of its advertisement packet;
Alert Level 2—The advertising node is requesting that any available master node acknowledge the receipt of its advertisement packet;
Alert Level 3—Data for Upload—node has captured data available for upload through a master node; and
Synchronize—The advertising node requests to connect with a device or sensor that can synchronize data (such as timer or location information).

By broadcasting the status via, for example, a portion of a header in an advertising data packet, one or more nodes within range of the broadcasting node can determine the node's status and initiate active connections if requested in the status message.

A request for more information from the advertising node may, in some embodiments, come in the form of a SCAN_REQ message. In general, an exemplary SCAN_REQ is a message sent from a scanning (listening) master node to an advertising node requesting additional information from the advertising node. In this example, the alert status bit may indicate to the scanning master node, for example, at an application layer, whether the advertising node is in a mode that will or will not accept a SCAN_REQ. In one embodiment, the non-connectable and discoverable modes of node advertising are in compliance with Bluetooth® Low Energy (BLE) standards.

In another embodiment, a node may have further different modes of operation while scanning or listening for other nodes. For example, a node's query or scanning mode may be active or passive. When a node is scanning while passive, the node will receive advertising data packets, but will not acknowledge and send SCAN_REQ. However, when a node is scanning while active, the node will receive advertising data packets, and will acknowledge receipt by sending a SCAN_REQ. A more detailed embodiment may provide the passive and active modes of scanning or inquiry in compliance with Bluetooth® Low Energy (BLE) standards.

In an embodiment, an exemplary node is scanning as it listens for other wireless nodes broadcasting on the short-range radio. An exemplary scanning node may capture, for example, a MAC address of the advertising node, a signal strength of the RF output signal transmitted from the advertising node, and any other metadata published by the advertising node (e.g., other information in the advertising data packet). Those skilled in the art will appreciate that the scope of "listening" when a node is scanning may vary. For example, the query may be limited. In other words, the scope of what a node is particularly interested in and for which it is listening may be focused or otherwise limited. In such a case, for example, the information collected may be limited to particular information from a targeted population of short-range wireless nodes advertising; but the information collection may be considered "open" where information from any advertising device is collected.

When nodes are advertising or scanning, an embodiment may make further use of status flags and additional modes when advertising or scanning as part of how nodes communicate and may be managed. In one example, when a scanning (listening) node receives an advertising data packet with the status flag indicating an Alert Level 1 or 2 status, and the scanning node is in "Passive" scanning mode, the node will switch to "Active" scanning mode for some interval. However, when the scanning node in this situation is already in an "Active" scanning mode, the node will send the SCAN_REQ message and receive a SCAN_RSP from the advertising node (e.g., a message providing the additional information requested from the advertising node). The scanning node will then switch back to a "Passive" scanning mode.

In another example, when an advertising (broadcasting) node receives a SCAN_REQ from a scanning node, the advertising node will consider that its advertising data packet has been acknowledged. Further, the advertising node will reset its "Alert" status flag back to an Alert Level 0 status. This allows the advertising node to effectively receive an acknowledgement to its advertisement without ever making a connection to the scanning node, which advantageously and significantly saves on power consumption.

In yet another example, when a scanning node receives an advertising data packet with an Alert Level 3 status flag set, the scanning node will attempt to make a connection with the advertising device. Once the connection is made, the advertising device will attempt to upload its data to the connected device Thus, an embodiment of the node advertise and query (scan) logic manager of code 325 may rely upon one or more status flags, advertising modes, scanning modes, as nodes communicate with each other in various advantageous manners.

Node Information Control & Exchange Manager

In an exemplary embodiment, the information control and exchange manager part of node control and management code 325 determines whether and how information may be exchanged between nodes. In the exemplary embodiment, the information control and exchange manager establishes different node operational states where information may be changed according to a desired paradigm for the state. In more detail, an embodiment of information control and exchange manager may establish different levels of information exchange between nodes with a "non-connectable advertising" state or mode of operation, a "discoverable advertising" state or mode, and a "general advertising" state or mode operation. When a node is in the "non-connectable advertising" mode, the node information exchange is limited. For example, the advertising node may broadcast information that is captured by one or more querying (scanning) nodes, but no two-way exchange of information happens.

When a node is in the "discoverable advertising" mode and a scanning node is in "Active" mode, the node information exchange in enabled both ways. For example, the advertising node sends the advertising packet, and in response the scanning node sends the SCAN_REQ packet. After the advertising node receives the SCAN_REQ requesting additional information, the advertising node sends the SCAN_RSP with the requested information. Thus, in the "discoverable advertising" mode there is a two-way exchange of information, but no active connection is made between the two nodes exchanging information.

Finally, for advanced two-way information exchange, an active connection may be used between nodes and information may be exchanged both ways to and from different nodes. In a more detailed embodiment, at this level of two-way information exchange, nodes are first identified and then authenticated as part of establishing the active connection. Once authenticated and thereafter actively connected to each other, the nodes may securely share information back and forth. In one example, a sensor node uploading previously captured environmental information to a master node may be in this mode or state. In another example, an ID node uploading the stored results of a node scanning operation to a master node may be in this mode or state. In yet another example, a master node sharing a timer and/or location information with corresponding nodes may be in this mode or state.

Node Power Manager

In an exemplary embodiment, the node power manager part of node control and management code 325 focuses on managing power consumption and the advantageous use of power (e.g., an adjustable level of RF output signal power) in a node. In general, nodes are either powered by a battery (such as battery 355 in an ID node), or by an interface (such as battery/power interface 470 in a master node) to an external power source. Examples of an external power source may include, in some embodiments, power supplied from an outlet or power connection within a facility, or power generated onboard a conveyance (e.g., automobile, truck, train, aircraft, ship, etc.). Those skilled in the art will appreciate that an interface to an external power source will be generally referred to as a "wired" power connection, and that node power manager may be informed whether a node is wired or powered off a battery, such as battery 355. Further embodiments may implement an interface to an external power source with wireless power transmission, such as via inductive coils.

In one embodiment, a node may manage power used when performing tasks. For example, a node may manage power when determining which node should perform a particular task. In more detail, the collective power consumption of a group of devices may be managed by electing to employ wired nodes, when feasible or desired, to accomplish a particular task, and saving the battery-powered nodes for other less energy burdensome or taxing tasks. In another embodiment, historic data may inform the system of the power needed to accomplish a particular task, and the system may make a determination of which node should accomplish the particular task based upon such historic data. In other embodiments, profile data may also be used to inform the system of the power needed to accomplish a particular task (e.g., a sensor profile that describes power requirements for operation of a sensor node that gathers sensor data over a certain period of time and under certain conditions). The system may also make a determination of which node should accomplish the particular task based upon such profile data.

In another example, the exemplary node power manager may manage power when determining how to best to use and adjust power to more accurately accomplish a particular task. In one embodiment, an RF signal output from a node (such as a short-range RF output signal from an ID node) may periodically move through a range of output power or simply switch between two or more settings that differ in a detectable manner. As disclosed in more detail below, the variability and dynamic adjustment of RF output signal power may allow other nodes (such as one or more master nodes) to see each node at the upper range of the RF output signal power, and only see nodes physically close to the advertising node at the lower range of signal power.

In another example, the exemplary node power manager may cause a change to a characteristic of its RF output signal power when the node has been associated to a physical place or another node by virtue of context data (such as context data 560 and association logic that utilizes that type of information). In one embodiment, the node may be instructed to change how often the node communicates and/or a characteristic of its RF output power to preserve power.

In yet another example, all advertising nodes may have their respective node power managers periodically cause each respective node to broadcast at a maximum RF output signal power level to ensure they still are within range of a scanning ID Node or Master Node. Doing so may increase the chance of being in communication range and allows the individual nodes to be properly located and managed within the network. The broadcast duration may be set or dynamically changed to allow pairing to occur if needed.

Rather than adjust the RF output signal power level, the exemplary node power manager may, in some embodiments, adjust the RF receiver sensitivity of a node. This allows for an adjustable range of reception (as opposed to merely an adjustable range of broadcast), which may similarly be used to manage power and enhance location determinations as discussed herein.

In yet another embodiment, a combination approach may be used in which the node power manager may concurrently and independently adjust more than one RF characteristic of a node. For example, en exemplary node power manager may adjust an RF output signal power level and also adjust the RF receiver sensitivity of a node as the node is located and associated with other nodes. Those skilled in the art will realize that this may be especially useful in an area with an unusually dense concentration of nodes, and a combination of changing RF output signal power levels An embodiment of the exemplary node manager may refer to a power profile (e.g., an exemplary type of profile data 330, 430) when adjusting a node's power characteristics (e.g., consumption of power, use of power, output signal frequency, duty cycle of the output put signal, timing, power levels, etc.).

Node Association Manager

In an exemplary embodiment, the node association manager part of node control and management code 325 focuses on how the nodes associate with other nodes in conjunction and consistent with the server-side association manager in code 525, as discussed in more detail below. Thus, exemplary node association manager, when executing in a node, directs how the node associates (e.g., enters an active connection mode) with one or more other nodes with input from the server.

The exemplary node association manager for a node may indicate through a Status Flag if the node requires an acknowledgement or connection, or if it has information available for upload to the backend. Thus, while a node may not be associated or actively connected yet to another node, a status of the node may be inferred from, for example, the status information in the node's broadcast header.

Regarding connections between nodes, there are generally secure connections and unsecure connections. While an embodiment may allow unsecure connections between one or more sets of nodes, other embodiments rely upon secure connections or authenticate pairings of nodes. In one embodiment, for a node to pair with another node, the exemplary node association manager first identifies the nodes to be associated and transmits an association request to the server. The request may include a specific request to pair the nodes and ask for the corresponding pairing credentials from the server, such as server 100. The server 100 may have staged pairing credentials on particular nodes based on information indicating the nodes would be within wireless proximity and future pairing may occur. Visibility to the node relationship may have been determined through scan-advertising, or $3^{rd}$ party data such as barcode scan information indicating the nodes to be within proximity currently or at a future state.

When connecting or not connecting to exchange information under the exemplary node information exchange modes described above, nodes generally operate in a number of states, which make up an exemplary advertise cycle for an exemplary ID node. Such an exemplary advertise cycle for a node is further explained below with reference to FIG. 8 and in conjunction and consistent with the server-side association manager in code 525, as discussed in more detail below.

Airborne Mode Program Module

In one embodiment, node control and management code 325 may also include an airborne mode program module (not shown). In another embodiment, the airborne mode program module may be implemented as a part of the node power manager program module of code 325. An exemplary airborne mode program module generally operates to manage the output power of the ID node's variable power short-range communication interface 375 when the ID node is operating in an aircraft. Operating a wireless device within an aircraft may, in some circumstances, have an unintentional impact on other electronic systems on the aircraft. In more detail, an embodiment of the airborne mode program module may operate to transition the ID node from different states or modes depending upon particular operations and/or operational conditions of the aircraft. For example, an exemplary airborne mode program module may operate to transition the ID node from one state or mode (e.g., a normal mode prior to takeoff, a disabled mode during takeoff, an airborne mode while aloft, a disabled mode during descent, and a normal mode after landing) based upon detected environmental conditions (e.g., pressure, altitude) and/or flight detail information associated with the aircraft. In this way, an ID node may be allowed to normally operate when onboard an aircraft, be disabled from operating at all in some circumstances, and be able to operate in an airplane mode that allows sensing and sensor data capture, but that may limit transmission of an RF output signal to avoid interference with the aircraft's onboard electronics. Further information related to a method of managing a wireless device (such as an ID node) in an aircraft is disclosed in greater detail in U.S. patent application Ser. No. 12/761,963 entitled "System and Method for Management of Wireless Devices Aboard an Aircraft," which is hereby incorporated by reference.

Node Data

As previously noted, volatile memory 320 may also include certain data (e.g., profile data 330, security data 335, association data 340, shared data 345, sensor data, and the like) generated as the ID node 120a executes instructions as programmed or loaded from memory storage 315. In general, data used on a node, such as an ID node, may be received from other nodes or generated by the node during operations.

In one embodiment, profile data 330 is a type of data that defines a general type of behavior for an ID node, such as a Broadcast Profile (discussed in more detail below). In another embodiment where ID node 120a is a BLE device, profile data 330 may include a Bluetooth® compatible profile related to battery service (exposing the state of a battery within a device), proximity between BLE devices, or messaging between BLE devices. Thus, exemplary profile data 330 may exist in volatile memory 320 and/or memory storage 315 as a type of data that defines parameters of node behavior.

In one embodiment, it may be desired to allow secured pairings of nodes. As will be explained in more detail below, as part of secure pairing of nodes, a request for pairing credentials is generated and sent to server 100. Thus, exemplary security data 335 (e.g., PIN data, security certificates, keys, etc.) may exist in volatile memory 320 and/or memory storage 315 as a type of data associated with providing secured relationships between nodes, such as the requested security credentials.

Association data, such as association data 340, generally identifies a connected relationship between nodes. For example, ID node 120*a* may become associated with the master node 110*a* as the ID node 120*a* moves within range of the master node 110*a* and after the server directs the two nodes to associate (with authorization). As a result, information identifying the relationship between ID node 120*a* and master node 110*a* may be provided to server 100 and may be provided, as some point, to each of ID node 120*a* and master node 110*a*. Thus, exemplary association data 340 may exist in volatile memory 320 and/or memory storage 315 as a type of data identifying associations between nodes.

Shared data 345 may exist in volatile memory 320 and/or memory storage 315 as a type of data exchanged between nodes. For example, context data (such as environmental data) may be a type of shared data 345.

Sensor data 350 may also exist in volatile memory 320 and/or memory storage 315 as a type of data recorded and collected from an onboard sensor or from another node. For example, sensor data 350 may include temperature readings from a temperature sensor onboard an ID node and/or humidity readings from a humidity sensor in another ID node (e.g., from another of the ID nodes within container 210 as shown in FIG. 2).

Thus, an ID node (such as node 120*a* shown in FIG. 3) is a lower cost wireless node that communicates with other ID nodes and master nodes via a short-range radio with variable RF characteristics, can be associated with other nodes, can broadcast to and scan for other nodes, associated with other nodes, and store/exchange information with other nodes.

Master Node

Figure 4:
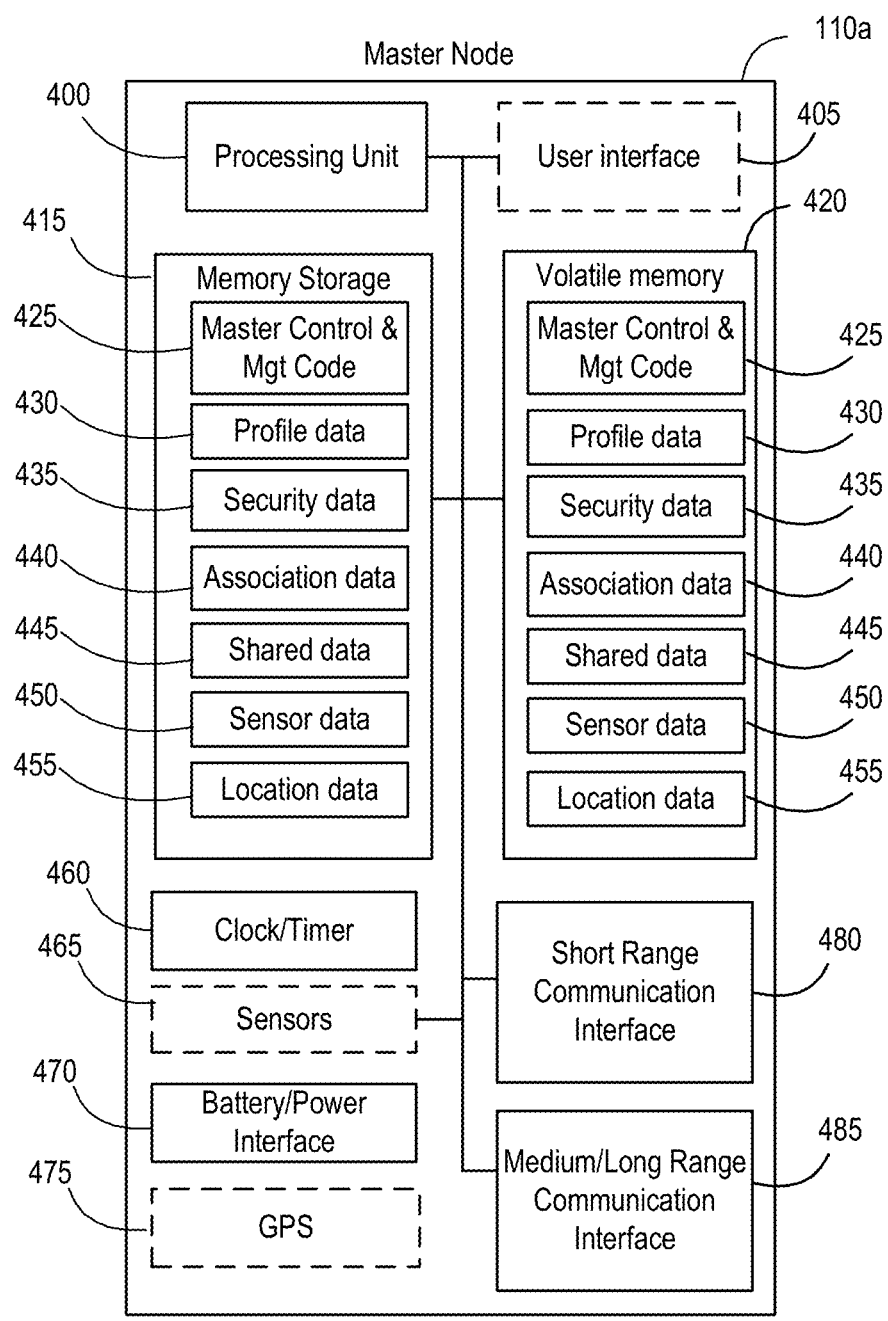
FIG. 4 is a more detailed diagram of an exemplary master node device in accordance with an embodiment of the invention.

A master node, such as master node 110*a* shown in more detail in FIG. 4, shares many ID node features but generally expands upon them in order to function as a bridge to the server 100. In general, while an ID node is a type of lower level node in an exemplary wireless node network, a master node is a type of higher level node. An exemplary master node may be in a fixed location or otherwise stationary, while other example master nodes may be implemented as movable and mobile devices.

Referring now to FIG. 4, exemplary master node 110*a* comprises a processing or logic unit 400 coupled to a short-range communication interface 485, memory storage 415, volatile memory 420, clock/timer 460, and battery/power interface 470. In some embodiments, the short-range communication interface 485 may have variable power characteristics, such as receiver sensitivity and RF output power level. Those skilled in the art will appreciate that processing unit 400 is logic, such as a microprocessor or microcontroller, which generally performs computations on data and executes operational and application program code and other program modules within the master node 110*a*.

In general, those skilled in the art will appreciate that the description of hardware with respect to ID node 110*a* in FIG. 4 applies to the similar hardware and software features appearing in each type of node, including a master node. Those skilled in the art will appreciate that exemplary master node 110*a* is a hardware-based component that may implement processor 400 with a single processor or logic unit, a more powerful multi-core processor, or multiple processors depending upon the desired implementation. In one embodiment, processing unit 400 may be implemented with a low power microprocessor and associated peripheral circuitry. Less complex microcontrollers or discrete circuitry may be used to implement processing unit 400 as well as more complex and sophisticated general purpose or dedicated purpose processors.

In yet another embodiment, exemplary processing unit 400 may be implemented by a low power ARM1176JZ-F application processor used as part of a single-board computer, such as the Raspberry Pi Computer Model B-Rev-2. The ARM application processor is embedded within a Broadcom® BCM2835 system-on-chip (SoC) deployed in the Raspberry Pi Computer. In this embodiment, the Raspberry Pi Computer device operates as a core of exemplary master node 110*a* and includes a Secure Digital memory card slot and flash memory card operating as memory storage 415, a 512 Mbyte RAM memory storage operating as volatile memory 420, an operating system (such as Linux) stored on memory storage 415 and running in volatile memory 420, and peripherals that implement clock/timer 460, and a power supply operating as a power interface 470.

Like short-range interface 375 in ID node 120*a*, exemplary master node 110*a* includes a short-range communication interface 480 as a programmable radio and an omni-directional antenna coupled to the processing unit 400. In some embodiments, the short-range communication interface 480 may have variable RF power characteristics, such as receiver sensitivity and/or RF output signal power level. In some embodiments, interface 480 may use an antenna with a different antenna profile when directionality may be desired. Examples of short-range communication interface 480 may include other hardware (not shown) for operatively coupling the device to a specific short-range communication path (e.g., a Bluetooth® Low Energy (BLE) connection path communicating at 2.4 GHz). While BLE is used in one embodiment to enable a short-range communication protocol, variable power short-range interface 480 may be implemented with other low power, short-range communication protocols, such as ultra-low power communication protocols used with ultra-wide-band impulse radio communications, ZigBee protocols, IEEE 802.15.4 standard communication protocols, and the like.

In one embodiment, various RF characteristics of the radio's transceiver, such as the RF output power and the RF receiver sensitivity may be dynamically and programmatically varied under control of processing unit 400. In other embodiments, further RF characteristics of the radio's transceiver may be programmatically varied, such as frequency, duty cycle, timing, modulation schemes, spread spectrum frequency hopping aspects, etc., as needed to flexibly adjust the RF output signal as needed depending upon a desired implementation and anticipated use of exemplary master node 110*a*. In other words, embodiments of master node 110*a* (or any other master node) may have programmatically adjustable RF characteristics (such as an adjustable RF output signal power, an adjustable RF receiver sensitivity, the ability to switch to a different frequency or frequency band, etc.).

In addition to the short-range communication interface 480, exemplary master node 110*a* includes a medium and/or long-range communication interface 485 to provide a communication path to server 100 via network 105. In one embodiment, communication interface 485 may be implemented with a medium range radio in the form of an IEEE 802.11g compliant WiFi transceiver. In another embodiment, communication interface 485 may be implemented with a longer range radio in the form of a cellular radio. In yet another embodiment, both a WiFi transceiver and a cellular radio may be used when best available or according to a priority (e.g., first attempt to use the WiFi transceiver if available due to possible lower costs; and if not, then rely on the cellular radio). In other words, an embodiment may rely upon the longer range cellular radio part of interface 485 as an alternative to the medium range WiFi transceiver radio, or when the medium range radio is out of reach from a connecting infrastructure radio within network 105. Thus, in these embodiments, medium and/or long-range communication interface 485 may be used to communicate captured node information (e.g., profile data 430, association data 440, shared data 445, sensor data 450, and location data 455) to server 100.

The battery/power interface 470 for master node 110*a* generally powers the circuitry implementing master node 110*a*. In one embodiment, battery/power interface 470 may be a rechargeable power source. For example, a master node may have a rechargeable power source along with a solar panel that charges the power source in order to help facilitate deployment of the master in a remote location. In another embodiment, battery/power interface 470 may be a non-rechargeable power source intended to be disposed of after use. In yet another embodiment, battery/power interface 470 may be a power interface connector (such as a power cord and internal power supply on master node 110*a*). Thus, when an exemplary master node is in a fixed or stationary configuration, it may be powered by a power cord connected to an electrical outlet, which is coupled to an external power source. However, other mobile master nodes may use an internal power source, such as a battery.

The clock/timer 460 for master node 110*a* generally provides one or more timing circuits used in, for example, time delay, pulse generation, and oscillator applications. In an embodiment where master node 110*a* conserves power by entering a sleep or dormant state for a predetermined time period as part of overall power conservation techniques, clock/timer 460 assists processing unit 400 in managing timing operations.

Optionally, an embodiment may also implement master node 110*a* as including one or more sensors 465 (similar to sensors deployed on ID node based Sensor nodes and described above with respect to FIG. 3). Additionally, an embodiment of master node 110*a* may also provide a user interface 405 to indicate status and allow basic interaction for review of captured node data and interaction with nodes and server 100. In one embodiment, user interface 405 may provide a display, interactive buttons or soft keys, and a pointing device to facilitate interaction with the display. In a further embodiment, a data entry device may also be used as part of the user interface 405. In other embodiments, user interface 405 may take the form of one or more lights (e.g., status lights), audible input and output devices (e.g., a microphone and speaker), or touchscreen.

As previously noted, an exemplary master node, such as master node 110*a*, may be positioned in a known fixed location or, alternatively, includes dedicated location positioning circuitry 475 (e.g., GPS circuitry) to allow the master node self-determine its location or to determine its location by itself. In other embodiments, alternative circuitry and techniques may be relied upon for location circuitry 475 (rather than GPS), such as location circuitry compatible with other satellite-based systems (e.g., the European Galileo system, the Russian GLONASS system, the Chinese Compass system), terrestrial radio-based positioning systems (e.g., cell phone tower-based or WiFi-based systems), infrared positioning systems, visible light based positioning systems, and ultrasound-based positioning systems).

Regarding memory storage 415 and volatile memory 420, both are operatively coupled to processing unit 400 in exemplary master node 110*a*. Both memory components provide program elements used by processing unit 400 and maintain and store data elements accessible to processing unit 400 (similar to the possible data elements stored in memory storage 315 and volatile memory 320 for exemplary ID node 120*a*).

In the embodiment shown in FIG. 4, memory storage 415 maintains a variety of executable program code (e.g., master control and management code 425), data similar to that kept in an ID node's memory storage 315 (e.g., profile data 430, security data 435, association data 440, shared data 445, sensor data 450, and the like) as well as other data more specific to the operation of master node 110*a* (e.g., location data 455 that is related to the location of a particular node). Like memory storage 315, memory storage 415 is a tangible, non-transient computer readable medium on which information (e.g., executable code/modules, node data, sensor measurements, etc.) may be kept in a non-volatile and non-transitory manner.

Like volatile memory 320 in ID node 120*a*, volatile memory 420 is typically a random access memory (RAM) structure used by processing unit 400 during operation of the master node 110*a*. Upon power up of master node 110*a*, volatile memory 120 may be populated with an operational program (such as master control and management code 425) or specific program modules that help facilitate particular operations of master node 110*a*. And during operation of master 110*a*, volatile memory 420 may also include certain data (e.g., profile data 430, security data 435, association data 440, shared data 445, sensor data 450, and the like) generated as the master node 110*a* executes instructions as programmed or loaded from memory storage 415.

Master Control & Management Code

Generally, an embodiment of master control and management code 425 is a collection of software features implemented as programmatic functions or program modules that generally control the behavior of a master node, such as master node 110*a*. In one embodiment, master control and management code 425 generally comprises several programmatic functions or program modules including (1) a node advertise and query (scan) logic manager, which manages how and when a node communicates; (2) an information control and exchange manager, which manages whether and how information may be exchanged between nodes; (3) a node power manager, which manages power consumption and aspects of RF output signal power and/or receiver sensitivity for variable short-range communications; (4) an association manager focusing on how the node associates with other nodes; and (5) a location aware/capture module to determine node location.

Master Node Program Modules and ID Node Modules

In an exemplary embodiment, program modules (1)-(4) of master node control and management code 425 generally align with the functionality of similarly named program modules (1)-(4) of node control and management code 325 as described above with respect to FIG. 3. Additionally, as node control and management code 325 may also comprise an airborne mode program module, those skilled in the art will appreciate and understand that master node control and management code 425 may also comprise a similar functionality airborne mode program module in order to allow advantageous operations of a master node while airborne. However, and consistent with examples set forth below, such modules may have some differences when in a master node compared with those controlling an ID node.

Location Aware/Capture Module

In addition to exemplary program modules (1)-(4) of code 425, an exemplary embodiment of master node control and management code 425 will further comprise an exemplary location aware/capture module related to node location (more generally referred to as a location manager module for a master node). In general, the exemplary location aware/capture module deployed in an exemplary master node may determine its own location and, in some embodiments, the location of a connected node. Embodiments of the exemplary location aware/capture module may work in conjunction with location manager program code residing and operating in a server (e.g., as part of server control and management code 525) when determining node locations of other nodes, as discussed in more detail herein.

In one embodiment, a master node may be positioned in a known, fixed location. In such an embodiment, the exemplary location aware/capture module may be aware that the master node location is a known, fixed location, which may be defined in a fixed, preset, or preprogrammed part of memory storage 415 (e.g., information in the location data 455 maintained in memory storage 415). Examples of such location information may include conventional location coordinates or other descriptive specifics that identify the location of the master node. In another embodiment where the master node may not be inherently known or a fixed location at all times (e.g., for a mobile master node), the exemplary location aware/capture module may communicate with location circuitry, such as GPS circuitry 475 on a master node, to determine the current location of the master node.

In an embodiment, the location of the master node may be communicated to the server, which may use this location information as part of managing and tracking nodes in the wireless node network. For example, if an exemplary master node is mobile and has determined a new current location using location circuitry 475, the master node may provide that new current location for the master node to the server. Additionally, when the master node's exemplary location aware/capture module determines the location of a node associated with the master node, the master node may also provide the location of that node associated with the master node to the server.

Server

Figure 5:
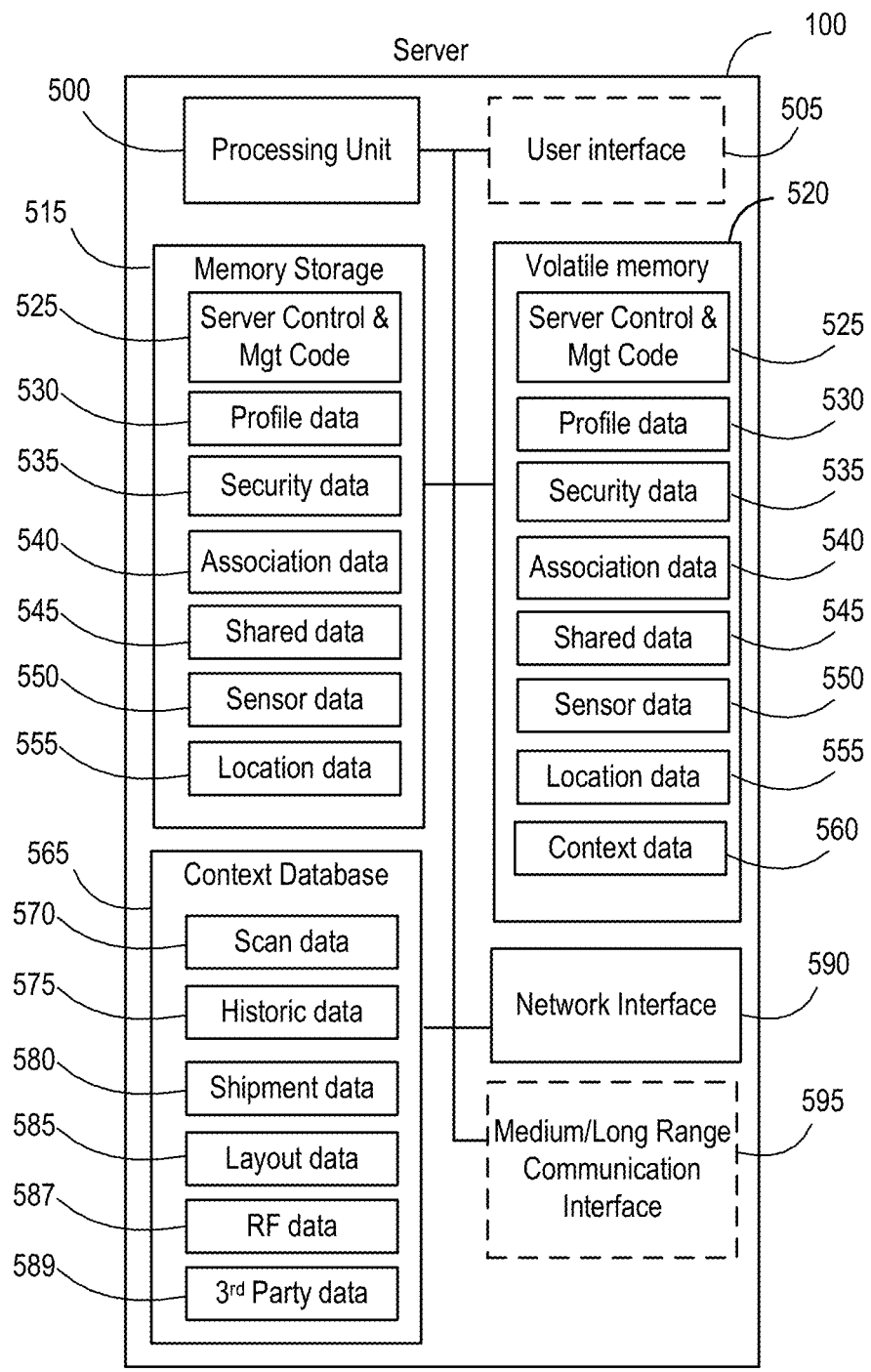
FIG. 5 is a more detailed diagram of an exemplary server in accordance with an embodiment of the invention.

While FIGS. 3 and 4 illustrate details of hardware and software aspects of an exemplary ID node and exemplary master node, respectively, FIG. 5 provides a more detailed diagram of an exemplary server that may operate as part of an exemplary wireless node network in accordance with an embodiment of the invention. In an exemplary embodiment, server 100 may be referred to as an Association and Data Management Server (ADMS) that manages the nodes, collects information from the nodes, stores the collected information from the nodes, maintains or has access to context data related to the environment in which the nodes are operating, and may provide information about the nodes (e.g., status, sensor information, etc.) to requesting entities. Further details on various embodiments that take advantage of this functionality are explained below. Those skilled in the art will appreciate that node density, geographic installation characterization, and network connectively are all types of examples of factors that may impact a final architecture desired for an embodiment of a wireless node network.

Referring now to FIG. 5, exemplary server 100 is shown as a networked computing platform capable of connecting to and interacting with at least the wireless master nodes. In other embodiments, exemplary server 100 is also capable of connecting to and interacting with one or more user access devices. Those skilled in the art will appreciate that exemplary server 100 is a hardware-based component that may be implemented in a wide variety of ways. For example, server 100 may use a single processor or may be implemented as one or more part of a multi-processor component that communicates with devices (such as user access devices 200, 205) and wireless nodes (such as master node 110*a*).

In general, those skilled in the art will further appreciate that server 100 may be implemented as a single computing system, a distributed server (e.g., separate servers for separate server related tasks), a hierarchical server (e.g., a server implemented with multiple levels where information may be maintained at different levels and tasks performed at different levels depending on implementation), or a server farm that logically allows multiple distinct components to function as one server computing platform device from the perspective of a client device (e.g., devices 200, 205 or master node 110*a*). In some regional deployments, an exemplary server may include servers dedicated for specific geographic regions as information collected within different regions may include and be subject to different regulatory controls and requirements implemented on respective regional servers.

Likewise, while the embodiment shown in FIG. 5 illustrates a single memory storage 515, exemplary server 100 may deploy more than one memory storage media. And memory storage media may be in differing non-transitory forms (e.g., conventional hard disk drives, solid state memory such as flash memory, optical drives, RAID systems, cloud storage configured memory, network storage appliances, etc.).

At its core, exemplary server 100 shown in FIG. 5 comprises a processing or logic unit 500 coupled to a network interface 590, which facilitates and enables operative connections and communications through network 105 with one or more master nodes as well as, in some embodiments, user access devices, such as devices 200, 205. In one embodiment, server 100 may include a medium and/or long-range communication interface 595 with which to more directly communicate with one or more master nodes. Using these communication paths as well as program code or program modules (such as server control and management code 525), the server 100 generally operates to coordinate and manage information related to an ID node as an item associated with the ID node physically moves from one location to another.

As a computing platform, the processing unit 500 of exemplary server 100 is operatively coupled to memory storage 515 and volatile memory 520, which collectively store and provide a variety of executable program code (e.g., server control and management code 525), data similar to that kept in a master or ID node's respective memory storage (e.g., profile data 530, security data 535, association data 540, shared data 545, sensor data 550, location data 555) and context data 560 related to the environment in which the nodes are operating (e.g., information generated from within the wireless node network and information created external to the wireless node network).

Like memory storage 315 and storage 415, memory storage 515 is a tangible, non-transient computer readable medium on which information (e.g., executable code/modules (e.g., server control and management code 525), node-related data (e.g., profile data 530, security data 535, association data 540, location data 555, etc.), measurement information (e.g., a type of shared data 545, sensor data 550, etc.), and information on the contextual environment for the nodes (e.g., context data 560) may be kept in a non-volatile and non-transitory manner.

Those skilled in the art will appreciate that the above identification of particular program code and data are not exhaustive and that embodiments may include further executable program code or modules as well as other data relevant to operations of a processing-based device, such as an ID node, a master node, and a server.

Context Data

As noted above, server 100 may access context data 560 as part of managing nodes in the wireless node network. The exemplary server 100 may contain a collection of such context data 560 in a context database 565 according to an embodiment. As illustrated in FIG. 5, exemplary context database 565 is a single database accessible by processing unit 500 internal to server 100. Those skilled in the art will readily understand that other configurations that provide an accessible collection of context data 560 are possible and contemplated within the scope and principles of embodiments of the invention. For example, context database 565 may be an externally accessible database (or multiple databases), such as an accessible storage maintained outside the server 100 via a dedicated interface or a network storage device (or network attached storage (NAS) unit). In yet another embodiment, the context database may be separately maintained by an external database server (not shown) that is distinct from server 100, but accessible through a communication path from server 100 to a separate database server (e.g., via network 105). Furthermore, those skilled in the art will appreciate that context database 565 may be implemented with cloud technology that essentially provides a distributed networked storage of collections of information (such as context data 560, sensor data 550, shared data 545, etc.) accessible to server 100.

Within context database 565, an exemplary embodiment of the collection of context data 560 may be maintained that generally relates to an environment in which the nodes are operating or anticipated to be operating. In more detail, the context data 560 may generally relate to what a similar node has experienced in a similar environment to what a given node is presently experiencing or is anticipated to experience as the given node moves.

Figure 22A:
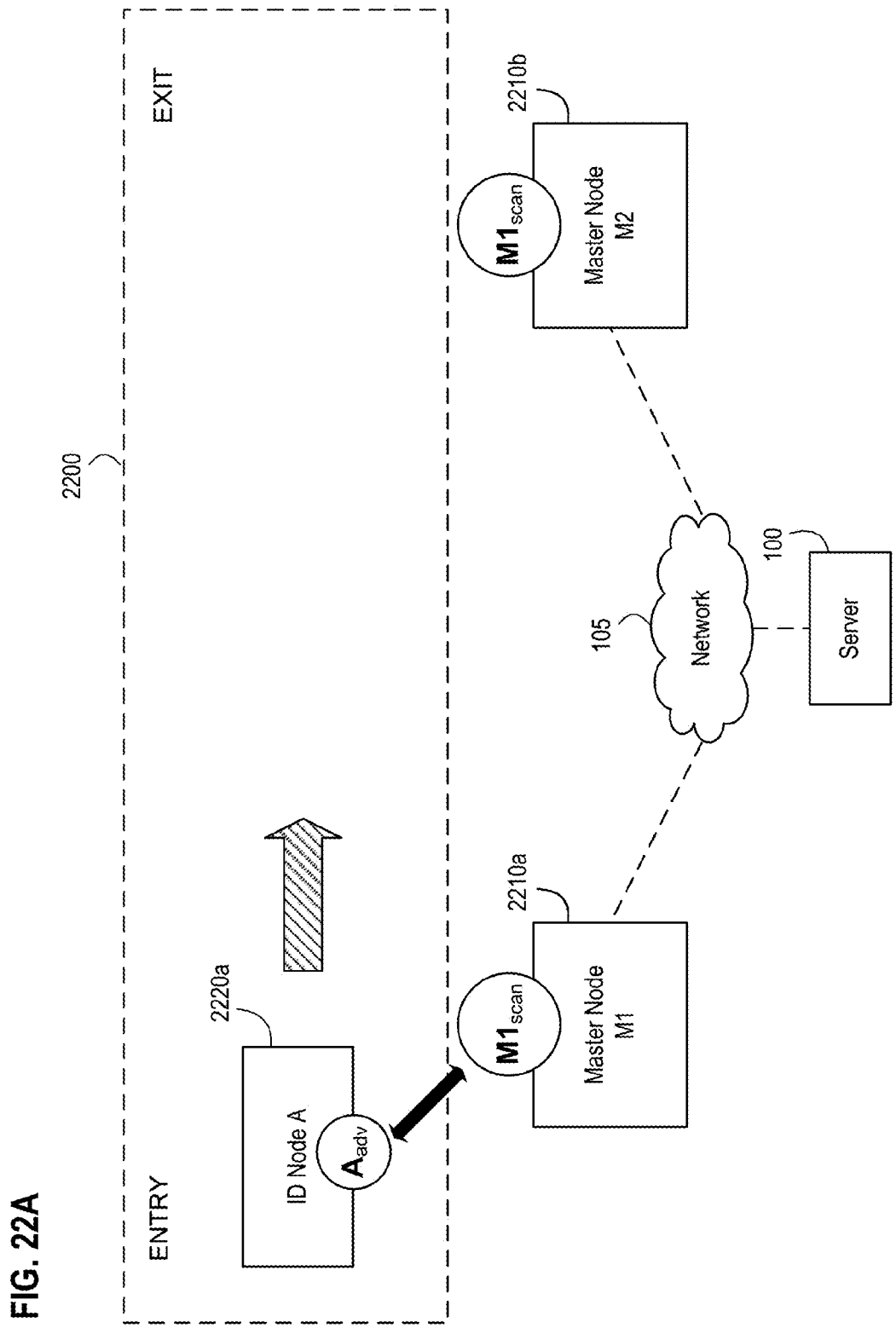
FIGS. 22A-22C are diagrams illustrating exemplary stages of an ID node moving through part of an exemplary transit path while associating with different master nodes in accordance with an embodiment of the invention.

In a general example, an environment in which a node may be actually or anticipated to be operating may include different types of environments—for example, an electronic communication environment (e.g., an RF environment that may be cluttered with signals or include materials or structure that may impede or otherwise shield RF communications), a physical environment of an anticipated path along with the identified node moves (e.g., temperature, humidity, security, and other physical characteristics), a conveyance environment related to how a node may move or be anticipated to be moving (e.g., speed and other parameters of a truck, airplane, conveyor system), and a density environment related to the density of nodes within an area near a particular node (e.g., how many nodes are anticipated to occupy a corridor, such as structure 2200 shown in FIG. 22A, or a storage facility through which a particular ID node is anticipated to transit on its shipping path).

In light of these different aspects of a node's operating environment, exemplary context data 560 may provide information related to different structures and conditions related to movement of an item (e.g., a particular type of courier device, vehicle, facility, transportation container, etc.). Such information may be generated by an entity operating the wireless node network, such as a shipping company. Additionally, exemplary context data 560 may include third party data generated external to the wireless node network. Thus, context data, such as data 560, may include a wide variety of data that generally relates to the environment in which the nodes are operating and may be used to advantageously provide enhanced node management capabilities in accordance with embodiments of the present invention.

In general, FIG. 5 illustrates exemplary types of context data 560 being maintained in database 565 and in volatile memory 520. Those skilled in the art will appreciate that context data 560 may also be maintained in other data structures, in addition to or instead of maintaining such information in a database. As illustrated in FIG. 5, exemplary types of context data 560 may include but are not limited to scan data 570, historic data 575, shipment data 580, layout data 585, RF data 587, and $3^{rd}$ party data.

Scan data 570 is generally data collected for a particular item related to an event. For example, when an item is placed in a package (such as package 130), a label may be generated and placed on the exterior of the package. The label may include a visual identifier that, when scanned by an appropriate scanning device capable of capturing, identifies the package. The information generated in response to scanning the identifier (a type of event), may be considered a type of scan data. Other scan data 570 may include, for example, general inventory data generated upon manual entry of information related to the package; captured package custodial control data; and bar code scan data.

Historic data 575 is generally data previously collected and/or analyzed related to a common characteristic. Historic data 575 embodies operational knowledge and know-how for a particular characteristic relevant to operations of the wireless node network. For example, the common characteristic may be a particular event (e.g., movement of an item from an open air environment to within a particular closed environment, such as a building), a type of item (e.g., a type of package, a type of content being shipped, a location, a shipment path, etc.), a success rate with a particular item (e.g., successful shipment), and the like. Another example of historic data 575 may include processing information associated with how an item has been historically processed as it is moved from one location to another (e.g., when moving within a particular facility, processing information may indicate the item is on a particular conveyor and may include information about the conveyor (such as speed and how long it is anticipated the item will be on the conveyor)).

Shipment data 580 is generally data related to an item being moved from one location to another location. In one embodiment, shipment data 580 may comprise a tracking number, content information for an item being shipped, address information related to an origin and destination locations, and other characteristics of the item being moved.

Layout data 585 is generally data related to the physical area of one or more parts of an anticipated path. For example, an embodiment of layout data 585 may include building schematics and physical dimensions of portions of a building in which a node may be transiting. An embodiment may further include density information associated with physical areas to be transited and anticipated numbers of potential nodes in those areas as types of layout data. In another example, an embodiment of layout data may include a configuration of how a group of packages may be assembled on a pallet, placed into a shipping container (e.g., a unit load device (ULD)) that helps move a collection of items on various forms with single mode or intermodal transport.

RF data 587 is generally signal degradation information about a signal path environment for a particular type of node and may relate to particular adverse RF conditions that may cause signal fluctuations, interference, or other degradation from the otherwise optimal signal path environment for that type of node. For example, RF data may include shielding effects when using a particular packaging or location, shielding effects when the package is within a particular type of container or assembled as part of a palletized shipment, shielding effects when particular content is shipped, and other physical and electronic interference factors.

Third party data 589 is an additional type of context data 560 that generally includes data generated outside the network. For example, third party data may include weather information associated with particular areas to be transited as the item is moved along an anticipated path from one location to another. Those skilled in the art will appreciate other types of third party data that relate to physical and environmental conditions to be faced by an item being moved from one location to another may also be considered context data 560.

The use of context data, such as context data 560 described above, advantageously helps server 100 better manage movement of items, provide better location determination, enhance intelligent operation and management of different levels of the wireless node network, and provide enhanced visibility to the current location and status of the item during operation of the wireless node network. In one embodiment, server control and management code 525 may provide such functionality that enables the wireless node network to be contextually aware and responsive.

Server Control & Management Code

Generally, server control and management code 525 controls operations of exemplary server 100. In an embodiment, server control and management code 525 is a collection of software features implemented as programmatic functions in code or separate program modules that generally control the behavior of server 100. Thus, exemplary server control and management code 525 may be implemented with several programmatic functions or program modules including, but not limited to, (1) a server-side association manager, which provides a framework for more robust and intelligent management of nodes in the wireless node network; (2) a context-based node manager, which enhances management of nodes in the wireless node network based upon context data; (3) a security manager, which manages secure pairing aspects of node management; (4) a node update manager, which provides updated or different programming for a particular node and shares information with nodes; (5) a location manager for determining and tracking the location of nodes in the network; and (6) an information update manager, which services requests for information related to the current status of a node or generally providing information about a node or collected from a node.

Server-Side Association Manager

The server-side association manager (also referred to as a server-side association management function) is generally a program module in exemplary code 525 that is responsible for intelligently managing the nodes in the wireless node network using a secure information framework. In an embodiment, this framework may be implemented to be a context-driven, learning sensor platform. The framework may also enable a way for information (such as RF scan, location, date/time, and sensor data) to be securely shared across nodes, a way to change the behavior of a node, and for a node to know it is considered "missing." The framework established during operation of the server-side association manager allows the network of nodes to be managed as a system with enhanced and optimized accuracy of determining the physical location of each ID Node. Further information regarding particular embodiments of such an association management framework and methods are explained below in more detail.

Context-Based Association Manager

The context-based node manager is generally a program module in exemplary code 525 that is responsible for incorporating context data as part of management operations to provide an enhanced data foundation upon which visibility of the nodes may be provided. In some embodiments, the context-based node manager may be implemented as part of the server-side association manager while other embodiments may implement the context-based node manager as a separate program module.

In one embodiment, the enhanced data foundation relies upon context data, such as context data 560 (e.g., scan data 570, historic data 575, shipment data 580, layout data 585, and other third party contextual data providing information regarding the conditions and environment surrounding an item and ID node moving from one location to another. Such context data (e.g., the network know-how, building layouts, and operational knowledge of nodes and shipping paths used with the wireless node network) may provide the enhanced building blocks that allow the server 100 to manage tracking and locating of nodes in a robustly enriched contextual environment. In an embodiment, context-based management provides visibility to the system through data analysis for when and how associations should be expected as the nodes travel through the wireless node network. In other embodiments, it may provide the foundation for better understanding RF signal degradation, which can be caused by the operating environment, packaging, package content, and/or other packages related to an item and its ID node.

Security Manager

The security manager module, which may be implemented separately or as part of the association manager module in exemplary server control and management code 525, helps with associating two nodes in the wireless node network by managing aspects of secure pairing of the nodes. In one embodiment, security manager module provides the appropriate pairing credentials to allow a node to securely connect to another node. Thus, when a node desires to connect to another node, an embodiment requires appropriate pairing credentials be generated by the server, provided to the nodes, and observed within the nodes to allow for a successful connection or association of nodes.

In operation, a node (such as master node 110a) identifies the address of the node (such as ID node 120a) to whom it desires to connect. With this address, the node prepares a pairing request and sends the request to the server 110. The server 100 operates under the control of the security manager module of the association manager, and determines whether the requesting node should be connected or otherwise associated with the other node. If not, the server does not issue the requested security credentials. If so and in accordance with the desired association management paradigm set by the association manager of code 525, server provides the requested credentials necessary for a successful wireless pairing and the establishment of secure communications between the associated nodes.

Node Update Manager

The exemplary server control and management code 525 may include a node update manager module that provides updated programming information to nodes within the wireless node network and collects information from such nodes (e.g., shared data 545, sensor data 550). The node update module may be implemented separately or as part of the association manager module in exemplary server control and management code 525.

Providing an update to a node's programming may facilitate and enable distribution of node functions to save power and better manage the nodes as a system. For example, one embodiment may alter the functional responsibility of different nodes depending on the context or association situation by temporarily offloading responsibility for a particular function from one node to another node. Typically, the server directs other nodes to change functional responsibility. However, in some embodiments, a master node may direct other nodes to alter functional responsibility.

Sharing information between nodes and with server (e.g., via an exemplary node update manager) facilitates collecting information from a node and sharing information with other nodes as part of an association management function of server 100. For example, one embodiment may collect and share RF scan data (a type of shared data 545), information about a node's location (a type of location data 555), system information about date/time (another type of shared data 545), and sensor measurements collected from sensor nodes (a type of sensor data 550).

Location Manager

The exemplary server control and management code 525 may include a location manager module that helps determine and track node locations. In a general embodiment, the location of a node may be determined by the node itself (e.g., a master node's ability to determine its own location via location circuitry 475), by a node associated with that node (e.g., where a master node may determine the location of an ID node), by the server itself (e.g., using location information determined by one or more techniques implemented as part of code 525), and by a combined effort of a master node and the server.

In general, an exemplary ID node may be directly or indirectly dependent on a master node to determine its actual physical location. Embodiments may use one or more methodologies to determine node location. For example and as more specifically described below, possible methods for determining node location may relate to controlling an RF characteristic of a node (e.g., an RF output signal level and/or RF receiver sensitivity level), determining relative proximity, considering association information, considering location adjustments for context information and an RF environment, chaining triangulation, as well as hierarchical and adaptive methods that combine various location methodologies. Further information and examples of how an exemplary location manager module may determine a node's location in accordance with such exemplary techniques are provided in more detail below.

Additionally, those skilled in the art will appreciate that it may also be possible to determine what constitutes an actionable location versus actual location based upon contextual information about the item being tracked. For example, a larger item may require relatively less location accuracy than a small item such that operational decisions and status updates may be easier implemented with knowledge of context. If the size of the item is known, the location accuracy can be tuned accordingly. Thus, if a larger item is to be tracked, or if the system's contextual awareness of it is such that lower location accuracy can be used, a stronger signal and thus wider area of scanning may be employed, which may help in situations where RF interference or shielding is an issue.

Information Update Manager

The exemplary server control and management code 525 may include an information update manager module that provides information related to operations of the wireless node network and status of nodes. Such information may be provided in response to a request from a device outside the wireless node network (such as user access device 200). For example, someone shipping an item may inquire about the current status of the item via their laptop or smartphone (types of user access devices), which would connect to server 100 and request such information. In response, the information update manager module may service such a request by determining which node is associated with the item, gathering status information related to the item (e.g., location data, etc.), and provide the requested information in a form that is targeted, timely, and useful to the inquiring entity.

In another example, a user access device may connect to server 100 and request particular sensor data from a particular node. In response, information update manager may coordinate with node update manager, and provide the gathered sensor data 545 as requested to the user access device.

Node Filtering Manager

An embodiment of exemplary server control and management code 525 may optionally comprise a node filtering manager, which helps manage the traffic of nodes with a multi-level filtering mechanism. The filtering essentially sets up rules that limit potential associations and communications. An example of such a node filtering management may define different levels or modes of filtering for a master node (e.g., which ID nodes can be managed by a master node as a way of limiting the communication and management burdens on a master node).

In one example, a "local" mode may be defined where the ID node only communicates and is managed by the assigned master node at the location where the last wireless node contact back to server 100 and/or where third party data indicates the assigned master node and ID node are in physical and wireless proximity. Thus, for the "local" mode of traffic filtering, only the assigned master node communicates and processes information from a proximately close and assigned ID node.

Moving up to a less restrictive filtering mode, a "regional" mode of filtering may be defined where the ID node may communicate and be managed by any master node at the location last reported back to server 100 and/or where third party data indicates the ID node is located. Thus, for the "regional" mode of traffic filtering, any master node near the ID node may communicate and process information from that ID node. This may be useful, for example, when desiring to implement a limit on associations and pairings to within a particular facility.

At the least restrictive filtering mode, a "global" mode of filtering may be defined as essentially system-wide communication where the ID node may be allowed to communicate and be managed by any master node. In other words, the "global" mode of traffic filtering allows any ID node within the wireless node network to communicate information through a particular master node near the ID node may communicate and process information from that ID node.

Thus, with such exemplary filtering modes, an ID node in a certain condition (e.g., distress, adverse environmental conditions, adverse conditions of the node, etc.) may signal the need to bypass any filtering mechanism in place that helps manage communications and association by using the "Alert" Status Flag. In such an example, this would operate to override any filtering rules set at the Master Node level in order to allow an ID node to be "found" and connect to another node.

Thus, exemplary server 100 is operative, when executing code 525 and having access to the types of data described above, to manage the nodes, collect information from the nodes, store the collected information from the nodes, maintain or have access to context data related to the environment in which the nodes are operating, and provide information about the nodes (e.g., status, sensor information, etc.) to a requesting entity.

Node Communication & Association Examples

Figure 22B:
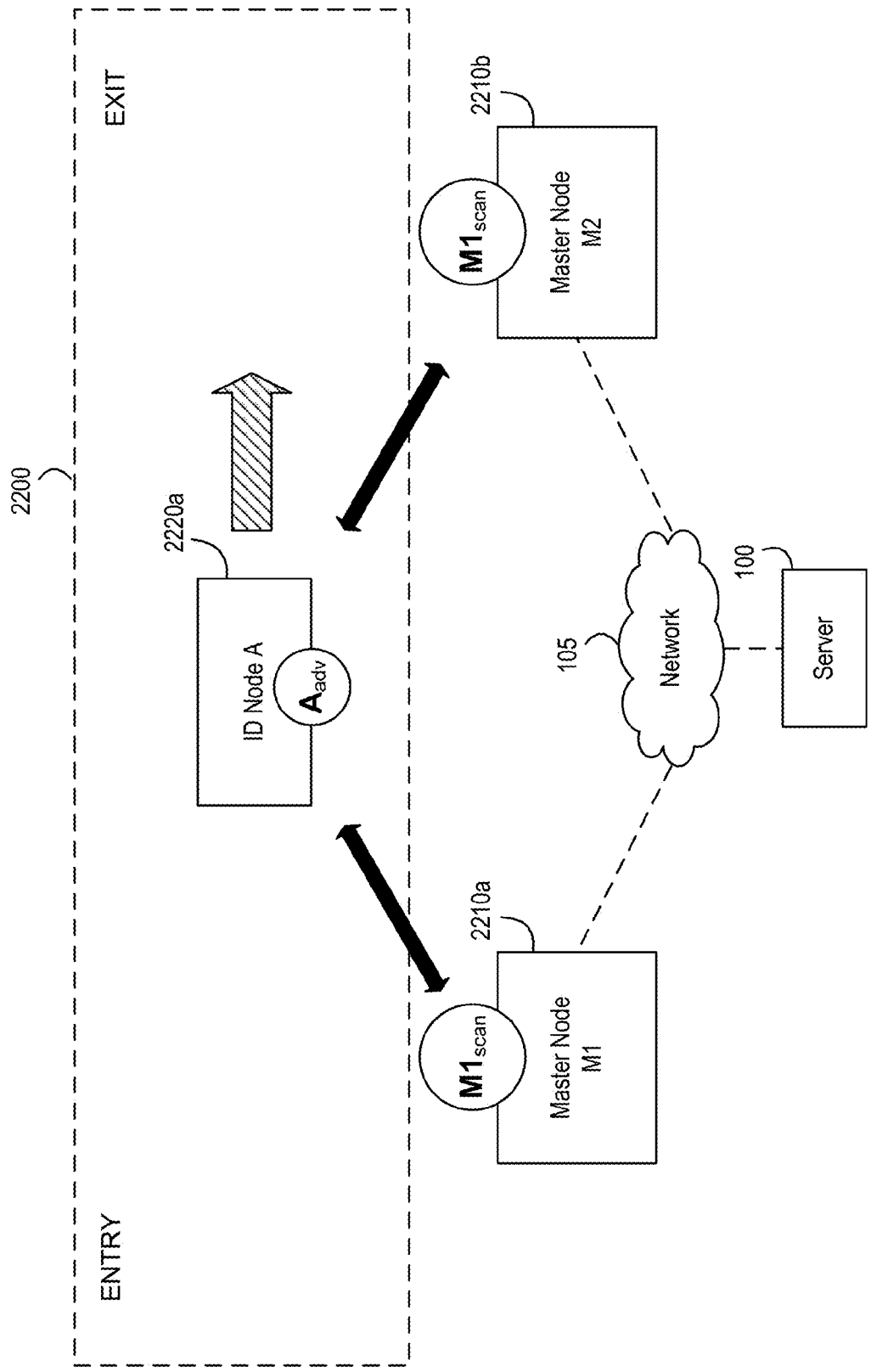
Figure 22C:
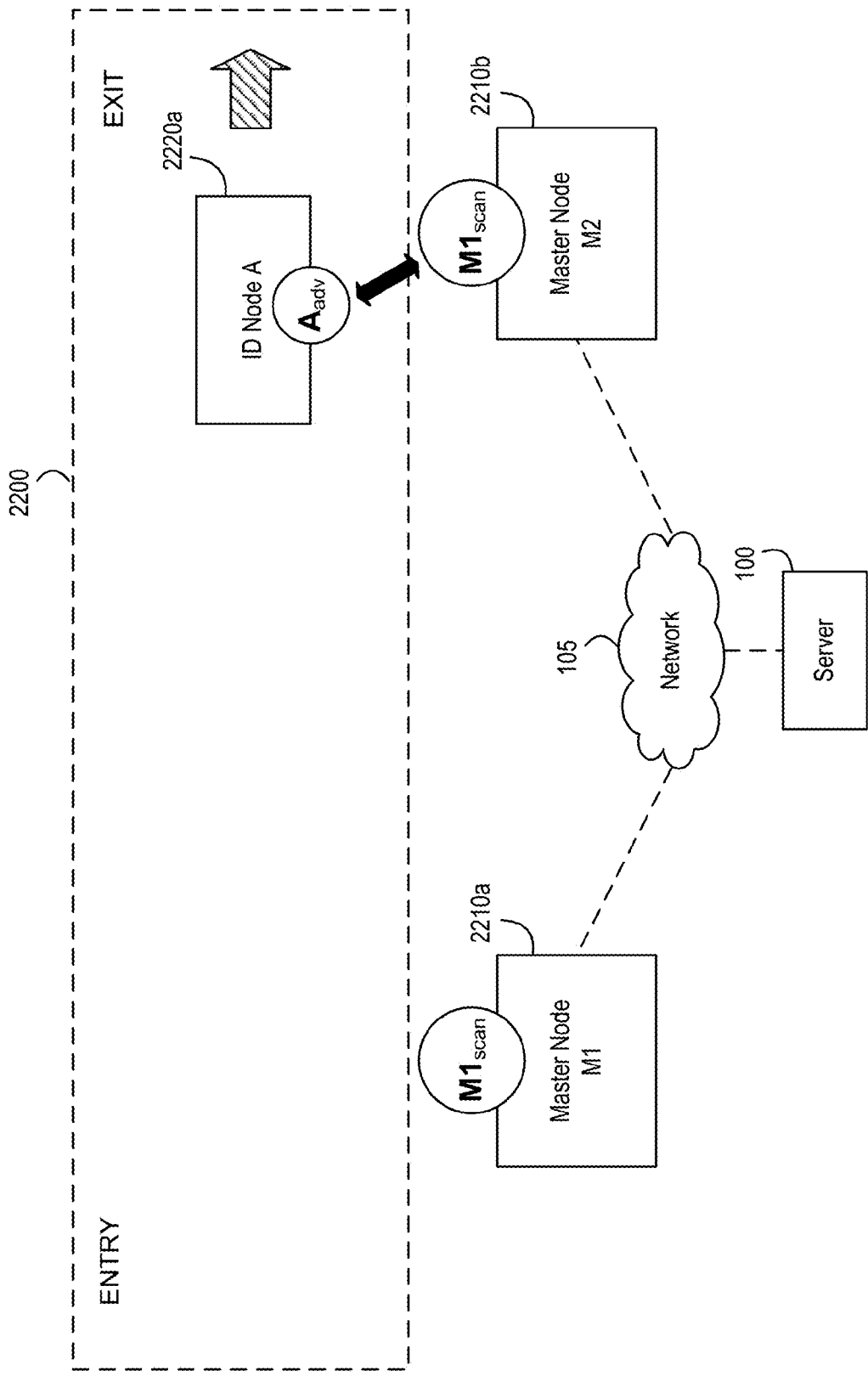

To better illustrate how exemplary management and communication principles may be implemented within an exemplary wireless node network, FIGS. 8-12 provide several examples of how exemplary components of the wireless node network may generally communicate (advertising & scanning), associate, and exchange information during different types of operations in various embodiments. FIGS. 22A-C also provide a more detailed application of such exemplary association and communication activities when an exemplary ID node moves along a transit path (e.g., through a corridor) and is tracked and managed by different master nodes and a server in an embodiment.

Node Advertising Cycle Example

As generally explained above, a node may have several different types of advertising states in which the node may be connectable with other nodes and may communicate with other nodes. And as a node moves within a wireless node network, the node's state of advertising and connection may change as the node disassociates with a previously connected node, associates with a new node, or finds itself not associated with other nodes. In some situations, a node may be fine and in normal operation not be connected or associated with another node. However, in other situations, a node may raise an issue with potentially being lost if it has not connected with any other node in a very long period of time. As such, a node may go through different types of advertising states in these different operational situations.

Generally, a node may be in a state where it is not connectable with other nodes for a certain period of time (also referred to as a non-connectable interval). But later, in another state, the node may want to be connected and advertises as such for a defined connectable period (also referred to as a connectable interval). As the node advertises to be connected, the node may expect to be connected at some point. In other words, there may be a selectable time period within which a node expects to be connected to another node. However, if the node is not connected to another node within that period of time (referred to as an Alert Interval), the node may need to take specific or urgent action depending upon the circumstances. For example, if a node has not been connected to another node for 30 minutes (e.g., an example alert interval), the node may change operation internally to look "harder" for other nodes with which to connect. More specifically, the node may change its status flag from an Alert Level 0 (no issue, operating normal) to Alert Level 2 in order to request that any available master node acknowledge receipt of the advertisement packet broadcasted by the node seeking a connection.

Figure 8:
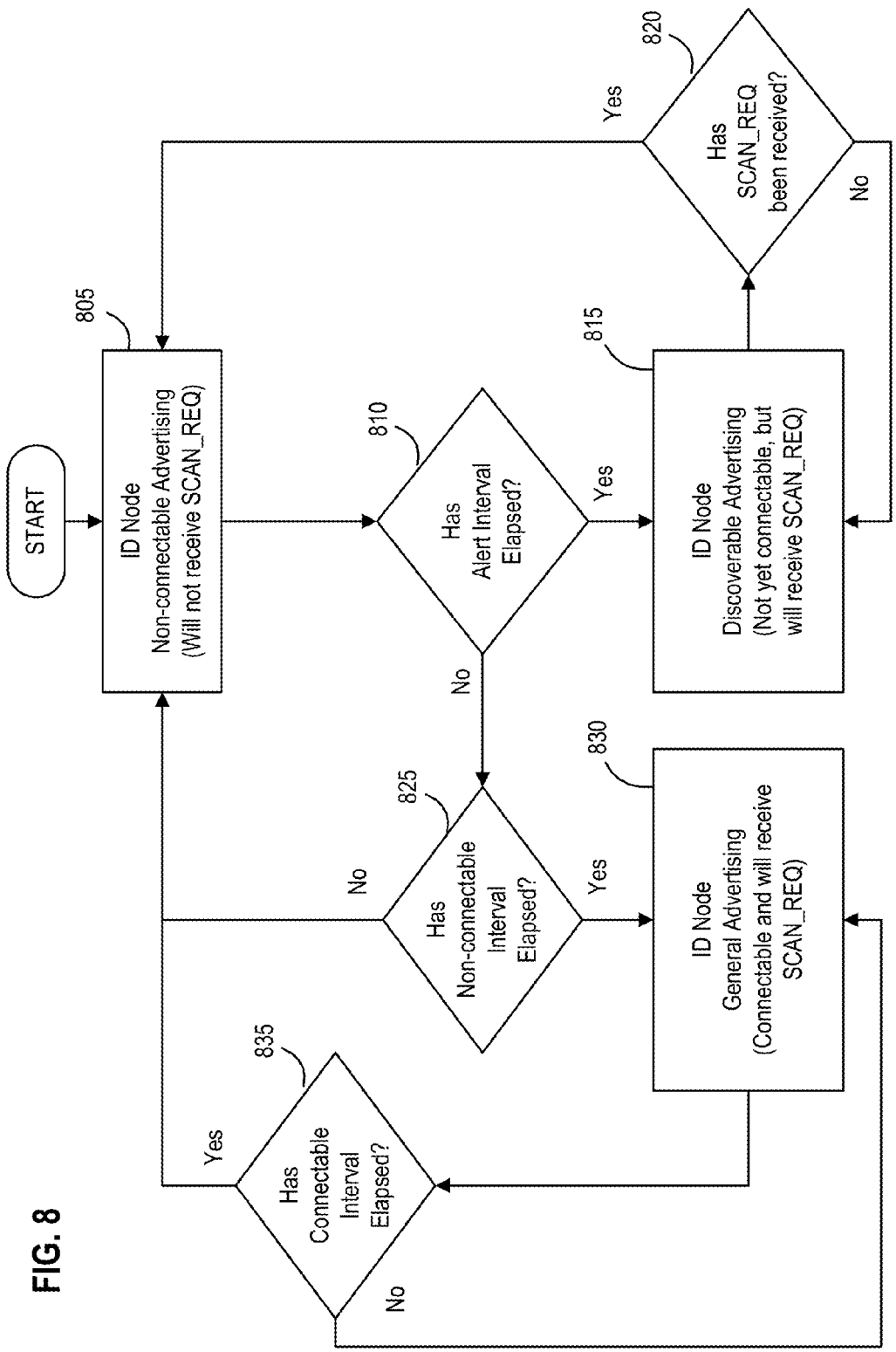
FIG. 8 is a state diagram illustrating exemplary states and transitions between the states as part of operations by an exemplary node in a wireless node network in accordance with an embodiment of the invention.

FIG. 8 is a diagram illustrating exemplary advertising states (or information exchange and node connectability states) and factors involved in transitions between the states by an exemplary ID node in a wireless node network in accordance with an embodiment of the invention. Referring now to FIG. 8, three exemplary states for a node are illustrated as part of an exemplary advertising cycle for the node—namely, an ID Node Non-Connectable Advertising state 805, an ID Node Discoverable Advertising state 815, and an ID Node General Advertising state 830. Transitions between these states will depend on factors related to expirations of the types of intervals described above. In an embodiment, the duration of each of these intervals will depend upon the system implementation and the contextual environment within which the ID node is operating. Such time intervals may, for example, be set by server 100 as part of data (e.g., profile data, association data, context data) provided to the node when updating the node and managing operations of the node.

Referring to the example illustrated in FIG. 8, an exemplary ID node may have an alert interval set at, for example, 30 minutes, and be in ID Node Non-Connectable Advertising state 805 with a non-connectable interval set at 5 minutes. In state 805, the ID node may broadcast or advertise, but is not connectable and will not receive a SCAN_REQ message (a type of request for more information sent to the advertising node from another node). Thus, the ID node in state 805 in this example may advertise in a non-connectable manner for at least 5 minutes but expects to be connected within 30 minutes.

If the alert interval has not yet elapsed (factor 810) and the non-connectable interval is still running (factor 825), the ID node simply stays in state 805. However, if the alert interval has not elapsed (factor 810) and the non-connectable interval elapses (factor 825), the ID node will enter a mode where it wants to try to connect to another node for a period of time (e.g., a 1 minute connectable interval) and will move to the ID Node General Advertising state 830 in the exemplary advertising cycle of FIG. 8. In state 830, as long as the connectable interval is running, the ID node will stay in this state where it is connectable to another node and will receive SCAN_REQ types of requests from other nodes in response to the advertising packets the ID node is broadcasting. However, when the connectable interval (e.g., the 1 min period) elapses or expires (factor 835), the ID node returns back to the Non-connectable Advertising state 805 for either the next time the non-connectable interval elapses (and the ID node again tries to connect in state 830) or the alert interval finally elapses (and the ID node finds itself in a situation where it has not connected to another node despite its efforts to connect in state 830).

When the alert interval finally elapses (factor 810), the ID node moves to the ID Node Discoverable Advertising state 815. Here, the ID node is not yet connectable but will receive a SCAN_REQ type of request from other nodes in response to advertising packets the ID node is broadcasting. In this state 815, the exemplary ID node may alter its status flag to indicate and reflect that its alert interval has expired and that the node is now no longer in normal operation. In other words, the ID node may change the status flag to a type of alert status being broadcasted to indicate the ID node urgently needs to connect with another node. For example, the status flag of the advertising packet broadcast by the ID node may be changed to one of the higher Alert Levels depending on whether the node needs to upload data (e.g., Alert Level 3 status) or synchronize timer or other data with another node (e.g., Synchronize status). With this change in status flag, and the ID node in state 815 broadcasting, the ID node awaits to receive a request from another node that has received the broadcast and requested more information via a SCAN_REQ message (factor 820) sent to the ID node from that other node. Once a SCAN_REQ message has been received by the ID node (factor 820), the ID node that went into the alert mode because it had not connected with another node within the alert interval can connect with that other node, upload or share data as needed, and then shift back to state 805 and restart the alert interval and non-connectable intervals.

Master Node to ID Node Association Example

Advertising (broadcasting) and scanning (listening) are ways nodes may communicate during association operations. FIGS. 9-12 provide examples of how network elements of a wireless node network (e.g., ID nodes, master nodes, and a server) may communicate and operate when connecting and associating as part of several exemplary wireless node network operations.

Figure 9:
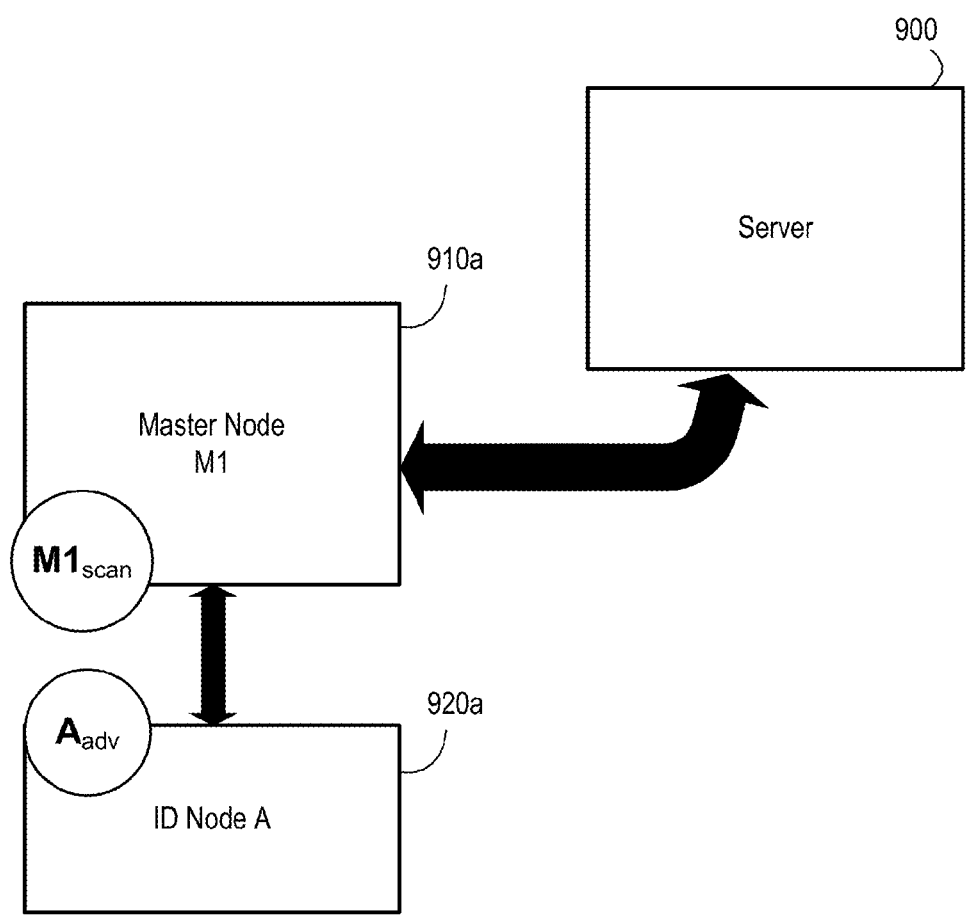
FIG. 9 is a diagram illustrating exemplary components of a wireless node network during an exemplary master-to-ID node association in accordance with an embodiment of the invention.

FIG. 9 is a diagram illustrating exemplary components of a wireless node network during an exemplary master-to-ID node association in accordance with an embodiment. Referring now to FIG. 9, exemplary master node M1 910a is illustrated within communication range of exemplary ID node A 920a. Master node M1 910a also has a communication path back to server 900. As shown, master node M1 910a is in a scanning or listening mode (e.g., indicated by the "M1$_{scan}$" label) while ID node A 920a is in an advertising or broadcasting mode (e.g., indicated by the "A$_{adv}$" label). In this example, M1 master node 910a has captured the address of ID node A 920a through A's advertising of at least one advertising data packet, and has reported it to the server 900. In this manner, the capturing and reporting operations effectively create a "passive" association between the nodes and proximity-based custodial control. Such an association may be recorded in the server, such as server 900, as part of association data, such as association data 540.

In another embodiment, passive association between a master node and ID node may be extended to an "active" association or connection. For example, with reference to the embodiment shown in FIG. 9, server 900 may instruct master node M1 910a to associate, connect, or otherwise pair with ID node A 920a, and forwards the required security information (e.g., PIN credentials, security certificates, keys) to master node M1 910a. Depending on the advertising state of ID node A 920a, ID node A 910a may only be visible (discoverable) but not connectable. In such a situation, the master node M1 910a must wait until ID node A 920a is in a connectable state (e.g., the ID Node General Advertising state) and can be paired. As discussed above with reference to FIG. 8, each ID node has a certain time window during each time period where it can be paired or connected.

In this example, when the ID node A 920a is successfully paired with master node M1 910a, ID node A 920a may no longer advertise its address. By default, only an unassociated device will advertise its address. A paired or associated node will only advertise its address if instructed to do so.

ID Node to ID Node Association Example

Figure 10:
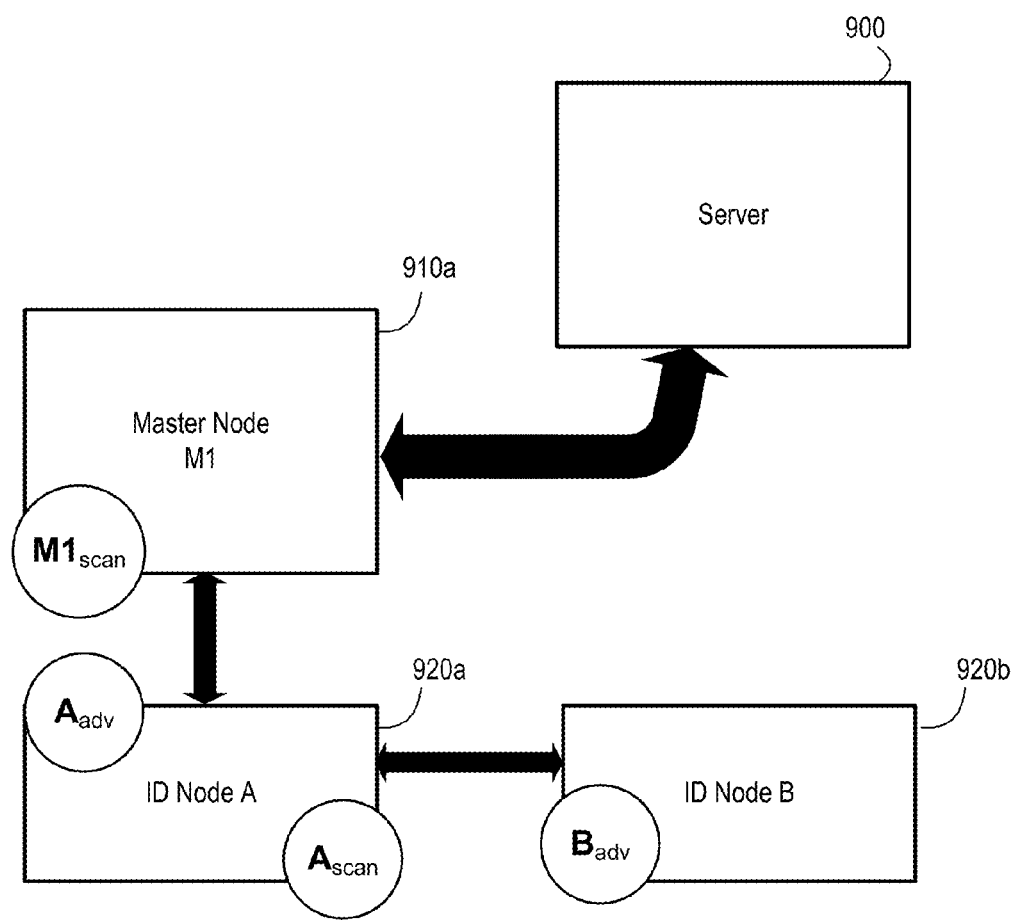
FIG. 10 is a diagram illustrating exemplary components of a wireless node network during an exemplary ID-to-ID node association in accordance with an embodiment of the invention.

In various embodiments, an ID node may associate with or connect to other ID nodes. FIG. 10 is a diagram illustrating exemplary components of a wireless node network during an exemplary ID-to-ID node association in accordance with an embodiment of the invention. Referring now to FIG. 10, exemplary master node M1 910a, ID node A 920a, and server 900 are similarly disposed as shown in FIG. 9, but with the addition of ID node B 920b, which is within communication range of ID node A 920a. In this example, ID node A 920a is running in query (scan) mode (e.g., A$_{scan}$) listening for ID node B 920b. When ID node A 910a detects ID node B 920b advertising (e.g., B$_{adv}$) with one or more advertising data packets as part of an advertised message from ID node B 920b, ID node A 920a identifies a status flag from the message indicating ID node B 920b has, for example, data (e.g., sensor data 350) for upload. As a result, ID node A 920a logs the scan result (e.g., as a type of association data 340) and, when next connected to master node M1 910a, ID node A 920a uploads the captured scan log information to the server 900. In this manner, the ID node scanning, capturing, and reporting operations effectively create a "passive" association between the different ID nodes. Such a passive association may be recorded in the server 900 as part of association data 540.

In another embodiment, passive association between two ID nodes may be extended to an "active" association or connection. For example, with reference to the embodiment shown in FIG. 10, based upon the captured status flag and uploaded information about ID node B 920b under that mode, the server 900 may issue a request to ID node A 920a through master node M1 910a to actively connect or pair with ID node B 920b for the purpose of downloading information from ID node B 920b. In one example, security credentials that authorize the active connection between ID node A 920a and ID node B 920b are downloaded to ID node A 920a from master node M1 910a, which received them from server 900. In another example, the requisite security credentials may have been pre-staged at ID node A 920a. And rather than rely upon an ID node to ID node connection, master node M1 may have connected directly with ID node B 920b if M1 was within communication range of ID node B 920b.

Information Query ID Node to Master Node Example

Figure 11:
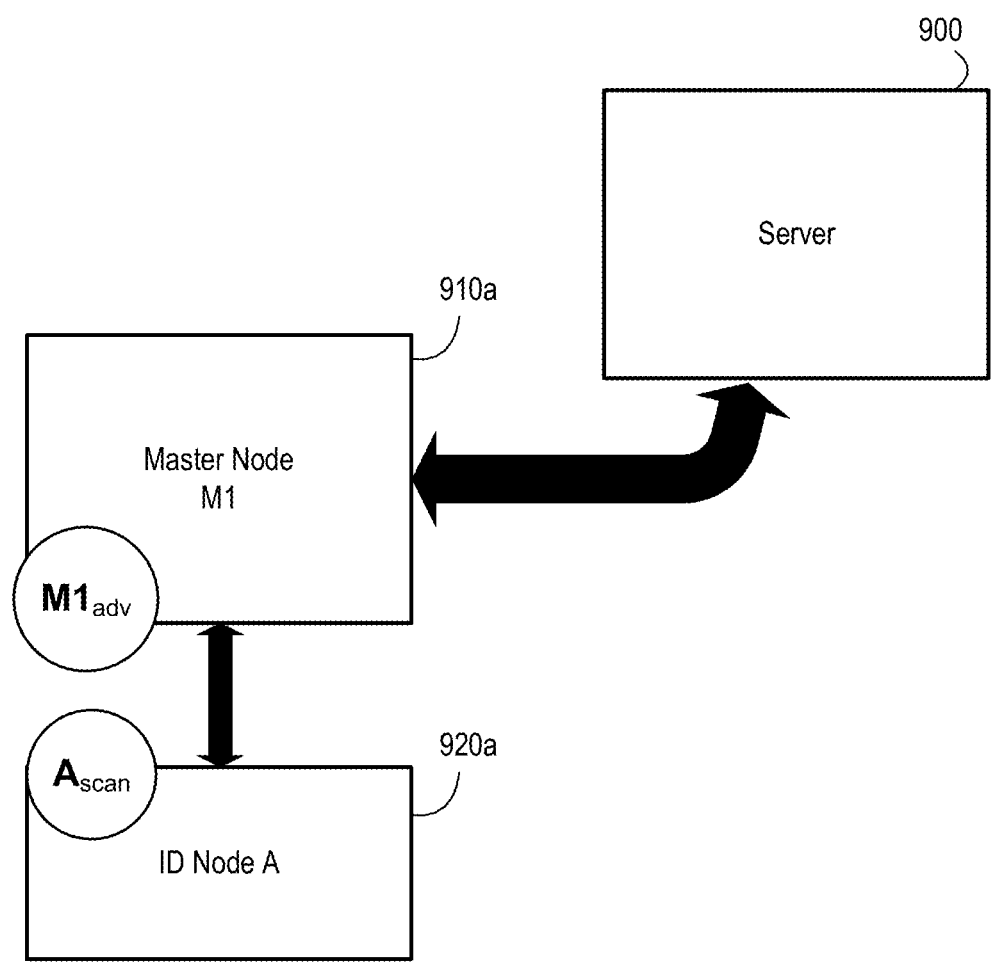
FIG. 11 is a diagram illustrating exemplary components of a wireless node network during an exemplary ID-to-master node query in accordance with an embodiment of the invention.

An exemplary ID Node may also issue queries to other nodes, both master nodes and ID nodes. FIG. 11 is a diagram illustrating exemplary components of a wireless node network during an exemplary ID-to-master node query in accordance with an embodiment of the invention. Referring now to FIG. 11, a similar group of nodes as shown in FIG. 9 appears, except that exemplary master node M1 910a is in an advertising or broadcasting mode (e.g., M1$_{adv}$) while ID node A 920a is in a scanning mode (e.g., A$_{scan}$). In this configuration, ID node A 920a may query master node M1 910a for information. In one embodiment, the query may be initiated through the ID node setting its status flag. The requested information may be information to be shared, such as a current time, location, or environmental information held by the master node M1 910a.

In a passive association example, ID node A 920a in A$_{scan}$ mode may have captured the address of master node M1 910a. However, since an ID node cannot directly connect to the server 900 to request pairing security credentials (e.g., security pin information that authorizes an active connection between ID node A 920a and master node M1 910a), a passive association and corresponding pairing will have been initiated from the master node. In another example, it may be possible for ID node A 920a to have the pairing credentials stored as security data 335 from a previous connection. This would allow ID node A 920a then to initiate the active association with master node M1 910a after a passive association.

Alert Level Advertising Example

Figure 12:
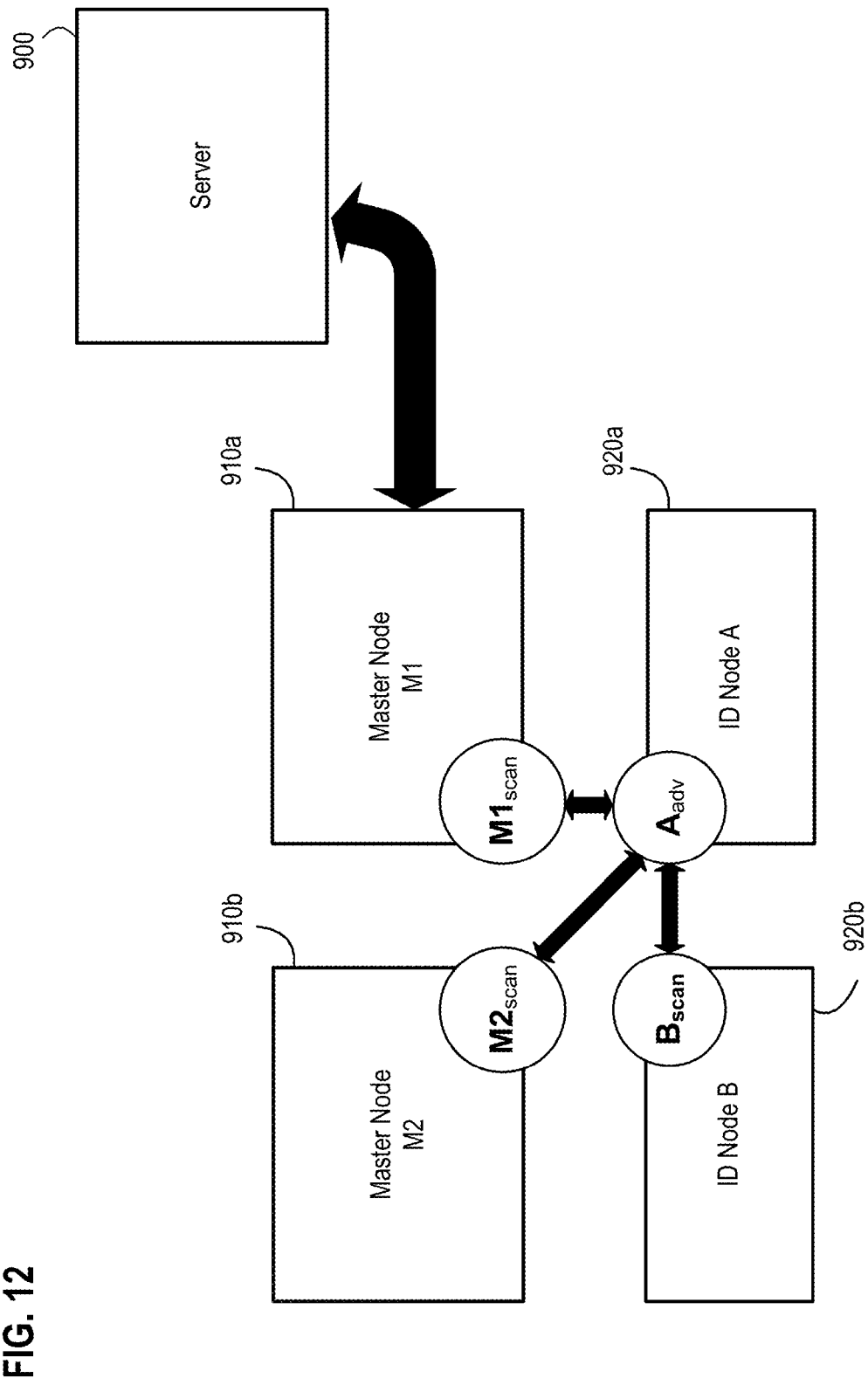
FIG. 12 is a diagram illustrating exemplary components of a wireless node network during an exemplary alert advertising mode in accordance with an embodiment of the invention.

As previously noted, a node may enter an alert stage or level in one or more embodiments. For example, if a node has not received an acknowledgement from a master node for an advertising packet within a set period (e.g., an Alert Interval as described in some embodiments), the node will enter a particular alert stage for more specialized advertising so that it may be "found" or pass along information. FIG. 12 is a diagram illustrating exemplary components of a wireless node network during an exemplary alert advertising mode in accordance with an embodiment of the invention. Referring now to FIG. 12, a similar group of nodes as shown in FIG. 9 appears, with the addition of another master node (master node M2 910b) and another ID node (ID node B 920b). Exemplary ID node A 920a is in an advertising or broadcasting mode (e.g., A$_{adv}$) while nodes M1, M2, and B are each in scanning mode (e.g., M1$_{scan}$, M2$_{scan}$, and B$_{scan}$). In this example and configuration as shown in FIG. 12, the status flag in an advertising message from ID node A 920a has been set to a particular alert level (e.g., Alert Level 2) in the header of the message, requesting any nearby master node to acknowledge it. In one example, this mode may be entered if ID node A 920a has not connected with another node for a set period or time. In another example, ID node A 920a may enter this specialized advertising mode upon received instructions (e.g., from server 900 or another nearby node) or a triggered condition (other than time), such as when a sensor input (such as light) is detected or otherwise registered and the node issues continuous updates of its address as a security feature. The ID node A 920a set at this alert level and in this specialized advertising mode is thus set in an active pairing mode, waiting for pairing credentials.

From a passive association perspective, any node in scanning mode can passively associate with such an advertising node (e.g., ID node A 920a in this alert mode). Thus, in an embodiment, the Alert Level 2 status flag in the advertising header broadcast by ID node A 920a indicates that urgent and active intervention is requested, rather than merely passively associate without an active connection.

From an active association perspective, any node that uploads the special advertising header of ID node A 920a may be forwarded the security credentials from the server 900. This would allow for the node receiving such credentials to actively associate or pair with ID node A 920a.

While FIG. 8 provides examples of how a node may advertise, and FIGS. 9-12 provide examples of how different exemplary devices (e.g., ID nodes, master nodes, and a server) may advertise and associate in different ways, FIGS. 22A-C provide a progressive set of illustrations that expand upon how associating and disassociating may be applied within an exemplary wireless node network. More specifically, FIGS. 22A-C show how associations and disassociations may occur when an exemplary ID node is tracked and managed by a server and different master nodes as the ID node moves through an exemplary transit path in accordance with an exemplary embodiment of the invention.

Referring now to FIG. 22A, a structure 2200 is shown having an entry and exit point. In one example, the structure 2200 may be a corridor or another part of a building or facility. In another example, structure 2200 may be a conveyor system that transports an item and its ID node from the entry point to the exit point. Master node M1 2210a is located near the entry point of structure 2200 while master node M2 2210b is located near the exit point. Those skilled in the art will appreciate that other master nodes may be disposed at additional points in structure 2200, but are not shown for sake of convenience and to simplify the association hand-off explanation that follows. Server 100 is operatively connected to each of master node M1 2210a and master node M2 2210b via network 105.

In one embodiment, server 100 has access to context data 560 related to the structure 2200, such as layout data 585 on dimensions and materials making up structure 2200. Context data 560 may include historic data 575 on how an ID node has operated and successfully been tracked as it traverses structure 2200 from the entry point to the exist point. For example, server 100 may have context data indicating structure 2200 is a conveyor that can transport an item and its ID node from the entry point to the exit point over a distance of 800 feet. The context data may further indicate typical items are moved at a certain speed on the conveyor of structure 2200 and a nominal time from the entry point to the exit point may be about 5 minutes. Thus, the server 100 has access to context data about the environment within with an ID node is operating and may leverage this to better and more accurately manage the ID node.

In FIG. 22A, ID node A 2220a is shown entering the structure 2200 at the entry point. Here, ID node A 2220a may be advertising in hopes of connecting with a master node as it enters structure 2200 with, for example, a non-connectable interval of 10 seconds with a connectable interval of 5 seconds. In this example, the server 100 knows that ID node A 2220a is located near the entry point and anticipates that ID node A 2220a should be coming near to master node M1 2210a at the entry point. Thus, server 100 may set the connectable and non-connectable intervals accordingly so as to provide a sufficient opportunity for ID node A 2220a to connect to the next master node along the predicted path of the ID node and in accordance with the speed of travel.

Additionally, server 100 may set the alert interval to 1 minute in this context. Here, if ID node A 2220a is not connected to another node within 1 minute, ID node A 2220a may broadcast or advertise with a message having a changed status flag that indicates an alert status so that ID node A 2220a can connect to a broader range of other nodes that see it is urgent for ID node A 2220a to connect and, essentially, be found. Depending on the context (e.g., the type of conveyor, the speed of the conveyor, the density of nodes near the entry point, etc.), those skilled in the art will appreciate that the server 100 can adjust the advertising cycle intervals to better accommodate the ID node's current environment.

When master node M1 2210a is scanning (listening), it may initially detect an advertising packet from ID node A 2220a during node A's non-connectable interval. But when ID node A 2220a changes advertising states and broadcasts as a connectable node in the general advertising state (i.e., during the connectable interval), master node M1 2210a may respond with a SCAN_REQ that acknowledge receipt of the broadcasted message and asks for further information from ID node A 2220a. Master node M1 2210a receives the requested information from ID node A 2220a, and then communicates with the server 100 to notify the server of its passive association with ID node A 2220a. Server 100 determines if active association is desired, and may authorize the active association between master node M1 2210a and ID node A 2220a by sending security credentials to master node M1 2210a, which allow the nodes to securely connect and share information. And master node M1 2210a may determine the location of ID node A 2220a (or server 100 may do so by directing master node M1 and/or ID node A), and provide the location of ID node A 2220a to server 100. Thus, server 100 is able to manage and track the location of ID node A 2220a as it enters structure 2220 via at least association.

In FIG. 22B, ID node A 2220a has traversed down part of the transit path through structure 2200 while remaining associated with master node M1 2210a. However, at some point master node M1 2210a and ID node A 2220a are disassociated at the direction of server 100 (or when they can no longer communicate). In one example where ID node A 2220a is on the conveyor within structure 2200, server 100 may instruct ID node A 2220a to go to a low power mode for a particular period of time in order to, for example, conserve ID node power. In another example, the low power mode may also provide better location accuracy. As the server 100 has access to the context data, the server 100 may know that ID node A 2220a was associated with master node M1 2210a near the entry point at a given time, and determine that ID node A 2220a will not be near the exit point until the end of the particular period of time. With the ID node A 2220a programmed this way, once the particular period elapses, the ID node A 2220a should be near the exit point and may again be placed into a normal operation mode so that it can seek to connect with master node M2 2210b.

Similar to the association process discussed with respect to ID node A and master node M1, ID node A 2220a and master node M2 2210b may be associated as ID node A 2220a approaches master node M2 2210b near the exit point. Once connected, the node locations and association data are updated on the server 100. And as ID node A 2220a continues to move through structure 2200, ID node A 2200a may arrive at the exit point as shown in FIG. 22C, where the node locations and association data are updated once again on the server 100.

Those skilled in the art will appreciate how such principles may be applied to further movements of an ID node as it is handed off (e.g., via active/passive associations and disassociations) between other master nodes and keeping track of these associations and node locations on the server 100. Additionally, as server 100 tracks and monitors associations, disassociations, and contextual environmental operations, server 100 essentially learns how to better use context information better track nodes, manage power used by ID nodes, and enhance accuracy for locations.

Those skilled in the art will also appreciate the general tradeoff with a level of RF power level and accuracy of location. If a node's RF power level is set high, it may advertise and connect with other nodes a longer distance away. But at such a high power level setting, the ability for the system to discriminate between and locate different nodes may be a challenge.

Association Management within a Wireless Node Network

As explained above in general, management of nodes may rely upon associations created and tracked between nodes. In some embodiments, the association relied upon may be an active association where the server expressly authorizes an active connection between nodes operating within the wireless node network. In other embodiments, the association relied upon may be a passive association where the master node (a type of managing node) is associated with the other node, but not actively connected to the other node. By virtue of the passive association, the server may be able to keep track of and manage the other node without requiring an active association. Thus, those skilled in the art will appreciate that in still other embodiments, associations relied upon by the server for managing a wireless node network may include both active and passive associations and may be generally authenticated or, more specially, authorize a secure connection that has a degree of protection for the connection and communications using that connection.

Those skilled in the art will also appreciate that the described embodiments of association management of nodes within a wireless node network fundamentally effect an improvement in the management technology of how nodes may be managed, tracked, and monitored within the network. Such an enhanced ability to manage nodes by their respective associations (e.g., active, passive) improves the overall operation of a wireless node network and applications that use such wireless node networks (e.g., technical fields such as logistics, shipping management, inventory management, and the like). In other words, the exemplary embodiments described herein with interrelated operations between nodes that desire to associate, and a server that keeps track of and may authorize such associations, provide a type of specially-adapted system that enhances and improves operations in technical fields such as logistics, shipping management, inventory management, and the like.

Figure 23:
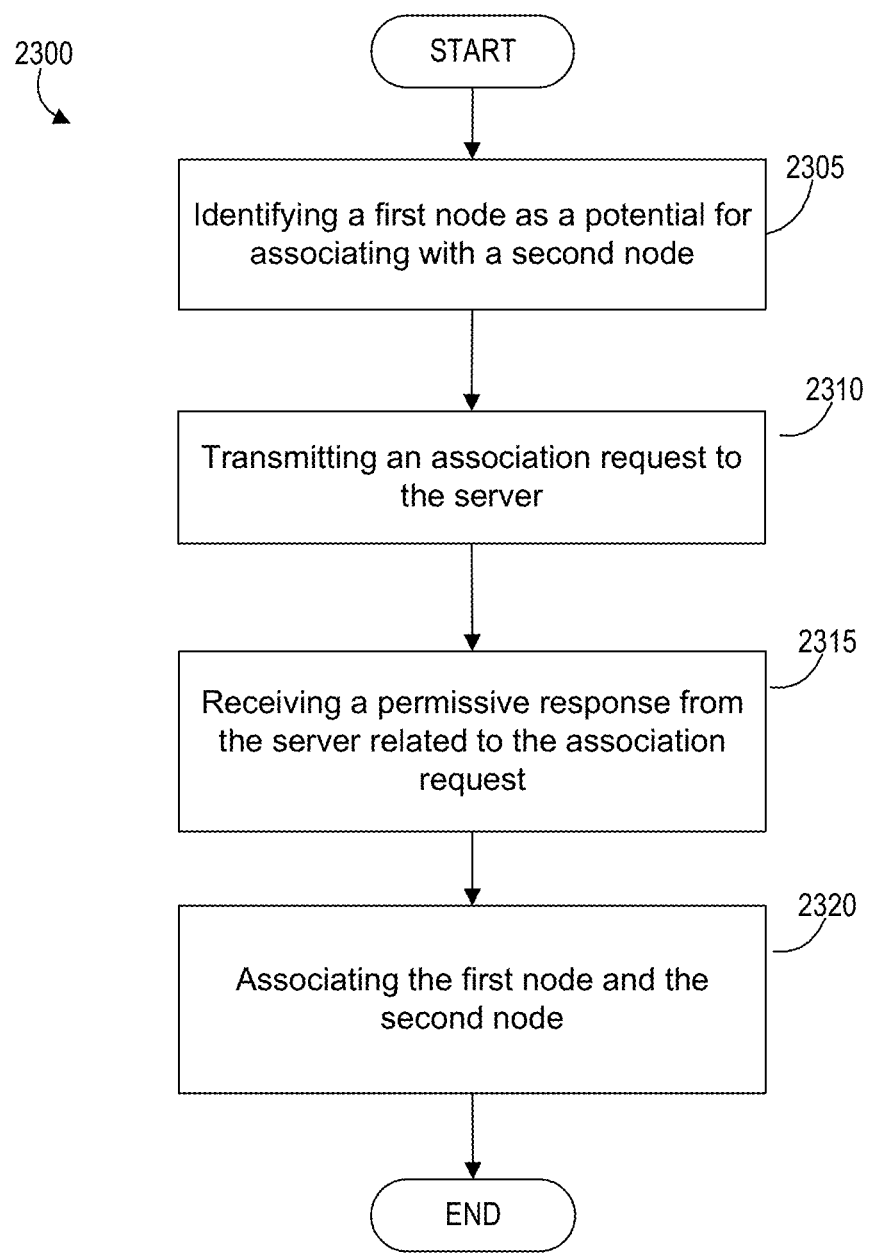
FIG. 23 is a flow diagram illustrating an example method for association management of a wireless node network in accordance with an embodiment of the invention.
Figure 24:
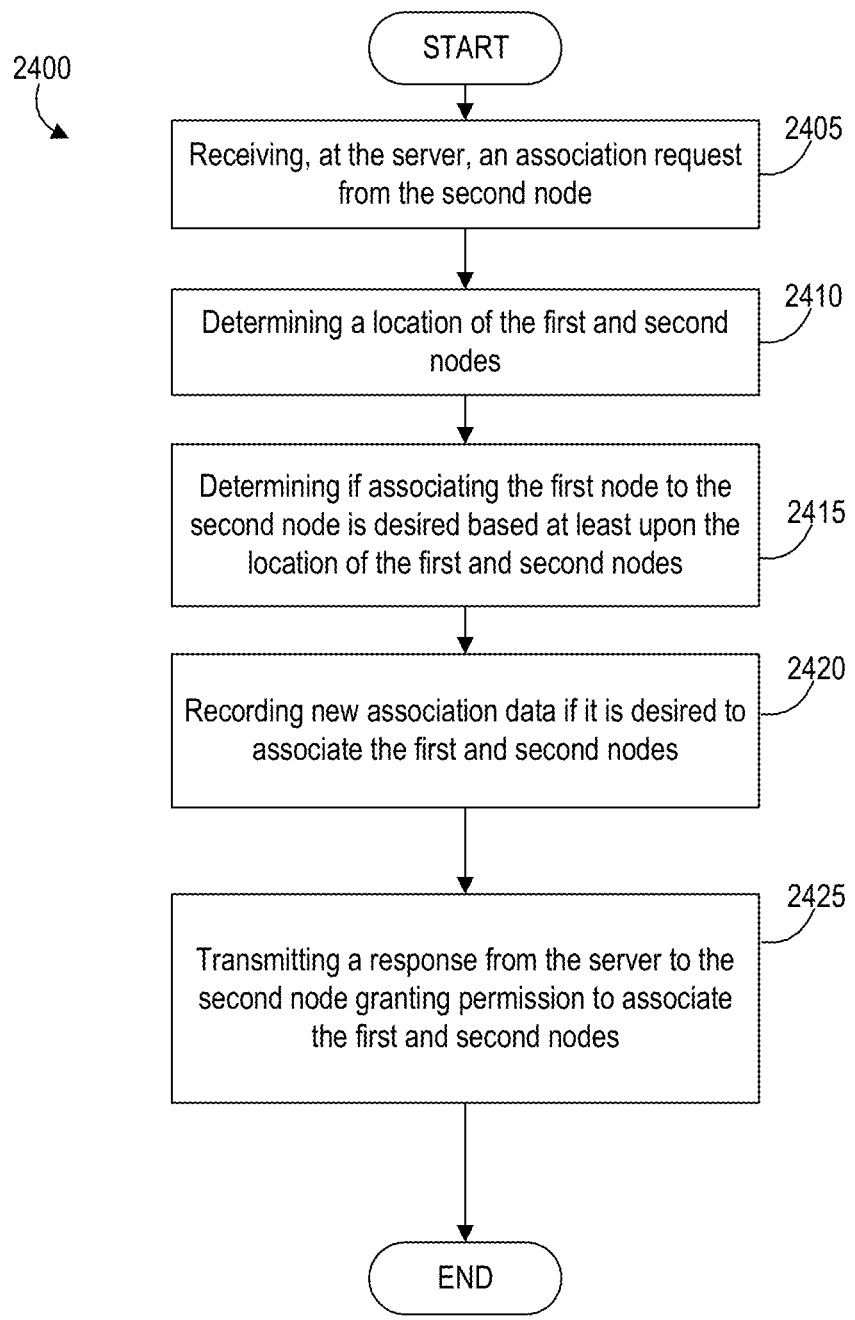
FIG. 24 is a flow diagram illustrating another example method for association management of a wireless node network in accordance with an embodiment of the invention.

In more detail, FIGS. 23-25 provide flow diagrams of exemplary methods for association management of a wireless node network having at least a plurality of nodes and a server in accordance with different embodiments of the present invention involving active and passive association examples. Those skilled in the art will appreciate that each of these exemplary methods for association management of a wireless node network may be implemented by instructions stored on a non-transitory computer-readable medium, which when executed perform the steps of the respective methods described below (e.g., methods 2300, 2400, and 2500) and the described variations of those methods.

Referring now to FIG. 23, method 2300 begins by identifying a first node as a potential for actively associating with a second node at step 2305. In one example, identifying the nodes for association may involve reviewing a message sent by the first node to determine status information related to the first node, and analyzing the status information to determine whether the first node should be associated with the second node. In a further example, the status information may comprise one of a plurality of different status levels indicating whether the first node is requesting a connection to the second node when at that particular status level.

Next, an association request is transmitted to the server in step 2310. In one example, the association request may identify the first node and second node to be associated and may request transmission of one or more appropriate security credentials (e.g., PIN credentials, security certificates, keys, and the like) that may be used by the nodes to enable the first and second node to securely connect and share data as part of associating. An embodiment may request only one credential as an authorization credential from the server. Other embodiments may use two credentials where one may be later uses as a credential with which to reply to challenges. For example, if an ID node is challenged, the ID node may send a reply authorization credential so that the master node can confirm the response and supply the ID node with the appropriate security credential for the authorized association. In some cases, an ID node may have been supplied with such a reply authorization credential (also generally referred to as a key) by the server.

At step 2315, the second node receives a permissive response from the server related to the association request. In an example, the permissive response may include receiving a first authorization credential and a second authorization credential from the server (which may be stored on the nodes). As such, the first authorization credential and the second authorization credential may be created by the server as a type of security data, and may be provided to authorize connecting the first node and the second node and securely sharing information between the first node and the second node.

With this authorization from the server, the first node and second node may be associated at step 2320. In one example, the method 2300 may associate the nodes by establishing an authorized connection from the second node to the first node based upon the authorization credential. And the method 2300 may securely provide shared data between the first node and the second node according to a profile established by the server after the first and second nodes are associated.

In an embodiment, the method 2300 may also comprise having the second node gaining responsibility for a node task after the second node is associated with the first node when responsibility for the task was previously with the first node. For example, when the second node is powered by an external power source and the first node is powered by a battery, this may advantageously shift the responsibility to a node that is better suited to perform the node task (e.g., has more power available or has a power source that does not need recharging or replacing).

FIG. 24 is a flow diagram illustrating another example method for association management of a wireless node network in accordance with an embodiment of the invention from the perspective of the server. Referring now to FIG. 24, method 2400 begins with the server receiving an association request sent from a second of the nodes at step 2405. The association request asks for permission to associate a first of the nodes to the second node.

At step 2410, the server determines a location (actual or relative) of the first node and second node. In one embodiment, the server may receive location data for the second node. For example, when the second node is a master node, the location data for the second node may be GPS coordinates for the current location of the master node, which provides this to the server. And in an embodiment, the server may determine a location of the first node using at least one of a plurality of location methods available to the server for locating the first node, such as those discussed in detail above (or a combination of such methods so that a more refined location of the first node is determined).

At step 2415, the server determines if associating the first node to the second node is desired based at least upon the location of the first node and the location of the second node. In one embodiment, it may be determined if associating is desired by determining if associating the first node to the second node is anticipated based upon context data. In another embodiment, it may be determined if associating is desired by identifying a current mode of filtering that limits potential nodes to be associated, and granting the permission to associate the first node to the second node only if the current mode of filtering allows the first node to be associated with the second node. For example, this may involve granting the permission only if the current mode of filtering defines that the second node is within a locational range of the first node consistent with the current mode of filtering. This may be defined by a particular filtering mode, such as a local, regional, or global filtering mode that operates to restrict nodes that may associate with other nodes. As such, the method may alter the current mode of filtering to another mode of filtering that allows the first node to be associated with the second node as a sort of override of the current filtering mode (e.g., depending upon an alert status of the first node).

At step 2420, the server records new association data if it is desired to associate the first node with the second node at step 2420. At step 2425, the server transmits a response to the second node granting the permission to associate the first node to the second node. In an embodiment, the server may first generate an authorization credential that authorizes connecting the first node and the second node and sharing information between the first node and the second node. This may be by looking up the credential information or by going through a process to create specific an authorization credential that allows the two nodes to actively pair and share data. With the authorization credential, the server may transmit them as the response.

In another example, the server may have pre-staged an authorization credential related to the second node and a third node if the server anticipates the second node will disassociate with the first node and later request to associate with the third node. For example, this may be done if the context indicates the second node (e.g., a master node) may be placed in a container and need to connect with the third node in the future when the second node may lose its connection to the server.

Method 2400 may also include the server receiving shared data from the second node. The shared data may originate from the first node or may have parts that originate from both the first and second nodes. For example, the second node may have received the permission to associate, and actively paired with the first node in a secure manner. The first node may have indicated it has data to upload (e.g., sensor data), and the second node may receive the data from the first node. Subsequent to that sharing, the second node may upload the shared sensor data from the first node by transmitting it to the server.

The method may further comprise instructing the second node to take over responsibility for a task previously performed by the first node after the second node is associated with the first node. For example, when the second node is powered by an external power source and the first node is powered by a battery, the responsibility for certain node performed tasks may be taken over by the node with a more robust power supply (e.g., the node powered by an external power source).

In more detail, the responsibility for certain tasks may be established, tracked and changed with a programmable profile. For example, in one embodiment, the server may establish a profile for how long the task responsibility would change. In some cases, the profile may define a period of time for how long a node having this profile would have responsibility for a certain task before it would revert back to a default node. In another example, a node (such as a master node) may have a default condition trigger (like a low power situation or when it cannot communicate with the server) that can override such a profile so that it does not take on more responsibilities under particular conditions.

Furthermore, an embodiment may have the master node deciding what other node may take on responsibility for certain node-related tasks. This may be helpful in situations where access to the server may be limited (e.g., an airborne environment). However, managing such a profile may be more easily accomplished in other embodiments with easier access to more types of context data on the server level.

In an embodiment that implements association management as a system, such an exemplary system for association management of a wireless node network may comprise a first node, a second node, and a server. The second node includes a node processing unit, a node volatile memory coupled to the node processing unit, a first communication interface coupled to the node processing unit, and a second communication interface coupled to the node processing unit. The first communication interface provides a short-range communication path between the first node and the second node and the second communication interface provides a longer range communication path between the second node and the server.

The server includes a server processing unit, a server volatile memory coupled to the processing unit, and a third communication interface that provides a longer range communication path between the server and the second communication interface of the second node.

The node volatile memory maintains at least a first program code section (e.g., master control and management code 425 or parts thereof) while the server volatile memory maintains at least a second program code section (e.g., server control and management code 525 or parts thereof).

When executing the first program code section resident in the node volatile memory, the node processing unit of the second node is operative to identify the first node as a potential for associating with the second node, transmit an association request over the second communication interface to the server, receive an association response (having at least authorization information generated by the server) over the second communication interface from the server, provide the authorization information to the first node, and associate the first node and the second node.

In one example, the node processing unit may be further operative to review status information related to the first node to determine whether the first node desires association with the second node. In another example, the node processing unit may be further operative to securely provide shared data between the first and second node after the first and second node are associated and in accordance with a sharing profile provided by the server. The sharing profile may define types of information to be securely shared between particular nodes.

When executing the second program code section resident in the server volatile memory, the server processing unit is operative to determine a location of the first node and second node, determine if associating the first node to the second node is desired based at least upon the location of the first node and the location of the second node, store new association data in the server volatile memory if it is desired to associate the first node with the second node, and transmit the authorization response to the second node granting the permission to associate the first node to the second node.

In one embodiment, the second node in the system may take over responsibility of a task previously handled by the first node after the second node is successfully associated with the first node. For example, when the second node is powered by an external power source and the first node is powered by a battery, the system may be more effectively and efficiently managed by reassigning a task (especially a task that involves a significant expenditure of power, a series of operations over a significant period of time, or both) to another node, such as the second node, which has more power available than the first node.

In another embodiment, the server processing unit may be further operative to set a current mode of filtering that limits potential nodes to be associated, and grant the permission to associate the first node to the second node only if the current mode of filtering allows the first node to be associated with the second node. In a further embodiment, the server processing unit may be further operative to alter (e.g., override) the current mode of filtering to a different mode of filtering. In this way, the server may adapt how nodes are managed and allow the first node to be associated with the second node if it is desired, such as then the first node is in an alert status level and urgently is requesting connection to a larger group of nodes than permitted under the current mode of filtering.

While the exemplary methods illustrated in FIGS. 23 and 24 focus on active associations, FIG. 25 is a flow diagram illustrating an example method for association management of a wireless node network having at least a plurality of nodes and a server in accordance with an embodiment, but from the perspective of a node that is to be passively associated with another node. Referring now to FIG. 25, method 2500 begins with a second of the nodes receiving a message broadcasted from a first of the nodes at step 2505. At step 2510, the second node captures an address of the first node from the message. At step 2515, the first node and the second node are associated by storing the captured address of the first node and an address of the second node as association data in a memory of the second node. At step 2520, the second node transmits the association data to the server.

At some point, the server may be updated by the second node with updated association data when the second node does not receive an additional message broadcast from the first node. For example, the second node and the first node may stay associated and securely connected for a period of time, but eventually the first node may move such that the connection is no longer viable or the first node may move closer to another node along the anticipated path it is traveling (e.g., an anticipated shipping path along a conveyor within a structure from an entry point of the structure but now closer to an exit point of the structure). As the first node travels on the conveyor, it may get closer to another node near the exit point and is better managed by an association with that other node near the exit point. Thus, the updated association data reflects that the first node is disassociated from the second node.

Method 2500 may further include having the second node determining a location of the first node, and updating the server with a current location of the second node and the determined location of the first node. Additionally, method 2500 may include receiving location information from the server that defines a refined location of the first node.

In an embodiment that implements passive association management as a managing node (e.g., a master node) in a wireless node having at least another node and a server, such an exemplary managing node comprises a processing unit, a first and second communication interface each coupled to the processing unit, a volatile memory coupled to the processing unit, and a memory storage coupled to the processing unit. The first communication interface provides a first communication path to the other node, can receive a message broadcast from the other node, and provide the message to the processing unit. The second communication interface providing a second communication path to the server.

The memory storage may maintain at least a node association manager module as program code to be executed by the processing unit. When the processing unit loads the module into volatile memory and executes instructions of the module, the processing unit is operative to receive the message from the first communication interface, capture an address of the another node from the message, store the captured address of the another node and an address of the managing node as part of association data in the memory storage, and transmit the association data to the server through the second communication interface.

In one example, the memory storage also maintains a location manager module and, when the processing unit also loads the location manager module into volatile memory and executes instructions of that module, the processing unit is operative to determine a location of the other node, determine a current location of the managing node (e.g., via GPS location signals), and update the server with the current location of the managing node and the determined location of the other node.

The managing node may be further operative to update the server with updated association data when the first communication interface does not receive an additional message broadcast from the other node. The updated association data may reflect that the other node is disassociated from the managing node.

Context Management within a Wireless Node Network

As explained above in general, management of nodes may rely upon the contextual environment of the nodes. As shown in FIG. 5, server 100 has access to a wide variety of different context data 560. Context data, such as data 560, may include a wide variety of data that generally relates to the environment in which the nodes are operating and may be used to advantageously provide enhanced node management capabilities in accordance with embodiments of the present invention. As such, the use of such context data provides a data foundation in an embodiment so that the server may better and more efficiently implement management tasks related to nodes in the network, and adjust such tasks to account for relevant context data as nodes move within the network (e.g., as an ID node moves with an item being shipped along an anticipated or predicted transit path from an origin to a destination). For example, the server take advantage of its ability to rely upon relevant context data to advantageously alter how it instructs a node operate, how it associates a node with the another node, how it can better locate a node, and how it can more efficiently track and respond to requests to report the location of the node.

FIG. 26 is a flow diagram illustrating an exemplary method for context management of a wireless node network in accordance with an embodiment of the invention. Referring now to FIG. 26, method 2600 begins at step 2605 by identifying, by the server, at least one of the nodes. In one example, such as that shown in FIG. 22a, server 100 may identify ID node A 2220a as part of communications received from master node M1 2210*a*. At step 2610, the server determines context data that relates to an operating environment of the identified node as the identified node moves within the operating environment.

In one embodiment, the context data may include one or more types of data, such as scan data, historic data, shipment data, RF data, and layout data. For the example shown in FIG. 22*a*, server 100 may access context data 560 (which may be kept in context database 565) to determine parts of the context data 560 that relate to the operating environment of ID node A 2220*a*. Such context data 560 may include, in this example, shipment data that relates the item being shipped that is connected to ID node A 2220*a*, scan data for when the item connected to ID node A 2220*a* was scanned upon entering structure 2200, historic data for how long it takes a node to traverse the conveyor located within structure 2200, and layout data on dimensions of structure 220. Those skilled in the art will appreciate that context data may include operational environment information created within the wireless node network or created by a third party (e.g., weather information related to the operating environment of ID node A 2220*a*).

While the server determines context data that relates to an operating environment of the identified node in one embodiment, such a current or anticipated operating environment for a node in a more detailed embodiment may include one or more types of environments. For example, the current or anticipated operating environment for a node may include an electronic communication environment, a physical environment of an anticipated path along with a node moves, a conveyance environment related to how a node moves, and a density environment related to the density of nodes within an area near a particular node identified by the server.

Back at step 2610, the determining step may involve determining the context data that relates to an anticipated operating environment of the identified node as the identified node moves in a predicted path towards a location of another node. In another example, the determining step may involve determining the context data that relates to the anticipated operating environment of the identified node and an anticipated operating environment of the another node as the identified node moves in the predicted path towards the another node for an expected association with the another node At step 2615, the server performs a management task related to the identified node with an adjustment made to account for the determined context data. When the determined context data (such as RF signal degradation information) indicates that no adjustment is actually needed when performing the task, no adjustment is made given the determined context data. Thus, those skilled in the art will appreciate that an adjustment may be made when needed contextually and is not required at all times.

In one embodiment, performing the management task may comprise generally instructing the identified node to alter its operation based upon the determined context data. For example, server 100 may perform the management task of instructing ID node A 2220*a* to change its connectable and non-connectable intervals as it approaches master node M1 (which server 100 knows from context data, such as scan data generated when node A entered structure 2200). Thus, in this example, server 100 is able to leverage enhanced visibility of ID node A 2220*a* based upon context data and advantageously alter the operation of node A to increase the node's chance of successfully associating with master node M1 2210*a*.

In other embodiment, performing the management task may comprise associating the identified node with another node with the adjustment made to alter an associating parameter based upon the determined context data. In other words, context data may be helpful as part of associating nodes. In one example, the associating parameter may include at least one altered timing interval related to associating the identified node with the other node, such as an alert interval or connectable interval. These intervals are parameters that may be altered as part of adjustments made when a server associates two nodes and, for example, sets the intervals to more appropriate time durations in order to enhance the chance and opportunity the nodes have to actively pair and securely share data as needed.

In yet another embodiment, performing the management task may comprise locating the identified node with an adjustment made to a power setting based upon the determined context data. In one example, the power setting adjustment is done to a master node in direct communication with the server. In another example, the power setting adjustment may be done to an ID node, which is passed this operational adjustment information from another node. In one embodiment, the power setting itself may comprise an output power level adjusted to account for an adverse condition in the operating environment of the identified node (e.g., a master node with an adjusted RF output signal level). The adverse condition may be, for example, an adverse RF communication environment where structure attenuates or otherwise impedes normal RF communications. In another example, the adverse condition may be a highly dense population of nodes close to the identified node.

In more detail, the output power level may be adjusted to account for a shielding condition in the operating environment of the first node. Such a shielding condition may be caused, for example, by one or more of packaging, package contents, proximate package, proximate package contents, and physical infrastructure in the operating environment of the first node. For example, if the identified node is located near a metal container, it is operating in an adverse RF communications environment where it may have its output power level increased based on this context data in order to better deal with the adverse shielding condition.

In still another embodiment, performing the management task may comprise providing the location of the identified node in response to a request received by the server related to a status of the identified node. For example, if server 100 receives a request from user access device 205 about the status of ID node A 2220*a*, server 100 is able to provide the location of node A as being within structure 2200, but refined as being close to the entry of the structure given the adjustment to account for contextual data, such as scan data related to the item being shipped with node A 2220*a*.

Those skilled in the art will appreciate that method 2600 as disclosed and explained above in various embodiments may be implemented on a server, such as server 100 illustrated in FIGS. 5 and 22A, running one or more parts of server control and management code 525 (e.g., the context based node manager). Such code may be stored on a non-transitory computer-readable medium such as memory storage 515 on server 100. Thus, when executing code 525, the server's processing unit 500 may be operative to perform operations or steps from the exemplary methods disclosed above, including method 2600 and variations of that method.

Node Location Determination Methodologies

As part of managing and operating a wireless node network in accordance with one or more embodiments of the invention, such as tracking ID node A 2220*a* in FIGS. 22A-C, determining a node's location is performed. As explained above, an exemplary ID node may be directly or indirectly dependent on a master node to determine its location. In the embodiments discussed and described herein, a location of a node may generally encompass a current or past location. For example, an embodiment that determines a node's location may be a current location if the node is not moving, but may necessarily determine the location as a past location should the node be in a state of motion.

Likewise, the term location alone may include a position with varying degrees of precision. For example, a location may encompass an actual position with defined coordinates in three-dimensional space, but use of the term location may also include merely a relative position. Thus, the term location is intended to have a general meaning unless otherwise expressly limited to a more specific type of location.

Determining node location may done by a master node alone, the server alone, or the master node working together with the server. And on such devices, embodiments may use one or more methodologies to determine a node's location and further refine the location. Such example methodologies may include, but are not limited to, determining node location may relate to controlling an RF characteristic of a node (e.g., an RF output signal level and/or RF receiver sensitivity level), determining relative proximity, considering association information, considering location adjustments for context information and an RF environment, chaining triangulation, as well as hierarchical and adaptive methods that combine various location methodologies. A more detailed description of these exemplary node location determination techniques is provided below.

Location Through Proximity

In one embodiment, a signal strength measurement between two or more nodes may be used to determine the proximity of the nodes. If neither node's actual location is known, one embodiment may infer a location relationship of the two nodes through proximity.

Proximity When Varying Power Characteristics

For example, an exemplary method of determining a node's location in a wireless node network of nodes may involve varying a node's power characteristic, such as the output power of one of the nodes. Generally and as explained with reference to FIG. 13, the power characteristic may be varied to identify closer ones of the nodes to the node broadcasting. The node broadcasting may transmit one or a series of signals while other nodes may report receiving one or more of the signals. Those other nodes that receive at least one signal broadcast from the transmitting node may be deemed part of a close group of nodes. And as the power characteristic is varied (increased or decreased or both), a closest group of nodes (or single node) may be identified as the smallest group of nodes of those that receive at least one signal from the broadcasting node. Accordingly, while not absolute, a type of location for the broadcasting node may be determined based on the closest one or group of nodes. This may be repeated for neighboring nodes to yield a set of closest node information for each of the nodes. In more detail, an exemplary set of closest node information for each of the nodes may include which nodes are closest (via the lowest power characteristic) and more robustly supplement this information with which other nodes are incrementally further away (via increasingly larger power characteristics). Thus, the set of closest node information provides the basis for a determination of how close the nodes in the network are to each other, which provides a type of location determination for each node.

Additionally, context data may be referenced in certain embodiments to further enhance determining how close the nodes are to each other. For example, combining the set of closest node information with context data, such as scan information that registers when an item changes custodial control in a delivery system, may further refine how to determine the location of the nodes. Scan and other context information will help determine if one or more of the nodes, for example, are known to be in the same container, vehicle or moving on a belt together. Thus, this type of context data may be integrated into a further step of refining how close the nodes are to each other based upon the context data.

In general, a location of a node based upon proximity may be determined when a power characteristic of nodes is changed or varied in a wireless node network. FIG. 28 is a flow diagram illustrating an exemplary method for location determination by varying a power characteristic of nodes in a wireless node network in accordance with an embodiment of the invention. Referring now to FIG. 28, method 2800 begins by at step 2805 by instructing a first of the nodes to vary the power characteristic for one or more signals broadcast by the first node. In a more detailed embodiment, such an instruction may cause the first node, for example, to incrementally decrease or incrementally increase the power characteristic (such as an output power level) between values.

At step 2810, method 2800 continues by identifying a first group of other nodes in the wireless node network that are near the first node based upon those of the other nodes that received at least one of the signals broadcast by the first node as the first node varies the power characteristic. In a further embodiment, step 2810 may incrementally identifying which of the first group of other nodes are receiving at least one of the broadcast signals as the first node incrementally varies the output power level of the signals broadcast. The incrementally identified nodes may be deemed a set of increasingly close nodes to the first node.

At step 2815, method 2800 continues by identifying a closest one or more of the other nodes as a smallest group of the other nodes that received at least one of the one or more signals broadcast by the first node as the first node varies the power characteristic.

At step 2820, method 2800 concludes by determining a location of the first node based upon the closest one or more of the other nodes. Thus, as the power characteristic is varied, the group of nodes that have received at least one of the signals broadcast by the first node may change and the smallest such group being a closest group of nodes (even if just one node) to the first node. In a more detailed embodiment, step 2820 may comprise determining the location of the first node based upon the closest one or more of the other nodes and the set of increasingly close nodes to the first node as the set of increasingly close nodes provides more detailed proximity information for a refined location determination.

Figure 14:
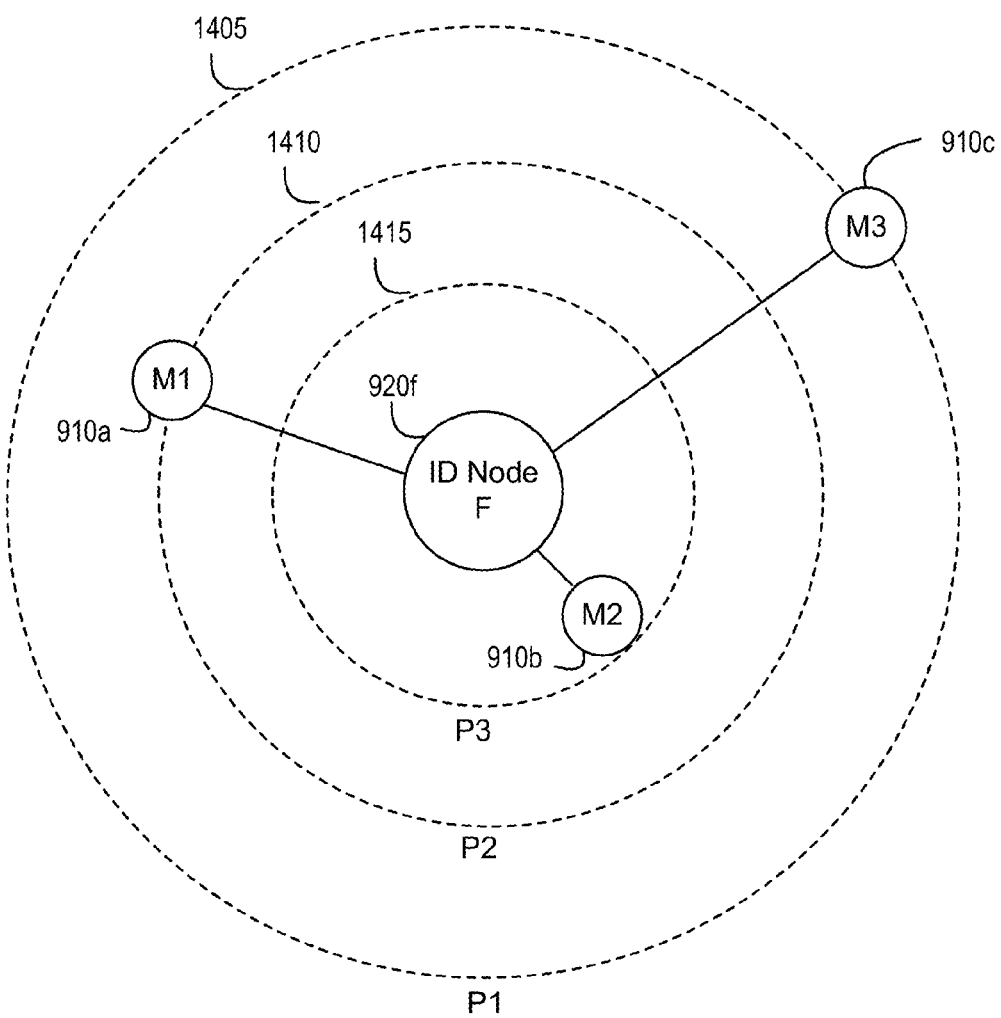
FIG. 14 is a diagram illustrating an exemplary location determination using ID node advertise in accordance with an embodiment of the invention.

For example, referring to FIG. 14, the set of increasingly close nodes to the ID node F 920*f* may include node M3 as being farthest away and M1 being closer than M3. When the power characteristic of ID node F incrementally decreases, and its output power level changes from P1 to P2, M3 can no longer receive the signal, but M1 and M2 still do. And as the power characteristic of ID node F continues to incrementally decrease, and its output power level is changed from P2 to P3, M1 can no longer receive the signal, but only M2 does as the last of the nodes closest to ID node F. Thus, in this example, determining the location of ID node F may be based upon the fact that M2 is the closest node and the set of increasingly close nodes include M1 and M3 with M1 being closer than M3.

In another embodiment, one or more further refinements to the first nodes location may be performed. In one example, steps 2805-2820 may be repeated where a second of the nodes is instructed to vary the power characteristic for one or more signals broadcast by the second node, and then method 2800 may further refine the location of the first node based upon a location of the second node. In a more detailed example, steps 2805-2820 may be repeated where a second of the nodes is instructed to vary the power characteristic for one or more signals broadcast by the second node, and then method 2800 may further the location of the first node based upon a location of the second node and a set of increasingly close nodes to the second node. With this increasingly cross-related information on what nodes are closer to other nodes and to what degree, which may be further repeated for additional nodes, embodiments may further refine the location of the first node within the network.

Method 2800 may further include determining context data related to the first node, and refining the location of the first node based upon the context data. In an embodiment where the power characteristic is output power level, the incremental changes in the output power level of the broadcast signal in steps 2805-2815 may be set according to the context data.

Method 2800 may also determine the context data to be related to the closest node to the first node, and refine the location of the first node based upon the context data. In still another example, method 2800 may determine the context data to be related to the incrementally identified nodes in the set of increasingly close nodes to the first node, and refining the location of the first node based upon the context data. For example, the closest node and the set of increasingly close nodes may have scan data that indicate they are within the same container. This exemplary context data may be used to further refine the location of the node being located, which may help efficiently determine that node is near the container. As such, those skilled in the will appreciate that context data for the node being located as well as nodes identified to be close to that node may provide relevant input to advantageously help further refine the location of the node.

Those skilled in the art will appreciate that method 2800 as disclosed and explained above in various embodiments may be implemented on a server apparatus, such as server 100 illustrated in FIGS. 5 and 22A, running one or more parts of server control and management code 525 (e.g., the location manager). Such code may be stored on a non-transitory computer-readable medium such as memory storage 515 on server 100. Thus, when executing code 525, the server's processing unit 500 may be operative to perform operations or steps from the exemplary methods disclosed above, including method 2800 and variations of that method.

An embodiment of such a server apparatus may include a server (such as server 100) operative to communicate with a plurality of nodes in the wireless node network. As explained with respect to FIG. 5, the server generally includes a server processing unit, a server volatile memory, a server memory storage, and at least one communication interface. In this embodiment, the volatile memory, memory storage, and communication interface are each coupled to the processing unit. The memory storage maintains at least a program code section and location data related to a location of one or more of the nodes. The communication interface provides a communication path operatively coupling the server with the nodes.

The server processing unit, as mentioned above, is operative when running the program code section, to perform the steps and operations as described above relative to method 2800 and variations of that method described above.

Proximity When Observing Signal Patterns and Strengths Over a Time Period

In another embodiment, an improved method for determining a node's location through proximity may include analyzing the signal patterns and strengths between an advertising node and a listening node. In one embodiment, a threshold may be set for association based on an observed message count and/or recorded signal strength within a specific time period may improve the ability to locate a node (e.g., an ID node) to that of another node (e.g., a master node). In some embodiments, the observed message count may be implemented as an averaged count over a repeated time periods. Further still, other embodiments may filter outlying observations in the observation data set to help improve the quality of data relied upon for setting a threshold for association and, as a result, determine a node's location.

In a more detailed example, an improved method for determining a node's location through proximity may show captured advertising message counts as a component for a node's location and determining a node's direction of travel. In this example, two exemplary master nodes (e.g., master node M1 910*a* and M2 910*b*) may capture advertising messages from one ID node (e.g., ID node A 920*a*). Master node M1 may observe and capture (e.g., record information related to the observation) 60 messages from ID node A within a 2 minute period, while master node M2 only observes and captures 7 advertising messages from ID node A within that same period. Based upon the difference in how often messages are observed from ID node A by master node M1 compared to those observed by master node M2, the system is able to determine that ID node A would more proximate to master node M1, and it's known location.

In a further embodiment, comparing the average time stamp of the captured records may allow the system can make a more accurate determination of location. For example, if the average captured message found on master node M2 is increasingly growing larger (e.g., taking longer for messages to go from ID node A to master node M2), this indicates ID node A is moving away from master node M2. If the average captured message found on master node M2 is growing increasingly larger while the average captured message found on master node M1 is increasingly growing smaller, this indicates ID node A is moving away from master node M2 and toward master node M1. Thus, over a number of observed time periods, the change in message timing (transmission to reception) may also be relied upon to enhance or refine a node's location.

In yet another embodiment, the observed signal strength may be a component in location determination and estimating direction of travel and may allow the system can make a more accurate determination of location. For example, two master nodes (M1 910*a* and M2 920*b*) may be capturing advertising messages from a node (ID node A 920*a*). M1 captures 60 messages from ID node A within 2 minutes, while M2 captures only 7 messages. The average signal strength observed for signals from ID node A by master node M1 is higher compared to the average signal strength observed by master node M2. Based upon this observed signal strength information, the system would determine that ID node A to be at M1, but a predicted path may indicate ID node A is heading towards M2. As the master nodes M1 and M2 continue to capture records, the system (e.g., management code 524 operating on server 900, which is in communication with M1 and M2) processes the continued feed of capture records from M1 and M2. With this observed signal strength information, the server 900 would expect that the count and average signal strength of messages from ID node A over the time period observed (2 minutes) to increase for observations at M2 and to decrease for observations at M1 when ID node A is physically moving closer to M2 and away from M1. Thus, the change in observed powers levels and in how often messages are observed may indicate actual node movement in an embodiment.

Basing node proximity location and node directional determinations on observed signal patterns and characteristic strengths over a period of time has the advantage of reducing the likelihood of unwanted and spurious signal anomalies causing an ID node's location to be incorrectly determined. And the above exemplary methods for determining movement characteristics of a node (e.g., moving closer to one node, moving closer to one but away from another, etc.) as part of refining the node location may be applied in combination with the various embodiments for determining node location described herein.

FIG. 27 is a flow diagram illustrating an exemplary method for proximity locating a node in a wireless node network based upon observed signal patterns and characteristic indications over a period of time in accordance with an embodiment of the invention. Referring now to FIG. 27, method 2700 begins at step 2705 by instructing a first and a second other nodes to detect any message broadcast from the one node over a period of time. The period of time may be set based upon a variety of factors, such as context data. In more detail, the period of time may be dynamically changed based upon context data as the one node moves into different contextual environments.

Method 2700 has the server receiving a first indication from the first other node at step 2710 and receiving a second indication from the second other node at step 2715. Finally, the method 2700 determines a location of the one node based upon a difference in the first indication and the second indication at step 2720.

The first indication is related to a characteristic of messages broadcast from the one node that are detected by the first other node during the period of time. Likewise, the second indication is related to the characteristic of messages broadcast from the one node that are detected by the second other node during the period of time. These indications may include, for example, a count of messages received by the respective other nodes, a transit time factor (e.g., an average transit time for a message to be detected after broadcast), and an average signal strength.

In one embodiment, the first indication may be a first count of messages broadcast from the one node that are detected by the first other node during the period of time, and the second indication may be a second count of messages broadcast from the one node that are detected by the second other node during the period of time. As such, determining the location of the one node may be the location that is closer to the first other node than the second other node when the first count is greater than the second count. Additionally, the method 2700 may further include determining an actual node movement direction for the one node based upon comparing the first count and the second count over a plurality of time periods. For example, the method 2700 may repeat observations over several of these time periods and track the first count and second count over time to determine which is increasing, which is decreasing, and determine movement of the one node based upon these measurements over time.

In another detailed embodiment, the first indication may be a first time factor of messages broadcast from the one node that are detected by the first other node during the predetermined time period, and the second indication may be a second time factor of messages broadcast from the one node that are detected by the second other node during the period of time. And an actual node movement direction for the one node may be based upon comparing the first time factor and the second time factor. In a more detailed embodiment, the first time factor may be an average transit time for a message detected at the first other node to go from the one node to the first other node, and the second time factor is an average transit time for a message detected at the second other node to go from the one node to the second other node. As such, determining the location of the one node may be that the location is closer to the first other node than the second other node when the first time factor is less than the second time factor.

In yet another embodiment, the first indication may be a first average signal strength of messages broadcast from the one node that are detected by the first other node during the period of time, and the second indication may be a second average signal strength of messages broadcast from the one node that are detected by the second other node during the period of time. As such, determining the location of the one node may be that the location is closer to the first other node than the second other node when the first average signal strength is greater than the second average signal strength.

The method 2700 may also include, in an embodiment, observing a degree of change in the first average signal strength and a degree of change in the second average signal strength over repeated time periods, and determining an actual node movement direction for the one node based upon comparing the degree of change in the first average signal strength and the degree of change in the second average signal strength.

In another embodiment, the method 2700 may also refine the determined location of the one node. In this embodiment, the method 2700 may further comprise refining the location of the one node based upon at least one of a first updated location received from the first other node and a second updated location received from the second other node. For example, when first other node is a mobile master node and it is the closer of the two nodes to the one node being located, the embodiment can take advantage of the location signaling onboard the first other node that provides the current location of the first other node. That current location data may be transmitted by the first other node to the server to update the server in its calculation of the location for the one node.

In still another embodiment, the method 2700 may layer context data with the determined location to refine the location of the node. Context data related to the one node may be determined by the server, and so the location of the one node may be refined based upon that context data. In another example, context data related to the closer of the first other node and the second other node when compared to the location of the one node. For example, the server may be aware that a particular master node is closer to the one node compared to a second master node, and that the particular master node is within a container. With this additional context data related to the particular master node, the server may refine the location of the one node based upon the context data. Other exemplary types of relevant context data may be relied upon when refining the location of the one node, such as context data of a particular shielding associated with the environment near the particular master node (e.g., a particular type of ULD having known RF shielding characteristics, etc.)

Additionally, the method 2700 may involve looking to see if the one node is behaving as expected. More specifically, a further embodiment of the method 2700 may further compare the location of the one node to a predicted path of the one node to determine if the one node is located outside the predicted path. This may allow the server to use learned, historic data when creating a predicted path, and keep track of the one node relative to being within an acceptable range associated with this predicted path. The method may also generate a notification if the one node is outside the predicted path. In this manner, actionable tasks can then be taken to locate the one node—e.g., changing filter mode options for nodes in that general area, etc.

Those skilled in the art will appreciate that method 2700 as disclosed and explained above in various embodiments may be implemented on a server, such as server 100 illustrated in FIGS. 5 and 22A, running one or more parts of server control and management code 525 (e.g., the location manager). Such code may be stored on a non-transitory computer-readable medium such as memory storage 515 on server 100. Thus, when executing code 525, the server's processing unit 500 may be operative to perform operations or steps from the exemplary methods disclosed above, including method 2700 and variations of that method.

Association Driven Locating with Variable RF Characteristics

As noted above, a signal strength measurement between two or more nodes may be used to determine relative distance between nodes. If one of the nodes has a known location (such as master node M1 910a), a relative location of one or more nodes within a range of the known location node is generally a function of how accurate the system may determine a distance between the node with known location and associated nodes. In other words, an embodiment may identify a relative location of an item and its related node by relying upon association-driven variable low-power RF output signals to determine a distance the node is from a known location.

Location Determination Through Master Node Advertise

Figure 13:
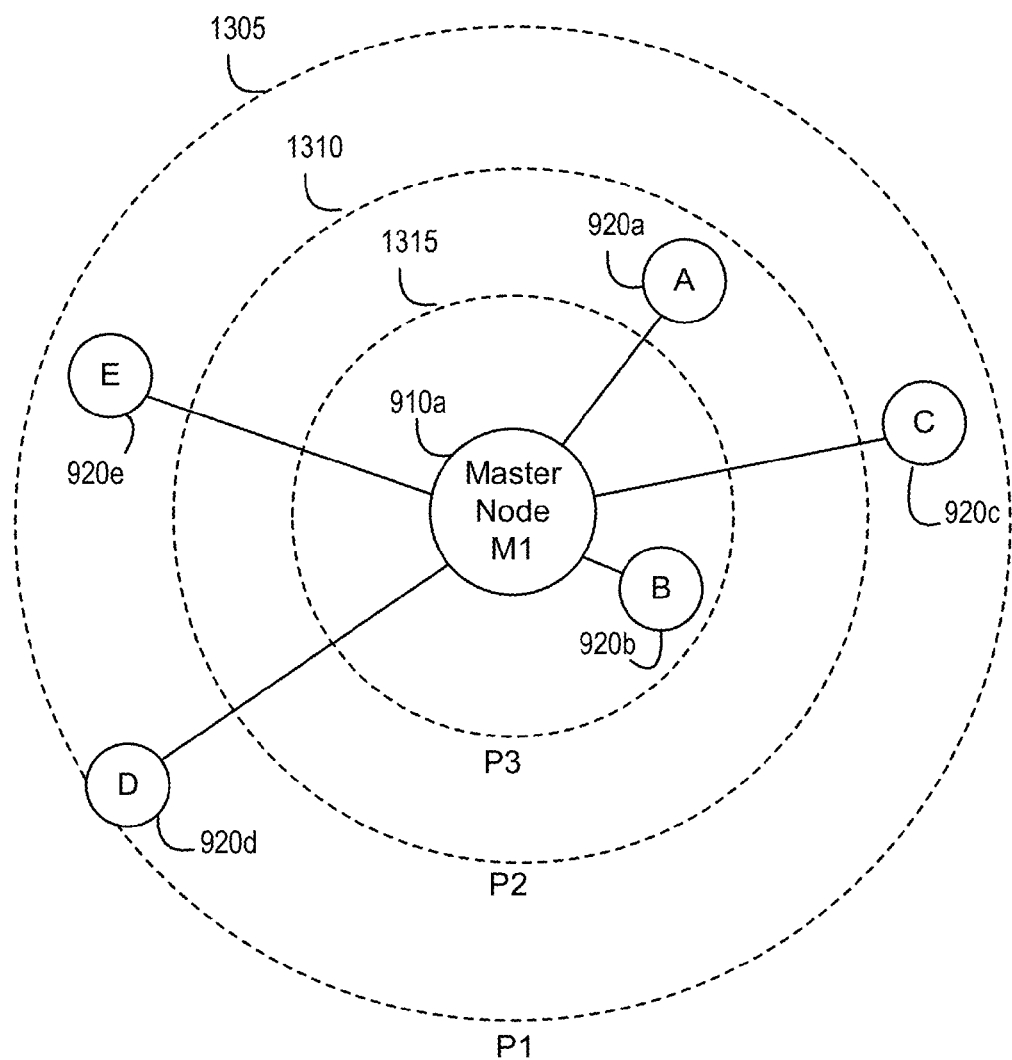
FIG. 13 is a diagram illustrating an exemplary location determination using master node advertise in accordance with an embodiment of the invention.

As generally mentioned above, determining node location may relate to controlling an RF characteristic of a node (e.g., an RF output signal level and/or RF receiver sensitivity level) and, more specifically, may involve aspects of controlling master node advertising. FIG. 13 is a diagram illustrating an exemplary location determination using master node advertise in accordance with an embodiment of the invention. In the illustrated embodiment shown in FIG. 13, a master node, such as master node M1 910a, with a known location is broadcasting an advertising message at varying RF output power levels. FIG. 13 illustrates the exemplary different RF output power levels as concentric ranges 1305-1315 about master node M1 910a. Thus, master node M1 910a may broadcast at a maximum power P1, related to range 1305, but may control the RF output power level and dynamically change the RF output power level to P2 and broadcast at a smaller range 1310, or to P3 and broadcast to an even smaller range 1315.

In the illustrated embodiment, receiving ID nodes A-E 920a-920e are in query (scan) mode and can each use the received signal at different levels to determine how far away from the transmitting M1 they are located. Those skilled in the art will appreciate that while the illustrated embodiment shown in FIG. 13 has the receiving nodes all as ID nodes, other embodiments may have receiving nodes be either master or ID nodes or a mixture.

In the exemplary embodiment of FIG. 13, the location for nodes A-E may be determined based upon the known location of master node M1 910a. That location, plus a range measurement when each of respective receiving nodes A-E last receives a signal from node M1, and factoring in a confidence factor of the range measurement, provides a location determination for the nodes according to variable RF signal power. Depending on a quality of the range measurement, the individual receiving nodes may or may not have an individually calculated location. In yet another embodiment, if third party or context data, such as scan information, is available, a refined location may be determined using such data as an additional confidence factor. As the communication range of M1 is limited from P1 to P3, the accuracy of location by association goes up.

In the illustrated example of FIG. 13, an exemplary method of determining a node's location may be described that uses master node advertising. First, when the master node M1's variable power short range communication interface 480 is set to P1, its maximum output, master node M1 910a is seen by each of ID nodes A-E 920a-920e. Based upon analytics or historic measurements, the open air performance (optimal range) of the radio in M1's variable power short range communication interface 480 at P1 power level may have been previously been found to be approximately 30 feet. Thus, without the need to examine RSSI levels from the individual ID nodes A-E 920a-920e and without the need for active calibration phases, the system may know that ID nodes A-E are within 30 feet of master node M1 910a.

Next, when the master node M1's variable power short range communication interface 480 is set to P2, a medium output level in this example, master node M1 is seen by nodes A and B. From previous analytics or historic measurements, it was determined the open air performance (optimal range) of the master node M1's variable power short range communication interface 480 running at P2 power level is approximately 15 feet. Thus, without the need to examine RSSI levels from the individual nodes, we know ID nodes A 920a and B 920b are within 15 feet of master node M1. Furthermore, we know the ID nodes no longer receiving the broadcasted RF signal from master node M1 910a (e.g., ID nodes C 920c, D 920d, and E 920e) are somewhere within 30 feet of master node M1 910a, but probably more than 15 feet away from M1.

And when the master node M1's variable power short range communication interface 480 is set to P3, its minimum output level in this example, it is seen by ID node B 920b. From previous analytics or historic measurements, it was determined the open air performance (optimal range) of the master node M1's variable power short range communication interface 480 running at P3 power level is approximately 5 feet. Thus, without the need to examine RSSI levels from the individual ID nodes, we know the location of ID node B 920b is within 5 feet of the known location of master node M1 910a.

The ranging steps, as discussed in the example above, may then be repeated for any of the identified nodes in order to build a more accurate picture of the relative location of each node. The granularity of RF characteristic settings (e.g., the RF output signal power level setting) will provide more granularity of location differentiation when performing the ranging steps. In one embodiment, the ranging steps may be performed over a set of gross RF characteristics settings (e.g., few settings over a wide range), and similar steps may then be performed over more select ranges for the RF characteristics settings.

FIG. 29 is a flow diagram illustrating an exemplary method for location determination using one or more associations of nodes in a wireless node network in accordance with an embodiment of the invention. Referring now to FIG. 29, method 2900 begins at step 2905 where a first of the nodes broadcasts one or more first messages at a first anticipated or predicted range distance. In one embodiment, the first anticipated range distance is an optimal range for the first node. For example, the first node's radio in its communication interface may have a maximum setting to allow the node to broadcast at maximized range assuming a clear environment. Such a setting provides a known anticipated range distance. In the example of FIG. 13, master node M1 910a may be broadcasting at a maximum power level P1 that reaches a first range distance from node M1. However, if node M1 is known to be within an adverse RF shielding environment, the first anticipated range distance may be a distance adjusted to account for the contextual environment of such shielding (e.g., a type of context data). Anticipated range distances may be adjusted depending upon one or more types of relevant context (e.g., one or more types of context data related to how an RF output signal from the node may be impeded).

At step 2910, method 2900 identifies which of the nodes associated with the first node received at least one of the first messages. In one embodiment, the first node may be able to access and review association data in its onboard memory storage as part of identifying which are the nodes associated with it. In one example, the associations with the first node may be passive associations (e.g., not actively paired and securely connected) or active associations (e.g., actively paired and able to securely connect and share data), or a combination of both types of associations.

Next, at step 2915, the first node broadcasts one or more second messages at a second anticipated range distance, which is incrementally smaller than the first anticipated range distance. In the example of FIG. 13, master node M1 910*a* may be the first node and now is broadcasting at a medium power level P2 that reaches a second anticipated range distance from node M1. By incrementally changing the RF power level in this manner, master node M1 910*a* now no longer can reach nodes C-E as shown in FIG. 13.

At step 2920, method 2900 concludes by determining a location of one or more of the identified associated nodes that did not receive any of the second messages but received at least one of the first messages, where the location is between the first and second anticipated range distances from the first node. Again, in the example of FIG. 13, master node M1 910*a* may determine the location of nodes C-E (given they did not receive the message sent out the second anticipated range distance at RF power level P2) to between the first anticipated range distance (when master node M1 was broadcasting at power level P1) and the second anticipated range distance (when master node M1 was broadcasting at power level P2) from the known location of master node M1.

In one embodiment, the method 2900 may also have the first node broadcasting one or more third messages at a third anticipated range distance (incrementally smaller range than the second anticipated range distance), and determining a location of one or more of the identified associated nodes that did not receive any of the third messages but received at least one of the second messages, where the location is approximately near the second anticipated range distance from the first node. Again, in the example of FIG. 13, by incrementally changing the power level down to P1 and broadcasting a third message at an anticipated range distance for that P1 level, the master node M1 can determine the location of node A (as node A received the second message but did not receive the third message) to be approximately near the anticipated range distance for P2 from the location of master node M1.

Additional embodiments of method 2900 may also refine such determined locations by updating the location of the first node. In one embodiment, the first node may be a mobile node. As such, refining may involve determining a current mobile location of the first node, and refining the location of the one or more of the identified associated nodes that did not receive any of the second messages but received at least one of the first messages based upon the current mobile location of the first node. Thus, as the first node moves and updates its own location (e.g., via GPS signals received by location circuitry 475 on a master node), the first node is able to leverage its own updated location and advantageously refine the location of nodes associated with it.

And, in some embodiments, the refined location of associated nodes may be transmitted to a server. This provides an update to the server, and aids in tracking and managing the location of nodes in the network. Again, referring back to the example of FIG. 13, master node M1 910*a* may take advantage of such a method for locating associated nodes, such as the locations of ID nodes A-E 920*a*-920*e*, and update server 100 with this new location data related to the current location of node M1 and any of the nodes associated with node M1.

Those skilled in the art will appreciate that method 2900 as disclosed and explained above in various embodiments may be implemented on a node (e.g., master node 110*a* in FIG. 4, master node M1 910*a* in FIG. 13, or master node M1 2210*a* in FIG. 22A) running one or more parts of master control and management code 425 (e.g., the location aware/capture module). Such code may be stored on a non-transitory computer-readable medium, such as memory storage 415 on master node 110*a*. Thus, when executing code 425, the master node's processing unit 400 may be operative to perform operations or steps from the exemplary methods disclosed above, including method 2900 and variations of that method.

In another embodiment, a node apparatus is described in a wireless node network that uses location determination by association as described with reference to the steps related to method 2900. As mentioned above, such as node apparatus may be implemented with a master node having a node processing unit, a node volatile memory, a node memory storage, and a first and second communication interface. Each of the memories and communication interfaces are coupled to the node processing unit. Further, the node memory storage maintains at least a program code section, association data, and location data and, at times, shipping information. The first communication interface provides a first communication path operatively coupling the node with a plurality of other nodes in the network, while the second communication interface provides a second communication path operatively and separately coupling the node with a server in the network.

In this embodiment, the node processing unit is operative to transmit one or more first messages via the first communication interface at a first anticipated range distance, and identify which of the others nodes that are associated with the first node received at least one of the first messages. In one embodiment, the node processing unit may be operative to access the association data in the node memory storage when identifying which of the nodes associated (e.g., passive, active, or both types of associations) with the first node received at least one of the first messages.

The first anticipated range distance may be an optimal transmission range for the first communication interface and, in a more detailed example, may be adjusted based upon context data (e.g., RF shielding inherent from the surrounding environment of the node). In yet another embodiment, the first anticipated range distance and the second anticipated range distance may be adjusted based upon one or more types of context data related to how an RF output signal transmit from the first communication interface may be impeded by an environment of the node.

The node processing unit is also operative to transmit one or more second messages via the first communication interface at a second anticipate range distance (incrementally smaller than the first anticipated range distance) and determine a location of one or more of the identified associated nodes that did not receive any of the second messages but received at least one of the first messages. That location is between the first anticipate range distance from a known location of the node and the second anticipated range distance from the known location of the node. In a further example, the node processing unit may be operative to store the determined location in the node memory storage as part of the location data.

The node processing unit may also be operative to transmit one or more third messages via the first communication interface at a third anticipated range distance (incrementally smaller range than the second anticipated range distance) and determine a location of one or more of the identified associated nodes that did not receive any of the third messages but received at least one of the second messages, where the location is between the second anticipated range distance from the known location of the node and the third anticipated range distance from the known location of the node.

In another embodiment, the node may be mobile and the node processing unit may be further operative to refine the location of the one or more of the identified associated nodes that did not receive the second message but received the first message by updating a location of the first node. In more detail, the node processing unit may be operative to determine a current mobile location of the first node (e.g., check with location circuitry onboard the node for valid GPS signals and a location lock based on such signals), and refine the location of the one or more of the identified associated nodes that did not receive any of the second messages but received at least one of the first messages based upon the current mobile location of the first node. The node processing unit may also be operative to transmit the refined location to the server over the second communication interface.

Location Determination through ID Node Advertise

While FIG. 13 provides an example of location determination through master node advertising, FIG. 14 focuses on location determination through ID node advertising. In particular, FIG. 14 is a diagram illustrating an exemplary location determination using ID node advertise in accordance with an embodiment of the invention. In the illustrated embodiment shown in FIG. 14, exemplary ID node F 920*f* is in an advertising mode but is without a known location. As with FIG. 13, FIG. 14 illustrates the exemplary different RF output power levels from ID node F 920*f* as concentric ranges 1405-1415 about ID node F 920*f*. Thus, ID node F 920*f* may broadcast at a maximum power P1, related to range 1405, but may control the RF output power level and dynamically change the RF output power level to P2 and broadcast at a smaller range 1410, or to P3 and broadcast to an even smaller range 1415. Master nodes M1-M3 910*a*-910*c* are disposed in various known locations relatively near ID node F 920*f*, which has an unknown location. As such, ID node F 920*f* may take advantage of the ability to adjust an RF characteristic, such as RF output signal power level, of its own short-range communication interface as part of how the system may determine location of ID node F through ID node advertising.

In the illustrated embodiment, an RF output signal power level of ID node F 920*f* may be varied or dynamically adjusted via programmable settings (such as profile settings or parameters) related to operations of variable power short range communication interface 375. Additionally, while an actual communication range may vary with the surrounding environment, a maximum anticipated communication range of the ID node's transmitter at each power level is known assuming an optimal operating environment or no substantial RF shielding or interference. Thus, a particular power level setting for a broadcasting node is inherently associated with a corresponding anticipated range distance.

In an exemplary method of determining a nodes location using ID node advertising, the RF output signal power level may be varied across multiple power levels to improve location through master node association. In more detail, when the ID node F's variable power short range communication interface 375 is set to P1, its maximum output, ID node F 920*f* is seen by each of master nodes M1-3 910*a*-910*c*. The anticipated open air performance or range distance (optimal range, or range based upon analytics or historic measurements) of the radio in ID node F's variable power short range communication interface 375 at P1 power level may have been previously been found to be approximately 30 feet. Thus, without any examination of RSSI levels from the individual master nodes, the system knows ID Node F is within 30 feet of master nodes M1-M3.

Next, when the ID node F's variable power short range communication interface 375 is set to P2, a medium output level in this example, ID node F 920*f* is seen by master nodes M1 910*a* and M2 910*b*. The anticipated open air performance or range distance (optimal range, or range based upon analytics or historic measurements) of the radio in ID node F's variable power short range communication interface 375 at running at P2 power level is approximately 15 feet. Thus, without any examination of RSSI levels from the individual nodes, we know master nodes M1 910*a* and M2 910*b* are within 15 feet of ID node F 920*f* in this example. Furthermore, we know the master node no longer receiving the broadcasted RF signal from ID node F 920*f* (e.g., master node M3 910*c*) is somewhere within 30 feet of ID node F 920*f*, but probably more than 15 feet away from node F in this example.

And when ID node F's variable power short range communication interface 375 is set to P3, its minimum output level in this example, ID node F 920*f* is seen by only master node M2 910*b*. The anticipated open air performance or range distance (optimal range, or range based upon analytics or historic measurements) of the radio in ID node F's variable power short range communication interface 375 at P3 power level is approximately 5 feet. Thus, without any examination of RSSI levels from the master nodes, we know the location of ID node F 920*f* is within 5 feet of the known location of master node M2 910*b* in this example.

The ranging steps with respect to the changed RF characteristics of an advertising ID node, as discussed in the example above, may then be repeated for any of the identified nodes in order to building a more complete picture of the relative location of each node.

Furthermore, the timing between such ranging steps may vary dynamically depending upon whether the node is moving. Those skilled in the art will appreciate that when moving, a quicker flow through such ranging steps will help to provide better accuracy given the movement of nodes. Thus, the time interval between instructing a node to broadcast one or more messages at a particular power level and then instructing that node to broadcast one or more messages at a different power level may be desired to be shorter when the node is moving, which can be determined based upon context data. For example, the context data may indicate the node is within a node package an on a moving conveyor system. As such, the node is moving relative to fixed master nodes that may be positioned along the conveyor system. Thus, server may have the first node perform the ranging steps where power is varied in relative quick succession compared to a situation where the context data indicates the node is not moving or is substantially stationary.

FIG. 30 is a flow diagram illustrating another exemplary method for location determination using one or more associations of nodes in a wireless node network in accordance with an embodiment of the invention. Referring to FIG. 30 and how it explains a particular way to locate a node using associations and master node one or more master node advertising techniques, method 3000 begins at step 3005 by instructing a first of the nodes to broadcast one or more first messages at a first power level, the first power level being related to a first anticipated range distance. In one example, the first anticipated range distance may be an optimal range for the first of the nodes (e.g., a transmission range that assumes there are no obstructions and a clear signal path between nodes). In another example, the first anticipated range distance may be an optimal range for the first node adjusted based upon context data (e.g., data related to the surrounding RF environment of the first node).

At step 3010, the method 3000 identifies which of the nodes associated with the first node have known locations at step 3010. For example, this type of identification may be accomplished by reviewing association data that indicates which of the nodes are associated with the first node (e.g., via passive association, via active association, or via a combination of both), determining which of the nodes are associated with the first node based upon the reviewed association data, and identifying which of those associated nodes have known locations.

The method 3000 continues at step 3015 by determining which of the identified associated nodes received at least one of the first messages. Next, the method 3000 instructs the first node at step 3020 to broadcast one or more second messages at a second power level, where the second power level is related to a second anticipated range distance and the second power level incrementally smaller than the first power level. In a further example, the first anticipated range distance and the second anticipated range distance may be adjusted based upon one or more types of context data related to how an RF output signal from the first node may be impeded.

At step 3025, method 3000 determines which of the identified associated nodes received at least one of the second messages. Method 3000 concludes at step 3030 where the method determines a location of the first node to be at or between the first anticipated range distance and the second anticipated range distance from each of the identified associated nodes that did not receive at least one of the second messages but received at least one of the first messages.

As mentioned above, determining the node's location may be improved when accounting for movement. As such, an embodiment of method 3000 may instruct the first node to broadcast the one or more second messages within a time interval after instructing the first node to broadcast the one or more first messages. The time interval may be predetermined in some implementations, but also may be a dynamically set parameter in other implementations based upon context data related to the first node. In more detail, the time interval may be reduced from a prior value when the context data related to the first node indicates the first node is moving, but may be increased from a prior value when the context data related to the first node indicates the first node is substantially stationary.

In another embodiment, method 3000 may further include instructing the first node to broadcast one or more third messages at a third power level. Such a third power level is related to a third anticipated range distance and incrementally smaller range than the second anticipated range distance. Thereafter, the method may determining the location of the first node to be at or between the second anticipated range distance and the third anticipated range distance from each of the identified associated nodes that did not receive any of the third messages but received at least one of the second messages.

In another embodiment, method 3000 may comprise refining the location of the first node with an updated location of one or more of the identified associated nodes that did not receive at least one of the second messages but received at least one of the first messages. For example, if the first node is associated with a mobile master node, the location of the first node may be refined with an updated location of the mobile master node (which may be closer to the first node than previously determined).

In a further embodiment, the first node in the operation of method 3000 may not be self-aware of its own location. In another embodiment, the first node in the operation of method 3000 may have been previously self-aware of the location of the first node but may no longer be self-aware of the location of the first node prior to broadcasting the one or more first messages. In more detail, the first node may no longer be self-aware of the location of the first node prior to broadcasting the first message because of a change in the environment surrounding the first node. Such a change in the environment may be, for example, when the first node has moved inside a structure (e.g., building, vehicle, aircraft, container, etc.) that blocks location signals from being received by the first node.

Those skilled in the art will appreciate that method 3000 as disclosed and explained above in various embodiments may be implemented on a node (e.g., master node 110a in FIG. 4) running one or more parts of master control and management code 425 (e.g., the location aware/capture module) to control operations of an ID node (such as ID node F in FIG. 14) as part of location determination via ID node advertising. Such code may be stored on a non-transitory computer-readable medium, such as memory storage 415 on master node 110a. Thus, when executing code 425, the master node's processing unit 400 may be operative to perform operations or steps from the exemplary methods disclosed above, including method 3000 and variations of that method.

From an apparatus perspective, an exemplary node apparatus in a wireless node network that uses location determination by association may comprises a node processing unit, node memory coupled to and used by the node processing unit (e.g., a node volatile memory and a node memory storage). The node memory storage maintains at least a program code section, association data, and location data. The node apparatus further includes a first communication interface that provides a first communication path coupled to the node processing unit and operatively coupling the node with a plurality of other nodes in the network. For example, the master node 110 illustrated in FIG. 4 includes such types of operational structure.

The node processing unit (e.g., processing unit 400 of master node 110a), when executing at least the program code section resident in the node volatile memory, is operative to perform specific functions or steps. In particular, the node processing unit is operative to communicate an instruction to a first of the other nodes (e.g., an ID node or master node temporarily operating as an ID node) via the first communication interface to cause the first other node to broadcast one or more first messages at a first power level, where the first power level is related to a first anticipated range distance.

The first anticipated range distance may be an optimal range for the first of the nodes and, in more detail, an optimal range for the first of the nodes adjusted based upon context data. In even more detail, the first anticipated range distance and the second anticipated range distance may be adjusted based upon one or more types of context data related to how an RF output signal broadcast from the first node may be impeded.

The node processing unit is also operative to identify which of the nodes associated with the first node have known locations. To do this, the node processing unit may access and review association data stored on the node memory storage (e.g., data indicating what nodes are passively or actively associated with the first other node), may determine which of the remaining other nodes are associated with the first other node based upon the reviewed association data, and may identify which of the remaining other nodes determined to be associated with the first other node have known locations.

The node processing unit is also operative to determine which of the identified associated nodes received at least one of the first messages, and to communicate another instruction via the first communication interface to the first node to cause the first node to broadcast one or more second messages at a second power level, where the second power level being is to a second anticipated range distance and incrementally smaller than the first power level.

Finally, the node processing unit is operative to determine which of the identified associated nodes received at least one of the second messages, and then determine a location of the first node to be at or between the first anticipated range distance and the second anticipated range distance from each of the identified associated nodes that did not receive at least one of the second messages but received at least one of the first messages.

In a further embodiment, the node processing unit may be operative to communicate a third instruction via the first communication interface to the first node to cause the first node to broadcast one or more third messages at a third power level. The third power level is related to a third anticipated range distance and incrementally smaller range than the second anticipated range distance. Additionally, the node processing unit may then be operative to determine the location of the first node to be at or between the second anticipated range distance and the third anticipated range distance from each of the identified associated nodes that did not receive any of the third messages but received at least one of the second messages.

In still another embodiment, the node processing unit is able to account for movement of the first node with a time interval between instructions sent to the first node. In particular, the node processing unit may be further operative to communicate another instruction via the first communication interface to the first node to broadcast the second messages within a time interval after instructing the first node to broadcast the first messages. In a more detailed example, the time interval may be dynamically set based upon context data related to the first node. In even more detail, the time interval may be programmatically reduced from a prior value when the context data related to the first node indicates the first node is moving (e.g., the first node is on a moving conveyor system) and/or the time value of the interval may be increased from a prior value when the context data related to the first node indicates the first node is substantially stationary (e.g., the node is within a node package recently placed in a storage area).

The node processing unit, in a further embodiment, may be operative to refine the location of the first other node with an updated location of one or more of the identified associated nodes that did not receive at least one of the second messages but received at least one of the first messages, and cause a second communication interface (e.g., medium/long range communication interface 485 coupled to processing unit 400) to transmit the refined location to the server.

From a server perspective, FIG. 31 is a flow diagram (similar to FIG. 30) illustrating yet another exemplary method for location determination using one or more associations of nodes in a wireless node network in accordance with an embodiment of the invention. Those skilled in the art will appreciate that while a server may operate to implement the steps as laid out in method 3000 and discussed above, FIG. 31 provides more details as to how a server processing unit (such as processing unit 500 running server code 525) may implement such a method at that level of the network via method 3100. In this more detailed embodiment, the server is communicating directly with a master node (e.g., a first node) to direct and control how the master node interacts with and causes operations to be undertaken on the ID node (e.g., a second node). Thus, step 3105 is similar to step 3005 but more precisely calls for communicating with a first node via a communication interface to cause a second node in the network to broadcast one or more first messages at a first power level at the request of the first node, where the first power level is related to and corresponds with a first anticipated range distance. Likewise, step 3120 is similar to step 3020 but more precisely calls for communicating with the first node via the communication interface to cause the second node to broadcast one or more second messages at a second power level at the request of the first node, the second power level being related to a second anticipated range distance and incrementally smaller than the first power level. The other steps of method 3100 are similar to those illustrated and explained above relative to method 3000, and that the similar principles will apply to method 3100.

Those skilled in the art will appreciate that method 3100 as disclosed and explained above in various embodiments may be implemented on a server (e.g., server 100 in FIG. 5) running one or more parts of server control and management code 525 to direct a master node to control operations of an ID node (such as ID node F in FIG. 14) as part of location determination via ID node advertising. Such code may be stored on a non-transitory computer-readable medium, such as memory storage 515 on server 100. Thus, when executing code 525, the server's processing unit 500 may be operative to perform operations or steps from the exemplary methods disclosed above, including method 3100 and variations of that method.

And similar to the node apparatus described above, one embodiment includes an exemplary server apparatus in a wireless node network that uses location determination by association. The exemplary server apparatus generally comprises a server processing unit, server memory coupled to and used by the server processing unit (e.g., a server volatile memory and a server memory storage). The server memory storage maintains at least a program code section, association data, and location data. The server apparatus further includes a communication interface coupled to the server processing unit and that provides access to a communication path operatively coupling the server with at least a first node in the network.

The exemplary server processing unit, when executing at least the program code section resident in the server volatile memory, is operative to perform specific functions or steps. In particular, the server processing unit is operative to communicate with the first node via the communication interface to cause a second node in the network to broadcast one or more first messages at a first power level at the request of the first node, where the first power level is related to a first anticipated range distance; identify which of the remaining nodes in the network associated with the second node have known locations; determine which of the identified associated nodes received at least one of the first messages; communicate with the first node via the communication interface to cause the second node to broadcast one or more second messages at a second power level at the request of the first node, where the second power level is related to a second anticipated range distance and incrementally smaller than the first power level; determine which of the identified associated nodes received at least one of the second messages; and determine a location of the second node to be at or between the first anticipated range distance and the second anticipated range distance from each of the identified associated nodes that did not receive any of the second messages but received at least one of the first messages. And in a further embodiment, the server apparatus' processing unit may be further operative to store the determined location in the server memory storage as part of the location data.

In another embodiment, the server apparatus' processing unit may be operative to communicate with the first node via the communication interface to cause the second node to broadcast the one or more second messages within a time interval after communicating with the first node to cause the second node to broadcast the one or more first messages. As previously mentioned, this type of time interval may dynamically set based upon context data related to the second node. Context data may also be used as set forth above with respect to the node apparatus but applied here to the second node—such was where the first anticipated range distance is the optimal range for the second node adjusted based upon context data.

Master Node Location Determination through Advertise

In another embodiment, a master node may no longer know its location. For example, such a situation may occur when a master node determines it's current location via GPS location circuitry 475, but the master node finds itself without access to an adequate number of GPS signals (e.g., it cannot determine a location due to the lack of a sufficient number of GPS signals from diverse GPS satellites). Such a situation may happen when the master node moves indoors is proximate to a structure that interferes with the location signals.

In an exemplary embodiment where a master node attempts to determine its own location via advertising techniques, the master node may detect a loss of location confidence (e.g., upon a loss of detected GPS signals; upon detecting a separate signal to processing unit 400 indicating the master node's location is unknown; when processing unit 400 senses movement (e.g., via accelerometers (not shown) or the like) but cannot confirm that the location circuitry 475 is providing updated location information for the node, etc.). In other words, the master node becomes aware that it no longer has a known location.

Next, the master node responds by beginning to broadcast one or more advertising messages in a similar way as ID node F 920*f* is described as doing with respect to FIG. 14. This is done so that the master node having an unknown location can advantageously leverage off the known locations of nearby other nodes. As such, an embodiment may allow a type of leveraged chaining effect whereby known locations of particular types of nodes may be used to extend location information to other nodes that do not know their locations (e.g., ID nodes) or nodes that have detected a loss of location confidence (e.g., master nodes). Thus, such an embodiment may be used to determine an indoor location of a master node (including equipment equipped with master node functionality) in cases where signals for the conventional onboard location circuitry 475 are not available.

Referring back to the exemplary method 3000 and FIG. 30, method 3000 may be such that the first node is not self-aware of the location of the first node. This may happen when the first node (e.g., an ID node) is actually a master node that was previously self-aware of its own location (e.g., via received GPS signals) but is no longer self-aware of its location (e.g., when the GPS signals can no longer be received), which has the master node changing operation to operate as an ID node prior to broadcasting the first message. In other words, the master node may no longer be self-aware of its location and begin operating as an ID node for purposes of location determination prior to broadcasting the first message because of a change in the environment surrounding the master node, such as when the master node has moved inside a structure that blocks location signals from being received by the master node. Thus, an embodiment may advantageously allow a node to adaptively alter operations when moving from a clear outdoor environment to an indoor environment. And a server may interact with such a master node while that master node is operating, for location purposes, as an ID node, temporarily.

Location with Improved RSSI Measurements

In another embodiment, a signal strength measurement between two or more nodes may be used to determine the proximity of the nodes by using one or more improvements to conventional RSSI measurements. In conventional RSSI measurements, such as with Bluetooth 4.0, those skilled in the art will appreciate that adaptive frequency hopping as part of spread spectrum techniques may cause undesirably cause the signal strength to fluctuate. In other words, the advantage of using frequency hopping and spread spectrum for security and avoidance of interference may have a negative impact on using such signals for stable proximity-based location determinations. Thus, it may be desired to emphasize stability of a signal and limits to fluctuation for purposes of location determination.

In one embodiment, a type of improvement for RSSI measurements may include reducing the number of channels and/or a corresponding frequency range in use during advertising from nodes. For example, a node may have processing unit 300/400 adaptively control variable power short range communication interface 375/480 to reduce the number of channels and/or the frequency range used during node advertising. Such a dynamic change may be implemented, in some embodiments, by altering the content of a particular type of profile data 330/430, such as an RF profile data that effectively defines RF characteristics of a node (e.g., frequency, power level, duty cycle, channel numbers, channel spacing, alternative fluctuation modes, etc.). In one further embodiment, a first fluctuation mode may be defined that provides a default or more standard communication protocol, such as the conventional frequency hopping, spread spectrum, and channel allocations for Bluetooth® communications. Other alternative modes (one or more) may be defined that alter one or more RF characteristics to provide increasingly more stable and less fluctuations of the RF output signal from a node. Thus, a node may be dynamically placed into one or more modes regarding such RF characteristics that increasingly emphasize stability of the node's RF output signal and limits fluctuation for purposes of enhanced location determination using RSSI measurements.

In another embodiment, a type of improvement for RSSI measurements may include ensuring visibility to and advantageously managing automatic gain control (AGC) circuitry (not shown) that may cause the RF output signal to vary for a node. For example, a node may include a type of AGC circuitry as part of variable power short range communication interface 375/480. This type of AGC circuitry may allow node processing unit 300/400 or other logic circuitry that is part of variable power short range communication interface 375/480 to limit fluctuations under certain conditions (e.g., when attempting to use RSSI location determination techniques). In this example, different AGC circuitry settings may be defined in exemplary RF profile data that effectively defines RF characteristics of a node (e.g., frequency, power level, duty cycle, channel numbers, channel spacing, alternative fluctuation modes, etc.). This is yet another example of how a node may be dynamically placed into one or more modes regarding such RF characteristics (including AGC circuitry settings) that increasingly emphasize stability of the node's RF output signal and limits fluctuation for purposes of enhanced location determination using RSSI measurements.

Location with Adjustments for Environmental Factors in RF Signal Quality

In general, those skilled in the art will appreciate that environmental factors may cause a communication signal, such as an RF signal, to fluctuate or be transmitted and received in a manner that undesirably varies depending upon a signal path environment. Passive physical interference factors (e.g., forms of electronic signal shielding) may be substantially close and cause drops in signal strength across the output ranges of the nodes. Additionally, active radio interference factors may vary across the RF output ranges of the nodes depending upon other active devices in the reception vicinity. Thus, the proximate environment of a node may have a multitude of adverse factors that impact communications and, as a result, the ability to locate the node.

In one embodiment, making location determinations may be enhanced by a data analytics type of approach that may adjust and account for different RF environmental factors for a similar type of node in a similar type of situation. For example, the quality of the RF output signal of a particular type of node and the corresponding physical range of that signal to a receiver of known sensitivity may be determined for a given environment. In this example, the system defines a maximum range of that signal based on a predetermined condition, such as open-air connectivity. This may assume an environment with no signal degradation due to interference or physical shielding. However, both interference and physical shielding may diminish the range of the RF output signal of a node. In a dynamically adaptive and learning manner, the system may collect information on how a particular type of node may operate in a particular environment under certain settings (e.g., reported signal strengths and corresponding settings for RF output signal power levels). This analysis of a similar environment may be repeated. In other words, through such data analytics of an anticipated environment to be faced by a similar node, signal loss information can be generated and applied as a type of context data (i.e., RF data) for a node in a similar environment to refine location determination. Thus, an exemplary embodiment may refine location determinations with adaptive signal loss characteristics based on a contextual appreciation of an anticipated environment (e.g., physical shielding such as packaging, package contents, proximate package, proximate package contents, and physical infrastructure causing signal variance) without requiring a calibration phase.

And advantageously combining those data points with $3^{rd}$ party data describing the physical environment, in which the node was located in at that time, may refine location even further. Such information may be used as RF data (a type of context data) in future efforts to manage and locate a similar type of node anticipated to be in a similar environment.

In more detail, in an embodiment that refines a location determination based upon context and data analytics to adjust for known RF impediments, the maximum physical range of a node's RF output signal relative to a receiver of known RF sensitivity is determined. In one example, this first range value may be referred to as a theoretical or nominal open-air range of a similar type transmitter-receiver node pair in a similar environment but with substantially no physical shielding or signal interference negatively impacting the signal range. A second range value, which may be considered an actual RF range value, may be the observed range of the signal in a similar environment but where there are contextual factors reducing the communication range, including physical shielding due to factors like packaging, package contents, proximate package, proximate package contents, physical infrastructure, interference from other radio sources, or shipper specific information such as vehicle or facility layout information. Through access to prior data analysis of the differing range values and with knowledge of the operational environment of the transmitting node was in (e.g., a similar environment to the proximate environment of the node), a refined location may be determined using an approximation of an actual RF output range that intelligently adjusts what may be anticipated to be the RF environment of the node. In other words, by knowing the appropriate contextual environment related to a node (such as signal degradation information on how a similar node operates in a similar environment), an improved location determination may be made to make intelligent yet efficient adjustments (such as communication distance adjustments) that provide a refined location of the node.

In one example, such as the example shown in FIG. 2, master node 110*b* is outside of a container (such as a Uniform Load Device (ULD) container 210 known to be used for transporting groups of items on aircraft) that has an ID node inside the container. A first or theoretical range value between master node 110*b* and ID node 120*b* may be determined to be 10 feet at a specific RF output power level when the package (and related ID node) may be known to be less than 10 feet away from the scanning node (e.g., master node 110*b*). A second range value at similar distances with similar types of nodes, but with incident RF signal loss as a result of communicating through the wall of the container 210, may be between 4 and 5 feet. If context data, such as $3^{rd}$ party information or scan data, indicates the transmitting node is within the ULD container 210, the system would expect the transmission range to be limited according to the data analytics associated with this known RF impediment (e.g., characteristics for transmitting through ULD container 210), thus reducing the possible scanning nodes that may see the broadcasting node within the ULD container, or require the transmitting node to increase its RF output power to be heard.

FIG. 32 is a flow diagram illustrating an exemplary method for location determination of a first node in a wireless node network based on context data in accordance with an embodiment of the invention. Referring now to FIG. 32, method 3200 begins at step 3205 with a network device (such as a master node or server) accessing a first type of the context data related to a proximate environment of the first node.

The first type of context data comprises signal degradation information on how a second node would operate in a similar environment to the proximate environment of the first node when the second node is a similar type as the first node. Thus, rather than calibrating with an actual measurement relative to the current proximate environment of the first node, the signal degradation information provides compensation information on what may be generally anticipated in a more general proximate environment based on how a similar type of node may operate in a similar environment. As the similar environment of the similar node is generally an approximation for what is anticipated to be the proximate environment of the first node, this advantageously avoids the need for an actual calibration of the proximate environment. In one embodiment, the signal degradation information may be based upon a difference in how the second node communicates when exposed to an adverse communication environment (such as a similar environment to the proximate environment of the first node) compared to how the second node would communicates when exposed to a nominal communication environment (such as an environment that is unencumbered by shielding and interference factors). Those skilled in the art will appreciate that a nominal communication environment need not be perfectly clear of all influences that shield or interfere with communications.

The types and aspects of signal degradation information may vary depending on a wide variety of factors. In one embodiment, the signal degradation information may be related to at least one of shielding and interference. Thus, signal degradation information may include both passive and active factors that impact the communication environment.

In another embodiment, the signal degradation environment may be based upon a degraded operation of the second node when the similar environment is an adverse communication environment. In more detail, the signal degradation information may be based upon a difference in how the second node communicates when exposed to the adverse communication environment compared to how the second node communicates when exposed to a substantially normal communication environment, such as an open air environment.

In still another embodiment, signal degradation information may relate to at least shipment data for one or more items being shipped (e.g., currently shipped or shipped in the past) and located in the proximate environment of the first node. For instance, a package near the first node may include metallic materials that may impede or block RF signals and the signal degradation information may relate to such information about close packages being shipped near the first node. In another example, the signal degradation information may relate to at least layout data for one or more physical structures in the proximate environment of the first node. In more detail, the layout data may be for one or more physical structures (e.g., walls, machinery, enclosures, and conveyances) in the proximate environment of the node near a predicted path for the first node. In yet another example, the signal degradation information relates to at least historic data on one or more analyzed prior operations of the second node.

At step 3210, the network device, such as a master node or server, may adjust an anticipated communication distance related to the first node based upon on the first type of the context data. In one example, the anticipated communication distance may be a theoretical broadcast distance based upon parameters of the device's radio. Such an anticipated communication distance is known as it is an estimate of the radio's range. In one example, the adjusted communication distance comprises an anticipated reduced range distance for a transmission from the first node. In another example, the adjusted communication distance comprises an anticipated reduced receiver sensitivity distance for the first node.

In yet another example, adjusting the communication distance may be accomplished by adaptively adjusting, by the network device, the communication distance based upon the signal degradation information and a second type of the context data. In other words, the communication distance may be adjusted based upon signal degradation information considered along with other types of context data, such as how the first node is being moved (such as an anticipated movement of the first node along a predicted transit path for the first node) or a density of other nodes near the first node.

At step 3215, the network device determines the location of the first node based upon the adjusted communication distance. In a further embodiment, the method may also update the adjusted communication distance by the network device based upon movement of the first node, and may refine the location of the first node with an updated adjusted communication distance. This may happen with the first node is a mobile master node capable of self-determining its own location.

Those skilled in the art will appreciate that method 3200 as disclosed and explained above in various embodiments may be implemented on a network device (e.g., exemplary master node 110a in FIG. 4 or server 100 in FIG. 5) running one or more parts of their respective control and management code to perform steps of method 3200 as described above. Such code may be stored on a non-transitory computer-readable medium, such as memory storage 415 on master node 110a or memory storage 515 on server 100. Thus, when executing such code, the respective network device's processing unit may be operative to perform operations or steps from the exemplary methods disclosed above, including method 3200 and variations of that method.

In more detail, an exemplary network device apparatus for determining a location of a first node in a wireless node network based on context data, the exemplary network device may include a processing unit, a volatile memory coupled to the processing unit, and a memory storage coupled to the processing unit. The exemplary network device further includes a communication interface coupled to the processing unit and that provides a communication path operatively coupling the network device with the first node in the network.

The memory storage for the device maintains at least a program code section and context data having at least signal degradation information. Such signal degradation information, as a type of context data, is information on how a second node would operate in a similar environment to a proximate environment of the first node when the second node is a similar type as the first node. Examples of signal degradation information may include those discussed above relative to step 3205 of method 3200.

When executing at least the program code section when resident in the volatile memory, the processing unit of the network device is operative to perform the steps noted and described above with respect to method 3200. In more detail, the processing unit is operative to at least connect with the memory storage to access the signal degradation information, adjust a communication distance (if needed) related to the first node based upon on the signal degradation information, determine the location of the first node based upon the adjusted communication distance, and store the determined location of the first node as location data on the memory storage.

Adjusting the communication distance by the processing unit may be accomplished as described above with regard to step 3210 of method 3200. And as mentioned above, the processing unit may be further operative to adaptively adjust the communication distance where other types of context data are also considered, such as movement and anticipated node movement as detailed out above.

In a further embodiment, the network device may be a mobile master node that includes location circuitry (such as GPS circuitry 475 of exemplary master node 110a shown in FIG. 4). In this embodiment, the processing of the network device may be further operative to determine a location of the network device based upon an output signal from the location circuitry received by the processing unit, and determine the location of the first node based upon the adjusted communication distance and the location of the network device. As such, the first type of the context data related to the proximate environment of the first node is based upon the determined location of the first node.

Those skilled in the art will also appreciate that in some operational environments, the signal degradation information may not require any adjustment to the communication distance in an embodiment. However, in other environments (e.g., adverse RF environments), the signal degradation information may provide a basis for adjusting the communication distance in the embodiment, even if not performed every time. Thus, an adjustment to the communication distance may not be needed in all proximate environments of the first node but may be performed, if needed, based on the proximate environment of the first node. It is the ability of an embodiment to adjust this communication distance when needed and if needed that advantageously allows for locating the first node with more accuracy.

Location Through Triangulation

Figure 15:
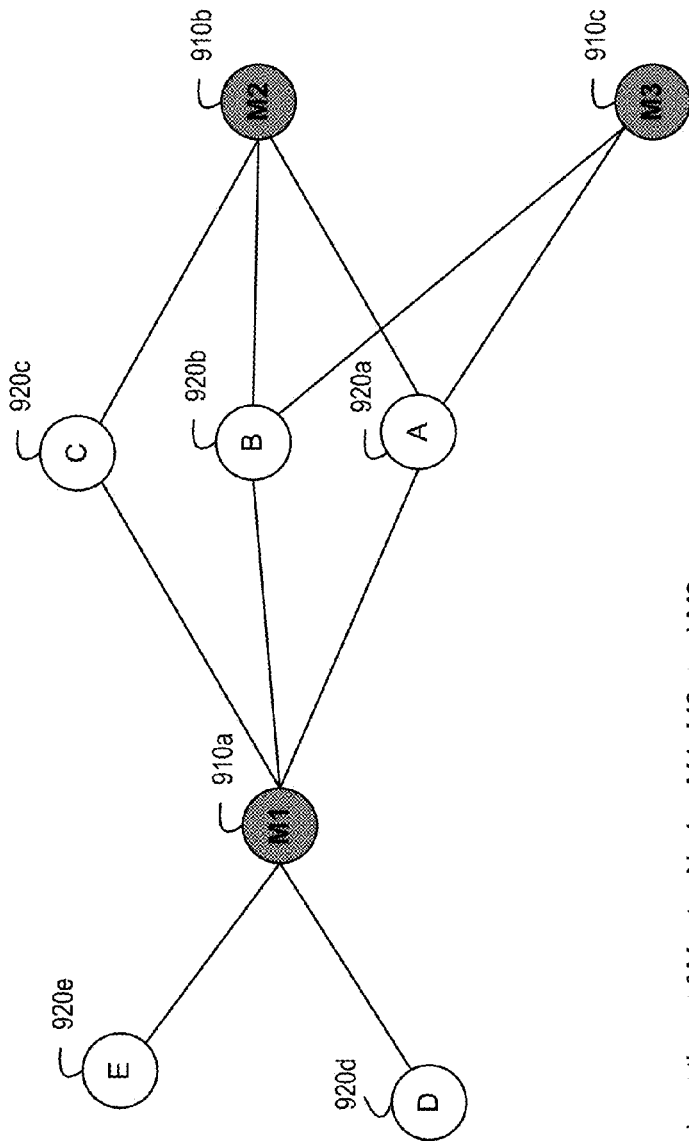
FIG. 15 is a diagram illustrating an exemplary location determination through triangulation in accordance with an embodiment of the invention.

In some embodiments, various methods for determining a node's location may rely upon, at least in part, triangulation techniques. In other words, as the wireless node network collects data on receiver-transmitter pairs, other methods for determining location of the individual nodes that utilize triangulation, at least in part, may become possible. FIG. 15 is a diagram illustrating an exemplary location determination through triangulation within a wireless node network in accordance with an embodiment of the invention. Referring now to the illustrated embodiment of FIG. 15, three exemplary master nodes M1-M3 910a-910c are shown with each master node having a known location. Exemplary ID nodes A-E 920a-920e are also shown where they are at least in communication range of one or more of exemplary master nodes MA-M3 910a-910c.

In this illustrated example, the master nodes M1-M3 may detect and collect advertising messages from ID nodes A-E at varying and known power levels. The captured information is forwarded by the master nodes M1-M3 to the backend server 100, where location determinations may be made. For example, factors like RSSI and visibility of each node at each power level may be used to determine, with a higher degree of accuracy, the location of nodes where sufficient information is available.

For an exemplary system to triangulate a node, three nodes with known locations must have seen the broadcasting node. In this example, two advertising ID nodes, A 920a and B 920b, were seen by the three nodes having known locations (master nodes M1-M3 910a-910c). Based upon the captured information, the locations of ID node A 920a and ID node B 920b are calculated.

Chaining Triangulation

Figure 16:
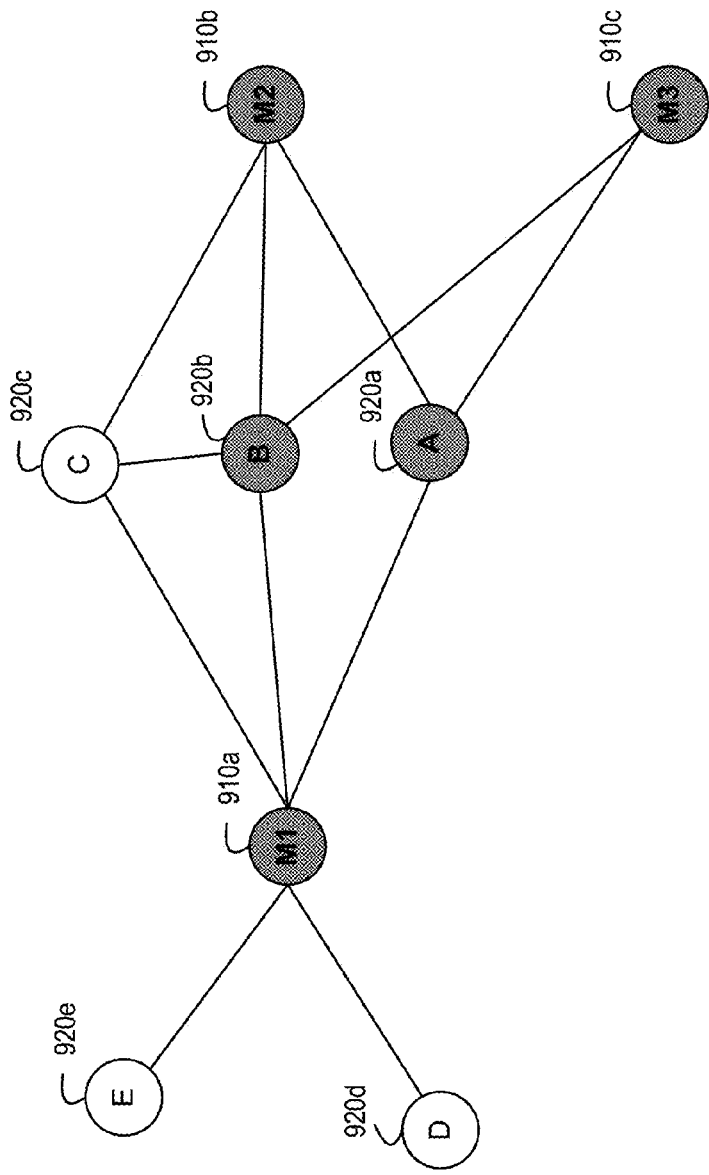
FIG. 16 is a diagram illustrating an exemplary location determination through chaining triangulation in accordance with an embodiment of the invention.

In another embodiment, a node with an inferred location may be used with triangulation techniques to determine a location of another node in a wireless node network. FIG. 16 is a diagram illustrating an exemplary location determination through chaining triangulation in accordance with an embodiment of the invention. The locations of ID nodes A 920a and B 920c have been determined by triangulating across master nodes M1-M3, as illustrated in the exemplary embodiment shown in FIG. 15. However, as illustrated in FIG. 16, the location of ID node C 920c may also be determined according to an embodiment.

For example, an exemplary method of determining a node's location through chaining triangulation begins with determining the calculated location of ID node B 920b (as explained with reference to FIG. 15). Next, a node closer to ID node B 920b may be used to get the missing third signal point needed for triangulation. This may be accomplished by placing ID node B 920b in a query (scan) mode such that it listens for a message from ID node C 902c. ID node C is instructed to advertise, thus providing a signal that may be captured by ID node B. After capturing the signal profile of C, ID node B may communicate or share the captured information and forward it along to the backend server 100 through either of the master nodes M1 or M2. The resulting location determination of ID node C 920c may have a higher level of position error due to it being partially based on a calculated reference (e.g., the location of ID node B), but the leveraged location determination of ID node C 920c may be sufficiently accurate (or be an actionable location) that useful information may be gleaned about ID node C 920c. For example, a leveraged or chained location determination of ID node C may indicate, with the help of context data, that nodes M1, M2, and ID node B are all close enough to ID node C that ID node C is determined to be within the same container nodes M1, M2, and ID node B.

Location Through Proximity to Triangulation (LP2T)

In an embodiment where chaining triangulation may determine location through proximity to triangulation (LP2T), a starting point may be determining the relative location of an ID node to a master node based on the proximity method, as explained above. However, when the relative location of the ID node has been determined, a more accurate or refined location of the ID node may be determined based upon the location of all master nodes that can capture the RF output signal broadcast from the ID node, and then triangulating based on observed signal strength of the ID node. In this example, the proximity-based location is used as an input in the triangulation calculation to estimate likely signal deterioration historically observed between a node at the proximity-determined location and scanning master nodes. In a further embodiment, by taking into account historic data on patterns of signal deterioration, a more accurate triangulation may be possible, leading to a more accurate location determination.

FIG. 33 is a flow diagram illustrating an exemplary method for determining a node location using chaining triangulation for one of a plurality of nodes in a wireless node network having a server in accordance with an embodiment of the invention. Such an exemplary node location need not be precise or exacting, but can be sufficiently accurate without absolutes.

Referring now to FIG. 33, method 3300 begins at step 3305 with the server receiving a location of a first of the nodes from the first node. Next, at step 3310, the server receives a location of a second of the nodes from the second node. For example, with reference to the example shown in FIG. 16, master nodes M1 910a and M2 910b may transmit their respective location coordinates from their respective onboard location circuitry to the server so that the server has the current locations of these two master nodes.

At step 3315, the server infers a location of a third of the nodes. For instance, in the example illustrated in FIG. 16, the server may infer the location of ID node B 920b. In one embodiment, inferring may comprise having the server determine a proximate-based location of the third node relative to another of the nodes having a known location, such that the proximate-based location operates as the inferred location of the third node.

In another embodiment, inferring the location of the third node may comprise having the server determine a relative location of the third node to the first node (as the node having a known location) or to the second node (as another node having a known location). Method 3300 may also, in another embodiment, include having the server adjust the inferred location of the third node to determine a refined location of the third node based upon third node context data related to the inferred location of the third node At step 3320, method 3300 concludes with the server triangulating the location of the one node based upon determined distances to each of the first and second nodes, and a determined distance of the one node to the inferred location of the third nodes.

In a more detailed embodiment, method 3300 may triangulate the location of the one node by accessing first node context data related to a contextual environment near the first node and second node context data related a contextual environment near the second node. Such contextual environments may include an environment of being on a conveyor system, or within a particular facility, or next to materials that may degrade or shield signals being received by the one node. Next, the more detailed triangulating may have the server adjust the determined distance of the one node to the location of the first node based upon the first node context data to provide a refined distance of the one node to the location of the of the first node. Then, the server may triangulate the location of the one node based upon the adjusted determined distance of the one node to the location of the first node, the adjusted determined distance of the one node to the location of second node, and a determined distance of the one node to the refined location of the third node.

In a further embodiment, method 3300 may also have the server transmitting an instruction so as to cause the server to transmit an instruction to cause the one node to broadcast a plurality of advertising signals over a period of time. In such an embodiment, the determined distance of the one node to the location of the first node may be based upon captured signals from the one node by the first node over the period of time and reported to the server by the first node. In another embodiment, the determined distance of the one node to the location of the second node may be based upon captured signals from the one node by the second node and reported to the server by the second node.

In still another embodiment, the server may transmit an instruction to cause the one node to broadcast a plurality of advertising signals at different power levels. In such an embodiment, the determined distance of the one node to the location of the first node may be based upon captured signals from the one node by the first node and reported to the server by the first node. In another embodiment, the determined distance of the one node to the location of the second node may be based upon captured signals from the one node by the second node and reported to the server by the second node.

In yet another embodiment, method 3300 may also have the server transmitting the location information out to a requesting entity (e.g., another node, a user access device, etc.) upon receipt of a request for a location of the one node from that entity.

Those skilled in the art will appreciate that method 3300 as disclosed and explained above in various embodiments may be implemented on a server (such as exemplary server 100 as illustrated in FIG. 5) running one or more parts of a control and management code (such as an code 525) to implement any of the above described functionality. Such code may be stored on a non-transitory computer-readable medium (such as memory storage 515 in an exemplary server). Thus, when executing such code, a processing unit of the server (such as unit 500) may be operative to perform operations or steps from the exemplary methods disclosed above, including method 3300 and variations of that method.

A server apparatus is also described in an embodiment for determining a location using chaining triangulation for one of a plurality of nodes in a wireless node network. The server apparatus generally comprises a server processing unit, a server volatile memory, a server memory storage, and a communication interface. The server volatile memory, server memory storage, and communication interface are each configured in the apparatus as coupled to the server processing unit. The server memory storage maintains at least a program code section and location data related to nodes in the network. In some embodiments, the server memory storage may also maintain context data, such as first node context data and second node context data. The communication interface provides a communication path operatively coupling the server with nodes in the network, such as a first and second node.

The server processing unit, when executing at least the program code section resident in the server volatile memory, is operative to perform various functions, such as the functions described in the steps above related to method 3300. In particular, the server processing unit is operative to receive a request over the communication interface for the location of the one node. Based on the request, the server processing unit is then operative to receive the respective locations of the first and second nodes, and store the locations as part of the location data kept on the server memory storage. The server processing unit is further operative to infer a location of a third of the nodes, and store the inferred location of the third node as part of the location data kept on the server memory storage. The server processing unit then is operative to triangulate the location of the one node based upon a determined distance of the one node to the location of the first node, a determined distance of the one node to the location of second node, and a determined distance of the one node to the inferred location of the third node. And finally, the server processing unit is operative to transmit the location information to the requesting entity over the communication interface in response to the request.

In one embodiment, the server processing unit may be further operative to infer the location of the third of the nodes by being operative to determine a proximate-based location of the third node relative to another of the nodes having a known location, where the proximate-based location operates as the inferred location of the third node.

In another embodiment, the server processing unit may be further operative to transmit an instruction over the communication interface to cause the one node to broadcast a plurality of advertising signals over a period of time. In this embodiment, the determined distance of the one node to the location of the first node may be based upon captured signals from the one node by the first node over the period of time and reported to the server by the first node. Alternatively, the determined distance of the one node to the location of the second node may be based upon captured signals from the one node by the second node and reported to the server by the second node.

In another embodiment, the server processing unit may be further operative to transmit an instruction over the communication interface to cause the one node to broadcast a plurality of advertising signals at different power levels. In such an embodiment, the determined distance of the one node to the location of the first node may be based upon captured signals from the one node by the first node and reported to the server by the first node. Alternatively, the determined distance of the one node to the location of the second node may be based upon captured signals from the one node by the second node and reported to the server by the second node.

In yet another embodiment, the server processing unit may be further operative to infer the location of the third node by being operative to determine a relative location of the third node to the first node or, alternatively, to the second node.

In still another embodiment, context data may be relied upon to refine locations. More specifically, the server processing unit may be further operative to adjust the inferred location of the third node to determine a refined location of the third node based upon third node context data related to the inferred location of the third node.

In a more detailed embodiment, the server memory storage may further maintains context data, and the server processing unit may be further operative to triangulate by being operative to access first node context data as part of the context data maintained on the server memory storage, where the first node context data is related to a contextual environment near the first node. Likewise, the server processing unit may be further operative to access second node context data as part of the context data maintained on the server memory storage, where the second node context data is related a contextual environment near the second node. The server processing unit may then be operative to adjust the determined distance of the one node to the location of the first node based upon the first node context data to provide a refined distance of the one node to the location of the of the first node. As such, the server processing unit may be operative to triangulate the location of the one node based upon the adjusted determined distance of the one node to the location of the first node, the adjusted determined distance of the one node to the location of second node, and a determined distance of the one node to the refined location of the third node.

Combined Methods for Determining Node Location

In light of the examples explained above for locating a node, one skilled in the art will appreciate that a further embodiment expressly contemplates using more than one of the above-described location determination techniques when determining a refined location of a node in a wireless node network. For example, such combination embodiments may apply an ordered or prioritized approach whereby a first location technique is applied to generate first location information regarding the location of a node in the wireless network. Thereafter, a second location technique may be selected from a hierarchy or prioritized set of techniques (some of which may work better in certain circumstances and be chosen or dynamically prioritized based upon the contextual environment), and applied to generate second location information regarding the location of the node or refining the location of the node. Other embodiments may apply additional location techniques to generate further refined location information.

In an embodiment, the information in the exemplary hierarchy generally identifies which technique may be preferred to be used initially as well as a ranked grouping or listing of when to apply other location techniques. Such information in the exemplary hierarchy may be fixed (based upon successful historic data and experience) or be dynamically altered over time as nodes may move relative to each other and, for example, based upon context data that provides more information relative to the a current or anticipated contextual environment.

Applying Node Location Determination in a Vehicular Environment

The various exemplary methods and techniques described above for determining the location of a node provide an advantageous way to locate a node. However, further embodiments may advantageously apply such methods and techniques in a vehicular environment when dealing with logistics operations where a node is to be located in a vehicle, moved within a vehicle, or removed for delivery from a vehicle.

Essentially, embodiments may use a package enabled with a node (generally referred to as a node package or node-enabled package) to ship one or more items and such a node package may be advantageously placed, located, moved, or removed for delivery in a vehicle/transportation/shipping/logistics environment. As explained throughout this description, a node package is generally a package to be shipped that is related to a particular node. The node and the related package travel together as part of the shipping process. In a general embodiment, the node may simply be within the package. In another embodiment, the node may be attached to the package (e.g., adhered to an interior portion of the package, fixed to a part of the package where one or more status indicators of the node may be visible through the package, etc.). In another embodiment, the node of the node package may be part of the package or the packaging materials used to comprise an exterior, interior, or separating/cushioning material within the node package. In more detail, the node may be integrated as part of the package or packaging materials (e.g., integrated as part of a pallet, a ULD container, a corrugated fiberboard box, and the like). In still another detailed embodiment, the node of the node package may be fully or partially embedded within the package or packaging materials used to help form a general container, which maintains an item to be shipped along with the node. As explained herein, FIGS. 75A, 75B, 76-78 provide various illustrations of different exemplary node-enabled packaging materials that may be used as part of a node package.

Figure 93:
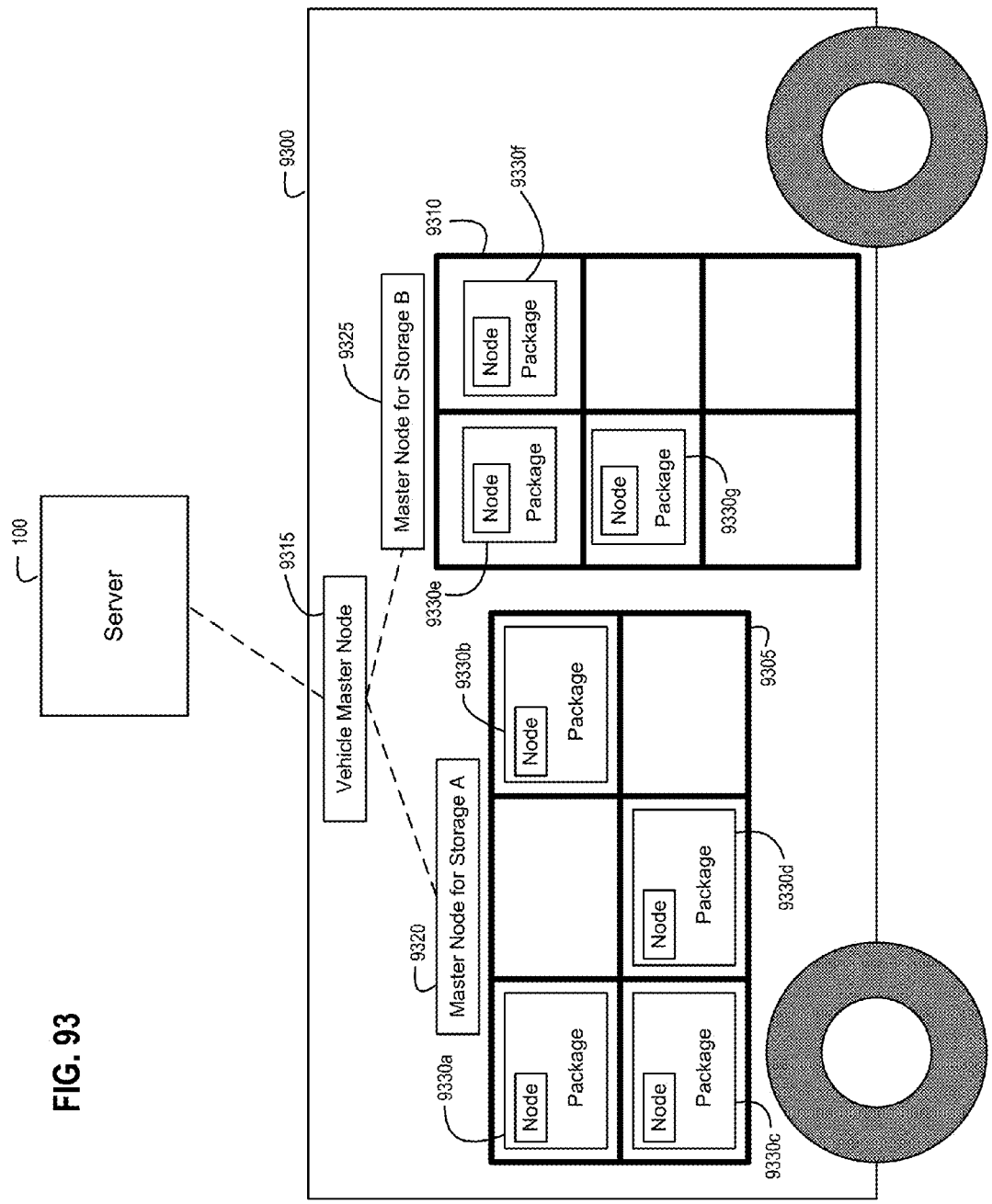
FIG. 93 is a diagram illustrating exemplary node packages located in an exemplary vehicle environment in accordance with an embodiment of the invention.

FIG. 93 is a diagram illustrating exemplary node packages located in an exemplary vehicle environment in accordance with an embodiment of the invention. Referring now to FIG. 93, exemplary vehicle 9300 is illustrated as an example of a general mobile logistics transport or conveyance carrying packages being shipped. Those skilled in the art will appreciate that vehicle 9300 may be implemented as various types of logistics conveyances (e.g., automobile, delivery van, autonomous vehicle, truck, trailer, train, aircraft, marine vessel (ship), etc.). Within exemplary vehicle 9300, packages may be placed, stored, and organized within different storage devices or units, such as storage unit A 9305 or storage unit B 9310. In general, a storage device or unit helps to maintain one or more packages in a configuration that helps to assure save shipment, minimize damage to the packages, and provide a way to organize what is being stored. Different embodiments of a storage unit may store a single package or may storage a wide variety of different types of packages that use different types of packaging materials (e.g., corrugated fiberboard boxes, wooden and non-wooden pallets, containers, etc.) and in large numbers.

Vehicle 9300 includes a vehicle master node 9315—an exemplary implementation of a master node, such as master node 110a shown and described with respect to FIG. 4. Vehicle master node 9315 is shown operative to communicate with server 100 over a longer-range communication interfaces (such as interface 485 on exemplary master node 110a) and operative to communicate with other nodes, such as master node 9320 associated with storage unit A 9305, master node 9325 associated with storage unit B 9310, and other nodes associated with parts of such storage units and node packages stored within the storage units. In more detail, each storage unit may include, in some embodiments, built-in nodes associated with particular shelves, lockers, receptacles, or other parts of the particular storage unit.

Thus, an exemplary storage unit (such as storage unit A 9305) may be a node-enabled storage unit used within a logistics vehicle to safely and intelligently transport node packages. As such, the exemplary storage unit may itself have a hierarchy of nodes (e.g., a master node, and one or more other nodes (ID nodes or other master nodes) assigned to different parts of the unit) and be operative to detect the location of particular node packages via the various location determination methods discussed herein as the node package is placed in a storage location within the unit, moved between storage locations of the unit or between different units, or simply removed from the storage location within the unit.

As shown in FIG. 93, various node packages 9330a-9330d may be kept in different storage locations of storage unit A 9305 within vehicle 9300. Similarly, other node packages 9330e-9330g are kept in portions of storage unit B 9310. Such node packages may be placed into particular storage locations according to shipping information related to the node packages. For example, the node packages may be placed into particular storage locations according to weights of the particular node packages, a planned loading scheme (such as according to an anticipated delivery schedule), to storage capacity of the particular different locations within the storage unit, or according to a storage type for the particular different locations (e.g., one location for storing envelope types of packages, another location for storing boxed container type of packages, another location for storing containerized packages (e.g., ULDs), etc.).

Figure 94:
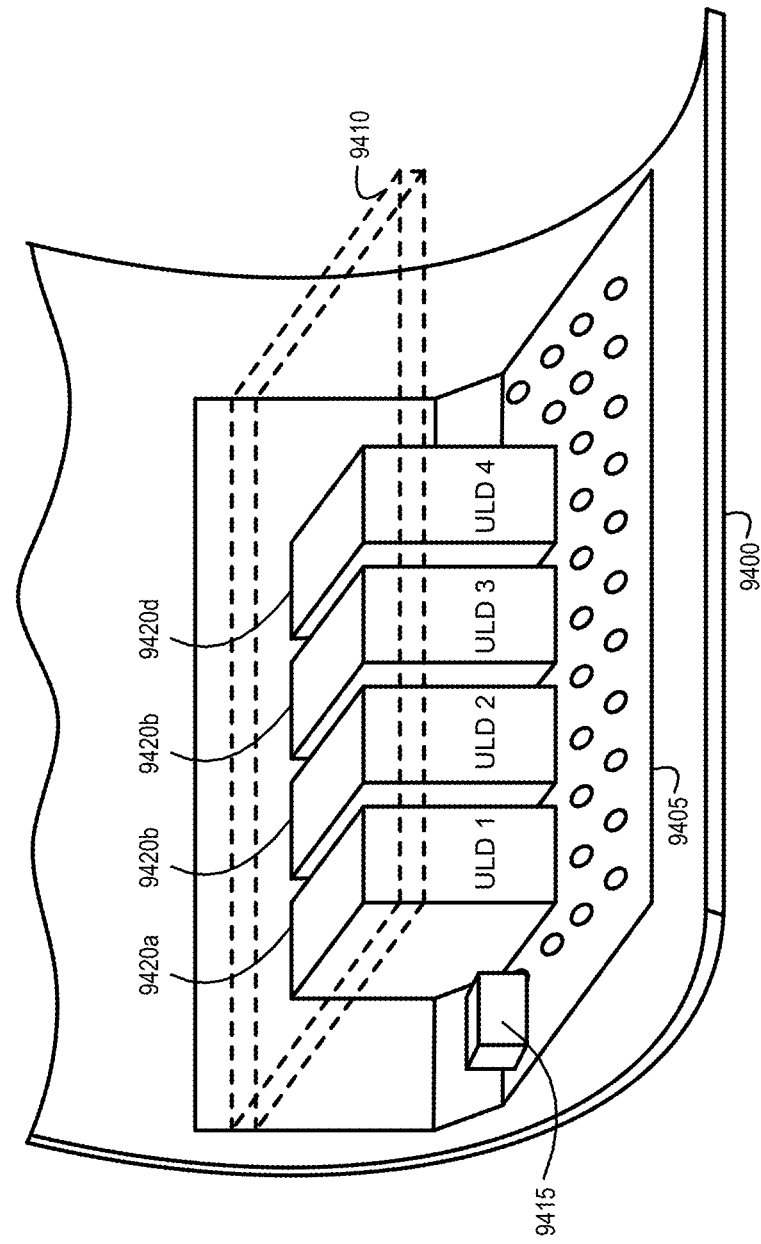
FIG. 94 is a diagram illustrating exemplary mobile storage units, such as ULDs, used as containers that help ship node packages in an exemplary airborne environment in accordance with an embodiment of the invention.

Shipping of containerized groups of packages (e.g., ULD types of containers made to optimize airborne logistics handling of packages) is an example of where a mobile storage unit (such as a movable unit load device (ULD)) may be deployed when shipping node packages in an airborne environment. FIG. 94 is a diagram illustrating exemplary mobile storage units, such as ULDs, used as containers that help ship node packages in an exemplary airborne environment in accordance with an embodiment of the invention. Referring now to FIG. 94, a cut-away perspective view of an exemplary aircraft fuselage 9400 is illustrated. In particular, an exemplary floor 9405 of a cargo storage area within fuselage 9400 is shown having multiple roller elements that help facilitate movement of cargo within the cargo area. Additionally, while not shown in FIG. 94, the cargo storage area and floor 9405 typically include structure and fastening points to help hold any cargo loaded within fuselage 9400. The cargo storage area within exemplary fuselage 9400 may be split into an upper area and a lower area by an additional floor 9410.

The cut-away perspective example illustrated in FIG. 94 shows a lower cargo area where various ULD containers 9420a-9420d are shown along with an airborne master node 9415, which is (depending on the aircraft's location and communication mode and status) operative to communicate with server 100—much like vehicle master node 9315 does as shown in FIG. 93. In general, the illustrated configuration of ULD containers 9420a-d is used similar to the storage units illustrated and described in FIG. 93. For example, each ULD container 9420a-d may have different storage locations within it and one or more master nodes (not shown) dedicated and attached internally so that they may track, monitor, and communicate with different node packages loaded within the ULD as well as other nodes and a server—much like the master node 9320 for storage unit A 9305 can track, monitor, and communicate with different node packages loaded within the storage unit as well as other nodes and server 100. Node packages within each ULD may communicate with nodes in the ULD and may communicate directly with airborne master node 9415 directly (or indirectly through other master nodes within the ULD). And as such, shipping information may be used when the node packages are placed into particular storage locations within a particular ULD according to weights of the particular node packages, a planned loading scheme for the ULDs (such as according to an anticipated delivery schedule), to storage capacity of the particular different locations within the ULD, or according to a storage type for the particular different locations.

In light of the exemplary vehicular environments shown in FIGS. 93 and 94 showing structure used when initially placing, storing, maintaining, locating, moving, and eventually removing a node package for delivery, those skilled in the art will appreciate that each of the embodiments described above related to methods for locating a node may be further enhanced when applied to an exemplary vehicular environment. For example, in one embodiment, determining a node's location may further comprise determining a location of the node-enabled package within a vehicle to be the location of the node. In a more detailed embodiment, the method that determines a node location may further generate a location message regarding where the node-enabled package is located within the vehicle based upon the determined location of the node. Such a message may be displayed to a user (e.g., logistics personnel that handle packages being shipped) on a user interface of a node or user access device operating as a node (e.g., smartphone or smart wearable device). For example, such a displayed message may be a type of an informed prompt ("Pickup Package X at Storage Location 01 in Storage Unit A") or strategic instruction ("Place Package X in Storage Location 01 in Storage Unit A") or ("Move Package X at Storage Location 01 in Storage Unit A to Storage Location 03 in Storage Unit B"). In some embodiments, the network device or node that determines the node's location may also provide such a display to the user, but in other embodiments, the location message may be transmitted to another node for display to the user.

In another embodiment, an exemplary method that determines a node's location may also access shipping information related to the node-enabled package and generate a relocation message regarding where the node-enabled package may be relocated within the vehicle based upon the determined location of the node and the accessed shipping information. Such a message may be displayed to a user similar to the location message described above—namely, that such a relocation message may be displayed to a user (e.g., logistics personnel that handle packages being shipped) on a user interface of a node or user access device operating as a node (e.g., smartphone or smart wearable device) and that in some embodiments, the network device or node that determines the node's location may provide such a display to the user, but in other embodiments, the relocation message may be transmitted to another node for display to the user.

In more detail, the shipping information may comprise weight information on the node-enabled package that is used in determining where to relocate or initially place the node-enabled package.

In another embodiment, such shipping information may be used to create a loading scheme to help organize where to locate or relocate the node-enabled packages. Thus, the location or relocation of the node-enabled package within the vehicle may be determined according to a loading scheme. In more detail, such a loading scheme may be related to an anticipated delivery schedule, where the node-enabled package may be placed within or removed from the vehicle according to the anticipated delivery schedule.

Logistics Applications of a Wireless Node Network

Figure 17:
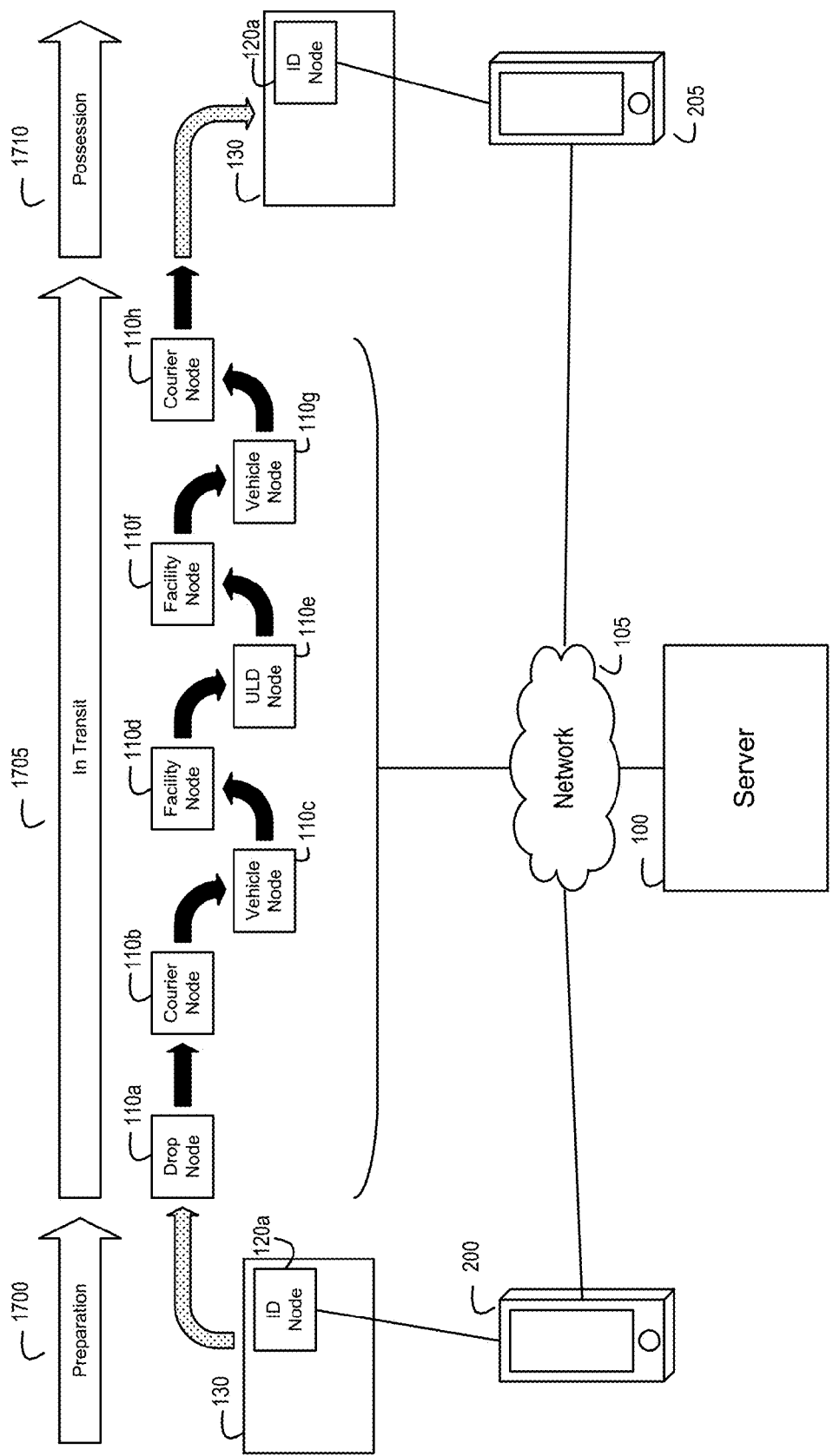
FIG. 17 is a diagram illustrating an example logistics operation using exemplary components of a wireless node network in accordance with an embodiment of the invention.

As described above, an exemplary wireless node network may be useful in a logistics application where an item is to be located. Further, such an exemplary wireless node network may also be useful in logistics applications where the item is moving between locations, and the network provides an enhanced level of visibility and management of the item within such a logistics environment. In other words, an embodiment of an exemplary wireless node network in accordance with one or more principles of the present invention helps enable enhanced logistical operations that manage information when shipping and tracking an item. FIG. 17 is a diagram illustrating an example logistics operation using exemplary components of a wireless node network in accordance with an embodiment of the invention. FIGS. 34A-34D are additional diagrams illustrating various examples of how different embodiments may also be deployed at various stages of an exemplary logistics operation.

Logistics Beyond Pickup and Delivery

Referring now to FIG. 17, an ID node 120*a* is illustrated as being deployed and associated with an item (e.g., package 130) to be shipped. As the package 130 is being prepared for shipping 1700, and is in transit as part of shipment 1705, and is in the possession of the intended recipient 1710, components of an exemplary wireless node network are deployed to manage information regarding the shipment during these three phases.

In a general example of using a wireless node network for managing logistics related to an item to be shipped, a shipping customer may initially register the item (such as package 130) with a node (such as an ID node) to be shipped from an origin location to a destination location. One or more management hand-offs of the item and node occurs as the item and the ID node collectively transit a path from the origin to the destination. Each hand-off may be based upon an awareness of the shipment path the ID node associated with package 130 will take as it is transferred through a shipping path from its origin to destination. Hand-off of the package 130 and ID node are managed and coordinated with master nodes (such as master nodes 110*a*-110*h*), which are managed by server 100, along the anticipated shipment path. During operation along the shipping path, server 100 receives information and updates from nodes, manages and authorizes hand-offs between different nodes, and tracks information related to current associations, shared data, sensor data available, locations of the nodes, and context data that helps to refine the location of nodes. Thus, with the ID node associated with package 130, the visibility of the package 130 may be extended for the customer beyond the conventional custodial control during transit 1705 as the shipping customer prepares the item for shipment 1700 prior to an initial drop-off and after delivery of the item to the recipient 1710.

In a more detailed embodiment, an exemplary method for managing logistics related to an item to be shipped using a wireless node network begins with registering a node with the item to be shipped. For example, the shipping customer may control user access device 200, and use device 200 to initially associate an ID node 120*a* and package 130 with a tracking number as part of preparing to ship the package 130 (a type of item). In one embodiment, device 200 may use a particular app or other program module resident and operating on device 200 to input the tracking number of the package 130. Device 200 then provides that information back to server 100 via network 105 to associate the tracking number with the package 130 and ID node 120*a*. Device 200, in some embodiments, may then print a label for the shipment of package 130 (and ID node 120*a*). In another embodiment, ID node 120*a* may be a pre-programmed node with pre-existing shipping and payment related information associated with it. Further details of a label-less shipping and payment in another embodiment are described below.

Concurrent with this action, the shipping customer may associate ID node 120*a* with package 130. For example, the shipping customer may place the ID node 120*a* within package 130 and, in some cases, physically attach the ID node 120*a* to a particular part of package 130. In another example, the shipping customer may place an exterior label on package 130 where the label itself includes ID node 120*a*. Other examples may effectively group ID node 120*a* with package 130 within a larger package, container, or pallet of items or packages that collectively travel together.

In this manner, device 200 may operate as a type of master node under control of the app or other program module, and be associated with the package 130 and ID node 120*a* from an association management perspective. For example, device 200 may operate via the app or other program module along with Bluetooth® hardware and software working on device 200 to communicate with ID node 120*a*. Other embodiments may rely on other short-range communication interfaces for device 200 to communicate with ID node 120*a*. And in one embodiment, device 200 may receive one or more security credentials from server 100 in order to connect and actively pair or connect with ID node 120*a*.

With at least the shipping information at the server 100, server 100 may determine a predicted shipping path for the package 130. In one embodiment, server 100 may have historic data indicating an optimal route for shipping an item from point A to point B that uses a particular shipping path (e.g., pick-up near A by a particular courier, transport by vehicle to a particular facility, further transport via aircraft to another facility near point B, and transport by vehicle to facilitate delivery by a courier at point B). In one example, the predicted path may only be for a portion of the route between two points, such as an origin point and a destination point.

In a further example, the predicted path (or part thereof) may be adjusted based on the contextual environment of an item being shipped. For instance, depending on context data (such as weather information, historic data on success for particular transit segments, capacity information for third party carriers, etc.), server 100 may alter the initially predicted shipping path to provide a refined predicted shipping path that is more optimized under the current conditions and context. This allows the server 100 to further anticipate which master nodes may be used along an anticipated shipping path (or refined shipping path), to help efficiently manage shipment of the package 130 to point B. Those skilled in the art will further appreciate that an embodiment may only partially identify what master nodes may be used along the anticipated shipping path (or refined shipping path), and that further master nodes may be identified as the package 130 is actively in route to point B depending on context data (e.g., master node availability, weather information, etc.).

In a more detailed example, server 100 may use sort data analytics to predict an appropriate shipping path along which the package 130 and the ID node 120*a* will travel, identifying predicted master nodes the ID node 120*a* will be within range of during its journey. In the example flow illustrated in FIG. 17, nodes 110*a*-110*h* refer to different master nodes along an exemplary predicted shipping path, which includes at least a pick-up and drop-off of ID node 120*a* and package 130 at an origin and destination, respectively.

In one example, the shipping customer may place package 130 and its associated ID node 120*a* in a drop box or repository for items to be shipped. In the illustrated example of FIG. 17, drop box is represented as drop node 110*a*. Essentially, drop node 110*a* may be implemented with a type of master node connected to or integrated into a drop box or locker unit type of logistics repository (more generally referred to herein as a node-enabled logistics receptacle). As the shipping customer physically places ID node 120*a* into drop node 110*a*, device 200 may hand-off ID node 120a to drop node 110a, update server 100 with this association information, and disassociate from ID node 120a. In this manner, the system has visibility into the status and location of an item (such as package 130) prior to pick-up from drop node 110a. Further details of an exemplary node-enabled logistics receptacle are described below.

At the drop node 110a, a courier may pick-up the package 130 and ID node 120a. The courier has a courier node 110b, which knows the tracking number and associated ID node 120a at time of pickup, or looks up the ID node 120a MAC address based on a captured tracking number (part of information broadcast or advertised by ID node 110a. Basically, the master node responsibility transfers to or is otherwise handed off to courier node 110b, which now acts as a master node actively connected and associated with ID node 120a (by virtue of communications from courier node 110b back to server that authorizes the association of ID node 110a with courier node 110b and disassociates drop node 110a with ID node 110a).

Similar handoffs occur between different master nodes and ID node 120a occur as package 130 and ID node 120a transit the anticipated shipping path in accordance with instructions sent to different master nodes by server 100. In one embodiment, associations are accomplished during such handoffs with security credentials requested, authorized, and transmitted to the appropriate master node. In another embodiment, associations are merely passive associations that do not require active and authorized pairings. Yet, the passive association still may allow the system to keep track of ID node 120a and package 130 as they transit the anticipated shipping path.

New associations (active and passive) and disassociations are updated to server 100. And server 100 may change programming in different nodes as package 130 and ID node 120a transit the shipping path—such as changing the operation of a master node (such as ULD node 110e) to shift to operating as an ID node while airborne or when GPS signals are lost. In another example, certain mobile types of node may have responsibilities changed to wired types of nodes as a way of preserving the power of a mobile type of node. If ID node 120a fails to associate for a certain interval and needs to be reacquired, ID node 120a may update its status flag to a particular Alert Stage and may attempt to communicate with an increasingly broader range of master nodes in order to be found.

During the transit, server 100 may share information with different nodes, such as context data, timer/clock data, environmental data, etc. Sensor data from the ID node 120a may be gathered via scans from a master node, and then forwarded back to server 100. And as server 100 manages the associations, handoffs, and information going to and coming from ID node 120a (via master nodes), server 100 is able to determine the location of ID node 120a using one or more of the various location determination techniques described above. As such, server 100 is able to provide information related to the ID node 120a and its related package 130 in response to requests for such information.

When package 130 and ID node 120a arrive at the destination (e.g., point B), courier node 110h may update server 100 once ID node 120a is placed at the destination and disassociated with courier node 110h. However, visibility need not end at such a drop-off event (such as arriving at the destination). The recipient customer's user access device 205 may act as another master node, and associate with ID node 120a after delivery. In one example, server 100 is notified by courier node 110h that delivery has been made. Thereafter, server 100 may notify device 205 with this information. In response, an app or other program module on device 205 may cause device 205 to operate as a node and to actively seek association with ID node 120a. When device 205 and ID node 120a connect and are given authorization by server 100 to actively associate, server 100 is notified and may provide further information to device 205 (e.g., sensor data, etc.) and may be able to determined updated location data about ID node 120a and package 130 after delivery has occurred. In another example, active association may not be needed between device 205 and ID node 120a as status information may still be gathered by device 205 via passive association, where the status information provides further visibility regarding the ID node 120 after delivery to the destination.

FIGS. 18 and 19 are flow diagrams illustrating various exemplary methods for managing a shipment of an item using a wireless node network, such as that illustrated in FIG. 17. Referring now to FIG. 18, exemplary method 1800 begins by transmitting shipping information to the server to register the ID node and the item to be shipped at step 1805 and associating the ID node to a first master node related to a predicted path for shipping the item at step 1810. At step 1815, the server is updated to reflect the association between the ID node and the first master node. Typically, this may come in the form or a communication from the first master node to the server. When the first master node is a user access device (e.g., one of a laptop computer, a desktop computer, a tablet device, a personal area network device, a smartphone device, and a smart wearable device) that is operated by a shipping customer, the server may be updated to become aware that the ID node is associated with the first master node prior to a pick-up event in the predicted path.

For example, a shipping customer may use their smartphone to enter shipping information and register that the ID node and the item (such as package 130) are to be shipped from an origin point to a destination point. Prior to when the item and ID node are picked up by an initial courier (e.g., from a drop box, locker unit, or other receptacle), the shipping customer's smartphone operates as the first master node and is associated with the ID node. As such, and with an update to the server, the server now has visibility into the status and location of the ID node prior to a pick-up event in the predicted shipping path from the origin point to the destination point.

The method 1800 may continue at step 1820 by disassociating the ID node and the first master node when associating the ID node and a second master node related to the predicted path as the ID node transits the predicted path. In one example, the ID node need not disassociate with the first master node commensurate with associating with the second master node. Thus, those skilled in the art will appreciate that the ID node may be associated with one or more master nodes at a given point in time and may be selectively disassociated with certain master nodes depending on the need for the ID node to securely share data with different master nodes.

At step 1825, the server is updated to reflect the disassociation between the ID node and the first master node (if that has occurred yet) and the association between the ID node and the second master node as the ID node continues to transit the predicted path. At step 1830, the method may associate the ID node to a third master node near an end of the predicted path for shipping the item, and then at step 1835 notifies the server to reflect the association between the ID node and the third master node.

In the method 1800, associating the ID node to the third master node in step 1830 may be performed after a drop-off event in the predicted path. The method may also rely upon context data to adjust for an environmental aspect of the predicted path when associating the ID node to any of the first, second, or third master nodes.

For example, after the item and ID node are delivered to or near the destination, the recipient's smartphone may operate as the third master node associated with the ID node. Data, such as sensor data, may be shared with the recipient while the recipient's smartphone operates as the third master node associated with the ID node. As such, and with an update to the server, the server now has visibility into the status and location of the ID node after a drop-off event.

Thereafter, the recipient may unregister the ID node and item given the item is now in the recipient's possession and control. For example, the recipient may remove the ID node from the item (e.g., the package 130), deactivate the ID node to otherwise power down the device, update the server regarding the deactivated status of the ID node (and the disassociation of ID node and the third master node), and then clean up and/or recharge the ID node for future use in shipping another item.

Method 1800 may also include receiving context data related to the predicted path. In one embodiment, such context data may advantageously allow for adjustments due to one or more environmental aspects of the predicted path when associating the ID node to any of the master nodes. For example, the context data may include scan data indicating the type of material in package 130 (the item), which may cause RF shielding issues with the ID node.

Referring now to FIG. 19, exemplary method 1900 is explained from the perspective of the server, which can authorize certain types of node associations. The server may be updated, in some embodiments, with association information when an ID node and a master node are passively associated. In such a situation, the nodes have not established an authorized association where they can securely share data. However, as method 1900 explains in more detail, an embodiment may manage a shipment of an item when active associations are established.

Method 1900 begins with the server receiving shipping information to register the ID node and the item to be shipped in step 1905. The method 1900 then provides a first set of authentication credentials (e.g., security pin information) to a first master node to permit the ID node to associate with the first master node related to a predicted path for shipping the item at step 1910. In one example, the first master node may be a user access device, such as a laptop computer, a desktop computer, a tablet device, a personal area network device, a smartphone device, or a smart wearable device. And step 1920 may be performed prior to a pick-up even in the predicted path.

At step 1915, the server receives an update to reflect the association between the ID node and the first master node. The method 1900 then provides a second set of authentication credentials to a second master node to permit the ID node to associate with the second master node and disassociate the ID node from the first master node as the ID node transits the predicted path at step 1920. At step 1925, the server then receives an update to reflect the association between the ID node and the second master node as the ID node continues to transit the predicted path (or a portion of a predicted path). When the ID node and the first master node disassociate, the server may also be updated.

In some examples, the method 1900 may have the server provide a third set of authentication credentials to a third master node to permit the ID node to associate with the third master node as the ID node reaches an end of the predicted path for shipping the item at step 1930. In some examples, this step may be performed after a drop-off event in the predicted path.

Finally, at step 1935, the server receives a notification that reflects the association between the ID node and the third master node. When the ID node and the second master node disassociate, the server may also be updated.

In method 1900, another embodiment has the server providing any of the master nodes with context data related to an environmental aspect of a part of the predicted path. For example, exemplary context data may include layout data related to a facility in which the ID node is moving between master nodes. In more detail, the received context data may be relied upon to adjust for an environmental aspect of the predicted path when associating the ID node to any of the first, second, or third master nodes.

In still another embodiment, method 1900 may also determining a location of the ID node based upon association information received by the server and location information related to at least one of the first, second, or third master nodes.

As previously discussed, the server may predict a transit route from a first point to a second point along at least a portion of the predicted path for shipping the item. In one example, the first point is an origin and the second point is a destination point with both being identified in the shipping information of the item. However in other examples, the first and second point along a predicted path may merely be interim points without encompassing the originating shipment point or the ultimate destination of the item being shipped. Further, another example may adjust the predicted path as the ID node transits the path. In this way, the server may adapt based upon, for example, context data, so as to optimize or at least account for a changing contextual environment when managing the shipment of an item.

In another embodiment, a non-transitory computer-readable medium is disclosed that contains instructions, which when executed on a processor (e.g., processor 500 of server 100), performs another embodiment of a method for managing a shipment of an item using a wireless node network having at least one ID node, a plurality of master nodes, and a server. In this embodiment, the exemplary method begins with the server receiving shipping information to register the ID node and the item to be shipped. The method predicting a first portion of a transit route for the item from a first point to a second point. For example, a first point may be the origin point and the second point may be the destination point—both of which are identified in the shipping information. In another example, the first and second points are any two points along the transit route. Furthermore, the transit route may be predicted as a series of portions or segments that may use particular types of master nodes during transit (e.g., master nodes used by a particular courier for pick-up, an anticipated vehicle used by the pickup courier, one or more anticipated facilities that may be used by the vehicle, an anticipated air route (e.g., an anticipated departing airport, an anticipated aircraft, anticipated types of containers such as a type of ULD or pallet used on the aircraft, and an anticipated arriving airport), a facility near the anticipated arriving airport, a vehicle used to carry the item, and a courier that may deliver the item at the destination point). Those skilled in the art will realized that some of the potential portions of an exemplary predicted path or transit route may be relatively simple for a local delivery, or may be quite complex from an intermodal perspective when the origin point and destination points are very far away from each other.

Next, the method authorizes a first master node to associate or connect with the ID node near the origin point. This may be done prior to a pick-up event for the ID node and item being shipped. For example, when the first master node is a user access device (e.g., a laptop computer, a desktop computer, a tablet device, a personal area network device, a smartphone device, and a smart wearable device) for the shipping customer, visibility as to the status and location of the ID node may be extended to prior to a pick-up event. In one embodiment, such an authorization is performed by the server 100 when it receives information from the first master node regarding the ID node, determines that the first master node and the ID node should be actively paired and associated, and the server 100 sends the appropriate security pin information as a type of authorization credentials that permit the first master node to actively pair and connect with the ID node. After the first master node is associated with the ID node, the server receives an update reflecting the association.

Next, the server may authorize a second master node to associate with the ID node as management responsibility of the ID node is handed off from the first master node to the second master node at the second point on the predicted transit route. In one embodiment, the method may authorize the first master node to disassociate with the ID node. However, in other embodiments, the first master node may stay associated with the ID node—even after the ID node is authorized to associate with the second master node. The server then receives an update to reflect the association between the ID node and the second master node as the ID node continues on the predicted first portion of the transit route.

The method may further authorize the second master node to disassociate with the ID node and a third master node to associate with the ID node as management responsibility of the ID node is handed off from the second master node to the third master node near the destination point on the predicted transit route. This may be done prior to a pick-up event for the ID node and item being shipped. For example, when the third master node is a user access device (e.g., a laptop computer, a desktop computer, a tablet device, a personal area network device, a smartphone device, and a smart wearable device) for the recipient, visibility as to the status and location of the ID node may be extended to after a drop-off event. After the third master node is associated with the ID node, the server receives a notification to reflect the association between the ID node and the third master node.

And during the method, the server may determine a location of the ID node based upon association information received by the server and location information related to at least one of the first, second, or third master nodes. As discussed above, various techniques are available for locating a node and, in some cases, adjusting for adverse RF environmental conditions with context data to more accurately refine the location of a node. As such, the server keeps track of the location of nodes in the wireless node network, and may provide that information (as well as other types of shared or sensor information) when requested and authorized to do so.

From a system perspective of such a logistics application of a wireless node network, an exemplary system is disclosed for managing a shipment of an item using a wireless node network. With reference to FIG. 17, the exemplary system generally comprises an ID node (such as node 120a), a plurality of master nodes (such as nodes 110a-110h), and a server (such as server 100). The ID node is registered to the item (such as package 130) being shipped. Each of the master nodes are predicted to be located at a different part of an anticipated transit route for the item as the item is shipped from an origin point to a designation point of the anticipated transit route. Each of the master nodes is operative to communicate with the ID node over a short-range communication path, and operative to communicate with other master nodes and the server 100.

The server operates to track and report a location of the ID node and a location of the master nodes. As shown in FIG. 17, server 100 relies on network 105 to communicate with different master nodes (110a-110h) as well as user access devices 200, 205 that may operate and function as a master node associated with ID node 120a at certain times. As previously discussed, server 100 may employ a variety of different techniques (or a combination of different techniques) for determining the location of ID node 120a or one of the other nodes in the network.

The server is also operative to facilitate the transfer of management responsibility of the ID node between different master nodes as the ID node moves along the anticipated transit route. For example, as discussed above, nodes communicate via broadcast and scanning methods, and may be associated under control of the server 100 as part of managing the wireless node network. In this way, a first of the master nodes may be associated with the ID node prior to a pick-up event for the ID node and item to be shipped. In one example, user access device 200 may operate as a master node and be associated with ID node 120a prior to being placed into drop node 110a and picked up by a courier from the receptacle related to that drop node 110a.

Later, a second of the master nodes may be associated with the ID node after the ID node is disassociated with the first of the master nodes at an intermediate point of the anticipated transit route. And, a third of the master nodes may be associated with the ID node after a drop-off event for the ID node and item to be shipped. For example, user access device 205 may operate as a master node and be associated with ID node 120a after the ID node 120a and item are dropped off at an intended destination point (e.g., a type of drop-off event).

In an embodiment of the system, each of the master nodes may be operative to update the server upon completing a disassociation or association with the ID node. This provides the server with association information with which it can use to manage and track the nodes in the wireless node network. When associating nodes, the server may be operative to transmit a set of authorization credentials to one of the master nodes and the ID node to authorize a desired association between the master node and the ID node. The server may also be operative to determine the location of the ID node based upon context data, such as information relating to an environmental aspect of a part of the anticipated transit path (e.g., RF shielding aspects of the item being shipped with the ID node or a container holding the ID node, building layout information, etc.).

Those skilled in the art will readily appreciate that operations of such an exemplary wireless node network, as set forth herein, are not limited to tracking just a package, but may be used to manage logistics and tracking of other types of items, such as an object or a person. Indeed, some embodiments provide enhanced capabilities that facilitate better tracking of items, objects, and people as they move to a more restrictive indoor environment, by using a low power ID node in advertising mode in the presence of one or more master nodes.

Proactive Shipping Label Generation

While FIG. 17 provides an overview of an example logistics operation as package 130 and related ID node 120a transit a shipping path, FIGS. 34A-D illustrate more detailed embodiments of operations at particular stages of an example logistic operation involving shipment of package 130 and related ID node 120a.

Figure 34A:
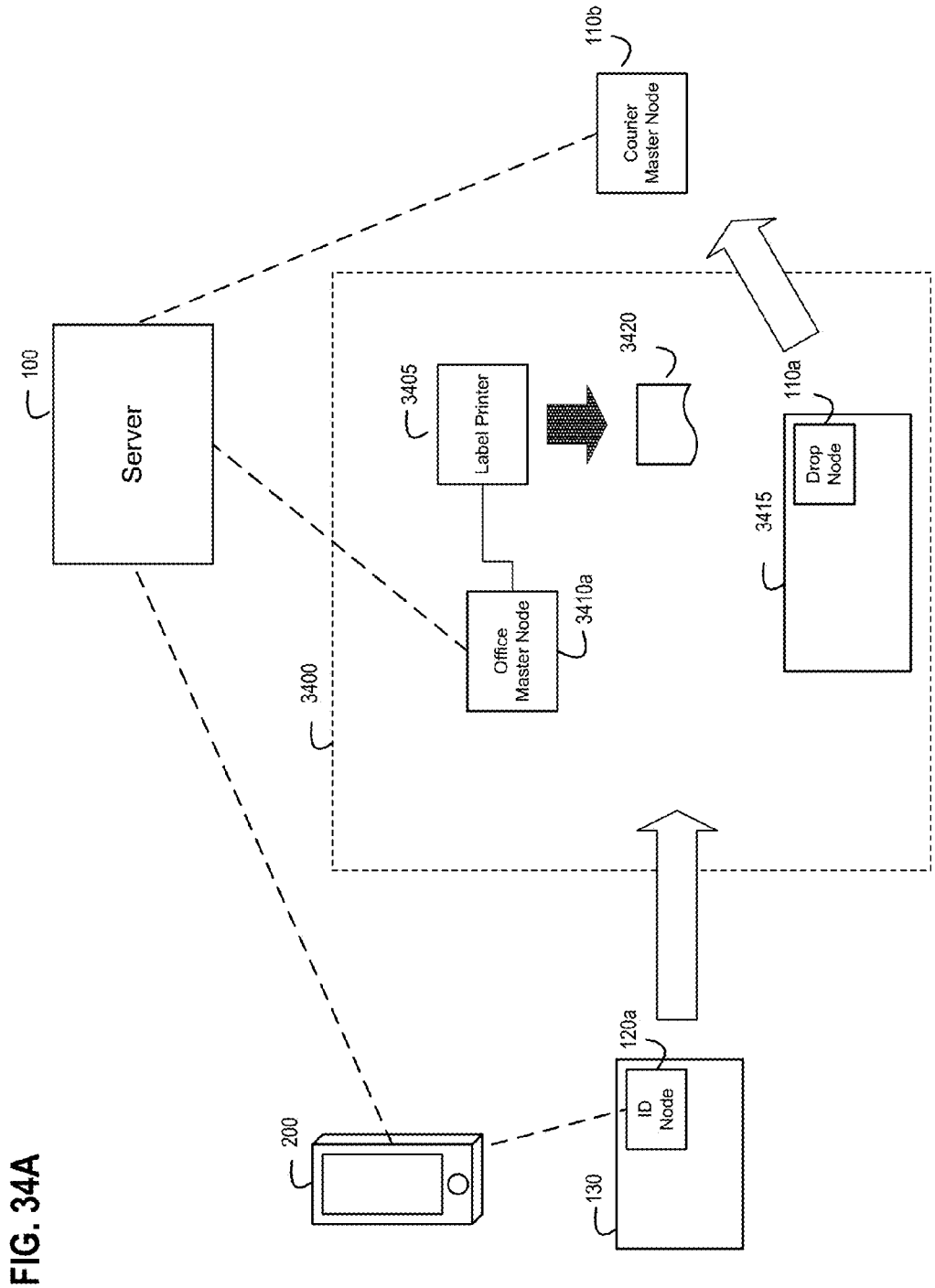
FIGS. 34A-34D are diagrams illustrating various exemplary stages of an example shipping and logistics operation using exemplary components of a wireless node network in accordance with an embodiment of the invention.

In one stage, the shipping customer is dropping off an item to be shipped at a shipping facility. FIG. 34A is a diagram showing an exemplary shipping facility that employs an exemplary wireless node network to help at this stage. Referring now to FIG. 34A, package 130 and related 120 node 120a are illustrated being taken by a shipping customer to a shipping facility 3400 (e.g., such as a FedEx® Office Print & Ship Center or the like). In a general example, the shipping customer has entered or otherwise provided or registered shipping information for an intended shipment of an item and that shipping information may be maintained on server 100.

When approaching the shipping facility, the shipping customer may interact with a wireless node system for generating a shipping label via a variety of embodiments of a node associated with the shipping customer. In one example, as shown in FIG. 34A, the shipping customer may approach the shipping facility 3400 with the item to be shipped already in a package 130, which has a node 120a (e.g., an ID node as illustrated or a mobile master node) in the package 130. In another example, the package 130 may have the node integrated as part of the package (generally referred to here as a "node package").

In another example, the shipping customer may simply approach the shipping facility with a smartphone 200 (a type of user access device) and the item to be shipped but without a package 130 or node 120a. Here, the smartphone 200 may operate as a type of master node that can use a longer range communication path to communicate with the shipping facility's master node 3410a. Doing so may use a particular app (a type of programmable code similar to that of code 425). And as the smartphone 200 gets closer to the shipping facility, the device may changes modes and operate as a type of ID node (e.g., using a shorter range communication path to communicate with the shipping facility's master node 3410a or in a temporary ID node mode that operates without the ability to self-locate via GPS when the shipping customer goes inside the shipping facility). Thus, the node associated with the shipping customer may be implemented in a variety of ways—e.g., ID node, master node, a user access device operating as a type of node—so that the shipping facility can proactively provide an enhanced customer experience with generating shipping labels, offering packages or specialized packaging materials, and offering tailored coupons for the shipping customer.

In one example where the shipping customer has already packaged the item into a package, prior to arriving at office 3400, the shipping customer may have registered package 130 and ID node 120a to be shipped from an origin point to a destination point. For example, the shipping customer may use their smartphone (e.g., a type of user access device 200) and a particular app (a type of programmable code) operable on that device to facilitate registration of package 130 and ID node 120a to be shipped, and to identify a desired drop-off location for the package 130 (and its related ID node 120a). As the shipping customer travels to the desired drop-off location (e.g., shipping facility 3400) and approaches the facility, the system is aware and anticipating the customer's arrival. An office master node 3410a may detect ID node 120a and proactively cause printer 3405 to generate a shipping label 3420 for package 130, and in some cases prompt shipping facility personnel regarding the shipping customer, generate a coupon, prompt the shipping customer directly about offers related to their retail experience in the shipping facility, and the like.

Figure 35:
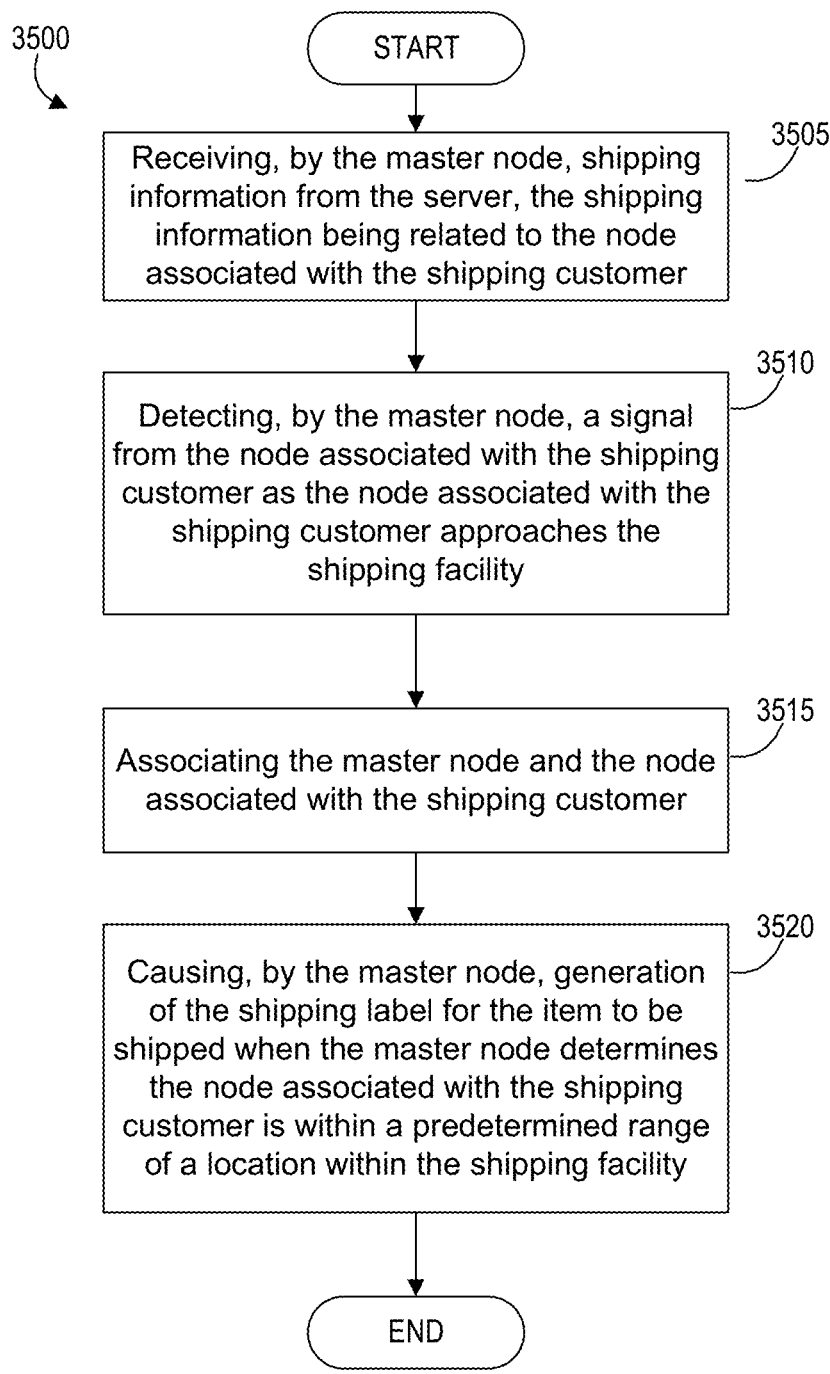
FIG. 35 is a flow diagram illustrating an exemplary method for generating a shipping label for an item to be shipped using a wireless node network in accordance with an embodiment of the invention.

FIG. 35 is a flow diagram illustrating an exemplary method for generating a shipping label for an item to be shipped using a wireless node network in accordance with an embodiment of the invention. Referring now to FIG. 35, method 3500 begins at step 3505 where the master node receives shipping information from the server. The shipping information is related to the node associated with the shipping customer.

As explained above in more detail, the node associated with the shipping customer may be implemented in embodiments of method 3500 as an ID node, a master node, a node package, a user access device operating as an ID node, a user access device operating as a master node, or a master node operating in a temporary ID node mode. And in more detail, the shipping customer's master node may be operative to transition how it communicates with the shipping facility's master node—namely being operative to transition from communicating over a longer range communication path but, when the shipping customer's master node can receive a signal from the master node associated with the shipping facility, switching over to communicating over a short range communication path. For example, a shipping customer's mobile master node (e.g., their smartphone operating an app that enables operation of the device as a mobile master node) may use a cellular or WIFI longer range communication range path as the shipping customer approaches the facility, and then transition to communicating with the facility's master node over a shorter range Bluetooth® communication path when the smartphone can received a signal from the facility's master node over that shorter range path.

At step 3510, method 3500 continues with the shipping facility's master node detecting a signal from the node associated with the shipping customer as the node associated with the shipping customer approaches the shipping facility. In the FIG. 34A example, the signal from the shipping customer's ID node 120a may be an advertising signal with header information indicating the ID node 120a is associated with package 130 and may be looking for nodes with which to associate (passively or actively). Once detected, the shipping facility's master node and the ID node are associated at step 3515.

At step 3515, method 3500 continues by associating the master node and the node associated with the shipping customer. Such an association may involve establishing a passive association between the facility's master node and the node associated with the shipping customer without requiring a secure connection between the master node and the node associated with the shipping customer. In another example, such an association may involve establishing an active association between the master node and the node associated with the shipping customer, where the active association reflects a secure connection between the facility's master node and the node associated with the shipping customer. And in a further embodiment, method 3500 may have the master node be operative to update the server with updated association data when the master node is no longer associated with the node. In the example shown in FIG. 34B, office master node 3410a may still be associated with ID node 120a when package 130 is placed within receptacle 3415. However, drop node 110a associated with receptacle 3415 may detect and associate with ID node 120a. And at some point in time, for example with the package 130 has been in receptacle 3415 for a particular duration or when the package 130 is picked up from receptacle 3415 by a courier, office master node 3410a may disassociate with ID node 120a. At that time, other nodes are associated with ID node 120a and may facilitate tracking and management with server 100.

At step 3520, method 3500 concludes with the facility's master node causing the generation of the shipping label for the item to be shipped. This happens when the facility's master node determines the node associated with the shipping customer is within a predetermined range of a location within the shipping facility. For example, referring to FIG. 34B, ID node 120a (as a type of node associated with the shipping customer) and package 130 are now within the shipping facility 3400 and closer to office master node 3410a, which may be deployed at a drop off counter location within the facility 340. As ID node 120a approaches office master node 3410a at that location or some other designated location within the shipping facility, the location of the ID node 120a will enter a predetermined range distance from office master node 3410a. At that point, office master node 3410a may instruct the printer 3405 (e.g., via wired or wireless connection) to generate a shipping label 3420 for the package 130 to be shipped. In another example, the office master node 3410a may determine the ID node 120a is within a predetermined range of a shipping department drop off receptacle 3415 (e.g., an example of a designated location within the shipping facility).

In a more detailed embodiment, the location within the facility may be a type of designated points, such a drop off location for the item and node (e.g., a desk, counter, receptacle, etc.), a generation location for the shipping label (e.g., an area near a printer within the shipping facility), and a pickup location for the shipping label (e.g., a desk, counter, receptacle, etc.).

In a further embodiment, the method 3500 may further include the shipping facility's master node determining that the node associated with the shipping customer is within the predetermined range of the designated location by instructing the node associated with the shipping customer to alter an RF power characteristic (e.g., an RF transmission power level) as part of locating the node associated with the shipping customer.

Figure 34B:
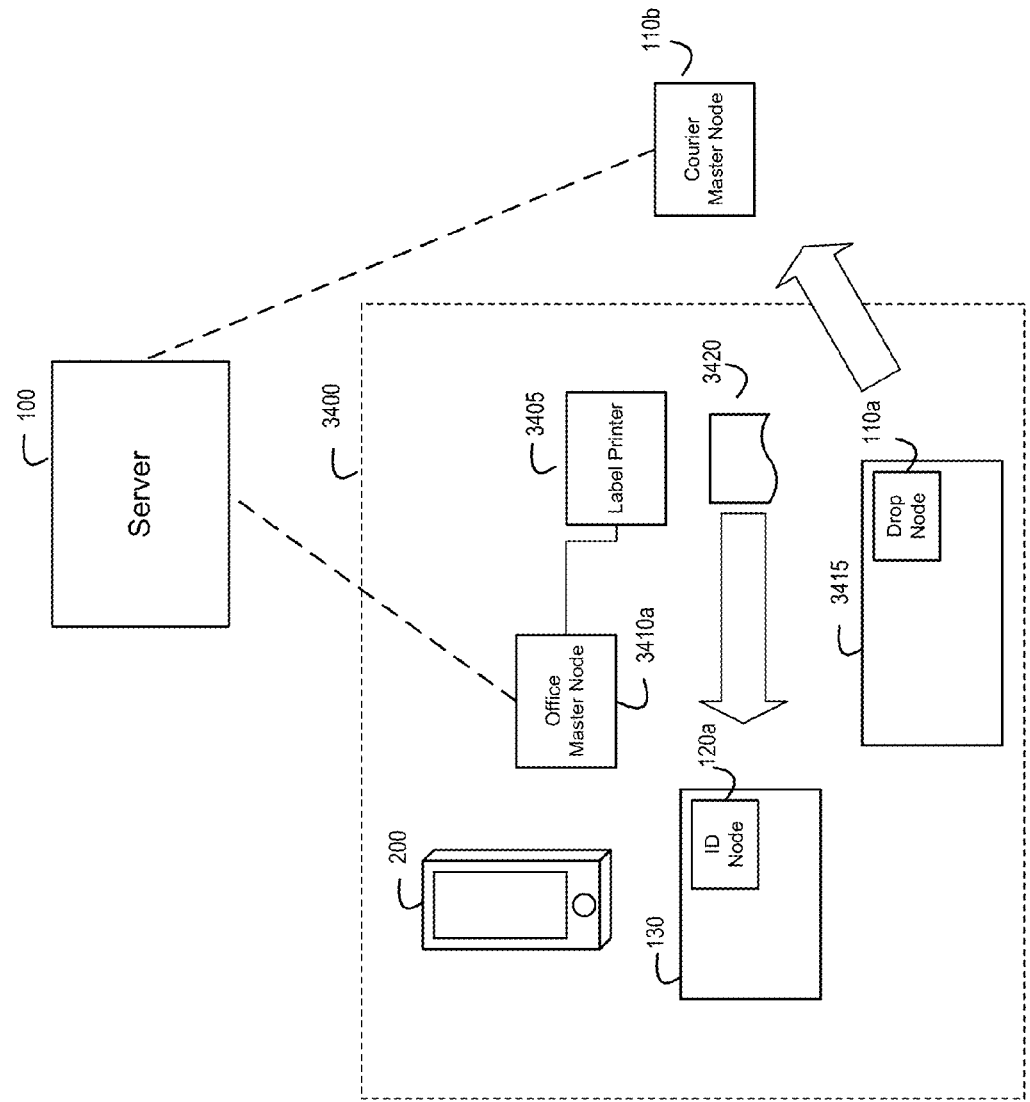

In general, an exemplary shipping label accompanies the item being shipped (and any ID node related to the item, such as ID node 120a within package 130). Examples of shipping label 3420 may include a human readable label with information, such as a tracking number associated with the shipping information, an address associated with the shipping information, information about a user shipping the item. And the label may also include one or more machine readable references, such as a scannable image (e.g., barcode) or scannable tag (e.g., RFID tag), to attach to the item to be shipped. As shown in FIG. 34B, the generated shipping label 3420 may be placed on package 130 prior to placement of package 130 (and ID node 120a) within receptacle 3415.

In still another embodiment, method 3500 may also include updating the server when the master node is no longer associated with the node associated with the shipping customer. The server may also be updated, in a further embodiment, with location metric information related to analytics on movement of the node associated with the shipping customer within the shipping facility. For example, as shown in FIG. 34A, as the office master node 3410a tracks the ID node 120a within shipping facility 3400, the master node may collect, record, and forward location metrics (e.g., position, time, movement directions) to server 100 as part of data analytics quantifying efforts to understand how and where the ID node and/or the shipping customer with their smartphone moves within the shipping facility 3400. In more detail, the office master node 3410a may track metrics related to how long the ID node 120a stays in receptacle 3415 before a courier picks up package 130. In still another embodiment, the office master node 3410a may track metrics related to how long it takes to print out certain types of shipping labels, and use such metrics (by the server or master node) to adjust the predetermined range distance so that the shipping label is optimally generated so to best assist the shipping customer and operations of the shipping facility 3400.

Those skilled in the art will appreciate other sales and shipping related logistics metrics may be tracked and uploaded to the server 100, so that server 100 can learn about operations within shipping facility 3400 and leverage use of that information as a type of historic data when attempting refine locations of nodes being tracked in the future. Thus, the node's movements and tracking information on that within the shipping facility provides a type of data source for analytics to help the facility understand the consumer experience—for the shipping customer when the node is, for example, the customer's smartphone; or for a package that is node-enabled and is processed within the shipping facility.

In another embodiment, method 3500 may have the facility's master node causing the generation of one or more additional shipping labels when the master node determines the node associated with the shipping customer is within a predetermined range of a location within the shipping facility. Thus, the shipping information may indicate the need for any additional shipping labels and the embodiment allows for the proactive generation of such labels.

In a further embodiment, method 3500 may also proactively provide the shipping customer with one or more coupons as part of their experience in coming to the shipping facility and interacting with the facility's wireless node network. In more detail, method 3500 may have the master node cause generation of a coupon for packaging material for the item to be shipped, or other consumables offered by the facility. Should the shipping customer be determined to be a priority customer (e.g., a frequent consumer of the facility, a designated representative of a corporate client of the shipping facility, or the like), an embodiment may have the facility's master node generating a notification for shipping facility personnel by the master node prior to generating the shipping label, the notification indicating that the shipping customer is the priority customer Additionally, certain embodiments may have the facility's master node providing messages to prompt different people. In one example, the master node may provide a message to a user access device operated by shipping facility personnel, where the message causes the user access device to display a prompt related to offering the shipping customer packaging material. In another example, the facility's master node may directly provide a message to the node associated with the shipping customer, where the message causes the node to display a prompt related to an offer for packaging material. In still another example, the facility's master node may provide a message to a user access device operated by shipping facility personnel, where the message causes the user access device to display a prompt related to offering the shipping customer a specialized packaging material for the item to be shipped based upon a value of the item being shipped as identified in the shipping information. Further still, the facility's master node may provide a message to a user access device operated by shipping facility personnel, where the message causes the user access device to display a prompt related to offering the shipping customer a specialized packaging material for the item to be shipped based upon an indication that the item to be shipped is fragile. As part of such prompting examples, further embodiments contemplate more interactive messages where the shipping customer may be able to, for example, select which type of specialized packaging material they want to use, or which type of coupons they would like to redeem.

Referring back to the example shown in FIG. 34A, office master node 3410a may interact with the printer 3405 directly or indirectly when causing generation of the shipping label in an embodiment. In one example, label printer 3405 is directly coupled to office master node 3410*a*. However, in another example, the label printer 3405 may be directly connected to another computer system (e.g., an order management system (not shown) that communicates directly or indirectly with server 100 and helps facilitate shipping orders and payment for the same). Thus, while not directly connected to office master node 3410*a*, office master node 3410*a* may still be able to communicate and cause the printer 3405 to generate the label 3420 via indirect connections (e.g., WiFi or wired LAN connection from office master node 3410*a* to the order management system, or network connections from office master node 3410*a* to server 100, which may communicate separately with printer 3405). Additionally, server 100 may be operative to cause printing to occur on printer 3405.

Those skilled in the art will appreciate that method 3500 as disclosed and explained above in various embodiments may be implemented on a network device, such as office master node 3410*a* illustrated in FIG. 34A, running one or more parts of master control and management code 425 to implement any of the above described functionality. Such code may be stored on a non-transitory computer-readable medium such as memory storage 415 on a master node (such as office master node 3410*a*). Thus, when executing code 425, the master node's processing unit 400 may be operative to perform operations or steps from the exemplary methods disclosed above, including method 3500 and variations of that method.

Payment Transactions Using Node Association

In the example shown in FIG. 34B, the shipping label 3420 may be on package 130 and the shipping customer may desire to pay for shipping the package 180 to its intended destination. In one embodiment, payment may be facilitated using an association established between nodes. In other words, the shipping customer may utilize a node, and based upon an association between the customer's node and the payment receiver's master node, a payment transaction may be conducted.

Figure 36:
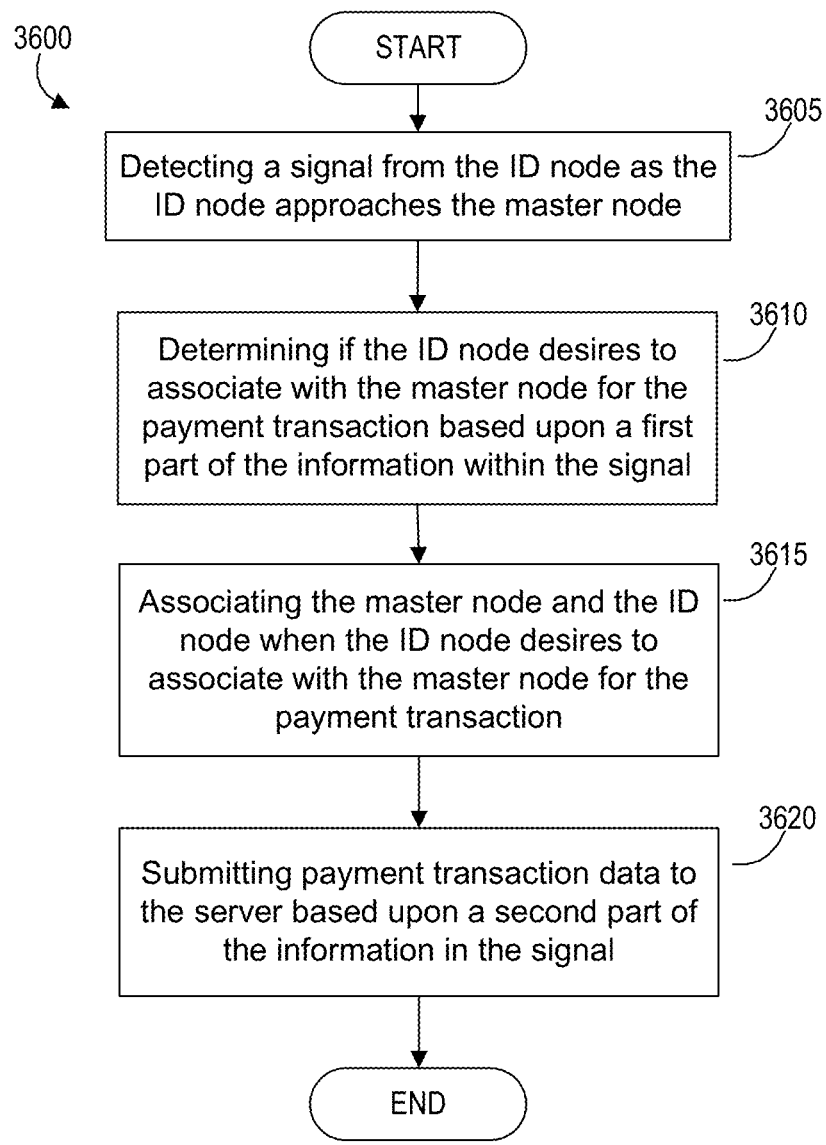
FIG. 36 is a flow diagram illustrating an exemplary method for conducting a payment transaction using a node association in a wireless node network in accordance with an embodiment of the invention.

FIG. 36 is a flow diagram illustrating an exemplary method for conducting a payment transaction using a node association in a wireless node network in accordance with an embodiment of the invention. Referring now to FIG. 36, exemplary method 3600 begins at step 3605 by detecting, by the master node, a signal from the ID node as the ID node approaches the master node, the master node being related to a payment receiver and the ID node being related to a payment provider.

At step 3610, determining, by the master node, if the ID node desires to associate with the master node for the payment transaction based upon a first part of the information within the signal. In one embodiment, the information within the signal includes header information of a signal broadcast from the ID node (e.g., a mobile user access device, such as a smartphone 200 of the shipping customer). The header information may include status information on whether the ID node is in a particular state (e.g., a discoverable advertising state, a general advertising state, or a non-connectable advertising state as discussed above with reference to FIG. 8). The information may also include an identification of a particular consumable (such as a product or service) to be purchased in the payment transaction, and in another part of the information, include an identification of a payment source for the payment transaction. In the example of FIG. 34B, mobile user access device 200 may broadcast a signal, which is detected by office master node 3410*a*. Part of the information broadcasted in the signal may identify the shipment to be purchased (e.g., shipment of package 130).

Another part of the information broadcasted may identify a payment source for the payment transaction. This may be a conventional currency based payment source (e.g., a bank account, a credit account, or the like) or may be a non-currency type of program (such as a rebate program, award point program, or other closed ecosystem type of program used to exchange value for products/services from the payment receiver). For example, the shipping customer may prepay for a desired amount of shipping credits with a specific shipping company and, in some implementations, allow integration of an embodiment with conventional payment systems such as the Google Wallet app, the Square Wallet app, or PayPal® payment systems. The prepaid shipping credits related to the shipping customer may, in some embodiments, be part of the shipping information, and in some cases, can be staged on a node (such as a smartphone 200 operating as an ID node). Staging payment credits with a particular node helps facilitate other payment services, such as cost-on-delivery (COD) type services. It also allows for a payment state to be preserved within the node as the package moves through a distribution or shipping network. In some embodiments, the payment state preserved on the node reflecting present credits may be updated (added or removed credits) as the node moves through the distribution or shipping network.

At step 3615, the master node associates with the ID node when the ID node desires to associate with the master node for the payment transaction. In one embodiment, associating may involve altering a broadcasting mode of the master node and instructing the ID node to alter its broadcasting mode to enable associating the master node and the ID node. In another embodiment, associating may involve establishing a passive association between the master node and the ID node without requiring a secure connection between the master node and ID node. However, in yet still another embodiment, associating the nodes may involve establishing an active and secure association between the master node and the ID node where the active association reflects a secure connection between the master node and ID node. Such an active and secure association may be facilitated with preloaded credentials, but in other embodiments such authority to associate may be requested from the server.

In a more detailed example, the master node may establish the active association with the ID node after receiving an acknowledgement from the ID node related to the payment transaction. This acknowledgement may be prompted, in one example, with a displayed prompt on the ID node (e.g., the screen of the shipping customer's mobile smartphone 200 operating as an ID node for purposes of paying for shipping of the package 130).

Referring back to the example of FIG. 34B, office master node 3410*a* may analyze the information broadcast in the signal (e.g., a Bluetooth® formatted short range transmission signal) from the mobile user access device 200 operating as an ID node when determining whether to associate with mobile user access device 200 for this purpose. If the office master node 3410*a* determines that the mobile user access device 200 desires to proceed with a payment transaction related to shipment of package 130 (based upon information in the signal), office master node 3410 then associates with the mobile user access device 200 operating as an ID node. For example, the office master node 3410*a* may receive information from server 100 related to the shipment of package 130, and know that the mobile user access device 200 is identified in a profile for the shipping customer, and that shipping information related to package 130 is in the system with a charge identified for the service of shipping package 130. Thus, based upon the shipping information and the profile information on the shipping customer related to the shipping information, office master node 3410a may only need to associate with the shipping customer's mobile user access device (e.g., smartphone 200) to proceed and complete the payment transaction for shipping package 130.

At step 3620, method 3600 concludes by submitting payment transaction data to the server. The payment transaction data is based upon another part of the information within the signal broadcast from the ID node (e.g., smartphone 200 in the example of FIG. 34B). In more detail, the payment transaction data may reflect an authorization to complete the payment transaction based upon the successful association of the master node and the ID node.

In one example, server 100 may receive the payment transaction data (e.g., acknowledgement that a successful association occurred for that transaction) and the server 100 may rely on data already resident in its server memory (e.g., related to the shipping information, prices for the shipping order, payment source information provided as part of entering the shipping information and initially registering the package 130 and ID node 120a) to then conclude the payment transaction. In another example, the server 100 may receive further information (such as updated payment source information) from the ID node (e.g., smartphone 200) as part of the payment transaction data via the associated master node.

In a further embodiment method 3600 may include steps where the mobile user access device operating as an ID node provides a user interface with displayed prompts as part of validating payment, authenticating payment, and a charge notification approval display. One or more prompts may appear on the user interface of the mobile user access device. Such prompts typically inform the operative of the device of information related to the transaction, or ask for further input related to the transaction. In such an embodiment, the operator of the mobile user access device may provide one or two-way interaction to approve, validate and otherwise authenticate a payment transaction conducted between the nodes.

While many embodiments may rely on authenticated connections where information may be more securely shared for the payment transaction, other embodiments may rely on unauthenticated connections (e.g., passive associations or active but not secure or authenticated connections). As such, the security aspect may come into play on the backend server that utilizes proprietary credits rather than conventional currency. For example, when a node package is dropped in a node-enabled logistics receptacle (such as a drop box), the customer may be automatically debited with a preauthorized account with the shipping entity. The shipping entity's backend server can keep track of the credits and debit the customer's account accordingly based on the detected deposit of the node package.

Those skilled in the art will appreciate that method 3600 as disclosed and explained above in various embodiments may be implemented on a network device, such as office master node 3410a illustrated in FIG. 34B, running one or more parts of master control and management code 425 to implement any of the above described functionality. Such code may be stored on a non-transitory computer-readable medium such as memory storage 415 on a master node (such as office master node 3410a). Thus, when executing code 425, the master node's processing unit 400 may be operative to perform operations or steps from the exemplary methods disclosed above, including method 3600 and variations of that method.

Likewise, those skilled in the art will appreciate that in light of the method 3600 described above and further details described therein, that an exemplary system of a server and master node associated with a payment receiver (e.g., a FedEx® Office Print & Ship Center) may be used for conducting a payment transaction using node association. In this embodiment, the master node is operative to communicate with the server and separately detects and is operative to communicate with an ID node for purposes of associating for a payment transaction where the master node's processing unit, when running the code 425, implements the steps described above related to method 3600.

Node-Enabled Shipping without a Shipping Label

Figure 37:
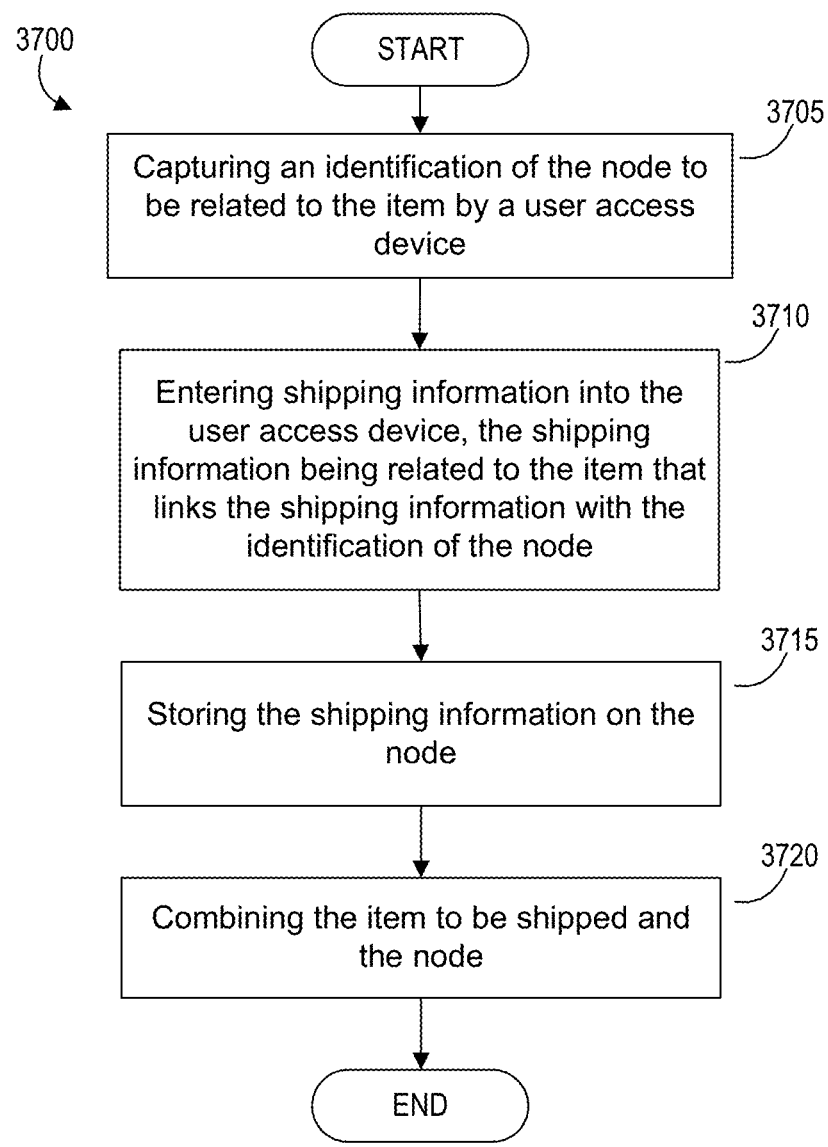
FIG. 37 is a flow diagram illustrating an exemplary method for preparing a node-enabled shipment of an item to be shipped using a wireless node network in accordance with an embodiment of the invention.

While the embodiment described with respect to FIG. 35 involves proactive generation of a shipping label for an item to be shipped, another embodiment using a wireless node network in accordance with an embodiment of the invention allows for node-enabled shipping without a shipping label. FIG. 37 is a flow diagram illustrating an exemplary method for preparing a node-enabled shipment of an item to be shipped using a wireless node network in accordance with an embodiment of the invention. Referring now to FIG. 37, method 3700 begins at step 3705 by capturing an identification of the node to be related to the item by a user access device. In different embodiments, the node may be implemented by an ID node, a sensor node, or a master node. In a more detailed embodiment, the node may be implemented as a mobile master node having at least one sensor onboard the master node for gathering environmental information about an environment near the master node.

For the node to be related to the item being shipped, identification of the node may be captured with the user access device (e.g., a smartphone, laptop computer, desktop computer, personal area network device, and the like as described herein) in a various ways. In one example, capturing the identification of the node may involve detecting an electronic identification of the node (such as a Bluetooth® signature or identifier (e.g., MAC address) for the node, a near field communication (NFC) code related to the node, an RFID identifier related to the node). In one embodiment where the RFID version is implemented with NFC, the user access device may be able to communicate via very short range NFC signals to capture the NFC code but then auto-associate the node using a less range restrictive communication path (e.g., Bluetooth® Low Energy or BLE). In another example, capturing the identification of the node may involve viewing a readable identifier of the node (such as a written label on the exterior of the node having an identification printed on the label). In still another example, capturing the identification of the node may involve scanning a machine-readable identifier of the node (such as a barcode).

At step 3710, shipping information is entered into the user access device. The shipping information is related to the item and includes a link between the shipping information (e.g., shipping customer, origin, destination, etc.) and the identification of the node.

At step 3715, the shipping information is stored on the node. The shipping information may be stored in a node's volatile memory, onboard memory storage, or both. In one embodiment, the shipping information may be uploaded to the server. In a more detailed embodiment, the shipping information may be transmitted to the server to pre-associate the shipping information for the node with another node (e.g., courier master node 110b shown in FIG. 34A) in the network related to a person (such as a courier) that will handle a logistics transaction for the item to be shipped. Exemplary logistics transactions may include picking up the item, dropping off the item, and the like. At pickup, the courier may optionally generate a shipping label to facilitate further logistics handling of the item being shipped; however, in other embodiments, no further label is needed as the node may communicate the necessary information for successful shipment to other nodes as it transits its path towards its shipment destination.

At step 3720, the item to be shipped is combined with the node. Typically, the item to be shipped may include a package for the item. The package may help protect the item as it is shipped to a destination. Thus, in one example, the item to be shipped may be combined with the node by placing the node within an interior of a package for the item to be shipped. Depending on the item being shipped, those skilled in the art will appreciate that the actual location of the node within the interior of the package may adversely impact how the node can communicate with other nodes.

In another example, the item to be shipped may be combined with the node by securely fixing the node to an interior surface of a package for the item to be shipped. In more detail, the node may be adhered to a side-wall or top interior surface within the package. Keeping the node in a fixed location proximate to a wall or top of the package my keep the contents of the package from interfering with the node (or communications from the node) and help avoid physical damage to the node from the contents of the package (the item being shipped).

In a further example, the node may be embedded as part of a package for the item to be shipped. In this example, the node may be integrated into the package or packaging materials and may be partially or entirely embedded within the package or packaging materials.

In yet a further example, the item to be shipped may be combined with the node by securely fixing the node to an exterior surface of a package for the item to be shipped. In this example, the node may be implemented in a relatively flat configuration so as to ensure the node stays fixed to the package as the item is shipped to its destination. In particular, the package may have a special location, such as a recessed location, which is accessible from the exterior of the package and where a shipping customer may place and securely fix the node.

In another embodiment, method 3700 may also include fixing an external notification to a package for the item to be shipped, the external notification providing notice that the package is a node shipment. The external notification in this embodiment is not a shipping label in that it does not include shipping information viewable on the exterior of the package. Instead, an exemplary external notification may display a simple message to alert shipping company personnel that the package includes a related node that may (e.g., via scanning, via communications with, via indirect passive analysis of signals from the node) be used to help track and manage the package as it is shipped without requiring a full shipping label.

Those skilled in the art will appreciate that method 3700 as disclosed and explained above in various embodiments may be implemented on a node, such as an exemplary ID node or sensor node illustrated in FIG. 3, or an exemplary master node as illustrated in FIG. 4, running one or more parts of their respective control and management code to implement any of the above described functionality. Such code may be stored on a non-transitory computer-readable medium, such as memory storage within such types of exemplary nodes. Thus, when executing such code, a processing unit within the respective node may be operative to perform the operations or steps from the various exemplary methods disclosed above where the shipping information is received by the user access device and the combining step may be implemented as issuing a message on the user interface of the user access device to combine the item to be shipped and the node.

Likewise, those skilled in the art will appreciate that in light of the method 3700 described above and further details described therein, that an exemplary system of a server and a node may be used for preparing a node-enabled shipment of an item to be shipped using a wireless node network according to an embodiment. The exemplary node in the system may comprise a node processing unit, a node memory storage coupled to the processing unit, and a communication interface coupled to the processing unit and operative to communicate with a user access device (e.g., smartphone 200 used by a shipping customer). Examples of the node may include an ID node, a sensor node, and a master node. In a more detailed embodiment, the node may be implemented as a mobile master node having at least one sensor onboard the master node for gathering environmental information about an environment near the master node.

The exemplary server in the system is operative to communicate with the node via the communication interface. However, those skilled in the art will appreciate that if the node is an ID node or sensor node, the server may separately communicate with the node indirectly through the shipping customer's user access device (operating as a master node) while the user access device communicates with the node through the communication interface.

The exemplary node's processing unit is operative to emit an identification of the node to be related to the item by the user access device. For example, the node may emit or otherwise transmit a short-range signal that identified the node and that identification may be related to the item being shipped after it is captured by the user access device (e.g., via Bluetooth® Low Energy communications). The node processing unit is further operative to receive shipping information from a user access device, the shipping information being related to the item and is linked with the identification of the node. The node processing unit is further operative to store the shipping information on the node (e.g., on the node memory storage) when the node and the item to be shipped are combined for shipping.

The node processing unit may be further operative to upload the shipping information to the server. The server, in one embodiment, may be operative to receive the shipping information from the node (e.g., when the node is a master node). In other embodiments, the server may be operative receive the shipping information from the user access device (e.g., when the node is an ID node or sensor node).

Node-enabled Logistics Receptacle

In FIGS. 34A and 34B, receptacle 3415 is a drop-box and/or pickup type of container (more generally referred to as a logistics receptacle) that may temporarily maintain custody of items being shipped (along with their respective ID nodes should one be present with the particular item). In some examples discussed here, receptacle 3415 is a simple container or receptacle for one or more packages to be shipped. The exemplary receptacle has an entrance opening through which an item being shipped (along with its related node) can pass as the item is deposited within a storage area of the receptacle. Thus, the storage area maintains the item being shipped and the related node after it is deposited within the receptacle.

In some embodiments, the receptacle may be implemented as a secure access receptacle or container (such as a locker type of logistics receptacle) having an entrance opening that is accessible to a shipping customer for depositing the item to be shipped (and its readable node), but once within the receptacle the item is secure and only removed from a secure storage area within the receptacle by someone with a key or combination. Such an example of a logistics receptacle may be useful when deployed in situations where personnel are not actively managing the receptacle.

An embodiment of receptacle 3415 may deploy this receptacle as a node-enabled assembly. In other words, in this other embodiment, receptacle 3415 may have an attached or integrated node (such as drop node 110a or ID node 110a or master node 120a) as part of the assembly making up receptacle 3415. Equipping the receptacle 3415 with such a node (e.g., an ID node, a sensor node, or a master node with or without sensors) in an embodiment provides a way to identify items being shipped that have related advertising nodes with the item as the items are left near or deposited in the receptacle (such as a drop box type of container). The node assembled with the receptacle operates to detect signals from nodes related to items being shipped. When detected, the receptacle's node associates with the node related to the item being shipped and based upon the location of the that node relative to the receptacle, the receptacle's node may alter a current inventory related to the receptacle that is stored in that node's memory storage. As the node related to an item being shipped (e.g., a node package) approaches the node-enabled logistics receptacle and is deposited into the temporary custody of the receptacle, the receptacle's node may instruct the node package to adjust its RF output signal (e.g., adjusting a broadcast profile for the node package). As such, the receptacle's node takes advantage of a new package node's communication profile as it helps facilitate the communication behavior of the new node within the receptacle's temporary managerial custody so there is less potential interference and disruption with communications to and from other nodes within the node-enabled logistics receptacle's custody (inside or near the receptacle).

Further details on various embodiments of an exemplary node-enabled logistics receptacle assembly appear in FIGS. 34A-34D, 85A, 85B, 86A, 86B, and 89A-89D. In some of these embodiments, the node within the node-enabled logistics receptacle assembly may include at least one sensor that monitors for a deposited package the custody of which is temporarily maintained by the node-enabled logistics receptacle assembly. As discussed more with respect to FIGS. 89A-89D, such a sensor may be implemented with one or more internal sensors, external sensors, and/or door sensors to help detect packages.

Figure 38:
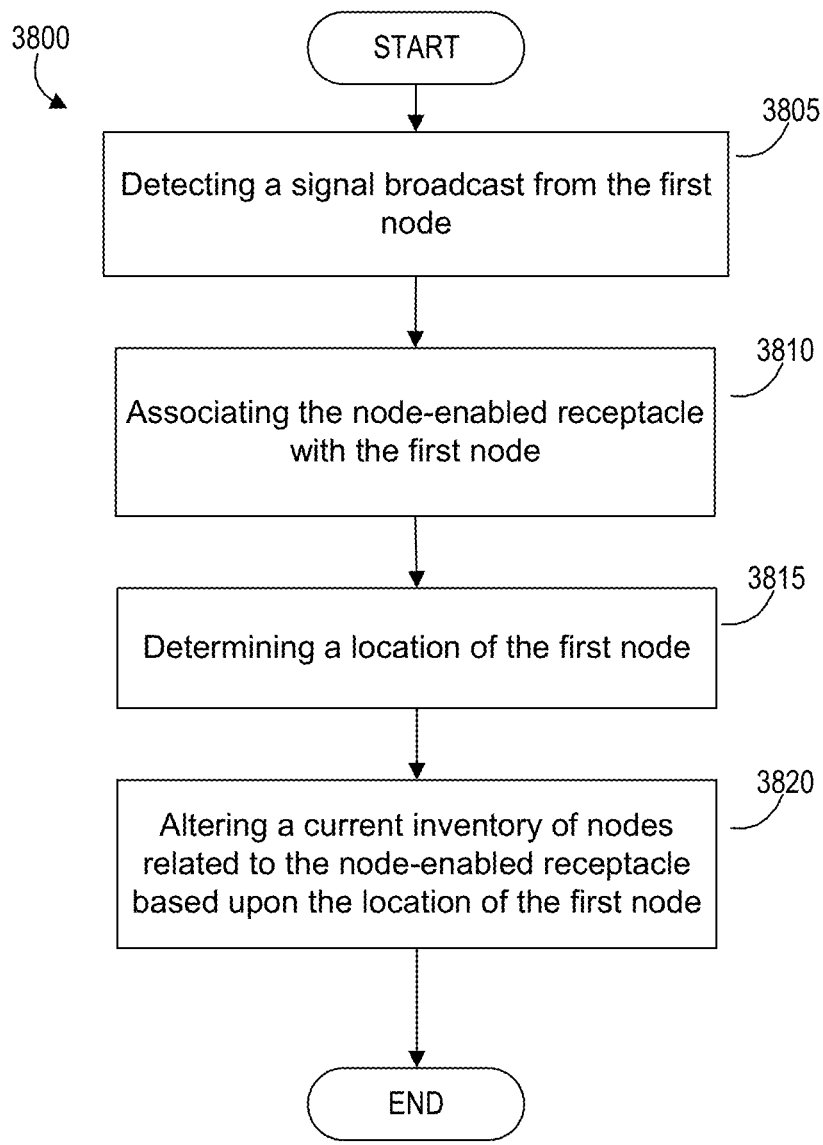
FIG. 38 is a flow diagram illustrating an exemplary method for operation of a node-enabled logistics receptacle in a wireless node network in accordance with an embodiment of the invention.

FIG. 38 is a flow diagram illustrating an exemplary method for operation of a node-enabled logistics receptacle in a wireless node network in accordance with an embodiment of the invention. Referring now to FIG. 38, method 3800 begins at step 3805 by detecting a signal broadcast from the first node. In the example shown in FIG. 34B, receptacle 3415 may be a node-enabled logistics receptacle where drop node 110a is incorporated into the assembly having receptacle 3415. As package 130 and ID node 120a approach drop node 110a embedded in receptacle 3415, drop node 110a detects a signal broadcast from ID node 120 related to the package 130 being shipped.

At step 3810, the node-enabled logistics receptacle associates with the first node. Back in the example of FIG. 34B, drop node 110a associates with ID node 120a. As ID node 120a approaches drop node 110a, drop node 110a may instruct ID node 120a to alter a power characteristic of its advertising signal (such as the RF output power level) in order to allow the drop node 110a to better locate the ID node 120a.

At step 3815, the location of the first node is determined by the node-enabled receptacle. As a fixed location installation, the physical address of the drop node 110a may be assumed to be identical to the receptacle itself. In other embodiments where drop node 110a is a master node, the location of the receptacle may not be fixed and drop node 110a may have location circuitry with which to determine the node-enabled receptacle's current mobile location.

In one embodiment, the method may detect if the first node is left within a vicinity of the node-enabled logistics receptacle based on the location of the first node. The vicinity of the node-enabled logistics receptacle may be an area sufficiently proximate to the node-enabled logistics receptacle to indicate that an item and node within the vicinity intends to be shipped. For example, the node-enabled logistics receptacle may detect that the item (e.g., package 130) and its related node (ID node 120a) are left immediately outside of the node-enabled receptacle, which may indicate (along with a current inventory) that the node-receptacle is full and in need of pickup. In one embodiment, the node-enabled logistics receptacle may send a message to a server regarding the need for pickup under certain circumstances (e.g., when a predetermined number of nodes are detected in the current inventory or there is at least one node detected outside the receptacle).

In another embodiment, the method may detect if the first node is within the node-enabled logistics receptacle based on the location of the first node. Depending on the size of the receptacle, this may be possible given the granularity of possible location determinations. And once the first node is detected within the node-enabled receptacle, it is deemed deposited for shipment and should be counted towards the current inventory.

At step 3820, the node-enabled logistics receptacle alters a current inventory of nodes related to the node-enabled logistics receptacle based upon the location of the first node. In one example, the inventory may include those nodes in the vicinity of the node-enabled receptacle. In another example, the inventory may only include those nodes detected to be within the node-enabled receptacle.

The method 3800 may also detect removal of the first node from the vicinity of the node-enabled logistics receptacle and from within the node-enabled logistics receptacle itself. Thus, the node-enabled logistics receptacle may be operative to manage a current inventory of nodes (and related items being shipped) and inform the server of such information. When the node embedded with the receptacle is implemented and operates as an ID node, the embedded node may be able to collect scan results from other ID nodes in the receptacle, and then transfer them to a master node. In other words, the node-enabled logistics receptacle is operative to transfer one or more results collected by the node-enabled logistics receptacle listening to at least one other ID node within the receptacle. However, if the embedded node is implemented and operates as a master node, the embedded node can directly update a server when the current inventory of nodes changes.

In another embodiment, when the embedded node (e.g., drop node 110a) is implemented and operates as a sensor node having one or more environmental sensors, the processing unit of the embedded node may be operative to detect an interior condition of the receptacle using the one or more environmental sensors. For example, if the interior condition of the receptacle is wet, the embedded node may want to immediately have the server notified. Thus, once the interior condition is known, the embedded node may transmit an environmental update on the interior condition of the receptacle to a master node, which is then operative to pass it on to the server.

The method 3800 may also include tracking inventory metric information as a type of productivity data. In one embodiment, inventory metric information about when each of the nodes in the current inventory of nodes arrive and depart from within the node-enabled logistics receptacle is tracked, and the embedded node may cause such inventory metric information to be sent to the server (e.g., directly transmitting the information to the server when the embedded node is a master node, or indirectly sending the information to the server via a connected master node when the embedded node is an ID node). Thus, in one example, the inventory metric information may be related to when pickup personnel and/or vehicles equipped with nodes arrive and depart at the location with the node-enabled receptacle.

In a further embodiment, method 3800 may also help manage RF communications of nodes within the custody or soon to be in the custody of the node-enabled logistics receptacle. Specifically, an embodiment of method 3800 may also comprise instructing the first node by the node-enabled logistics receptacle to change an output power setting on the first node to a different power level when the location of the first node places the first node in a temporary custody of the node-enabled logistics receptacle. In more detail, such a step of instructing the first node by the node-enabled logistics receptacle to change the output power setting on the first node to the different power level may comprise adjusting a broadcast setting of a broadcast profile for the first node. For example, the exemplary method discussed with respect to FIG. 52 and the accompanying description explain how a broadcast setting may be adjusted as part of a node's broadcast profile that defines how a node communicates.

Those skilled in the art will appreciate that method 3800 as disclosed and explained above in various embodiments may be implemented on a node, such as an exemplary ID node or sensor node illustrated in FIG. 3, or an exemplary master node as illustrated in FIG. 4, running one or more parts of their respective control and management code to implement any of the above described functionality. Such code may be stored on a non-transitory computer-readable medium, such as memory storage within such types of exemplary nodes. Thus, when executing such code, a processing unit within the respective node may be operative to perform operations or steps from the exemplary methods disclosed above, including method 3800 and variations of that method.

Node-Enabled Packaging

Figure 55:
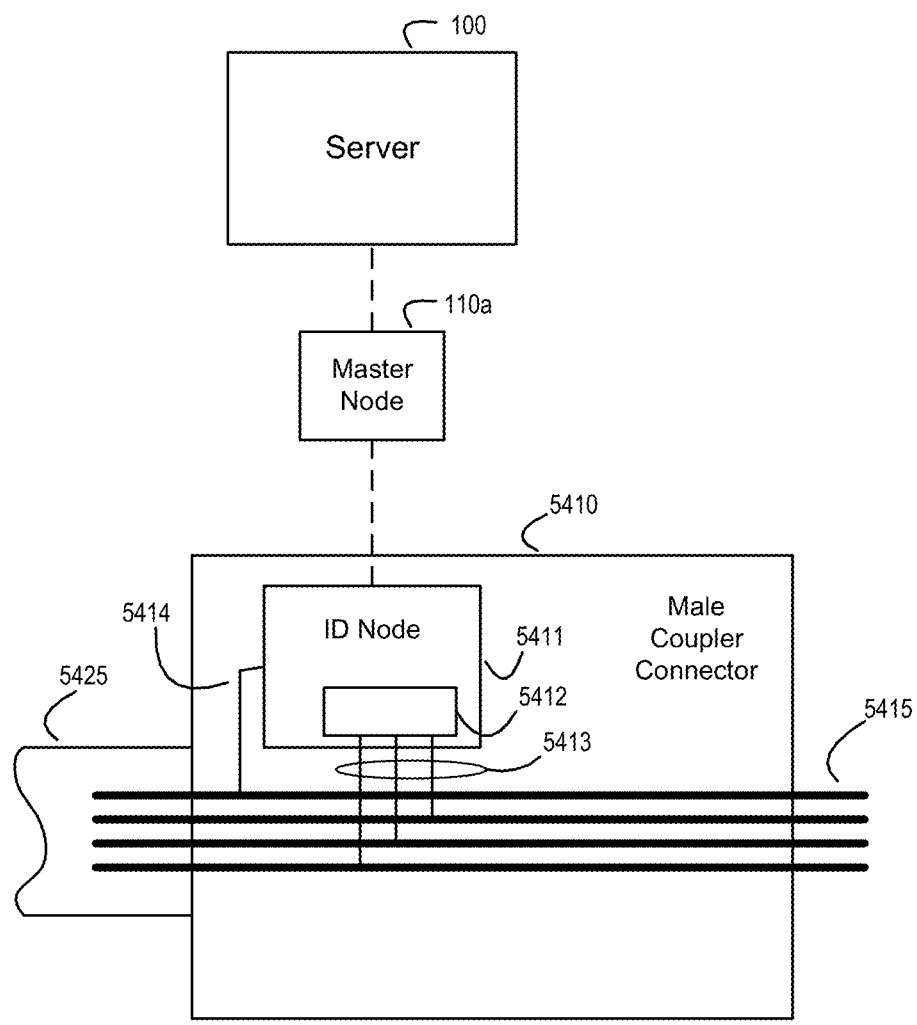
FIG. 55 is a more detailed diagram illustrating the exemplary coupler connector between two systems having an integrated node in accordance with an embodiment of the invention.

Embodiments of nodes in an exemplary wireless node network may be part of different types of electrical components (such as a coupler connector as shown in FIG. 55), but may also be advantageously integrated into or otherwise be part of a container (such as a package) commonly used to ship items. One type of container used for shipping an item is a corrugated fiberboard box (also referred to commonly as a "cardboard box" or "cardboard package"). Among its uses, a corrugated box may be used by manufacturers of products to ship items, such as products, to retail distributors or to end users, and used by the general public to ship materials, gifts, or other items to friends and relatives. When used in such a manner, the corrugated box operates as a package for the item being shipped.

As explained in an embodiment above, a package may be enabled with a node (generally referred to as a node package or node-enabled package) when shipping one or more items in the package. And as noted, in a general embodiment, the node may simply be placed within the package while in other embodiments, the node may be attached to the package (e.g., adhered to an interior portion of the package, fixed to a part of the package where one or more status indicators of the node may be visible through the package, etc.) or may be part of the package or the packaging materials used to comprise an exterior, interior, base, or separating/cushioning material within the node package. In more detail, the node may be integrated as part of the package or packaging materials (e.g., built-into a part of a box or pallet structure). In still another detailed embodiment, the node of the node package may be fully or partially embedded within the package or packaging materials used to help form a general container, which maintains an item to be shipped along with the node. As explained below in more detail, FIGS. 75A, 75B, 76-78 provide various illustrations of different node-enabled packaging materials that may be used as part of a node package.

In an embodiment, exemplary packaging material may be used as at least part of a shipping container (e.g., box, enclosure, etc.) in a variety of forms. For example, the packaging material may be used as a base, sides, and sealable lid from one or more sheets of packaging material to create and form the container itself, such as a corrugated fiberboard box. In another example, the exemplary packaging material may be used as packaging separator material where one or more sheets may be configured in various orientations and with uniform or non-uniform surfaces to separate distinct items being shipped together from each other within the same package container. In still another example, the exemplary packaging material may be used as cushioning material for an item relative to an interior base, side, or lid surface so that the item being shipped is more protected from impacts to the package container. In some embodiments, such packaging material may form the container alone. In other embodiments, the packaging material may act as separator material as well as cushioning material. And in still other embodiments, the packing material may operate as all three—the material making up the container, the separator materials, and the cushioning material.

As discussed in more detail below, a node (such as an ID node or master node) may be generally assembled as part of such packaging material in an embodiment. For example, the node may be placed within a recessed part of the packaging material and held in place, it may be adhered to an interior surface of the packaging material, it may be integrated as part of the packaging material, and may be embedded within the packaging material where some or none of the node is exposed outside the packaging material. Such node-enabled packaging material may then be made available to a shipping customer as part of a consumer product (e.g., a node-enabled shipping box) that can be purchased for later use when shipping an item.

Figure 75A:
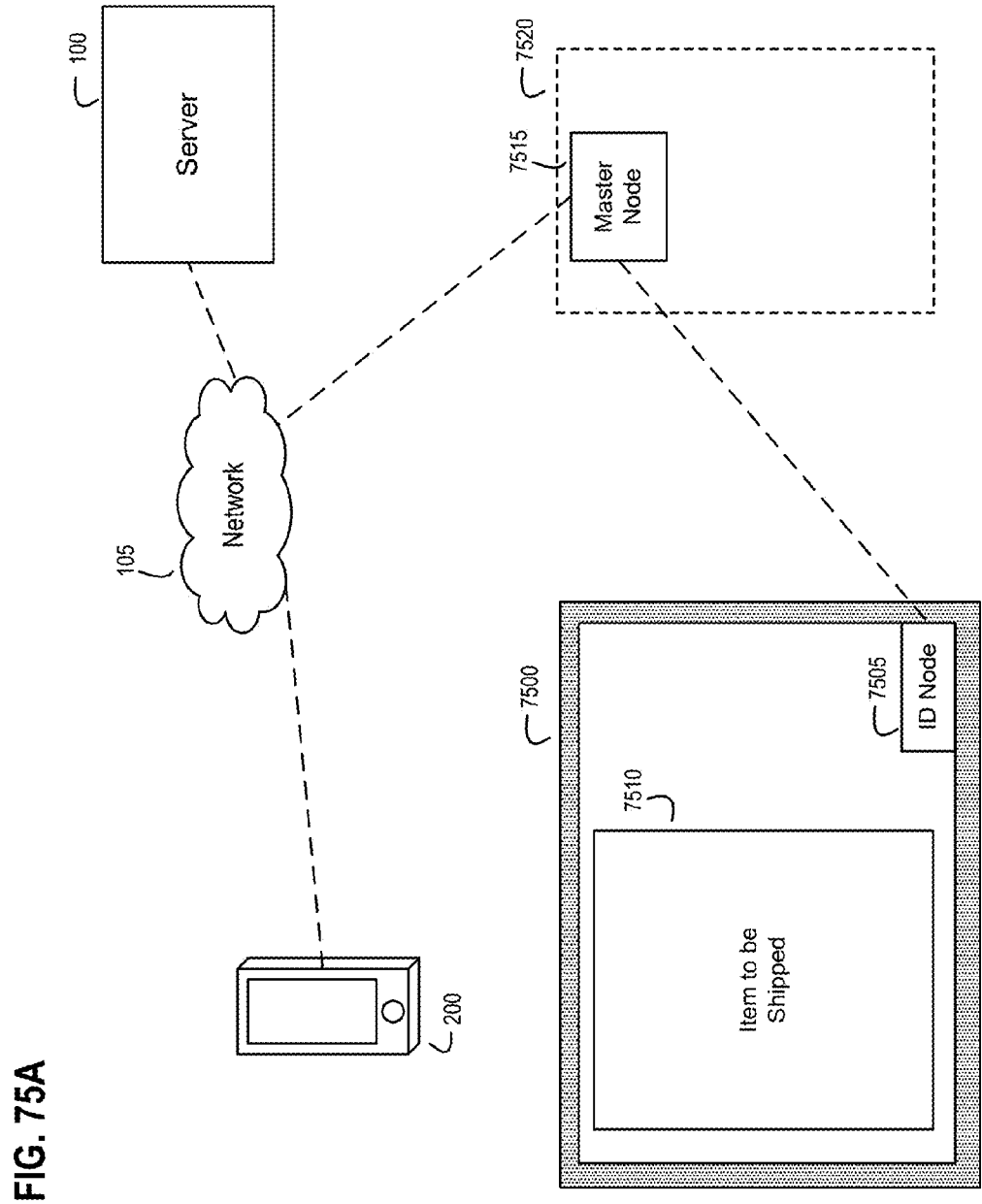
FIG. 75A is a diagram illustrating an exemplary container using node-enabled packaging material as part of an exemplary wireless node network in accordance with an embodiment of the invention.

FIG. 75A is a diagram illustrating an exemplary container using node-enabled packaging material as part of an exemplary wireless node network in accordance with an embodiment of the invention. Referring now to FIG. 75A, exemplary container 7500 (e.g., a box or other package) is illustrated that contains an item to be shipped 7510. Exemplary ID node 7505 is shown as part of packaging material (such as fiberboard material) that makes up container 7500. As shown, ID node 7505 is attached with adhesive to an interior surface of container 7500. Those skilled in the art will appreciate that while the container 7500 is shown as a cardboard box, in other embodiments, the container may have packaging material made from other materials, such as metal, plastic, closed-cell extruded polystyrene foam (such as the Styrofoam™ brand from The Dow Chemical Company), or other materials used to make containers within which an item may be shipped.

Figure 75B:
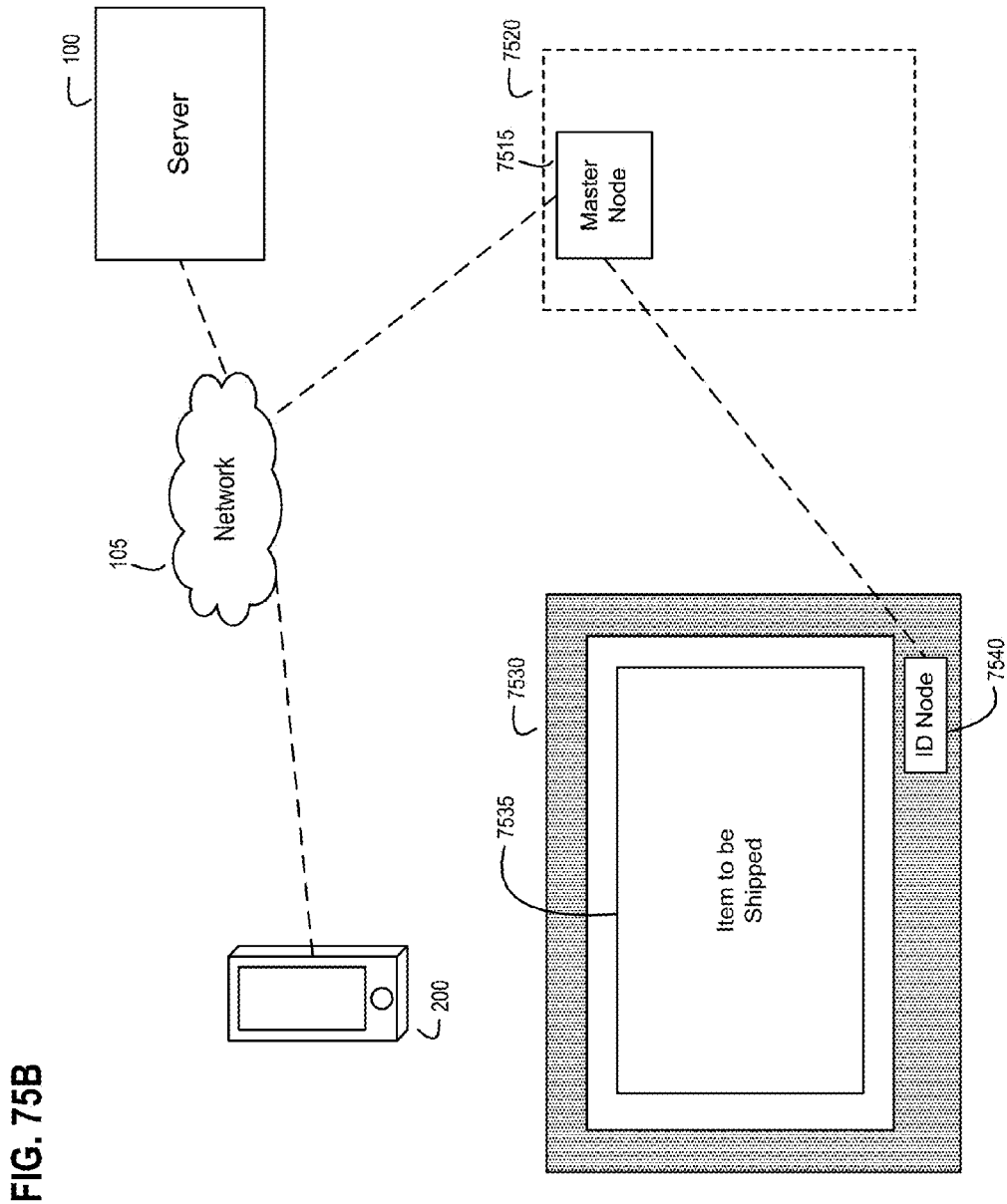
FIG. 75B is a diagram illustrating another exemplary container using node-enabled packaging material as part of an exemplary wireless node network in accordance with an embodiment of the invention.

In other embodiments, ID node 7505 may be embedded within the packaging material. For example, FIG. 75B is a diagram illustrating another exemplary container using node-enabled packaging material as part of an exemplary wireless node network in accordance with an embodiment of the invention. Referring now to FIG. 75B, exemplary container 7530 is shown being made with packaging material (such as corrugated fiberboard, plastic, closed cell foam, a foam injected interior with roto-molded side walls, a combination of different materials, etc.) where the ID node 7540 is embedded within a sheet of the packaging material making up at least part of container 7530. Those skilled in the art will appreciate that a general embodiment of such a "sheet" may have planar surfaces; however, other embodiments may have an exemplary sheet of packaging material in the form of a block or other shape (without requiring planar surfaces) as long as packaging material is disposed between the surfaces.

Figure 76:
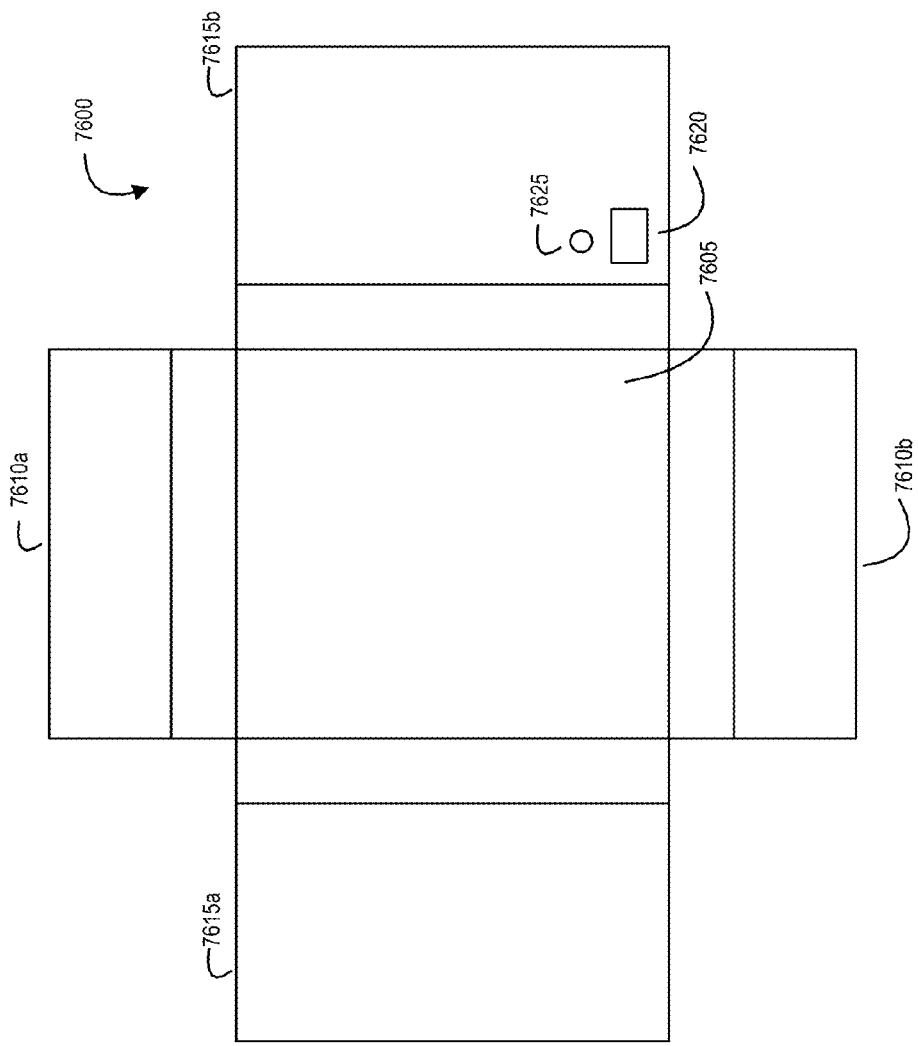
FIG. 76 is a diagram illustrating a view of an exemplary container sheet using node-enabled packaging material as part of an exemplary wireless node network in accordance with an embodiment of the invention.

FIG. 76 is a diagram illustrating a view of an exemplary container sheet using node-enabled packaging material as part of an exemplary wireless node network in accordance with an embodiment of the invention. Referring now to FIG. 76, exemplary container sheet 7600 is illustrated as a single sheet of packaging material, such as fiberboard material. Sheet 7600 includes fold lines that separate sheet 7600 into distinct parts of a container formed from the sheet 7600. In the illustrated embodiment, a base panel 7605 appears central to the sheet 7600 and has extension panels 7610a, 7610b, 7615a, 7615b that become the side walls and lid sections when assembled (as shown in perspective in FIG. 77).

In this exemplary embodiment, one of the panels 7615b includes a recessed node region 7620 where a node may be mounted. As shown in FIG. 76, the recessed node region 7620 in sheet 7600 may initially be open and accessible for mounting a master node or ID node. Mounting, for example, may be accomplished by adhesive or other restraints (tape, etc.). In one example, the node may be placed in the recessed region 7620 and an adhesive label may be place over the node while also overlapping onto the extension panel 7615b. Thus, the adhesive label may hold the node in place within region 7620 but may allow for replacement of the node so that the node and/or the container formed from sheet 7600 may be reused in other scenarios with other components.

Additionally, in the illustrated exemplary embodiment, panel 7615b includes an opening. The opening allows a status light (not shown) from the node to be aligned and mounted. In one embodiment, the status light may be integral to the node itself and, thus, the opening may appear within recessed region 7620. In another embodiment, the status light may be electrically coupled (e.g., via wire or traces internal to panel 7615b) to the node within the recessed region 7620 with the light being physically separate from the node.

In another embodiment, sheet 7600 has no opening for the light to be shown through the sheet, but may yet still provide light from the status light visible from outside the assembled container from sheet 7600. For example, at least a portion of the packaging material making up the recessed portion 7620 may be clear or translucent to allow for light (or at least a glow of light) to be apparent from outside the assembled container from sheet 7600. In another example, the status light may be disposed on the node placed within recessed region 7620, and facing the exterior of the container when assembled from sheet 7600. A small part of the packaging material making up extension panel 7615b may have a see through membrane (e.g., clear tape or the like) right where it would align with the status light.

As previously explained with respect to exemplary ID and master nodes, an exemplary status light used with such nodes may also indicate a shipment state (such as a status of the shipped item, or a status along the transit journey for the shipped item in the container of packaging material). The status light may also, in another embodiment, indicate a sensed error or exceeded threshold by the node.

Figure 77:
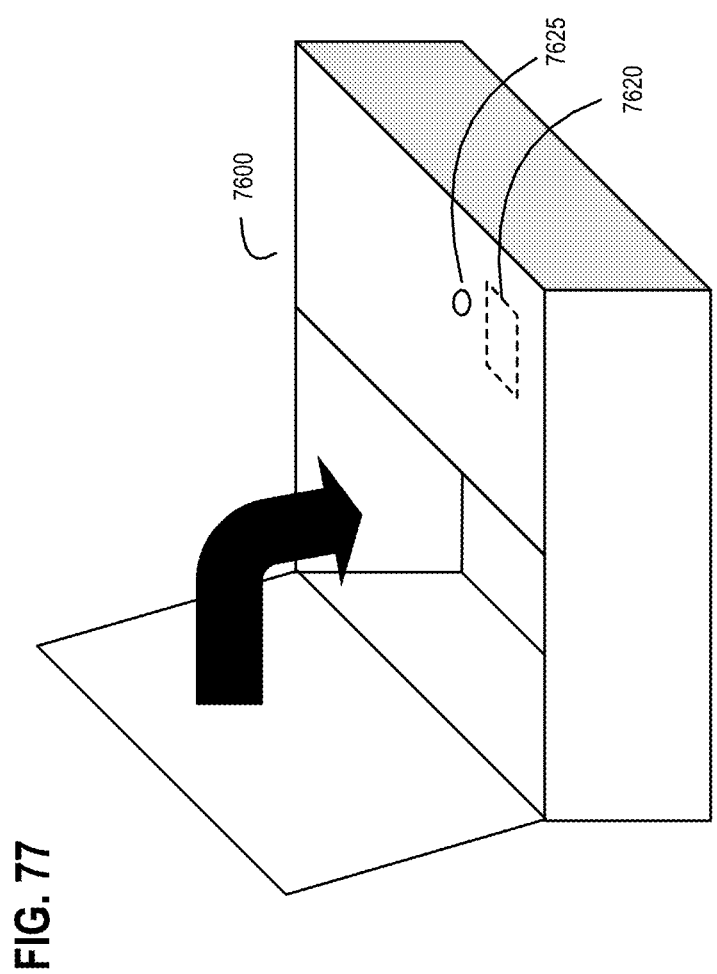
FIG. 77 is a diagram illustrating a perspective view of an exemplary assembled container using node-enabled packaging material as part of an exemplary wireless node network in accordance with an embodiment of the invention.

FIG. 77 is a diagram illustrating a perspective view of an exemplary assembled container using node-enabled packaging material as part of an exemplary wireless node network in accordance with an embodiment of the invention. Referring now to FIG. 77, a container may be assembled or, more generally, formed from the sheet 7600 and used to package an item (such as item 7535 or 7510) to be shipped. As the extension panels are folded along the fold lines shown in FIG. 76, the container takes form. Once the node and status light (if used in opening 7625) are integrated as part of the packaging material that forms at least a part of the container, the item to be shipped may be placed within the container and the container may be sealed. Typically, sealing is done after activating the node, but depending on how activation may be accomplished with the node integrated as part of the container, activation may occur after the container is sealed as well.

Figure 78:
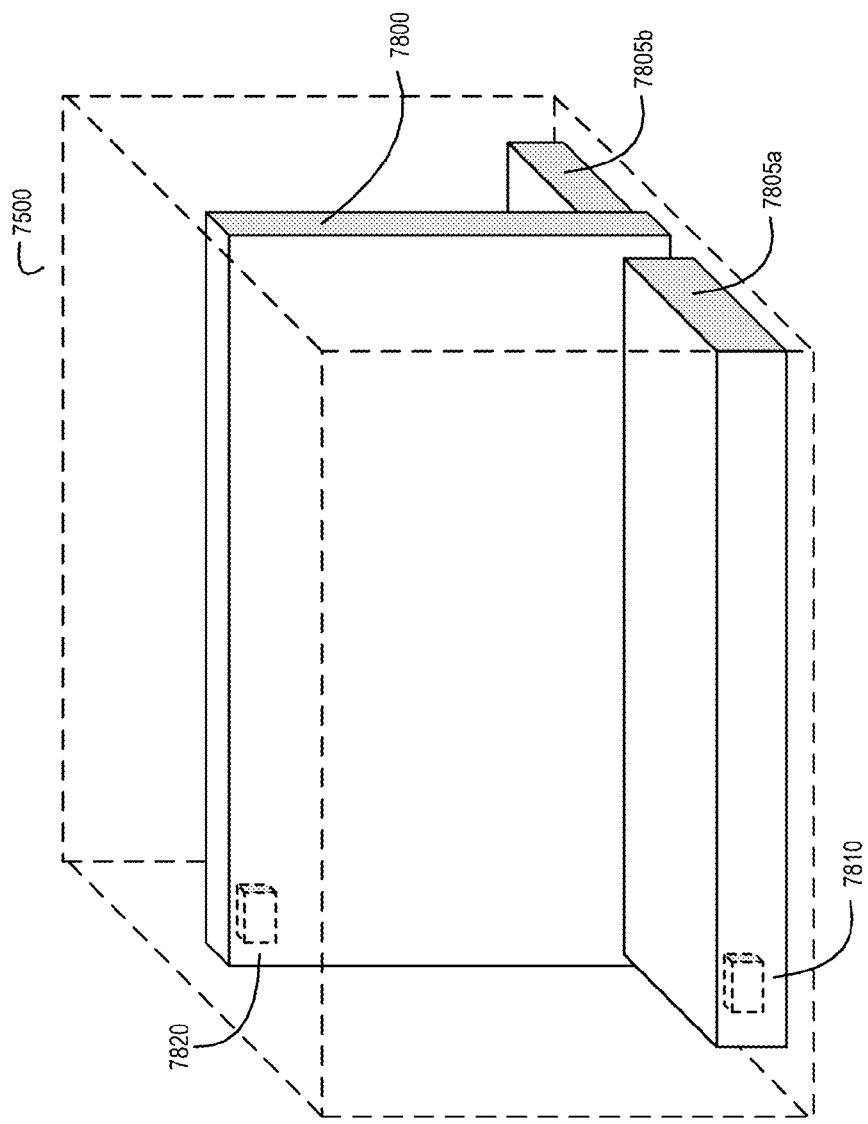
FIG. 78 is a diagram illustrating a perspective view of exemplary node-enabled packaging material implemented with exemplary packaging separator sheet material and exemplary cushioning material in accordance with an embodiment of the invention.

In some embodiments, the item to be shipped may need further support and care to make sure it arrives undamaged. To facilitate such undamaged transit for an item to be shipped, separator packaging material and/or cushioning packaging material are often used. In some embodiments, the packaging material making up such separator packaging material and/or cushioning packaging material may also include a node integrated in one or more of these packaging materials and operative to be a node in a wireless node network. FIG. 78 is a diagram illustrating a perspective view of exemplary node-enabled packaging material implemented with exemplary packaging separator sheet material and exemplary cushioning material in accordance with an embodiment of the invention. Referring now to FIG. 78, container 7500 is shown again but this time showing an interior of the container 7500. Specifically, the interior of container 7500 is shown having separator packaging material 7800 and cushioning packaging materials 7805a, 7805b disposed within it. Exemplary separator packaging material 7800 is shown deployed essentially bisecting the interior region of the container 7500, and providing a protective segmentation of the interior so that more than one item may be shipped in container 7500 without damage. And in an embodiment, separator packaging material 7800 may have a node 7820 integrated as part of the material (e.g., attached to, embedded within, etc.). Likewise, exemplary cushioning packaging material 7805a, 7805b is shown deployed along the base of container 7500 provides a protective cushioning barrier for an item within container 7500 and may have a node 7810 integrated as part of the material. Such node-enabled packaging material may be reused in a variety of shipping scenarios, may be sold in sheets that can be custom cut and fit to the particular shipping customer's intended container, separator, or cushioning requirements (while retaining the integrated node).

Another embodiment includes a node-enabled apparatus for packaging an item to be shipped. The apparatus generally comprises packaging material and an ID node integrated as part of the packaging material. The packaging material is used as part of a container that packages the item to be shipped. For example, as discussed above regarding FIGS. 75A, 75B, and 76-78, such packaging material may be part of the panels making up the structure of the container, separator sheets deployed as part of the container to keep items separated from each other within the container, or cushioning material used to protect the packed items from the base, walls, and lid of the container. Thus, in one embodiment the packaging material may comprise one from a group consisting of a fiberboard container sheet, a packaging separator sheet, and cushioning material sheet.

The ID node integrated as part of the packaging material of the node-enabled apparatus is operative to communicate directly with a master node (e.g., exemplary master node 110a shown in FIG. 4 or master node 7515 illustrated in FIGS. 75A-B) in a wireless node network but is unable to directly communicate with a server (e.g., server 100 shown in FIGS. 5 and 75A-B) in the wireless node network. In more detail, the ID node further comprises a processing unit and a communication interface coupled to the processing unit. The communication interface provides a communication path (e.g., a short range communication path, such as a Bluetooth® formatted communication path) to the master node. The communication interface can also receive a message broadcast from the master node and provide the message to the processing unit.

The ID node in the apparatus further comprises a volatile memory coupled to the processing unit and a memory storage coupled to the processing unit. Examples of such memory are shown in FIG. 3 as memory storage 315 and volatile memory 320. The memory storage maintains code for execution by the processing unit and shipping information related to the container and the ID node integrated as part of the packaging material. During operation of the ID node, the code (e.g., node management and control code 325) may be loaded from memory storage and run in volatile memory.

The ID node in the apparatus also comprises a power source for energizing the ID node. For example, such a power source may be battery 355. In one embodiment, the power source within the ID node may initially be assembled to have a non-conductive strip that interrupts any possible current flow out of the power source and into the circuitry of the ID node as a way of best preserving the life of the power source. This embodiment allows the consuming shipping customer to purchase the node-enabled apparatus for a future use when shipping an item, and allow the customer to remove the non-conductive strip from between the power source (e.g., a terminal of battery 355) and a power terminal for the ID node that is normally coupled to the power source.

The processing unit of the ID node in the apparatus, when executing the code, is operative to receive the shipping information from a first node (e.g., a master node) in the wireless node network, cause an advertising signal to be broadcast over the communication interface to the master node, and share at least a part of the shipping information with the master node. In more detail, sharing such information may be accomplished when the server provides an authorization to actively connect and associate with the master node (which may be preauthorized or requested from the server when the master node detects the advertising signal).

In a further embodiment, the node-enabled apparatus may also include a status light indicative of an activated state of the ID node. For example, an exemplary status light may be implemented with a low power LED light source coupled to circuitry on ID node that interfaces with such circuitry and can be driven by the processing unit. In one embodiment, the processing unit may be further operative to cause the status light to blink in a designated pattern upon receiving the shipping information. This may allow the shipping customer a way to confirm that the node-enabled apparatus is operating and ready to be sealed within the container. For example, upon receipt of the shipping information, the processing unit may send control signals to the interface circuitry coupled to the LED status light and the control signals may cause the light to blink on and off a predesignated number of times to visually reflect receipt of the shipping information. Other embodiments may have the processing unit exercising the light in other patterns to indicate different types of status conditions and provide additional feedback to the shipping customer or package handling personnel or light sensing machines that may process or sort the package container.

In another embodiment, the status light may be disposed within the packaging material but viewable from outside the container. In one example, the status light may be disposed within the packaging material without an opening, but be close enough to the exterior so that light may "glow" appear viewable (or partially viewable) from outside the container. The status light may be disposed in a translucent part of the packaging material advantageously located so it may be seen or easily scanned.

In another example, as discussed above with respect to FIG. 76, an exemplary ID node may be disposed within recessed region 7620 and have a status light viewable through opening 7625 or, if the light is part of the body of the ID node, a status light viewable through an opening (not shown) in recessed region 7620.

In still another embodiment, the packaging material may include an opening and the status light may be disposed in a configuration within the packaging material where the status light aligns with the opening. As shown in FIG. 76, for example, an exemplary opening 7625 may be aligned with a separately mounted status light coupled to the ID node.

The ID node integrated as part of the packaging material in the apparatus may further comprise a switch coupled to the power source for allowing the power source to energize the ID node. For example, as shown in FIG. 3, ID node 120a includes a magnetic switch that is magnetically activated when the switch detects a set of magnetic field changes. In more detail, the detected set of magnetic field changes detected by the switch may further comprise a series of magnetic field changes over a period of time that defines an activation pattern. Such a pattern may be actuated by physical movement of a magnetic field source (e.g., a magnet) near the node in such a timed manner as to present the series of magnetic field changes over time.

In another embodiment, the ID node integrated as part of the packaging material in the apparatus may further comprise a logical input to the processing unit that allows the power source to energize the ID node.

In one embodiment, the packaging material may include at least a sheet of packaging material, such that the ID node integrated as part of the packaging material may be embedded within the sheet of packaging material. For example, the ID node 7540 shown in FIG. 75B is embedded within a sheet of packaging material making up a panel base of the container 7530.

Figure 79:
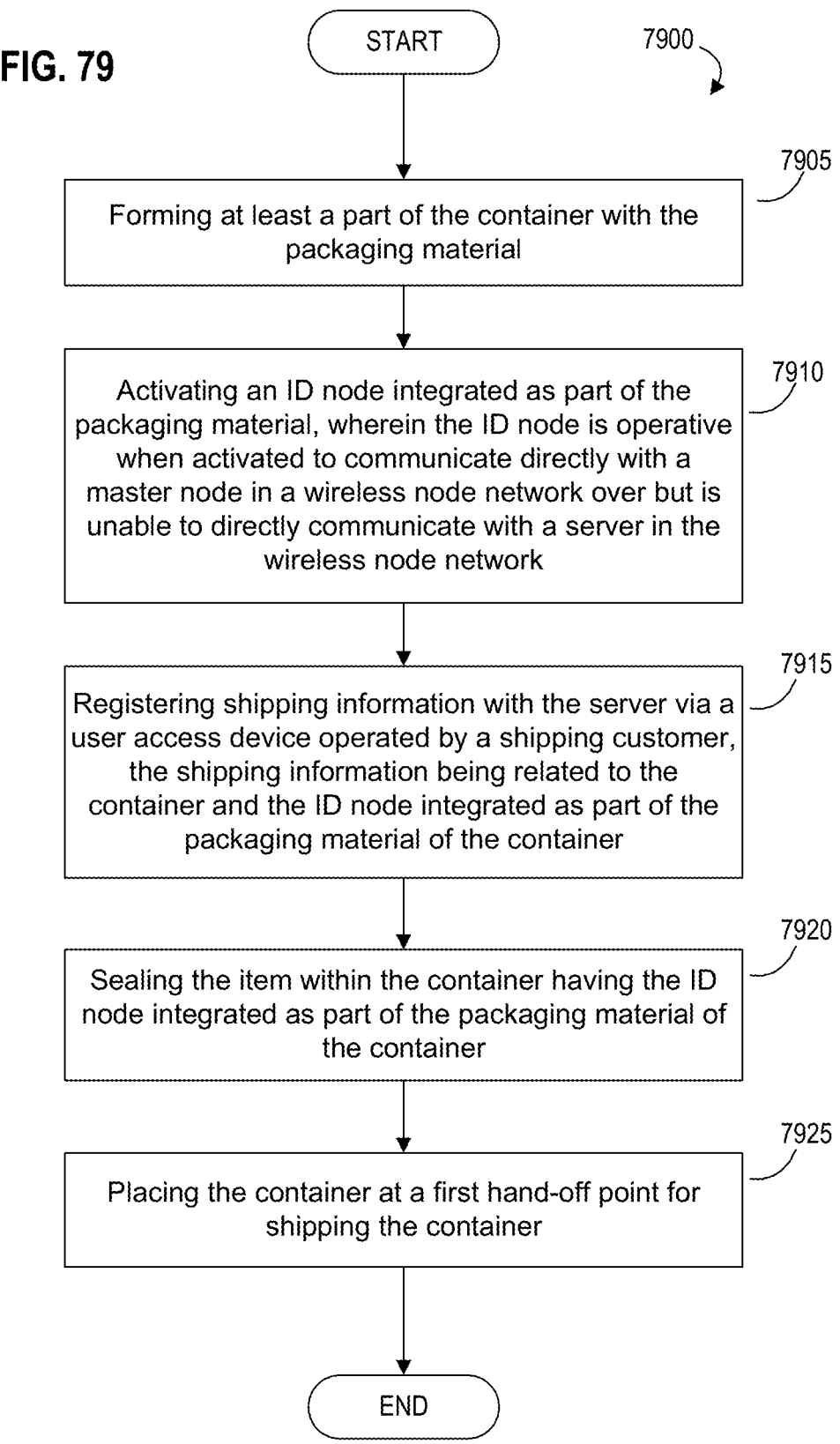
FIG. 79 is a flow diagram illustrating an exemplary method using node-enabled packaging material as part of a container for an item to be shipped in accordance with an embodiment of the invention.

Typical embodiments of such a node-enabled apparatus may include a container advantageously having an integrated or embedded ID node within the packaging material making up the container. How such node-enabled packaging material may be used is also the subject of various embodiments. FIG. 79 is a flow diagram illustrating an exemplary method using node-enabled packaging material as part of a container for an item to be shipped in accordance with an embodiment of the invention.

Referring now to FIG. 79, method 7900 begins at step 7905 by forming at least a part of the container with the packaging material. In one embodiment, the packaging material may comprise one from a group consisting of a fiberboard container sheet, a packaging separator sheet, and cushioning material sheet.

At step 7910, method 7900 continues by activating an ID node integrated as part of the packaging material. The ID node is operative to communicate directly with a master node in a wireless node network over but is unable to directly communicate with a server in the wireless node network. For example, as shown in FIG. 75A, ID node 7505 can communicate directly with master node 7515 (associated with and part of node-enabled logistics receptacle or node-enabled drop box 7520) but is unable to directly communicate with server 100. Instead, ID node 7505 relies on the hierarchy of master node 7515, which is able to communicate directly with server 100 through network 105.

In one embodiment of method 7900, activating the node integrated as part of the packaging material may be accomplished in various ways. For example, the node may have sensors built into the packaging material such that as the material forms a container and a lid part of the container is closed, the sensors detect such a closing and responds by activating the node. In another example, two surfaces of the packaging materials may have built-in sensors, which when pressed together activate the node. And as explained above, another example may deploy a magnetic switch that, when changing states under the appropriate magnetic stimulus, may activate the node.

Activating the node may cause the node to energize from a completely unpowered condition. In another example, activating the node may cause the node to move from a lower energy consumption state (e.g., a standby mode) to a higher functioning state or fully functioning state. As such, prior to activation, a node may remain in an exemplary standby mode where part of the node functions but does so while attempting to minimize the consumption of energy. For example, an exemplary node may keep its communication interface(s) powered down (e.g., radio off) when in standby, but power such circuitry on when activated so that the node can begin to communicate with other nodes or the server in the wireless node network.

In one embodiment, activating the ID node may further comprise causing a power source within the ID node (e.g., battery 355 of exemplary ID node 120a) to energize the ID node integrated as part of the packaging material of the container and to turn on a status light of the ID node.

At step 7915, method 7900 continues by registering shipping information with the server via a user access device operated by a shipping customer, the shipping information being related to the container and the ID node integrated as part of the packaging material of the container. As explained with reference to FIG. 2, an exemplary user access device in various embodiments (such as device 200) may be implemented with a desktop computer, laptop computer, tablet (such as an Apple iPad® touchscreen tablet), a personal area network device (such as a Bluetooth® device), a smartphone (such as an Apple iPhone®), a smart wearable device (such as a Samsung Galaxy Gear™ smartwatch device, or a Google Glass™ wearable smart optics) or other such devices capable of communicating over network 105 with server 100, over a wired or wireless communication path to master node and ID nodes. And as shown in the example illustrated in FIG. 75A, user access device 200 may be a smartphone operated by a shipping customer running an app (that may implement code 425 explained above) to allow direct access to server 100. In one example, the customer may have purchased container 7500 (which has integrated node 7505) at a shipping facility, a retail outlet, or via an online order for such a node-enabled apparatus.

In a more detailed embodiment, registering may comprise entering a destination address for the container into the user access device as a first part of the shipping information; entering a tracking number into the user access device as a second part of the shipping information (where the tracking number is related to the container); entering a node identification (e.g., a MAC address related to the ID node integrated as part of the packaging material of the container) into the user access device as a third part of the shipping information; and causing the user access device to transmit the shipping information to the server.

Additionally, registering may comprise entering container content information that describes the item to be shipped in the container made from the packaging material. In one particular example, the container content information may further comprise customs information for a customs declaration on the item in the container. Once generated and supplied to the server, such container content information may be programmed into and stored within memory of the ID node integrated as part of the packaging material.

At step 7920, method 7900 may continue by sealing the item within the container having the ID node integrated as part of the packaging material of the container. And at step 7925, method 7900 continues by placing the container at a first hand-off point for shipping the container.

In one embodiment, the placing step may further comprise providing the container to a courier associated with the master node near the first hand-off point. For instance, in the example illustrated in FIG. 75A, master node 7515 may be associated with a courier. As the courier receives the container 7500 having the integrated ID node 7505, the courier's master node 7515 associates with the ID node 7505 at the hand-off point (e.g., a mail room in an office building, a package storage room at a shipping facility, etc.).

However, in another embodiment, the placing step may further comprise depositing the container in a node-enabled logistics receptacle serviced by a courier, where the node-enabled logistics receptacle is at the first hand-off point. Referring back to the example illustrated in FIG. 75A, master node 7515 may be part of a node-enabled logistics receptacle or, more generally, a node-enabled logistics receptacle 7520 that can received package containers being shipped and hold them for one or more couriers to service the unit and pick up relevant package containers being shipped.

Proactive Re-Route Notification Using a Node-Enabled Logistics Receptacle

Other embodiments may have one or more nodes in a wireless node network facilitating proactive notification of a shipping customer as the customer attempts to ship a package. The shipping customer may have input and otherwise provided shipping information to a server for the package to be shipped, and then be traveling on their way to the shipping facility (e.g., such as a FedEx® Office Print & Ship Center or the like) to drop off the package. Dropping off the package with the facility, for example, may be where the package begins its anticipated transit from an origin location to a destination location.

One issue that may be encountered is when the shipping facility is unable to accept the package for some reason (e.g., the facility is closed, particular equipment may be inoperable, scheduled pickup by a courier has already occurred, the facility cannot handle the type of item to be shipped, and the like). In general, an embodiment where certain network devices in a wireless node network are deployed may provide proactive notification to the shipping customer to re-route the customer away from the facility that is unable to accept the package, and towards an alternative shipping solution (e.g., another facility, a node-enabled logistics receptacle, etc.) so that the customer may still have the package shipped.

Figure 80:
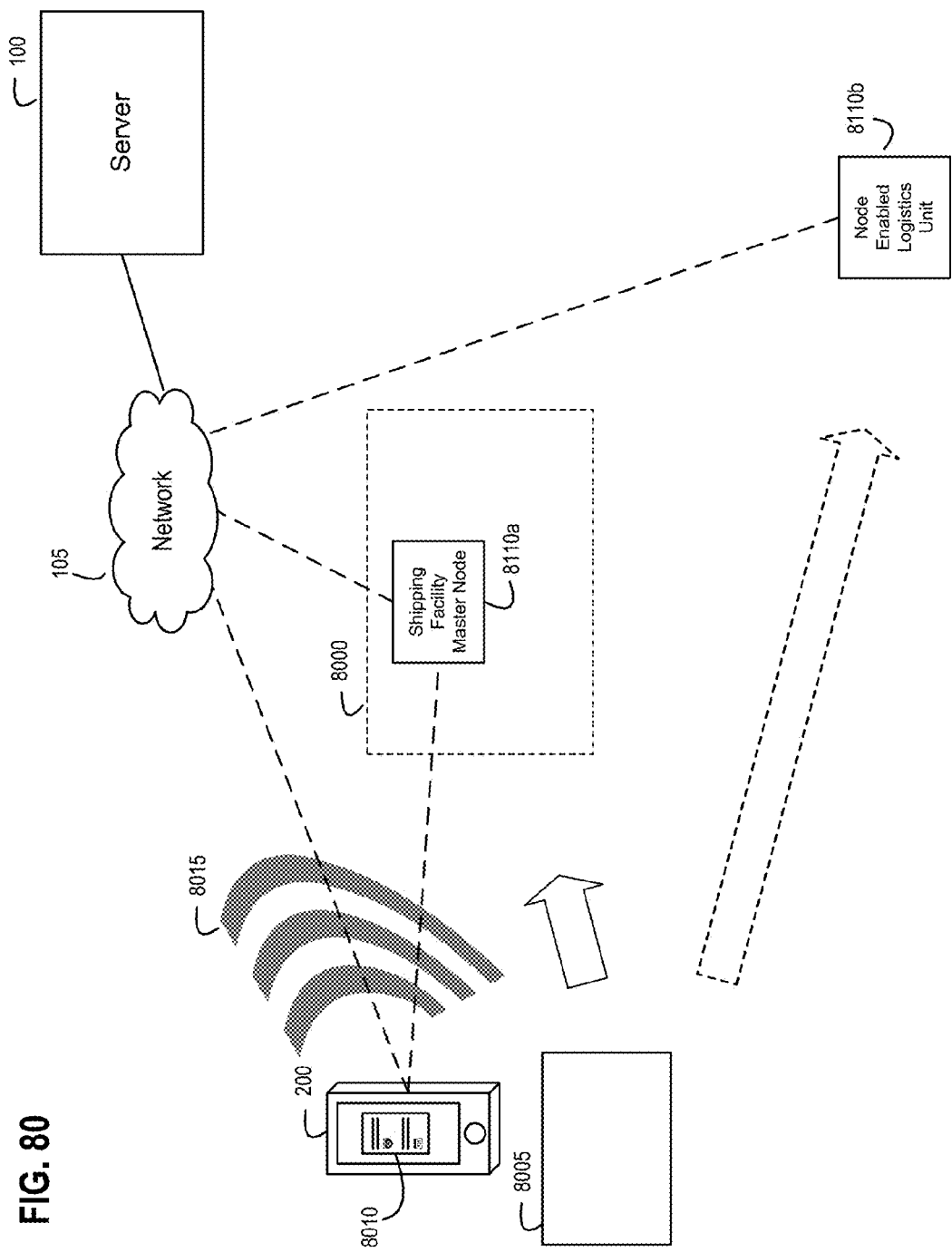
FIG. 80 is a diagram illustrating an exemplary user access device and package approaching an exemplary shipping facility where an exemplary system notifies a shipping customer about an alternative shipping solution in accordance with an embodiment of the invention.

FIG. 80 is a diagram illustrating an exemplary user access device and package approaching an exemplary shipping facility where an exemplary system notifies a shipping customer about an alternative shipping solution in accordance with an embodiment of the invention. Referring now to FIG. 80, a shipping customer's smartphone 200 (a type of user access device) and the package 8005 are shown approaching an exemplary shipping facility 8000. The facility 8000 has deployed within or around it a shipping facility master node 8110*a*, similarly structured and programmed as set forth for exemplary master node 110*a* in FIG. 4. As such, shipping facility master node 8110*a* is operative to directly communicate with server 100 via network 105.

In an embodiment, the shipping customer's smartphone 200 may execute an app (not shown) that in essential parts operates as code 325 or 425 to make smartphone 200 operate as an exemplary ID node or exemplary master node, respectively. As such, smartphone 200 may interact with server 100, for example, to upload shipping information on the package 8005 to be shipped. Likewise, smartphone 200 may exercise its Bluetooth® communication hardware and software (e.g., RF transceiver, program stacks, profiles, and the like) as a short-range communication interface to broadcast advertising signals 8015. As smartphone 200 approaches and gets close enough to shipping master node 8110*a*, the master node 8110*a* may begin to detect the signals 8015. Such signals 8015 may include information in the status header that indicates smartphone 200 is looking to associate with another node. In one embodiment, once associated, the master node 8110*a* may access server 100 to gather further information (e.g., shipping information). In another embodiment, the master node 8110*a* may receive such information directly from the smartphone 200 after the active association between the smartphone 200 and the shipping facility master node 8110.

At this point, the shipping customer may continue approaching the shipping facility 8000 and enter the facility 8000 to ship the package 8005 if the facility 8000 is open and accepting packages for shipment. However, rather than simply arrive at facility 8000 and find out then that the package cannot be shipped from there as intended, an embodiment may provide a proactive notification about an alternative shipping solution to the smartphone 200 (as a type of user access device). Those skilled in the art will appreciate that smartphone 200 may be implemented by others types of user access devices, such as a laptop computer, a tablet device, a personal area network device, or a smart wearable device. And in more detail, an embodiment may provide a proactive notification about an alternative shipping solution to the user access device based upon the shipping information and a shipping status for the shipping facility.

In general, the shipping status relates to the ability or inability of the facility to accept and ship the package. Status information may be available on the shipping master node 8110*a* and/or server 100 that reflects such a shipping status. Likewise, such network devices may also be able to determine or identify an alternative shipping solution, such as a nearby shipping facility open later that facility 8000 or a close by node-enabled logistics receptacle. Other examples of an alternative shipping solution may include logistics receptacles, such as a conventional non-node-enabled drop box, secure locker unit or other drop off receptacle. As such, an exemplary proactive notification may provide directions to such an alternative shipping solution's location (the nearest 24-hour shipping facility, a close by node-enabled logistics receptacle, etc.).

In a more detailed embodiment, the proactive notification may be a beginning message of a two-way interactive dialog between the user of the smartphone 200 looking to find a suitable alternative shipping solution and the master node or server providing other alternatives, relevant information about each alternative (e.g., distance from the user's current location, hours of operation, types of courier service offered, different types of shipping service offered, a schedule of future pickup times). Additionally, the user of the smartphone 200 may be provided, as part of such a two-way dialog started with the proactive notification, an offer for premium or prioritized pickup to be schedule for a selected node-enabled logistics receptacle.

For example, if the shipping customer using smartphone 200 is unable to have facility 8000 ship the package 8005, the proactive notification sent to smartphone 200 may include directions 8010 to a close by node enabled logistics receptacle 8110*b*. Furthermore, the shipping customer using smartphone 200 may be presented with options for other alternative shipping solutions (e.g., other locations with other logistics receptacles or shipping facilities). Additionally, in an embodiment, the shipping customer using smartphone 200 may elect to go to node-enabled logistics receptacle 8110*b* and pay to have pickup prioritized at that particular unit. For example, such a payment may cause the receptacle 8110*b* to quickly report the pending package in its custody to server 100 for a quicker pickup than normally provided with standard shipping services. As such, payment may be made by the shipping customer using smartphone 200 (e.g., using wireless payment options with node associations as discussed in more detail herein), and schedule information for courier pick-up of packages within node-enabled logistics receptacle 8110*b* may be prioritized.

Figure 81:
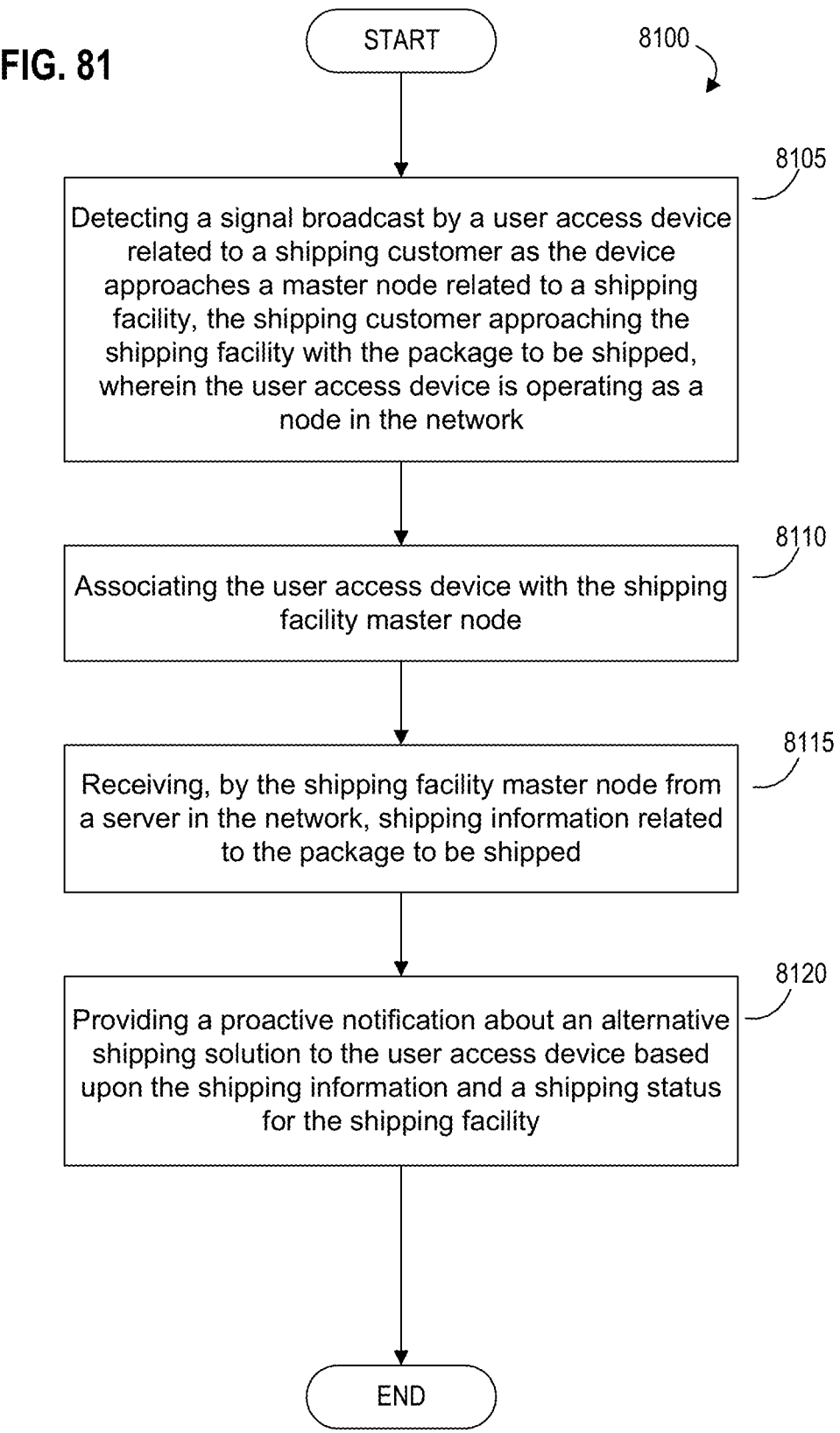
FIG. 81 is a flow diagram illustrating an exemplary method for proactively notifying a shipping customer using a wireless node network about an alternative shipping solution when shipping a package in accordance with an embodiment of the invention.

FIG. 81 is a flow diagram illustrating an exemplary method for proactively notifying a shipping customer using a wireless node network about an alternative shipping solution when shipping a package in accordance with an embodiment of the invention. Method 8100 begins at step 8105 by detecting a signal broadcast by a user access device related to a shipping customer as the device approaches a master node related to a shipping facility, where the shipping customer is approaching the shipping facility with the package to be shipped. In another embodiment of method 8100, the user access device may detect a signal broadcast by the master node related to the shipping facility as a prelude to associating in step 8110.

Here, the user access device (e.g., smartphone 200 as shown and explained in FIG. 80) is operating as a node in the network. In a more detailed embodiment, the user access device may be operating as an ID node in the network, and as such may be operative to directly communicate with the shipping facility master node but unable to directly communicate with the server in the network. However, in another embodiment, the user access device may be operating as another master node in the network, such that the device can directly communicate with the shipping facility master node and directly communicate with the server in the network. Indeed, an example smartphone 200 may have an app that allows it to operate as a master node in some instances and as an ID node in other instances.

At step 8110, method 8100 continues by associating the user access device with the shipping facility master node. This may be accomplished with establishing a passive or active connection between the device and the master node. The active connection may allow for secured sharing of information, such as shipping information in one embodiment.

At step 8115, method 8100 continues with an embodiment where, rather than receive the shipping information from the user access device, the shipping facility master node receives the shipping information related to the package to be shipped from the server. In one example, this may be done after the shipping facility master node associates with the user access device. However, in another example, the shipping facility master node may have received the shipping information prior to associating with the user access device. Thus, the server may have pre-staged the shipping information with the shipping master node in anticipation of the shipping customer bringing the package to the facility (such as facility 8000) for shipping.

Additionally, in another embodiment the shipping facility master node may be pre-staged with service information. For example, such service information may outline or otherwise define classes of acceptable shipping services provided by the shipping facility. In more detail, such service information may also include alternative shipping solution information to be provided to the user access device.

At step 8120, method 8100 continues by providing a proactive notification about an alternative shipping solution to the user access device based upon the shipping information and a shipping status for the shipping facility. For example, exemplary shipping information may identify a particular shipping service desired, and the shipping status information for the facility may indicated that desired service is not offered or is temporarily offline (e.g., due to equipment maintenance issues, inability to accept more due to being a maximum capacity, or the like).

In one embodiment, the step of providing the proactive notification to the user access device may be performed by one of the shipping facility master node and the server. For example, an embodiment may have more details on what other alternative shipping solutions are available on the back-end server 100, rather than maintaining such information on shipping facility master node 8110*a*. However, in another embodiment, shipping facility master node 8110*a* may be a robust computing platform and its memory storage may contain such information depending on the implementation and so it can offload the server 100 from needing to respond with such a notification or, in more detailed embodiments, interactive messaging between the device 200 and the system (e.g., master node 8110*a* or server 100).

In several other embodiments, the shipping status for the shipping facility may be implemented in various ways. In a general embodiment, the shipping status for the shipping facility may comprise whether the shipping facility is unable to accept any package for shipment. In a more detailed example, the shipping status may comprise whether the shipping facility is not currently open for business. The shipping customer may be attempting to drop off the package to be shipped after normal business hours for the facility, or at least when a shipping department portion of the shipping facility is not currently open for business. In yet another detailed example, the shipping status may comprise whether the shipping facility is unable to accept one or more categories of shipments related to the package (such as dangerous goods, or types of pickup entities that may not service the shipping facility).

In another example, the shipping status for the shipping facility may comprise whether the shipping facility is no longer scheduled for a pickup event by a desired shipping courier identified in the shipping information. For instance, the shipping customer may be approaching the shipping facility after the last pickup by a courier for that day. In more detail, when the shipping information identifies a desired shipping courier, that particular shipping courier may not be scheduled to come to the shipping facility that day while other couriers may still be scheduled to pick-up packages identified to be handed off to them for further shipping through their respective shipping entity's logistics network.

In still another example, the shipping status for the shipping facility may comprise whether the shipping facility is unable to accept a package for shipment by a desired shipping service identified in the shipping information. For instance, a single shipping entity may provide a faster shipping service (e.g., overnight) and a more standard shipping service that costs less than the faster service. The shipping status, in such a situation, may indicate that while it can accept packages for the standard shipping server, it cannot ship any more packages with the faster shipping service that day given the logistics resources already deployed by the shipping entity.

In another embodiment, the proactive notification about the alternative shipping solution may include information about an alternative shipping facility that is able to accept the package for shipment as the alternative shipping solution. In the example shown in FIG. 80, smartphone 200 may receive an exemplary proactive notification as the device approaches facility 8000 where the notification includes a name of another shipping facility, location, hours of service, and types of service provided by one or more shipping entities.

In still another embodiment, the proactive notification about the alternative shipping solution may comprise information about a node-enabled logistics receptacle that is able to accept the package for shipment as the alternative shipping solution. In more detail, the information about the node-enabled logistics receptacle that is able to accept the package for shipment may include directions to the node-enabled logistics receptacle. For instance, such a notification may include information that identifies node-enabled logistics receptacle 8110*b*, which may be available to intelligently accept, track, report, and manage the location and status of package 8005 immediately upon receipt. And that information may include directions 8010 to be shown to the shipping customer via a user interface on device 200.

In an even more detailed embodiment, the step of providing the proactive notification about the alternative shipping solution may comprise determining, by the server, a location of the user access device; determining if the shipping information and the shipping status for the shipping facility indicate the shipping facility is unable to accept the package for shipment; identifying a node-enabled logistics receptacle near the shipping facility (e.g., unit 8110*b* near facility 8000) as the alternative shipping solution; and transmitting the proactive notification to the user access device, where the proactive notification provides directions to the identified node-enabled logistics receptacle.

And in a further embodiment of method 8100, the identifying step explained above may further comprise determining which one of a plurality of node-enabled logistics receptacles is a closest unit to the user access device with a capacity to accept the package for shipment; and identifying the determined one of the node-enabled logistics receptacles to be the alternative shipping solution comprising the node-enabled logistics receptacle near the shipping facility. Here, there may be a large number of potential alternative shipping solutions and the master node or server may determine which is closest. Alternatively, a set of choices for close units within a prompted range may be provided where the notification is a beginning message in a more interactive exchange to proactively help the shipping customer ship the package in an efficient manner.

Those skilled in the art will appreciate that method 8100 as disclosed and explained above in various embodiments may be implemented on a master node (such as exemplary master node 110a as illustrated in FIG. 4, and shipping facility master node 8110a in FIG. 80), running one or more parts of a control and management code (such as code 425) to implement any of the above described functionality. Such code may be stored on a non-transitory computer-readable medium (such as memory storage 415 in an exemplary mobile master node). Thus, when executing such code, a processing unit of the master node (such as unit 400) may be operative to perform operations or steps from the exemplary methods disclosed above, including method 8100 and variations of that method.

Self-Assessing a Location for Node-enabled Logistics Receptacle

Figure 82B:
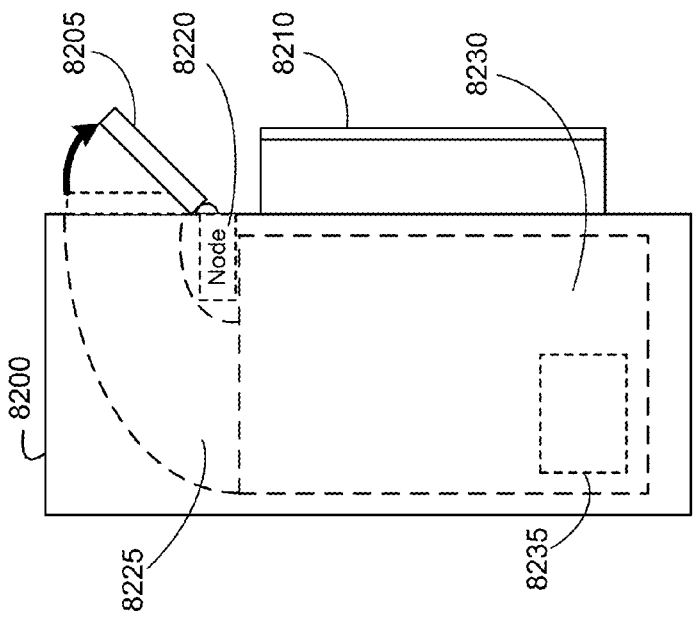
FIG. 82B is a diagram illustrating a side and internal view into the exemplary node-enabled logistics receptacle of FIG. 82A in accordance with an embodiment of the invention.
Figure 82A:
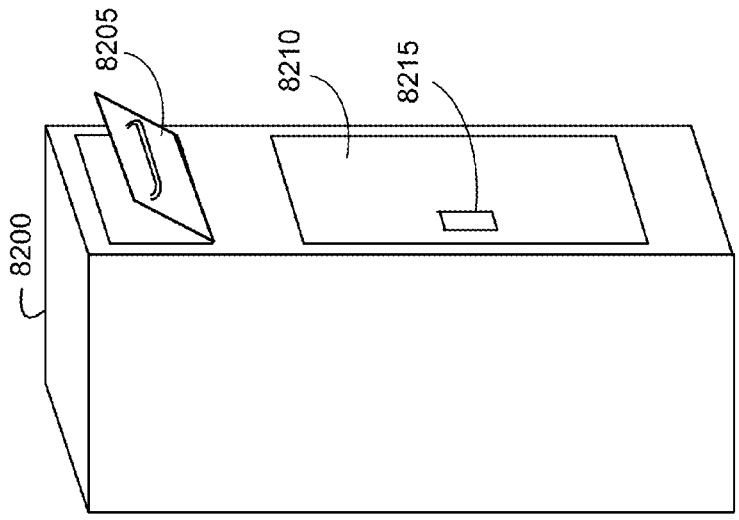
FIG. 82A is a perspective diagram illustrating an exterior view of an exemplary node-enabled logistics receptacle in accordance with an embodiment of the invention.

As described above, an embodiment may implement a node as part of or connected/attached to a logistics receptacle, such as a shipping drop box or secure locker unit. FIGS. 82A and 82B illustrate an exemplary node-enabled logistics receptacle. Referring now to FIG. 82A, exemplary node-enabled logistics receptacle 8200 is illustrated in perspective having a deposit entrance 8205 and a payload access door 8210. The node-enabled logistics receptacle 8200 is typically placed in an accessible location where shipping customers may have access to receptacle 8200. In operation, a shipping customer may articulate and open a door at the deposit entrance 8205 so that the receptacle 8200 may receive a package. Once the package is placed within the receptacle 8200, and the shipping customer closes the door at the deposit entrance 8205, the package is then maintained within the receptacle. In other words, the exemplary node-enabled logistics receptacle 8200 can receive and temporarily maintain custody of a package being shipped, and it does so with an entrance opening 8205 through which the package is received by the receptacle and a temporary storage area within the receptacle where the package is temporarily and securely maintained until an authorized pickup. Typically, a shipping entity's courier personnel may arrive and pickup any deposited packages using payload access door 8210 and security lock 8215.

FIG. 82B is a diagram illustrating a side and internal view into the exemplary node-enabled logistics receptacle 8200 of FIG. 82A in accordance with an embodiment of the invention. Referring now to FIG. 82B, more details of the exemplary node-enabled logistics receptacle 8200 are shown. For example, the node-enabled logistics receptacle 8200 is shown having a node 8220 as part of the receptacle structure. In one embodiment, node 8220 may be implemented as an ID node; in other embodiments, node 8220 may be implemented as a more complex master node. Node 8220 may be integrated or embedded within the node-enabled logistics receptacle 8200. Other embodiments may simply have the node 8220 attached to some part of the node-enabled logistics receptacle 8200, such as to an accessible portion of the interior regions 8225, 8230 of node-enabled logistics receptacle 8200. With such a removable implementation of node 8220, various service operations related to the node 8220 may be easier to accomplish (e.g., replacement of the node, replacement of the node's battery, replacement of the node's sensor(s), adding more memory to the memory onboard the node, and the like).

In operation, a shipping customer may insert a package 8235 through the opening 8205 by opening a door for the opening. The package, such as package 8235, may then be placed within a first interior region 8225. In some embodiments, those skilled in the art will appreciate that the node-enabled logistics receptacle 8200 may include further structure to accept the package 8235 in region 8225 while preventing removal of any packages or items from within the node-enabled logistics receptacle 8200.

Once within region 8225, the package 8235 then drops into or otherwise moves into a second interior region 8230. Region 8230 is typically used as a temporary storage area within the receptacle 8200 where the package 8235 can be temporarily and securely maintained until an authorized pickup. In one example, a shipping entity's courier personnel may arrive and pickup any deposited packages using payload access door 8210 and security lock 8215.

And as discussed in more detail with respect to other embodiments disclosed herein (e.g., embodiments illustrated in FIGS. 89A and 89B), an exemplary node-enabled logistics receptacle may be able to sense when a package having a node (generally referred to as a "node package") is approaching, and in some embodiments can detect when a node package or non-node package has been deposited within the receptacle.

One issue that may be faced related to deploying a node-enabled logistics receptacle, such as receptacle 8200, at a particular location is assessing whether the location is a suitable location for the node-enabled logistics receptacle. If the location does not have a suitable amount of potential shipping customers that may use the receptacle, the costs of deploying such a node-enabled logistics receptacle may not be justified. Additionally, business and consumer activity surrounding a particular location may change over time. Such business and consumer activity may have initially justified placement of the node-enabled logistics receptacle at the particular location, but an embodiment may allow for on-going and future re-assessments of whether keeping the node-enabled logistics receptacle at that location is justified.

Figure 83:
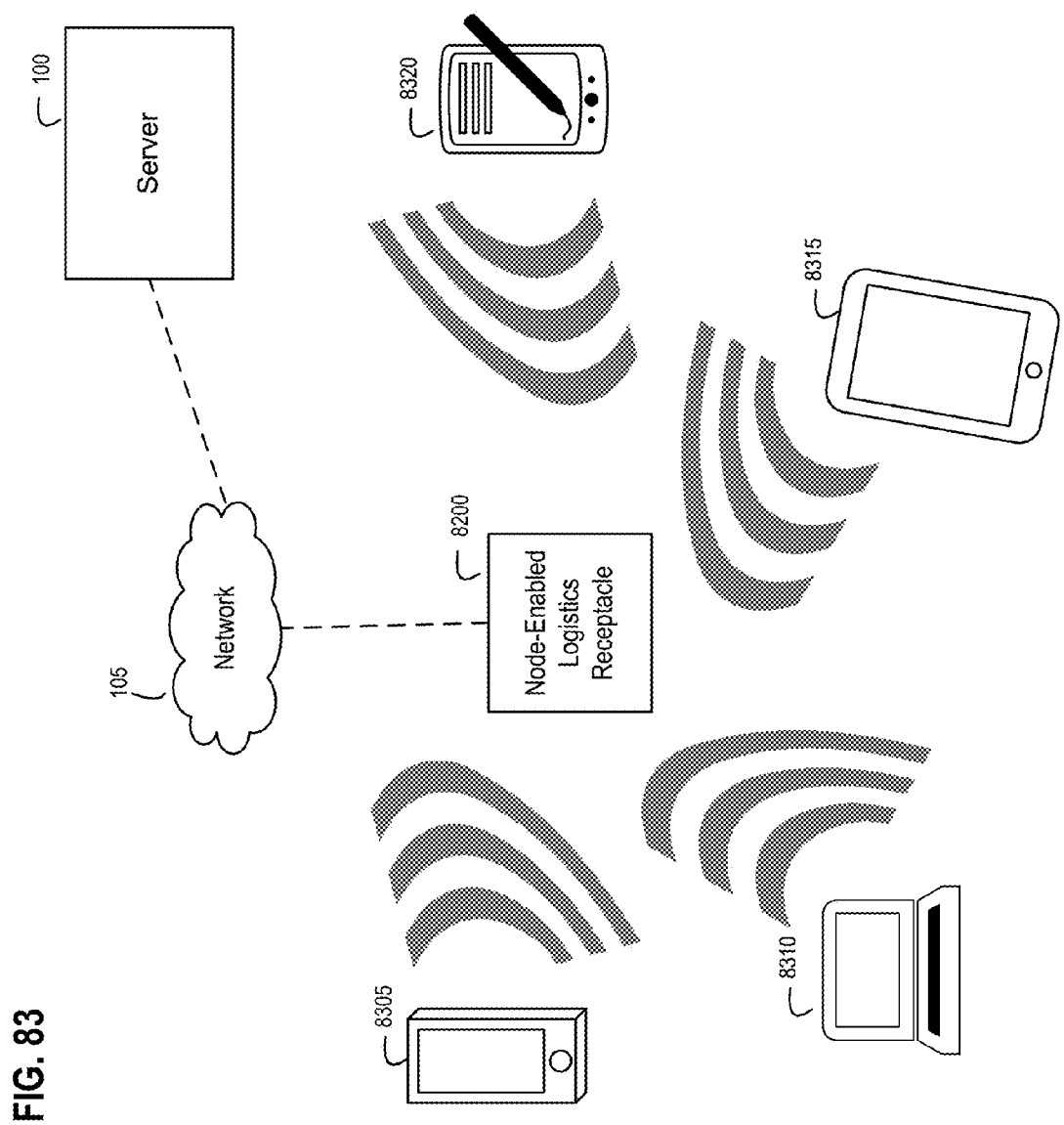
FIG. 83 is a diagram illustrating an exemplary node-enabled logistics receptacle that can assess the suitability of a current location of the exemplary node-enabled logistics receptacle in accordance with an embodiment of the invention.

In one embodiment, a node-enabled logistics receptacle, such as exemplary node-enabled logistics receptacle 8200, is able to self-assess its current location. For example, FIG. 83 is a diagram illustrating an exemplary node-enabled logistics receptacle that is operative to assess the suitability of a current location of the exemplary node-enabled logistics receptacle in accordance with an embodiment of the invention. Referring now to FIG. 83, an embodiment is shown where node-enabled logistics receptacle 8200 is operative to communicate directly with a server 100 over network 105. Thus, the node 8220 within receptacle 8200 in this embodiment is a master node. However, in another embodiment, node 8220 within receptacle 8200 may be implemented with an ID node, and node-enabled logistics receptacle 8200 may be operative to directly communicate with a master node (not shown) in the wireless node network, which can then directly communicate with server 100.

The logistics receptacle 8200, as explained with reference to FIGS. 82A and 82B, can receive and temporarily maintain a package being shipped. And as shown in FIG. 82B, the receptacle has an entrance opening through which the package is received and a temporary storage area (such as region 8230) where the package is temporarily and securely maintained until an authorized pickup.

The node-enabled logistics receptacle also comprises a node assembled with the receptacle such that there is a general relationship between the node and the receptacle. The node, for example, may be assembled with the receptacle by being attached to, integrated as part of, or fully or partially embedded within the structure of the receptacle. In one embodiment, the node may be implemented with ID node 120a illustrated in FIG. 3; likewise, in another embodiment, the node may be implemented with master node 110a illustrated in FIG. 4.

In more detail, the node assembled with the logistics receptacle further comprises a node processing unit, a node memory storage, and at least one communication interface. The node memory storage is coupled to the node processing unit and maintains code for execution by the node processing unit and a user criteria level related to wireless communication signal activity near the embedded node assembled with the receptacle.

The communication interface (or each communication interface when there are multiple interfaces) is/are coupled to the node processing unit. The communication interface is generally operative to detect a signal broadcast from a wireless user access device (such as a smartphone) and communicate with another network device in the wireless node network (such as an ID node, a master node, or the server).

The node processing unit, when executing the code maintained on the node memory storage, is operative to perform various functions that collectively allow the node-enabled logistics receptacle to assess a current location for a node-enabled logistics receptacle. In more detail, the node processing unit is operative to detect a level of wireless communication signal activity on the at least one communication interface. In the example illustrated in FIG. 83, the node-enabled logistics receptacle 8200 is shown to be detecting wireless communication signal activity on its communication interface (e.g., medium/long range communication interface 485 when the node is a master node like node 110a shown in FIG. 4). As shown in FIG. 83, receptacle 8200 is operative to detect activity from four different wireless devices, such as smartphone 8305, laptop computer 8310, tablet device 8315, and personal area network device 8320.

The node processing unit is also operative to record the detected level of wireless communication signal activity over a predetermined period of time in the node memory storage. Thus, in the example shown in FIG. 83, the node processing unit within node 8220 of receptacle 8200 may record the detected level of wireless communication signal activity over a week, for example, in onboard memory within the node 8220. The activity level may, for example, be recorded as a number of signals detected, the signal strength of the signals detected (e.g., based on a received signal strength indication or RSSI), or a combination thereof. Other embodiments may record the activity level as signals detected during specific time intervals (e.g., during convention business hours, before business hours, during a lunch time interval, after business hours, during rush hour, during certain days of the week, during holiday periods, and the like).

The node processing unit is also operative to compare the recorded level of wireless communication signal activity to the user criteria level for the node-enabled logistics receptacle maintained in the node memory storage. Based upon the comparison of the recorded level and the user criteria level, the node processing unit is operative to assess the current location for the node-enabled logistics receptacle. If the processing unit assesses that the current location does not meet the user criteria level, the unit may transmit an alert message to another network device in the network.

In one embodiment, the alert message may provide the recorded level of wireless communication signal activity over the predetermined period of time to at least one of a master node in the network or a server in the network. For example, in the FIG. 83 example, node-enabled logistics receptacle 8200 is shown as operative to communicate directly with the server 100 via network 105 (i.e., not through an intermediary wireless node in the wireless node network before getting to server 100). However, another embodiment may have node-enabled logistics receptacle 8200 communicating the alert message to another node (e.g., a master node not shown in FIG. 83), which may forward the alert message or otherwise notify the server 100 about the alert message.

In another embodiment, the node processing unit is further operative to detect the level of wireless communication signal activity by being operative to detect a number of signals broadcast by at least one wireless user access device. Thus, the number of signals broadcast by one or more than one wireless user access devices (e.g., one or more network devices from a group comprising a laptop computer, a tablet device, a personal area network device, a smartphone device, and a smart wearable device) may be the detected level of wireless communication signal activity. The wireless user access device(s) have users that may interact with one or more network devices of a wireless node network, such as the node in the node-enabled logistics receptacle.

In a more detailed embodiment, the user criteria level may be a threshold number of signals broadcast by the at least one wireless user access device and detected by the node-enabled logistics receptacle. In other words, the node-enabled logistics receptacle may listen for and record indications of a level of potential customers that may use the receptacle. As such, this embodiment may consider a threshold number of detects signals from wireless user access devices to be a suitable user criteria level.

In still another embodiment, the detected level wireless communication signal activity over the predetermined period of time further may be based upon a number of detected signals broadcast by at least one wireless user access device and a strength of each of the detected signals broadcast by the at least one wireless user access device, and further still, the user criteria level may be a threshold number of detected signals broadcast by the at least one wireless user access device. In an even more detailed embodiment, the user criteria level may be a threshold number of detected signals broadcast by the at least one wireless user access device having at least a threshold strength. And in yet a further detailed embodiment, the user criteria level may be a threshold number of detected signals broadcast by the at least one wireless user access device having a minimum relative received signal strength (such as an RSSI that effectively focuses the relevant group of detected signals to those within a reasonable range from the node-enabled logistics receptacle.

Figure 84:
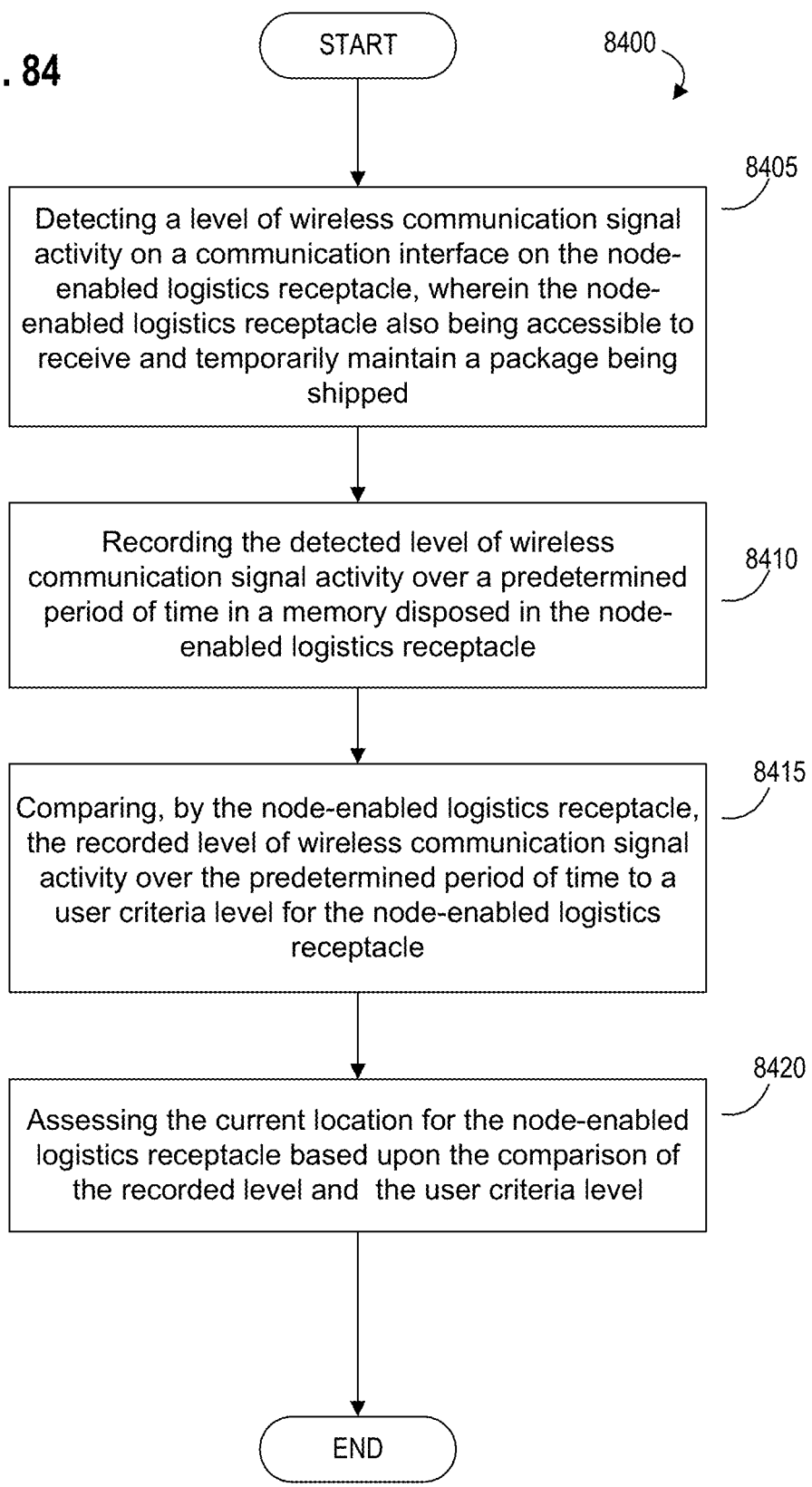
FIG. 84 is a flow diagram illustrating an exemplary method for assessing a current location for a node-enabled logistics receptacle in accordance with an embodiment of the invention.

FIG. 84 is a flow diagram illustrating an exemplary method for assessing a current location for a node-enabled logistics receptacle in accordance with an embodiment of the invention. Referring now to FIG. 84, method 8400 begins at step 8405 by detecting a level of wireless communication signal activity on a communication interface on the node-enabled logistics receptacle, where the node-enabled logistics receptacle can receive and temporarily maintain a package being shipped. For example, as shown in FIGS. 82A and 82B, node-enabled logistics receptacle 8200 can receive and temporarily maintain package 8235 in region 8230 as it is being shipped and can detect, as shown in FIG. 83, a level of wireless communication signal activity from network devices (such as wireless user access devices—e.g., smartphone 8305, laptop computer 8310, tablet device 8315, and personal network device 8320).

In a further embodiment of method 8400, the detecting step may comprise detecting the level of wireless communication signal activity as detecting a number of signals broadcast by one or more wireless user access devices that allow a user to interact with one or more network devices of a wireless node network. Examples of a wireless user access device may be a network device, such as a laptop computer, a tablet device, a personal area network device, a smartphone device, and a smart wearable device. Additionally, method 8400 may have the user criteria level being a threshold number of signals broadcast by the at least one wireless user access device and detected by the node-enabled logistics receptacle.

In a more detailed embodiment of method 8400, the detected level wireless communication signal activity over a predetermined period of time may be based upon a number of detected signals broadcast by at least one wireless user access device and a strength of each of the detected signals broadcast by the at least one wireless user access device (e.g., an RSSI based strength of the detected signals). Additionally, in such an embodiment, the user criteria level may further be implemented in a variety of useful ways, such as with a threshold number of detected signals broadcast by the at least one wireless user access device; with a threshold number of detected signals broadcast by the at least one wireless user access device having at least a threshold strength; and with a threshold number of detected signals broadcast by the at least one wireless user access device having a minimum relative received signal strength.

At step 8410, method 8400 continues by recording the detected level of wireless communication signal activity over a predetermined period of time in a memory disposed in the node-enabled logistics receptacle. At step 8415, method 8400 continues by comparing, by the node-enabled logistics receptacle, the recorded level of wireless communication signal activity over the predetermined period of time to a user criteria level for the node-enabled logistics receptacle. And at step 8420, method 8400 concludes by assessing the current location for the node-enabled logistics receptacle based upon the comparison of the recorded level and the user criteria level.

In a further embodiment, method 8400 may also include transmitting an alert message to another network device in the network when the node-enabled logistics receptacle assesses the current location does not meet the user criteria level. Additionally, the alert message may provide the recorded level of wireless communication signal activity over the predetermined period of time to at least one of a master node in the network or a server in the network.

Those skilled in the art will appreciate that method 8400 as disclosed and explained above in various embodiments may be implemented on node-enabled logistics receptacle having an ID node (such as exemplary ID node 120a as illustrated in FIG. 3) or a master node (such as exemplary master node 110a as illustrated in FIG. 4), running one or more parts of a control and management code (such as code 325 for an ID node based node-enabled logistics receptacle or code 425 for a master node based node-enabled logistics receptacle) to implement any of the above described functionality. Such code may be stored on a non-transitory computer-readable medium (such as memory storage 315 or 415 in the respective exemplary nodes). Thus, when executing such code, a processing unit of the node (such as unit 300 or unit 400) may be operative to perform operations or steps from the exemplary methods disclosed above, including method 8400 and variations of that method.

Proactive Status Reporting from a Node-enabled Logistics Receptacle

Servicing of a conventional logistics receptacle (e.g., a shipping drop-box or secure locker unit) may be performed without proactive reporting from the receptacle itself. However, in the embodiments described below, an exemplary node-enabled logistics receptacle may proactively facilitate more efficient and effective pick up of packages being shipped and management of logistics receptacle resources that allow a shipping customer to drop off a package for shipment.

FIGS. 82A and 82B and the accompanying description above provide a basic description of an exemplary node-enabled logistics receptacle. Additionally, FIG. 85A is a diagram illustrating an exemplary node-enabled logistics receptacle with a master node assembled within the logistics receptacle and ready to receive a package in accordance with an embodiment of the invention. Referring now to FIG. 85A, node-enabled logistics receptacle 8500 is illustrated having a master node 8505 assembled within it (similar to node 8220 within receptacle 8200 shown in FIG. 82B and exemplary master node 110a shown in FIG. 4). In FIG. 85A, a package 8235 to be shipped is outside node-enabled logistics receptacle 8500 prior to depositing the package 8235 into the node-enabled logistics receptacle 8500. Once deposited within node-enabled logistics receptacle 8500, FIG. 85B illustrates the package 8235 within the node-enabled logistics receptacle 8500 in accordance with an embodiment of the invention.

Figure 85B:
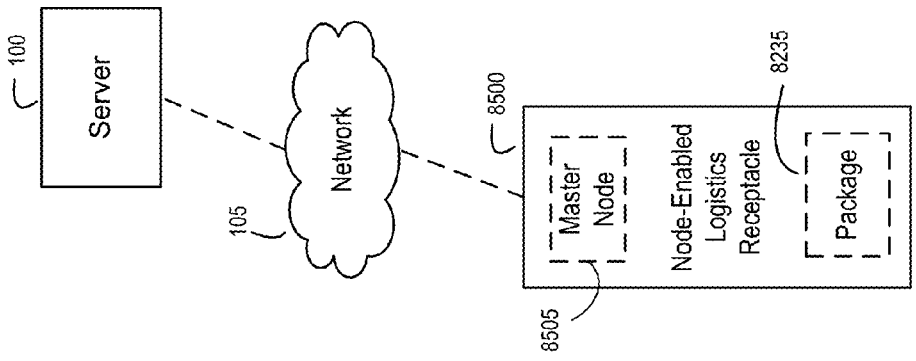
FIG. 85B is a diagram illustrating the exemplary node-enabled logistics receptacle with the master node assembled within the logistics receptacle of FIG. 85A with the package within the node-enabled logistics receptacle in accordance with an embodiment of the invention.
Figure 85A:
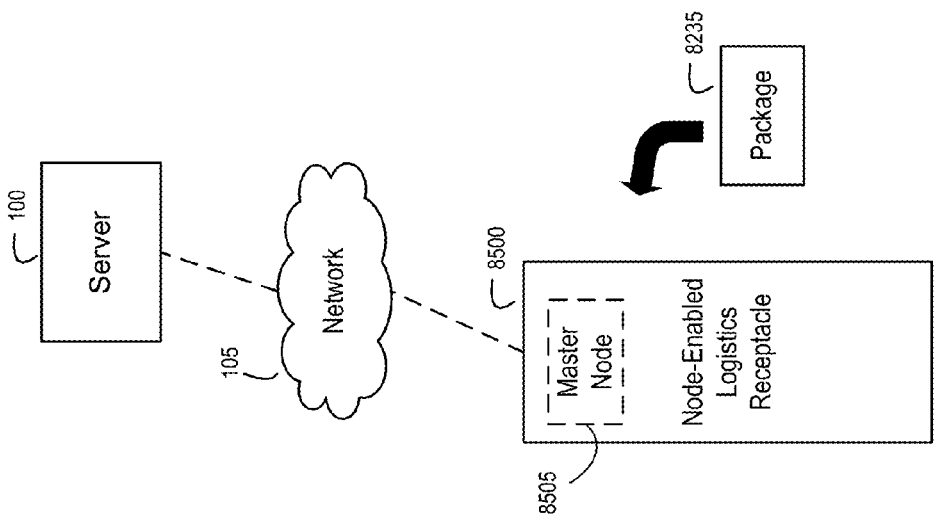
FIG. 85A is a diagram illustrating an exemplary node-enabled logistics receptacle with a master node assembled within the logistics receptacle and ready to receive a package in accordance with an embodiment of the invention.

As shown in FIGS. 85A and 85B, master node 8505 is operative to communicate within the wireless node network with various network devices—e.g., with other nodes (such as ID nodes and master nodes) as well as communicate directly with server 100. Thus, the exemplary node-enabled logistics receptacle 8500 is able to provide information related to its contents through master node 8505 to server 100.

Figure 86B:
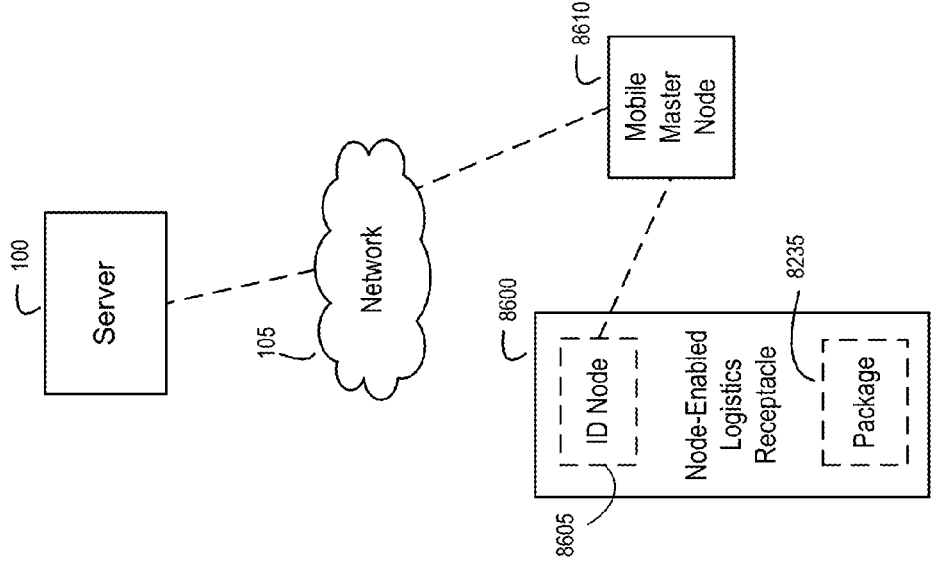
FIG. 86B is a diagram illustrating the exemplary node-enabled logistics receptacle with the ID node assembled within the logistics receptacle of FIG. 86A with the package within the node-enabled logistics receptacle in accordance with an embodiment of the invention.
Figure 86A:
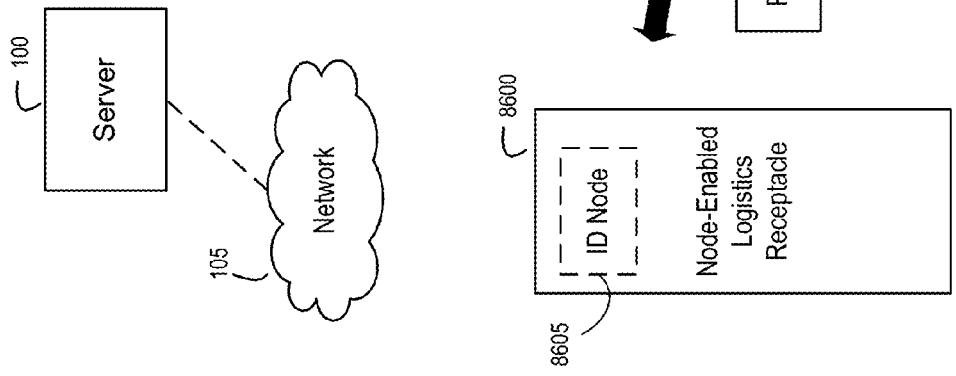
FIG. 86A is a diagram illustrating an exemplary node-enabled logistics receptacle with an ID node assembled within the logistics receptacle and ready to receive a package in accordance with an embodiment of the invention.

Similar to the node-enabled logistics receptacle 8500 shown in FIGS. 85A and 85B, another exemplary node-enabled logistics receptacle is illustrated in FIGS. 86A and 86B. However, the node assembled with the receptacle in FIGS. 86A and 86B is an ID node instead of a master node. In more detail, FIG. 86A is a diagram illustrating an exemplary node-enabled logistics receptacle with an ID node assembled within the logistics receptacle and ready to receive a package in accordance with an embodiment of the invention. Referring now to FIG. 86A, node-enabled logistics receptacle 8600 is illustrated having an ID node 8605 assembled within it (similar to node 8220 within receptacle 8200 shown in FIG. 82B and exemplary ID node 120a shown in FIG. 3). In FIG. 86A, package 8235 to be shipped is outside node-enabled logistics receptacle 8600 prior to depositing the package 8235 into the node-enabled logistics receptacle 8600. Once deposited within node-enabled logistics receptacle 8600, FIG. 86B illustrates the package 8235 within the node-enabled logistics receptacle 8600 in accordance with an embodiment of the invention.

In some embodiments, the package 8235 may be temporarily left in the custody of the node-enabled logistics receptacle 8600 without being actually within the receptacle as shown in FIG. 86B. In more detail, in some environments, the node-enabled logistics receptacle 8600 may not be able to fit the package through a package door used by customers to deposit packages within receptacle 8600. However, the node-enabled receptacle 8600 may be able to communicate with a node package left outside of the receptacle—e.g., if package 8235 were deposited within a small distance of receptacle 8600 the node 8605 may be able to detect signals coming from the node in package 8235, associated with the node package 8235, and temporarily gain a type of managerial custody of the package 8235. For non-node packages, the node within the node-enabled logistics receptacle may use additional sensors discussed below with reference to FIGS. 89A-D.

In a further embodiment where no external sensors are incorporated as part of the node-enabled logistics receptacle to sense the presence of a package outside the receptacle, third party data may be used by the server in predicting the likelihood of a package being left outside the node-enabled logistics receptacle. For example, such third party data may include information on relevant weather and crime statistics for the area where the node-enabled logistics receptacle is located. Using such data, sensor inputs and drop off patterns, the server may be able to predict, for a certain day, whether to exclude that particular node-enabled logistics receptacle from being services.

As shown in FIGS. 86A and 86B, ID node 8605 is operative to communicate within the wireless node network with certain network devices—e.g., with other nodes (such as ID nodes and master nodes) but cannot communicate directly with server 100. Thus, the exemplary node-enabled logistics receptacle 8600 is able to provide information related to its contents only through an intermediary node, such as mobile master node 8610, to server 100. In more detail, as mobile master node 8610 approaches ID node 8605 assembled within and part of node-enabled logistics receptacle 8600, master node 8610 may be broadcasting advertising packets that are detected by ID node 8605. Through association (e.g., a passive or active connection between ID node 8605 and mobile master node 8610), ID node 8605 may then be able to broadcast status information related to the content status of the node-enabled logistics receptacle 8600. For example, upon detecting the advertising signal from mobile master node 8610, ID node 8605 may broadcast a signal that includes status information as part of the header information of the broadcasted advertising packet from ID node 8605. Such status information may indicate what packages are within node-enabled logistics receptacle 8600 and may also include a request to pick up one or more packages within the receptacle generally or, in a more detailed example, with specificity as to the required shipping courier that may service the receptacle 8600.

While an embodiment with node-enabled logistics receptacle 8600 may wait until a mobile master node, such as mobile master node 8610, comes within communication range in order to report the status information so that such information may be uploaded to the server 100, other embodiments where the node-enabled logistics receptacle 8500 includes a master node 8505 may more frequently report the status information directly to the server 100 without requiring an intermediary node (e.g., a master node, or in some cases an associated ID node that forwards the status information as a type of shared information with another master node, which then uploads that status information to server 100). Additionally, in situations where the likelihood of a mobile master node passing nearby may be lower than desired, a node-enabled logistics receptacle that includes a master node assembled within it may be a better solution to be deployed than one with an ID node assembled within it.

In one embodiment, a node-enabled logistics receptacle apparatus (such as exemplary node-enabled logistics receptacle 8500 or 8600) can proactively report its content status and comprises a logistics receptacle and a node assembled with the receptacle. As shown in the example of FIGS. 82A and 82B, the logistics receptacle can receive and temporarily maintain a package (such as package 8235) being shipped. The receptacle has an entrance opening (such as opening 8205) through which the package is received and a temporary storage area (such as region 8230) where the package is temporarily and securely maintained until an authorized pickup.

The node assembled with the receptacle (such as node 8220, master node 8505, or ID node 8605) comprises a node processing unit, a node memory storage, and at least one communication interface. The node memory storage is coupled to the node processing unit, and maintains code for execution by the node processing unit along with at least a content status related to one or more packages currently maintained within the logistics receptacle. The communication interface is also coupled to the node processing unit, and is operative to communicate with another network device (such as another node or a server) in the wireless node network.

The node processing unit, when executing the code maintained on the node memory storage, is operative to perform various functions when proactively reporting a content status of the node-enabled logistics receptacle. In more detail, the node processing unit is operative to update the content status stored in the node memory storage based upon whether the logistics receptacle has received a package and is temporarily maintaining custody the package. The node processing unit is also operative to broadcast status information over the at least one communication interface, where the status information relates to the updated content status for the logistics receptacle.

In a further embodiment, the node processing unit of the node-enabled logistics receptacle apparatus may be further operative to transmit a request for shipping information related to the package received over the communication interface, and may be further operative to receive the requested shipping information related to the package over the communication interface.

In another embodiment, the node processing unit may be further operative to identify a shipping courier for the package from the requested shipping information received.

In several more detailed embodiments, the status information broadcast may comprise a request to pick up the package from the node-enabled logistics receptacle; a request for the identified shipping courier to pick up the package from the node-enabled logistics receptacle; or a request to pick up at least one package from the node-enabled logistics receptacle when a number of packages temporarily maintained within the logistics receptacle is more than a pickup threshold. Such a pickup threshold may be, for example, a number of packages sensed to be within the receptacle (e.g., via node sensing, impact sensing, a combination of node and impact sensing, scanning as the package is inserted), a weight of the packages within the receptacle obtained via a built-in scale or weight sensor at the bottom of the interior storage region (e.g., region 8230), optically detecting when packages within the region are taller than a predetermined threshold height using another sensor disposed within the interior storage region (e.g., a light beam and light detector).

Additionally, another embodiment of the apparatus may have the node processing unit being further operative to update the content status stored in the node memory storage based upon whether the node processing unit detects the package has been removed from within the logistics receptacle. And, the node processing unit may be further operative to broadcast updated status information over the at least one communication interface, where the updated status information comprises a message indicating there is no need for a shipping courier to service the node-enabled logistics receptacle. For example, if there are no packages within the node-enabled logistics receptacle, there would be no need for a shipping courier to adhere to a preexisting schedule to travel to and check the receptacle for packages. In a similar example, if there are no packages within the node-enabled logistics receptacle for a particular shipping courier (i.e., the receptacle is serviced by different shipping couriers), there would be no need for that particular shipping courier to adhere to a preexisting schedule to travel to and check the receptacle for packages that they are responsible to pick up.

And similar to the embodiments shown in FIGS. 85A and 85B, the node assembled with the receptacle in the apparatus may comprise a master node (such as master node 8505) operative to communicate directly to a server in the wireless node network. As such, the node processing unit may be further operative to broadcasting the status information over the at least one communication interface directly to the server in the wireless node network.

And similar to the embodiments shown in FIGS. 86A and 86B, the node assembled with the receptacle in the apparatus may comprise an ID node operative to communicate directly to a master node in the wireless node network. As such, the node processing unit may be further operative to broadcast the status information over the at least one communication interface directly to the master node in the wireless node network, with the master node being operative to forward the status information to a server in the wireless node network.

In another embodiment, an exemplary node-enabled logistics receptacle apparatus comprises a logistics receptacle and a node assembled with the receptacle essential the same as that described above. However, in this additional embodiment, the node processing unit, when executing the code maintained on the node memory storage, is operative to detect a signal via the at least one communication interface, the signal having been broadcast from a master node in the wireless node network; access the content status stored in the node memory storage the node-enabled logistics receptacle; and causing the at least one communication interface to broadcast status information to the master node related to the content status for the node-enabled logistics receptacle.

Additionally, the node processing unit may be further operative to request shipping information related to the package from the master node. In more detail, the node processing unit may be further operative to receive the requested shipping information related to the package from the master node. In still more detail, the node processing unit may be further operative to identify a shipping courier for the package from the requested shipping information received.

And in more detail, the status information may comprise a request to pick up the package from the node-enabled logistics receptacle, or a request for the identified shipping courier to pick up the package from the node-enabled logistics receptacle.

FIG. 87 is a flow diagram illustrating an exemplary method for proactively reporting a content status of a node-enabled logistics receptacle in a wireless node network in accordance with an embodiment of the invention. Referring now to FIG. 87, method 8700 begins at step 8705 by updating the content status stored in memory onboard the node-enabled logistics receptacle based upon whether the node-enabled logistics receptacle has received a package and is temporarily maintaining custody of the package. In a more detailed embodiment, method 8700 may also have the node-enabled logistics receptacle request shipping information related to the package received (e.g., from a master node or directly from a server if the receptacle is assembled with a master node in it). Additionally, method 8700 may include the node-enabled logistics receptacle receiving the requested shipping information related to the package, and identifying a shipping courier for the package from the requested shipping information received. For example, a shipping courier for the package may be associated with and identified from the shipping server selected (e.g., a very time-definite shipping service may indicate and identify FedEx Express as the shipping courier).

In a few more detailed embodiments, method 8700 may have the status information comprising a request to pick up the package from the node-enabled logistics receptacle; or a request for the identified shipping courier to pick up the package from the node-enabled logistics receptacle; or a request to pick up at least one package from the node-enabled logistics receptacle when a number of packages in the temporarily custody of the node-enabled logistics receptacle is more than a pickup threshold.

At step 8710, method 8700 concludes by broadcasting status information related to the updated content status for the node-enabled logistics receptacle. For example, in one embodiment this may include broadcasting the status information from a master node in the node-enabled logistics receptacle directly to a server in the wireless node network. In another embodiment, this may involve broadcasting the status information from an ID node in the node-enabled logistics receptacle directly to a master node in the wireless node network, where the master node is operative to forward the status information to a server in the wireless node network. As such, the status information may be forwarded or otherwise uploaded to the backend server, which can then make use of such proactive reporting rather than the reactive post-visit report from courier after a scheduled visit (which may or may not be needed).

With such updated content status information provided to the backend server, the server can analyze the updated information, third party weather information, crime statistics, and other sensor data and/or drop off patterns with the particular node-enabled logistics receptacle to predict a need for pickup services. In other words, the server may use this proactive notification of status information related to the updated content status when determining whether to deploy pickup services for the particular node-enabled logistics receptacle.

Additionally, method 8700 may also include updating the content status stored in the memory onboard the node-enabled logistics receptacle based upon whether the node-enabled logistics receptacle detects the package has been removed from within the node-enabled logistics receptacle. Furthermore, method 8700 may also include broadcasting updated status information, which may comprise a message indicating there is no need for a shipping courier to service the node-enabled logistics receptacle.

Those skilled in the art will appreciate that method 8700 as disclosed and explained above in various embodiments may be implemented on node-enabled logistics receptacle having an ID node (such as exemplary ID node 120*a* as illustrated in FIG. 3 and ID node 8605 as illustrated in FIGS. 86A and 86B) or a master node (such as exemplary master node 110*a* as illustrated in FIG. 4 and master node 8505 as illustrated in FIGS. 85A and 85B), running one or more parts of a control and management code (such as code 325 for an ID node 8605 based node-enabled logistics receptacle 8600 or code 425 for a master node 8505 based node-enabled logistics receptacle 8500) to implement any of the above described functionality. Such code may be stored on a non-transitory computer-readable medium (such as memory storage 315 or 415 in the respective exemplary nodes). Thus, when executing such code, a processing unit of the node (such as unit 300 or unit 400) may be operative to perform operations or steps from the exemplary methods disclosed above, including method 8700 and variations of that method.

Figure 88:
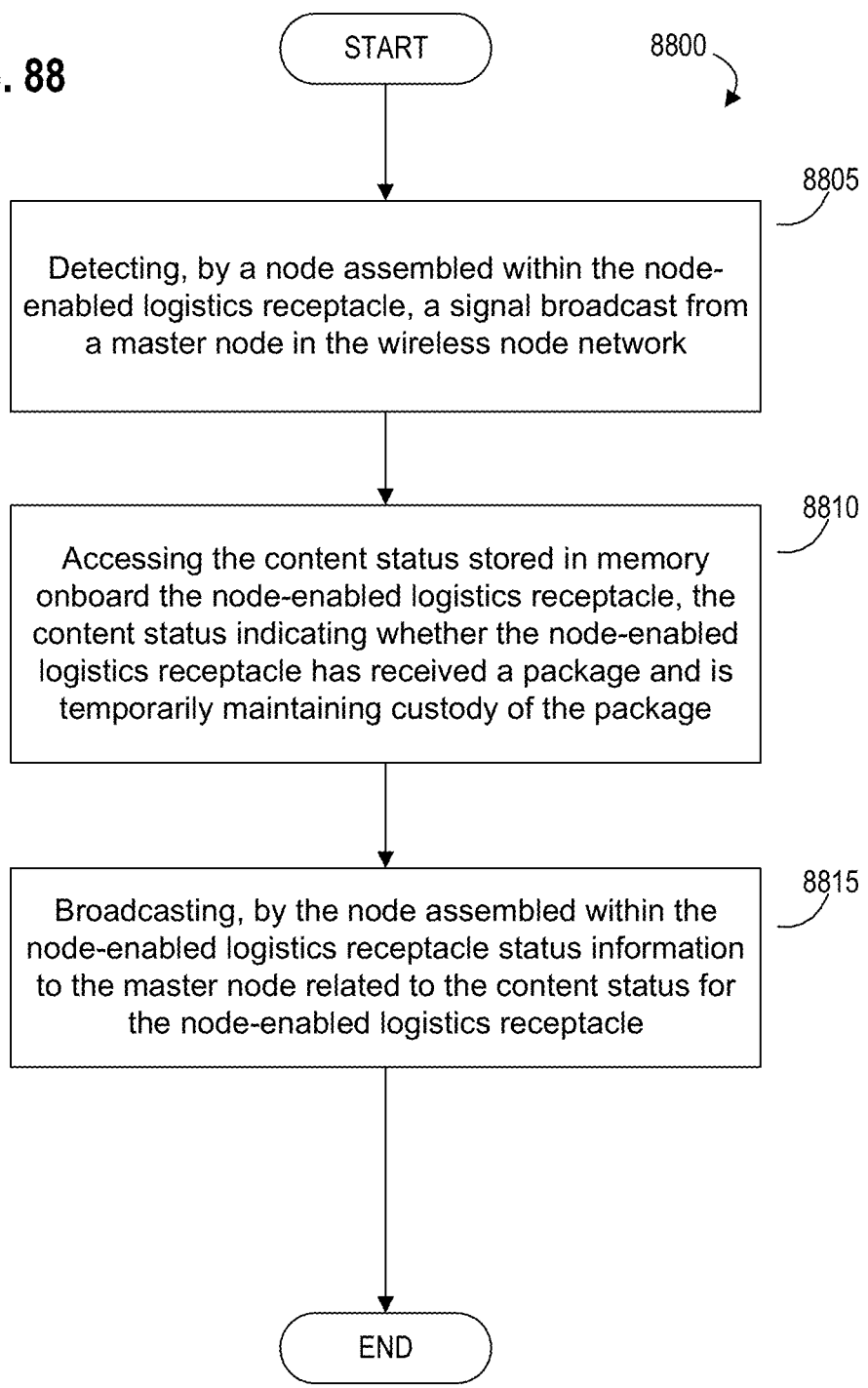
FIG. 88 is a flow diagram illustrating another exemplary method for proactively reporting a content status of a node-enabled logistics receptacle in a wireless node network in accordance with an embodiment of the invention.

FIG. 88 is a flow diagram illustrating another exemplary method for proactively reporting a content status of a node-enabled logistics receptacle in a wireless node network in accordance with an embodiment of the invention. Referring now to FIG. 88, method 8800 begins at step 8805 with a node assembled within the node-enabled logistics receptacle detecting a signal broadcast from a master node in the wireless node network. For example, as shown in FIG. 86B, mobile master node 8610 may be broadcasting an advertising signal that is detected by ID node 8605 assembled as part of node-enabled logistics receptacle 8600.

At step 8810, method 8800 continues by accessing the content status stored in memory onboard the node-enabled logistics receptacle. Here, the content status indicates whether the node-enabled logistics receptacle has received a package and is temporarily maintaining custody of the package. In the example shown in FIG. 86B, such content status information stored in node memory storage of node-enabled logistics receptacle 8600 indicates a package 8235 is being maintained within the receptacle 8600.

At step 8815, method 8800 concludes with the node assembled within the node-enabled logistics receptacle broadcasting status information to the master node related to the content status for the node-enabled logistics receptacle. For example, as shown in FIG. 86B, ID node 8605 within receptacle 8600 may associate with mobile master node 8610 and, as part of that association or after actively associating, broadcasts status information to mobile master node 8610.

In a further embodiment, method 8800 may include requesting, from the master node by the node assembled within the node-enabled logistics receptacle, shipping information related to the package. And in more detail, method 8800 may also have the node assembled within the node-enabled logistics receptacle receiving the requested shipping information related to the package. And in even more detail, method 8800 may identify a shipping courier for the package from the requested shipping information received.

And in more detailed embodiment, the status information may comprise a request to pick up the package from the node-enabled logistics receptacle, or a request for the identified shipping courier to pick up the package from the node-enabled logistics receptacle.

Those skilled in the art will appreciate that method 8800 as disclosed and explained above in various embodiments may be implemented on node-enabled logistics receptacle having an ID node (such as exemplary ID node 120*a* as illustrated in FIG. 3 and ID node 8605 as illustrated in FIGS. 86A and 86B) or a master node (such as exemplary master node 110*a* as illustrated in FIG. 4 and master node 8505 as illustrated in FIGS. 85A and 85B), running one or more parts of a control and management code (such as code 325 for an ID node 8605 based node-enabled logistics receptacle 8600 or code 425 for a master node 8505 based node-enabled logistics receptacle 8500) to implement any of the above described functionality. Such code may be stored on a non-transitory computer-readable medium (such as memory storage 315 or 415 in the respective exemplary nodes). Thus, when executing such code, a processing unit of the node (such as unit 300 or unit 400) may be operative to perform operations or steps from the exemplary methods disclosed above, including method 8800 and variations of that method.

Node-enabled Logistics Receptacle—Detecting Packages

In an exemplary logistics system, different types of packages may be used to ship items. For example, and as explained in several embodiments herein, one type of package may have its own node related to it (e.g., placed within the package, attached to the package, integrated as part of the package or the materials making up the package) and may be generally referred to as a node package or node-enabled package. In one example, such a package may have a node simply placed within the package along with the item to be shipped. In another example, the node may be attached to, part of, integrated into, or embedded within (fully or partially) the package or packaging materials. In contrast, another type of package is not node-enabled. In other words, packages may include those that are node-enabled and those that are not.

To handle aspects of shipping such diverse types of packages, another embodiment takes advantage of one or more features of a node-enabled logistics receptacle to be able to detect and differentiate the different types of packages. FIGS. 89A-89D show aspects and features of different embodiments of a node-enabled logistics receptacle that can detect different types of packages, while FIG. 90 explains an exemplary method for doing so.

Figure 89A:
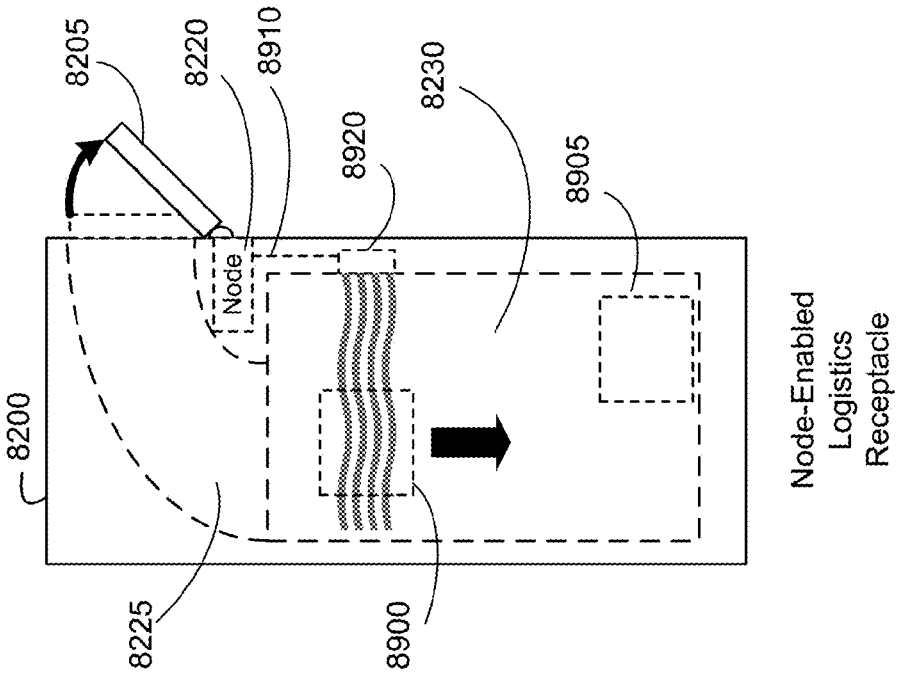
FIG. 89A is a diagram illustrating an exemplary node-enabled logistics receptacle with a node and an exemplary sensor assembled within the logistics receptacle in accordance with an embodiment of the invention.

In more detail, FIG. 89A is a diagram illustrating an exemplary node-enabled logistics receptacle with a node and an exemplary sensor assembled within the logistics receptacle in accordance with an embodiment of the invention. Referring now to FIG. 89A, an exemplary node-enabled logistics receptacle 8200 is shown in side view with internal structure illustrated with dotted lines, similar to the embodiment shown in FIG. 82B. For ease of discussion, exemplary node-enabled logistics receptacle 8200 shown in FIG. 89A is similar to that as shown in FIG. 82B for elements that appear in common in both figures. In addition, the exemplary node 8220 within the receptacle 8200 illustrated in FIG. 89A further includes one or more sensors that assist with detecting and differentiating packages as they are deposited within the exemplary node-enabled logistics receptacle 8200.

In more detail as shown in the embodiment of FIG. 89A, node 8220 further includes a sensor pad or plate 8915, which is coupled, via wiring 8910, to node 8220. In operation, the sensor 8915 responds to stimulus (e.g., an impact force or weight, etc.) and produces a responsive sensor signal, which is provided on wiring 8910 to the node processing unit within node 8220. As such, the embodiment of node 8220 shown in FIG. 89A is a type of sensor node that detects the deposit of any package within the receptacle 8220. Thus, as one or more packages 8900, 8905 are deposited within node-enabled logistics receptacle 8200 (e.g., deposited within the interior storage region 8230), an example of sensor pad/plate 8915 senses an impact from the deposited package or measures the weight of the package added to within the receptacle 8200. Thus, exemplary embodiments of sensor 8915 may be implemented as a pressure pad, pressure plate, impact sensor, or measurement scale that is responsive to force (e.g., momentary, constant, etc.) exerted by packages deposited within the interior storage region 8230 of the node-enabled logistics receptacle 8200 against the bottom of the region 8230.

Figure 89B:
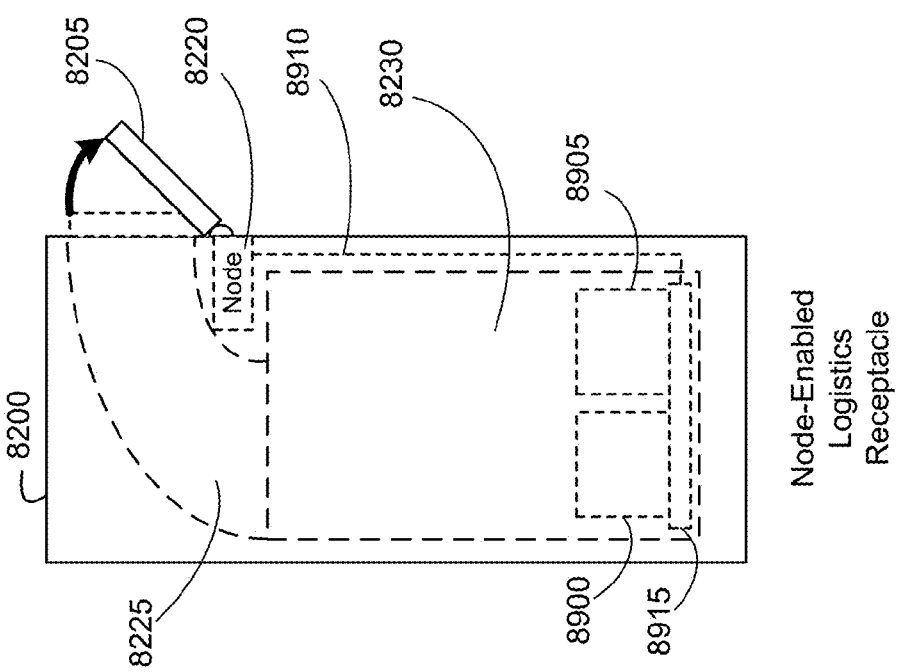
FIG. 89B is a diagram illustrating an exemplary node-enabled logistics receptacle with a node and another type of exemplary sensor assembled within the logistics receptacle in accordance with an embodiment of the invention.

In another embodiment, such as the embodiment illustrated in FIG. 89B, node 8220 may further include a sensor 8920, which is also coupled, via wiring 8910, to node 8220 in this embodiment. In operation, the sensor 8920 is typically disposed on a side wall of region 8230 where it detects movement within a part of the node-enabled logistics receptacle 8200. Thus, in one example, sensor 8920 may be a sensor that relies upon a type of echolocation (e.g., ultrasonic sensor that sends out ultrasonic waves to determine movement based upon a change in the returned energy sensed by the sensor). In an example shown in FIG. 89C, sensor 8925 may be a light sensor where a package, which is moving from the opening 8205 and through the top interior part 8225 of receptacle 8200 to enter and travel through the interior storage region 8230, breaks a light being sensed or detected by sensor 8925, which then generates a responsive sensor signal. Example sensors may include a light source (not shown) within the sensor or rely upon an external light source (e.g., laser) disposed opposite the sensor 8920. In another embodiment, the broken light beam indicating movement within the region of interest may simply cause a change in the signal generated by the sensor (e.g., a temporary drop in voltage indicative of the time the light beam was broken).

Other embodiments may use sensors 8920, 8925 as band of multiple sensors disposed at different locations within the receptacle 8200. For example, such a band of sensors making up sensors 8920, 8925 may extend in one or more dimensions of the region covered. Thus, such a band of sensors may provide more extensive coverage within regions of receptacle 8200 to better capture movement of a package (e.g., the deposit of any type of package within receptacle 8200) or attempts to insert a package within receptacle 8200 (e.g., sensing movement with sensor 8925 but not sensing movement with sensor 8920 given that the package could not fit into the receptacle).

Additional embodiments may implement sensor 8920 with a scanner capable of capturing barcode scan information from an exterior label present on the package being deposited. As such, node 8220 may be operative to interact with sensor 8920 and capture scan information related to the particular package being deposited even if the package is not a node-enabled package.

A counter (implemented as part of the circuitry that comprises node 8220) may also be used in various embodiments to track the total number of packages detected to have been deposited within the interior storage region 8230 of node-enabled logistics receptacle 8200. Additionally, as the receptacle 8200 is serviced by a courier, who may pick up one or more, but potentially not all packages, the counter may be updated to reflect a change in the number of packages within the region 8230.

Figure 89C:
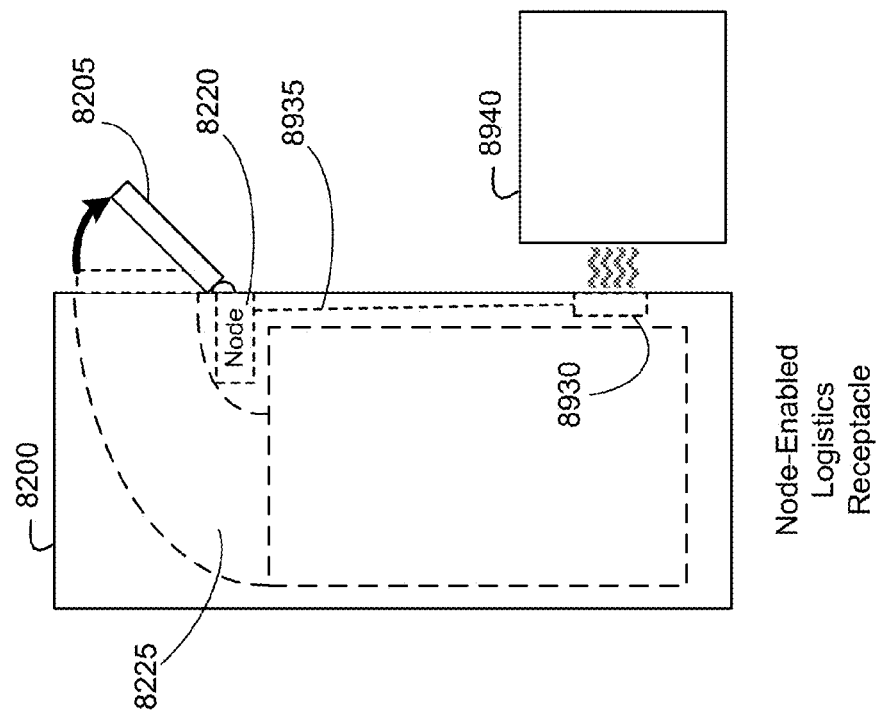
FIG. 89C is a diagram illustrating another exemplary node-enabled logistics receptacle with a node and still other types of exemplary sensors used as part of the node-enabled logistics receptacle in accordance with an embodiment of the invention.

In still another embodiment, such as the embodiment illustrated in FIG. 89C, node 8220 of exemplary node-enabled logistics receptacle 8200 may further include a door sensor that detects movement of the door shown in FIG. 89C hinged to cover opening 8205. Such a sensor would be coupled, via wiring (not shown for purposes of clarity in the Figure), to node 8220 in this embodiment.

In operation, the door sensor is typically disposed on a side wall of region 8225 where it detects movement of the door covering opening 8205 via conventional contact switches or magnetic switches. Another example of door sensor may be incorporated as part of or within a hinge for the door covering opening 8205. Like sensor 8925 described above, the door sensor may help to identify whether there are any packages placed outside node-enabled logistics receptacle 8200 (e.g., sensing movement of the door sensor but not sensing movement with sensor 8920 within the interior of the receptacle given that the package could not fit into the receptacle).

Figure 89D:
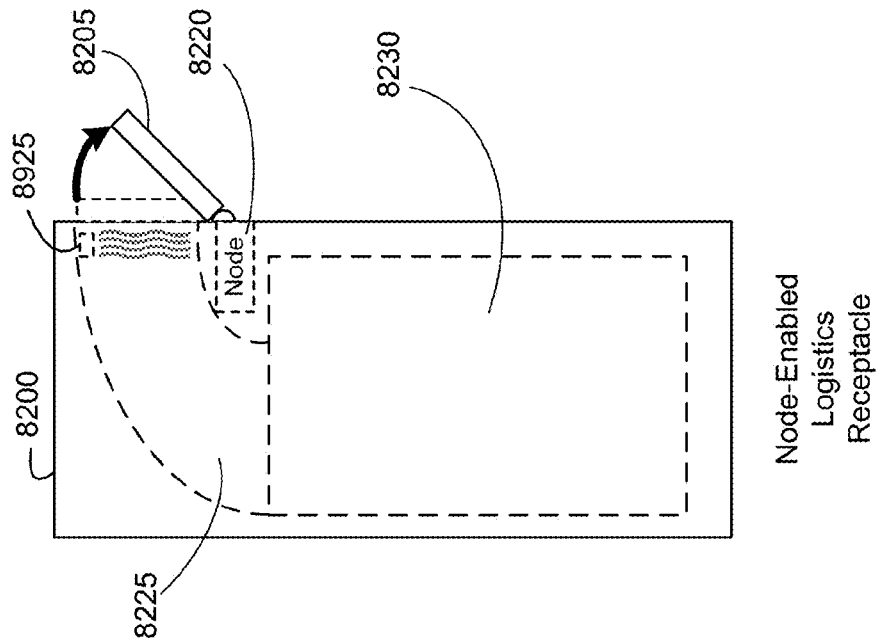
FIG. 89D is a diagram illustrating still another exemplary node-enabled logistics receptacle with a node and further other types of exemplary sensors used as part of the node-enabled logistics receptacle in accordance with an embodiment of the invention.

Additionally, one or more external sensors may be deployed in other embodiments to help detect one or more packages outside the receptacle but that are temporarily in the management custody of the node-enabled logistics receptacle while not being within region 8230. FIG. 89D is a diagram illustrating an exemplary node-enabled logistics receptacle with a node and an exemplary external sensor that may be used as part of the node-enabled logistics receptacle in accordance with an embodiment of the invention. Referring now to FIG. 89D, receptacle 8200 is shown with node 8220 as in FIGS. 89A-C. However, in FIG. 89D, node 8220 is coupled via wiring 8935 to an external sensor 8930 that is operative to monitor an area or region near the receptacle 8220. While only one external sensor 8930 is shown in FIG. 89D for simplicity, those skilled in the art will appreciate that other embodiments may employ multiple external sensors to cover different, distinct, or overlapping areas or regions near the node-enabled logistics receptacle.

External sensor 8930 may sense (via motion detection as explained above with respect to sensors 8920 and 8925) the presence of package 8940. If package 8940 is detected to be within a designated area near the receptacle 8200 for a period of time, node 8220 may consider package 8940 to be within its temporary custody despite being outside the receptacle 8200. In more detail, node 8220 may use sensor 8930 to help keep track of node and non-node packages deposited outside the receptacle. Here, for example, once a certain number (such as even one) of packages are detected outside the receptacle but within the temporary custody of the receptacle 8200, node 8220 may update the content status for the receptacle and broadcast status information to reflect the one or more packages being outside the receptacle but within the temporary custody of the receptacle.

Thus, an embodiment of the node-enabled logistics receptacle may determine whether the receptacle has received the package and is temporarily maintaining custody of the package based upon a detection result from at least one sensor deployed as part of the node-enabled logistics receptacle, and that sensor may be implemented as an internal sensor (such as sensors 8920 and 8925), an external sensor (such as 8930), a door sensor, or the like as described herein.

In another embodiment, a node-enabled logistics receptacle apparatus is described for use in a wireless node network (e.g., a network of nodes, such as ID nodes and master nodes, and a server) that detects a plurality of package types. The node-enabled logistics receptacle apparatus comprises a logistics receptacle and a node assembled with the receptacle. For example, as shown in FIGS. 82A and 82B as well as FIGS. 89A and 89B, the logistics receptacle can receive and temporarily maintain a package (such as packages 8235, 8900, and 8905) being shipped. The receptacle has an entrance opening (such as opening 8205) through which the package is received and an internal storage region (such as region 8230) where one or more packages are temporarily and securely maintained until an authorized pickup.

The node assembled with the receptacle (such as node 8220 illustrated in FIGS. 89A-89D but consistent with the common structure of an ID node or a master node as illustrated and described with respect to FIGS. 3 and 4) comprises a node processing unit, a node memory storage, and at least one communication interface. The node memory storage is coupled to the node processing unit, and maintains code for execution by the node processing unit along with logged detection information about different package types within the receptacle. The communication interface is also coupled to the node processing unit, and is operative to communicate with another network device (such as another node or a server) in the wireless node network.

The node processing unit, when executing the code maintained on the node memory storage, is operative to perform various functions when detecting a plurality of package types. In more detail, the node processing unit is operative, when executing such code, to detect a first type of package (a node-enabled package) by receiving a signal broadcast from a node within a first package prior to sensing a deposit of the first package within the node-enabled logistics receptacle. The node processing unit is also operative to detect a second type of package (not a node-enabled package) by sensing a deposit of a second package within the node-enabled logistics receptacle without receiving a signal broadcast from a node within the second package. The node processing unit is then operative to log the detections of the first type of package and the second type of package as the detection information stored on the node memory storage, and cause the communication interface to transmit a notification to another network device (such as a server or a master node) within the wireless node network about the logged detection of the first type of package and the second type of package.

For example, in the illustrated example of FIGS. 89A-89D, if node 8220 is an ID node, then the communication interface is a shorter range communication interface capable of communicating with a master node in the hierarchy of node types within the wireless node network. However, if node 8220 is implemented as a master node, then the communication interface may be a longer range communication interface capable of directly communicating with the server without needing an intermediary master node when reporting detected types of packages deposited in the node-enabled logistics receptacle.

In a more detailed embodiment, the node processing unit may be further operative to detect the first type of package by being operative to receive, via the communication interface, the signal broadcast from the node within the first package within a predetermined time interval prior to sensing the deposit of the first package within the node-enabled logistics receptacle. For example, as the node-enabled package approaches the location of the node-enabled logistics receptacle, the node assembled with the receptacle (e.g., node 8220) may attempt to associate with the node-enabled package. In more detail, such associating may be merely a passive association where the node processing unit is not yet actively connected to the node-enabled package, but detects an advertising signal being broadcast from the node-enabled package. In another example, such associating may be accomplished with an active association that allows for an authorized connection between the node-enabled package and the node-enabled logistics receptacle.

In another more detailed embodiment, the node assembled with the receptacle may comprise a sensor (e.g., sensor 8915, sensor 8920, sensor 8925, the door sensor, and/or external sensor 8930) coupled to the node processing unit. As such, the node processing unit may be further operative to detect the second type of package by being operative to sense the deposit of the second package within the node-enabled logistics receptacle based upon a sensor signal provided by the sensor to the node processing unit. For example, in the embodiment shown in FIG. 89A, node 8220 is operative to sense the deposit of a package that is not node-enabled (e.g., package 8905) based upon a sensor signal provided from sensor 8915 through wiring 8910 to interface circuitry within node 8220.

In further embodiments that are more detailed regarding the sensor, the sensor may be deployed within the internal storage region of the node-enabled logistics receptacle. For example, the sensor may be implemented as a motion detector coupled to the node assembled with the receptacle. As such, the motion detector may sense movement of the first package and the second package as the packages are respectively deposited within the interior storage region, and may provide the sensor signal to the node processing unit related to the sensed movement. Such an embodiment is illustrated in FIG. 89B, where sensor 8920 may detect movement of the packages 8900, 8905 as they are deposited within interior storage region 8230.

In another example, the sensor may be implemented as an impact sensor coupled to the node assembled with the receptacle. As such, the impact sensor may register a change in pressure exerted against a bottom surface of the interior storage region in response to an object deposited within the interior storage region, and may provide the sensor signal to the node processing unit related to the sensed impact. Such an embodiment is illustrated in FIG. 89A, where sensor 8915 may detect an impact of each of the packages 8900, 8905 as they are deposited within interior storage region 8230 and onto a sensor plate or pad of the sensor 8915.

In still another example, the sensor may be implemented as a measurement scale coupled to the node assembled with the receptacle. As such, the measurement scale measures a weight of an object (such as a package—e.g., package 8900 or 8905) deposited within the interior storage region and provides the sensor signal to the node processing unit related to the measured weight. Such an embodiment is illustrated with reference to FIG. 89A, where sensor 8915 may be a scale that can incrementally weigh the packages 8900, 8905 as they are deposited within interior storage region 8230. As each package is deposited within interior storage region 8230 and comes to rest, the package and item being shipped within the package exert a force on the sensor 8915. The measured weight can be determined from the sensor signal sent to the node 8220, which can keep track and log when packages are deposited and how much they incrementally weigh so as to provide further contextual information regarding what is in the node-enabled logistics receptacle.

In the context of such exemplary node-enabled logistics receptacles that can deter different package types, FIG. 90 is a flow diagram illustrating an exemplary method for detecting a plurality of package types within a node-enabled logistics receptacle in a wireless node network in accordance with an embodiment of the invention. Referring now to FIG. 90, method 9000 begins at step 9005 by detecting a first type of package by receiving a signal broadcast from a node within a first package (a node-enabled package) prior to sensing a deposit of the first package with the node-enabled logistics receptacle. Such a deposit may be within the receptacle as shown in FIGS. 89A and 89B or may be in an area monitored and near the receptacle as shown in FIG. 89C (e.g., for oversized packages where an external sensor may detect a deposit of such a package outside the receptacle after a period of time with the package remaining there). Those skilled in the art will appreciate that any such deposits are considered to have the package be with the temporary custody of the node-enabled logistics receptacle—regardless of whether the deposit is within the receptacle or adjacent and outside the receptacle.

In another embodiment, detecting the first type of package may comprise receiving the signal broadcast from the node within the first package within a predetermined time interval prior to sensing the deposit of the first package within the node-enabled logistics receptacle. In more detail, the step of receiving the signal broadcast from the node within the first package may be accomplished by associating the node within the first package with the node assembled within the node-enabled logistics receptacle.

At step 9010, method 9000 continues by detecting a second type of package by sensing a deposit of a second package (not a node-enabled package) within the node-enabled logistics receptacle without receiving a signal broadcast from a node within the second package. Another embodiment of method 9000 may detect a second type of package by sensing the deposit of the second package outside the node-enabled logistics receptacle without receiving a signal broadcast from the second package. Thus, sensing the deposit of the second package may simply be that the deposit is to the temporary custody of the node-enabled logistics receptacle (either within the receptacle or in an area near to but outside the receptacle).

As such, method 9000 is able to detect both node-packages and packages that include those that are not node-packages. In another embodiment, detecting the second type of package may further comprise sensing the deposit of the second package within the node-enabled logistics receptacle using a sensor coupled to a node assembled within the node-enabled logistics receptacle. Such a sensor may be deployed within an interior storage region of the node-enabled logistics receptacle.

In general, the sensor may take several exemplary forms—such as an internal sensor, an external sensor or a door sensor (e.g., as shown in FIGS. 89A-89D). In more detail, the sensor may comprise at least one of an internal sensor disposed within the internal storage region of the receptacle, an external sensor that monitors an area outside but near the logistics receptacle, and a door sensor that monitors the entrance opening of the receptacle (typically covered by a door). In a more detailed example, the sensor may comprise a motion detector coupled to the node assembled within the node-enabled logistics receptacle. As such, the motion detector may sense movement of the first package and the second package when deposited within the interior storage region of the node-enabled logistics receptacle and may provide the sensor signal to the node processing unit related to the sensed movement.

In another example, the sensor may comprise an impact sensor coupled to the node assembled within the node-enabled logistics receptacle. As such, the impact sensor may register a change in pressure or force exerted against a bottom surface of the interior storage region in response to an object deposited within the interior storage region and may provide the sensor signal to the node processing unit related to the sensed impact.

In still another example, the sensor may comprise a measurement scale coupled to the node assembled within the node-enabled logistics receptacle. As such, the measurement scale may measure a weight of an object (such as a package) deposited within the interior storage region and may provide the sensor signal to the node processing unit related to the measured weight.

At step 9015, method 9000 continues by logging the detections of the first type of package and the second type of package. In one embodiment, the detections are logged in memory, such as memory storage in node 8220 of FIGS. 89A and 89B. With this logged information on detections of node-enabled packages and detections of packages that are not node-enabled (e.g., based on a difference between the detected deposits of all packages and subtracting out those that are confirmed to be node-enabled packages via the signal detection or association).

And so at step 9020, method 9000 concludes by notifying another network device within the wireless node network about the logged detection of the first type of package and the second type of package. For example, if the node assembled within the node-enabled logistics receptacle is implemented with an ID node, the other network device may be a master node, which can receives the notification and forward a message to the server regarding the logged detections as necessary or desired. Alternatively, should the node assembled within the node-enabled logistics receptacle is implemented with a master node, greater opportunities are presented to directly communicate logged detections to the server rather than need to involve an intermediary node, such as another master node.

Those skilled in the art will appreciate that method 9000 as disclosed and explained above in various embodiments may be implemented on node-enabled logistics receptacle having a node (such as exemplary ID node 120*a* as illustrated in FIG. 3, exemplary master node 110*a* as illustrated in FIG. 4, or node 8220 as illustrated in FIGS. 89A and 89B), running one or more parts of a control and management code (such as code 325 or code 425) to implement any of the above described functionality. Such code may be stored on a non-transitory computer-readable medium (such as memory storage 315 or 415 in the respective exemplary nodes). Thus, when executing such code, a processing unit of the node (such as unit 300 or unit 400) may be operative to perform operations or steps from the exemplary methods disclosed above, including method 9000 and variations of that method.

Deployment of Pickup Services with Multiple Pickup Entities

In another exemplary logistics system, an exemplary node-enabled logistics receptacle may have packages in its temporary custody that are intended to be serviced for pickup by more than one pickup entity. For example, a first shipping customer may desire and pay for shipping a first package by a particular pickup entity, such as FedEx® Express, while another shipping customer may desire and pay for shipping another package by a different pickup entity, such as FedEx® Ground. Generally, an approach to servicing the packages deposited and temporarily maintained in a conventional logistics receptacle (such as a drop box or secure locker unit) involves an existing schedule where one or more pickup entities (e.g., a shipping courier) travels to the receptacle to perform a pickup service on packages in the receptacle. This may be time consuming and unpredictable. Additionally, it typically leads to unnecessary trips at times for a particular pickup entity and wasteful of the entity's resources.

In some instances, things are complicated even more where a receptacle may not be serviced by more than one pickup entity. This may require the shipping customer dropping off a package to be shipped to find an appropriate location that can be serviced by that particular pickup service, even when multiple pickup services are available as a way to provide the customer a selection of shipping options from one shipping entity. From the shipping entity's perspective, requiring a different receptacle for each pickup entity is also wasteful. And simply putting all packages into a common receptacle without more incurs time consuming work for each different pickup service entity sending a courier to pick up their specific packages from the common receptacle.

Figure 91:
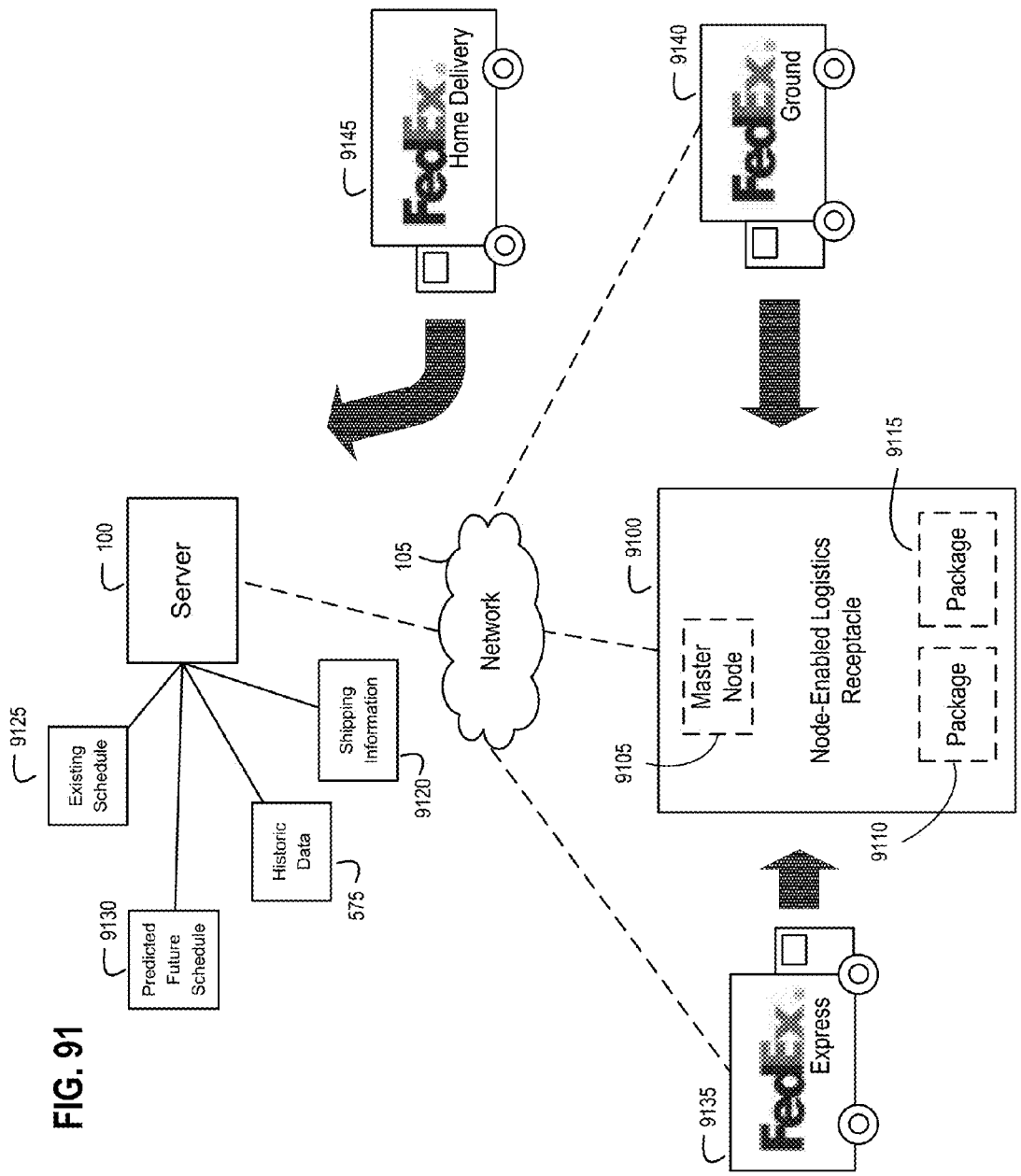
FIG. 91 is a diagram illustrating an exemplary node-enabled logistics receptacle that reports a current status of packages to a server for enhanced deployment of pickup services by pickup entities in accordance with an embodiment of the invention.

In another embodiment, a node-enabled logistics receptacle (e.g., node-enabled drop box or node-enabled locker unit) so that packages may be dropped for shipping and picked up by multiple pickup entities from the same receptacle in a more efficient and enhanced manner. FIG. 91 is a diagram illustrating an exemplary node-enabled logistics receptacle that reports a current status of packages maintained within the receptacle to a server for enhanced deployment of pickup services by pickup entities in accordance with an embodiment of the invention. Referring now to FIG. 91, an exemplary node-enabled logistics receptacle 9100 is illustrated in communication with server 100 over network 105. Such an exemplary node-enabled logistics receptacle 9100 is similar to that as described and shown in other figures (e.g., FIGS. 82A, 82B, 85A, 85B, 86A, 86B, 89A, 89B). And as shown in FIG. 91, exemplary node enabled logistics receptacle 9100 includes a node (e.g., master node 9105) assembled with the receptacle itself, and is temporarily maintaining two packages (e.g., package 9110, package 9115).

The exemplary node-enabled logistics receptacle 9100 is operative, through code running on the processing unit of master node 9105, to send a message to server 100 to report the current status of packages in the receptacle 9100. In more detail, node-enabled logistics receptacle 9100 is operative, through code (such as code 425) running on the processing unit (such as unit 400) of master node 9105, to send a message to server 100 where the message identifies a plurality of packages (such as packages 9110, 9115) currently maintained within the node-enabled logistics receptacle 9100 ready for pickup. The message is transmitted through a communication interface that is part of master node 9105, through network 105, and is received by server 100.

Exemplary server 100, as explained in more detail with respect to FIG. 5, is an apparatus that includes at least one server processing unit (such as processing unit 500), at least one server memory storage (such as memory storage 515), and a communication interface (such as network interface 590). As explained above with reference to FIG. 5, server 100 may be implemented as a single computing system, a distributed server (e.g., separate servers for separate server related tasks), a hierarchical server (e.g., a server implemented with multiple levels where information may be maintained at different levels and tasks performed at different levels depending on implementation), or a server farm that logically allows multiple distinct components to function as one server computing platform device from the perspective of a client device (e.g., devices 200, 205 or master node 110*a*). In some embodiments, an exemplary server may include one or more servers dedicated for specific geographic regions as information collected within different regions may include and be subject to different regulatory controls and requirements implemented on respective regional servers. Likewise, while the embodiment shown in FIG. 5 illustrates a single memory storage 515, exemplary server 100 may deploy more than one memory storage media. And memory storage media may be in differing non-transitory forms (e.g., conventional hard disk drives, solid state memory such as flash memory, optical drives, RAID systems, cloud storage configured memory, network storage appliances, etc.).

Additionally, the exemplary server apparatus' memory storage is coupled to the server processing unit. While not shown in FIG. 91 (but shown as part of exemplary server 100 illustrated in FIG. 5), the server memory storage in server 100 maintains code for execution by the server processing unit. Additionally, server memory storage may maintain shipping information 9120 about a plurality of packages (such as packages 9110, 9115) currently maintained within the node-enabled logistics receptacle 9100 ready for pickup.

The communication interface of the server apparatus is coupled to the server processing unit and is operative to communicate with at least the node-enabled logistics receptacle in the wireless node network. For example, the network interface 590 of exemplary server 100 shown in FIG. 5 is a type of communication interface that is coupled to processing unit 500 and, as shown in FIG. 91, is operative to communicate over network 105 with at least node-enabled logistics receptacle 9100 as well as other network devices in a wireless node network (e.g., other master nodes) and other servers or computing devices that are capable of communicating over network 105.

The server processing unit of the server apparatus, when executing the code maintained on the server memory storage, is operative to perform certain functions that allow for deploying a plurality of pickup entities to a node-enabled logistics receptacle (such as receptacle 9100) in a wireless node network. In more detail, the processing unit, when executing the code, is operative to receive a message from the node-enabled logistics receptacle over the communication interface where the message identifies a plurality of packages currently maintained within the node-enabled logistics receptacle ready for pickup. For instance, in the illustrated example of FIG. 91, the processing unit of server 100 may be operative to receive a message prepared and transmitted by master node 9105 within node-enabled logistics receptacle 9100. Such a message identifies package 9110 and package 9115 as being currently maintained within the node-enabled logistics receptacle 9100 and ready for pickup.

The processing unit, when executing the code, is also operative to access the server memory storage to obtain shipping information related to the identified plurality of packages currently maintained with the node-enabled logistics receptacle. For example, server 100 may access shipping information 9120, which is information related to shipping of packages 9110 and 9115.

From this proactive notification facilitated by the node-enabled logistics receptacle, the processing unit, when executing the code, is then operative to identify which of the plurality of pickup entities need to be deployed to provide one or more pickup services at the node-enabled logistics receptacle based upon the shipping information. For example, the shipping information 9120 relating to package 9110 may identify FedEx® Express as the appropriate pickup entity to provide a pickup service for package 9110 at receptacle 9100 while the information 9120 relating to package 9115 may identify FedEx® Ground as the appropriate pickup entity to provide a pickup service for package 9115 at receptacle 9100.

In one embodiment, the server processing unit may be further operative to cause the communication interface to transmit a pickup request to the identified ones of the pickup entities regarding the one or more pickup services to be performed at the node-enabled logistics receptacle. Accordingly, in the example shown in FIG. 91, server 100 may transmit the pickup request to a courier vehicle 9135 given FedEx® Express was one of the identified pickup entities that needs to pick up a package (e.g., package 9110) at node-enabled logistics receptacle 9100. Likewise, server 100 may transmit the pickup request to another courier vehicle 9140 given FedEx® Ground was another of the identified pickup entities that needs to pick up a package (e.g., package 9115) at node-enabled logistics receptacle 9100.

In another embodiment, the server processing unit may be further operative to update historic data for the node-enabled logistics receptacle related to the identified ones of the pickup entities, and store the updated historic data in the server memory storage. As explained earlier with respect to FIG. 5, historic data is generally data previously collected and/or analyzed related to a common characteristic. Historic data 575 embodies operational knowledge and know-how for a particular characteristic relevant to operations of the wireless node network. Here, exemplary historic data relates to what pickup entities are needed for packages deposited in a particular receptacle. Accordingly, in the example shown in FIG. 91, server 100 may update such historic data 575 for the node-enabled logistics receptacle 9100 related to the identified ones of the pickup entities (e.g., FedEx® Express and FedEx® Ground), and store the updated historic data 575 in the server memory storage within server 100.

In still another embodiment, the server processing unit may be further operative to predict a future pickup schedule for the node-enabled logistics receptacle based upon the updated historic data. For example, as shown in FIG. 91, server 100 may predict a future pickup schedule 9130 for the node-enabled logistics receptacle 9100 based upon the updated historic data 575. Thus, the more packages are deposited that require pickup service at a particular node-enabled logistics receptacle by a particular pickup entity, the more the server is able to learn from the proactive notifications from the particular node-enabled logistics receptacle.

In a further embodiment, the server processing unit may be further operative to cause the future pickup schedule to be transmitted over the communication interface to those of the pickup entities having a predicted pickup service in the future pickup schedule for the node-enabled logistics receptacle. In this way, the advantage of the proactive notifications from the particular node-enabled logistics receptacle may be leveraged in an even more broad way.

In some embodiments, server 100 may have an existing schedule 9125 of which pickup entities are scheduled to provide pickup services for a particular receptacle. As such, the server processing unit may be further operative to notify a previously scheduled one of the pickup entities over the communications interface if the previously scheduled one of the pickup entities is not one of the identified ones of the pickup entities regarding the one or more pickup services to be performed at the node-enabled logistics receptacle. For example, as shown in FIG. 91, server 100 may contact a pickup entity, such as FedEx® Home Delivery (e.g., via a message to a previously designed courier vehicle 9145 for that pickup entity) to let it know that it no longer needs to perform pickup services at node-enabled logistics receptacle 9100. So, as shown in FIG. 91, courier vehicle 9145 for FedEx® Home Delivery can avoid wasting time, effort, and cost of an unnecessary stop and continue to another stop to pick up or drop off other packages.

In a more detailed embodiment, the server processing unit may be further operative to cause the communication interface on the server to transmit the pickup request by being operative to access an existing pickup schedule (such as schedule 9125) maintained in the server memory storage. In more detail, the existing pickup schedule may comprise one or more existing scheduled pickup services at the node-enabled logistics receptacle. The server processing unit may then be operative to notify (using the server's communication interface) one of the pickup entities that is on the existing pickup schedule (e.g., schedule 9125) but that is not currently identified as one of the plurality of pickup entities that they do not need to provide one or more pickup services at the node-enabled logistics receptacle based upon the shipping information 9120.

Further, an additional embodiment may have the server processing unit being operative to revise the existing pickup schedule 9125 based on the identified ones of the plurality of pickup entities that need to provide one or more pickup services at the node-enabled logistics receptacle based upon the shipping information.

Figure 92:
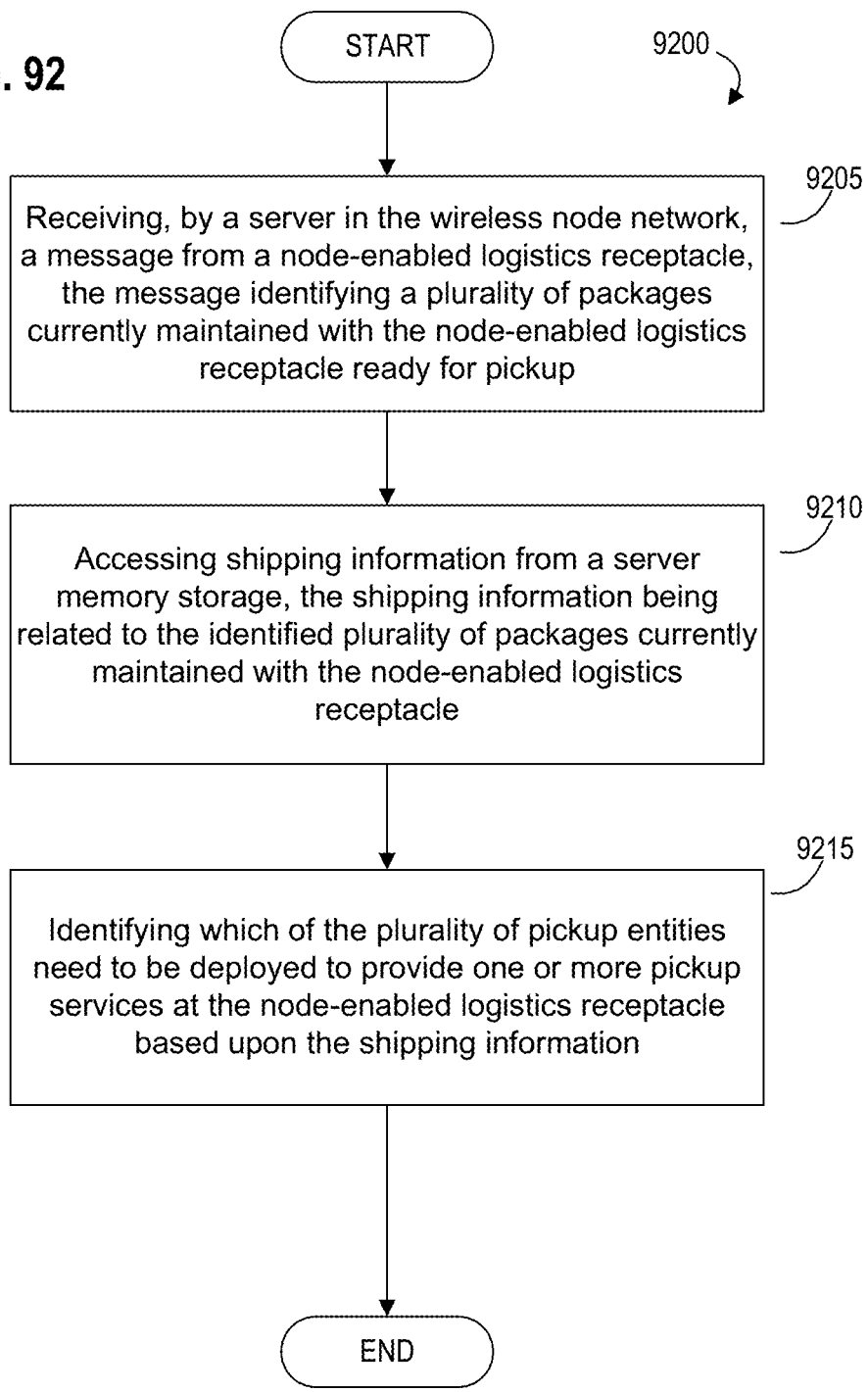
FIG. 92 is a flow diagram illustrating an exemplary method deploying a plurality of pickup entities to a node-enabled logistics receptacle in a wireless node network in accordance with an embodiment of the invention.

While FIG. 91 and the above description focus on the server apparatus and its operation with node-enabled logistics receptacle 9100 when deploying various pickup entities, FIG. 92 is a flow diagram illustrating an exemplary method deploying a plurality of pickup entities to a node-enabled logistics receptacle in a wireless node network in accordance with an embodiment of the invention. Referring now to FIG. 92, method 9200 begins at step 9205 with a server in the wireless node network receiving a message from a node-enabled logistics receptacle. The message identifies a plurality of packages currently maintained within the node-enabled logistics receptacle ready for pickup.

At step 9210, method 9200 continues by accessing shipping information from a server memory storage. The shipping information is related to the identified plurality of packages currently maintained with the node-enabled logistics receptacle.

At step 9215, exemplary method 9215 concludes by identifying which of the plurality of pickup entities need to be deployed to provide one or more pickup services at the node-enabled logistics receptacle based upon the shipping information.

In a further embodiment, method 9200 may also include the step of transmitting a pickup request by the server over a communication interface of the server to the identified ones of the pickup entities regarding the one or more pickup services to be performed at the node-enabled logistics receptacle. For instance, in the example illustrated and explained in FIG. 91, if the identified ones of the pickup entities that need to perform pickup services at node-enable logistics receptacle 9100 are the pickup entities FedEx® Express and FedEx® Ground (that respectively operate courier vehicles 9135 and 9140), server 100 may transmit a pickup request to each of these vehicles via network 105.

In a more detailed embodiment, method 9200 may transmit the pickup request by accessing an existing pickup schedule maintained in the server memory storage, where the existing pickup schedule comprising one or more existing scheduled pickup services at the node-enabled logistics receptacle. Then, method 9200 may notify one of the pickup entities that is on the existing pickup schedule but that is not identified as one of the plurality of pickup entities that it does not need to provide one or more pickup services at the node-enabled logistics receptacle based upon the shipping information. Further still, method 9200 may also include revising the existing pickup schedule based on the identified ones of the plurality of pickup entities that need to provide one or more pickup services at the node-enabled logistics receptacle based upon the shipping information.

In yet another embodiment, method 9200 may include updating historic data for the node-enabled logistics receptacle related to the identified ones of the pickup entities, and predicting a future pickup schedule for the node-enabled logistics receptacle based upon the updated historic data. In more detail, method 9200 may also involve transmitting the future pickup schedule to those of the pickup entities having a predicted pickup service in the future pickup schedule for the node-enabled logistics receptacle.

In still another embodiment, method 9200 may also include notifying a previously scheduled one of the pickup entities if the previously scheduled one of the pickup entities is not one of the identified ones of the pickup entities regarding the one or more pickup services to be performed at the node-enabled logistics receptacle.

Those skilled in the art will appreciate that method 9200 as disclosed and explained above in various embodiments may be implemented on server network device (such as exemplary server 100 as illustrated in FIG. 5 and as illustrated in FIG. 91), running one or more parts of a server control and management code (such as code 525) to implement any of the above described functionality. Such code may be stored on a non-transitory computer-readable medium (such as memory storage 515). Thus, when executing such code, one or more processing units of the server (such as processing unit 500) may be operative to perform operations or steps from the exemplary methods disclosed above, including method 9200 and variations of that method.

Shipment Merging for Multi-part Shipments

In some examples, an item to be shipped may be part of a multiple package shipment (also referred to as a multi-part shipment, multi-piece shipment, or MPS). In general, an MPS involves a set of items being shipped to the same location. For example, the set of items may be a set of related items (such as parts to a desktop computer—e.g., a display, a keyboard and mouse, and a desktop computer chassis having a power supply, disk drives, graphics boards, peripheral interfaces, and a motherboard). Each item in the set may be separately packaged. Some items may be purchased as off the shelf items, and then included in the set of items as a re-sold item by the set supplier (e.g., a computer manufacturer). And even when a single entity manufactures each item in the set, there are instances when separately packaging each item is cost effective and desired.

As is often the case with a set of shipped items, it may be desired for the items to be delivered together. For example, if one of the items in the set is missing (such as a display from an ordered computer), the rest of the items in the set may be of little use to the recipient until that last item arrives. Indeed, there are instances (such as for purposes of clearing a customs holding area) where further movement or delivery of a set of items may be delayed when one or more items in the set become separated during the shipment process.

In an embodiment, various nodes in a wireless node network may be deployed to help facilitate the potential for a quicker and more efficient shipment of a set of items. For example, a shipping customer may deposit the set of packaged items (with each packaged item having a related node) with a shipping company so that the set is shipped to a destination. In one embodiment, all items in the set enter a shipping operation at the same time with their respective shipping information identifying each item in the set. However, in another embodiment the items may enter the shipping operation at differing times but still have shipping information identifying each item in the set.

Figure 34C:
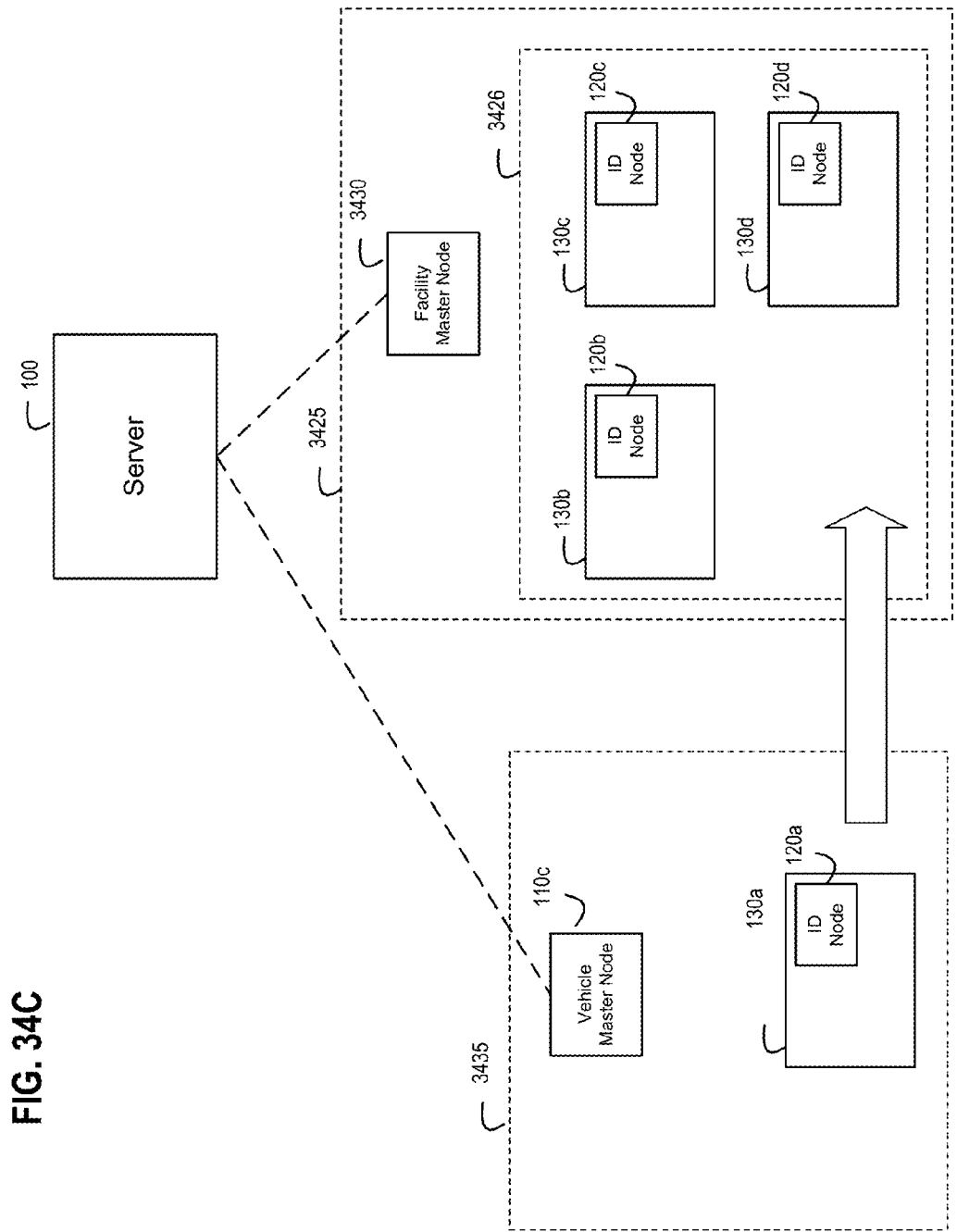

FIG. 34C provides an illustration of an exemplary mid-shipment stage in a shipping and logistics operation. Referring now to FIG. 34C, a set of packages 130a-130d is illustrated as having arrived or approaching an exemplary shipment facility 3425. Each of the packages 130a-130d includes a related ID node 120a-120d, respectively. In each of the packages 130a-130d is an item that is part of a set of items shipped. Thus, the related ID nodes 120a-120d represent a group of ID nodes where reach ID node is related to a different packaged item in the set.

As shown in the embodiment of FIG. 34C, one item from the set is in package 130a with ID node 120a. That package 130a and ID node 120a are currently located in a vehicle 3435 approaching facility 3425, where the remaining packages 130b-130d in the set are currently located in the exemplary shipping facility 3425 during transit to the set's destination. The vehicle 3435 has a vehicle master node 110c, while the facility 3425 has a facility master node 3430. In one example, facility 3425 has numerous master nodes deployed within and around it, but such other master nodes are not shown in FIG. 34C. Likewise, in such an example, facility master node 3430 may be associated with a particular part of the facility, such as a holding or containment area 3436 (such as a customs holding area) within facility 3425. Those skilled in the art will appreciate that while holding area 3426 may be explained in terms of temporarily holding packaged items for purposes of customs, other types of storage areas, receptacles, or general containments may similarly operate to temporarily maintain packaged items in a separate region (e.g., area of a loading dock, storage facility, warehouse, a secured room, a special fenced area, etc.) for other purposes as part of shipping a set of packaged items to a common destination.

Figure 39:
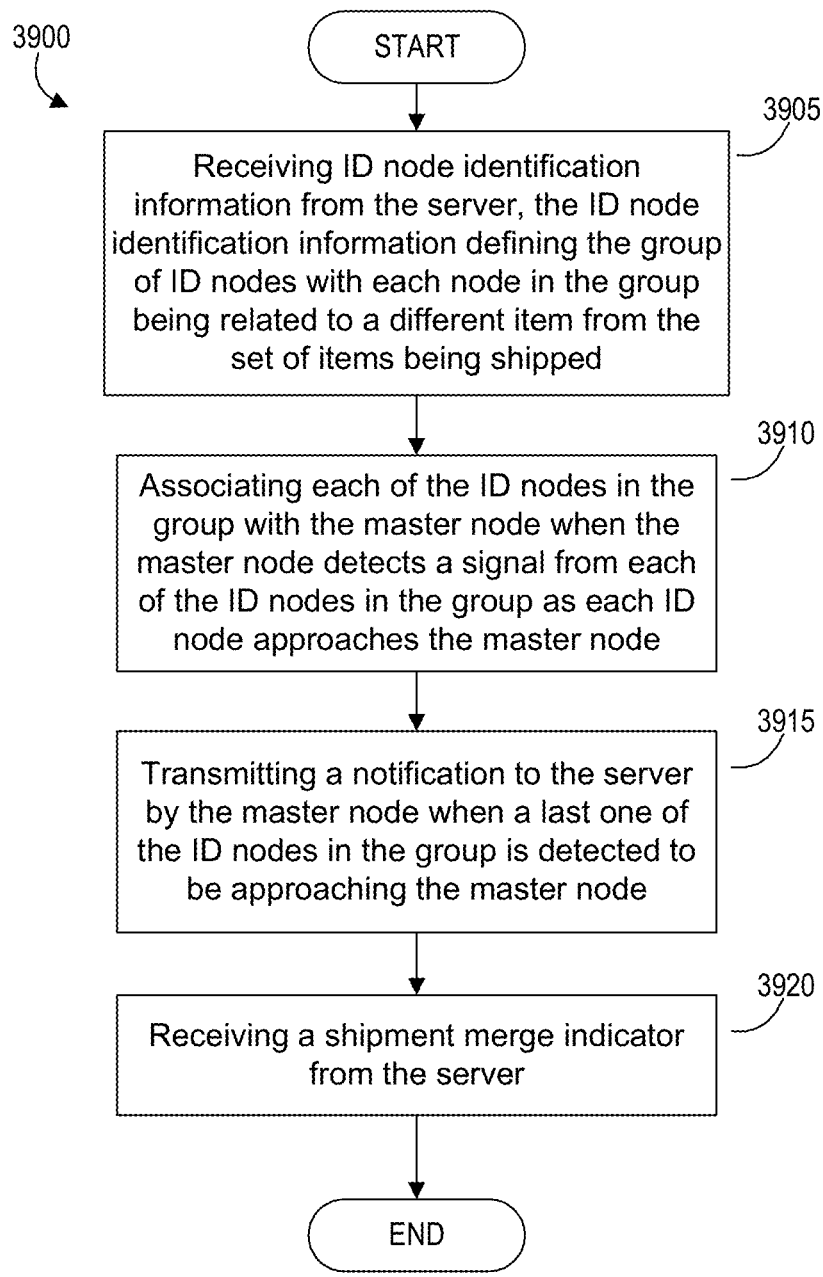
FIG. 39 is a flow diagram illustrating an exemplary method for shipment merging in a wireless node network in accordance with an embodiment of the invention.

FIG. 39 is a flow diagram illustrating an exemplary method for shipment merging of a set of items being shipped using a wireless node network. Referring now to FIG. 39, method 3900 begins at step 3095 with the master node receiving ID node identification information from the server. The ID node identification information defines the group of ID nodes where each ID node from the group is related to a different item in the set of items being shipped. In one example, the ID node identification information may be derived from and be part of shipping information related to the set of items being shipped (such as shipping information related to packages 130a-130b and their respectively identified ID nodes 120a-120d as shown in FIG. 34C).

In one embodiment, the master node may be associated with a containment. For example, the containment may be a holding area, such as a customs holding area. In another example, the containment is merely a designated part of a facility or, more specifically, as secured portion of a facility.

At step 3910, method 3900 continues by associating each of the ID nodes in the group of ID nodes with the master node when the master node detects a signal from each of the ID nodes in the group as each of the ID nodes in the group approaches the master node. In one example, associating may be implemented by establishing a passive association between the master node and each of the ID nodes in the group of ID nodes without requiring an authorized connection between the master node and each of the ID nodes in the group of ID nodes. However, in another example, associating may be establishing an active association that reflects an authorized connection.

At step 3915, the master node transmits a notification to the server when a last one of the ID nodes in the group is detected to be approaching the master node.

At step 3920, the master node receives a shipment merge indication from the server. The shipment merge indication reflects that the set of items has been merged to a single shipment. For example, the shipment merge indication may be an authorization for the set of items to be released from the containment. In another example, this authorization may be a customs clearance notification authorizing release of the set of items from the containment as a single merged shipment.

In a further embodiment, such an authorization may be the result of one or more prompted messages. In more detail, method 3900 may include generating an authorization prompt message by the master node, where the authorization prompt requests an authorization for the set of items to be released from the containment. The master node may then transmit the authorization prompt message to another network device in the wireless node network (e.g., a user access device, such as a laptop computer, operated by personnel that manage the containment). The master node may then receive the authorization in response to the authorization prompt message.

And as a result of receiving the shipment merge indication, the method 3900 may also instruct each of the ID nodes in the group to store customs information (such as information related to the shipment merge indication, authorization to be released from the containment, the customs clearance notification, or any other customs related paperwork and related duties and fees) in a memory of the respective each of the ID nodes in the group of ID nodes.

In one embodiment, the method 3900 may also include disassociating each of the ID nodes in the group of ID nodes from the master node after the master node determines a collective location of the group of ID nodes is outside a predetermined vicinity of the containment and after the master node receives the shipment merge indicator. In the example of FIG. 34C, once packages 130a-130d (and their related ID nodes 120a-120d) are moved outside a predetermined boundary of the containment area 3426 but master node 3430 has received the shipment merge indication from server 100, it is permitted for the set of packages 130a-130d to move on and be disassociated with facility master node 3430.

However, in another embodiment, when any of the ID nodes in the group of ID nodes are detected by the master node as being located outside of the containment after the master node receives the shipment merge indication, the master node may notify the server. The server may follow-up to locate the detected ID node and alert appropriate personnel or other systems as a way of causing local follow-up actions in facility 3425 relative to that detected ID node.

Those skilled in the art will appreciate that method 3900 as disclosed and explained above in various embodiments may be implemented on a node, such as an exemplary master node as illustrated in FIG. 4, running one or more parts of their respective control and management code 425 to implement any of the above described functionality. Such code may be stored on a non-transitory computer-readable medium, such as memory storage 415 within an exemplary master node. Thus, when executing such code, a processing unit within the respective node may be operative to perform operations or steps from the exemplary methods disclosed above, including method 3900 and variations of that method.

Figure 40:
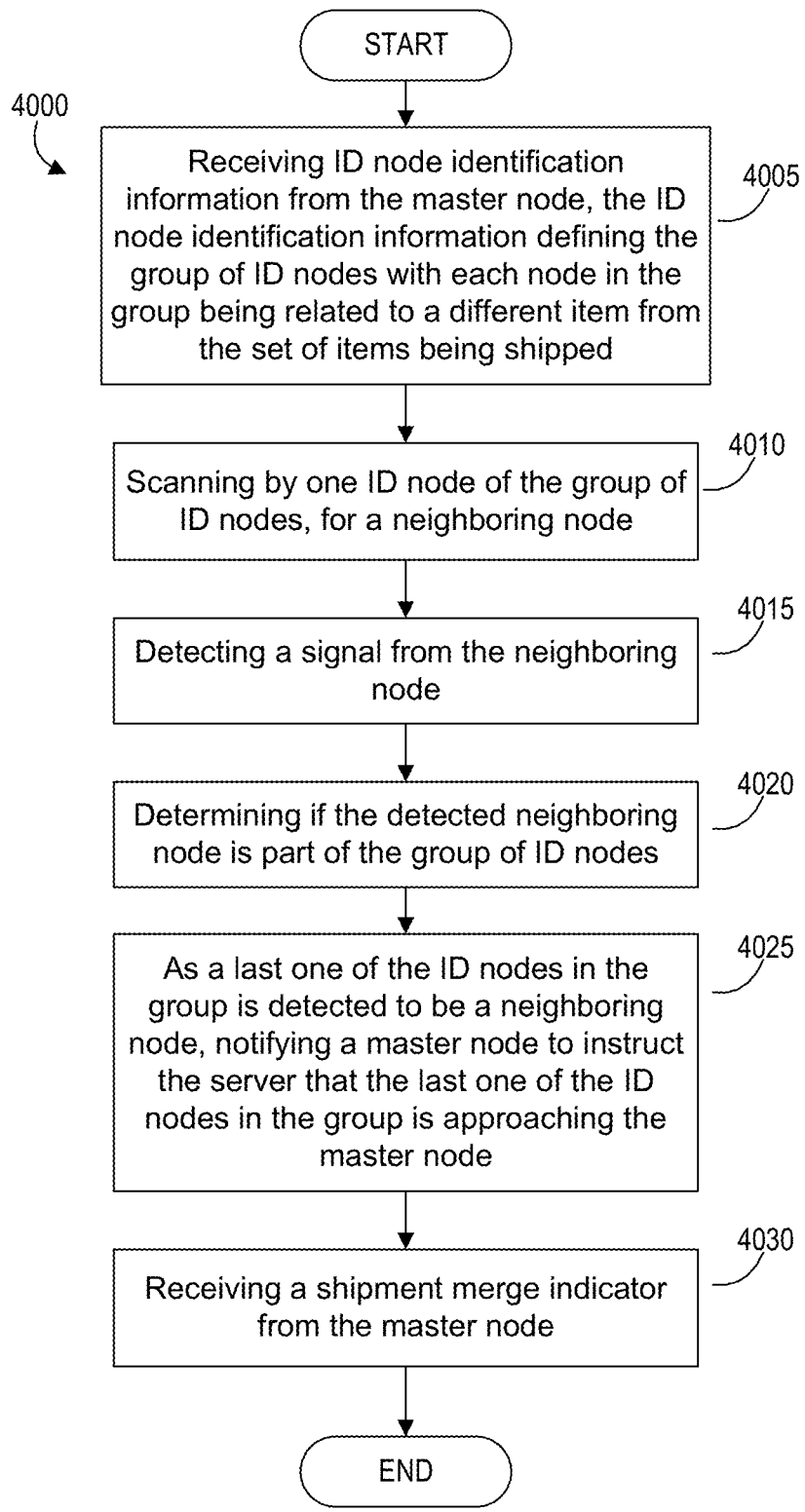
FIG. 40 is a flow diagram illustrating another exemplary method for shipment merging in a wireless node network in accordance with an embodiment of the invention.

While FIG. 39 describes operations of an exemplary method for shipment merging from the perspective of exemplary master node operations, such as facility master node 3430 in FIG. 34*c*, operations of shipment merging in another embodiment may also be explained from the perspective of exemplary ID node operations. FIG. 40 is a flow diagram illustrating another exemplary method for shipment merging of a set of items being shipped using a wireless node network. Referring now to FIG. 40, method 4000 begins at step 4005 by receiving ID node identification information from the master node. The ID node identification information defines the group of ID nodes and each ID node from the group is related to a different item from the set of items being shipped. In one example, the ID node identification information may be derived from and be part of shipping information related to the set of items being shipped (such as shipping information related to packages 130*a*-130*b* and their respectively identified ID nodes 120*a*-120*d* as shown in FIG. 34C).

At step 4010, scanning, by one ID node of the group of ID nodes, for a neighboring node. In the FIG. 34C example, ID node 120*b* may scan its general vicinity for any close ID nodes within communication range (e.g., a type of neighboring node).

At step 4015, the ID node from the group detects a signal from the neighboring node and at step 4020, it can determine if the detected neighboring node is part of the group of ID nodes based upon the signal broadcast from the neighboring node. In the example illustrated in FIG. 34C, ID node 120*b* may detect neighboring nodes 120*c* and 120*d*, which are identified as part of the group of nodes related to the set of packages 130*a*-130*d* being shipped. However, ID node 120*b* may not yet detect node 120*a*, which is in vehicle 3435. Thus, ID nodes 120*b*-120*d* may be aware that one ID node (and its related item in the package) from their group is missing.

At step 4025, as a last one of the ID nodes in the group of ID nodes is detected to be the neighboring node, method 4000 notifies a master node to instruct the server that the last one of the ID nodes in the group of ID nodes is approaching the ID node. Thus, in the FIG. 34C example, ID node 120*b* may detect a last of the ID nodes in the example group (i.e., ID node 120*a*) is approaching ID node 120*b*. Upon this detection and recognition that ID node 120*a* is the last of the group to be detected as a neighboring node (e.g., from the advertising signal broadcast by ID node 120*a* as it comes within communication range of ID node 120*b*), ID node 120*a* (or another of the ID nodes in the group that are associated with facility master node 3430) may notify facility master node 3430.

At step 4030, the master node responds by sending a shipment merge indication that is received by the ID nodes from the group. In one example, one of the ID nodes from group receives the shipment merge indication, and can let others of the ID nodes from the group know of this (e.g., via secure information sharing between connected nodes). The shipment merge indication reflects that the set of items has been merged to a single shipment. In another example, the shipment merge indication may be an authorization for the set of items to be released from the containment. In yet another example, this authorization may be a customs clearance notification authorizing release of the set of items from the containment as a single merged shipment.

And as a result of receiving the shipment merge indication, the method may have one or more of the ID nodes in the group storing customs information (such as information related to the shipment merge indication, authorization to be released from the containment, the customs clearance notification, or any other customs related paperwork and related duties and fees) in a memory of the respective each of the ID nodes in the group of ID nodes.

Those skilled in the art will appreciate that method 4000 as disclosed and explained above in various embodiments may be implemented on a node, such as an exemplary ID node as illustrated in FIG. 3, running one or more parts of their respective control and management code 325 to implement any of the above described functionality. Such code may be stored on a non-transitory computer-readable medium, such as memory storage 315 within an exemplary ID node. Thus, when executing such code, a processing unit 300 within the respective node may be operative to perform operations or steps from the exemplary methods disclosed above, including method 4000 and variations of that method.

Delivery Notification Using a Wireless Node Network

As an item being shipped and its related node (e.g., an ID node or a mobile master node) transit a shipping path from an origin to a destination, the intended recipient awaits the item. In one example, such as that shown in FIG. 34D, an exemplary delivery point stage of a shipping operation is illustrated where an embodiment may facilitate delivery to a fixed type of delivery point (e.g., a mailroom) and issue a notification to the intended recipient using a wireless node network. In general with reference to FIG. 34D, an exemplary delivery point 3440 is shown associated with a master node 3445, which is in communication with server 100. Package 130 and related ID node 120*a* are initially associated with courier master node 110*h* (also operative to communicate with server 100). As the packaged item 130 and ID node 120*a* approach the delivery point (with master node 3445 being located substantially near to the delivery point 3440), master node 3445 may detect advertising signals from ID node 120*a*. Based on those signals, master node 3445 may determine shipping information related to the approaching ID node 120*a*, and be able to notify an intended recipient of package 130 when the ID node 120*a* is substantially near the delivery point 3440.

Figure 41:
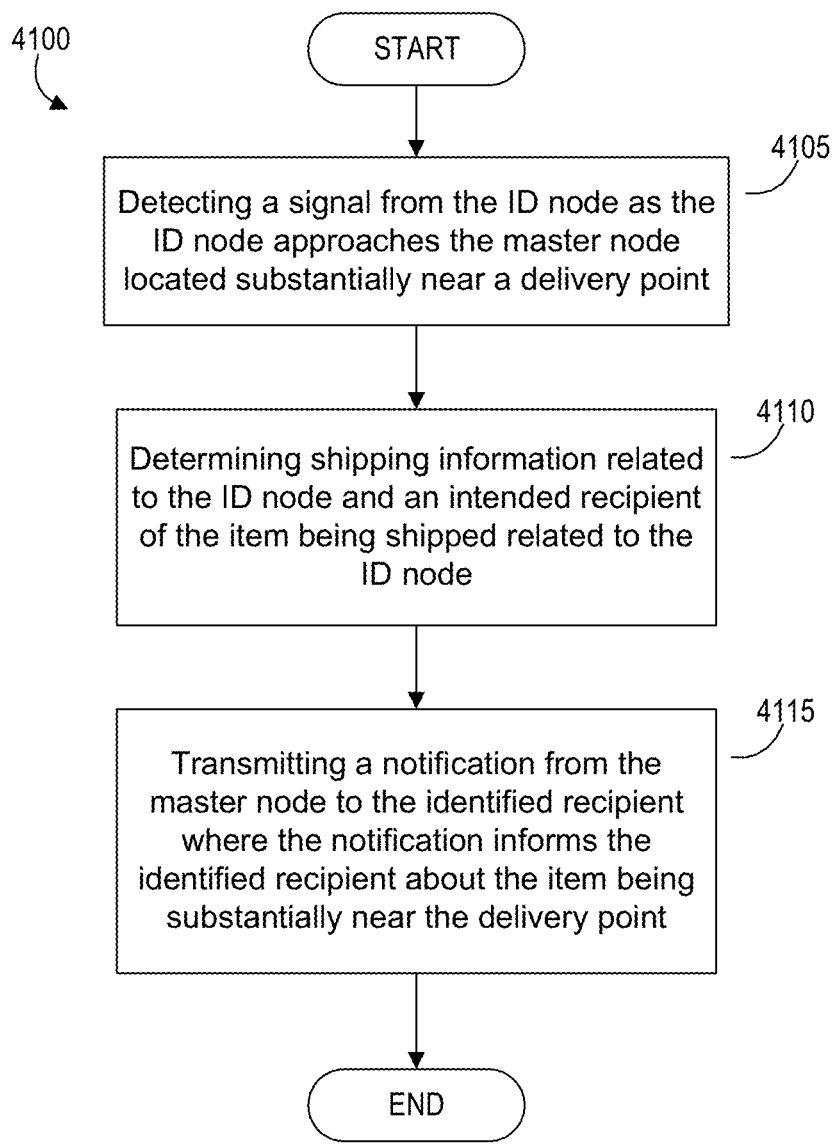
FIG. 41 is a flow diagram illustrating an exemplary method for delivery notification using a wireless node network in accordance with an embodiment of the invention.

FIG. 41 is a flow diagram illustrating an exemplary method for delivery notification using a wireless node network in accordance with an embodiment of the invention. Method 4100 begins at step 4105 where the master node detects a signal from the ID node (e.g., ID node 120*a* related to an item being shipped in package 130) as the ID node approaches the master node located substantially near a delivery point. While package 130 is shown with related ID node, an embodiment may implement such an ID node with a mobile master node temporarily operating as an ID node (for example, when the mobile master node is indoors and no longer receives satellite location signals but remains operative as a node in the wireless node network nonetheless).

An exemplary delivery point in this embodiment may take various forms. For example, in one embodiment, the delivery point may be a designated shipping area, delivery area, or a general package handling area. Further, other examples of an exemplary delivery point may include a logistics receptacle, such as a controlled access locker system. And additional examples may have the delivery point being indoors or outdoors.

In one example, the signal detected may be an advertising signal from the ID node. In the more detailed example of FIG. 34D, ID node 120a may be placed in an advertising mode by courier master node 110h so that as ID node 120a approaches the delivery point 3440, ID node 120a may begin advertising with broadcasted signals having status and identification information within the header of such broadcasted advertising signals. With master node 3445 substantially near the delivery point 3440, master node 3445 is able to scan for signals broadcast from approaching ID nodes (such as ID node 120a) and may determine the identification of the ID node based upon the broadcast signal from the ID node. In a further embodiment, server 100 may instruct courier master node 110h when to have ID node 120a begin broadcasting signals and may instruct master node 3445 when to begin scanning for ID node 120a.

The delivery point 3440 in this illustrated example may generally be a designated shipping area that handles receipt of shipped items (such as package 130). In a more detailed example, delivery point 3440 may be implemented as a mailroom of a business office or a designated drop off point at a facility (e.g., a loading dock where vehicles transfer packaged items being shipped, a storage room that may temporarily maintain packaged items being shipped, a shipping desk staffed with shipping personnel responsible for further distribution of a packaged item, a mobile pickup vehicle (autonomous or driven by personnel) responsible for further distribution of a packaged item within the facility. Those skilled in the art will appreciate that, in one embodiment, a delivery point may generally be near a final shipping destination (such as that illustrated in FIG. 34D where the final destination is the location of delivery point 3440 where an intended recipient may pick up the shipped item). Likewise, those skilled in the art will appreciate that the same principles may apply to an embodiment where the delivery point may be an intermediate shipping transfer point in the overall shipping path for a packaged item being shipped (such as the containment area 3426 within facility 3425 shown in FIG. 34C and where the intended recipient may be personnel in charge of containment area 3426).

At step 4110, the master node determines shipping information related to the ID node and an intended recipient of the item being shipped. In one example, the master node may determine the shipping information based upon the identification of the ID node (e.g., using the broadcast signal header information broadcast from ID node 120a). In one embodiment, the shipping information related to the ID node approaching may already be resident on the master node. In such a situation, server 100 may have transmitted the relevant shipping information for package 130 and ID node 120a to master node 3445 as pre-staged shipping information (identifying at least the intended recipient and how to notify that entity) before ID node 120a is detected as approaching. This pre-staged shipping information may be part of a larger amount of shipping information for multiple ID nodes (and their related items being shipped) or may be specific pre-staged shipping information limited to the particular ID node anticipated by the server to be approaching (which may require less memory storage requirements on the master node). However, in another embodiment, the shipping information may not be already resident on the master node. In that situation, upon detection of the signal from the approaching ID node, the master node may request shipping information from the server by notifying the server that the master node and approaching ID node are now associated (e.g., an established passive association without requiring an authorized connection between the master node and ID node, or an established active association reflecting an authorized connection between the master node and ID node), and receiving shipping information from the server in response. Thus, the master node may determine the appropriate shipping information using the ID node identification, and may involve requesting the shipping information from the server if it is not already resident on the master node.

At step 4115, the master node transmits a notification to the identified recipient. The notification informs the identified recipient about the item being substantially near the delivery point. Notification may be in a variety of forms and formats, such as but not limited to an email message, a text message, an audio message, visual indicator, or other alert type of communication.

In one example, transmitting the notification to the identified recipient may be directly accomplished between the master node and the intended recipient. For instance, in the example of FIG. 34D, master node 3445 may broadcast a message directly to an intended recipient, such a recipient identified by the shipping information as having a user access device (e.g., smartphone 205) registered in a profile for delivery notification. Master node 3445 may be able to communicate directly with smartphone 205 via one of a variety of communication paths directly with master node 3445 (e.g., Wi-Fi, Bluetooth, etc.). In another example, transmitting the notification to the identified recipient may be indirectly accomplished between the master node and the intended recipient via, for example, the server. For instance, with reference to the example shown in FIG. 34D, master node 3445 may forward the notification to the server 100, which causes the server 100 to send the notification to the intended recipient via smartphone 205.

The method may also, in another embodiment, have the master node determine that the ID node is within a predetermined range of the delivery point by instructing the ID node to alter an RF transmission power level as the ID node approaches the delivery point before transmitting the notification to the intended recipient. For example, the server may be able to dynamically set the predetermined range of the delivery point based upon context data (such as the layout of the facility where the delivery point is located). For instance, server 100 may configure master node 3445 to use a 25 foot range from the location of the ID node 120a to the delivery point 3440 as a notification threshold. Thus, master node 3445 may instruct ID node 120a to alter signals broadcast from the ID node 120a as the node approaches delivery point 3440, and master node 3445 will notify the intended recipient when it determines ID node 120 is within the threshold 25 foot range from the delivery point 3440. As such, the server is able to adjust and adapt based upon, for example, what courier is dropping off ID node 120 or how fast it is anticipated that courier will move (e.g., a type of context data).

Figure 34D:
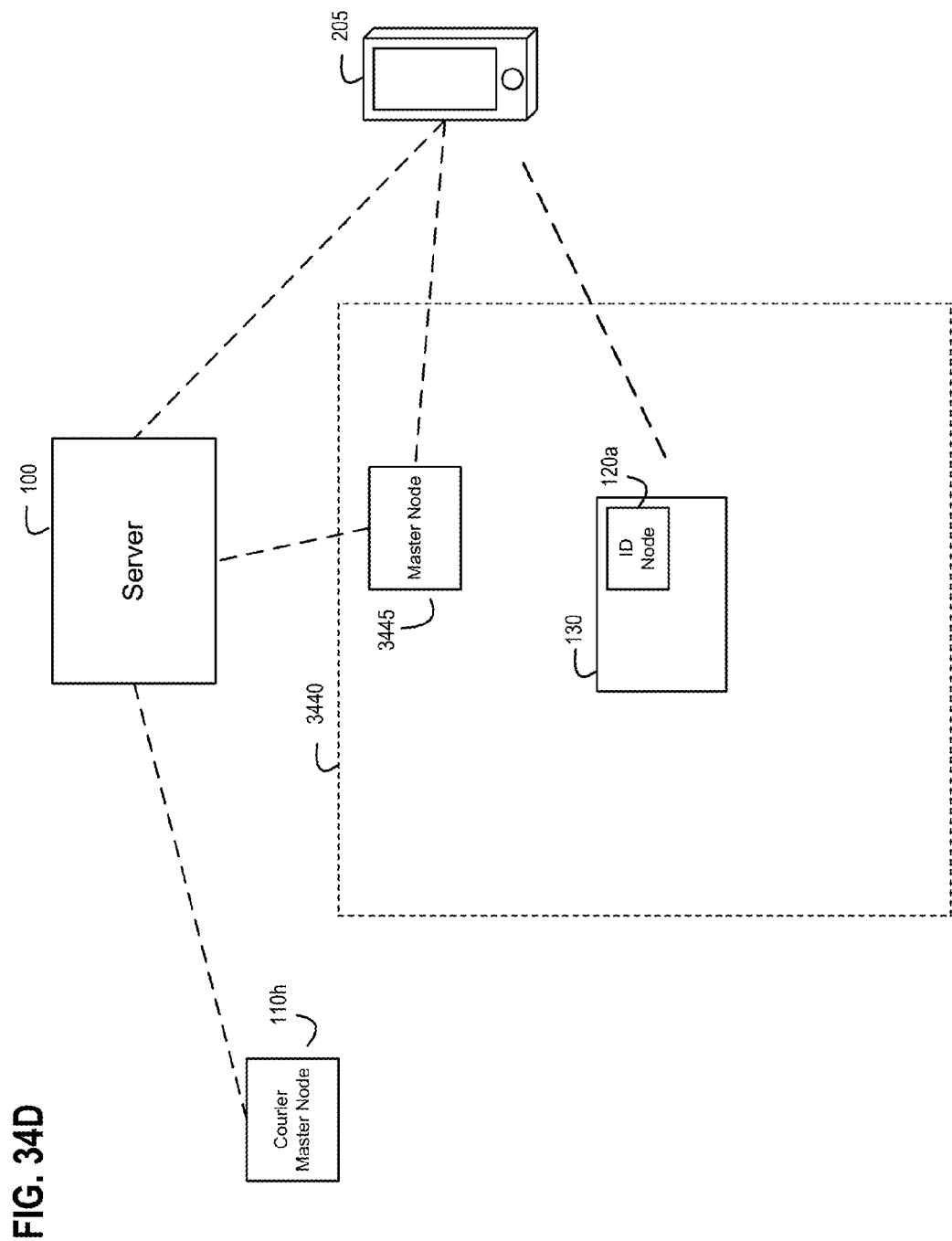

Those skilled in the art will appreciate that method 4100 as disclosed and explained above in various embodiments may be implemented on a node, such as an exemplary master node as illustrated in FIG. 4 or master node 3445 illustrated in FIG. 34D, running one or more parts of a control and management code 425 to implement any of the above described functionality. Such code may be stored on a non-transitory computer-readable medium, such as memory storage 415 within an exemplary master node. Thus, when executing such code, a processing unit 400 within the respective master node may be operative to perform operations or steps from the exemplary methods disclosed above, including method 4100 and variations of that method.

In more detail, another embodiment may include a master node for delivery notification. The exemplary master node may comprise a node processing unit and a node memory storage coupled to the node processing unit. The node memory storage maintains code for execution by the node processing unit and shipping information related to an ID node and a related item being shipped. The exemplary master node also comprises first and second communication interfaces each of which being coupled to the node processing unit. The first communication interface being operative to communicate with the ID node while the second communication interface is operative to communicate with the server.

When executing the code maintained on the node memory storage, the node processing unit is operative to perform steps from the exemplary methods as described above. In more detail, the node processing unit is operative to detect a signal from the ID node on the first communication interface as the ID node approaches the master node located substantially near a delivery point (such as a designated shipping area), access the node memory storage to determine the shipping information related to the ID node and an intended recipient of the item being shipped from the shipping information, and instruct the second communication interface to transmit a notification from the master node to the intended recipient where the notification informs or otherwise alerts the identified recipient about the item being substantially near the delivery point.

Related to determining shipping information, the node processing unit may, in some embodiments, be further operative to determine an identification of the ID node based upon the signal from the ID node, and determine the shipping information based upon the identification of the ID node. Related to transmitting the notification, the node processing unit may, in some embodiments, make use of an indirect notification path and forward the notification to the server from the master node with an instruction (implied or express) to cause the server to send the notification to the intended recipient.

Figure 101A:
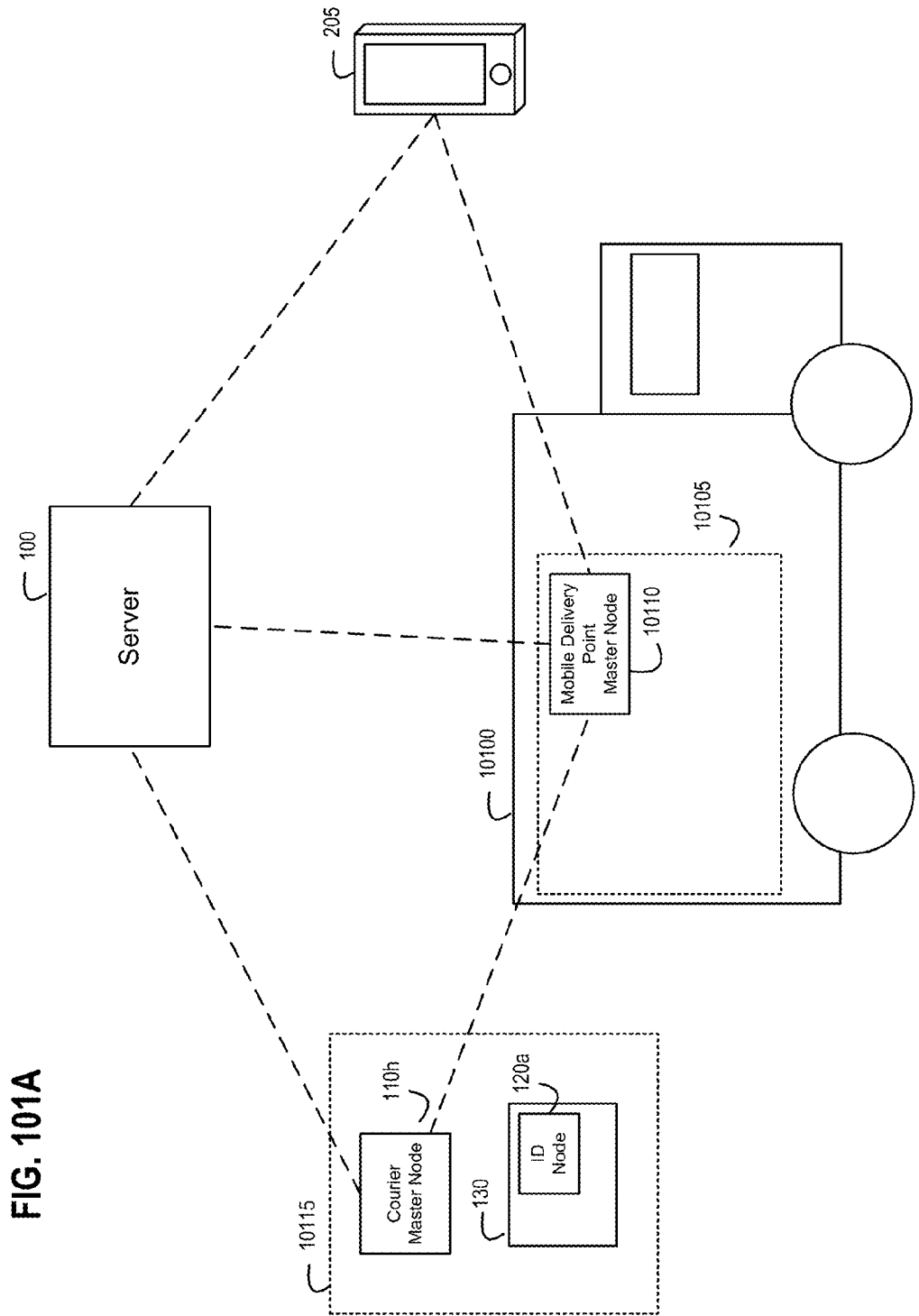
FIGS. 101A-101B are diagrams illustrating different points in time for an exemplary delivery notification stage involving an exemplary mobile delivery point in accordance with an embodiment of the invention.
Figure 101B:
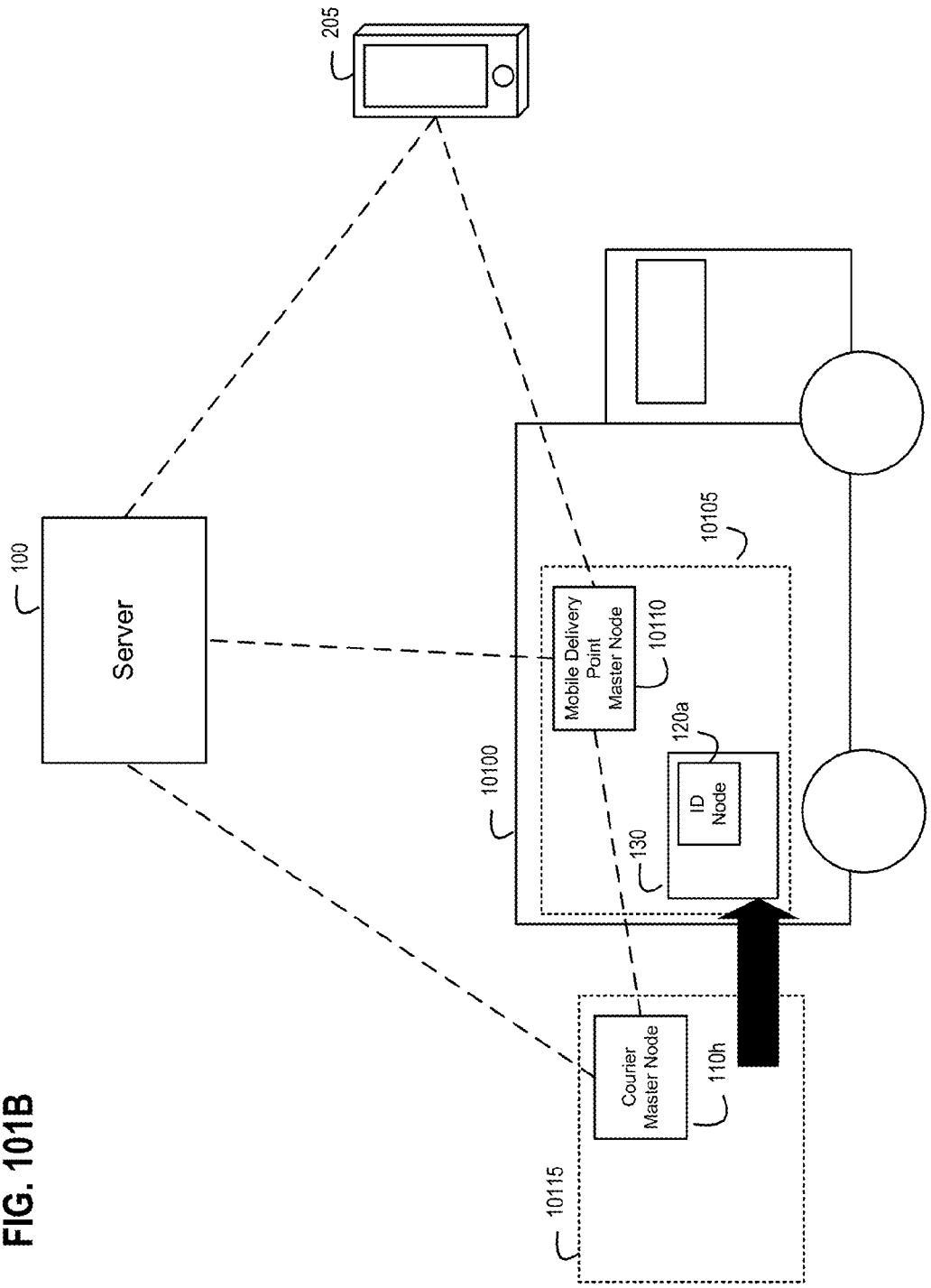
Figure 103:
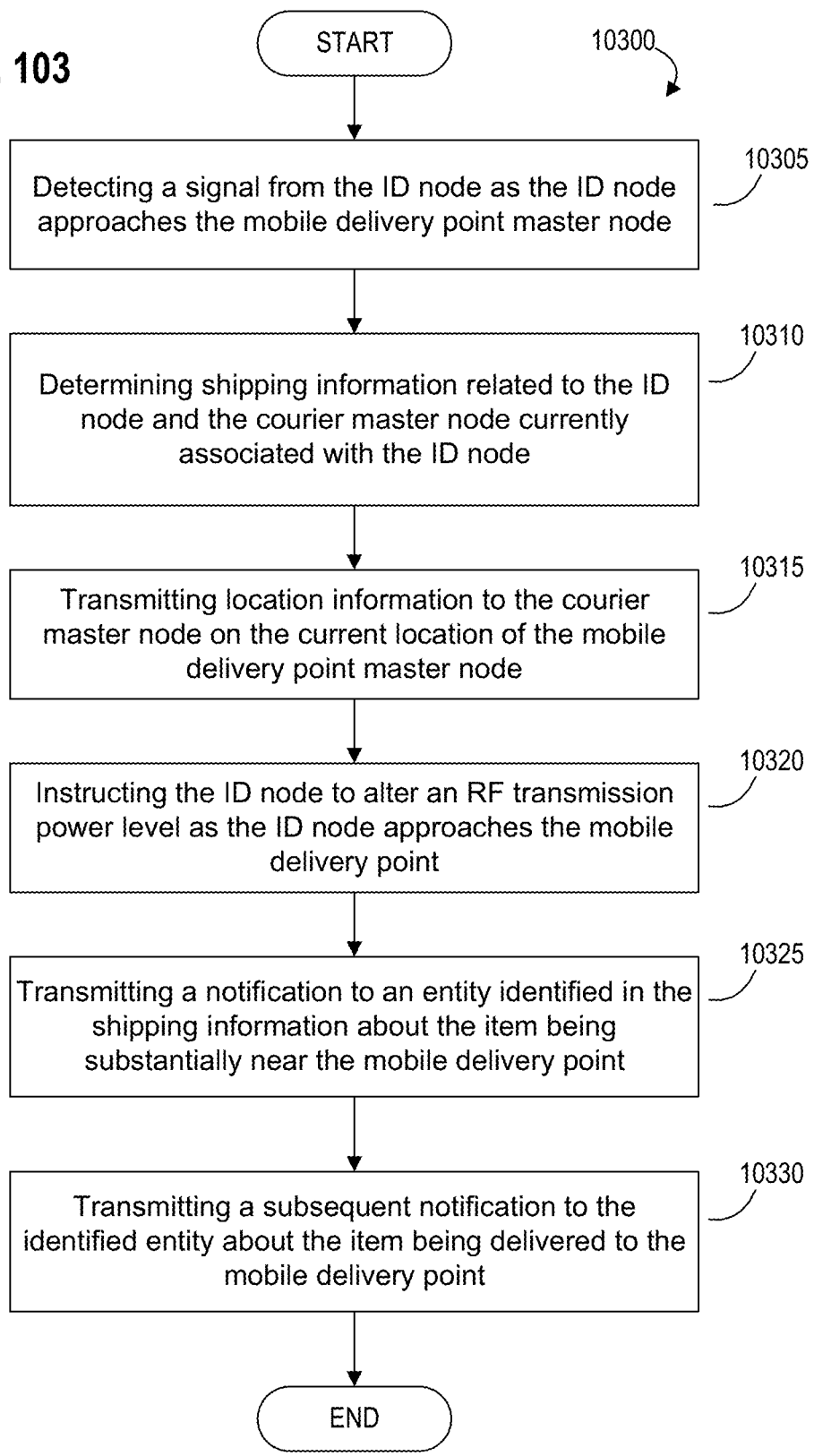
FIG. 103 is a flow diagram illustrating an exemplary method for delivery to a mobile delivery point and notification of an identified entity in accordance with an embodiment of the invention.

While FIGS. 34D and 41 describe an embodiment where the delivery point usually remains in a fixed location, other embodiments may involve a delivery to a mobile delivery point, such as a vehicle (e.g., car, van, truck, train, ship/boat, aircraft, and the like). Delivery to such a moving or movable delivery point may find the responsible courier having authorized access to the movable delivery point, but may pose some additional challenges given the location of the delivery point is not fixed. FIGS. 101A and 101B illustrate an example of another exemplary delivery point stage in a shipping operation where an embodiment may facilitate the delivery and delivery notification for an item being shipped to a mobile type of delivery point using a wireless node network. And while FIG. 102 illustrates an exemplary method of node operations that helps facilitate delivery to the mobile delivery point with notification to an intended recipient, FIG. 103 illustrates another exemplary method of node operations that helps facilitate delivery to the mobile delivery point with notification to an identified entity other than the intended recipient of the item being shipped.

In general and with reference to FIG. 101A, an exemplary mobile delivery point 10100 is shown associated with a mobile delivery point master node 10110, which is operative to communicate with server 100. Package 130 and related ID node 120*a* are initially associated with a courier 10115 having a courier master node 110*h* (also operative to communicate with server 100). In this embodiment, the delivery point 10100 may be mobile, such as a movable car or truck where the intended recipient desires to have the package 130 placed within or otherwise delivered. Thus, embodiments of the mobile delivery point master node 10110 may be implemented by a node on the vehicle (generally referenced as a vehicle node), such as a master node, an ID node, a master node operating as an ID node, or an ID node operating in a pseudo master node mode.

As the package 130 and ID node 120*a* approach the mobile delivery point 10100, mobile delivery point master node 10110 may detect advertising signals from ID node 120*a*. Based on the signals, mobile delivery point master node 10110 may determine shipping information related to the approaching ID node 120*a* and determine that courier master node 110*h* is currently associated with the ID node 120*a*. Mobile delivery point master node 10110 is then able to send location information (such as GPS coordinates or context data related to the mobile deliver point) to courier master node 110*h* as a way to assist and help guide the courier 10115 responsible for the package 130 with delivery to the mobile delivery point 10100. For example, mobile delivery point master node 10110 may send courier master node 110*h* location information on the vehicular mobile delivery point 10100, and that location information may include GPS coordinates and/or context data, such as a vehicular identification (e.g., Vehicle Identification Number or VIN, a license plate, an airplane tail number, or other tracking name or code affixed to the vehicle), a vehicular type (e.g., car, van, truck, private airplane), a vehicular color, a vehicular make (e.g., Ford, GM, Lear, Cessna), a vehicular make (e.g., F-150 truck, Piper Cub airplane), a parking level or area (e.g., level 3 in a parking garage, a temporary visitor parking area), and a parking space number (e.g., space #13 in the parking garage, hanger #44 at a private airport). In this manner, the vehicular node (mobile delivery point master node 10110) is context aware and leverages this knowledge so as to help guide the courier to the mobile delivery point with precise location information and/or contextually relevant information that allows the courier to quickly and easily identify the mobile delivery point and make the delivery.

When the ID node 120*a* is substantially near the mobile delivery point 10100 (more particularly, a storage area 10105 within vehicle 10100), the mobile delivery point master node 10110 may also notify the intended recipient of package 130 (via a message to smartphone 205). And as shown in FIG. 101B, the mobile delivery point master node 10110 may also notify the intended recipient and/or another entity (e.g., a shipping entity for the item, a business entity related to the mobile delivery point) when the ID node 120*a* and package 130 have actually been delivered to the mobile delivery point 10100. Thus, in some embodiments as explained in more detail with respect to FIG. 103, delivery notification may not necessarily require information on the intended recipient but may involve sending a notification upon delivery to the shipper and/or to a business that may own the mobile delivery point (e.g., a rental company that owns vehicle 10100).

In a further embodiment, delivery may be automatically acknowledged via node signatures and reported by the mobile delivery point master node. For example, the ID node and the mobile delivery point master node may become associated as they approach each other and, once delivery is acknowledged through node interactions (e.g., passive or active authorized associations between the ID node with the item being shipped and the mobile delivery point master node that is authorized to receive the item), the mobile delivery point master node may notify the server about the acknowledged delivery. In some embodiments, such node interactions to acknowledge delivery may use security data (such as security data 335 implemented with cryptographic keys, PIN data, etc.) maintained by the ID node and the mobile delivery point master node in their respective memories as discussed above relative to acknowledged deliveries and security data used when authorizing and authenticating such transactions via node interactions.

In yet another embodiment, mobile delivery point master node 10100 may control the authorized entry or access to storage area 10105 in one embodiment via communication with courier master node 110*h* or, in another embodiment, by detecting ID node 120*a* being proximate storage area 10105. Locking elements (electronic door locks, electronic trunk locks or actuators) may be operated with signals from mobile delivery point master node 10100 to provide or control access within the mobile delivery point 10100 (e.g., access to within storage area 10105 of vehicle 10100). Such authorized access entry to storage area 10105 may further involve verifying or validating access codes or keys provided by courier master node 110*h* or other security measures to ensure storage area 10105 has limited access only by those authorized (e.g., courier 10115) by the intended recipient. In another embodiment, an unlock key set may be separately communicated to the courier master node 110*h* (pre-staged or received upon coming close to the mobile delivery point. Other embodiments may use other types of keys as disclosed herein (e.g., rotating type of key based on time, fixed type of key, pre-staged key received when associating with the ID node and package initially, etc.).

FIG. 102 is a flow diagram illustrating an exemplary method for delivery notification using a wireless node network in accordance with another embodiment of the invention. Referring now to FIG. 102, method 10200 begins at step 10205 where the mobile delivery point master node detects a signal from the ID node as the ID node approaches the mobile delivery point master node. Here, the mobile delivery point master node is related to a mobile delivery point (such as vehicle 10100) and the ID node is related to an item being shipped (such as package 130). In more detail, such a vehicle may be related to the intended recipient and may be accessible by delivery personnel associated with the courier master node, such as the courier having custody of package 130 and actually doing the delivering.

Method 10200 proceeds to step 10210 where the mobile delivery point master node determines shipping information related to the ID node, an intended recipient of the item being shipped, and the courier master node currently associated with the ID node. In a further embodiment of method 10200, this determination may be accomplished after the mobile delivery point master node determines an identification of the ID node based upon the detected signal from the ID node, and then determines the shipping information, the intended recipient, and the courier master node based upon the identification of the ID node.

In still a further embodiment of method 10200, such a determination as performed in step 10210 may be implemented with the mobile delivery point master node notifying the server that the mobile delivery point master node and the ID node are associated; and then receiving responsive information from the server about the shipping information, the intended recipient, and the courier master node currently associated with the ID node.

At step 10215, method 10200 has the mobile delivery point master node transmitting location information to the courier master node. The location information comprises a current location of the mobile delivery point master node at the mobile delivery point. For example, mobile delivery point master node 10110 shown in FIG. 101A may transmit a message to courier master node 110*h* (directly or via a relayed message using server 100). The message includes location information, such as the current GPS coordinates, for mobile delivery point master node 10110. As such, courier 10115 is made aware of where mobile delivery point 10100 is specifically located, which facilitates an easier delivery as the ID node 120*a* approaches the general area where mobile delivery point 10100 is located.

In a further embodiment where the mobile delivery point is a vehicle, step 10215 may also have the mobile delivery point master node transmitting location information that may further comprise context data related to the vehicle. In other words, location information may include more precise location data (e.g., GPS coordinates, altitude level, and the like) and/or less precise types of location data, such as context data available to the mobile delivery point master node as contextually relevant information that allows the courier to quickly and easily identify the mobile delivery point and make the delivery. Examples of such relevant context data may include a vehicular identification (e.g., Vehicle Identification Number or VIN, a license plate, an airplane tail number, or other tracking name or code affixed to the vehicle), a vehicular type (e.g., car, van, truck, private airplane), a vehicular color, a vehicular make (e.g., Ford, GM, Lear, Cessna), a vehicular model (e.g., an F-150 truck from Ford Motor Company, a Cub airplane from Piper Aircraft), a parking level or area (e.g., level 3 in a parking garage, a temporary visitor parking area), and a parking space number (e.g., space #13 in the parking garage, hanger #44 at a private airport).

In another embodiment, method 10200 may include step 10220 where the mobile delivery point master node instructs the ID node to alter an RF transmission power level as the ID node approaches the mobile delivery point. This may be helpful in when the mobile delivery point is located near structure that may otherwise attenuate ID node transmissions or when the mobile delivery point is in a high node density environment.

At step 10225, method 10200 has the mobile delivery point master node transmitting a notification to the identified recipient in order to inform the intended recipient that the item being shipped is substantially near the mobile delivery point. In other embodiments, this notification may occur when the item is within a threshold distance or reception range from the mobile delivery point master node. An advantage here is that the intended recipient may be directly contacted by the mobile delivery point master node without needing to then relay the notification through the server, which may help offload the backend operations and provide for quicker notifications.

However, in other embodiments, transmitting the notification may desirably involve forwarding, by the mobile delivery point master node, the notification to the server, which then causes the server to send the notification to the intended recipient. In more detail, notifying may be accomplished by notifying the server that the mobile delivery point master node has established a passive association with the ID node without requiring an authorized connection between the mobile delivery point master node and ID node. Further still, another embodiment may implement notifying by notifying the server that the mobile delivery point master node has established an active association with the ID node reflecting an authorized connection between the mobile delivery point master node and ID node.

In a further embodiment, method 10200 may also include transmitting updated location information by the mobile delivery point master node to the courier master node. For example, if vehicle 10100 shown in FIG. 101A moves, mobile delivery point master node 10110 may subsequently transmit its updated location via location information sent to courier master node 110h. This may be done, for example, after the vehicle 10100 moves a threshold distance from its prior reported location. In another example, this may be done periodically until the courier delivers the package 130, as shown in FIG. 101B, to the vehicle 10100.

In still another embodiment, method 10200 may also have the mobile delivery point master node transmit a warning notification to the courier master node if the ID node is determined, by the mobile delivery point master node, to be moving away from the mobile delivery point master node. In such a situation, the courier may be lost or, at least, is moving in a direction that appears to make delivery more difficult. The warning notification may allow the courier to alter its course and be aware that it was moving away from the intended delivery of the package 130 to the mobile delivery point.

Once delivery has occurred, step 10230 of method 10200 has the mobile delivery point master node transmitting a subsequent notification to the intended recipient about the item being delivered to the mobile delivery point. In more detail, the subsequent notification may inform the intended recipient that the item has been delivered to the mobile delivery point. In a further embodiment, such a subsequent notification may also inform the intended recipient that the mobile deliver point (e.g., vehicle 10100) has be re-locked after the delivery so to allow the recipient additional peace of mind with respect to the opted mobile delivery point operation.

Those skilled in the art will appreciate that method 10200 as disclosed and explained above in various embodiments may be implemented on a node, such as an exemplary master node as illustrated in FIG. 4 or mobile delivery point master node 10110 illustrated in FIGS. 101A and 101B, running one or more parts of a control and management code 425 to implement any of the above described functionality. Such code may be stored on a non-transitory computer-readable medium, such as memory storage 415 within an exemplary mobile delivery point master node. Thus, when executing such code, a processing unit 400 within the respective mobile delivery point master node (as described below, for example) may be operative to perform operations or steps from the exemplary methods disclosed above, including method 10200 and variations of that method.

From another perspective, another embodiment may include a mobile delivery point master node for delivery notification involving a mobile delivery point using a wireless node network having at least an ID node, a courier master node, and a server. The exemplary mobile delivery point master node may comprise a node processing unit and a node memory storage coupled to the node processing unit. The node memory storage maintains code for execution by the node processing unit; shipping information related to an ID node and a related item being shipped; and identification information related to the courier master node currently associated with the ID node. The exemplary mobile delivery point master node also comprises first and second communication interfaces each of which being coupled to the node processing unit. The first communication interface being operative to communicate with the ID node while the second communication interface is operative to communicate with the server.

When executing the code maintained on the node memory storage, the node processing unit of the mobile delivery point master node is adapted and operative to perform steps from the exemplary methods as described above relative to method 10200. In more detail, the node processing unit is adapted and operative to detect a signal from the ID node via the first communication interface as the ID node approaches the mobile delivery point master node, the mobile delivery point master node being related to the mobile delivery point (e.g., such as when a vehicle is the mobile delivery point and the vehicle's master node operates as the mobile delivery point master node), the ID node being related to an item being shipped; access the node memory storage to determine the shipping information related to the ID node, an intended recipient of the item being shipped, and the courier master node currently associated with the ID node; cause the location information to be transmitted to the courier master node, where the location information comprises a current location of the mobile delivery point master node at the mobile delivery point; and instruct the second communication interface to transmit a notification from the mobile delivery point master node to the identified recipient, where the notification informs the intended recipient about the item being substantially near the mobile delivery point or being actually delivered to the mobile delivery point.

As previously noted, while FIG. 102 illustrates an embodiment where an intended recipient may be notified related to delivery to a mobile delivery point, FIG. 103 illustrates another exemplary method of node operations that helps facilitate delivery to a mobile delivery point but where the notification may be sent to one or more entities other than the intended recipient of the item being shipped. As explained above, in some instances, pre-delivery and delivery confirmation notification related to a mobile delivery point may not need to go to the ultimate recipient of the item being shipped. For example, in one embodiment, a mobile delivery point master node itself may acknowledge delivery with a secure signoff or handoff from the courier master node, and the delivery-related notifications may go to one or more other entities, such as an entity identified in the shipping information.

Such an identified entity may be related to the mobile delivery point (e.g., a shipping company responsible for the overall logistics of shipping the item to the mobile delivery point or a business entity related to the mobile delivery point, such as a rental car company related to a rental car that is used as the mobile delivery point). In these examples, the mobile delivery point master node associated with the mobile delivery point may send a notification to one of these identified entities that may or may not include the intended recipient. For example, a courier master node may deliver a package having an ID node to a time-shared car, such as a Zipcar® automobile. The package here may, for example, include groceries or office supplies ordered online. In this example, the Zipcar® automobile may be equipped with a vehicle node that operates as a type of mobile delivery point master node. As such, the node in the Zipcar® automobile may notify a shipping company responsible for delivering the package when the package is substantially near that particular Zipcar® automobile and, for example, again after it has received the package and ID node to confirm delivery to the shipping company and without the need to know the intended recipient. In some cases, the intended recipient may also be notified, if desired. In other cases, the Zipcar® business may be notified as a business entity related to the mobile delivery point via a message directly to the business or via a message sent by the backend server. In still further cases, multiple combinations of entities may be notified by the mobile delivery point master node (directly or indirectly via the server) related to an impending and confirmed delivery of the package.

FIG. 103 is a flow diagram illustrating an exemplary method for delivery notification using a wireless node network in accordance with another embodiment of the invention where notification is to an identified entity, which may be one or more entities other than the intended recipient of the packaged item being shipped. Referring now to FIG. 103, method 10300 begins at step 10305 where the mobile delivery point master node detects a signal from the ID node as the ID node approaches the mobile delivery point master node. Here, as with exemplary method 10200, the mobile delivery point master node in method 10300 is related to a mobile delivery point (such as vehicle 10100) and the ID node is related to an item being shipped (such as package 130, which represents the item and its packaging).

At step 10310, method 10300 has the mobile delivery point master node determining shipping information related to the ID node and the courier master node currently associated with the ID node. In one embodiment, the shipping information related to the ID node and the courier master node currently associated with the ID node may be pre-staged on the mobile delivery point master node. As such, determining such information may be accomplished by accessing the information on the mobile delivery point master node's memory. However, those skilled in the art will appreciate that in another embodiment, the shipping information related to the ID node and which courier master node is currently associated with the ID node may be determined by requesting such information from the server 100. In more detail, step 10310 may further comprise notifying the server that the mobile delivery point master node and the ID node are associated, and receiving, by the mobile delivery point master node, responsive information from the server about the shipping information and the courier master node currently associated with the ID node.

At step 10315, the mobile delivery point master node transmits location information to the courier master node currently associated with the ID node. The location information includes a current location of the mobile delivery point master node at the mobile delivery point. In an example embodiment where the mobile delivery point is a vehicle (such as that shown in FIGS. 101A and 101B), step 10315 may also have the mobile delivery point master node transmitting location information that may further comprise information known to the mobile delivery point master node about its contextual environment—i.e., context data related to the vehicle. In other words, various embodiments may have location information including more precise types of location data (e.g., GPS coordinates, altitude level, and the like) and/or less precise types of location data, such as context data available to the mobile delivery point master node as contextually relevant information that allows the courier to quickly and easily identify the mobile delivery point and make the delivery. Examples of such context data may include a vehicular identification (e.g., Vehicle Identification Number or VIN, a license plate, an airplane tail number, or other tracking name or code affixed to the vehicle), a vehicular type (e.g., car, van, truck, private airplane), a color of the vehicle, a make or brand name of the vehicular (e.g., Ford, GM, Lear, Cessna), a model of the vehicle (e.g., an F-150 truck from Ford Motor Company, a Caravan airplane from the Cessna Aircraft Company), a parking level or area (e.g., level 3 in a parking garage, a temporary visitor parking area), and a parking space number (e.g., space #13 in the parking garage, hanger #44 at a private airport).

At step 10320, the mobile delivery point master node may instruct the ID node to alter an RF transmission power level as the ID node approaches the mobile delivery point. As noted above with respect to method 10200, this may be helpful when the mobile delivery point is located near structure that may attenuate ID node transmissions or when the mobile delivery point is in a high node density environment.

At step 10325, method 10300 has the mobile delivery point master node transmitting a notification to an entity identified in the shipping information. This informs the identified entity that the item is substantially near the mobile delivery point. In other embodiments, this notification may occur when the item is within a threshold distance or a certain reception range from the mobile delivery point master node.

The entity notified is identified from the shipping information. This may allow the shipping customer to select and setup details on who or what is to be notified just before and upon delivery. As such, the identified entity may not be the intended recipient of the shipped item in the package 130. In a more detailed embodiment, the identified entity may be an entity related to the mobile delivery point itself, such as one of a shipping entity for the item, a business entity related to the mobile delivery point, and an intended recipient of the item or a combination thereof. In yet another embodiment where the mobile delivery point is a vehicle, the vehicle may be unrelated to the intended recipient but may be related to the business entity, and the vehicle may be accessible by delivery personnel associated with the courier master node. In still another embodiment, the vehicle may be unrelated to the intended recipient at the time of delivery only later to become related to the intended recipient (e.g., delivery to a specific rental car prior and then later assigning that specific rental car to the intended recipient).

In other embodiments, transmitting the notification to the identified entity may take a less direct approach in that it may desirably involve forwarding the notification to the server by the mobile delivery point master node. This then causes the server to send the notification to the identified entity. In more detail, notifying may be accomplished by notifying the server that the mobile delivery point master node has established a passive association with the ID node without requiring an authorized connection between the mobile delivery point master node and ID node. Further still, another embodiment may implement notifying by notifying the server that the mobile delivery point master node has established an active association with the ID node reflecting an authorized connection between the mobile delivery point master node and ID node.

In a further embodiment, method 10300 may also include transmitting updated location information by the mobile delivery point master node to the courier master node. For example, if vehicle 10100 shown in FIG. 101A moves, mobile delivery point master node 10110 may subsequently transmit its updated location via location information sent to courier master node 110h. This may be done, for example, after the vehicle 10100 moves a threshold distance from its prior reported location. In another example, this may be done periodically until the courier delivers the package 130, as shown in FIG. 101B, to the vehicle 10100.

In still another embodiment, method 10300 may also have the mobile delivery point master node transmit a warning notification to the courier master node if the ID node is determined, by the mobile delivery point master node, to be moving away from the mobile delivery point master node. In such a situation, the courier may be lost or, at least, is moving in a direction that appears to make delivery more difficult. The warning notification may allow the courier to alter its course and be aware that it was moving away from the intended delivery of the package 130 to the mobile delivery point.

Once delivery has occurred, step 10330 of method 10300 may have the mobile delivery point master node transmitting a subsequent notification to the identified entity about the item being delivered to the mobile delivery point. In more detail, the subsequent notification may inform the identified entity that the item has been delivered to the mobile delivery point. In a further embodiment, such a subsequent notification may also inform the identified entity that the mobile deliver point (e.g., vehicle 10100) has been re-locked after the delivery.

Those skilled in the art will appreciate that method 10300 as disclosed and explained above in various embodiments may be implemented on a node, such as an exemplary master node as illustrated in FIG. 4 or mobile delivery point master node 10110 illustrated in FIGS. 101A and 101B, running one or more parts of a control and management code 425 to implement any of the above described functionality. Such code may be stored on a non-transitory computer-readable medium, such as memory storage 415 within an exemplary mobile delivery point master node. Thus, when executing such code, a processing unit 400 within the respective mobile delivery point master node may be operative to perform operations or steps from the exemplary methods disclosed above, including method 10300 and variations of that method as described above.

In another perspective, another embodiment may include a mobile delivery point master node for delivery notification using a wireless node network having at least an ID node, a courier master node, and a server. The exemplary mobile delivery point master node may comprise a node processing unit and a node memory storage coupled to the node processing unit. The node memory storage maintains code for execution by the node processing unit (such as one or more parts of the control and management code 425); shipping information related to an ID node and a related item being shipped; and identification information related to the courier master node currently associated with the ID node. The exemplary mobile delivery point master node also comprises first and second communication interfaces each of which being coupled to the node processing unit. The first communication interface is operative to communicate with the ID node while the second communication interface is operative to communicate with the server.

When executing the code maintained on the node memory storage, the node processing unit of the mobile delivery point master node is adapted and operative to perform steps from the exemplary methods as described above relative to method 10300 and its variations as described above. In more detail, the node processing unit is adapted and operative (via execution of the code) to detect a signal from the ID node via the first communication interface as the ID node approaches the mobile delivery point master node (where the mobile delivery point master node is related to a mobile delivery point and the ID node is related to an item being shipped); access the node memory storage to determine the shipping information related to the ID node and the courier master node currently associated with the ID node; cause the location information to be transmitted to the courier master node (where the location information comprises a current location of the mobile delivery point master node at the mobile delivery point); and instruct the second communication interface to transmit a notification to an entity identified in the shipping information, where the notification informs the identified entity about the item being substantially near or being actually delivered to the mobile delivery point.

Order Pickup Using a Wireless Node Network

In another embodiment, picking up an order placed with a retail facility may be advantageously facilitated using a master node and a mobile user access device operating as an advertising ID node within a wireless node network. A retail order may generally be an item purchased that may be picked up from a facility. In a more detailed example, a customer submits an order to a retail establishment, such as a FedEx® Office Print & Ship Center, for an item. In one example, the ordered item may include a number of specifically printed documents bound together in a desired way (e.g., spiral bound with distinct covers). The exemplary order may be submitted by the customer in person at the retail establishment (more generally referred to as a facility). In another example, the order may be submitted online to the retail establishment by the customer via a website where the customer may have an account or profile. Such an account or profile may identify the customer and identify and register a mobile user access device that may be used when picking up the order. In both the in-person and online order submission paths for an exemplary order, an order management system for the retail establishment may receive information about the order (e.g., an identification of the customer, specific information on what items were ordered, an identification of a mobile user access device to be used when picking up the order, etc.) and help to fulfill the order for the customer.

Figure 42:
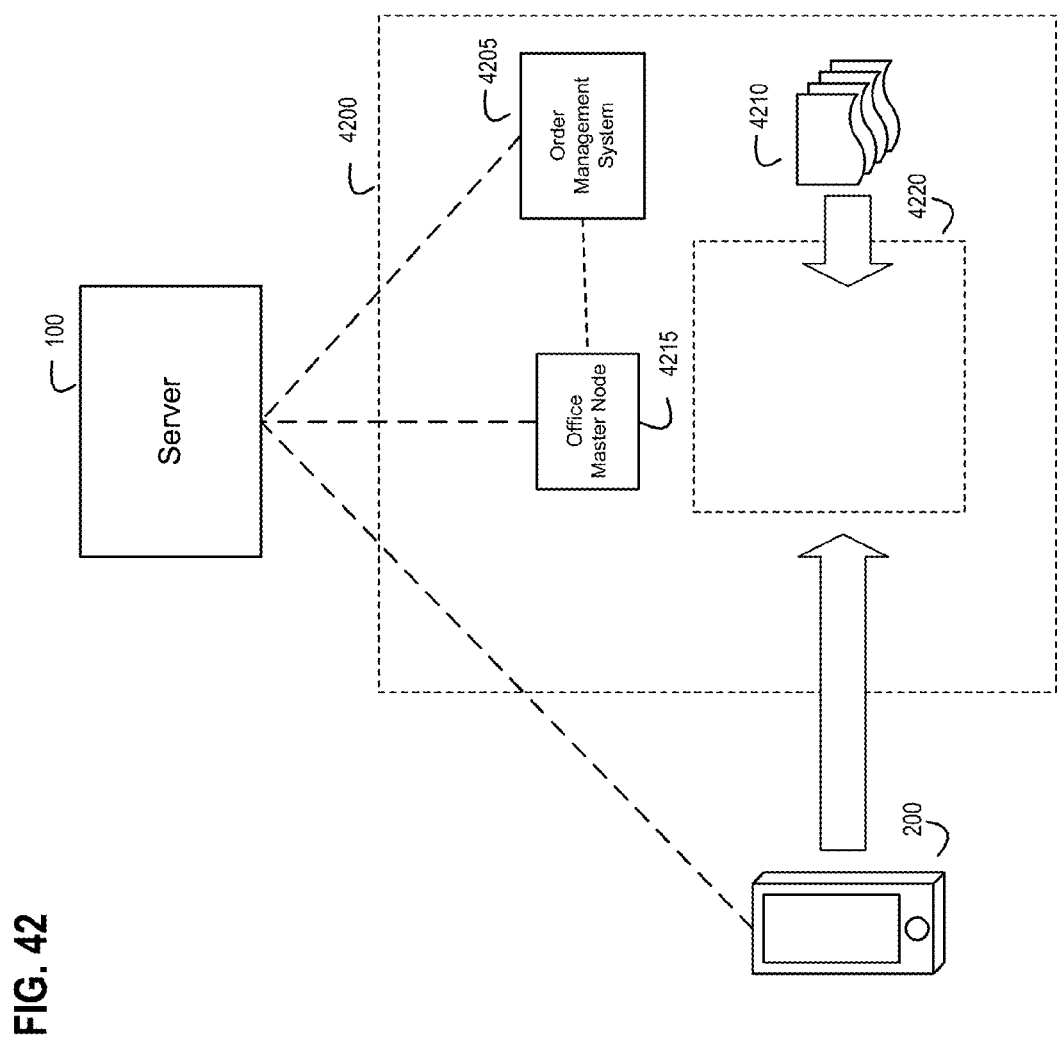
FIG. 42 is a diagram illustrating an example environment for picking up an order using exemplary components of a wireless node network in accordance with an embodiment of the invention.

FIG. 42 is a diagram illustrating an example environment for picking up an order using exemplary components of a wireless node network in accordance with an embodiment of the invention. Referring now to FIG. 42, an exemplary order management system 4205 is illustrated that may have received the order and is generally responsible for the order and its fulfillment. Those skilled in the art will appreciate that order management system 4205 may be implemented by a wide variety of computer-based systems, such as server-type sales management systems involved in online sales management, order fulfillment, and order status reporting.

In the illustrated example, exemplary order management system 4205 is related to facility 4200 where the order 4210 is to be picked up. The facility 4200 also has a related office master node 4215 deployed at or near a designated order fulfillment area 4220 (more generally a pickup point) where a previously submitted order for one or more items are made available to customers. In one example, the order may be a print order generated by a printer. In another example, the order may be a 3D print order generated by a 3D printer. In further examples, the order may be other retail items.

In one example, the office master node 4215 may be at or substantially near a customer pickup counter (a more specific pickup point). Office master node 4215 is operative to communicate with server 100 as part of the wireless node network. Server 100 may be separate from order management system 4205 in one embodiment, but server 100 may also function as the order management system 4205 in other embodiments depending on how the retail establishment elects to deploy its server computing resources.

As shown in FIG. 42, a mobile user access device 200 registered to pick up the order approaches the facility 4200. An exemplary mobile user access device may be implemented in a wide variety of forms, such as a laptop computer, a tablet device, a personal area network device, a smartphone device, and a smart wearable device. Furthermore, those skilled in the art will appreciate that code operative on the exemplary mobile user access device 200 (e.g., an app on a smartphone) may be used along with the conventional features of the mobile user access device to communicate over a short-range communication path, such as a Bluetooth® Low Energy enabled RF communication path, and allow the mobile user access device to operate as an advertising ID node as described herein. In other words, the mobile user access device 200 may operate as an advertising ID node when it approaches the facility 4200 in an embodiment in order to facilitate pickup of the order. As the mobile user access device 200 approaches and when the office master node 4215 detects a signal from the mobile user access device 200 operating as an advertising ID node, the office master node 4215 associates with the mobile user access device 200.

The office master node 4215, having an identification of the mobile user access device 200 being registered to the order, may notify the order management system 4205 upon detecting such a signal from the mobile user access device 200. In another embodiment, office master node 4215 may wait for such notification, and continue to determine the location of the mobile user access device 200 operating as an advertising ID node as the device 200 keeps approaching the master node, and notify the order management system 4205 when the device 200 is within a predetermined range of the pickup point in facility 4200. Thus, office master node 4215 and device 200 operating as an ID node may allow for a proactive notification of and integration into the order management system 4205 so that the order 4210 may be ready by the time device 200 (and the customer carrying device 200) arrive at the pickup point.

Figure 43:
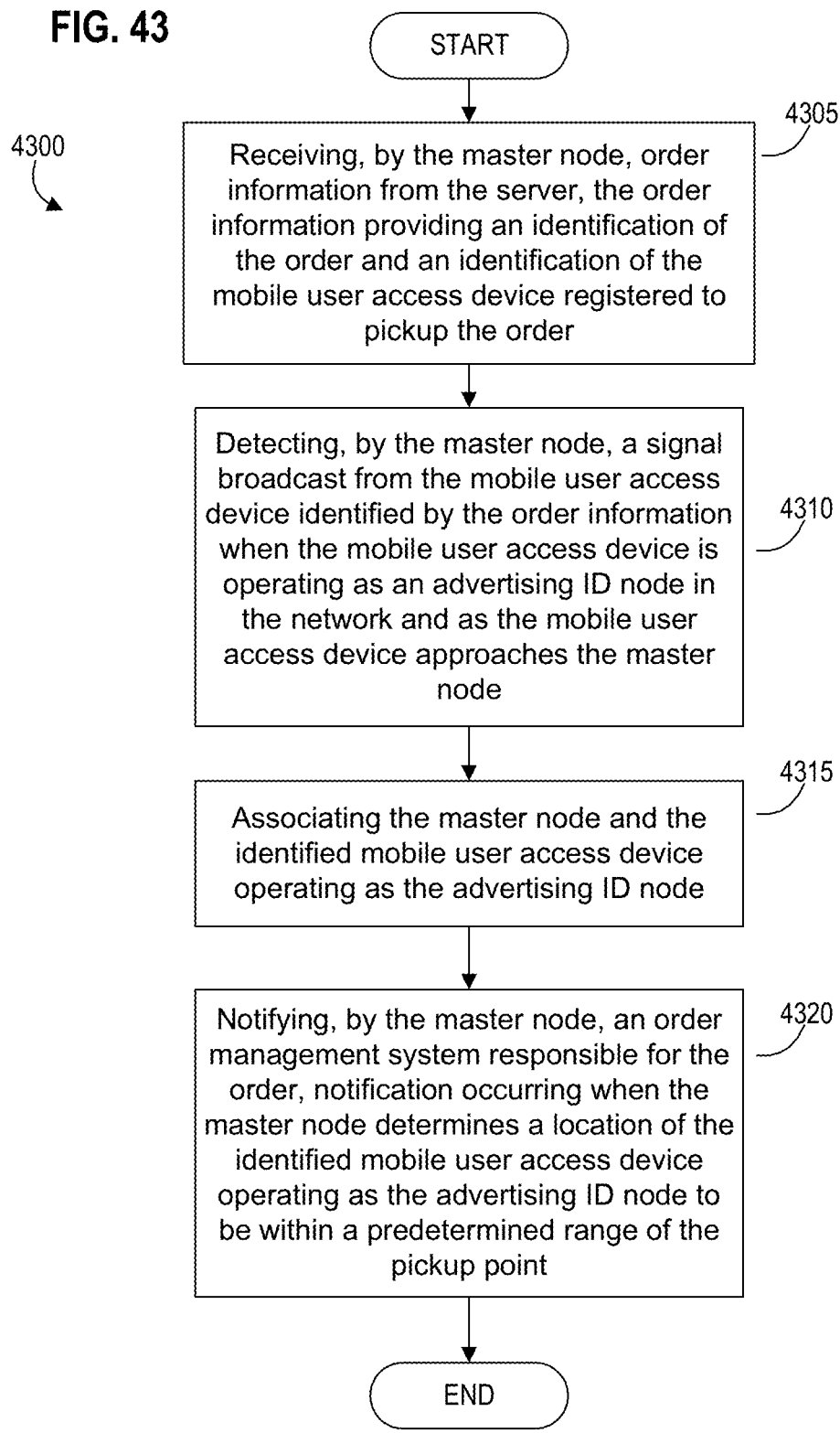
FIG. 43 is a flow diagram illustrating an exemplary method for picking up an order using a wireless node network in accordance with an embodiment of the invention.

FIG. 43 is a flow diagram illustrating an exemplary method pickup of an order using a wireless node network in accordance with an embodiment of the invention. Referring now to FIG. 43, exemplary method 4300 begins at step 4305 where a master node associated with a pickup point receives order information from a server. The order information provides an identification of the order and an identification of a mobile user access device registered for the pickup of the order. The pickup point, in one embodiment, may be a designated location where the order will be available, such as an order fulfillment area in a facility, a pickup desk or counter within a retail establishment, or the like.

At step 4310, detecting, by the master node, a signal broadcast from the mobile user access device identified by the order information when the mobile user access device is operating as an advertising ID node in the network and as the mobile user access device approaches the master node. In one embodiment, master node may be able to detect the signal is from the particular mobile user access device registered with the order because the identification of the mobile user access device may appear in header information of the signal broadcast from the mobile user access device when operating as the advertising ID node. For example, smartphone 200 illustrated in FIG. 42 may be operating as an ID node by advertising or broadcasting a signal (such as an advertisement packet similar to that shown in FIG. 7) formatted with header information that identifies a Bluetooth® Low Energy (BLE) signature (e.g., a MAC address or other header information) related for this particular smartphone 200. Thus, in this example, the exemplary app (not shown) resident on smartphone 200 is able to control such BLE signals emitted and read BLE signals received to operatively enable smartphone 200 to function as an advertising ID node.

At step 4315, method 4300 continues by associating the master node and the identified mobile user access device operating as the advertising ID node. The association may be passive or active depending on a desire to securely share information with the mobile user access device. Thus, in one embodiment, the associating at step 4315 may further comprise establishing a passive association between the master node and the identified mobile user access device operating as the advertising ID node without requiring an authorized connection between the master node and the identified mobile user access device operating as the advertising ID node. However, in another embodiment, such associating may further comprise establishing an active association between the master node and the identified mobile user access device operating as the advertising ID node reflecting an authorized connection between the master node and the identified mobile user access device operating as the advertising ID node. In more detail, establishing an active association may involve the master node determining when the identified mobile user access device operating as the advertising ID node is connectable, requesting authorization from the server to associate with the identified mobile user access device operating as the advertising ID node, and receiving the requested authorization from the server to allow the authorized connection between the master node and the identified mobile user access device operating as the advertising ID node.

At step 4320, the master node notifies an order management system responsible for the order (such as order management system 4205 shown in the example of FIG. 42). This notification occurs when the master node determines a location of the identified mobile user access device operating as the advertising ID node to be within a predetermined range of the pickup point. In another embodiment where the master node, the notifying step may comprise transmitting a message from the master node to the server, where the message causes the server to notify the order management system that the identified mobile user access device related to the order is approaching the pickup point to receive the order.

Method 4300 may further include steps that provide feedback to the mobile user access device prior to pick up. In more detail, such steps may include the master node receiving an order update message from the order management system where the order update message reflects a status of the order. For example, if the order is not yet ready for pickup, the master node may inform the customer by transmitting a pickup status message to the identified mobile user access device operating as the advertising ID node. However, if the order is ready for pickup or if there is other status information to convey to the designated pickup device, the pickup status message provides a proactive way of doing so.

In a further embodiment, the pickup status message may cause the identified mobile user access device operating as the advertising ID node to display one or more prompts (e.g., prompted messages) on a user interface of the identified mobile user access device. For example, the prompt may be related to picking up the order, validating that the order has been picked up, and/or paying for the order.

Those skilled in the art will appreciate that method 4300 as disclosed and explained above in various embodiments may be implemented on a master node, such as an exemplary master node as illustrated in FIG. 4 or office master node 4215 illustrated in FIG. 42, running one or more parts of a control and management code 425 to implement any of the above described functionality. Such code may be stored on a non-transitory computer-readable medium, such as memory storage 415 within an exemplary master node. Thus, when executing such code, a processing unit 400 within the respective master node may be operative to perform operations or steps from the exemplary methods disclosed above, including method 4300 and variations of that method.

In another embodiment, an exemplary master node for pickup of an order at a pickup point using a wireless node network comprises a node processing unit at its core. The master node also comprising a node memory storage, a first communication interface, and a second communication interface—each of which being coupled to the node processing unit. The node memory storage maintains code for execution by the node processing unit (such as control and management code 425) and order information having an identification of the order and an identification of the mobile user access device registered to pick up the order. For example, the order may be a print order submitted by a customer having an account or profile information with a FedEx a FedEx® Office Print & Ship Center that is associated with the order. Thus, the customer may have registered one or more mobile user access devices on the account or profile. As a result, such registered mobile user access device or devices may be considered identified or registered to pick up the order even though the customer need only use one of the registered devices when picking up the order.

In the master unit, the first communication interface coupled to the node processing unit is operative to communicate with the mobile user access device operating as an advertising ID node over a short-range communication path, such as over a Bluetooth® Low Energy formatted signal communication path. Instead of using this short-range communication path, the second communication interface of the master node is coupled to the node processing unit and operative to communicate with the server. In one example, the communication path for the master node to communicate with the server is a wireless higher-speed, longer-range communication path when compared to the short-range communication path of the first communication interface.

The node processing unit, when executing the code maintained on the node memory storage, is operative to perform steps substantially similar to those described above with respect to method 4300. More specifically, the node processing unit is operative to receive the order information from the server and maintain the order information on the node memory storage, and receive a signal detected by the first communication interface and broadcast from the mobile user access device when the mobile user access device is operating as an advertising ID node in the network and approaching the first communication interface. The node processing unit may be operative, in a more detailed embodiment, to determine if the signal detected by the first communication interface is from the identified mobile user access device by analyzing header information of the signal broadcast from the mobile user access device operating as the advertising ID node The node processing unit is further operative to associate the master node and the identified mobile user access device operating as the advertising ID node. In one embodiment, the node processing unit may associate the master node and the identified mobile user access device operating as the advertising ID node by being further operative to establish a passive association between the master node and the identified mobile user access device operating as the advertising ID node without requiring an authorized connection over the first communication interface between the master node and the identified mobile user access device operating as the advertising ID node. In another embodiment, the node processing unit may associate the master node and the identified mobile user access device operating as the advertising ID node by being further operative to establish an active association between the master node and the identified mobile user access device operating as the advertising ID node reflecting an authorized connection over the first communication interface between the master node and the identified mobile user access device operating as the advertising ID node. The node processing unit may, in even more detail, be operative to establish the active association by being further operative to (1) determine when the identified mobile user access device operating as the advertising ID node is connectable, (2) transmit an authorization request over the second communication interface to the server, and (3) receive an authorization response from the server over the second communication interface to allow the authorized connection between the master node and the identified mobile user access device operating as the advertising ID node. As such, the authorized connection may use the first communication interface to share information between the master node and the mobile user access device.

The node processing unit is operative to determine if a location of the identified mobile user access device operating as the advertising ID node is within a predetermined range of the pickup point. When the message being transmitted when the identified mobile user access device operating as the advertising ID node is determined to be within a predetermined range of the pickup point, the node processing unit is still further operative to transmit a message over the second communication interface to notify an order management system responsible for the order.

In another embodiment of the master node, the node processing unit may transmit the message over the second communication interface to notify the order management system by being further operative to transmit an intermediate message to the server to cause the server to notify the order management system that the identified mobile user device related to the order is approaching the pickup point to receive the order.

In still another embodiment, the node processing unit may be further operative to receive an order update message from the order management system over the second communication interface where the order update message reflects a status of the order. And the node processing unit may also be operative to transmit a pickup status message to the identified mobile user access device operating as the advertising ID node over the first communication interface, where the pickup status message informs the identified mobile user access device of the status of the order.

Managing Delivery Using Node Signatures

As described in several of the embodiments, a signal broadcast or advertised by an exemplary node in a wireless node network provides a type of signature for the node. This signature may be detected and applied in a variety of embodiments to facilitate, for example, package delivery and payment on delivery (also referred to as cost on delivery or COD). The example illustrated in FIG. 34D was previously discussed in terms of delivery notification as package 130 and ID node 120a approached master node 3445 associated with delivery point 3440. However, managing delivery to the intended recipient (such as a customer using mobile user access device 205) may be enhanced in an embodiment as described in more detail below when the recipient's mobile user access device 205 operates as a master node that detects the ID node 120a related to package 130 as device 205 gets close enough to ID node 120a.

Notably, FIG. 34D illustrates an embodiment where master node 3445 is in communication with server 100. As explained with reference to FIG. 41, the intended recipient may be notified of delivery of package 130 and related ID node 120a when the ID node 120 approaches a delivery point 3440 (such as a shipping area, loading dock, mail room, and the like). However, after mobile user access device 205 may be notified that the packaged item (and its related ID node 120a) is substantially near delivery point 3440, the intended recipient using mobile user access device 205 may approach the package 130 and ID node 120a as part of the delivery.

In this example, mobile user access device 205 may be functioning as an exemplary master node with a short-range communication path to ID node 120a and with a longer-range communication path to server 100. As previously explained above, an embodiment of device 205 may be implemented as a mobile user access devices (such as a smartphone) and may operate as an exemplary master node (such as master node 110*a* of FIG. 4) that communicates and associates with ID nodes and other master nodes, as described herein, and communicates with the server 100. In more detail, this may be accomplished with the processor in the user access device, peripheral circuitry coupled to the processor, and an app or other code executing in mobile user access device 205 as master control and management code 425 along with relevant master node related data (as explained in more detail in FIG. 4). The exemplary app or program module implementing master control and management code 425 on device 205 may leverage, for example, use of an existing Bluetooth® Low Energy (BLE) communication capability of the device 205 (e.g., a type of short range communication interface 480 for an exemplary master node 110*a*) in a format and manner as described herein as a master node (e.g., as explained in FIGS. 6-12). This allows device 205 to advertise signals having exemplary packet messages as short-range signals and associate (passively or actively in an authorized manner) with other nodes in the network (such as master node 3445 or ID node 120*a*).

FIG. 44 is a flow diagram illustrating an exemplary method for managing a delivery of an item being shipped using a wireless node network in accordance with an embodiment of the invention. Referring now to FIG. 44, method 4400 begins at step 4405 where the mobile user access device operative to function as the master node receives shipping information from the server. The shipping information is related to the item being shipped and includes an identification of the ID node related to the item being shipped. In the example of FIG. 34D, the exemplary shipping information is related to the item within package 130 and includes an identification of ID node 120*a* related to the item being shipped.

At step 4410, the mobile user access device operative to function as the master node detects a signal broadcast from the ID node as the ID node comes within a communication range of the mobile user access device operative to function as the master node. In one example, the signal is an advertising packet message transmitted from ID node 120*a*.

At step 4415, the method associates the ID node and the mobile user access device operating as the master node to acknowledge the delivery of the item and, at step 4420, the mobile user access device operating as the master node notifies the server with a notification about the acknowledged delivery.

In one embodiment, associating may comprise establishing a preauthorized connection between the ID node and the mobile user access device operating as the master node to acknowledge the delivery of the item. In more detail, establishing the preauthorized connection may be based upon a previously authorized acceptance condition that occurs automatically when the mobile user access device operating as the master node detects the signal broadcast as an advertising signal from the ID node. Thus, in one embodiment, the preauthorized connection may be automatically established (without the need for an prompted acknowledgement) as soon as the ID node's advertising signal is detected by the mobile user access device operating as the master node. However, in another embodiment, the preauthorized connection may be automatically established when the mobile user access device operating as the master node is located within a threshold distance from the ID node. The mobile user access device operating as the master node (device 205 in FIG. 34D) may periodically determine the location of ID node 120*a* relative to its own location as part of establishing the preauthorized connection.

In another embodiment, associating may comprise establishing a preauthorized connection between the ID node and the mobile user access device operating as the master node to acknowledge the delivery of the item for automatic payment on delivery purposes. In this embodiment, the method may also notify the server by the mobile user access device operating as the master node with a notification indicating the successfully established preauthorized connection. The mobile user access device operating as the master node may also instruct the server to complete a payment transaction related to the item being shipped at a rate charged lower than if an active prompted connection was established for payment on delivery purposes between the ID node and the mobile user access device operating as the master node. Thus, a COD customer may be able to create an acceptance condition (e.g., when the customer's mobile user access device operating as a master node receives a signal from the ID node related to the packaged item being shipped) that preauthorizes a connection and allows for a payment transaction for the item to be completed without some other kind acknowledgement or active feedback from the COD customer.

In another embodiment, associating may comprise establishing an active prompted connection between the ID node and the mobile user access device operating as the master node to acknowledge the delivery of the item after receiving a prompted acknowledgment of the delivery of the item. For example, rather than an automatic connection upon detecting the ID node's advertising signal, an active acknowledgement from the customer that ordered the item is needed to acknowledge delivery of the item.

In still another embodiment, associating may comprise establishing an active prompted connection for payment on delivery purposes between the ID node and the mobile user access device operating as the master node. And, as such, method may further include notifying the server by the mobile user access device operating as the master node. Here, the notification may indicate a successfully established active prompted connection for payment on delivery purposes and instruct the server to complete a payment transaction related to the item being shipped.

Those skilled in the art will appreciate that method 4400 as disclosed and explained above in various embodiments may be implemented on a node, such as an exemplary master node as illustrated in FIG. 4 and implemented as a type of mobile user access device, running one or more parts of a control and management code 425 to implement any of the above described functionality. Such code may be stored on a non-transitory computer-readable medium, such as memory storage 415 within an exemplary master node. Thus, when executing such code, a processing unit 400 within the respective master node may be operative to perform operations or steps from the exemplary methods disclosed above, including method 4400 and variations of that method.

In another embodiment, a system for managing a delivery of an item being shipped using a wireless node network may be used to perform similar steps. In more detail, the system comprises a server and a master node in communication with the server. The master node comprises a node processing unit and a node memory coupled to the node processing unit. The node memory maintaining code for execution by the node processing unit and shipping information related to the item being shipped. The shipping information comprises an identification of an ID node related to the item being shipped. With this information, the node processing unit is operative, when executing the code, to receive the shipping information from the server and maintain the shipping information on the node memory, and receive a signal detected by the first communication interface and broadcast from the ID node. The signal is detected as the ID node comes within a communication range of the first communication interface. The node processing unit is further operative to associate the ID node and the master node to acknowledge the delivery of the item, and transmit a message over the second communication interface to notify the server about the acknowledged delivery.

In a particular embodiment, the master node comprises a mobile user access device, such as a laptop computer, a tablet device, a personal area network device, a smartphone device, and a smart wearable device. More specifically, the master node is a mobile user access device operating as a master node.

In several different embodiments, the node processing unit is operative to associate the ID node and the master node in particular ways. In one example, the node processing unit may associate the ID node and the master node by being further operative to establish a preauthorized connection between the ID node and the master node to acknowledge the delivery of the item. In another example, the node processing unit may associate the ID node and the master node by being further operative to establish a preauthorized connection between the ID node and the master node to acknowledge the delivery of the item for automatic payment on delivery purposes. In still another example, the node processing unit may associate the ID node and the master node by being further operative to establish an active prompted connection between the ID node and the master node to acknowledge the delivery of the item after the master node receives input from a user of the master node, the input being a prompted acknowledgment of the delivery of the item. And in yet another example, the node processing unit may associate the ID node and the master node by being further operative to establish an active prompted connection for payment on delivery purposes between the ID node and the master node.

In still another embodiment, the node processing unit may be further operative to notify the server over the second communication interface where the notification indicates a successfully established active prompted connection for payment on delivery purposes. The notification may also instruct the server to complete a payment transaction related to the item being shipped.

Multi-Entity Management of Location Services

A node, for example an ID node, may have multiple distinct users (or more generally entities) each with a possible desire to independently administer the node and access its collected data. In such a situation, exemplary methods for managing hand-off and custodial chain of the node and its data may be helpful.

In the example shown in FIG. 17, for instance, essentially three entities are illustrated as managing ID node 120a—e.g., a sender as a first entity that operates user access device 200 during the preparation phase 1700, a shipping entity (e.g., FedEx) that operates or is related to various master nodes during the shipment or transit phase 1705, and a recipient as a third entity that operates user access device 205 during the possession phase 1710.

In a general embodiment, ID node 120a may start in possession of the sender, as shown in FIG. 17 during the preparation phase 1700. In this example, the sender's (shipping customer's) user access device 200 (e.g., a smartphone) also functions as a master node through at least one program module of code (e.g., an app, an application, or several interacting program modules operating as code 425) running on their device. This master node code communicates with the backend server 100, which has server-side software to help manage master-to-ID node associations (as discussed above regarding the server-side association manager program module in exemplary code 525).

In one example, the ID node 120a may have been associated with the master node (user access device 200) previously by a request issued from the sender's device 200 to the server 100 (via network 105) resulting in authorized access. This may give the holder of that authorization certain rights to the data to be collected and management of the ID node 120a. As will be explained in more detail below, exemplary authorizations provided by server 100 may include certain privileges that authorize such rights under particular circumstances and for particular types of information (e.g., paid for privileges, limited access privileges, access to data collected, access to location information, privileges to track an item associated with the ID node over time, etc.).

When the sender initiates shipment with a shipping entity, such as FedEx, and associates the ID node 120a with the shipment data, the initially granted privilege is transferred back to the shipping entity through the server 100, which instructs a likely first master node in the shipping entity's network to see the package 130 having ID node 120a to accept advertising messages from ID node 120a. For example, the master node may be part of a drop box (e.g., drop node 110a), a locker system and/or a handheld courier device (e.g., courier node 110b). When such a master node reports seeing the package 130 (e.g., by detecting an advertising signal from ID node 120a), the prior privilege for the sender's device 200 to directly access the ID node 120a is terminated. Active access to ID node 120a at that point remains limited to the shipping entity until the package is delivered to the recipient. When delivered to the recipient, their user access device 205 (e.g., another smartphone), running the master node software (such as code 425), can issue a request to the server 100 asking to take over control of the ID node. If the server grants the request to have such destination privileges based on particular conditions (e.g., payment, limited scope of control or access to data, etc.), the data associated with the ID node 120a after the transition of ownership is made available to the to the recipient user access device 205. If not granted, the data ownership and management for ID node 120a remains with the shipping entity.

In another embodiment, when an ID node is associated with an entity outside of the shipping entity (e.g., with the sender's user access device 200 or the recipient's user access device 205), the application on their device would allow for management of where the collected data should be stored. For example, the collected data in the ID node may only be visible to the entity outside of the shipping entity (via their master node operating device) and not uploaded to the server 100 unless directed to do so and allowed by server 100. Hosting of this data may be part of a service offered to the user by shipping entity that operates and manages server 100. Regardless of where data is held, for management functions, the ID node may still periodically communicate to the server 100 to check for updates of software and instructions.

FIGS. 64-66 are flow diagrams illustrating exemplary methods for multi-entity management of an ID node from various operational perspectives. In more detail, FIG. 64 is a flow diagram illustrating an exemplary method for multi-entity management of an ID node in a wireless node network in accordance with an embodiment of the invention from the perspective of exemplary ID node operations. Referring now to FIG. 64, method 6400 begins at step 6450 by associating the ID node with a first entity user access device. The first entity user access device is operating as a master node in the network (such as the previously described sender's device 200 operating as a master node). As such a master node, the first entity user access device is operative to communicate directly with a server in the network over a first (e.g., longer range) communication path and separately communicate with the ID node over a second (e.g., shorter range) communication path. And the ID node is operative to communicate directly with the first entity user access device over the second communication path but is unable to directly communicate with the server.

At step 6410, the ID node provides the associated first entity user access device with access to data collected by the ID node if authorized by an initial privilege, which was provided by the server to the first entity user access device. In one embodiment, the initial privilege may comprise a paid privilege to access the data collected by the ID node. For example, the sender may pay when obtaining ID node 120a to be able to access information related to the node as the node is used. In another embodiment, the initial privilege may comprise a paid privilege to be provided a location of the ID node. So for example, the sender may pay for a specific type of information, such as to be informed of the current location of the ID node 120a or the package 130 with the ID node 120a. In a further embodiment, the initial privilege may comprise a paid privilege to track an item associated with the ID node over time. And in the same example, the sender may pay for an even more specific service related to the data gathered and collected—namely, for a tracking service for the item packaged in package 130 related to ID node 120a.

Other options may allow the sender to customize how they want to store or maintain data collected by the ID node. In one embodiment, the initial privilege may comprise a privilege for the first entity user access device to manage where the data collected by the ID node is stored. In more detail, the initial privilege may comprise a paid privilege to have the data collected by the ID node uploaded to the first entity user access device over the second communication path. Thus, the data may be shared with the device operating as a master node. In a further embodiment, the initial privilege may comprise a paid privilege to have the data collected by the ID node also uploaded to the server from the first entity user access device over the first communication path.

At step 6415, the ID node is associated with a shipping entity master node in the network. For example, as shown in FIG. 17, ID node 120a may be associated with drop node 110a (a type of master node operated by a shipping entity, such as FedEx). While method 6400 includes the ID node changing custodial control to only one shipping entity master node, those skilled in the art will appreciate with reference to FIG. 17 that custodial control and handoff of ID node 120a may happen with several different shipping entity master nodes (e.g., courier node 110b, vehicle node 110c, facility node 110d, ULD node 110e, facility node 110f, delivery vehicle node 110g, and courier node 110h) before handoff to the recipient may occur for delivery.

At step 6420, the ID node provides the associated shipping entity master node with access to the data collected by the ID node based upon a transferred privilege, which is provided by the server to the shipping entity master node.

At step 6425, the ID node is associated with a second entity user access device. In another embodiment, method 6400 may have the ID node restricting the first entity user access device from directly accessing the data collected by the ID node after the ID node is associated with the shipping entity master node.

At step 6430, the ID node provides the associated second entity user access device with access to the data collected by the ID node if authorized by a destination privilege provided by the server to the second entity user access device. In one embodiment, the destination privilege may comprise a paid privilege to access any of the data collected by the ID node. In another embodiment, the destination privilege may comprise a paid privilege to access only a limited portion of the data connected by the ID node. For example, some of the data collected may not be of interest to the consumer, but some may be interesting and valued enough to cause a consumer to pay for even the limited portion of the data (e.g., specific types of data, only limited or periodic samples of certain data, only a summary of the data, etc.).

In a further embodiment, the data collected by the ID node while the ID node is associated with the shipping entity master may remain owned by the shipping entity related to the shipping entity master node when the second entity user access device is not authorized by the destination privilege. Thus, if rights to such data are not granted, the shipping entity may maintain ownership of the data and control of the ID node.

And in another embodiment, method 6400 may allow the ID node to request system updates (e.g., software updates for any code on the ID node) from the server by the ID node regardless of where the data collected by the ID node is stored.

Those skilled in the art will appreciate that method 6400 as disclosed and explained above in various embodiments may be implemented on an ID node (such as exemplary ID 120a as illustrated in FIGS. 3 and 17), running one or more parts of a control and management code (such as code 325) to implement any of the above described functionality. Such code may be stored on a non-transitory computer-readable medium (such as memory storage 315 in an exemplary ID node). Thus, when executing such code, a processing unit of the ID node (such as unit 300) may be operative to perform operations or steps from the exemplary methods disclosed above, including method 6400 and variations of that method.

FIG. 65 is a flow diagram illustrating an exemplary method for multi-entity management of an ID node in a wireless node network from the perspective of a shipping customer entity in accordance with an embodiment of the invention. Referring now to FIG. 65, method 6500 begins at step 6505 by executing a program module of code (such as master node control and management code 425) on a first entity user access device to enable operation of the first entity user access device as a master node. As such, the first entity user access device is operative to communicate directly with a server over a first communication path (as a master node) and separately communicate with the ID node over a second communication path (as a master node). And the ID node is operative to communicate directly with the first entity user access device over the second communication path but unable to directly communicate with the server.

At step 6510, method 6500 continues by transmitting a request to the server from the first entity user access device. The request is for an authorization to associate with the ID node and to provide an initial privilege related to data to be collected by the ID node. In one embodiment, the authorization and the initial privilege are separate data items, however in other items both are implemented as part of the authorization (e.g., the initial privilege may be at least one authorized task or privilege approved by the server to be performed between the master node and the ID node).

In one embodiment, the initial privilege may comprise a paid privilege or, in more detail, a paid privilege for access to the data collected by the ID node. Method 6500 may also include receiving, by the first entity user access device, a location of the ID node if authorized by the initial privilege. And method 6500 may further include receiving, by the first entity user access device, a tracking update on the ID node if authorized by the initial privilege.

At step 6515, method 6500 continues by receiving the authorization and the initial privilege from the server, and then associating the first entity user access device with the ID node at step 6520. At step 6525, method 6500 continues with the first entity user access device receiving data collected by the ID node if authorized by the initial privilege.

At step 6530, method 6500 concludes by managing the data collected by the ID node. For example, in one embodiment, the managing step may further comprise managing where the data collected by the ID node is maintained in accordance with the initial privilege. For instance, the initial privilege may allow the data collected by the ID node to be uploaded by the first entity user access device to the server over the first communication path.

Additionally, method 6500 may also include where the initial privilege no longer authorizes the first entity user access device to receive the data collected by the ID node once the ID node associates with a shipping entity master node.

Those skilled in the art will appreciate that method 6500 as disclosed and explained above in various embodiments may be implemented on a master node (such as exemplary master node 110a as illustrated in FIG. 4 when implemented with a sender's user access device, such as device 200 in FIG. 17), running one or more parts of a control and management code (such as code 425) to implement any of the above described functionality. Such code may be stored on a non-transitory computer-readable medium (such as memory storage 415 in an exemplary device 200 operating as a master node). Thus, when executing such code, a processing unit of the device (such as unit 400) may be operative to perform operations or steps from the exemplary methods disclosed above, including method 6500 and variations of that method.

FIG. 66 is a flow diagram illustrating an exemplary method for multi-entity management of an ID node in a wireless node network from the perspective of recipient entity in accordance with an embodiment of the invention. Referring now to FIG. 66, method 660 begins at step 6605 by executing a program module of code (such as code 425) on a recipient entity user access device to enable operation of the recipient entity user access device as a master node. As such, the recipient entity user access device is operative to communicate directly with a server over a first communication path (as a master node) and separately communicate with the ID node over a second communication path (as a master node). The ID node is operative to communicate directly with the recipient entity user access device over the second communication path but unable to directly communicate with the server.

At step 6610, method 6600 continues by transmitting a request to the server from the recipient user access device. The request is for an authorization to associate with the ID node and a destination privilege related to data to be collected by the ID node. In one embodiment, the authorization and the destination privilege are separate data items, however in other items both are implemented as part of the authorization (e.g., the destination privilege may be a specific authorized task or privilege approved by the server to be performed between the master node and the ID node).

In one embodiment, the destination privilege may comprise a paid privilege. In more detailed embodiment, the destination privilege may comprise a paid privilege to access only a limited portion of the data connected by the ID node. And in another embodiment, the destination privilege may allow the data collected by the ID node to be uploaded by the recipient user access device to the server over the first communication path.

At step 6615, method 660 continues by receiving the authorization and the destination privilege from the server. At step 6620, method 660 then associates the recipient user access device with the ID node. And at step 6625, method 6600 concludes with the recipient user access device receiving data collected by the ID node if authorized by the destination privilege.

In a further embodiment, method 660 may have management of the data collected by the ID node to be limited to the server if the data collected by the ID node is not authorized to be received by the recipient user access device under the destination privilege.

Those skilled in the art will appreciate that method 6600 as disclosed and explained above in various embodiments may be implemented on a master node (such as exemplary master node 110a as illustrated in FIG. 4 when implemented with a recipient's user access device, such as device 205 in FIG. 17), running one or more parts of a control and management code (such as code 425) to implement any of the above described functionality. Such code may be stored on a non-transitory computer-readable medium (such as memory storage 415 in an exemplary device 200 operating as a master node). Thus, when executing such code, a processing unit of the device (such as unit 400) may be operative to perform operations or steps from the exemplary methods disclosed above, including method 6600 and variations of that method.

An ID node managed by multiple entities using a wireless node network is described in another embodiment. The ID node comprises at least a node processing unit, a node memory coupled to the processing unit, and a short-range communication interface coupled to the node processing unit. The node memory maintains code for execution by the processing unit and data collected by the ID node during operations of the node. And the short-range communication interface is operative to directly communicate with a master node in the network over a short-range communication path but unable to directly communicate with a server in the network.

The node processing unit of the ID node, when executing the code maintained on the node memory, is operative to associate the ID node with a first entity user access device, where the first entity user access device operates as the master node and can communicate directly with the server over a longer range communication path and separately communicate with the ID node over the short-range communication path.

The node processing unit is also operative to provide the first entity user access device with access to the data collected by the ID node if authorized by an initial privilege, which was provided by the server to the first entity user access device. In one embodiment, the initial privilege may comprise a paid privilege to access the data collected by the ID node. In another embodiment, the initial privilege may comprise a paid privilege to be provided a location of the ID node. In yet another embodiment, the initial privilege may comprise a paid privilege to track an item associated with the ID node over time.

In still another embodiment, the initial privilege may be related to managing the data collected. For example, one embodiment of the initial privilege may comprise a privilege for the first entity user access device to manage where the data collected by the ID node is stored, such as uploaded from the node memory to the first entity user access device over the short-range communication path via the short-range communication interface. In another embodiment, the initial privilege may comprise a privilege to have the data collected by the ID node uploaded to the server from the first entity user access device over the longer range communication path.

The node processing unit is also operative to associate the ID node with a shipping entity master node in the network. In one embodiment, the node processing unit may be further operative to restrict the first entity user access device from directly accessing the node memory for the data collected by the ID node after the ID node is associated with the shipping entity master node.

The node processing unit is operative to provide the associated shipping entity master node with access to the data collected by the ID node based upon a transferred privilege, which was provided by the server to the shipping entity master node. The node processing unit is then operative to associate the ID node with a second entity user access device, where the second entity user access device operates as another master node and can communicate directly with the server over the longer range communication path and separately communicate with the ID node over the short-range communication path.

And finally, the node processing unit is also operative to provide the associated second entity user access device with access to the data collected by the ID node if authorized by a destination privilege provided by the server to the second entity user access device. In one embodiment, the destination privilege may comprise a paid privilege to access any of the data collected by the ID node. In another embodiment, the destination privilege may comprise a paid privilege to access only a limited portion of the data connected by the ID node. And in still another embodiment, the data collected by the ID node while the ID node is associated with the shipping entity master remains owned by a shipping entity related to the shipping entity master node when the second entity user access device is not authorized by the destination privilege.

In a further embodiment, the node processing unit may also be further operative to request a system update regardless of where the data collected by the ID node is stored.

Dynamic Node Adaption within a Wireless Node Network

As noted in the logistics examples described above, an embodiment of a node may operate in different ways depending upon its desired application. For example, a master node may have different operating modes—one that is typically a default or normal operating mode where it is able to locate itself and operate as a higher level node in the wireless node network. However, under certain circumstances, an exemplary master node may change to an alternative operating mode and essentially function similar to a lower level node in the wireless node network. This may happen on a temporary basis when an environmental change is detected, such as when the master node loses GPS signal lock and can no longer detect location signals with which to determine its own location. Rather than simply go inoperative, an embodiment of a master node advantageously alters its operating mode to a temporary ID node mode, and continues operations within the wireless network as a non-locating type of master node (e.g., it may be able to still communicate with the server but is unable to self-locate). Thus, an embodiment may allow a master node that becomes "lost" due to environmental circumstances to remain functional in the network, associate with other nodes, help transfer shared data through connections with other nodes, and revert back to its normal operation when the master node is able to locate itself again.

As previously noted, exemplary master nodes 110a, 110b, 110c illustrated in FIG. 2 are deployed and connected to network 105 (and by virtue of those respective connections, to server 100) as well as to each other. ID nodes 120a, 120b, 120e are connected to various master nodes. However, ID nodes 120c and 120d are shown in FIG. 2 connected to ID node 120b but not to any of the master nodes. This may be the case if ID nodes 120b, 120c, 120d are associated with different items (e.g., packages) within a larger container 210 (or grouped together on a pallet). In such an embodiment, only ID node 120b remains within the wireless communication range of any master node. However, in one embodiment, ID node 120b may actually be a different master node that, because it is placed within container 210 and shielded from receiving location signals, is operating in an alternative mode to function temporarily as an ID node (e.g., ID node 120b shown in FIG. 2). While the master node (operating as ID node 120b) remains in container 210, it may be unable to operate as a master node and may operate as an ID node (a master node operating in a temporary ID node mode) that can remain in a communication relationship with ID nodes 120c and 120d. After changing operational modes, node 120b (the master node operating in a temporary ID node mode) may associate with another master node (such as master node 110b) and forward information from ID nodes 120c, 120d. But after being removed from within container 210, node 120b may revert back to the normal operating mode of a master node.

FIGS. 20 and 21 are flow diagrams illustrating various exemplary methods for dynamically changing an operational mode of node operations in a wireless node network. Those skilled in the art will appreciate that each of these exemplary methods for dynamically changing a configuration of one or more nodes in a wireless node network may be implemented by instructions stored on a non-transitory computer-readable medium, which when executed perform the steps of the respective method.

Referring now to FIG. 20, exemplary method 2000 begins at step 2005 where a first of the master nodes detects an environmental change related to a first of the master nodes (e.g., no longer being able to receive a location signal). In a more detailed example, the environmental change may be when at least the first of the master nodes is within a container that substantially impedes reception of the location signal by the first of the master nodes. In other words, the first master node may no longer be able to determine its own location because of a change in the surrounding environment, such as materials near or around the master node or building structure that acts as a shield to prevent or operatively impair reception of location signals (e.g., GPS signals).

In a further example, the environmental change may be an anticipated environmental change related to the first of the master nodes. For example, the server may notify the first of the master nodes that it is about to be placed within a container. Thus, the first of the master nodes becomes aware of the upcoming environmental change and may include steps to complete urgent tasks (e.g., sharing of data, completing locating tasks, etc.) prior to the experiencing the different environmental.

In response to detecting the environmental change, the method 2000 has the first of the master nodes changing its operational mode to a temporary ID node mode where the first of the master nodes no longer can self-determine its location at step 2010. In one embodiment, the temporary ID node mode may have the first of the master node performing all normal operations of an exemplary higher level node in the network (compared with the ID node) that do not rely upon self-determined locations. For example, the master node operating in the temporary ID node mode may be able to communicate with the server while not being able to self-locate like a normal master node. In another embodiment, the temporary ID node mode may have the first of the master nodes operating in a more limited way so as to mimic an ID node (e.g., with an altered signature to broadcast when advertising) so that other master nodes will believe the master node operating in the temporary ID node mode is an ID node for purposes of associating (passive or active).

And in a further embodiment, the first of the master nodes may be operating in the temporary ID node mode while remaining in a communication relationship with at least one ID node. Thus, for example, when a master node is placed in an adverse RF environment and loses reception of its location signals, the master node may remain associated (e.g., an active authorized connection) with this ID node.

At step 2015, method 2000 continues by notifying the server by the first of the master nodes that the first of the master nodes is operating in the temporary ID node mode. And at step 2020, method 200 concludes by associating the first of the master nodes operating in the temporary ID node mode with a second of the master nodes. Such associating may be accomplished by the first of the master nodes advertise to the second of the master nodes regarding a request to connect with the second of the master nodes, receiving a response from the second of the master nodes, and sending a reply to the second of the master nodes with information requested.

Method 2000 may further include forwarding information (e.g., sensor data) gathered by the ID node to the second of the master nodes via the first master node operating in the temporary ID node mode. In more detail, the master node operating in the temporary ID node mode may provide extended visibility to other ID nodes (e.g., ID nodes 120c and 120d within container 210) and relay or forward information from those ID nodes not in direct contact with the second master node (and thus the server).

Additionally, method 2000 may also include changing the operational mode for the first of the master nodes to a normal operational mode upon detecting a second environmental change related to the first of the master nodes, the normal operational mode being where the first of the master nodes can self-determine its location again. Thus, the first of the master nodes may adapt and still be useful in the wireless node network when an environmental change limits certain functionality of the master node (e.g., its self-locating ability) until the environment related to the master node changes again and that functionality is no longer limited.

Those skilled in the art will appreciate that method 2000 as disclosed and explained above in various embodiments may be implemented on an exemplary master node, such as master node 110a illustrated in FIG. 4, running one or more parts of master control and management code 425 to implement any of the above described functionality. Such code may be stored on a non-transitory computer-readable medium such as memory storage 415 on a master node (such as master node 110a). Thus, when executing code 425, the master node's processing unit 400 may be operative to perform operations or steps from the exemplary methods disclosed above, including method 2000 and variations of that method.

While FIG. 20 illustrates exemplary steps from method 2000 from the perspective of master node actions and steps, FIG. 21 illustrates and provides an explanation of an exemplary embodiment where a method for managing a dynamically changing operational mode of node operations in a wireless node network may occur from the perspective of server actions. Referring now to FIG. 21, exemplary method 2100 begins at step 2105 by receiving a notification by the server from a first of the master nodes reporting an environmental change related to the first of the master nodes. In one example, the environmental change may be an anticipated environmental change related to the first of the master nodes. In more detail, the anticipated environmental change may comprise, for example, an adverse RF environment anticipated to be exposed to the first of the master nodes (such when the first of the master nodes is anticipated to be moved within a container, such as a ULD, that may impede reception of a location signal (such as a GPS signal) by the first of the master nodes).

In another embodiment, method 2100 may also have the server updating context data consistent with the environmental change. For example, when the first master node is placed in the ULD and it loses reception of GPS signals, the server updates relevant types of context data to reflect this environmental change related to the first master node.

At step 2110, method 2100 continues by recording a logical change of the first of the master nodes to be operating in a temporary ID node mode as a result of the environmental change. For example, the logical change essentially has the first master node temporarily operating in the temporary ID node mode with ID node like features as a result of, for example, a detected lack of location signal reception (e.g., GPS signal loss), being exposed to an adverse RF environment that impedes reception of a location signal, being in a container that shields an interior of the container from reception of the location signal, being in a shielded structure (e.g., indoors within a building where GPS signals are difficult to pick up), and being substantially near shielding material (e.g., being placed next to metal objects that may adversely interfere with RF signal reception). In another embodiment, the temporary ID node mode may be characterized as still allowing the first of the master nodes to communicate with the server while no longer being able to self-determine its location.

At step 2115, method 2100 concludes by authorizing the first of the master nodes operating in the temporary ID node mode to associate with a second of the master nodes. In an airborne example, the second master node may be a dedicated master node within an aircraft that has location circuitry and an antenna on the outside of the aircraft so that it maintains GPS signal lock yet allows the second master node to communicate with nodes inside onboard containers (e.g., the first master node that is operating in the temporary ID node mode as a result of its inability to detect GPS signals within the container). In one example, method 2100 may also include receiving information (e.g., sensor data gathered by a node or other shared data) from the second of the master nodes as forwarded information from the first of the master nodes when operating in the temporary ID node mode In another embodiment, method 2100 may also include recording another logical change of the first of the master nodes back to a normal operational mode as a result of a second environmental change related to the first of the master nodes. For example, the first of the master nodes may now be removed from being within a ULD container. As a result, the first of the master nodes may adaptively change back to its normal operational mode where it can self-determine its location again.

Those skilled in the art will appreciate that method 2100 as disclosed and explained above in various embodiments may be implemented on an exemplary server, such as server 100 illustrated in FIG. 5, running one or more parts of server control and management code 525 to implement any of the above described functionality. Such code may be stored on a non-transitory computer-readable medium such as memory storage 515 on a server (such as server 100). Thus, when executing code 525, the server's processing unit 500 may be operative to perform operations or steps from the exemplary methods disclosed above, including method 2100 and variations of that method.

Similar to such exemplary methods, an exemplary dynamically configurable wireless node network is disclosed. The exemplary network comprises a plurality of master nodes and a server in communication with the master nodes. The master nodes include at least a first master node and a second master node. Each of the master nodes is a higher complexity node (compared with an ID node) and has a normal operating mode where the respective master node is operative to determine its own position (amongst other functions). The master nodes also have a temporary ID node mode where the respective master node is no longer operative to determine its own position.

The first master node is operative to detect an environmental change related to the first master node and temporarily alter a current operating mode of the first master node from the normal operating mode to the temporary ID node mode. The second master node, when operating in the normal operating mode, is operative to associate with the first master node when the first master node is operating in the temporary ID node mode. In a further embodiment, the first master node operating in the temporary ID node mode may be further operative to return to functioning as the first master node in the normal operating mode upon detecting a second environmental change. The second environmental change may be when the first master node receives a location signal to allow the first master node to determine its own location and return to functioning as the first master node in the normal operating mode. In yet another embodiment, the first master node may also be operative, when operating in the temporary ID node mode, to receive sensor information and forward the sensor information to the second master node. This sensor information may be sensor data received from an ID node that remained in communication with the first master node, even after the first master node changed to operating in the temporary ID node mode.

In one embodiment, the server may be operative to receive a notification from the first master node reporting the environmental change, record a logical change of the first master node to be operating in the temporary ID node mode, and authorize the second master node to associate with the first master node when the first master node is operating in the temporary ID node mode. For example, the server may upon receipt of the notification and recording the logical change, instruct other master nodes to recognize a signature or identification of the first master node as a type of ID node for purposes of node management, association, location determination, and sharing of information.

In another embodiment, the environmental change comprises an inability of the first master node to sufficiently receive and determine a position based upon a location signal (such as a GPS signal). In more detail, the environmental change may further comprise the first master node being exposed to an adverse RF environment (such as being placed near shielding material) that impedes reception of the location signal by the first master node.

Figure 95:
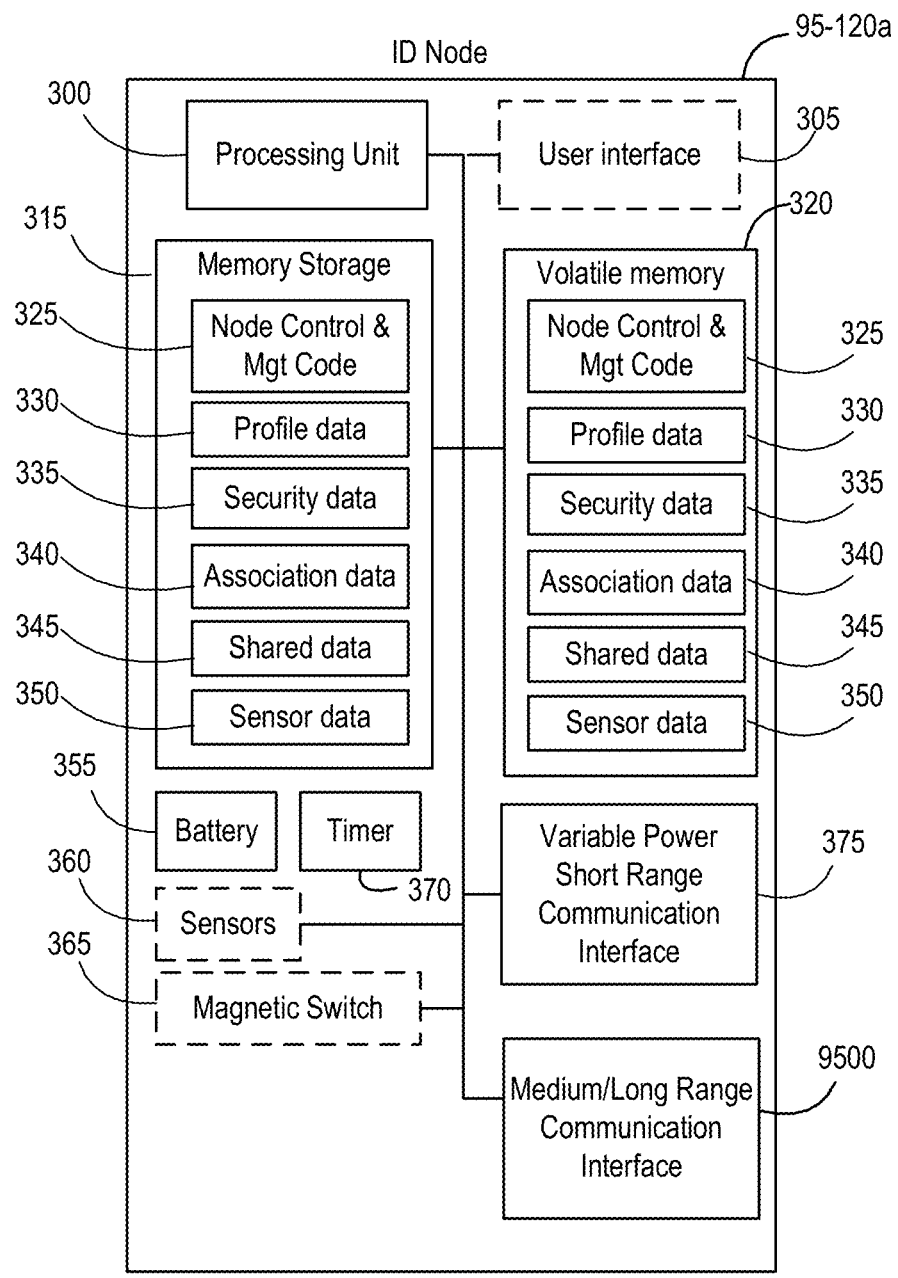
FIG. 95 is a diagram illustrating an exemplary ID node device adapted to operate in a pseudo master node mode in accordance with an embodiment of the invention.
Figure 96:
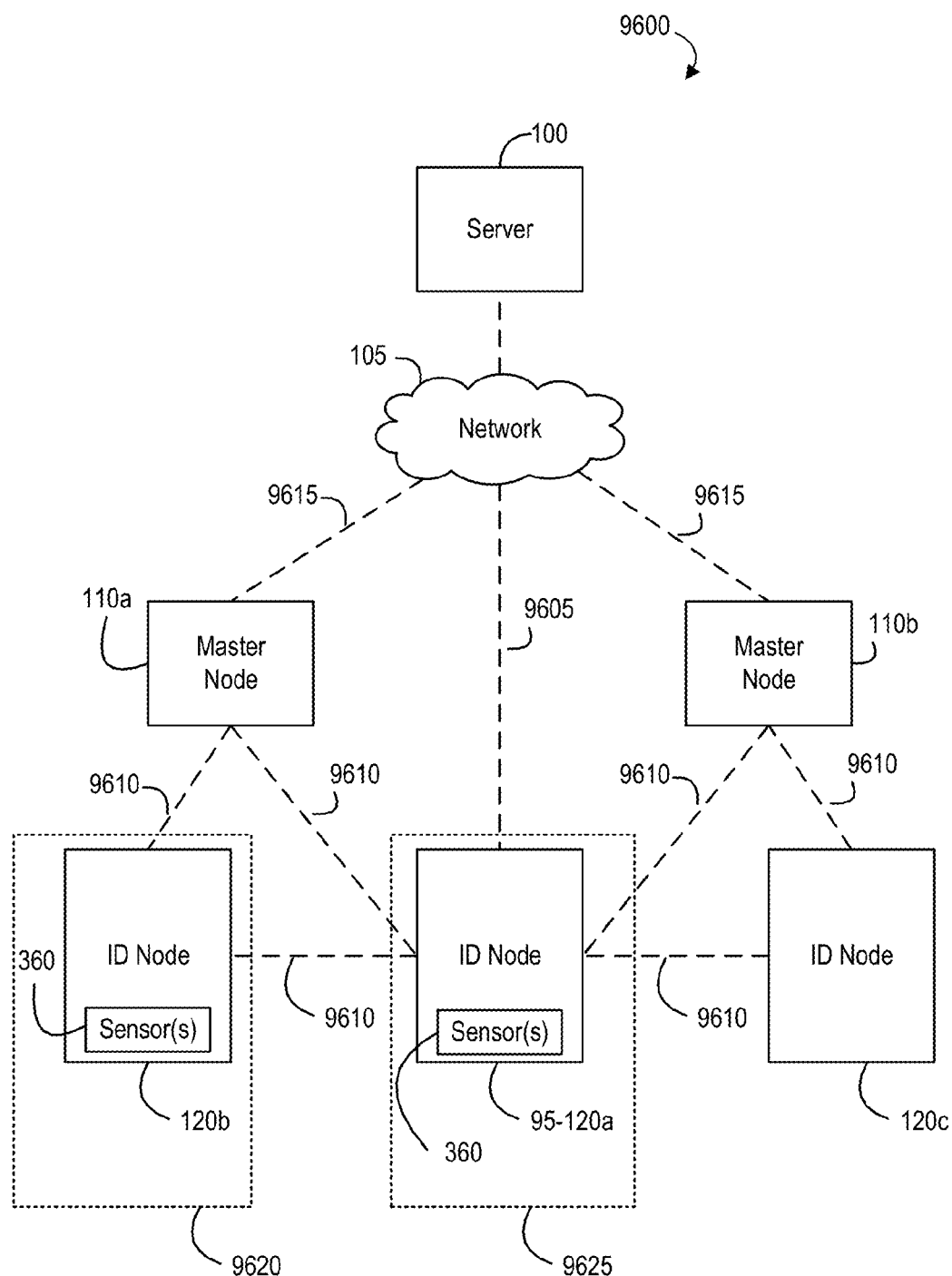
FIG. 96 is a diagram illustrating an exemplary hierarchical wireless node network in accordance with an embodiment of the invention.
Figure 97:
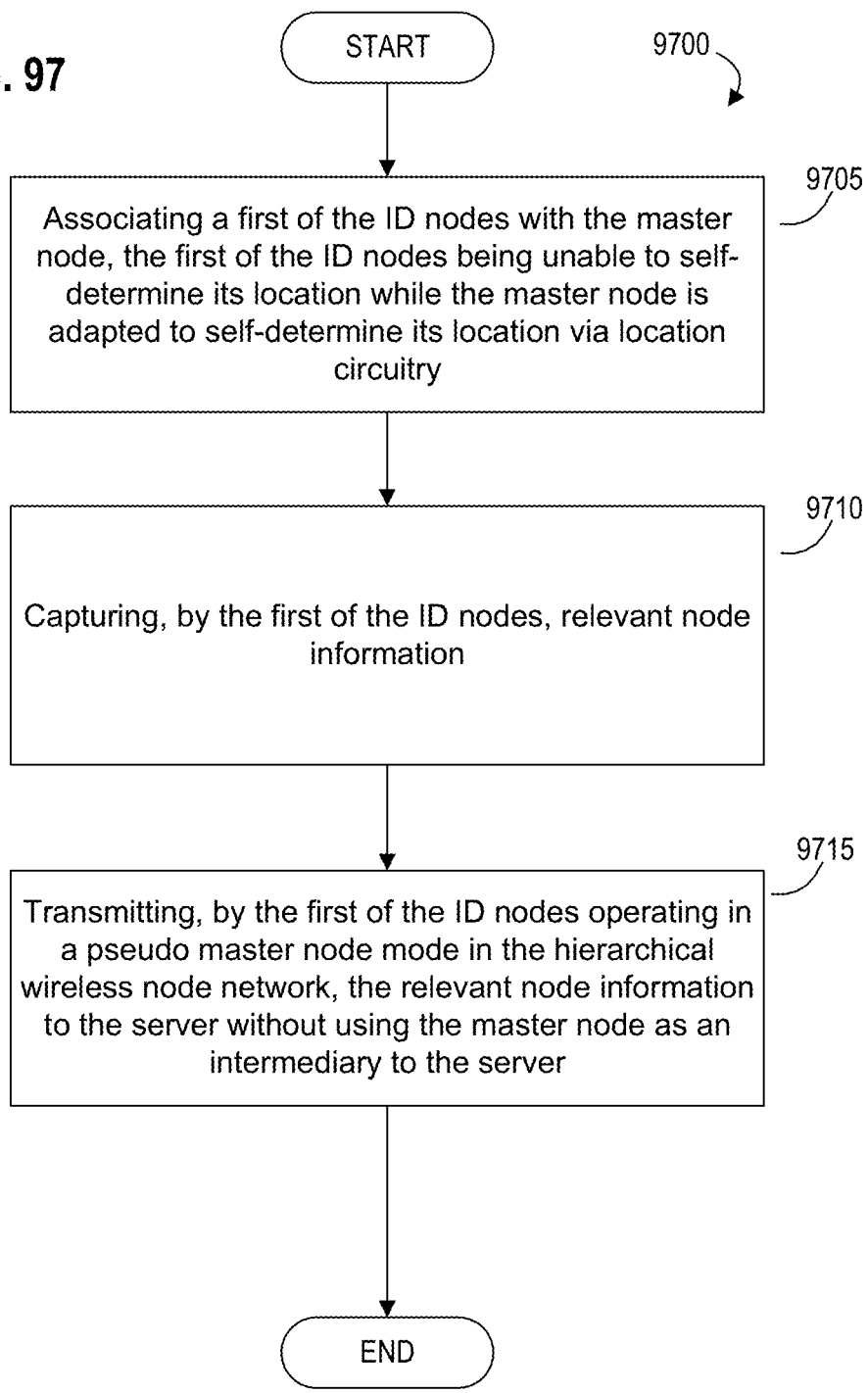
FIG. 97 is a flow diagram illustrating an exemplary method for node communication within a hierarchical wireless node network in accordance with an embodiment of the invention.

While the above examples relative to FIGS. 20 and 21 describe embodiments where a master node may operate in a temporary ID node mode depending upon its desired application, FIGS. 95-97 describe additional embodiments where an ID node may be adapted to operate in a different mode, such as a pseudo master node mode that avoids the need for an ID node to communicate through an intermediary node when messaging the server. For example, an ID node may typically operate in a default or normal operating mode where it is unable to self-determine its location as well as limit direct communication to a short range communication path (e.g., Bluetooth®). However, in some situations, the ID node may be adapted and operative to communicate on other communication paths, such as a longer range communication path directly to the server without the need for an intermediary node (e.g., a master node) when desiring to forward information from the ID node to the server. Additionally, while the ID node in such a pseudo master node mode may still be limited in its inability to self-determine location (e.g., the ID node would remain without location circuitry, such as GPS circuitry), such an ID node may provide master node like connectivity for other ID nodes in the network in order to enhance the ability to report on relevant node information from one or more ID nodes to the server. Further, while the pseudo master node may not have the ability to self-determine location absent input from other nodes in one exemplary embodiment, such a pseudo master node may still be aware of what nodes are in its proximity.

FIG. 95 is a diagram illustrating an exemplary ID node device similar to ID node 120*a* shown in FIG. 3, but further adapted to operate in a pseudo master node mode in accordance with an embodiment of the invention. Referring now to FIG. 95, exemplary ID node 95-120*a* is shown the same as illustrated in FIG. 3 but with an additional communication interface 9500 (e.g., an LTE radio using Internet Protocol version 6 or IPv6), which enables the ID node 95-120*a* to send and receive messages over a medium/long range communication path (e.g., a WiFi path to the Internet) rather than have to rely solely upon a shorter range communication path (e.g., a Bluetooth® formatted short range path). In this embodiment, the specially adapted ID node 95-120*a* may thus be operative to report relevant node information (such as sensor data) to a server in a wireless node network in a much more efficient manner. In other words, when deployed as part of an exemplary hierarchical wireless node network of ID nodes, master nodes, and a server, the specially adapted ID node 95-120*a* may enable a more robust yet more economical solution for node communication without the need for relying on intermediary nodes (such as a master node) for such communication purposes.

FIG. 96 is a diagram illustrating such an exemplary hierarchical wireless node network in accordance with an embodiment of the invention. Referring now to FIG. 96, exemplary hierarchical wireless node network 9600 is illustrated having three different levels of network devices. Generally, a first level includes ID nodes (more basic and less costly network node devices), a next level up includes master nodes (more sophisticated with the ability to self-locate using dedicated positioning or location circuitry onboard the node), and then a top level that includes a more sophisticated server. Normally, devices in each level can communicate with those devices in the next level above or below in the hierarchy. However, when an ID node is adapted to operate in a pseudo master node mode by having the ability to also communicate with a server, it effectively bypasses the need to have a master node in an intermediary role and, at times, can provide more efficient communication back to the server.

In more detail, on a first level of the exemplary hierarchical wireless node network 9600, FIG. 96 shows multiple ID nodes, such as ID node 120*b*, ID node 120*c*, and ID node 95-120*a*. While ID node 120*c* is not shown associated with a particular package, ID node 120*c* and ID node 95-120*a* are respectively shown disposed within packages 9620 and 9625. Additionally in this embodiment, while ID node 120*c* is shown not having sensors, ID nodes 120*b* and 95-120*a* each include a respective set of sensors 360 similar to those described with respect to FIG. 3. The sensors 360 (e.g., temperature, light, or moisture sensors) typically generate sensor data (e.g., sensor data 350) in operation. As such, the sensor data may be related to at least one condition of the respective packages. Such sensor data is a type of relevant node information that may be useful to quickly have available at the backend server (e.g., server 100).

In the same example shown in FIG. 96, a second level of the network 9600 is populated with at least one master node (such as master nodes 110a and 110b). As shown in FIG. 4, such a master node may include specific location circuitry (such as GPS circuitry 475) with which to self-determine its location. In other words, a master node can determine its own position without reliance on input from other network nodes. And additionally, as discussed in more detail above, these master nodes are adapted and operative to associate with ID nodes that are within a communication range of the respective master nodes.

And in the example shown in FIG. 96, a third level of the network 9600 is populated with a server, such as server 100. FIG. 5 and the textual description accompanying FIG. 5 above provides more detail on such a server. As shown in FIG. 96, server 100 may communicated with other nodes in the network 9600 over network 105.

In operation, an embodiment of network 9600 allows for robust communication between the network devices shown in FIG. 96 and described above. In one embodiment, ID node 95-120a is adapted and operative to perform certain functions related to node communication as it is disposed within such a network 9600. In more detail, ID node 95-120a is adapted and operative to associate itself with master node 110a. Doing so allows for ID node 95-120a to determine its location with help from master node 110a using one of the node locationing techniques described herein. Thus, ID node 95-120a is unable to self-determine its location.

ID node 95-120a may also be adapted and operative to capture relevant node information. In a general embodiment, relevant node information may be information generated or gathered by a node in the network 9600 where the information is related to operations of the network or items associated with the network (such as packages in transit that are associated with and monitored with sensors in certain nodes). In more detail, the relevant node information in an embodiment may comprise at least one of profile data, security data, association data, shared data, and sensor data. Examples of such profile data, security data, association data, shared data, and sensor data are respectively described above relative to FIGS. 3 and 95, which include profile data 330, security data 335, association data 340, shared data 345, and sensor data 350 as examples of relevant node information.

Such relevant node information may be captured directly by ID node 95-120a or more indirectly by another node that provides such information to ID node 95-120a. For example, ID node 95-120a may capture relevant node information using sensors 360 onboard ID node 95-120a. Such sensors 360 in node 95-120a may detect information related to package a condition of package 9625.

In another example, ID node 95-120a may associate with another ID node 120b (e.g., via passive association or active association) and receive other relevant node information from the other ID node 120b over a short range communication path 9610 (e.g., Bluetooth® radio path). In this way, ID node 95-120a may capture the other relevant node information from a broadcast signal originating from ID node 120b. Such other relevant node information may include information about the condition of package 9620.

ID node 95-120a may also be adapted and operative to transmit, in a pseudo master node mode, the relevant node information to the server 100 without using a master node (e.g., master nodes 110a, 110b) as an intermediary to the server 100. Those skilled in the art will appreciate that arming the master nodes in a wireless node network may have advantages when consolidating and managing communications with the server in the network, but that deploying an ID node at a lower level that can communicate with the server directly (i.e., without using a master node as an intermediary network device or node in communications with the server) may also allow for situations where a master node may be temporarily offline, out of communication range to the ID node, or when the relevant node information may be more efficiently sent to the server directly. Accordingly, an exemplary pseudo master node mode for an ID node is a mode of operation that enables such direct communications to the server (as a master node normally does) but advantageously does not require the ID node to self-determine its location or position (which would otherwise require dedicated location circuitry onboard the ID node). Thus, such an ID node as ID node 95-120a operates like a typical master node with respect to its ability to communicate with the server but still operates like a typical ID node with respect to self-locating.

In a more detailed embodiment, ID node 95-120a may be adapted and operative to transmit such relevant node information by generating a message for the server and then broadcasting the message on a longer range communication path. In this embodiment, the message includes the relevant node information and is formatted for the longer range communication path (such as a longer range WiFi path) when compared to a shorter range communication path (such as a short range Bluetooth® path) used to communicate between the ID nodes. Broadcasting the message on the longer range communication path to the server 100 can be done while avoiding the need to first send the message to a master node (such as master node 110a or 110b) during transit to the server 100.

In still another detailed embodiment, ID node 95-120a may be adapted and operative to transmit such relevant node information by first determining a desired communication path for a message including the relevant node information. The desired communication path may be either a first communication path or a second communication path. The first communication path includes one of the master nodes (such as master node 110a or master node 110b) operating as an intermediary to the server 100, while the second communication path does not include and avoids the need for a master node operating as an intermediary to the server 100.

In this other detailed embodiment, ID node 95-120a may be further adapted and operative to transmit such relevant node information by then formatting the message for the server and broadcasting it. In this embodiment, the format of the message is one suitable for broadcasting on the determined desired communication path. Thus, when broadcasting the message on the second communication path to the server, such broadcasting may avoid the need to first send the message to the master node during transit to the server.

FIG. 97 is a flow diagram illustrating an exemplary method for enhanced node communication within a hierarchical wireless node network having a plurality of ID nodes on a first level, a master node on a second level, and a server at a third level in accordance with an embodiment of the invention. Referring now to FIG. 97, method 9700 begins at step 9705 by associating a first of the ID nodes with the master node. The first ID node is unable to self-determine its location while the master node is adapted to self-determine its location via location circuitry.

Method 9700 continues at step 9710 with the first ID node capturing relevant node information. As described above with respect to FIG. 96, an embodiment may have the relevant node information comprising at least one of profile data, security data, association data, shared data, and sensor data. In more detail, the sensor data may comprise data collected from one or more sensors in communication with the first of the ID nodes. For example, the sensor data may include temperature and moisture data collected from sensors 360 operatively coupled through interfacing and buffering circuitry onboard ID node 95-120a as shown in FIG. 96. As such, the data collected from the one or more sensors may relate to one or more conditions of a package 9625 associated with the first ID node (i.e., ID node 95-120a).

In a further embodiment of method 9700, the capturing step may further comprise the first ID node capturing the relevant node information from a broadcast originating from a second of the ID nodes associated with the first of the ID nodes. As such, the sensor data may include data collected from one or more sensors in communication with the second of the ID nodes. For example, the sensor data may include temperature data collected from sensors 360 operatively coupled through interfacing and buffering circuitry onboard ID node 120b (as a second ID node) as shown in FIG. 96. As such, the data collected from the one or more sensors may relate to one or more conditions of a package 9620 associated with the second ID node (i.e., ID node 120b).

Method 9700 concludes at step 9715 with the first ID node operating in a pseudo master node mode in the hierarchical wireless node network to transmit the relevant node information to the server without using the master node as an intermediary to the server. As previously noted, this may be advantageous to exclude the master node as an intermediary in some circumstances where speed is more important or access to a master node may be somewhat impaired.

In a further embodiment of method 9700, the transmitting step may be implemented with the first ID node generating a message for the server and broadcasting the message to the server. The message may include the relevant node information and be formatted for a longer range communication path when compared to a shorter range communication path used to communicate between the ID nodes. The message may be broadcast by the first ID node on the longer range communication path to the server while advantageously avoiding the need to first send the message to the master node during transit to the server.

In yet another more detailed embodiment of method 9700, the transmitting step may have the first ID node determining a desired communication path for a message including the relevant node information. The desired communication path may include one of a first communication path and a second communication path, where the first communication path includes the master node operating as a communication intermediary to the server. In contrast, the second communication path would not include the master node operating as the intermediary to the server. Next, the ID node formats the message for the server according to the desired communication path and then broadcasts the message on the desired communication path to the server while avoiding the need to first send the message to the master node during transit to the server when the desired communication path is the second communication path.

Those skilled in the art will appreciate that method 9700 as disclosed and explained above in various embodiments may be implemented on an ID node (such as exemplary ID node 95-120a as illustrated in FIGS. 95-96) running one or more parts of a control and management code (such as code 325) to implement any of the above described functionality. Such code may be stored on a non-transitory computer-readable medium (such as memory storage 315 in an exemplary ID node). Thus, when executing such code, a processing unit of the node (such as unit 300) may be operative to perform the method and various steps as disclosed above.

In still another series of embodiments, a node may have the ability to adaptively change or alter its advertising message format as a way of enhancing system operations within a wireless node network. Embodiments may change the message format to one of various different types of shortened formats (i.e., also called a variable broadcast format) depending upon, for example, a desired degree of change from a full-format that provides a larger amount of information balanced against a shortened format that may specifically identify the broadcasting node to certain other nodes with less information broadcasted.

In particular, FIGS. 98A-98C, FIG. 99, and FIG. 100 describe additional embodiments where an exemplary node (e.g., an ID node or master node) may change its advertising message broadcast format when the node changes state, such as when a change in the relative environment of the node is detected. In general, once such a changed state is detected (e.g., a change in node density near the node or a change in how the node may be moving), the node may be adapted to communicate in a different or alternative format, such as a shortened or truncated format when compared to an initial or first format for the advertising message. By dynamically altering how the node formats an advertising message depending upon changes in the relative environment of the node, the node allows for more compact and efficient communication in the wireless node network within which the node operates and enhanced system operation. More particularly, embodiments of such a dynamic altering of node advertising message format may allow for shorter communication bursts, which accommodates system operations when there is a relatively high density of nodes operating in a given area.

Those skilled in the art will appreciate that an embodiment may have the node detecting a state change and then, in response, altering its advertising message broadcast format by itself, while other embodiments may have the broadcasting node (e.g., an ID node) receiving a control or command message from another node (e.g., a master node) that causes the broadcasting node to change or alter its advertising message broadcast format to a type of shortened format (e.g., a global shortened format, a nested shortened format, or a local shortened format).

Figure 98A:
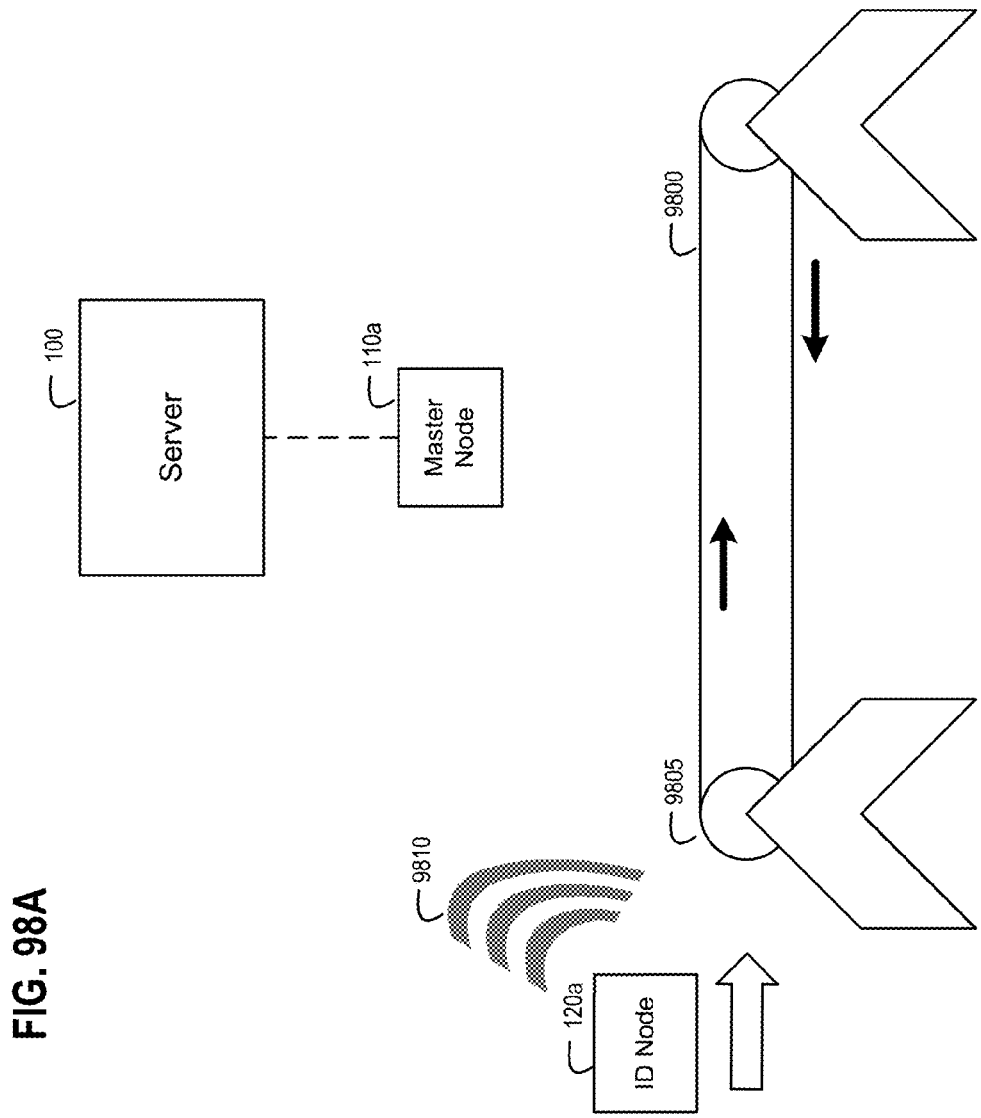
FIGS. 98A-98C are a series of diagrams illustrating various configurations of an exemplary node as it adaptively alters how it formats a broadcasted advertising message in response to detected state changes for the node in accordance with an embodiment of the invention.
Figure 98B:
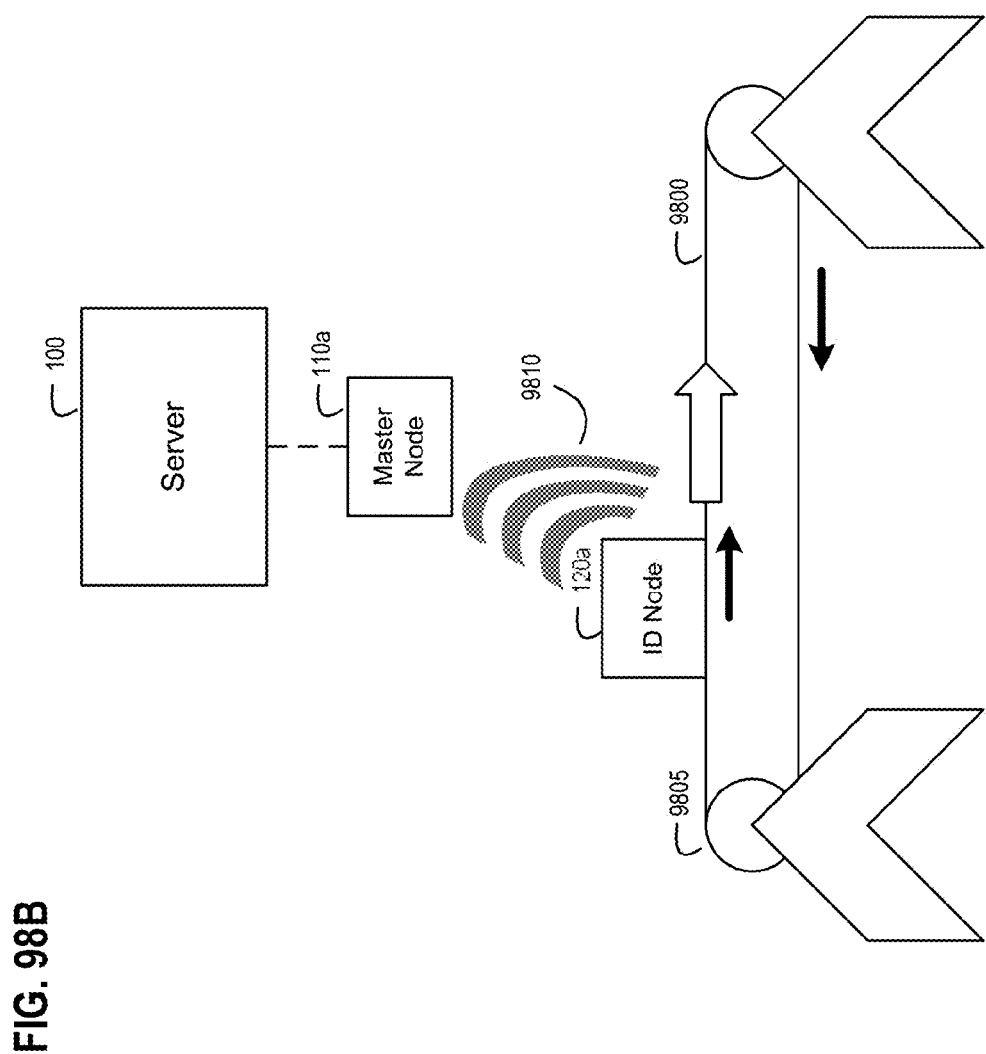
Figure 98C:
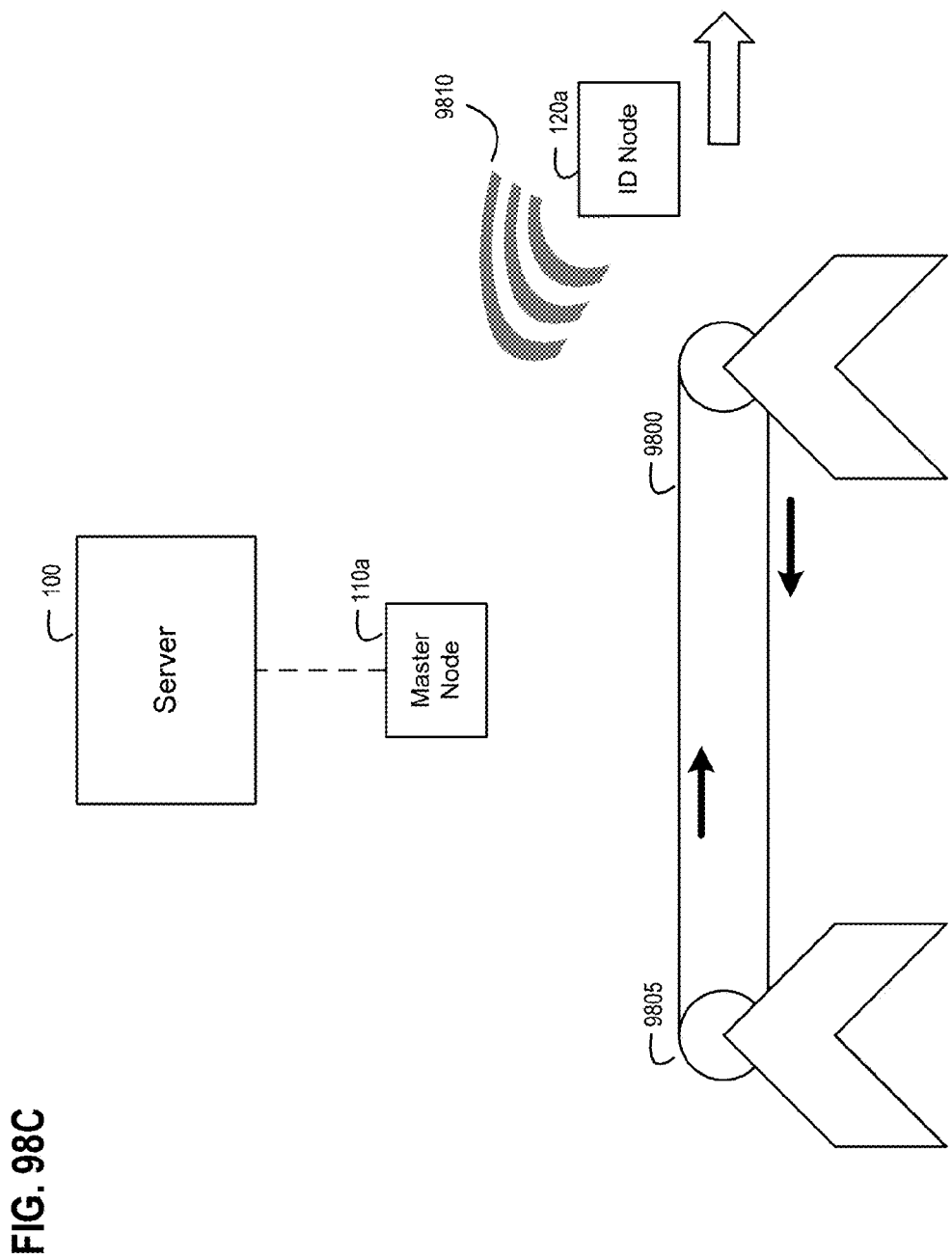

FIGS. 98A-98C present a series of exemplary diagrams that generally illustrate various embodiments where an exemplary node adaptively alters how it formats a broadcasted advertising message in response to detected state changes for the node. Referring now to FIG. 98A, an exemplary node (i.e., ID node 120a) is shown in motion as it approaches a conveyor system 9805, which has a moving conveyor belt 9800. The exemplary node 120a may be associated with a package, container, vehicle, or other object or person in motion. And as explained with reference to FIG. 3, the exemplary node 120a may have at least a processing unit 300, volatile memory 320, memory storage 315, and a communication interface 375 for communicating with other nodes (such as master node 110a, which is further operative to communicate with server 100). In an embodiment, an exemplary adaptive messaging program section may be implemented as part of node control and management code 325, which is maintained in the node's memory storage 315. The exemplary adaptive messaging program code section implements and controls how node 120a may generate and dynamically format advertising messages being broadcast from node 120a via Bluetooth® Low Energy (BLE) wireless signals 9810 being transmitted from the communication interface on node 120a. The exemplary adaptive messaging program code section may, in some embodiments, implements and controls how node 120*a* may respond to commands, messages or other signals received from other nodes that responsively cause node 120*a* to generate and dynamically format advertising messages being broadcast from node 120*a*

In an embodiment and in light of the ID node functionality discussion above related to FIG. 3, node 120*a* shown in FIG. 98A may be adapted and operative to load the adaptive messaging program section into the node's volatile memory and, when executing at least the adaptive messaging program code section when resident in the node's volatile memory, node 120*a* is further adapted and operative to dynamically format advertising messages. In more detail, an embodiment of the processing unit in node 120*a* running the adaptive messaging program code section is adapted and operative to generate an advertising message in a first format (e.g., such as the full format shown and illustrated with respect to FIGS. 6-7) and cause the communication interface to broadcast the advertising message in the first format when the node device is in a first state. For example, as shown in FIG. 98A, node 120*a* is in a state of transit as it moves towards conveyor system 9805. As the node 120*a* approached the conveyor system 9805, the node 120*a* may begin broadcasting an advertising message in a normal format as it attempts to associate with master node 110*a*. Thus, the state or, more specifically, the relative environment of the node 120*a* is that node 120*a* is moving in transit and approaching conveyor system 9805.

FIG. 98B illustrates the same embodiment as shown in FIG. 98A, but after the node 120*a* has detected a state change associated with a changed relative environment of the node 120*a*. This may be accomplished when the node 120*a* switches between broadcasting the advertising message in a first (e.g., full length) format and scanning or listening for an anticipated or known node signature indicative of a type of changed relative environment of the node 120*a*. Upon detection of such a node signature while scanning, node 120*a* detects such a state change. As shown in FIG. 98A, an embodiment may have node 120*a* detecting the node signature of master node 110*a* as a state change as node 120*a* approaches conveyer system 9805 given that master node 110*a* is associated with the system 9805. Thus, simply detecting the signature of master node 110*a* may be enough to indicate a change in the relative environment surrounding node 120*a* in one embodiment.

Referring back to the example shown in FIG. 98B, another embodiment has node 120*a* detecting a different movement aspect in that it has been placed on a moving conveyor belt 9800 of conveyor system 9805 and is no longer moving in transit approaching the conveyor system 9805. Thus, in this example embodiment, the changed relative environment of node 120*a* may be from a detected change in the movement aspect of node 120*a*—such as whether the node 120*a* is moving relative to known structure. Such detection may be accomplished, for example, by receipt of a signal with location and/or context information from another node (e.g., master node 110*a*) or by reference to location and/or context information maintained by the node itself. In still another embodiment, the changed relative environment may be from a detected change in a node density near the node 120*a*—such as whether node 120*a* is entering an area having a very large number of other nodes (e.g., a container or ULD).

In more detail, the change in the movement aspect of node 120*a* shown in FIG. 98B may be considered to reflect that the node 120*a* is substantially stationary relative to some proximate structure, such as the conveyor belt 9800. In an embodiment such as that illustrated in FIG. 98B, the proximate structure to the node (e.g., conveyor belt 9800) may be moving while being substantially stationary relative to the node device (e.g., node 120*a* placed on the belt 9800). In another embodiment, such proximate structure may be stationary along with the node (e.g., node 120*a* placed in a temporary storage room). Thus, given such proximate structure may have known location information and attributes (e.g., linear speed of the belt, time it takes to transit from one point to another along the conveyor belt, the location or context information describing a temporary storage room, etc.), a simplified, shortened, truncated, or abbreviated format for further advertising messages may be used given what is known or can be implied about the relative environment of the node.

In a more detailed embodiment, such proximate structure may comprise at least one of a conveyance device associated with the node device or a package containing device for the node device. For example, a conveyance device associated with the node that may help move the node may include, but is not limited to, a conveyor belt, a trailer, a truck, an aircraft, a train, and a delivery vehicle (e.g., a car, van, and the like). In another example, a package containing device may include, but is not limited to, a facility, room, bin, container, pallet, or a unit load device (ULD) type of transportation storage. Such package containing devices are generally able to take on and have temporary custody of the node device while such conveyance devices are generally able to move the node device between locations.

To adapt to the detected state change of node 120*a*, an embodiment of the processing unit in node 120*a* running the adaptive messaging program code section is adapted and operative to alter the first format of the advertising message to a shortened format comprising an identifier for node device, where the identifier is derived from the changed relative environment of the node device; and then causing the communication interface to broadcast the advertising message using the shortened format.

In an embodiment, the shortened format is relative to the standard or longer format used for advertising messages. Essentially, the shortened format allows for the recipient of an advertising message using the shortened format to be informed of which node is advertising and the changed state for that node. Thus, an abbreviated message may be generated according to the shortened format, which is then used when the node processing unit causes further advertising messages to be broadcast by the communication in that shortened format.

FIG. 98C illustrates the same embodiment as shown in FIGS. 98A and 98B, but after the node 120*a* has detected a further state change associated with yet another changed relative environment of the node 120*a*. In this particular example, node 120*a* has detected a different movement aspect in that it is no longer on the moving conveyor belt 9800 of conveyor system 9805 and is now moving in transit away from the conveyor system 9805. Thus, the node processing unit of node 120*a* is further adapted and operative to dynamically alter a variable broadcast format of the advertising message when detecting at least one further state change of the node device. In one embodiment, the variable broadcast format of the advertising message comprises two different formats—a longer format with more information related to the node and a shorter format with less or minimal additional information related to the node. However, further embodiments may implement the variable broadcast format of an advertising message with more than two different formats to best suit the information needs balanced with the communication and node density requirements for the system.

FIG. 99 is a flow diagram illustrating an exemplary method for adaptive node communication within a wireless node network having a plurality of nodes in accordance with an embodiment of the invention. Referring now to FIG. 99, exemplary method 9900 begins at step 9905 with a first of the nodes generating an advertising message in a first format. In one example, the first format for the advertising message is the format as shown in FIG. 6 or 7. Such a format provides valued information in the header that can be useful as described herein relating to passive association and communication aspects.

At step 9910, method 9900 continues with the first of the nodes broadcasting the advertising message in the first format when the first of the nodes is in a first state. As discussed above and shown in the embodiment illustrated in FIG. 98A, exemplary node 120a broadcasts an advertising message while in a state of transit as it moves towards conveyor system 9805. The advertising message is in a normal format as it attempts to associate with master node 110a. Thus, the first state or, more specifically, the first relative environment of the node 120a as shown in FIG. 98A is currently that node 120a is moving in transit and approaching conveyor system 9805.

At step 9915, exemplary method 9900 continues by detecting a state change for the first of the nodes. The state change is associated with a changed relative environment of the first of the nodes, such as a change in a node density near the first of the nodes or a change in a movement aspect of the first of the nodes. For a state change involving a change in the movement aspect of the node, a further embodiment may have the first of the nodes being substantially stationary relative to a proximate structure. In another embodiment, the proximate structure (e.g., a conveyor belt 9800) may be moving while being substantially stationary relative to the first of the nodes (e.g., node 120a placed on and supported by the moving conveyor belt 9800). In further examples, the proximate structure may comprise at least one of a package containing device for the first of the nodes or a conveyance device associated with the first of the nodes. In different embodiments, a conveyance device may include a conveyor belt, a truck, a trailer, an aircraft, a train, and a delivery vehicle. Further, in other embodiments, the package containing device may include a facility, a room, a bin, a container, a pallet, and a unit load device (ULD) type of transportation storage.

If no state change is detected in step 9915, method 9900 proceeds back to step 9910 to continue broadcasting advertising messages in the first format. However, if a state change is detected, method 9900 proceeds to step 9920 where method 9900 continues by adapting to the detected state change by altering the first format of the advertising message to a shortened format. The shortened format may comprise an identifier for the first of the nodes, where the identifier is derived from the changed relative environment of the first of the nodes.

In a more detailed embodiment of method 9900, step 9920 may have the first of the nodes generating an abbreviated version of the advertising message according to the shortened format, and then broadcasting the abbreviated version of the advertising message in response to detecting the state change. In other words, one embodiment may simply shorten the message using the shortened format (e.g., by simply cutting out certain information), but another embodiment may create a different abbreviated version of the full length message using the shortened format (e.g., by replacing some of the information with more compact versions of information in the shortened format rather than simply cutting it out).

At step 9925, method 9900 continues by detecting a further state change. If no further state change is detected in step 9925, method 9900 proceeds back to step 9910 to continue broadcasting advertising messages in the shortened format. However, if a further state change is detected, method 9900 proceeds to step 9930 where method 9900 continues by dynamically altering the format (also referred to as a variable broadcast format in some embodiments) of the advertising message based upon the detected further state change of the first of the nodes. For example, the format of the advertising message may be altered back to the first format. However, in other embodiments the format of the advertising message may be further varied to accommodate and corresponding to a further change in the relative environment of the first of the nodes.

Those skilled in the art will appreciate that method 9900 as disclosed and explained above in various embodiments may be implemented on a node (such as exemplary ID node 120a as illustrated in FIGS. 98A-98C) running one or more parts of a node control and management code (such as an exemplary adaptive messaging program code section implemented as part of node control and management code 325) to implement any of the above described functionality. Such code may be stored on a non-transitory computer-readable medium (such as memory storage 315 in exemplary ID node 120a). Thus, when executing such code, a processing unit of the node (such as unit 300) may be operative to perform the method and various steps as disclosed in the various embodiments described above.

While FIG. 99 and method 9900 describe embodiments of operational steps taken by an exemplary node that is, itself, broadcasting an advertising message and changing the format of that message to a shortened format, other embodiments may have the broadcasting node responding to instructions or command messages sent from another node as part of adapting its variable broadcast format to a type of shortened format. For example, master node 110a shown in FIG. 98A may detect the broadcasted advertising message 9810 from ID node 120a, detect a state change of ID node 120a when that node is placed upon conveyor system 9805, and then may instruct ID node 120a to broadcast using a shortened format. In such an example, master node 110a may be adapted and operative to control when and how the ID node 120a broadcasts its advertising message, and may control which type of shortened format may be useful to deploy under the particular circumstances faced by ID node 120a.

Notably, in an embodiment from the perspective where one node device controls how another node adapts its advertising message format, master node 110a may be deployed as an example of such a controlling node device. As explained with reference to FIG. 4, such an exemplary master node 110a may include a processing unit 400; a volatile memory 420 coupled to the processing unit 400; a memory storage 415 coupled to the processing unit 400; and a communication interface (e.g., short range communication interface 480) also coupled to the processing unit 400 and providing access to other nodes (such as ID node 120a) in a wireless node network. In this embodiment, an exemplary adaptive messaging program code section may be implemented as part of master control and management code 425, which is maintained in the master node's memory storage 415 and can be loaded into and executed by processing unit 400 while in the volatile memory 420. The exemplary adaptive messaging program code section implements and controls how master node 110a may dynamically control how another node (e.g., ID node 120a) alters the format of advertising messages being broadcast from that other node via, for example, Bluetooth® Low Energy (BLE) wireless signals 9810 transmitted from node 120a.

In an embodiment and in light of the master node functionality discussion above related to FIG. 4, master node 110a shown in FIG. 98A may be adapted and operative to load the adaptive messaging program code section into the master node's volatile memory 420 and, when executing at least the adaptive messaging program code section when resident in the master node's volatile memory, master node 110*a* may be further adapted and operative to dynamically control how another node formats advertising messages. In more detail, an embodiment of the processing unit in master node 110*a* running the adaptive messaging program code section may be adapted and operative to receive an indication from the communication interface, where the indication reflects that the communication interface detected an advertising message in a first format being broadcast by the ID node. For example, master node 110*a* may detect advertising message 9810 being broadcast by ID node 120*a* in a full format (e.g., similar to that shown in FIGS. 6-7).

The embodiment of the processing unit in master node 110*a* running the adaptive messaging program code section may be adapted and operative to detect a state change relative to one of the nodes, such as ID node 120*a*. The state change detected may be associated with a changed relative environment of the ID node 120*a*. Based upon the detected state change, the processing unit is also adapted and operative to instruct the communication interface to broadcast a command to the one node that causes the one node to alter the first format of the advertising message to a shortened format. The shortened format comprises at least an identifier for the one node derived from the node's changed relative environment.

In various embodiments, the changed relative environment may take different forms. For example, in one embodiment, the changed relative environment may be a change in a node density near the one node broadcasting the advertising message. In another embodiment, the changed relative environment may be a change in a movement aspect of the node. Such a change in the movement aspect may reflect that the node is substantially stationary relative to a proximate structure, which may be moving while being substantially stationary relative to the broadcasting node. The proximate structure may be a package containing device for the broadcasting node (such as a facility, a room, a bin, a container, a pallet, and a unit load device (ULD) type of transportation storage) or a conveyance device associated with the broadcasting node (such as a conveyor belt, a truck, a trailer, an aircraft, a train, and a delivery vehicle).

As noted above, the processing unit of the master node device is adapted and operative to instruct the communication interface broadcast or transmit a command to the broadcasting other node. Such a command causes that other node to change to a shortened format when broadcasting subsequent advertising messages. In more detail, the command may cause the other node to broadcast the advertising message according to a variable broadcast format as the shortened format. In other words, the shortened format may vary and need not be a singular type of shortened format to use in all situations; instead, the format may be tailored for various degrees of compaction and identity specificity. For example, further embodiments explained in more detail below may have such a variable broadcast format including different types of shortened formats (such as a shortened global format, a shortened nested format, and a shortened local format) that may be separately deployed to help make for more efficient wireless node communications within the network.

In more detail, an embodiment of the shortened global format may include a global identifier of the broadcasting node (e.g., ID node 120*a*) derived from the node device that detects the state change (e.g., master node 110*a*). The global identifier of the broadcasting node may further include a full identifier for the node device detecting the state change and a shortened reference to the broadcasting node. For example, master node 110*a* may have a full identifier of M123456 while the broadcasting ID node 120*a* may have a full identifier of I123456. As such, an exemplary shortened global format for the broadcasting ID node 120*a* may be implemented as M1234546-1, which is a type of global identifier for ID node 120*a* derived from the master node detecting the state change (e.g., "M123456") along with a shortened reference (e.g., the "-1") representing ID node 120*a* that indicates its relationship to master node 110*a* in a type of shorthand reference. Thus, the shortened global format may be helpful in situations where more compact communications are desired and there is the desire to avoid the communication overhead involved with contacting a backend server (e.g., server 100) to determine the master node related to the broadcasting ID node.

The nested format may be helpful in situations where a hierarchy of nodes is involved, such as when an ID node is placed within a ULD having its own master node, and the ULD is placed within a vehicle having its own master node. An embodiment of the shortened nested format may include a nested identifier of the broadcasting node (e.g., ID node 120*a*) relative to the node device that detects the state change (e.g., master node 110*a*). The nested identifier may further include one or more hierarchical references to higher level other nodes associated with the broadcasting node. Such a nested identifier may indicate the broadcasting node's relationships with the higher level other nodes and may include a shortened reference to the broadcasting node. For example, an exemplary broadcasting ID node may use a full identifier of I123456 while an exemplary ULD containing the ID node may use an identifier of U123456 and an exemplary vehicle that maintains the ULD may use an identifier of V123456. As such, an exemplary shortened nested format for the broadcasting ID node may be implemented as VUI123456-1-1. Such an exemplary nested format has the broadcasting ID node referenced as UI123456-1 relative to the ULD, but as placed within the vehicle, the broadcasting ID node is then able to use a nested type of referencing as VUI123456-1-1. Other ID nodes within the same ULD and vehicle may be shortened to VUI123456-1-2, VUI123456-1-3, and so forth where the "-2" and "-3" are shortened references to the other ID nodes in the same ULD. And broadcasting ID node within another ULD placed within the same vehicle may use a shortened nested format of VUI123456-2-1, where the "-2" indicates a shortened reference to the other ULD. Thus, such an exemplary shortened nested format for a broadcasting node allows the format itself to indicate where the node was when it was renamed, which avoids the communication overhead involved with contacting the backend server to determine such information. This may provide the advantage of a quicker responsiveness when the system needs to generate and transmit alert types of communications (as opposed to simply tracking types of communications).

The shortened local format may be helpful in situations that are highly contained and use of the shortened local format need only make sense to one node (e.g., master node 110*a* that detected the change but that may have no other master nodes near it). An exemplary embodiment of the shortened local format may include a local identifier of the broadcasting node (e.g., ID node 120*a*) derived from an abbreviated node reference for the node device detecting the state change (e.g., master node 110*a*). More specifically, the abbreviated node reference for the node device detecting the state change may include a collapsed reference to that node device and a shortened reference to the broadcasting node. In the example where the broadcasting ID node 120*a* uses an identifier of I123456, an example of the shortened local format to be used by that broadcasting ID node may be M1-1, which is derived from an abbreviated node reference to the master node 110*a* (i.e., M123456) that detected the state change. As such, the "M1" in the example is a collapsed reference to the M123456 full identifier of the master node 110*a* detecting the state change, while the "-1" is a shortened reference to the broadcasting ID node 120*a*. Thus, using M1-1 allows for a greater degree of format compaction but at the expense of ease of identification.

And while such types of shortened formats may be deployed by the broadcasting node at the direction and control of the master node, a further embodiment of such a master node device may have the node processing unit in the master node being further adapted and operative to instruct the broadcasting node to alter the shortened format of the advertising message back to the first format when the master node detects at least one further state change of the broadcasting node (such as when ID node 120*a* is detected to be at the end of conveyor system 9805 and transitioning to moving while off the conveyor belt 9800 as shown in FIG. 98C).

FIG. 100 is a flow diagram illustrating an exemplary method for adaptive node communication within a wireless node network having at least a master node and an ID node in accordance with an embodiment from the operational perspective of the master node device that controls how the broadcasting ID node changes advertising message formats. Referring now to FIG. 100, method 10000 begins at step 10005 where the master node scans for an advertising message being broadcast by an ID node where the message uses a first format. For example, as shown in FIG. 98A, master node 110*a* may be scanning for an advertising message broadcast by ID node 120*a* where the message uses a full format as shown in FIGS. 6-7.

At step 10010, method 10000 continues by detecting such an advertising message. If no advertising message is detected, step 10010 has method 10000 continuing to scan in step 10005. However, if such an advertising message is detected in step 10010, method 10000 proceeds to step 10015 where the master node detects a state change relative to the ID node. The state change is associated with a changed relative environment of the ID node. In one embodiment, the changed relative environment may be a change in a node density near the ID node. In another embodiment, the changed relative environment may be a change in a movement aspect of the ID node. More specifically, the change in the movement aspect of the ID node may reflect that the ID node is substantially stationary relative to a proximate structure (which may be moving while being substantially stationary relative to the ID node). An exemplary proximate structure may implemented by a package containing device for the ID node (such as a facility, a room, a bin, a container, a pallet, and a unit load device (ULD) type of transportation storage) or a conveyance device associated with the ID node (such as a conveyor belt, a truck, a trailer, an aircraft, a train, and a delivery vehicle).

If a state change is not detected at step 10015, step 10015 returns to step 10005 to keep scanning. However, if such a state change is detected, step 10015 proceeds to step 10020 where the master node instructs the ID node to alter the first format of the advertising message to a shortened format, which comprises an identifier for the ID node that is derived from the changed relative environment of the ID node. In a more detailed embodiment, the instructing step may be accomplished when the master node transmits a control or command message to the ID node, wherein the control or command message causes the ID node to broadcast the advertising message according to a variable broadcast format as the shortened format.

In an embodiment of method 10000, such a variable broadcast format may be at least one of a shortened global format, a shortened nested format, and a shortened local format. In more detail, an embodiment of method 10000 may use an exemplary shortened global format having a global identifier of the ID node derived from the master node detecting the state change. The global identifier of the ID node may further comprise a full identifier for the master node detecting the state change and a shortened reference to the ID node.

Another embodiment of method 10000 may use an exemplary shortened nested format having a nested identifier of the ID node, where the nested identifier includes hierarchical references to higher level nodes associated with the ID node. The nested identifier may also indicate the ID node relationships with the higher level nodes, and may further comprise a shortened reference to the ID node.

Still another embodiment of method 10000 may use an exemplary shortened local format having a local identifier of the ID node derived from an abbreviated node reference for the master node detecting the state change. Further, the abbreviated node reference for the master node detecting the state change may comprise a collapsed reference to the master node and a shortened reference to the ID node.

And in a further embodiment, method 10000 also includes instructing, by the master node, the ID node to alter the shortened format of the advertising message back to the first format when the master node detects at least one further state change of the ID node.

Those skilled in the art will appreciate that method 10000 as disclosed and explained above in various embodiments may be implemented on a node (such as exemplary master node 110*a* as illustrated in FIGS. 98A-98C) running one or more parts of a master control and management code (such as an exemplary adaptive messaging program code section implemented as part of master control and management code 425) to implement any of the above described functionality. Such code may be stored on a non-transitory computer-readable medium (such as memory storage 415 in exemplary master node 110*a*). Thus, when executing such code, a processing unit of the node (such as unit 400) may be operative to perform the method and various steps as disclosed in the various embodiments described above.

Enhanced Energy Management Aspects
Context Adjustment of Output Power

Figure 45A:
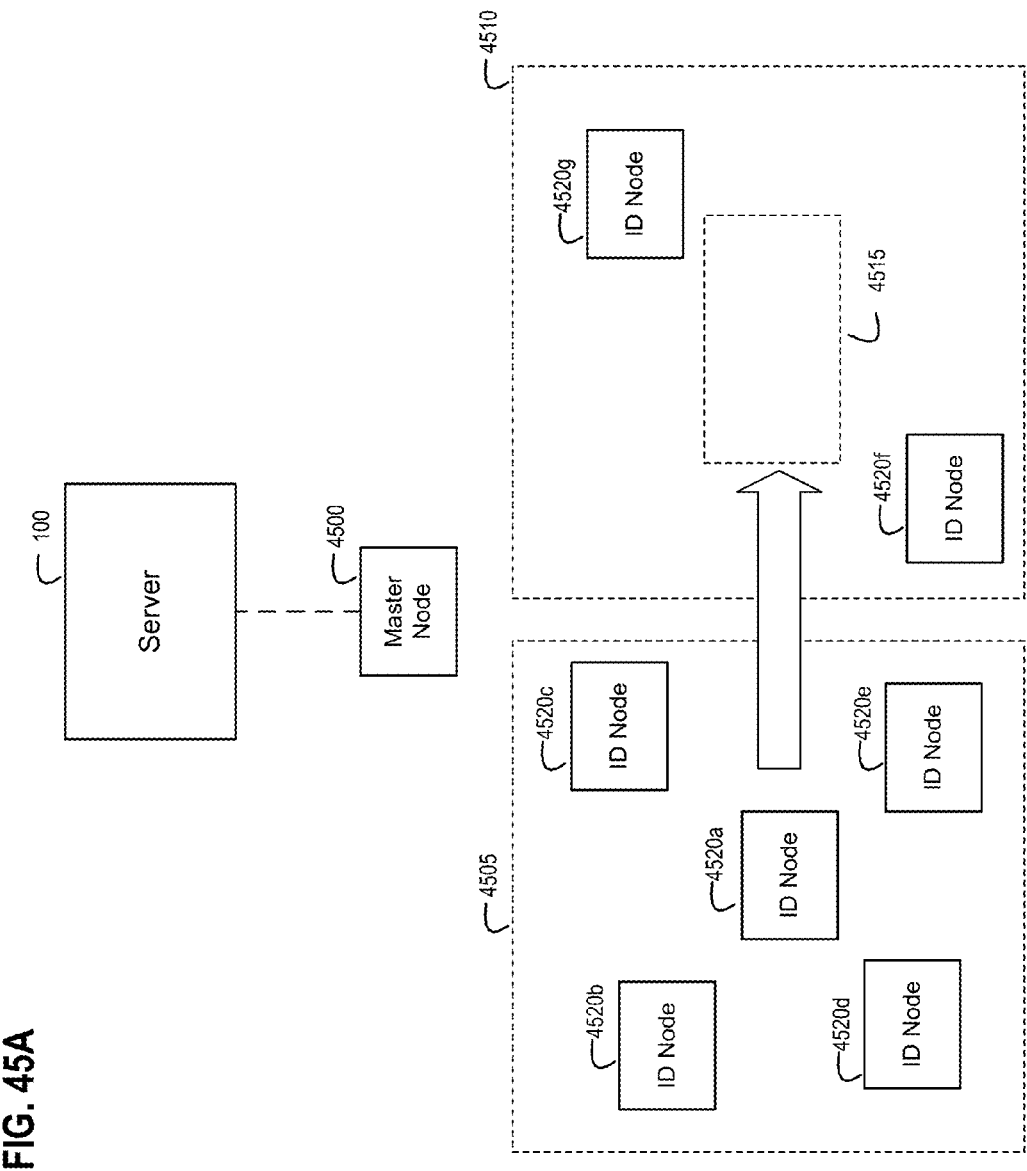
FIGS. 45A-45C are collectively a series of diagrams illustrating an example environment where a node is located in and may move between areas having different operating node densities and adaptively adjust node power in accordance with an embodiment of the invention.
Figure 45B:
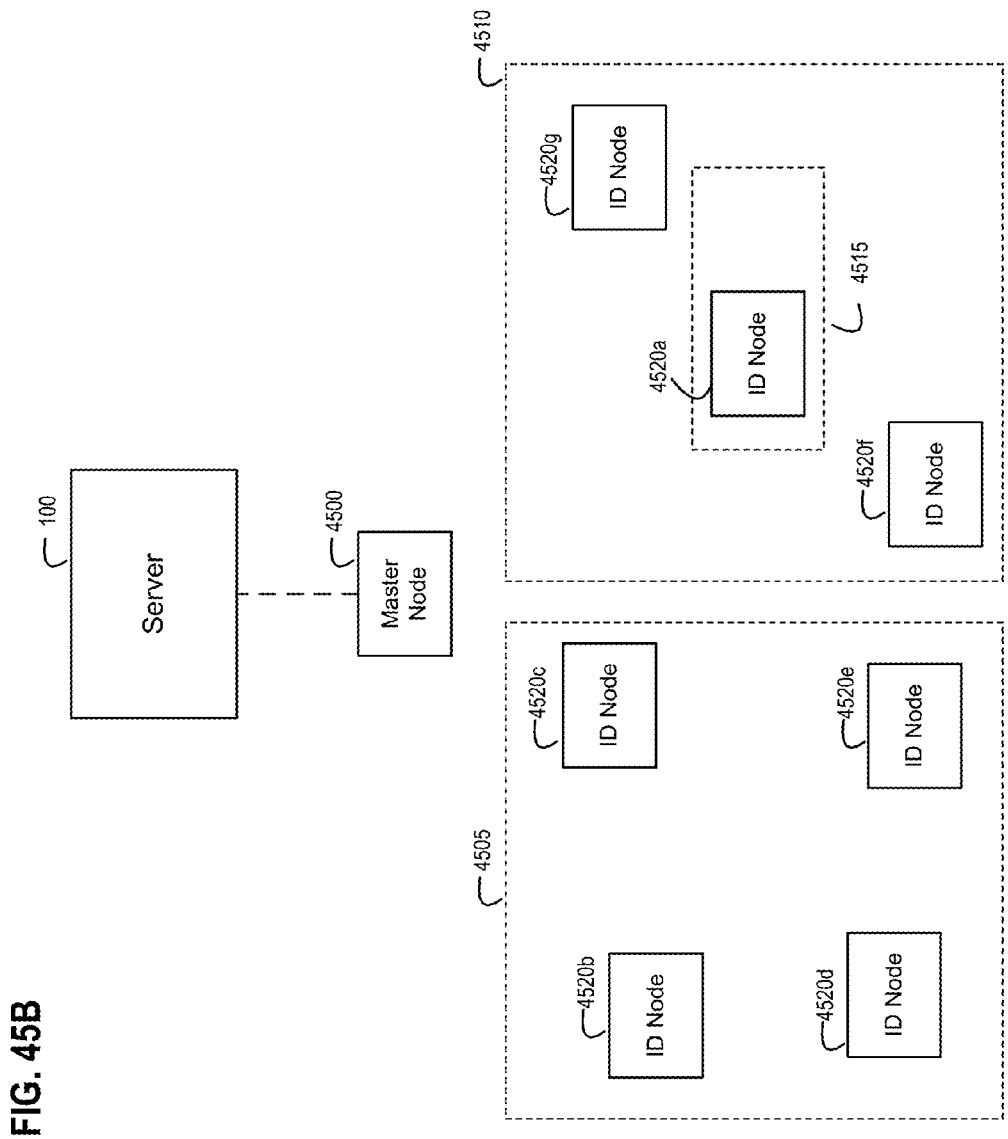
Figure 45C:
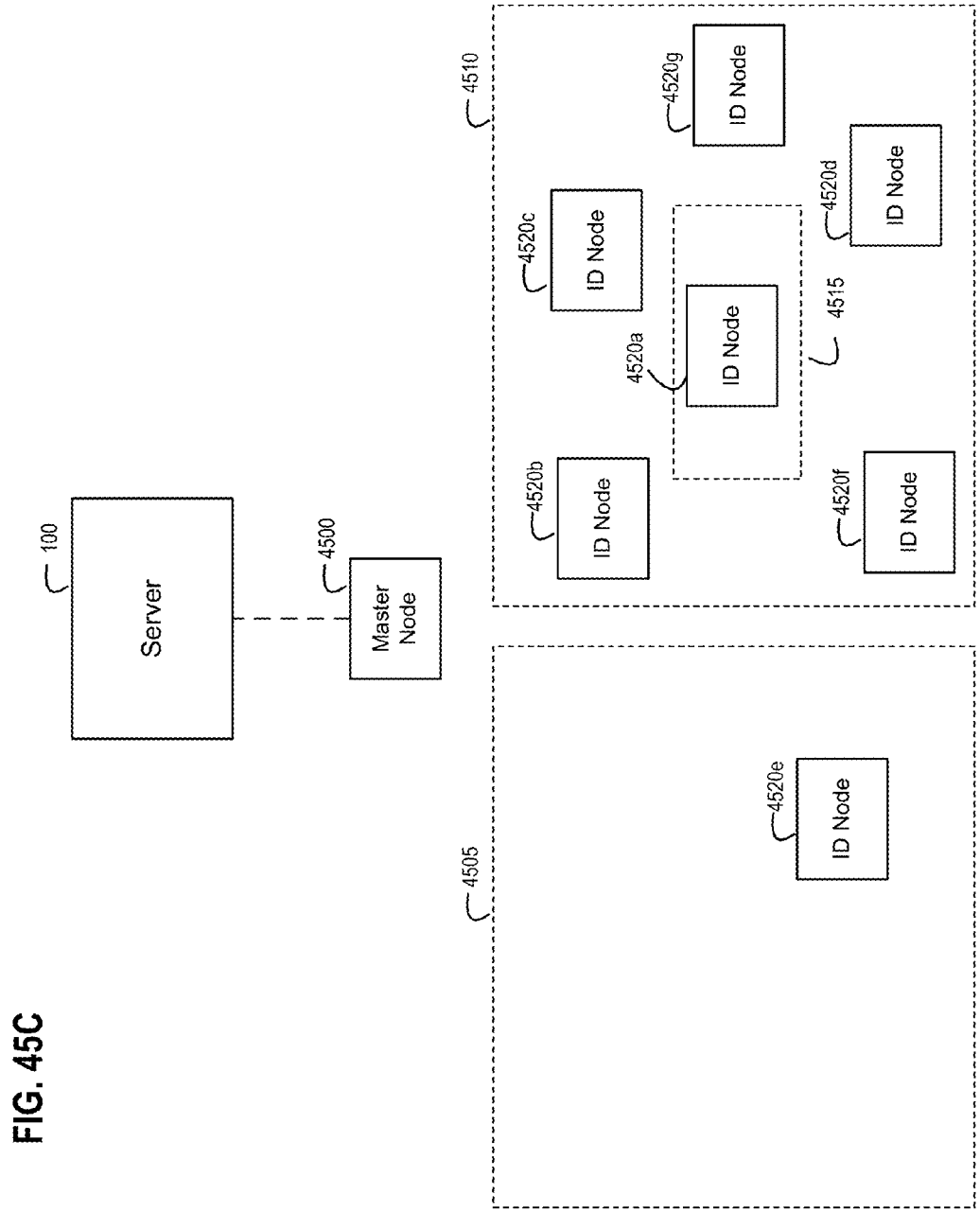

In some embodiments, the ability to adaptively adjust a node's broadcasting or advertising signal power may have certain advantages and particular uses during operations of a wireless node network. FIGS. 45A-45C are collectively a series of diagrams illustrating an example environment where a node is located in and may move between areas having different operating node densities and adaptively adjust node power in accordance with an embodiment of the invention. Referring now to FIG. 45A, server 100 and master node 4500 are deployed as part of an exemplary wireless node network. Master node 4500 is illustrated to be in communication with server 100 (such as through a second communication interface (e.g., medium/long range communication interface 485 for exemplary master node 110*a*). While FIG. 45A-45C do not expressly show lines between the various nodes, those skilled in the art will appreciate that each of the nodes (e.g., master node 4500 and ID nodes 4520*a*-4520*g*) have the capacity to communicate with each over and form associations over short-range communication interfaces, such as a Bluetooth® interface. The server 100 (with relayed commands by master node 4500) or the master node without direction from sever 100 are operative to fix an output power setting of any of ID node 4520*a*-4520*g* and be able to update that level depending on the circumstances. While not shown in FIGS. 45A-45C, server 100 may, in other embodiments, have relayed commands through one or more other master nodes so that the server 100 is operative to fix an output power setting of any ID node or master node. And likewise, master node 4500 without direction from sever 100 may be operative to fix an output power setting of any other master node in the network.

As shown in FIG. 45A, ID nodes 4520*a*-4520*g* are located in two different areas. Specifically, ID nodes 4520*a*-4520*e* are located within a first area 4505 while ID nodes 4520*f* and 4520*g* are located within a second area. In one example, the first area 4505 may be a storage facility, room, vehicle, container, or other bounded area. The second area 4510 may also be a storage facility, room, vehicle, container, or other bounded area. In a particular example, the first area 4505 is a storage room where packages and their related ID nodes are temporarily stored as the items in the packages are being shipped. The second area, in this particular example, is a sorting facility having a conveyor system at a particular point 4515 (such an entry point to the conveyor system) within the area 4510.

In a general embodiment, when a node passes a certain point (such an exit point of the first area 4505), the output power level being broadcast from the node may be changed depending upon a detected or determined change in the operating node density in the next area (or, in some embodiments, an anticipated next area).

In the example of FIG. 45A, one of the ID nodes (ID node 4520*a*) is going to be moved from the first area 4505 to the second area 4510. ID node 4520*a* is initially located in the first area 4505, which has a density of 4 other nodes operating within that area (e.g., ID nodes 4520*b*-4520*e*). In contrast, the second area 4510 has 2 other nodes operating within that second area (e.g., ID nodes 4520*f* and 4520*g*). As shown in FIG. 45B, ID node 4520*a* has moved from the first area 4505 to the second area 4510 (more specifically, to a designated entry point 4515 of the conveyor system). With the second area 410 having an operating node density less than the first area 4505, either server 100 or master node 4500 may adapt the output power setting of ID node 4520*a* to correspond with the reduced operating node density, and update the output power setting on ID node to a higher power level.

FIG. 46 is a flow diagram illustrating an exemplary method for adaptive adjustment of node power level in a wireless node network depending upon operating node densities when a node (such as ID node 4250*a*) moves to a new area in accordance with an embodiment of the invention. The embodiment with exemplary method 4600 is explained in terms of actions by a server, but in light of the discussion above regarding FIG. 45A, those skilled in the art will further appreciate that such operational steps may also be performed, in another embodiment, by a master node without direction of the server.

Referring now to FIG. 46, method 4600 begins with the server fixing an output power setting on a first of the nodes to a first power level when the first node is located in a first area where the first power level corresponds to a density of the nodes operating within the first area. In more detail, the first power level may correspond to a density of the scanning nodes operating within the first area. In the example of FIG. 45A, server 100 may fix the output power setting on ID node 4520*a* (via relayed commands by master node 4500) to a low power level given the operational node density in the first area 4505 is currently 4 nodes in that area.

At step 4610, the server detects if the first node has moved to a second area. For example, server 100 may receive updated location data from master node 4500 that indicates ID node 4520*a* is moving towards and now into second area 4510. In one embodiment, detecting may include tracking the location of the first node as the first node moves from within the first area to within the second area, and determining when the location of the first node has moved to within the second area.

In another embodiment, detecting by the server in step 4610 may be detecting if the first node is anticipated to be moving from the first area to the second area. In other words, the server may anticipate movement of the first node and detect an anticipated movement of the first node from the first area to the second area. In more detail, the server may detect if the first node is anticipated to be moving from the first area to the second area by accessing context data related to an expected transit path of the first node. In another embodiment, method 4600 may also have the server predicting at least a portion of a predicted path for the first node, where the portion of the predicted path includes the expected transit path of the first node from the first area to the second area.

At step 4615, the server adapts the output power setting on the first node to a second power level when the first node is located in the second area. The second power level corresponds to a density of the nodes operating within the second area. Thus, a change in operating node density between the two areas can be accommodated with the adapted output power setting on the first node. For example, the second power level may be higher than the first power level when the density of the nodes operating within the second area is less than the density of the nodes operating within the first area. Likewise, the second power level may be lower than the first power level when the density of the nodes operating within the second area is greater than the density of the nodes operating within the first area.

In a more detailed embodiment, the adapting step may have the server adapting the output power setting on the first node to the second power level when the first node is passing a point in the second area, such as an entry point of a conveyor system disposed within the second area. The point may be a designated point or an anticipated point in different embodiments. In the example of FIG. 45B, ID node 4520*a* has moved within second area 4510 and is passing the designated conveyor system entry point 4515 within second area 4510. As such, server 100 may adapt the output power setting on ID node 4520*a* to a different power level based upon the different operational node density within second area 4510.

In a further embodiment, method 4600 may have the server accessing context data related to the designated point in the second area to anticipate a density of the nodes expected to be operating within a proximate environment of the designated point, and may have the server updating the output power setting on the first node to a third power level when the server detects the node is approaching the designated point in the second area. In this embodiment, the third power level may correspond to the density of the nodes expected to be operating within the proximate environment of the designated point, which may be different than simply the nodes operating within the second area.

In yet another embodiment, method 4600 may also have a second node with its output power setting adapted but in this situation the second node can do this based upon shared data from the first node. In more detail, method 4600 may further comprise adapting, by a second of the nodes, an output power setting on the second node to the second power level based upon shared data received by the second node from the first node. More particularly, the first node has its output power setting adapted and changed to the second power level as recited in method 4600 but then shares that second power level as a type of shared data with the second node. Here, if the server knows the second node is with the first node (e.g., traveling together as part of a multi-piece shipment, moving on the same conveyor belt system in proximity to each other, etc.), the ability to share the power level information allows for more efficient wireless node network operations.

In still another embodiment, the method 4600 may be implemented as performed by a mobile master node instead of a server. In other words, an exemplary mobile master node in such an embodiment can self-adapt its output power setting without requiring direction from the server. In more detail, the exemplary method is similar to that set forth above in method 4600 except that the first of the node perform each of the steps and the first node may be a mobile master node. In such an embodiment, context data related to the expected transit path of the mobile master node may be pre-loaded in the memory storage of the mobile master node.

Those skilled in the art will appreciate that method 4600 as disclosed and explained above in various embodiments may be implemented on a network device, such as exemplary server 100 as illustrated in FIG. 5 or an exemplary master node as illustrated in FIG. 4 (or master node 4500 illustrated in FIGS. 45A-45C), running one or more parts of a control and management code (such as code 425 for a master node device or code 525 for a server device) to implement any of the above described functionality. Such code may be stored on a non-transitory computer-readable medium (such as memory storage 415 within an exemplary master node or memory storage 515 within an exemplary server). Thus, when executing such code, a processing unit (such as unit 400 within a master node or unit 500 within a server) may be operative to perform operations or steps from the exemplary methods disclosed above, including method 4600 and variations of that method.

In yet another embodiment, an apparatus (such as a server or master node) is described for adaptive adjustment of node power level in a wireless node network. The apparatus comprises a processing unit and a memory coupled to the processing unit. The memory maintains code for execution by the processing unit (such as code 425 or code 525) and operational node density information related to a first area and a second area (such as areas 4505 and 4510 illustrated in FIG. 45A-45C). The apparatus further comprises a communication interface coupled to the processing unit. The communication interface operates to communicate with at least a first of a plurality of nodes in the network.

The processing unit of the apparatus, when executing the code maintained on the memory, is operative to perform particular steps and operations similar to those explained above with respect to the various embodiments of method 4600. In particular, the processing unit is operative to fix an output power setting on a first of the nodes to a first power level when the first node is located in a first area, where the first power level corresponds to a density of the nodes operating within the first area. This may be accomplished by sending a message over the communication interface to the first node as an instruction to fix the output power setting of the first node to the first power level. The processing unit is then operative to detect if the first node has moved to a second area. In one example, this may be accomplished by having the node processing unit being operative to track the location of the first node as the first node moves from within the first area to within the second area, and determine when the location of the first node has moved to within the second area.

In another example, the processing unit may be further operative to detect by being operative to detect if the first node is anticipated to be moving from the first area to the second area. In more detail, the memory may maintain context data related to an expected transit path of the first node, and the processing unit may be further operative to detect if the first node is anticipated to be moving from the first area to the second area by being operative to access the context data on the memory, and using the context data to determine if the first node is anticipated to be moving from the first area to the second area.

When the first node is located in the second area, the processing unit is operative to adapt the output power setting to a second power level, which corresponds to a density of the nodes operating within the second area. In one example, the second power level may be higher than the first power level when the density of the nodes operating within the second area is less than the density of the nodes operating within the first area. In another example, the second power level may be lower than the first power level when the density of the nodes operating within the second area is greater than the density of the nodes operating within the first area.

In another embodiment, the processing unit may be operative to adapt by adapting the output power setting on the first node to the second power level when the first node is passing a designated point in the second area. More specifically, in this other embodiment, the memory may contain context data related to the designated point in the second area, and the processing unit may be further operative to access the context data to anticipate a density of the nodes expected to be operating within a proximate environment of the designated point, and then update the output power setting on the first node to a third power level when the server detects the node is approaching the designated point in the second area, the third power level corresponding to the density of the nodes expected to be operating within the proximate environment of the designated point.

The processing unit is then operative to transmit a message over the communication interface to the first node to update the output power setting on the first node to the second power level.

In another embodiment, the processing unit of the apparatus may also be operative to predict at least a portion of a predicted path for the first node, wherein the at least portion of the predicted path comprises the expected transit path of the first node from the first area to the second area.

Thus, embodiments may adaptively adjust a node power level via the output power level broadcast from the node depending upon a detected or determined change in the operating node density in the next area (or, in some embodiments, an anticipated next area).

Proximity Adjustment of Output Power

Other embodiments may adaptively adjust a node power level via the output power level broadcast from the node depending upon whether a threshold number of other nodes are operating near or proximate to the first node or whether a threshold signal strength level is detected near the first node. Thus, such a threshold may be set relative to the number of nodes or signal strength level detected as a measure of crowded node operations.

Such a threshold may be set by the server as a type of context data, which could depend upon the contextual environment (e.g., a facility in which the first node is operating, a layout of the facility, machinery within the facility, RF signal degradation information about the surrounding environment, etc.). For example, when it is detected or determined that a lot of ID nodes are in a room (via numbers of nodes or signal strength levels), the power of one or more of the ID nodes can be dropped down to eliminate excess transmissions and/or noise, which may allow the nodes to better communicate and locate each other with enhanced granularity.

Looking back at FIG. 45B, ID node 4520a finds itself within second area 4510 and with two other ID nodes (e.g., ID nodes 4520f and 4520g) operating near ID node 4520a. In this situation, the transmissions and noise emitting from the nodes may be tolerable such that an output power setting of ID node 4520a may be originally set as a medium level. However, over time, ID nodes 4520b-4520d may also move from the first area 4505 to the second area 4510, as illustrated in FIG. 45C. As a result and referring to FIG. 45C, ID node 4520a now finds itself having 5 nodes operating near it. If the server 100 set the threshold (under the contextual circumstances) to 4, then the number of nodes operating near or proximate to ID node 4520a exceeds the threshold and the output power setting is changed to an adapted level (e.g., a low RF output power level), which is different from the original level (e.g., a medium RF output power level). Those skilled in the art will appreciate that while a low or medium level is disclosed as exemplary output power settings, an embodiment may have a specific power level and may change in increments relative to the extent the number of other nodes operating proximate ID node 4520 exceed the threshold. The ability to flexibly set the threshold by the server and the ability to adaptively set the output power settings to levels that make sense in the particular context of the node of interest may further enhance node operations in an exemplary embodiment of the wireless node network.

As previously noted, the server 100 (with relayed commands by master node 4500) or the master node without direction from sever 100 are operative to fix or adapt an output power setting of any of ID node 4520a-4520g and be able to update that level depending on the circumstances. While not shown in FIGS. 45A-45C, server 100 may, in other embodiments, have relayed commands through one or more other master nodes so that the server 100 is operative to fix or adapt an output power setting of any ID node or master node. And likewise, master node 4500 without direction from sever 100 may be operative to fix an output power setting of any other master node in the network.

Figure 47:
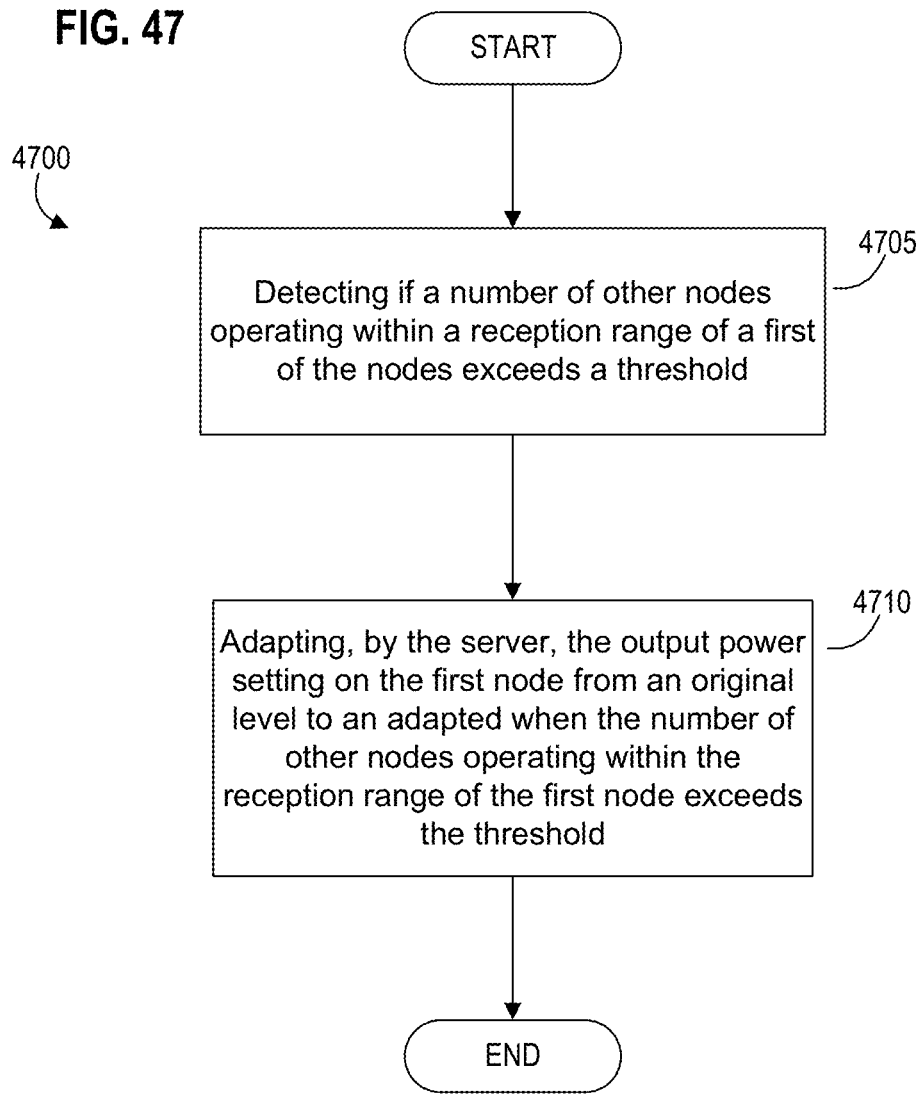
FIG. 47 is a flow diagram illustrating an exemplary method for adaptive adjustment of node power level in a wireless node network depending upon a threshold of operating nodes within a given area in accordance with an embodiment of the invention.

FIG. 47 is a flow diagram illustrating an exemplary method for adaptive adjustment of node power level in a wireless node network depending upon a threshold of operating nodes within a given area in accordance with an embodiment of the invention. The embodiment with exemplary method 4700 is explained in terms of actions by a server, but in light of the discussion above regarding FIGS. 45B-45C, those skilled in the art will further appreciate that such operational steps may also be performed, in another embodiment, by a master node without direction of the server.

Referring now to FIG. 47, method 4700 begins at step 4705 with the server detecting if a number of other nodes operating proximate a first of the nodes exceeds a threshold. In one embodiment, the number of other nodes operating proximate the first node may comprise a number of other nodes operating within a first communication area around the first node. For example, the first communication area around the first node may be defined by a transmission range around the first node or by a reception range from the first node. In another example, the first communication area around the first node may be defined by a first transmission range around the first node adjusted based upon context data related to an environment proximate the first node. Exemplary context data, such as context data 560, may include information on anticipated signal degradation for a similar environment to the environment proximate the first node (e.g., a type of RF data 587).

At step 4710, method 4700 concludes with the server adapting an output power setting on the first node from an original level to an adapted level when the number of other nodes operating proximate the first node exceeds the threshold. In one embodiment, the adapted level may comprise an RF output signal level that is decreased relative to the original level. For example, the decreased RF output signal level of the adapted level may be based upon or commensurate with the extent the number of other nodes operating proximate the first node exceeds the threshold. Thus, if a relatively large number of nodes are operating proximate the first and that greatly exceeds the threshold, then the adapted level may be significantly decreased. However, if the number of nodes operating proximate the first only barely exceeds the threshold, then the adapted level may only be slightly decreased. Those skilled in the art will appreciate that the amount of any decrease and setting of any threshold will be subject to the details of the implementation and intended environment where the node is expected to operate within.

Method 4700, in a further embodiment, may also include altering the output power setting to the original level when the server detects the number of other nodes operating proximate the first node no longer exceeds the threshold. Thus, the adaptive nature of an embodiment may compensate for going over the threshold as well as coming back under the threshold so as to better enhance node communications and the ability to locate a node within an exemplary wireless node network.

Those skilled in the art will appreciate that method 4700 as disclosed and explained above in various embodiments may be implemented on a network device, such as exemplary server 100 as illustrated in FIG. 5 or an exemplary master node as illustrated in FIG. 4 (or master node 4500 illustrated in FIGS. 45B-45C), running one or more parts of a control and management code (such as code 425 for a master node device or code 525 for a server device) to implement any of the above described functionality. Such code may be stored on a non-transitory computer-readable medium (such as memory storage 415 within an exemplary master node or memory storage 515 within an exemplary server). Thus, when executing such code, a processing unit (such as unit 400 within a master node or unit 500 within a server) may be operative to perform operations or steps from the exemplary methods disclosed above, including method 4700 and variations of that method.

In another embodiment, another exemplary method that may be implemented by a server is described for adaptive adjustment of node power level in a wireless node network having a plurality of nodes and a server. The method uses a threshold based upon signal strength level measured at the first node, rather than a number of nodes operating within an area around the first node. In particular, an embodiment of the method begins by detecting, by the server, if a signal strength level near a first of the nodes exceeds a threshold. The method continues by adapting, by the server, an output power setting on the first node from an original level to an adapted level when the signal strength level near the first node exceeds the threshold.

Furthermore, the adapted level may comprise an RF output signal level that is decreased relative to the original level based upon the extent the detected signal strength exceeds the threshold. And even further, the method may include altering the output power setting to the original level when the server detects the signal strength level no longer exceeds the threshold.

In still another embodiment, another exemplary method that may be implemented by a server is described for adaptive adjustment of node power level in a wireless node network having a plurality of nodes and a server. The method relies upon a location of the first node as a condition for adapting the output power setting of the node. In particular, an embodiment of the method begins by detecting, by the server, if a first of the nodes is located in an RF restricted area. The method continues by adapting, by the server, an output power setting on the first node from an original level to an adapted level when the first node is located in the RF restricted area. The method may include altering the output power setting to the original level when the server detects the signal strength level no longer exceeds the threshold. Thus, a server apparatus may implement such a method related to operating around and within restricted RF areas (such as on an aircraft or in medical facilities where RF interference is an issue).

In yet another embodiment, an apparatus (such as a server or master node) is described for adaptive adjustment of node power level in a wireless node network. The apparatus comprises a processing unit and a memory coupled to the processing unit. The memory maintains code for execution by the processing unit (such as code 425 or code 525) and location data regarding the nodes. The apparatus further comprises a communication interface coupled to the processing unit. The communication interface operates to communicate with at least a first of a plurality of nodes in the network.

The processing unit of the apparatus, when executing the code maintained on the memory, is operative to perform particular steps and operations similar to those explained above with respect to the various embodiments of method 4700. In particular, the processing unit is operative to access the location data on the memory, identify how many of the nodes are operating proximate the first node based upon the location data, and then detect if the identified number of other nodes operating proximate the first node exceeds a threshold. In one embodiment, the number of other nodes operating proximate the first node may comprise a number of other nodes operating within a first communication area around the first node. In one example, the first communication area around the first node may be defined by a transmission range around the first node or by a reception range from the first node. In more detail, the first communication area around the first node may be defined by a first transmission range around the first node adjusted based upon context data related to an environment proximate the first node. Such context data may, for example, include information on anticipated signal degradation (e.g., RF data 587) for a similar environment to the environment proximate the first node.

The processing unit is then operative to adapt an output power setting on the first node from an original level to an adapted level when the identified number of other nodes operating proximate the first node exceeds the threshold. In one embodiment, the adapted level comprises an RF output signal level that may be decreased relative to the original level based upon the extent the number of nodes operating proximate the first node exceeds the threshold.

In another embodiment of the apparatus, the processing unit may be further operative to transmit a message to the first node to alter the output power setting to the original level when the number of nodes operating proximate the first node no longer exceeds the threshold.

In a more specific embodiment, a master node is described for adaptive adjustment of node power level in a wireless node network of a plurality of other nodes and a server. The master node comprises a master node processing unit and a master node memory coupled to the processing unit. The master node memory maintains code (such as code 425) for execution by the master node processing unit and location data regarding the other nodes. The master node further comprises a first communication interface coupled to the master node processing unit and operative to communicate with at least a first of the of other nodes in the network. And the master node also comprises a second communication interface coupled to the server.

The master node processing unit, when executing the code maintained on the master node memory, is operative to perform particular steps and operations similar to those explained above with respect to the various embodiments of method 4700. In particular, the master node processing unit is operative to receive a threshold setting from the server over the second communication interface, access the location data on the master node memory, identify how many of the nodes are operating proximate the first node based upon the location data, and then detect if the identified number of other nodes operating proximate the first node exceeds the threshold setting received from the server.

In one embodiment, the number of other nodes operating proximate the first node may comprise a number of other nodes operating within a first communication area around the first node. In one example, the first communication area around the first node may be defined by a transmission range around the first node. In more detail, the first communication area around the first node may be defined by a first transmission range around the first node adjusted based upon context data related to an environment proximate the first node. Such context data may, for example, include information on anticipated signal degradation (e.g., RF data 587) for a similar environment to the environment proximate the first node.

The master node processing unit is then operative to adapt an output power setting on the first node from an original level to an adapted level when the identified number of other nodes operating proximate the first node exceeds the threshold. In one embodiment, the adapted level comprises an RF output signal level that may be decreased relative to the original level based upon the extent the number of nodes operating proximate the first node exceeds the threshold setting received from the server.

In another embodiment of the apparatus, the processing unit may be further operative to transmit a message to the first node to alter the output power setting to the original level when the number of nodes operating proximate the first node no longer exceeds the threshold setting received from the server.

Power Profile Management

One of the advantageous aspects of certain embodiments may come from how a master node can adjust settings on the ID node, which cannot communicate directly with the server. In some embodiments, the master node is able to accomplish adjusting a broadcast setting of an ID node using a type of broadcast profile for the ID node. In general, a profile generally contains information that defines the behavior of the ID node device. In one example, a broadcast profile (e.g., information stored as profile data 330) may contain information that defines how an ID node broadcasts signals and communicates with other nodes.

Referring back to the exemplary embodiment shown in FIG. 34C, as ID node 120*a* approaches facility master node 3430, master node 3430 may detect an advertising signal from ID node 120*a* when ID node 120*a* is within range. After associating with the ID node 120*a*, facility master node 3430 is able to change or adjust a broadcast profile for ID node 120*a* so that ID node 120*a* behaves or communicates in a manner that appropriate and dictated by master node 3430 (or via instructions sent from server 100 to facility master node 3430).

In another example, a node may be associated with structure, such as a ULD or drop box receptacle. As such, the node would be aware of characteristics of the structure (e.g., via context data about the structure) and may have a predetermined value (e.g., a default value) for a broadcast setting (e.g., an RF transmission output power level setting) for nodes entering the structure. In such an example, the interior space of the structure may be the interior of a commonly used drop box receptacle. The node associated with the receptacle may detect an ID node approaching, associate with the approaching ID node, and adjust a current RF output power level to an updated (e.g., lower) RF output power level as the detected ID node enters the interior of the drop box receptacle. In another embodiment, the adjustment to the updated RF output power level may occur prior to entering the structure. This may be accomplished by modifying the broadcast profile for the node entering the structure so that, for example, the node causes less disruption within a confined interior of the structure. In some situations, an ID node may have a default broadcast profile in memory onboard (e.g., the information in profile data 330) to be used whenever the ID node is associated with certain structure (e.g., a ULD, drop box receptacle) or another node associated with such structure.

FIG. 52 is a flow diagram illustrating an exemplary method for adjusting a broadcast setting of a node in a wireless node network having a master node and a server in accordance with an embodiment of the invention. Referring now to FIG. 52, method 5200 begins at step 5205 with the master node detecting an advertising signal from the node. In one embodiment, the node may be an ID node (such as ID node 120*a*) capable of communicating directly with the master node but incapable of communicating directly with the server in the wireless node network. In a more detailed, such an ID node may have pre-staged context aware data residing on the node and be operative to self-adjust its broadcast setting to an updated value based on the pre-staged context data.

At step 5210, method 5200 continues by establishing an active association with the node. In one embodiment, the active association of the master node and the detected node may reflect a secure connection between the master node and node. In this way, the master node may securely share information with the node.

At step 5215, method 5200 continues by determining an updated value for the broadcast setting of the node. In a general embodiment, the broadcast setting of the node is setting related to characteristic aspects of a signal (such as an advertising signal) broadcast from the node. Examples of such a broadcast setting may include an RF transmission output power level setting, a frequency setting, and a timing setting. In more detail, the RF transmission output power level setting may be a specific power level that may or may not be adjusted based upon context data (e.g., signal degradation information generally stored as RF data). Likewise, a more detailed example may adjust the frequency setting as a carrier frequency of the signal output from the node or the interval frequency in how often the signal is transmitted from the node. Exemplary timing settings may include other types of settings related to the signal broadcast from the node, such as duty cycle settings, etc.

In one embodiment, the updated value for the broadcast setting may be accessed on memory of the master node and determined by the master node itself (e.g., such as with adjustments made for context data). In another embodiment, the updated value for the broadcast setting may be received from the server and stored on the master node's memory.

At step 5220, method 5200 concludes by adjusting the broadcast setting of the node from a current value to the updated value. In one embodiment, the updated value may be a predetermined value related to a structure, where the structure is associated with the master node. In another embodiment, the updated value is a default broadcast value related to an interior of the structure, where the structure is a shipping container associated with the master node. Thus, when a particular part of a structure (e.g., the interior of a ULD) has been characterized with a similar node, the system may predetermine that a node entering such a structure should have its broadcast profile modified. For example, adjusting the broadcast setting of the node may involve modifying the broadcast profile of the node, where the broadcast profile defines the broadcast setting used when the node communicates with the master node. An exemplary broadcast profile may include different types of broadcast settings (e.g., RF transmission output power level setting, a frequency setting, a timing setting) that are relied upon by the node when broadcasting signals.

Those skilled in the art will appreciate that method 5200 as disclosed and explained above in various embodiments may be implemented on a master node, such as exemplary master node illustrated in FIG. 4, running one or more parts of a control and management code (such as code 425 for a master node device) to implement any of the above described functionality. Such code may be stored on a non-transitory computer-readable medium (such as memory storage 415 within an exemplary master node). Thus, when executing such code, a processing unit (such as unit 400 within a master node) may be operative to perform operations or steps from the exemplary methods disclosed above, including method 5200 and variations of that method.

In yet another embodiment, a master node is described for adjusting a broadcast setting of a node in a wireless node network. The master node comprises a processing unit and a memory coupled to the processing unit. The memory maintains code for execution by the processing unit (such as code 425) and an updated value for the broadcast setting of the node. The master node further comprises a first communication interface and a second communication interface, both of which are coupled to the processing unit. The first communication interface is operative to communicate with the node in the network, and the second communication interface is operative to communicate with a server in the network.

The processing unit of the master node, when executing the code maintained on the memory, is operative to perform particular steps and operations similar to those explained above with respect to various embodiments of method 5200. In particular, the processing unit is operative to detect that the first communication interface receives an advertising signal from the node, establish an active association with the node and store association data on the memory to reflect the active association between the master node and the node, access the updated value from the memory, and transmit a message to the node over the first communication interface, the message instructing the node to adjust a current value of the broadcast setting of the node to the updated value. In one embodiment, the node may be an ID node operative to communicate directly with the master node over the first communication interface but incapable of communicating directly with the server. And in another embodiment, the processing unit may be further operative to receive the updated value from the server over the second communication interface.

In still another embodiment of the master node, the processing unit may be further operative to modify a broadcast profile of the node, where the broadcast profile defines the broadcast setting used when the node communicates with the master node. The processing unit may then be operative to transmit the message by being operative to transmit information to the node over the first communication interface, where the transmitting information reflects the modified broadcast profile.

Enhanced Power-Related Alerts

As most mobile components in an exemplary wireless node network have a power source, such as a battery, that runs down over time with normal usage, an embodiment of the network may find an exemplary network device (such as an ID node or mobile master node) in a situation where power is running low. In such an embodiment, a network device, such as an ID node or master node, may advantageously notify other network devices (and in some cases, the server) of their current location and that they are running low on power in order to help prevent network devices unexpectedly and needlessly becoming inoperative due to lack of power. In general, the network device may send out an alert that its battery needs to be changed and its location.

As shown in FIG. 3, an exemplary ID node 120a includes a battery 355, which is a type of power source. Similarly, as shown in FIG. 4, an exemplary master node 110a may include a battery 470 (especially for mobile master nodes). In one embodiment, the processing unit of the respective network device (such as processing unit 300 of ID node 120a or processing unit 400 of master node 110a) may have an ability to detect the power status of the device (e.g., a current voltage level available across the terminals of the battery, within one of a range of voltages, etc.). In another embodiment, additional voltage detection circuitry may be incorporated as part of the power source or interfacing circuitry between the power source and the processing unit such that the processing unit is able to receive an indication of the current power status of the power source (and of the device given that the power source provides power for the device). For example, an exemplary processing unit 300 of an ID node may include buffer circuits that may interface with a voltage detection circuit, which is coupled to the output of the battery 355. The processing unit 300 may be operative to use its buffer circuitry and an output of the voltage detection circuit to detect a current power status of the battery.

With a detected power status, processing unit 300 may compare that current measurement with a threshold to determine an appropriate response. In one example, an exemplary threshold may be a designated voltage level. In another example, multiple thresholds may be employed where each time the current power status drops below a different threshold, a different type of enhanced power alert notification may be broadcasted and elicit a different type of response from devices that receive the notification. For example, a node may have several different thresholds—an initial "low" level threshold, a lower "urgent" level threshold, and an even lower "critical" level threshold. When the power source on the node goes below each of these different thresholds, different alert levels may be assigned.

In a further embodiment, an exemplary threshold may be based upon context data. For example, a threshold may be based on how much is remaining of the anticipated shipment journey, generally referred to as a shipment journey status. Thus, if the context data indicates that a node is in the midst of being shipped and is only 25% into its anticipated shipment journey, the threshold level may be higher than if only 10% of the anticipated shipment journey is left. In other words, when there is only 10% of the journey left, there is more comfort with a lower detected power status than if the node is only 25% into the journey and still has 75% of the journey (which, according to further context data, may require operations well beyond a predicted point of power depletion).

In a more detailed example, the node may further respond by only performing certain ones of prioritized functions or operations once the detected power status is lower than a threshold. In other words, the exemplary node may be operative to prioritize operations as an appropriate response to when the detected power status is below a threshold level.

In general, an alert level may be assigned by the network device reporting a low power situation. The alert level provides a general mechanism by which to externally indicate the severity of a low power condition on a particular network device. For example, a first alert level may be when the detected current power status is less than the initial "low" threshold; a second alert level may be when the detected current power status is below the lower "urgent" level threshold; and a third alert level may be when the detected current power status is below the "critical" level threshold. Actions to be taken with a node reporting such alert levels may depend on the contextual environment and location of the node.

FIG. 53 is a flow diagram illustrating an exemplary method for enhanced power notification from an ID node in a wireless node network having a master node and a server in accordance with an embodiment of the invention. Those skilled in the art will appreciate that the general steps recited specific to actions taken by an ID node (i.e., a node capable of communicating directly with the master node but incapable of communicating directly with the server) in this embodiment may be similarly taken by a mobile master node (i.e., a node capable of communicating directly with the server and separately communicating with an ID node) that is running low on power. Referring now to FIG. 53, method 5300 begins at step 5305 where the ID node detects a current power status for the ID node. In one embodiment, the power status may be a numeric voltage reading on the power source of the ID node. In another embodiment, the power status may be a qualitative range determination (such as one of multiple ranges of power for the power source on the ID node).

At step 5310, method continues by determining a current location of the ID node. In general, a location of the node may be relative to other nodes or structures or places, but may also be more precise, such as a set of coordinates (e.g., GPS coordinates identifying a location in three dimensions). In one embodiment, the current location may be stored as location data on the ID node. In another embodiment, the current location may be determined by the node (e.g., via location circuitry) or by requesting the node's a location from an associated node.

At step 5315, method 5300 concludes where the ID node broadcasts an enhanced power alert notification when the current power status of the ID node is below a threshold. The enhanced power alert notification is a message or signal that indicates that the current power status of the ID node is below the threshold and includes the current location of the ID node. In another embodiment, the enhanced power alert notification may also include a request for a replacement power source for the ID node. In still another embodiment, the enhanced power alert notification may also include a request to recharge an existing power source in the ID node. In this way, the exemplary notification provides an identification of the node issuing it along with relevant information about the notification and the low power event/condition leading up to it.

In another embodiment, method 5300 may also include the step of assigning an alert level based upon the current power status for the ID node, and broadcasting the enhanced power alert notification to include at least the current location of the ID node and the assigned alert level as a more detailed way to enhance the notification function. The assigned alert level may instruct the master node to take a responsive action when the master node receives the broadcasted enhanced power alert notification, where the responsive action depends on the assigned alert level.

In more detail, the assigned alert level part of the enhanced power alert notification may instruct the master node to notify the server (e.g., notify the server about the current location of the ID node and the assigned alert level) after the master node receives the broadcasted enhanced power alert notification.

And in a further embodiment, method 5300 may also include receiving, by the ID node, an alert response from the master node, where the alert response changes a broadcast setting for the ID node. For example, a master node may receive the broadcasted enhanced power alert notification from the reporting ID node, and be instructed by the server to have the reporting ID node change how often the node broadcasts given its location and where the server expects the reporting node to be headed (e.g., a storage facility in transit where the battery can be replaced).

In another embodiment, method 5300 may also include prioritizing one or more operations within the ID node to conserve power when the current power status of the ID node is below the threshold. Thus, the ID node may intelligently manage its onboard operations while also alerting other network devices about its power status.

Further still, an embodiment of method 5300 may establish the threshold as a value based upon context data related to the ID node. In more detail, the threshold may be a value based upon context data related to a shipment journey status for the node. Thus, context data may inform the ID node about where it is along its shipment journey, which can be used to dynamically determine a contextually appropriate value for the threshold and when the ID node should be issuing such enhanced power alert notifications.

Those skilled in the art will appreciate that method 5300 as disclosed and explained above in various embodiments may be implemented on an ID node, such as exemplary ID node illustrated in FIG. 3, running one or more parts of a control and management code (such as code 325 for an ID node type of network device) to implement any of the above described functionality. Such code may be stored on a non-transitory computer-readable medium (such as memory storage 315 within an exemplary ID node type of network device). Thus, when executing such code, a processing unit (such as unit 300 within an ID node) may be operative to perform operations or steps from the exemplary methods disclosed above, including method 5300 and variations of that method.

Likewise, those skilled in the art will further appreciate that another embodiment of method 5300 as disclosed and explained above may be implemented on a mobile master node instead of an ID node. Both types of network devices use power sources of a finite nature, and thus an exemplary mobile master node may also take advantage of such a method for enhanced power notification from the master node when the master node's power source becomes low.

In yet another embodiment, a network device (such as an ID node or a master node) capable of enhanced power notification is described. The network device comprises a processing unit and a memory coupled to the processing unit. The memory maintains code for execution by the processing unit (such as code 425 if implemented as a master node or code 325 if implemented as an ID node). The network device further comprises a short-range communication interface coupled to the processing unit and operative to communicate with another network device in the network. And the network devices further comprises a power source coupled to the processing unit and providing power for the network device.

The processing unit of the network device, when executing the code maintained on the memory, is operative to perform particular steps and operations similar to those explained above with respect to various embodiments of method 5300. In particular, the processing unit is operative to detect a current power status of the power source, determine a current location of the network device, and broadcast an enhanced power alert notification over the short-range communication interface when the current power status of the power source is below a threshold. The enhanced power alert notification indicates that the current power status of the power source is below the threshold and including the current location of the network device.

In one embodiment, the processing unit of the network device is operative to communicate directly with a master node in the wireless node network over the short-range communication interface but unable to communicate directly with a server in the wireless node network.

In another embodiment, the network device may also include a longer-range communication interface coupled to the processing unit and be operative to communicate with a server in the wireless node network. In more detail, the network device may further include location circuitry (such as a GPS chip) coupled to the processing unit and operative to receive at least one location signal and provide the current location of the network device to the processing unit as part of determining the current location of the network device. In still another embodiment, the processing unit of the network device may be operative to determine the current location of the network device by accessing data maintained on the memory, where the data represents the current location of the network device.

Enhanced Logistics Operations

Magnetically Altering Node Operation

A variety of enhanced embodiments may be achieved with a magnetically actuated node. While nodes communicate through their respective communication interfaces via conventional electronic (or electromagnetic waves) signals (such as with Bluetooth® enabled communications or NFC for short range communications and WiFi for medium/longer range communications) another medium of control and communication for a node relates to magnetic fields and, more specifically, to detecting a change in a magnetic field in the proximate environment of a node. In various embodiments disclosed below, a magnetic switch (e.g., a reed switch) may be deployed as part of a node's peripheral circuitry and may be used to alter the operation of a management function for the node.

Figure 48A:
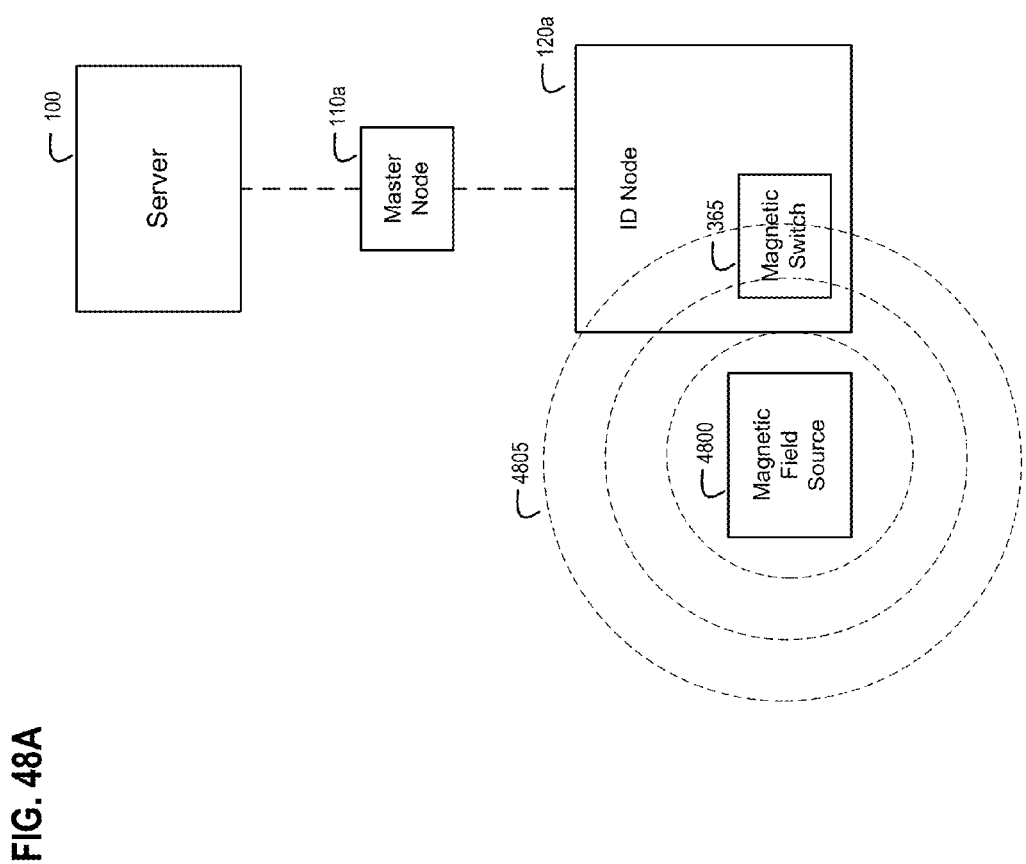
FIGS. 48A-48C are diagrams illustrating various configurations of an example wireless node network environment having an exemplary magnetically actuated node in accordance with an embodiment of the invention.

FIG. 3, as described above, shows magnetic switch 365 being part of or, in some instances, integrated into an ID node. FIGS. 48A-48C, 49A-49B, and 50A-50B show example configurations of a wireless node network deploying different embodiments of a magnetically actuated node. Referring now to FIG. 48A, the exemplary network includes server 100, master node 110*a*, and ID node 120*a*. Server 100 is in communication with master node 110*a*. And master 110*a* operates at a middle level of the network in communication with ID node 120*a* (typically on a separate communication interface than the communication path to server 100). As shown in FIG. 48A, ID node 120*a* includes a magnetic switch 365, which enables the ID node 120*a* (along with programming in code 325 of ID node 120a) to magnetically alter an operation of ID node 120a as explained in more detail in the below embodiments.

In FIG. 48A, magnetic switch 365 in ID node 120a is exposed to and detects a magnetic field 4805 from a magnetic field source 4800. When exposed to such a magnetic field 4805, magnetic switch 365 alters its switch configuration from either open to closed or closed to open. Various embodiments of a magnetic switch 365 may be employed with various poles and various throws depending on the particular needs of the implementation. For example, magnetic switch 365 may be a simple single pole, single throw switch that closes when exposed to a magnetic field. Other examples of a magnetic switch may be more complex with multiple inputs and outputs (multiplexer like configuration), but still controlled via a change in magnetic field.

Figure 48B:
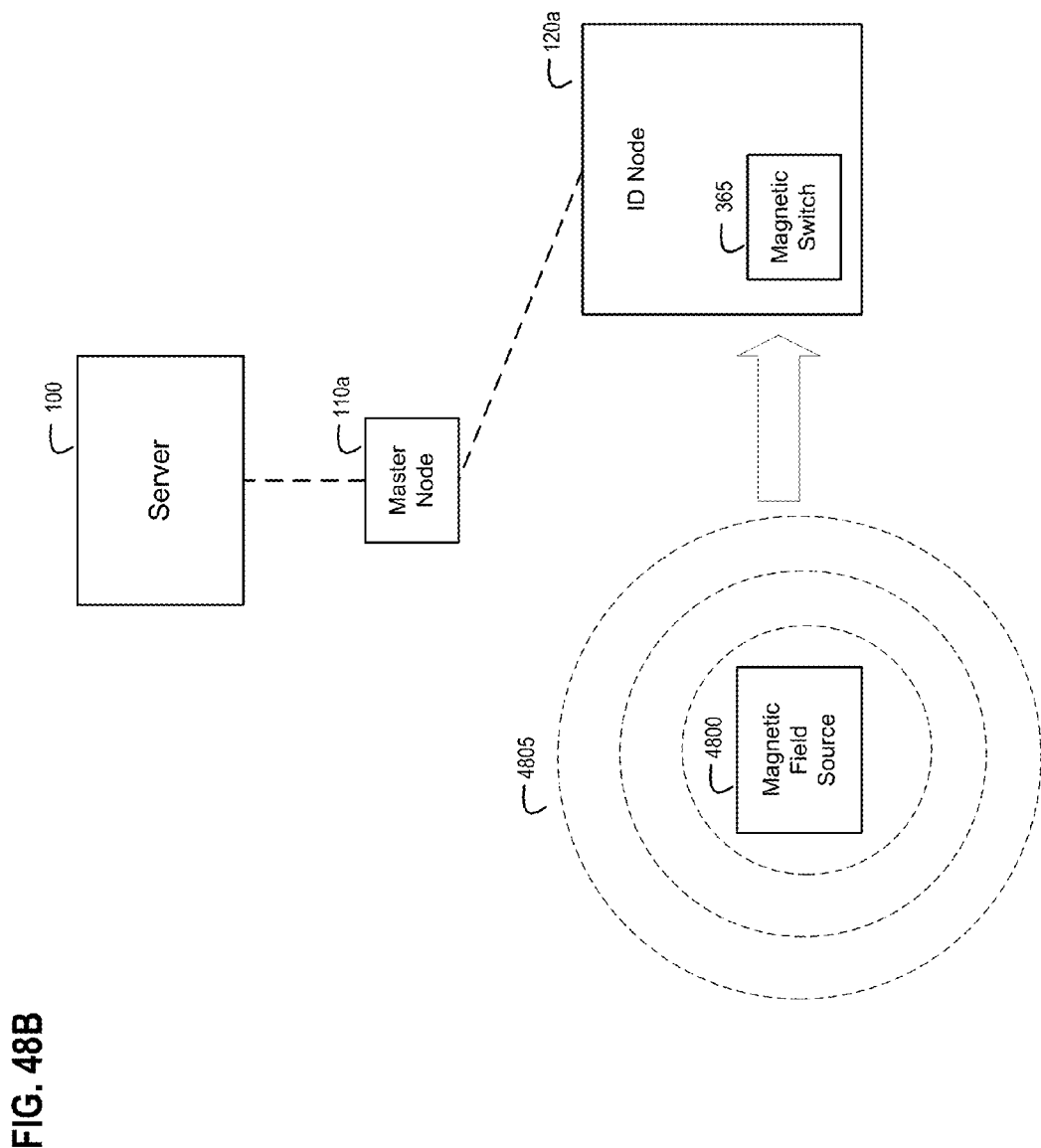
Figure 48C:
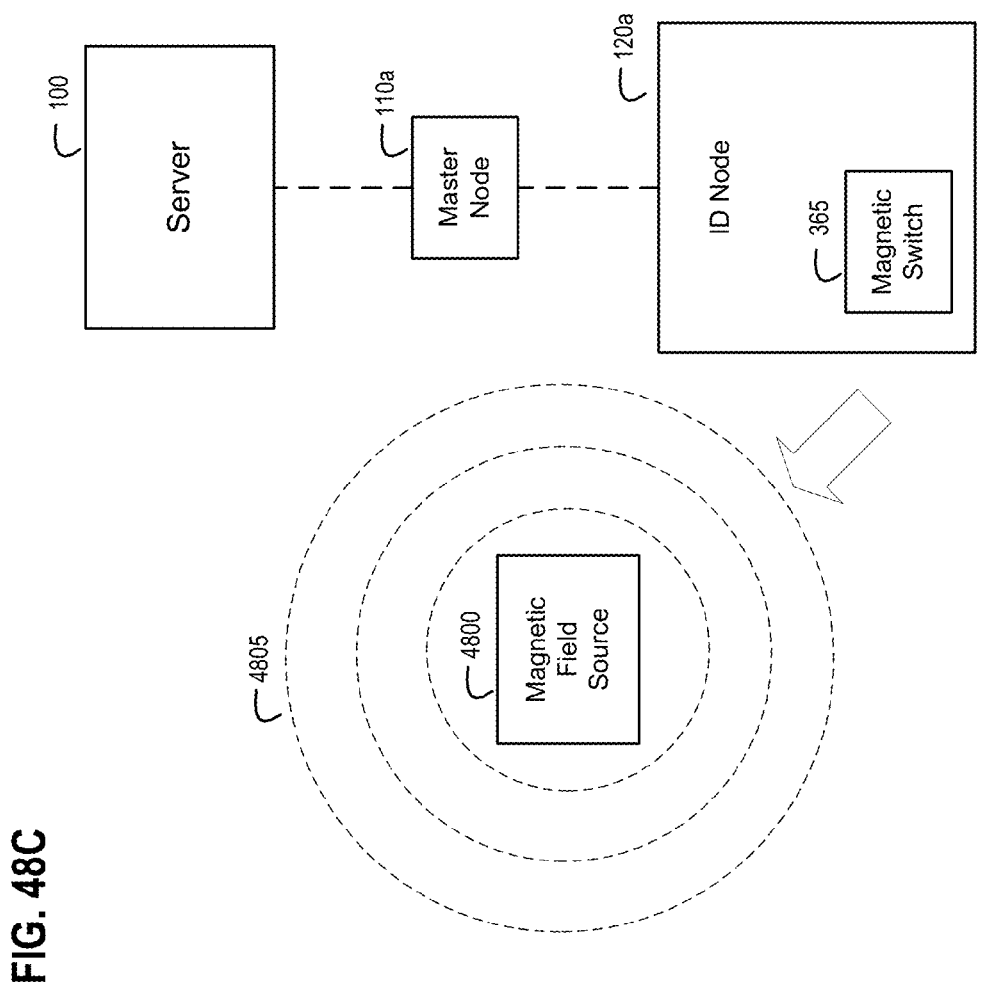

In FIG. 48B, ID node 120a moves away from magnetic field source 4800 and the magnetic fields 4805 emanating from the source. At a certain distance away from source 4805, magnetic switch 365 in ID node 120 may detect that the magnetic field in the proximate environment of ID node 120 is no longer the same and has changed compared to the situation illustrated in FIG. 48A. In other words, with a detected change in magnetic field (e.g., the substantial absence of field 4805), magnetic switch 365 actuates to a different state (e.g., from open to closed or vice versa) such that the ID node 120a may alter its operation in response. For example, when magnetic switch 365 changes states, this may cause a signal to be sent to the processing unit 300 of ID node 120a so that the ID node 120a may take action and alter its operation in response. Those skilled in the art will appreciate that, as shown in FIG. 48C, essentially the same response may be achieved in the ID node 120a if instead of moving the ID node 120a from a stationary magnetic field source 4800, and an example configuration moves the source 4800 relative to a stationary ID node 120a.

In a more detailed application embodiment, a customer may be ready to ship a package. The package may include a related ID node, or the ID node may be added to the package when the customer packages the item for shipment. In this embodiment, the ID node may have a magnet related to it that is initially held in a position that is next to or at least substantially proximate to the ID node so that the magnetic field generated by the magnet keeps the ID node in a low or unpowered state. When the customer desires to the ship the item and use the ID node as part of the packaged shipment of the item, the customer would remove the magnet, which can then energize and power the ID node. In a further embodiment, the removed magnet may be stored. Further, another embodiment may have the customer place and human/machine readable label or node identifier that indicates the packaged item is node-enabled (by a human reading the label or a scanner analyzing the label).

When the change in magnetic field is detected, for example by magnetic switch 365, embodiments may alter various types of management functions of ID node 120a. In general, a management function of ID node 120 is a function that impacts the operation of the node. Exemplary management functions of a node may include, but are not limited to, changing a power condition of the node (e.g., powering up the node, changing to a lower energy consumption mode, overriding a power setting previously established by a master node or server), transmitting an alert (e.g., notifying other nodes of the ID node's location, sending out a security alert related to an object associated with the ID node), changing association data related to the node, and logging usage information for the node, an item related to the node, or a moveable object separate from the node.

Figure 49A:
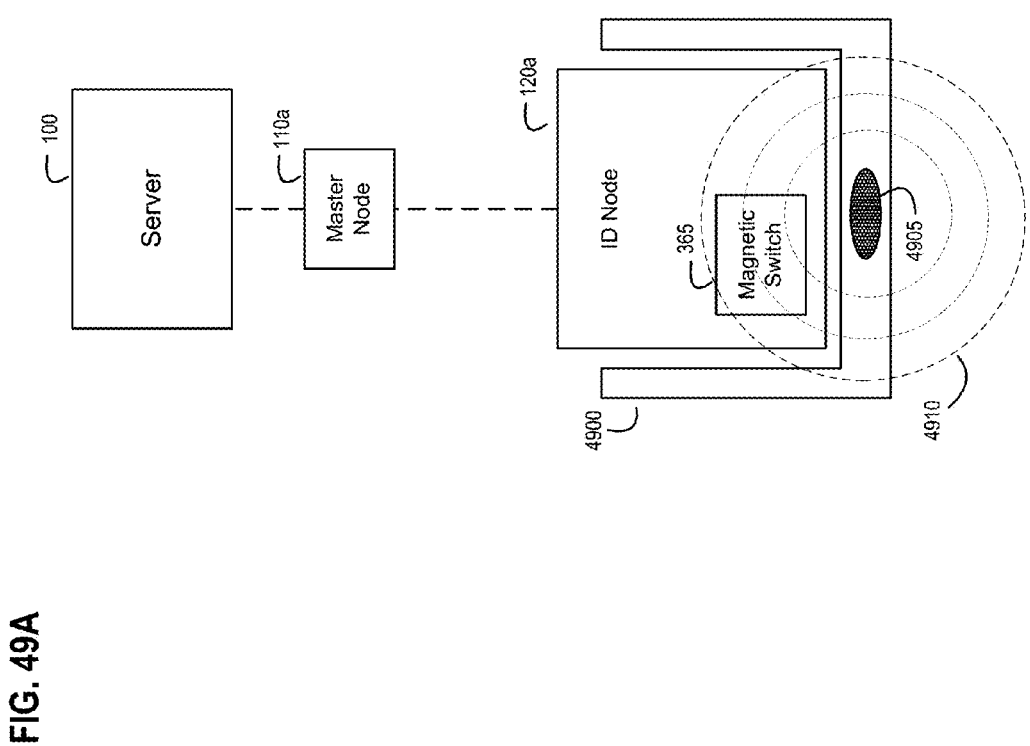
FIGS. 49A-49B are diagrams illustrating an example wireless node network environment having an exemplary magnetically actuated node and an exemplary magnetic placement support in accordance with an embodiment of the invention.
Figure 49B:
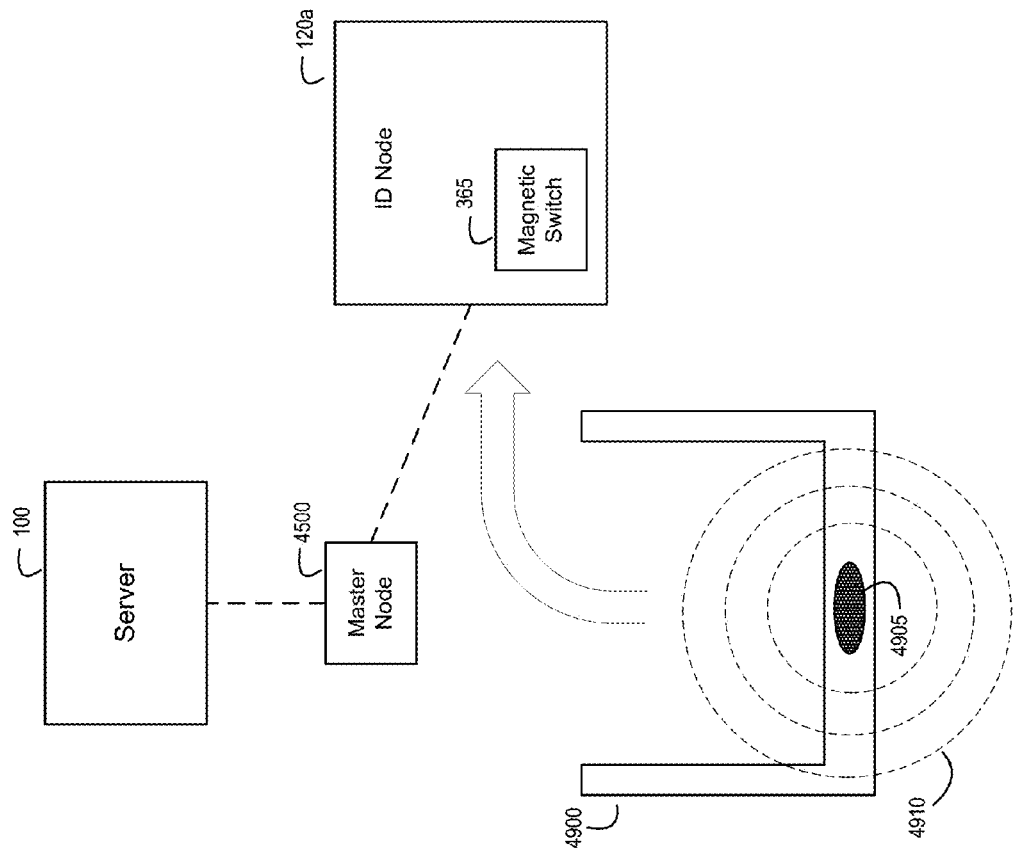

In more detail, referring to FIG. 49A, ID node 120a is shown being held in place by placement support 4900, which may in one example be a holster that holds the ID node 120a in place but may allow the ID node 120a to be easily moved off or out of placement support 4900 when desired. As shown in the example of FIG. 49A, placement support 4900 includes a magnetic field source 4905 that emanates a magnetic field 4910. When ID node 120a is moved out of placement support 4900, as shown in FIG. 49B, magnetic switch 365 is no longer exposed and can detect magnetic field 4910 and, as a result, changes states, which may cause a signal to be sent to the processing unit 300 of ID node 120a. And in response, a management function of ID node 120a may be altered.

Figure 50A:
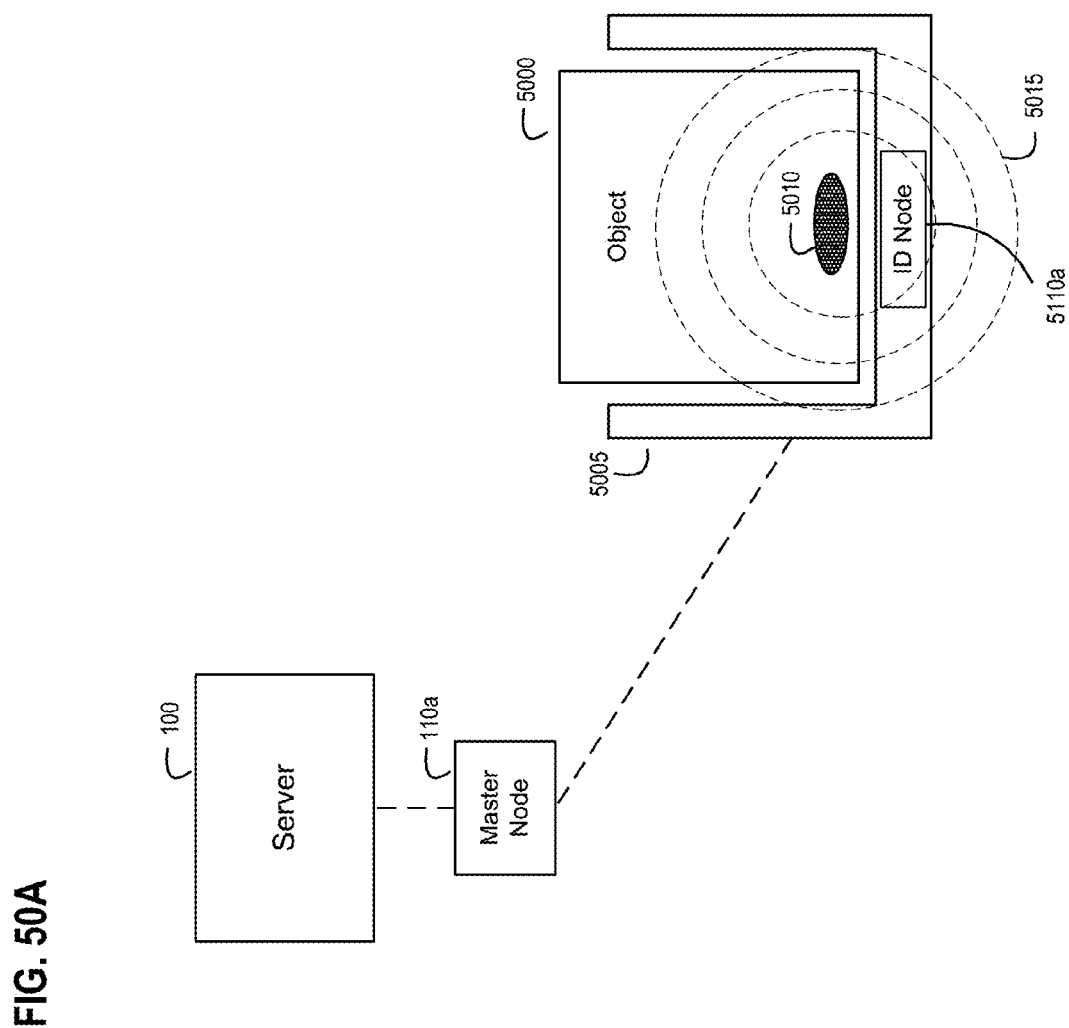
FIGS. 50A-50B are diagrams illustrating an example wireless node network environment having an exemplary magnetically actuated node integrated into an exemplary placement support for a moveable magnetic object in accordance with an embodiment of the invention.
Figure 50B:
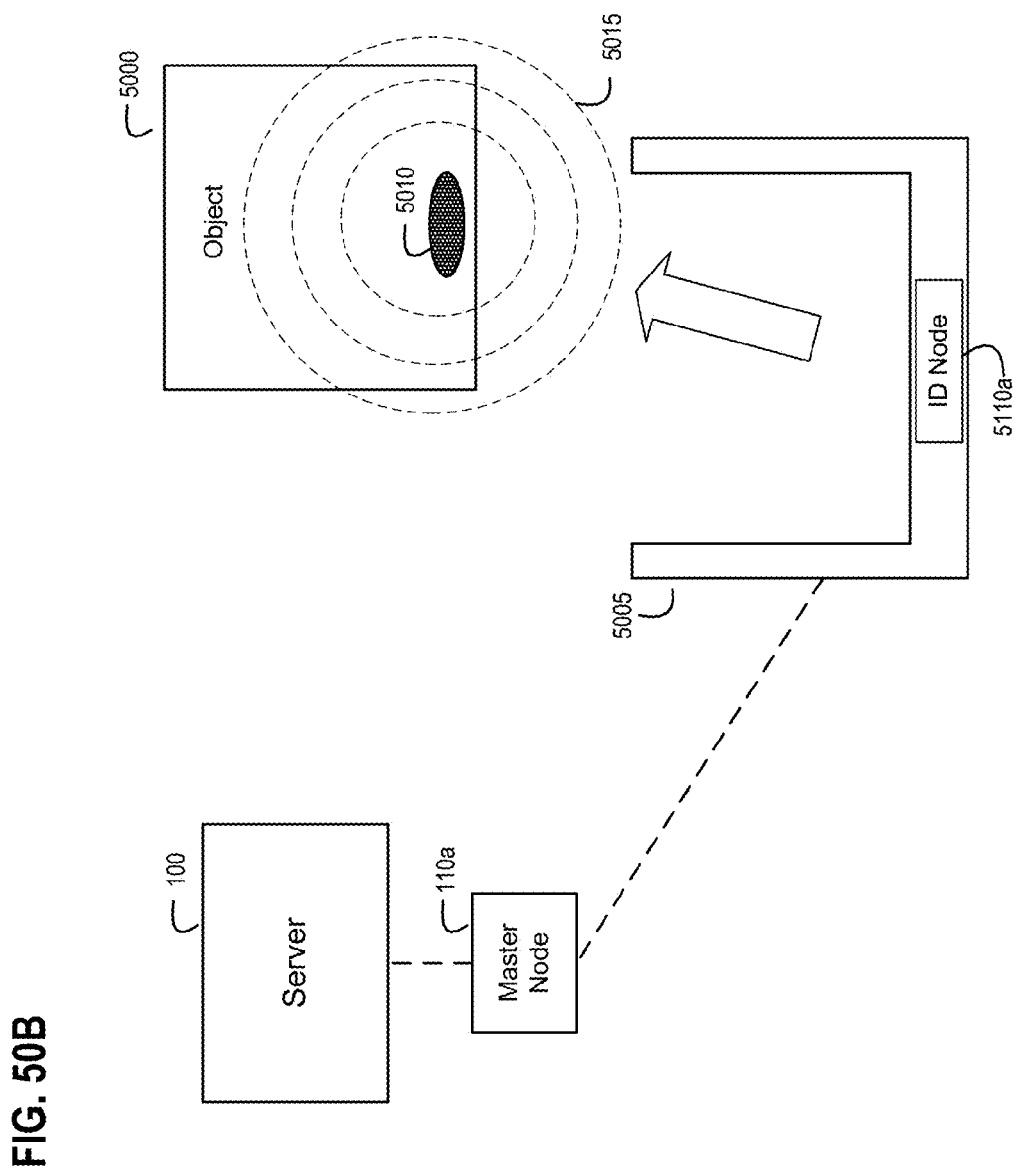

Another example configuration is shown in FIG. 50A, where ID node 5110a is part of placement support 5005, which supports object 5000. Object 5000 includes or has attached to it a magnetic field source 5010 emanating a magnetic field 5105. Thus, object 5000 is an example of a movable magnetic object relative to ID node enabled structure, such as placement support 5005. Those skilled in the art will appreciate that other types of structure may be used to house or hold an ID node near a moveable magnetic object. Likewise, those skilled in the art will appreciate that other types of structure may be used to house or hold a magnetic source relative to an ID node.

In the example of FIG. 50A, a magnetic switch within ID node 5110a may be exposed to the magnetic field 5105. However, when the object 5000 is moved from placement support 5005 and the magnetic switch in ID node 5110a (in placement support 5005) is no longer exposed to the magnetic field 5105, this change in magnetic fields causes a change in state for the magnetic switch and a responsive altering of a management function in ID node 5110a.

FIG. 51 is a flow diagram illustrating an exemplary method for magnetically altering an operation of a node in a wireless node network having a master node and a server in accordance with an embodiment of the invention. Referring now to FIG. 51, method 5100 begins at step 5105 the node detecting one or more magnetic field changes in a proximate environment of the node. In one example, the one or more magnetic field changes reflect an increase in a magnetic field in the proximate environment to the node. In another example, the one or more magnetic field changes reflect a decrease in a magnetic field in the proximate environment to the node. For example, with reference to FIG. 49A-49B, the change in magnetic fields in the proximate environment to ID node 120a would be an increase when ID node 120a is moved off, out of, or away from placement support 4900 (which includes a magnetic field source 4905 in it). In an example where placement support 4900 is a holster or other type of holder and ID node 120a is part of an item placed in and out of the holster, the fields would be increasing when placing the item and ID node 120a in the holster 4900 but decreasing when removing the item and ID node 120a from the holster 4900.

In one embodiment, the detecting step may further comprise sensing an altered configuration of a magnetic switch integrated within the node. For example, magnetic switch 365 may be in one state (e.g., open) when exposed to magnetic field 4910 in FIG. 49A, but may shift to be in another state (e.g., closed) when that magnetic field 4910 is decreased when ID node 120a is moved from placement support 4900 in FIG. 49B. The resulting change in circuit state for magnetic switch 365 (or more generally a different configuration of the switch) may be sensed by the processing unit on ID node 120*a*, which can then react and alter a management function of ID node 120*a*.

In another embodiment, the detecting step may comprise having the node detect the one or more magnetic field changes in the proximate environment to the node when the node has been separated from a placement support for the node, and where the placement support includes the source of the magnetic field. This embodiment is exemplified in FIGS. 49A-49B, where placement support 4900 includes magnetic field source 4905 and ID node 120*a* is separated from that support 4900 as shown in FIG. 49B.

At step 5110, method 5100 continues with the node altering a management function of the node in response to detecting the magnetic field changes. For an ID node deployed in a wireless node network and being in communication with a higher level master node, which is in further communication with a server, the ability to be magnetically actuated to generally alter an operational or management function of the ID node is advantageous. Various embodiments may alter a node's operation based upon the change in magnetic fields in a variety of ways.

In one example, the altering step may be accomplished when the node changes a power condition of the node in response to the detected one or more magnetic field changes. In more detail, the node may change the power condition of the node by selectively energizing the node from a power source (e.g., a battery 355) by actuating a magnetic switch integrated into the node (such as switch 365 in ID node 120*a* shown in FIG. 3) to enable powered operation of the node in response to the detected one or more magnetic field changes. In that detailed example, the magnetic switch may be wired within the node to separately be able to cut on and off a power signal that energized all or at least part of the ID node. As such, the change in magnetic field operates as a control mechanism by which the ID node may be turned on from an off position (or more generally made to change a power state within the ID node—e.g., from a low power state to an alert or higher power state).

In another example, the altered management function may be having the node override a power setting previously established in response to a server command. For example, the node may have recently received a command from a server (via a message from a master node), and the node responded to the command by changing a power setting on the node. For instance, the node may have set its RF output power level to a minimum power level. However, in response to the detected change in magnetic field, the node may override that power setting as a type of altered management function of the node.

In another example, the altered management function may comprise transmitting an alert, such as a security alert or movement alert. More specifically, the altered management function may comprise having the node transmit certain relevant information to the master node as a way or reporting what was detected. The relevant information may, for example, include a movement alert along with location information related to the node. The movement alert related to the node may update the master node that the node has been moved, which may be of concern if the expectation is that the node should not be moving. This may cause the master node to also forward such information on to the server depending on the content of the movement alerts (e.g., a particular level of the alert indicating a quantified extent of urgency and immediacy for continued hierarchical reporting up to the server). The location information related to the node may help inform the master node of any existing or new location or movement direction for the reporting node.

In another embodiment, the movement alert may indicate a change from between moving states—where the node is moving or no longer moving. In an example, a trailer hitch and related trailer ball may be used together. The ball may be equipped with a magnet (e.g., with support 4900 of FIG. 49B implemented as the ball) and the hitch contains a node with a magnetic switch (e.g., with ID node 120*a* and magnetic switch 365 as the node and magnetic switch, respectively). The magnetic switch may, for example, be internal to the node or externally exposed for ease of physical pairing and durability. When the magnetic switch connection between the two is changed (e.g., opened), it indicates to the backend server system (through the uploaded node data), that the trailer no longer is connected to the towing vehicle. This may be used for yard management of trailers through their location, productivity of applications, and security applications where the alert is both a movement alert and a security alert. Those skilled in the art will appreciate that in another embodiment (such as that illustrated in FIGS. 50A and 50B), the ball and hitch implementation may be reversed.

In an exemplary security embodiment, the movement alert may be used as a security trigger where detected change in magnetic fields may indicate an object may have been illicitly removed. In such a situation, the node may immediately start reporting its status. When the message has been communicated through a master node to the backend server, the server may determine if the break of the connection was expected or the result of an illicit action Transmitting the alert may, in another embodiment, be accomplished by transmitting the alert by the node to a predetermined set of nodes in the network defined by a filtering mode set by the server. For example, the server may set a "local" or "regional" filtering mode (as explained with respect to the Node Filtering Manager part of exemplary server control and management code 525) as a way to manage communications between nodes and an anticipated communication burden on a master node. The predetermined set of nodes defined by the filtering mode may be those master nodes which the node is allowed to contact and with whom the node may associate.

In still another example, the altered management function comprises altering association data related to the node. Association data, such as association data 340 maintained in memories 320 and 315 on ID node 120*a*, may reflect a logical connection that is tracked. For example, the association may be a passive or active connection of the ID node 120*a* with other nodes (such as master node 110*a*), and/or an association with one or more objects (e.g., vehicles, buildings, and places).

In a further example, altering association data may involve changing the association data to reflect a change in an inventory management aspect of an item related to the node. Use of an exemplary wireless node network may have nodes associated with items in an inventory (e.g., an inventory of trucks, ULD containers, pallets, etc.). In general, an inventory management aspect of an item related to a node is an aspect of how to manage an inventory of such items. In more detail, changing an inventory management aspect may involve changing the association data to indicate movement of the item related to the node, disposal of the item from the inventory, or adding the item to the inventory. For example, a trailer may associated with a magnetically actuated node and the trailer's node is positioned proximate a magnetic field source that is stationary. When the trailer moves from a storage spot, the movement of the trailer and its node away from the stationary magnetic field causes a change in magnetic fields near the node. As a result, the change in magnetic fields may be detected, and association data may be changed to indicate movement of the trailer. This may also be accompanied by an alert, such as a security alert related to movement of the trailer.

In another embodiment, the altered management function comprises logging usage information for an item related to the node. The detected change in magnetic field may, in some situations, represent movement or use of the item related to the node. For example, in the moving trailer example from above, the detected change in magnetic fields may indicate the trailer is being put into use and the node may log usage information for the trailer as a resulting type of altered management function. Such usage information may include, for example, time-related data on when the item has been moved relative to a source of the magnetic field. In other examples, the usage information may also or alternatively include location data on where the item is moving, or sensor information collected by various environmental sensors on the node to reflect an exposed environment being logged as the item is being used.

In one embodiment, the node may be part of a placement support for a moveable object having a source of the magnetic field. In general, a placement support may generally be structure that holds, couples to, or is placed next to a moveable object (such as a holster and gun relationship) where the placement support and the object are typically used together. In a more detailed embodiment, the altered management function may comprise logging usage information for the moveable object having the source of the magnetic field. In the embodiment shown in FIGS. 50A-50B, the node 5110*a* is stationary while object 5000 is moveable and the object includes magnetic field source 5010 that produces magnetic field 5015. As moved, the object 5000 (shown in FIG. 50B) is separated from the placement support 5005 and being used for a particular purpose. For example, object 5000 may be implemented as equipment (e.g., a handgun, a scanning tool, a piece of mobile test equipment) while placement support 5005 may be implemented as a holder or support for the equipment (e.g., a holster for the handgun, a holster for the scanning tool, a charging cradle for the mobile test equipment, etc.). As the object is moved, the magnetic field changes and usage information on the object may be collected and logged. Such usage information may include information related to time and location data.

In a more detailed example, the stationary node may be incorporated into or simply be part of a holster. The movable object may be implemented as a scanning gun having a magnet within it so that when the scanning gun is placed in the holster, the magnetic field emanating from the magnet are detected by and exposed to a magnetic switch in the holster's node. When the scanning gun is removed for use scanning codes or labels, the magnetic field is no longer exposed to the node in the holster, and the node responds to this change in magnetic field by logging usage information about the scanning gun.

At step 5115, method 5100 concludes by transmitting, by the node to the master node, information about the altered management function to be forwarded to the server. For example, an ID node may transmit a message to an associated master node where the message reports the altered management function (e.g., logged usage information, an alert about movement of the item, etc.). The message also will have the master node forwarding it to the server so that the server may be kept up to date on the ID node and updates from it, such as whether it is moving, whether inventory is changing, whether items that are moving are a security issue, etc.

Additionally, method 5100 may involve a selection of which management function to alter. In other words, the detecting of changing magnetic fields may allow for an alternative type of command input for a wireless node. For example, a type of code may be used for a particular number and/or duration of magnetic field changes detected, which may collectively indicate a certain management function to be altered by the node. In more detail, the multiple magnetic field changes may include a series of magnetic field changes over a period of time. These changes may be a detected pattern of changes. As such, the node's magnetic switch integrated within a magnetically actuated node may be implemented such that it may detect (or in combination with the node processing unit) the series of magnetic field changes over the period of time.

In a more detailed embodiment, multiple conditions may be monitored for detection from the magnetic field changes. For example, when there is a detected change on the magnetic switch, based upon a first stage or a first condition, the node monitors and attempts to detect a second stage or second condition while also causing a first management function to be changed. In other words, an embodiment may nest conditions and different altered management functions based upon the different conditions (e.g., setting alerts based upon movement, time or other conditions).

Those skilled in the art will appreciate that method 5100 as disclosed and explained above in various embodiments may be implemented on a node, such as exemplary ID node 120*a* as illustrated in FIG. 5 (or ID node 120*a* illustrated in FIGS. 48A-48C and 49A-49B, or ID node 5110*a* illustrated in FIGS. 50A-50B), running one or more parts of a control and management code (such as code 325) to implement any of the above described functionality. Such code may be stored on a non-transitory computer-readable medium (such as memory storage 315 within an exemplary ID node). Thus, when executing such code, a processing unit (such as unit 300 within a ID node) may be operative to perform operations or steps from the exemplary methods disclosed above, including method 5100 and variations of that method.

In yet another embodiment, a magnetically actuated node (such as an ID node) is described for magnetically altering an operation of the node in a wireless node network. The magnetically actuated node comprises a node processing unit, and a node memory coupled to the node processing unit. The node memory maintains code for execution by the node processing unit, such as code 325. The magnetically actuated node further comprises a first communication interface coupled to the node processing unit and is operative to communicate directly over a first communication path with a master node. The master node is deployed in communication with a server in the network over a second communication path.

The node further includes a magnetic switch having an output coupled to the node processing unit. The control of the magnetic switch is responsive to one or more magnetic field changes in a proximate environment of the magnetically actuated node.

The node also includes a power source for selectively energizing the magnetically actuated node. In one embodiment, the power source is a battery that provides electrical power to the components of the node. In one embodiment, the exemplary power source may be coupled to the magnetic switch such that the magnetic switch operates as a switch between the power source and the rest of the components of the node (or at least a subset of the components of the node).

The processing unit of the node, when executing the code maintained on the memory, is operative to perform particular steps and operations similar to those explained above with respect to the various embodiments of method 5100. In particular, the processing unit is operative to alter a management function of the magnetically actuated node when the magnetically actuated switch responds to the one or more magnetic field changes and sends a response signal from the output of the magnetically actuated switch to the node processing unit, and transmit a message to the master node, the message comprising information about the altered management function to be forwarded to the server.

In a related embodiment, the magnetically actuated node may further include a second communication interface and location circuitry. The second communication interface may be coupled to the node processing unit and operative to communicate over the second communication path with the server. The location circuitry has an input coupled to an antenna that receives location signals, such as GPS signals. The location circuitry also may have an output coupled to the node processing unit such that the circuitry receives one or more location signals in the input from the antenna and provide a determined location of the magnetically actuated node on the output to the node processing unit.

In another embodiment where the shipping ID node may be further utilized as an alarm sensor, the node may be configured or attached relative to a door along with a magnet on the door jamb (or vice versa). Upon opening of the door, the magnet and the node (having the magnetic switch) are separated causing a detection of a magnetic field change. As such, the node may transmit an alarm message to another node (or user access device operating as a node) or to the server for further distribution of the alarm message. Thus, an embodiment of the ID node may be used after the package is delivered as a type of mobile intrusion detection system.

Integrated Node in Communications Coupler or Adaptor

In one embodiment, a network device, such as an ID node or master node, may also be useful in a remote monitoring situation and especially when monitoring signals exchanged between conveyances (e.g., between a tractor and its trailer, between two trailers, between different railway vehicles, between a towing maritime vehicle and a towed barge, etc.). By monitoring such signals using a node, the wireless node network may be used to detect when there are problems (e.g., the trailer is disconnected from its tractor) and report a status without having to interfere with the electronic systems communicating onboard the respective conveyances. As such, an embodiment may monitor without having to interfere or make changes to any detected data or communications between such conveyances.

Conventionally, tractors and trailers (like many other types of known conveyances or means for transportation) may be mechanically coupled together so that the tractor can pull the trailer with its cargo in an efficient and cost effective manner. Various links between the tractor and the trailer may provide vehicle subsystems with power or other signals to operate, e.g., lights, brakes. Thus, hydraulic, pneumatic, electrical, and other subsystems on the tractor/trailer combination may have associated electrical conductors and pneumatic lines running there between so these subsystems can operate appropriately and in a coordinated fashion onboard the two conveyances.

In some situations, the electrical subsystems of both the tractor and trailer operate in a manner which requires coordination between the electrical components on each to operate the tractor/trailer combination safely and effectively. Conventionally, in order to coordinate such operation and to supply power from the tractor to the trailer, a seven-pin connector has been used by the trucking industry to accomplish these and other electrical objectives. The connector includes two mated and coupler connectors that can be disengaged or engaged to permit the tractor and trailer combination to be connected in order to communicate and disconnected when the tractor and trailer need to separate. These seven-pin connectors also are well known and have been specified by the Society of Automotive Engineering "SAE" according to the standard number J560 (hereinafter referred to as "SAE J560").

Figure 54:
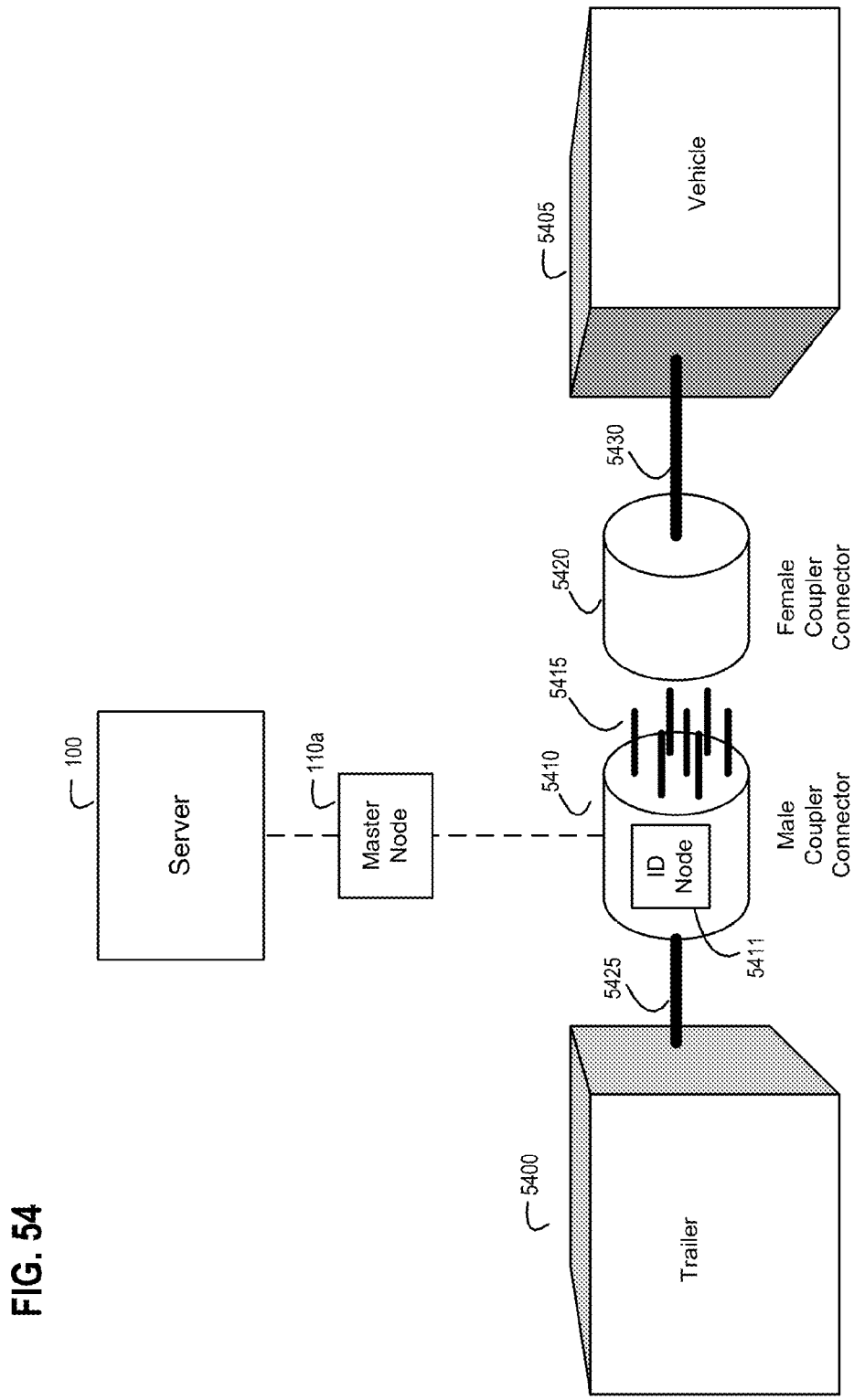
FIG. 54 is a diagram illustrating an exemplary coupler connection between two conveyance systems having an integrated node in accordance with an embodiment of the invention.

FIG. 54 is a diagram illustrating an exemplary coupler connection between two conveyance systems having an integrated node in accordance with an embodiment of the invention. Referring now to FIG. 54, a vehicle 5405 (such as a tractor or truck) and its trailer 5400 are illustrated in a simplistic manner as being connected together. Specifically, an electronic system aboard vehicle 5405 (such an anti-lock braking system (ABS) for the vehicle) communicates with an electronic system aboard trailer 5400 (such as the ABS system for the trailer) over a coupler connection that provides a communication path (e.g., multiple power and signal lines) for signals passing between the vehicle 5405 and trailer 5400. In more detail, as shown in the example illustrate in FIG. 54, an exemplary coupler connection may include a set of mated coupler connectors—e.g., male coupler connector 5410 and female coupler connector 5420. Male coupler connector 5410 is shown having pins 5415 extending from a face of the connector and a cable 5425 on the back of the connector. Those skilled in the art will appreciate that cable 5425 is operatively connected to an electronic system, such as an ABS system, onboard trailer 5400. The pins 5415 from the male coupler connector 5410 mate with sockets (not shown in detail) in female coupler connector 5420, which has a similar cable 5430 to a similar electronic system onboard vehicle 5405.

In one embodiment, a node (generally referred to as a network device) may be deployed and disposed within the coupler connection. As shown in FIG. 54, an ID node 5411 is shown integrated as part of the male coupler connector 5410 and connectable to master node 110b, which may communicate with server 100 in an exemplary wireless node network. In general, node 5411 can be powered (or charged) through a power line passing through the coupler connection. The node 5411 may essentially monitor, detect, and record data that appears on the signal lines passing through the coupler connection, and provide such data wirelessly via broadcasts from the node. As such, node 5411 is able to detect when trailer 5400 is disconnected from vehicle 5405 as well as monitor the operating conditions of the vehicle 5405 and trailer 5400 to the extent such conditions are apparent from any of the signals passing through the coupler connection.

FIG. 55 is a more detailed diagram illustrating the exemplary coupler connector between two systems having an integrated node in accordance with an embodiment of the invention. Referring now to FIG. 55, male coupler connector 5410 is shown in more detail with ID node 5411, pins 5415, and cable 5425. More specifically, male coupler connector 5410 is shown with ID node 5411 integrated as part of the coupler and, more generally, disposed within the coupler. In another embodiment, a similar ID node may be integrated within a female coupler instead of the male coupler.

As shown in FIG. 55, pins 5415 are essentially ends of signal lines that pass through the coupler connector 5410 and extend out of the face of coupler connector 5410. In this example, one of the signal lines is a power line that may provide power from vehicle 5405 to trailer 5400. As such, ID node 5411 may take advantage of the power line, which may be connected with a power connection 5414 to ID node 5411. Those skilled in the art will appreciate that power connection

5414 may include both a ground and a supply voltage in order to energize and power circuitry within ID node 5411.

And as shown in FIG. 55, ID node 5411 also includes signal monitor circuitry 5412 that has a collective input (e.g., the separate connections 5413 to different signal lines in the coupler connector 5410) and an output (not shown) coupled to the processor of the ID node 5411. In general, the output provides detected data from the signal lines being monitored on inputs 5413 to the processing unit. In more detail, the signal monitor circuitry 5412 may be implemented using peripheral circuitry described for an ID node with respect to FIG. 3 (e.g., various peripherals such as timer circuitry, USB, USART, general-purpose I/O pins, IR interface circuitry, DMA circuitry, additional logic chips, and relays that make up the ID node).

While FIGS. 54 and 55 illustrate an exemplary integrated ID node disposed within a coupler connection as part of one of the mated coupler connectors, other embodiments may not require a special integrated node coupler connector dedicated to a particular conveyance, such as a vehicle 5405 or trailer 5400. In particular, an embodiment may deploy a node (more generally a network device) as part of an adapter that can be part of a coupler connection. With such a node-enabled adapter being placed in-line with an existing convention mated coupler connector pair, a greater applicability may be achieved as the adapter may be used in less dedicated situations.

Figure 56:
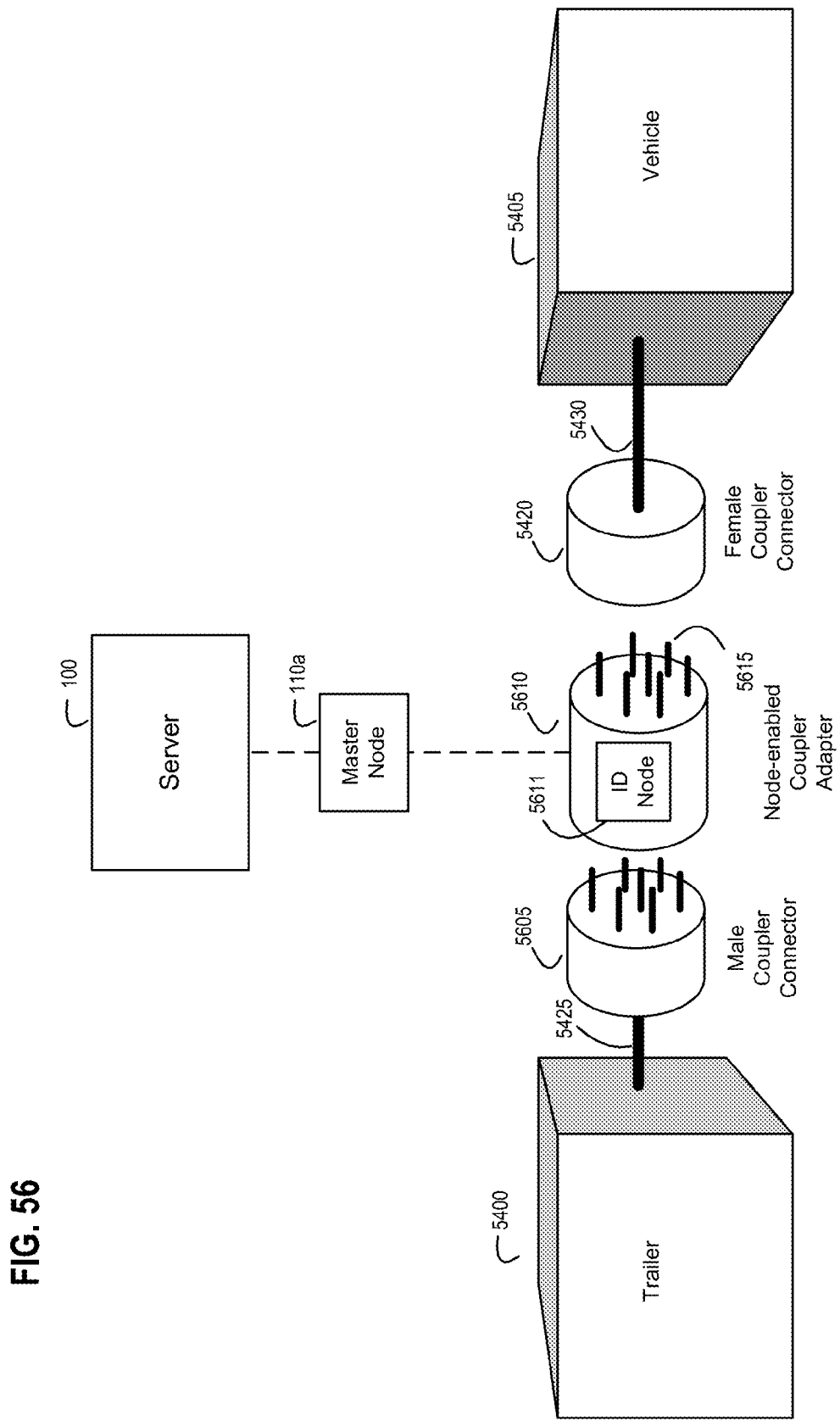
FIG. 56 is a diagram illustrating another exemplary coupler connection between two conveyance systems having an adapter node in accordance with an embodiment of the invention.

FIG. 56 is a diagram illustrating another exemplary coupler connection between two conveyance systems having an adapter node in accordance with an embodiment of the invention. As shown in FIG. 56, an exemplary adapter 5610 is disposed between a mated set of coupling connectors (male coupler connector 5605 and female coupler connector 5420). The adapter 5610 is essentially a plug adapter between the connectors and includes an ID node 5611 integrated within the adapter 5610 in much the same way as ID node 5411 is shown integrated within connector 5410 in more detail in FIG. 55.

While FIGS. 54-56 are illustrated showing exemplary conveyances as a vehicle 5405 and a trailer 5400, other types of conveyances or modes of transportation may also be applicable. In more detail, such exemplary conveyances may include, but are not limited to, different types of vehicles (e.g., an automobile, a truck, a tractor, farm equipment, construction equipment, marine vehicles, a locomotive, etc.) and trailers (as well as barges, trams, buses, other railway vehicles, etc.).

Additionally, those skilled in the art will appreciate that such integrated nodes as ID node 5611 and 5411 may be deployed in non-conveyance examples in other embodiments between disparately located electronic modules that need to communicate over a connecterized communication path. For example, a generator may be temporarily deployed to provide power and a node may be integrated into an adapter or connector as part of a coupler connection between the generator and what may be powered by the generator. Thus, the node may provide information related to the status of the generator without interfering with the operation of the generator.

Figure 57:
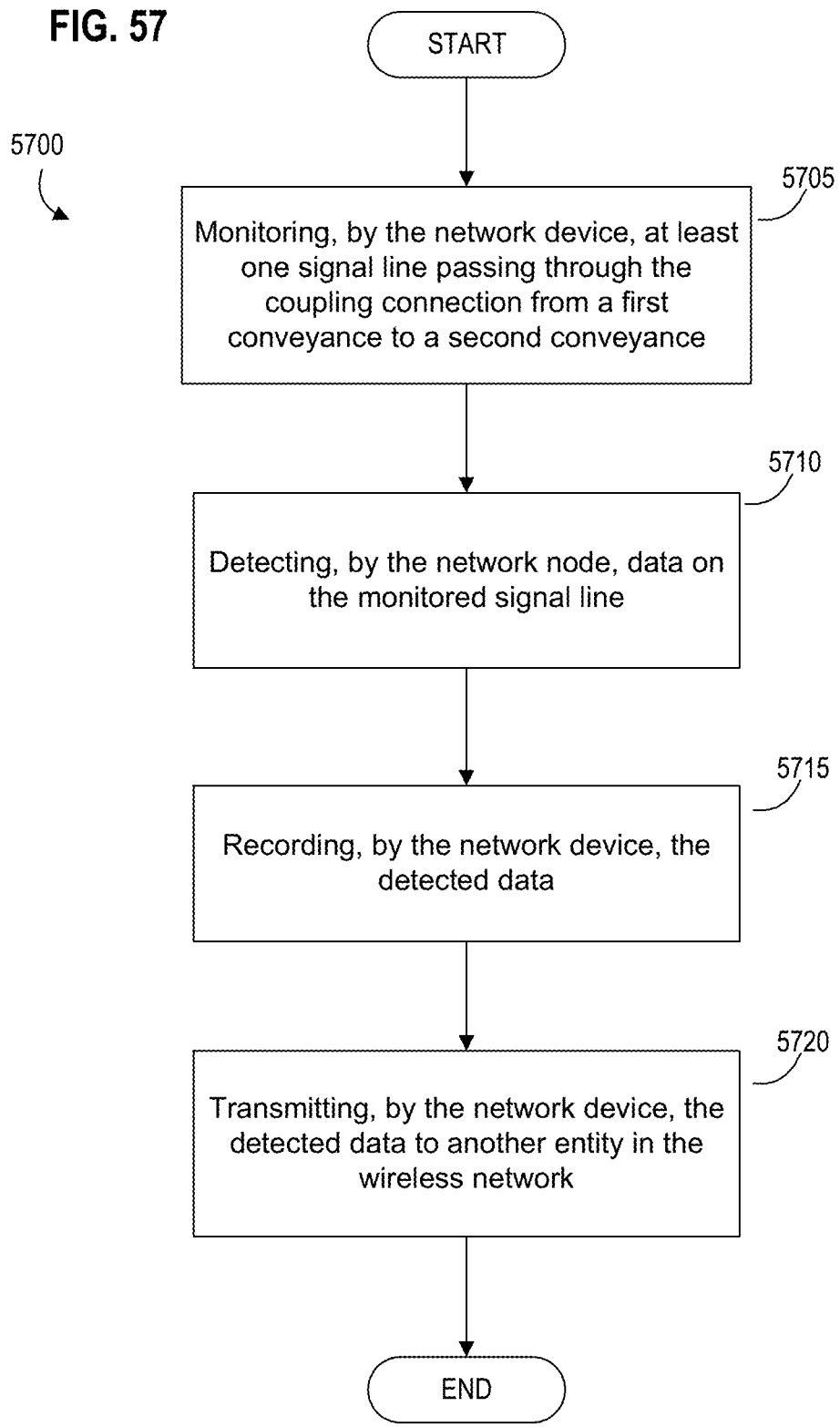
FIG. 57 is a flow diagram illustrating an exemplary method for monitoring at least one signal passing through a coupling connection having a network device that communicates on a wireless node network in accordance with an embodiment of the invention.

FIG. 57 is a flow diagram illustrating an exemplary method for monitoring at least one signal passing through a coupling connection having a network device that communicates on a wireless node network in accordance with an embodiment of the invention. Referring now to FIG. 57, method 5700 begins at step 5705 with the network device monitoring at least one signal line passing through the coupling connection from a first conveyance to a second conveyance (e.g., one or more of the lines monitored by connections 5413 of signal monitoring circuit 5412 in ID node 5411 shown in FIG. 55).

As mentioned, a network device is a general designation for a component, in the wireless node network in embodiments. In one embodiment, the network device may be an ID node operative to communicate directly with a master node in the wireless network but not operative to communicate directly with a server (another entity in the wireless node network). In another embodiment, the network device is a master node operative to communicate directly with a server as another entity in the wireless node network.

The coupling connection, for example, may comprise a mated set of connectors such that the network device may be integrated into one of the mated connectors. In the example shown in FIG. 55, ID node 5411 (a type of network device) is illustrated as being integrated into the male coupling connector 5410. However, those skilled in the art will appreciate that such a network device may also be integrated into the female coupling connector 5420.

In one embodiment, the coupling connection comprises an adapter disposed between a mated set of coupling connectors and, as such, the network device is integrated as part of the adapter. For example, FIG. 56 illustrates an exemplary adapter 5610 having ID node 5611 (a type of network device) integrated as part of adapter 5610. In another embodiment, the adapter may be disposed between a mated set of anti-lock braking system connectors linking a vehicle to a trailer.

Referring back to step 5705, method 5700 monitors at least one signal line passing through the coupling connection from the first conveyance to the second conveyance. In one embodiment, the first conveyance is a vehicle and the second conveyance is a trailer. A vehicle, in this embodiment, is a general term for a transport, and may include (as noted above) an automobile, a truck, a bus, a tractor, farm equipment, construction equipment, marine vehicles, a locomotive (a type of railway vehicle). Likewise, an exemplary trailer is a general term for transport equipment that is towed or pushed, such as a barge, carriage cars on trams, railway cars (another type of railway vehicle) towed or pushed by a locomotive. Other examples of conveyances may include a maritime conveyance (e.g., marine vessel, tugboat, ship, boat) where a second conveyance may be implemented as a maritime barge that is coupled to the towing maritime vessel and having a coupling connection between various electronic systems on the respective conveyances.

At step 5710, the network device detects data on the monitored signal line. For example, as shown in FIG. 55, data on one or more of the signal lines going through cable 5425 and connector 5410 may be detected using connections 5413 of signal monitoring circuitry 5412 on ID node 5411. For example, the data may include useful electronic information flowing from one conveyance to another (and vice versa) indicating a status of operations between and/or of the respective conveyances. In another example, such monitoring may detect when the first conveyance and the second conveyance are disconnected based upon the monitored status of the at least one signal line.

In a more general embodiment, the detecting step may further have the network device detecting a change in state for the coupling connection. For example, the change in state for the coupling connection may reflect a change in power flowing from the first conveyance to the second conveyance. When one of the conveyances begins drawing more power through the coupling connection, this change in the coupling connections state may be recorded and reported to another node or server in the wireless node network.

In a further example, the change in state for the coupling connection may reflect a changed RF environment detected by the network device. Thus, detecting more RF signals above a threshold amount or a change in RF power levels over a threshold level may reflect a change in state for the coupling connection and the related first and second conveyances to warrant reporting such a change. In more detail, one of the conveyances may have a characteristic RF signature, which may be reported with such a change in state.

At step 5715, the network device records the detected data. For example, ID node 5411 shown in FIG. 55 may record data detected on the three signal lines monitored in volatile memory 320 and memory storage 315 for an exemplary ID node. In another example, sensors 360 may implement signal monitoring circuitry 5412 and include onboard monitoring memory to temporarily record the data being monitored. The processing unit within ID node 5411 may, at some point, move the data from memory within the sensor 360 to a larger capacity memory storage 315 for longer-term storage before sharing or uploading the data to other network entities, such as master node 110a and server 100.

At step 5720, the network device transmits the detected data to another entity in the wireless network. For example, ID node 5411 shown in FIG. 55 may access the recorded data and transmit that data as the detected data over a communication interface to master node 110a, which may forward the data to server 100. In an embodiment where the network device is a master node, that master node may transmit the detected data to another master node or directly to the server.

In one embodiment, transmission of the detected data to another entity in the network may comprise providing a message to a server in the wireless network (directly if the network device is a master node, or indirectly if the network device is an ID node). The message may include the recorded data and a notification of a status related to the first conveyance and the second conveyance, such as that they are disconnected.

In still another embodiment, method 5700 may have the network device receiving power from a power line passing through the coupling connection. For example, as shown in FIG. 55, ID node 5411 receives power from a power line passing through the male coupler connector 5410 via a power connection 5414.

Those skilled in the art will appreciate that method 5700 as disclosed and explained above in various embodiments may be implemented on network device, such as an ID node (e.g., exemplary ID node 120a as illustrated in FIG. 3, ID node 4511 as illustrated in FIGS. 54 and 55, or ID node 5611 as illustrated in FIG. 56) or a master node (e.g., exemplary master node 110a as illustrated in FIGS. 4, and 54-56), running one or more parts of a control and management code (such as code 325 when the network device is implemented as an ID node or code 425 when the network device is implemented as a master node) to implement any of the above described functionality. Such code may be stored on a non-transitory computer-readable medium (such as memory storage 315 within an exemplary ID node or memory storage 415 within an exemplary master node). Thus, when executing such code, a processing unit of the network device (such as unit 300 within an ID node or unit 400 within a master node) may be operative to perform operations or steps from the exemplary methods disclosed above, including method 5700 and variations of that method.

In yet another embodiment, an apparatus is described for monitoring at least one signal passing from a first conveyance to a second conveyance. The apparatus comprises a coupling connection and a network device disposed within the coupling connection. The coupling connection provides a communication path for one or more signals passing between the first conveyance and the second conveyance, such as ABS signals passing through a connection between a tractor and a trailer.

The network device is in connection with signals passing through the coupling connection, and further comprises a processing unit, a memory, a communication interface, and a signal monitor circuit. The memory is coupled to the processing unit and maintains code for execution by the processing unit. The memory, at times, may also maintain detected and recorded data as explained in more detail below. The communication interface is coupled to the processing unit and operative to communicate with another network device (such as an ID node, a master node, or a server) in a wireless node network.

In one embodiment where the network device is an ID node, the communication interface may be a short-range communication interface such that the processing unit of the network device is operative to communicate directly with a master node as the another network device in the wireless node network over the short-range communication interface but unable to communicate directly with a server in the wireless node network.

In another embodiment where the network device is a master node, the network device may also include a longer-range communication interface coupled to the processing unit. This longer-range communication interface may be operative to communicate with a server in the wireless node network.

The signal monitor circuit of the network device has an input and output. The input is coupled to the one or more signal lines passing through the coupling connection on the communication path between the first conveyance and the second conveyance. The output provides detected data from the at least one signal line to the processing unit.

The processing unit of the network device, when executing the code maintained on the memory, is operative to perform particular steps and operations similar to those explained above with respect to the various embodiments of method 5700. In particular, the processing unit is operative to monitor the detected data provided from the signal monitor circuit, record the detected data to the memory for sharing with the another network device in the wireless node network, and transmit the recorded data over the communication interface to the another network device in the wireless network. The processing unit, in various further embodiments, may also be operative to perform steps as described in more details above with respect to the embodiments of method 5700.

Distributed Operation Applications

Sharing Shipment Condition Information Between Nodes

Rather than require network devices, such as ID nodes or master nodes, to always obtain certain types of data (e.g., environmental data, location data) from the backend server, an embodiment may allow a network device to share data with another network device in certain situations for more efficient network operations. In other words, an embodiment may distribute the operation of sharing certain types of data from the server to allow more efficient node-to-node sharing of the data.

In general, certain information may be shared between nodes (types of network devices) when, for example, the nodes and their respective packages are traveling together. For example, context data may indicate nodes and their respective packages are traveling together (e.g., context data may indicate certain nodes are part of a group of packages confined on a pallet or within a ULD). In such a situation, a node may need to know information about additional context data generally referred to as shipment condition information (such as location information, ambient or anticipated environmental information, updated system information, and the like related to shipping of the packages). This shipment condition information may be obtained by a node seeking such information from a node already possessing such information if it is authorized.

Generally, exemplary shipment condition information may exist or be generated or obtained in various ways. For example, shipment condition information may be generated from sensor data (e.g., environment, temperature, light, pressure, humidity). In another example, shipment condition information may be provided to a node by the server on request. In still another example, the shipment condition information may be pre-staged by the server on the node so that the node need not send the server a request for such information in the first place.

Additionally, exemplary shipment condition information may take different forms. For example, the shipment condition information may include environmental information, location information, updated system information needed for consistent and coordinated node operations, and the like.

In various embodiments, nodes may be authorized to share such shipment condition information by various means. For example, a node may be authorized to share such information with another node by requesting authority to do so from the server or having requested such authority before so as to be pre-authorized for the current sharing opportunity. In another example, a node may be pre-authorized to share only certain types of shipment condition information (e.g., a first node is authorized to share only temperature information with a second node, but not other types of shipment condition information).

FIG. 58 is a flow diagram illustrating an exemplary method for sharing shipment condition information in a wireless node network having a plurality of network devices and a server in accordance with an embodiment of the invention. Referring now to FIG. 58, method 5800 begins at step 5805 where a first node (one of the network devices) detects an advertising signal broadcast from a second node (another of the network devices). The first node is related to a first package, while the second node is related to a second package. For example, the first node may be related to one package in a palletized shipment of packages where the second node may be related to another package in the palletized shipment. These two nodes are being shipped and will travel together during at least part of the shipping transit journey.

In one embodiment, the first node may receive the shipment condition information from another of the network devices (e.g., an ID node, a master node, or the server) in the network before storing the shipment condition information on the memory in the first node.

In another embodiment, the first node may receive the shipment condition information from a sensor before storing the shipment condition information on the memory in the first node. For example, as shown in FIG. 3, ID node 120a includes sensors 360, which may gather environmental information (such as information on light, temperature, humidity, pressure, altitude, magnetic field strength, acceleration, vibration, impact, and orientation) about a proximate environment to the first node, such as an environment physically proximate and/or proximate in time. In other words, the shipment condition information may be environmental information about a physically proximate environment to the first node in one embodiment (such as the temperature outside a node, which may be used along with context data on packaging materials to estimate shipment condition temperature within the package).

In another embodiment, the shipment condition information may be environmental information about an environment anticipated to be proximate the first node at some time in the future. In more detail, ID node 120s may gather humidity information about the area and region surrounding the ID node 120a and store that information as shipment condition information in memory storage 315 as part of shared data 345. In another embodiment, the shipment condition information may comprise location information about the first node or updated system information (such as a common time setting dictated by the server so that all network devices are coordinated).

At step 5810, method 5800 associates the first node and the second node. Associating the first and second node may establish an authorized connection between the two nodes that may allow for secure sharing of information. Such an association may also be recorded as association data on the nodes.

At step 5815, method 5800 continues where the first node accesses the shipment condition information from the memory in the first node. For example, ID node 120a may access memory storage 315 to access exemplary shipment condition information maintained as shared data 345. Those skilled in the art will appreciate that if the first node is implemented as a master node in an embodiment, exemplary master node 110a (as illustrated in FIG. 4) may likewise access memory storage 415 to access exemplary shipment condition information maintained as shared data 445.

In more detail, the first node may access the shipment condition information as pre-staged information stored in the memory in the first node.

At step 5820, method 5800 concludes with the first node transmitting the shipment condition information to the second node if the first node is authorized to share the shipment condition information with the second node. In one embodiment, the first node may transmit the shipment condition information to the second node if the first node was pre-authorized to share the shipment condition information with the second node. In another embodiment, the first node may transmit the shipment condition information to the second node if the first node was pre-authorized to share a designated type of shipment condition information with the second node and the shipment condition information accessed is the designated type of shipment condition information.

In another embodiment, method 5800 may also have the first node setting a status flag to indicate the first node has shipment condition information to be shared. In a more detailed example, the status flag may be information in an advertising signal broadcast by the first node (e.g., in a header of an advertising packet message broadcast by the first node after obtaining the shipment condition information to be shared).

In still another embodiment, method 5800 may also include the first node receiving a request from the second node in response to the advertising signal broadcast by the first node, where the request asks for the first node to directly share the shipment condition information with the second node without requesting the shipment condition information from the server. Thus, an embodiment using information from the advertising signal (e.g., the status flag) may indicate that the first node has shipment condition information available to be shared via the signal information such that when the second node receives the signal, the second node may request the information, log and update relevant updated settings with the shared shipment condition information (e.g., a new clock reading, a new temp reading) without having to upload from the backend server.

Those skilled in the art will appreciate that method 5800 as disclosed and explained above in various embodiments may be implemented on a network device, such as an ID node (e.g., exemplary ID node 120a as illustrated in FIG. 3) or a master node (e.g., exemplary master node 110a as illustrated in FIG. 4), running one or more parts of a control and management code (such as code 325 when the network device is implemented as an ID node or code 425 when the network device is implemented as a master node) to implement any of the above described functionality. Such code may be stored on a non-transitory computer-readable medium (such as memory storage 315 within an exemplary ID node or memory storage 415 within an exemplary master node). Thus, when executing such code, a processing unit of the network device (such as unit 300 within an ID node or unit 400 within a master node) may be operative to perform operations or steps from the exemplary methods disclosed above, including method 5800 and variations of that method.

While FIG. 58 explained an embodiment for sharing shipment condition information from the perspective of the network device (e.g., ID node or master node) having the information and sharing it with another node, FIG. 59 explains a similar embodiment for requesting shared shipment condition information from the perspective of the network device receiving that shared information. In other words, FIG. 59 is a flow diagram illustrating an embodiment with an exemplary method for requesting shared shipment condition information after one of the network devices senses another of the network devices has such information. Referring now to FIG. 59, method 5900 begins at step 5905 where a second node detects an advertising signal broadcast from a first node. The first node is one of the network devices and is related to a first package, while the second node is another of the network devices and is related to a second package.

At step 5910, the second node determines that the first node has shipment condition information to share based upon status information in the advertising signal broadcast from the first node. In one embodiment, the shipment condition information may have been generated by the first node (such as sensor data generated by a first node having sensors). In another embodiment, the shipment condition information may have been generated by the server and provided to the first node. In yet another embodiment, the shipment condition information may comprise pre-staged data stored on a memory of the first node.

In an embodiment, the shipment condition information may include environmental information about a proximate environment to the first node (such as at least one of light, temperature, humidity, pressure, altitude, magnetic field strength, acceleration, vibration, impact, and orientation). In other embodiments, this proximate environment may be a physically proximate environment to the first node or an environment anticipated to be proximate the first node at another time. In still another embodiment, the shipment condition information may comprise location information about the first node.

In yet another embodiment, the shipment condition information may comprise updated system information, such as a new clock reading for the node to use so that operations may be better coordinated and more synchronized.

At step 5915, method 5900 associates the first node and the second node. As explained with respect to step 5810 in FIG. 58, associating the first and second node may establish an authorized connection between the two nodes that may allow for secure sharing of information. Such an association may also be recorded as association data on the nodes.

At step 5920, the second node transmits a request for the shipment condition information if the status information indicates the first node has the shipment condition information to share. Thus, the second node is informed of the availability of sharable data via the status information and, if such data is desired, transmits the request.

At step 5925, method 5900 concludes when the second node receives the shipment condition information from the first node if the first node is authorized to share the shipment condition information with the second node. In one embodiment, the second node receives the shipment condition information from the first node if the first node was pre-authorized to share the shipment condition information with the second node. In another embodiment, the second node receives the shipment condition information from the first node if the first node was pre-authorized to share a designated type of shipment condition information with the second node and the shipment condition information requested is the designated type of shipment condition information Those skilled in the art will appreciate that method 5900 as disclosed and explained above in various embodiments may be implemented on a network device, such as an ID node (e.g., exemplary ID node 120a as illustrated in FIG. 3) or a master node (e.g., exemplary master node 110a as illustrated in FIG. 4), running one or more parts of a control and management code (such as code 325 when the network device is implemented as an ID node or code 425 when the network device is implemented as a master node) to implement any of the above described functionality. Such code may be stored on a non-transitory computer-readable medium (such as memory storage 315 within an exemplary ID node or memory storage 415 within an exemplary master node). Thus, when executing such code, a processing unit of the network device (such as unit 300 within an ID node or unit 400 within a master node) may be operative to perform operations or steps from the exemplary methods disclosed above, including method 5900 and variations of that method.

In another embodiment, a system is disclosed for sharing shipment condition information in a wireless node network. The system generally comprises a first node in the network and a second node in the network. The first node in the system is related to a first package being shipped and generally comprises a first processing unit, a first memory, and a first communication interface. The first processing unit is coupled to each of the first memory and the first communication interface. The first memory maintains a first code (e.g., code 325 or code 425 depending on whether the node is an ID node or master node) for execution by the first processing unit. The first memory also maintains the shipment condition information.

In a further embodiment, the first node may also be implemented as a sensor node (another type of network device similar to an ID node as discussed above in more detail) and include a sensor coupled to the first processing unit. The sensor may generate sensor data as the shipment condition information maintained in the first memory.

The second node in the system is related to a second package being shipped and generally comprises a second processing unit, a second memory, and a second communication interface. The second processing unit is coupled to each of the second memory and the second communication interface. The second memory maintains a second code (e.g., code 325 or code 425 depending on whether the node is an ID node or master node) for execution by the second processing unit.

During operation of the system, the first node and the second node are operative under the control of their respective codes, to interact and share the shipment condition information under certain conditions. In particular, the first processing unit of the first node, when executing the first code maintained on the first memory, is operative to access the shipment condition information on the first memory and broadcast an advertising signal over the first communication interface. The advertising signal broadcast has status information on whether the first node has the shipment condition information to share. The first processing unit is also operative to receive a request from the second node over the first communication interface. The request asks the first node for the shipment condition information. The first processing unit is further operative to associate the first node and the second node, and transmit the shipment condition information to the second node over the first communication interface if the first node is authorized to share the shipment condition information with the second node.

In one embodiment, the first processing unit of the first node may also be operative to receive the shipment condition information from a server in the wireless node network. In another embodiment, the shipment condition information maintained on the first memory may comprise at least one of pre-staged data, environmental information (such as light, temperature, humidity, pressure, altitude, magnetic field strength, acceleration, vibration, impact, and orientation) about a proximate environment to the first node (such as a physically proximate environment or an environment proximate in time with respect to the node), location information about the first node, and/or updated system information (such as a time setting).

Additionally, the second processing unit of the second node, when executing the second code maintained on the second memory, is operative to detect the advertising signal broadcast from the first node and determine that the first node has the shipment condition information to share based upon the status information in the advertising signal broadcast from the first node. The second processing unit in the system is then operative to transmit the request for the shipment condition information to the first node over the second communication interface if the status information indicates the first node has the shipment condition information to share, and receive the shipment condition information from the first node when the first node is authorized to share the shipment condition information with the second node.

In a further embodiment of the system, the first processing unit may be further operative to receive an authorization from the server in the wireless node network, where the authorization permits the first node to share the shipment condition information with the second node. In another example of the system, the first processing unit may be further operative to transmit the shipment condition information to the second unit over the first communication interface if the first node was pre-authorized to share the shipment condition information with the second node. In still another example of the system, the first processing unit may be further operative to transmit the shipment condition information to the second unit over the first communication interface if the first node was pre-authorized to share a designated type of shipment condition information with the second node and the shipment condition information accessed in the first memory is the designated type of shipment condition information.

Hierarchical Sensor Network for Multi-piece Shipments

As mentioned above, certain types of shipments may include a set of packaged items. In some situations, such related packages may be grouped together and shipped as together (such as on a shipping pallet or within a shipping container). Those skilled in the art will appreciate that related packages being shipped together may be referred to as a multi-piece shipment that may share the same origin and destination (or at least share a portion of a predicted shipping route where the packages are intended to be shipped together). In an embodiment, a network of hierarchically configured nodes may be used to provide information about the shipment, more specifically, different parts of the shipment, as the multi-piece shipment is being shipped.

In general, a master node is higher in the hierarchy than an ID node. A master node is generally more complex and more expensive than an ID node, which advantageously allows a distribution of sensing functions to the lower complexity, lower cost ID nodes. In one embodiment, the higher complexity master node is able to communicate directly with a server over a first (e.g., longer range) communication path, while being able to communicate with the lower level and complexity ID nodes over a second (e.g., shorter range) communication path different from the first.

Figure 60B:
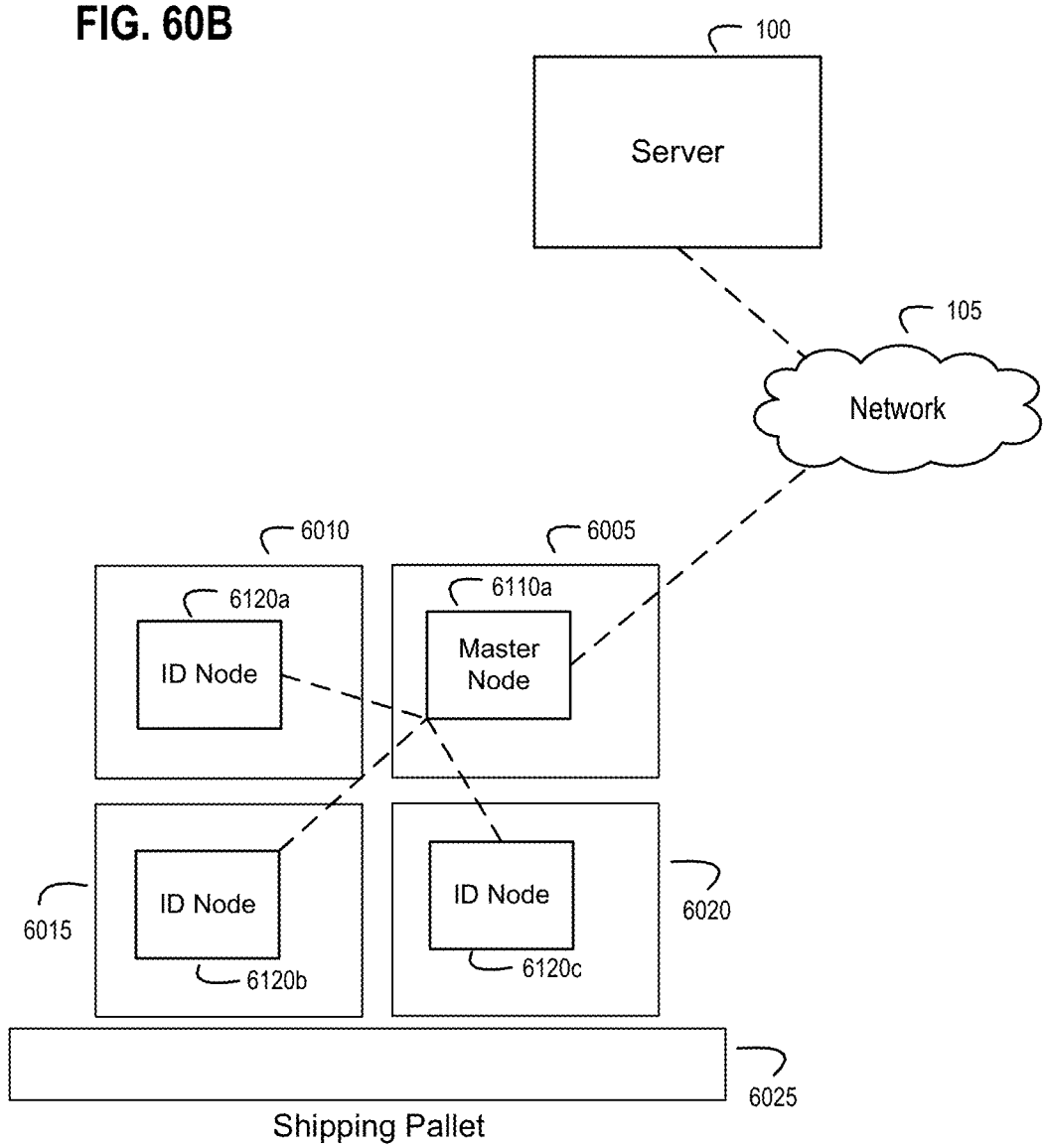
FIG. 60B is a diagram illustrating an exemplary group of nodes associated with a multi-piece shipment on an exemplary shipping pallet in accordance with an embodiment of the invention.

FIG. 60A is a diagram illustrating an exemplary group of nodes associated with a multi-piece shipment of packages in an exemplary shipping container in accordance with an embodiment of the invention. Referring now to FIG. 60A, shipping container 6000 is shown having packages 6005, 6010, 6015, and 6020 within container 6000. Within each of the packages is a network device—in particular, a mobile master node 6110a is placed within package 6005, ID node 6120a is placed within package 6010, ID node 6120b is placed within package 6015, and ID node 6120c is placed within package 6020. Mobile master node 6110a can communicate with server 100 via the network 105, but can also communicate with each of the ID nodes 6120a-6120c via a short range communication path (e.g., a Bluetooth® enabled communication path shown with dashed lines in FIGS. 60A and 60B).

A shipping customer may selectively identify a group of packages within the set of packages in the container or on the pallet. Thus, an embodiment may allow the shipping customer to identify a group or "cloud" of nodes based on the packages selected so that the shipping customer may monitor those packages and the shipment conditions within and around them. Additionally, an embodiment may allow the shipping customer to be proactively notified when the personalized cloud of nodes detects when a package is leaving the group. For example, if an ID node reports shipment condition information for a particular package that includes location information for that ID node, and that location information diverges from the location information gathered from other ID nodes in other packages in the group, the mobile master node may notify the server, which may access shipping information on the group and proactively contact the shipping customer in a designated manner (e.g., via an email message, a phone call, a text message, or the like).

In one embodiment, when initially preparing the set of packages 6005-6020 for shipment as a group, the nodes may be placed and enabled within their respective packages to function as a hierarchical sensor network of nodes as one or more of the ID nodes sense shipment condition information relevant to particular packages in the group while being managed by mobile master node 6110a. For example, such a network may be implemented as a personal cloud of nodes that may sense shipping condition information on some or all of the packages in the group.

While the embodiment illustrated in FIG. 60A has the packages being placed and confined into a shipping container 6000 (such as a ULD) as a group, another embodiment may place the node-enabled packages on the same shipping pallet 6025 as shown in FIG. 60B. In one embodiment, a shipping pallet is a type of flat transport structure that supports packaged and unpackaged items in a stable fashion so as to be moved about as a unit. Exemplary shipping pallets may confine the packages via strapping, stretch wrap, or other covering material that helps to hold the packages in place on the pallet.

Those skilled in the art will appreciate that embodiments may have a grouped set of packages where not all of the packages are node-enabled. For example, nodes may be placed and enabled within only packages having select exterior facing positions with the group of packages. This may help to cost effectively monitor for humidity and light detected as a result of damage to the exterior ones of the packages as they are arranged in the container or pallet. In another example, including nodes in only a portion of the packages may help effectively monitor for temperature at designated parts of the configured group of packages and avoid the expense and operational overhead incumbent when all packages in the group are node-enabled.

In an embodiment, the ability to require the only one of the nodes placed in the packages of the group be a mobile master node of higher complexity and cost, allows for an overall lower cost implementation for a sensor network to monitor a group of packages.

Figure 61:
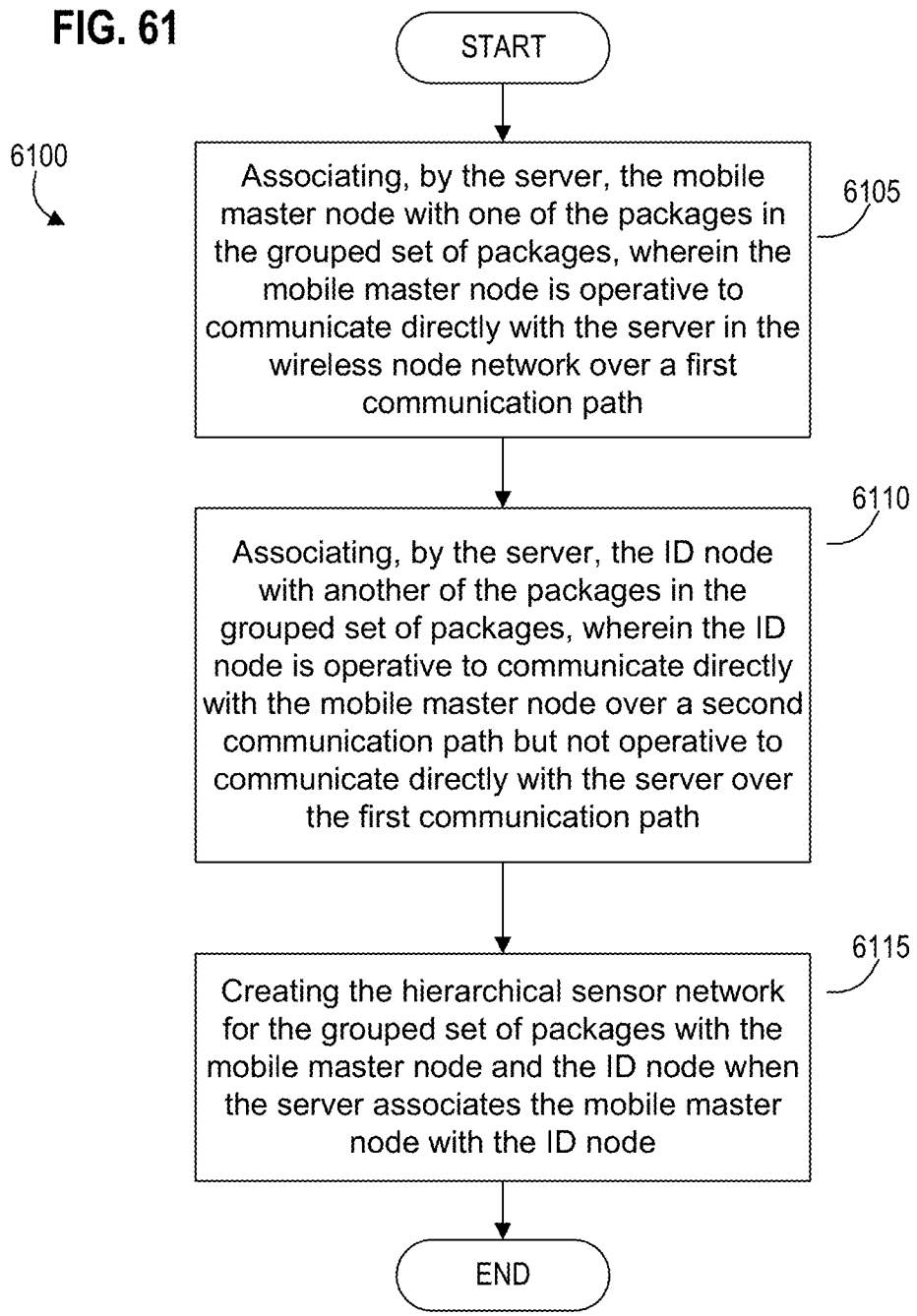
FIG. 61 is a flow diagram illustrating an exemplary method of server operations when creating a hierarchical sensor network for a grouped set of packages being shipped in accordance with an embodiment of the invention.

FIG. 61 is a flow diagram illustrating an exemplary method of server operations when creating a hierarchical sensor network for a grouped set of packages being shipped in accordance with an embodiment of the invention. Referring now to FIG. 61, method 6100 begins at step 6105 with the server associating the mobile master node with one of the packages in the grouped set of packages. In one embodiment, the associating is commonly direct (e.g., with nodes in direct contact with each other as part of the association process) but may be indirect in other embodiments (e.g., using scanned machine readable or human readable association information). Such associating may take the form of recording association data to reflect the association between the mobile master node and the package. The mobile master node is operative to communicate directly with the server in the wireless node network over a first communication path, such as a longer range communication path.

In one embodiment, the grouped set of packages may comprise a palletized group of packages being shipped together. For example, as shown in FIG. 60B, packages 6005-6020 are a palletized group of packages secured to shipping pallet 6025. However, in another embodiment, the grouped set of packages may comprise a group of packages together within a shipping container, such as container 6000 shown in FIG. 60A.

At step 6110, method 6100 continues with the server associating the ID node with another of the packages in the grouped set of packages, where the ID node is operative to communicate directly with the mobile master node over a second communication path but not operative to communicate directly with the server over the first communication path. Such associating of the ID node may take the form of recording association data to reflect the association between the ID node and the relevant package.

At step 6115, method 6100 concludes by creating the hierarchical sensor network for the grouped set of packages with the mobile master node and the ID node when the server associates the mobile master node with the ID node.

Method 6100 may, in a further embodiment, have the server associate an additional ID node with one or more of the remaining ones of the packages; and update the hierarchical sensor network to further comprise each of the associated additional ID nodes. Thus, such an exemplary hierarchical sensor network may include more than one ID node and may not require all of the packages to include a node.

In yet another embodiment, method 6100 may also include having one or more of the ID nodes shipping condition information related to their respective package. Exemplary shipping condition information may, in various embodiments, include environmental information and location information about a particular ID node (more specifically, the package associated with the ID node).

In still another embodiment, the ID node may share the sensed shipping condition information with the mobile master node. As such, the master node may then provide the shared sensed shipping condition information to the server.

And in another embodiment, method 6100 may have the server managing power consumption of the hierarchical sensor network by transmitting a power management instruction to the master node by the server. The power management instruction causes the mobile master node to alter at least one operation of the mobile master node and the ID node to change power consumption by at least one of the mobile master node and the ID node. For example, the mobile master node may be able to shift to a lower power state for a period of time while the ID node is gathering data only one a periodic basis (e.g., turning on, gathering sensor data, turning off, turning on again after a set period of time, gathering more sensor data, then turning off again, and so on).

Those skilled in the art will appreciate that method 6100 as disclosed and explained above in various embodiments may be implemented on a server (such as exemplary server 100 as illustrated in FIGS. 5, 60A, and 60B) running one or more parts of a control and management code (such as code 525) to implement any of the above described functionality. Such code may be stored on a non-transitory computer-readable medium (such as memory storage 515 in an exemplary server). Thus, when executing such code, a processing unit of the server (such as unit 500) may be operative to perform the various steps as disclosed above.

Figure 62:
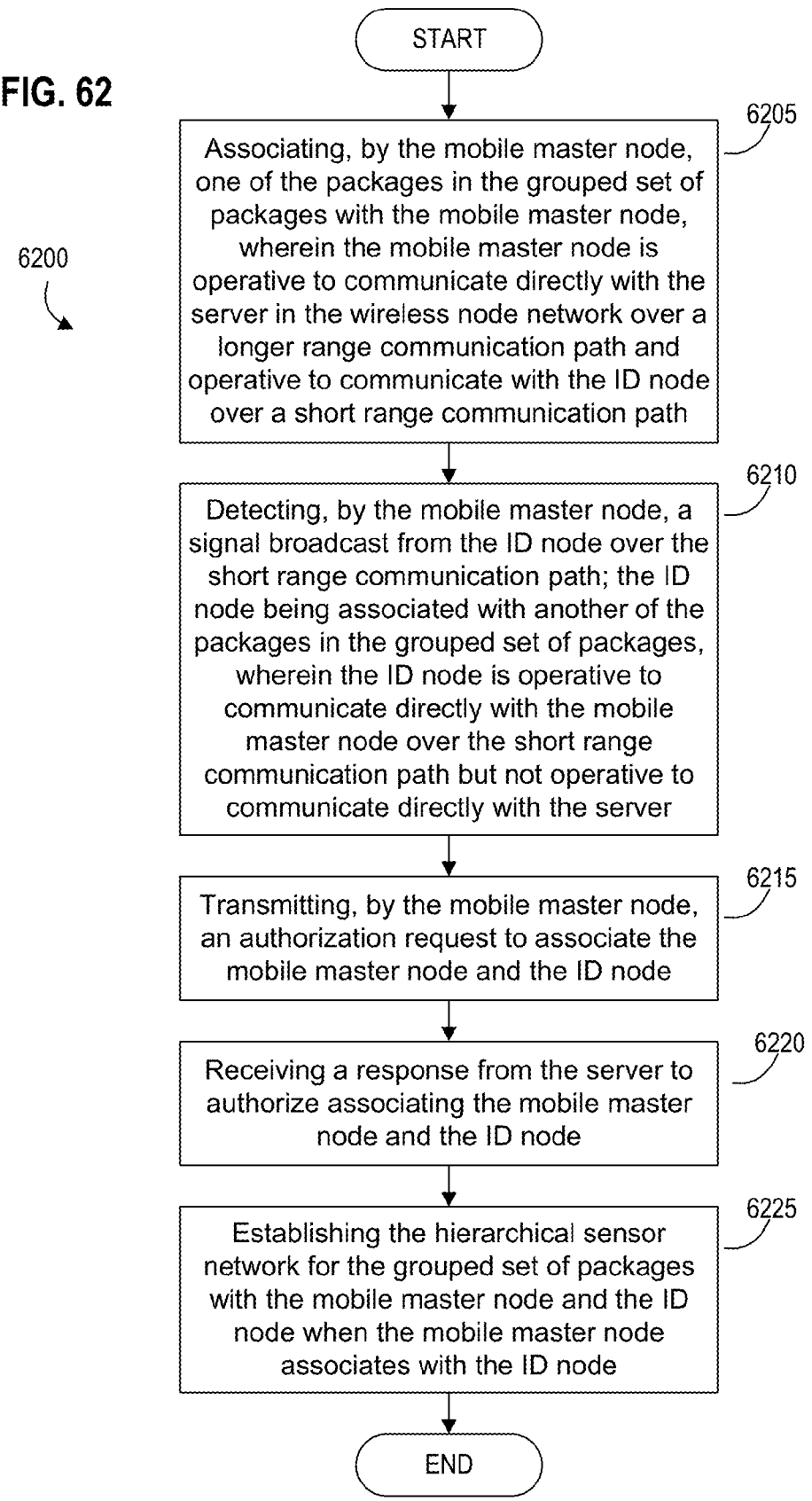
FIG. 62 is a flow diagram illustrating an exemplary method of master node operations when creating a hierarchical sensor network for a grouped set of packages being shipped in accordance with an embodiment of the invention.

While FIG. 61 illustrates exemplary steps for creating a hierarchical sensor network from the perspective of exemplary server operations and the above description expands upon that, FIG. 62 is a flow diagram illustrating an exemplary method of master node operations when creating a hierarchical sensor cloud for a grouped set of packages being shipped in accordance with an embodiment of the invention. Referring now to FIG. 6200, method 6200 begins at step 6205 with the mobile master node associating with one of the packages in the grouped set of packages with the mobile master node. Here, the mobile master node is operative to communicate directly with the server over a longer range communication path and operative to communicate with the ID node over a short range communication path.

In one embodiment, the grouped set of packages may comprise a palletized group of packages being shipped together where in another embodiment they may comprise a group of packages together within a shipping container.

At step 6210, the mobile master node detects a signal broadcast from the ID node over the short range communication path (such as a Bluetooth® enabled limited RF communication range). The ID node is associated with another of the packages in the grouped set of packages, and is operative to communicate directly with the mobile master node over the short range communication path but not operative to communicate directly with the server.

At step 6215, the mobile master node transmits an authorization request to associate the mobile master node and the ID node. And at step 6220, the mobile master node receives a response from the server to authorize associating the mobile master node and the ID node.

Finally, at step 6225, method 6200 establishes the hierarchical sensor network for the grouped set of packages with the mobile master node and the ID node when the mobile master node associates with the ID node.

In another embodiment, method 6200 may also include having the mobile master node associating an additional ID node with each of the remaining ones of the packages, wherein the hierarchical sensor network further comprises each of the associated additional ID nodes. Additional embodiments may include less than all of the remaining ones of the packages being associated with ID nodes.

In a further embodiment of method 6200, the mobile master node may receive shipping condition information from the ID node. In more detail, the shipping condition information may comprise at least one of environmental information (such as temperature, humidity, light, etc.) and location information related to the ID node. Further still, another embodiment of method 6200, the mobile master node may provide the shared shipping condition information received from the ID node to the server.

In yet another embodiment, method 6200 may also include having the mobile master node receiving a power management instruction from the server. The mobile master node may implement the power management instruction to manage power consumed by the mobile master node and the ID node. For example, the mobile master node may instruct the ID node to alter an operation of the ID node in order to change the power consumed by the ID node. In another example, the mobile master node may alter an operation of the mobile master node in order to change the power consumed by the mobile master node.

Those skilled in the art will appreciate that method 6200 as disclosed and explained above in various embodiments may be implemented on a mobile master node (such as exemplary master node 110a as illustrated in FIG. 4, and master node 6110a in FIGS. 60A, and 60B), running one or more parts of a control and management code (such as code 425) to implement any of the above described functionality. Such code may be stored on a non-transitory computer-readable medium (such as memory storage 415 in an exemplary mobile master node). Thus, when executing such code, a processing unit of the master node (such as unit 400) may be operative to perform operations or steps from the exemplary methods disclosed above, including method 6200 and variations of that method.

In addition to aspects involving the internal operations of the server and mobile master node, an embodiment may create an exemplary hierarchical sensor network as a way of putting such a network together and enabling it. Specifically, FIG. 63 is a flow diagram illustrating an exemplary method of creating a hierarchical sensor network for a grouped set of packages being shipped in accordance with an embodiment of the invention. Referring now to FIG. 63, method 6300 begins at step 6305 by placing the mobile master node within one of the packages in the grouped set of packages. Here, the mobile master node is operative to communicate directly with a server in the wireless node network over a first communication path (such as a longer range communication path). In contrast, the ID node is operative to communicate directly with the master node over a second communication path (such as a shorter range communication path) but is not operative to communicate directly with a server over the first communication path.

In one embodiment, the grouped set of packages may comprise a palletized group of packages being shipped together while in another embodiment they may comprise a group of packages together within a shipping container.

At step 6310, method 6300 continues by placing an ID node within another of the packages in the grouped set of packages. At step 6315, method 6300 enables the mobile master node and the ID node with power. And at step 6320, method 6300 concludes by activating the hierarchical sensor network for the grouped set of packages by causing the server to associate the mobile master node with the ID node.

In a further embodiment, method 6300 may also place an additional ID node within each of the remaining ones of the packages, and enable each of the additional ID nodes placed within each of the remaining ones of the packages. Thus, the enabled each of the additional ID nodes is powered and discoverable by the mobile master node and added to the hierarchical sensor network when the enabled each of the additional ID nodes is associated with the mobile master node.

In still another embodiment, method 6300 may place an additional ID node within a remaining one of the packages and enable the additional ID node placed within the remaining one of the packages. Thus, the enabled additional ID node is powered and discoverable by the mobile master node and added to the hierarchical sensor network when the enabled additional ID node is associated with the mobile master node And in yet another embodiment, method 6300 may also include selecting the packages in the grouped set of packages as a monitored group of packages to be shipped together for at least a portion of a shipping path from an origin to a destination From a system perspective, an embodiment is described of a hierarchical sensor system for a set of packages being shipped. The system generally comprises a mobile master node and a plurality of ID nodes. The mobile master node is associated with one of the packages in the set of packages. The mobile master node is operative to communicate with a server over a longer range communication path.

Each of the ID nodes in the system is associated with one of the remaining packages in the set of packages and includes a sensor that collects shipment condition information (e.g., environmental information, location information). And each of the plurality of ID nodes is operative to communicate with the mobile master node over a short range communication path but unable to directly communicate with the server.

In another embodiment, the mobile master node may further comprise a sensor that collects shipment condition information about the one of the packages in the set of packages. Thus, different embodiments may deploy one or more sensors as part of the mobile master node or any of the ID nodes that may make up the hierarchical sensor system.

The mobile master node in the system is further operative to receive the collected shipment condition information from the ID nodes over the short range communication path and update the server over the longer range communication path with summary shipment condition information related to each of the packages in the set of packages, the summary shipment condition information being based upon the collected shipment condition information from the ID nodes. For example, such summary shipment condition information may be a compilation of environmental and location information collected related to packages in the set of packages.

In a further embodiment, the set of packages may comprise a group of packages identified by shipping information to be related and shipped together, where the shipping information is maintained on the server and defined by a shipping customer. This allows for a more personal selection of which packages may make up the group of packages, and allow more flexibility and visibility for tracking purposes to a shipping customer. And those skilled in the art will appreciate that the set of packages may, in some embodiments, comprise a palletized group of packages being shipped together while, in other embodiments, comprise a group of packages together within a shipping container (such as a ULD).

Autonomous Node-enabled Vehicle Logistics Applications

Exemplary elements of a wireless node network may also be applied in embodiments involving autonomous vehicle transports that are able to pick-up, carry, hand-off, and deliver packaged items as part of an exemplary logistics system. By incorporating a mobile master node into the autonomous vehicle, and using other nodes at different locations, an embodiment of the mobile master node may be able to manipulate and control the other nodes so as to navigate to a shipping location or, more generally, a waypoint (e.g., a pickup point, a drop-off point, or a delivery point) along an anticipated transit route for a packaged item.

Node-based Navigation for Autonomous Transport Vehicles

Figure 67A:
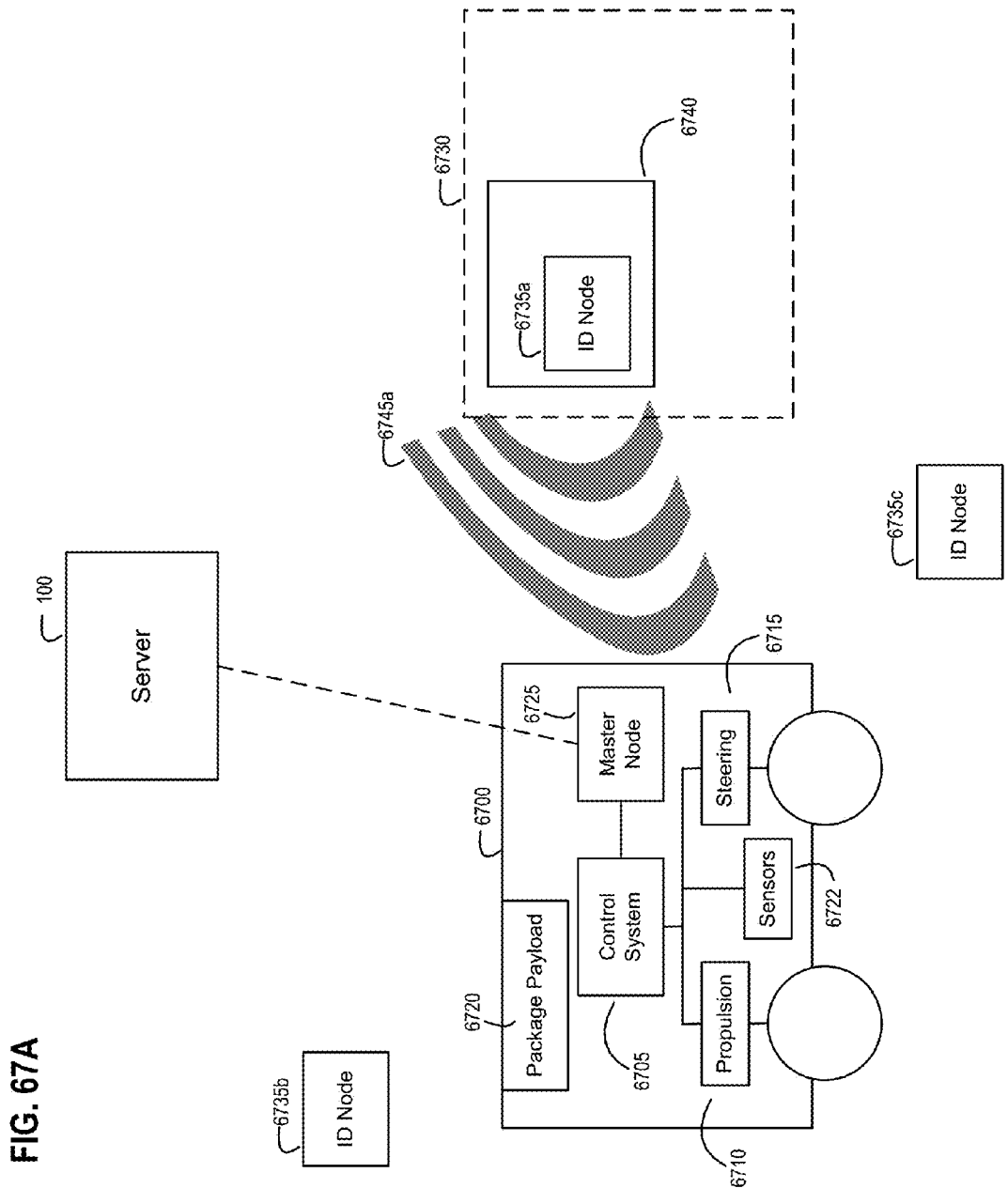
FIGS. 67A-67D are diagrams illustrating an exemplary node-enabled autonomous transport vehicle in various stages of navigating using nodes in a wireless node network in accordance with an embodiment of the invention.

FIGS. 67A-67D are diagrams illustrating an exemplary node-enabled transport vehicle in various stages of navigating using nodes in a wireless node network in accordance with an embodiment of the invention. Referring now to FIG. 67A, an exemplary node-enable transport vehicle is illustrated based upon an autonomous vehicle 6700. Examples of such an autonomous vehicle may be implemented as a pilotless, driverless, or unmanned means of transportation, such as a drone, automobile, truck, bus, tractor, aerial vehicle, railway vehicle, or marine vehicle. The vehicle 6700 may be implemented in a variety of sizes that may depend upon, for example, the types of packages to be transported, the environment in which the vehicle 6700 will be running (e.g., inside, outdoors), the accuracy required in movement (e.g., width for operations, turn around spacing, etc.), and the anticipated payload and articulating loading and unloading mechanisms (e.g., robotic arms, cranes, drop-down conveyor belts to help load and unload packages, etc.).

As shown in FIG. 67A, the exemplary autonomous vehicle 6700 incorporates a master node 6725 and employs a control system 6705 and sensors 6722 to navigate from one location to another location via a propulsion system 6710 and a steering system 6715 while carrying packages in a package payload. The master node 6725 (e.g., node 400 as shown and described in FIG. 4) is operative to communicate with server 100 over a longer-range communication interface (e.g., interface 485 as shown on master node 110a in FIG. 4). In one embodiment, the master node 6725 may be integrated into and be part of a processor-based system within the electronics onboard autonomous vehicle 6700. In another embodiment, the master node 6725 may be implemented as a standalone separate unit that may be added and/or fixed to a part of the autonomous vehicle 6700 (e.g., a storage compartment, a weather sealed compartment, etc.). Additionally, while node 6725 appears as a master node in FIGS. 67A-67D, other embodiments may implement node 6725 as an ID node. Further still, there may be embodiments where node 6725 associated with the autonomous transport vehicle may be implemented a master node temporarily operating as an ID node (e.g., as in when a master node can no longer self-determine its own location).

Those skilled in the art will appreciate that, depending upon the implementation of the autonomous vehicle 6700 (e.g., an autonomous truck, an unmanned autonomous flying drone quad-copter, an autonomous railway vehicle), the types of control systems 6705, propulsion systems 6710, steering systems 6715, and onboard sensors 6722 will vary in order to successfully have the vehicle 6700 navigate to a location on its own power and control. For example, an autonomous railway vehicle may be implemented with a hybrid diesel electric propulsion system in order to tow a large number of railcars having a vast package payload, but with a simple steering system given the implementation. In another example, an autonomous quad-copter drone vehicle may have four motors or engines as its collective propulsion system and have a more advanced steering system given the larger number of actuators used to fly such an aerial vehicle in stable flight.

Exemplary sensors 6722 on vehicle 6700 are typically used to help guide the vehicle 6700 when moving and avoid obstacles. For example, one embodiment may use ultrasonic sensors to detect objects in close proximity (e.g., walls, curbs, doors, packages, etc.). Other examples of sensors may include RADAR, LiDAR (using a laser to illuminate an object and analyzing the reflected light), computer vision with image processing and recognition, infrared sensors (e.g., forward looking infrared or FLIR technology), and the like. Those skilled in the art will appreciate that such sensors may scan and create useful images and maps to help avoid obstacles.

Exemplary control system 6705 is disposed within or on the autonomous vehicle 6700. The control system 6705 has the capacity to sense its environment as input, navigate between locations, and control propulsion and steering in response to the sensed and navigation inputs. The control system 6705 has a collective output coupled to the control input of the autonomous vehicle (e.g., inputs to the propulsion system 6710 and steering system 6715). In more detail, the exemplary control system 6710 further has at least one input for receiving an instruction on a desired movement for the autonomous vehicle (e.g., control instructions to start/stop the vehicle, accelerate or slow down the vehicle, turn the vehicle, and make the vehicle go in a particular direction (e.g., forward, backward, left, right, up, down) and produces a control signal on the output responsive to the instruction received.

In some embodiments, control system 6705 may also include guidance equipment, such as a compass, gyroscope, accelerometer, inertial sensors, GPS receiver circuitry, and the like. In one example, the control system may include an inertial navigation system (not separated shown in FIG. 67A) that is capable of operating in hostile RF environments (e.g., indoors, within shielded facilities, underwater, etc.).

As shown in FIG. 67A, master node 6725 is a mobile master node onboard autonomous vehicle 6700, which is capable of moving under its own control and propulsion from one location to another location in response to control input. Additionally, FIG. 67A shows various ID nodes 6735a-6735c at different locations relative to vehicle 6700. In one embodiment, the ID nodes may operate by broadcasting advertising signals to help the node-enabled autonomous vehicle 6700 navigate. Generally, the mobile master node 6725 is able to identify an ID node at a desired location (e.g., a waypoint along an anticipated route for package pickup, transport, or delivery), associate with that ID node, instruct that ID node to lower the broadcasting power, and determine a direction where the ID node is located based on sensing the lowered broadcasting power. The gradual or incremental lowering of ID node output power helps to indicate where the ID node is located and where the mobile master node should be headed. This may be repeated for the next waypoint in a series of waypoints.

Figure 67B:
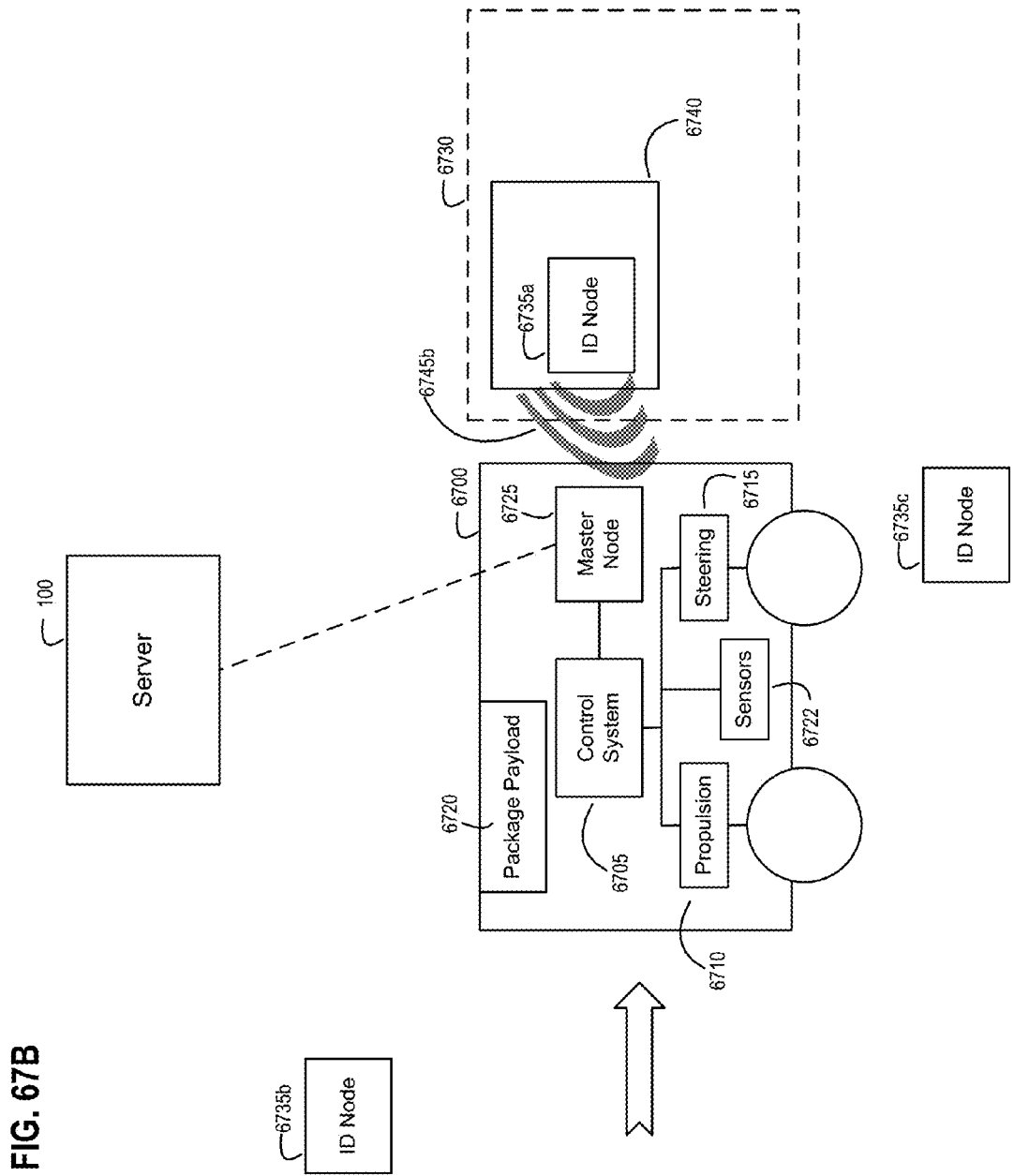

In more detail, FIG. 67A illustrates ID node 6735a within package 6740 at a shipping location 6730 (e.g., a front door, a shipping dock, a storage room) with other ID nodes (such as ID nodes 6735b, 6735c) in the general area. ID node 6735a is broadcasting an advertising signal at a high power, which corresponds to a larger broadcast range 6745a. Upon detecting this signal from ID node 6735a, mobile master node 6725 in vehicle 6700 may instruct ID node 6735a to lower the broadcast output power. Thus, as shown in FIG. 67B, mobile master node 6725 may detect that ID node 6735a has lowered its output signal to a lower power 6745b, which then allows mobile master node to determine a general direction of the ID node 6735a and move in that direction (e.g., provide the determined direction as an input to control system 6705, which controls movement and steering through propulsion system 6710 and steering system 6715). Thus, mobile master node 6725 and the ID node 6735a may be used to help guide and navigate when the vehicle 6700 needs to move to the shipping location 6730 to pick-up one or more packages there, drop off one or more packages there, or simply use that location 6730 as a waypoint so that vehicle 6700 can then move on to the next waypoint in an anticipated route and ultimately get to its desired destination.

In some embodiments, the node-enabled autonomous vehicle 6700 may use a central courier vehicle (e.g., truck, van) as a type of base from which to make runs to different addresses to pick up one or more packages for shipment, or drop off one or more packages for delivery. In such an embodiment, the central vehicle from which the node-enabled autonomous vehicle 6700 departs and returns may include a ramp or other articulating loading and unloading mechanisms (e.g., robotic arms, cranes, drop-down conveyor belts to help load and unload the various autonomous vehicles as they leave and return to the central vehicle, etc.).

In other embodiments, the node-enabled autonomous vehicle 6700 may ferry one or more packages from one location (such as a courier vehicle) to another location (such as another courier vehicle). In still other embodiments the node-enabled autonomous vehicle 6700 may ferry or transport packages between storage locations in a shipping facility or off a truck and into an entrance of a sorting facility using exemplary articulating loading and unloading mechanisms (e.g., robotic arms, cranes, drop-down conveyor belts to help load and unload packages, etc.).

Figure 67C:
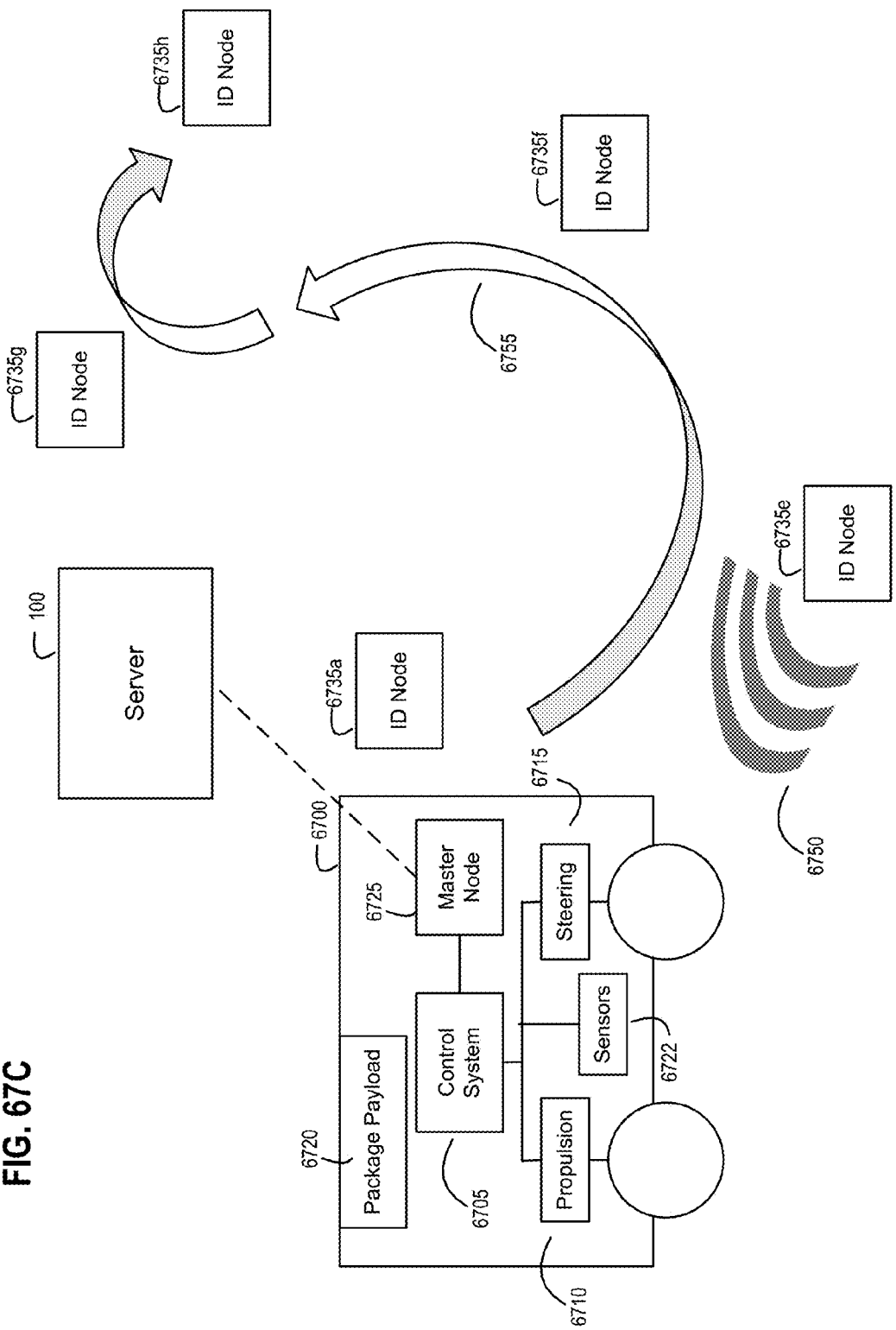

FIG. 67C illustrates an embodiment where the ID nodes may be used as a series of waypoints. Referring now to FIG. 67C, vehicle 6700 may have arrived near ID node 6735A (as shown and explained with respect to FIGS. 67A and 67B), but now is moving on to another waypoint at ID node 6735e (and then ID nodes 6735f, 6735g, and 6735h as further waypoints in the series). Mobile master node 6725 embedded in node-enabled autonomous vehicle 6700 may instruct ID node 6735e to lower its output signal 6750 so that the master node 6725 can identify a direction towards that ID node and cause the vehicle 6700 to move in that direction.

Figure 67D:
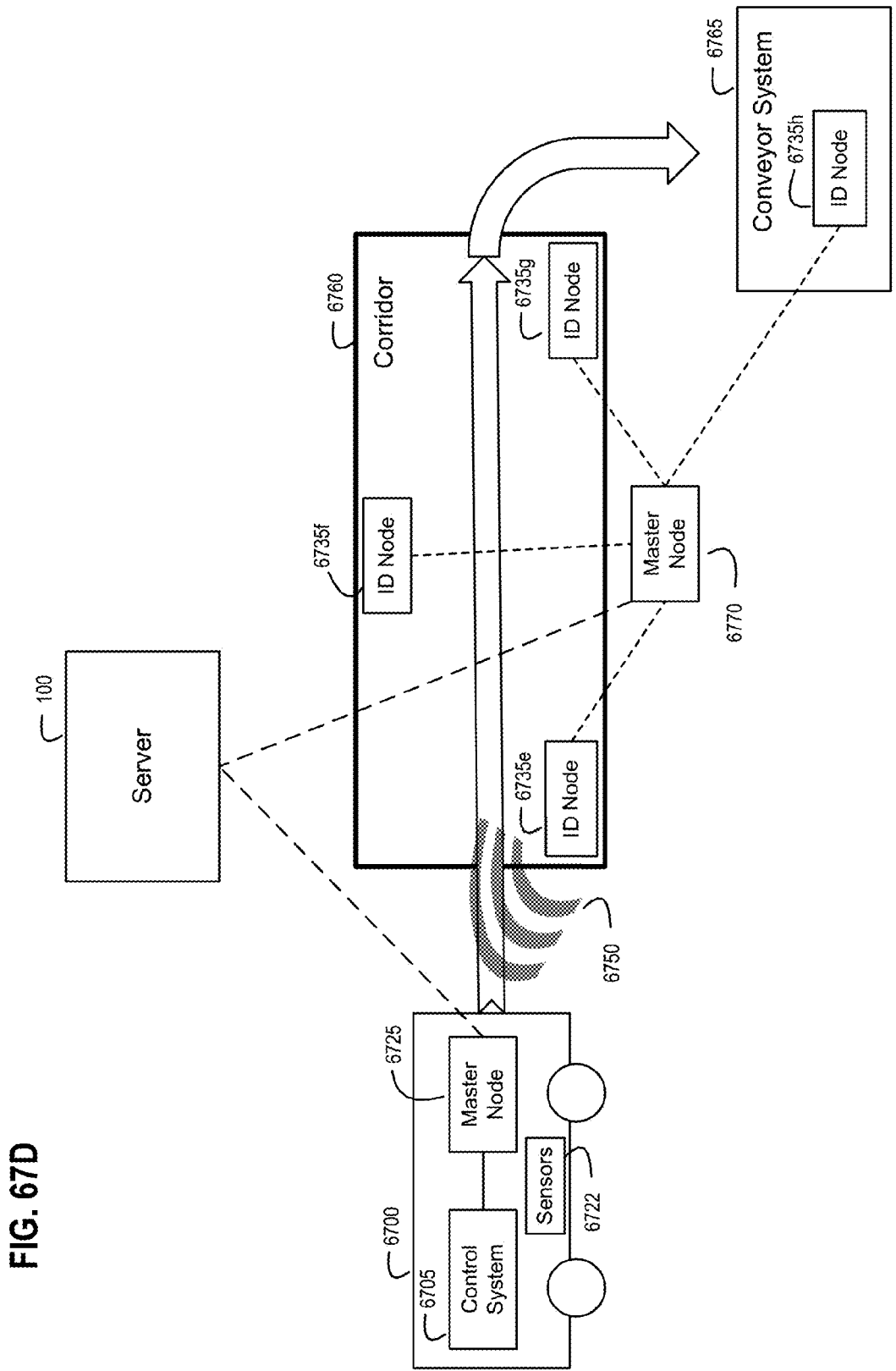

FIG. 67D illustrates a further embodiment where an exemplary node-enabled autonomous vehicle 6700 has an anticipated route that will take it through a corridor 6760 and towards a conveyor system 6765 within a shipping facility (such as a package sorting facility). In this example and within such a facility, the exemplary node-enabled autonomous vehicle 6700 may transport packages to be placed onto the conveyor system 6765 for processing, scanning, sorting, and further distribution logistics activities. In doing so, the node-enabled autonomous vehicle 6700 is able to navigate along the anticipated route via waypoint associated with broadcasting ID nodes along the way. For example, as node-enabled autonomous vehicle 6700 approaches the entrance to corridor 6760, mobile master node 6725 within vehicle 6700 may detect an advertising signal 6750 being broadcast from ID node 6735e. Additionally, mobile master node 6725 may rely on and use context data about the corridor and the surrounding anticipated environment to better navigate from ID node to ID node along the route. Such exemplary context data relates to the anticipated operating environment of the ID node—e.g., mobile master node 6725 may access context data identifying that corridor 6760 is dimensionally 75 feet long and 10 feet wide and provide layout information for the corridor (e.g., turns along the way, etc.). Proximity data may also be gathered from sensors 6722 as the vehicle 6700 moves along the route from ID node to ID node (each of which may be managed and associated with different master nodes 6770 before they associate with and are controlled by mobile master node 6725). Thus, as the mobile master node 6725 controls the respective ID nodes along the route, the broadcast characteristics of the different ID nodes may be detected by the mobile master node 6725 such that it navigates towards a final destination (e.g., a loading area for conveyor system 6765).

FIG. 68 is a flow diagram illustrating an exemplary method for navigating to a shipping location by an autonomous transport vehicle using a plurality of nodes in a wireless node network in accordance with an embodiment of the invention. Referring now to FIG. 68, method 6800 begins at step 6805 with a mobile master node associated with the autonomous transport vehicle detecting a signal broadcast from an ID node associated with the shipping location. The mobile master node is one of the plurality of nodes and can communicate directly with a server in the wireless node network over a first communication path. The ID node is another of the plurality of nodes and can communicate directly with the mobile master node over a second communication path but is not able to communicate directly with the server over the first communication path.

In one embodiment, method 6800 may also include the mobile master node receiving an identification of the ID node from the server. For example, server 100 may have anticipated or predicted a route using one or more ID nodes and transmit an identification (e.g., a MAC address or other identifier) associated with ID node 6735a shown in FIG. 67A. In this embodiment, the detecting step may comprise detecting the identification of the ID node from the signal broadcast from the ID node.

In one embodiment, the shipping location may comprise one from a group consisting of a delivery point, a drop-off point, and a pickup point. In another example, the shipping location may be a waypoint in an anticipated route. In a more detailed example, the shipping location may be implemented as a first waypoint of a plurality of waypoints on an anticipated route as the mobile master node approaches a transit destination for a package transaction. Each of the plurality of waypoints is associated with a different ID node. For example, as shown in FIG. 67C, different waypoints may be associated with different ones of ID nodes 6735e, 6735f, 6735g, and 6735h.

At step 6810, method 6800 has the mobile master node instructing the ID node to lower a power level of the signal broadcast from the ID node. For example, mobile master node 6725 in FIG. 67A instructs ID node 6735a to lower the power level 6745a of the signal being broadcast, which is then shown at the lowered power level 6745b in FIG. 67B.

At step 6815, the mobile master node identifies the signal broadcast from the ID node with the lowered power level. In this way, the ID node can be distinguished from other ID nodes broadcasting in the area around the node-enabled autonomous vehicle 6700 having mobile master node 6725.

At step 6820, the mobile master node determines a direction of the ID node relative to the mobile master node based upon the detected signal with the lowered power level. The mobile master node, for example, is able to distinguish the ID node broadcasting the lower power level signal and determine a direction towards that ID node.

At step 6825, the mobile master node navigates to the ID node associated with the shipping location based upon the determined direction. In one embodiment, such navigation may be accomplished by navigating to the ID node as the power level of the signal is incrementally decreased over time as the mobile master node approaches the ID node.

In another example where the mobile master node is associated with a control system of an autonomous vehicle transport (such as control system 6705 of node-enabled autonomous vehicle 6700), such navigating may be accomplished when the mobile master node provides the determined direction to an input of the control system to cause the autonomous vehicle transport to stop moving when a current location of the mobile master node is within a predetermined range of the ID node.

In a more detailed example, navigating may be accomplished by first accessing context data that relates to an operating environment of the ID node, and then navigating to the ID node referencing the accessed context data as the power level of the signal is incrementally decreased over time and as the mobile master node approaches the ID node. For example, the referenced context data may provide layout and dimensional information along the anticipated route of the vehicle as it approaches the ID node.

In a still more detailed example, navigating may be accomplished by first accessing context data that relates to an anticipated operating environment of the ID node, gathering proximity sensor data from at least one sensor deployed on the autonomous vehicle transport, and then navigating to the ID node with reference to the accessed context data and the proximity sensor data as the power level of the signal is incrementally decreased over time and as the mobile master node approaches the ID node. In such an embodiment, the operating environment of the ID node may be within a shipping facility, such as a package sorting facility (such as the exemplary facility illustrated in FIG. 67D having a corridor 6760 and a conveyor system 6765 where node-enabled autonomous vehicle 6700 may navigate through corridor 6760 using waypoints of ID nodes before dropping off one or more packages at the conveyor system 6765.

Method 6800 may also, in a further embodiment, have the mobile master node transmit an updated location of the mobile master node to the server as the mobile master node approaches the ID node. The updated location of the mobile master node may be determined using location circuitry (such as a GPS chipset and antenna) on the mobile master node.

In another example, the mobile master node may be associated with a control system of an autonomous vehicle transport, such that the updated location of the mobile master node is determined based at least in part upon a determined position from an inertial navigation unit deployed on the autonomous vehicle transport. In still another example, the updated location of the mobile master node may be determined based upon an onboard location provided by location circuitry on the mobile master node (such as the GPS chipset and antenna) when available and, when the onboard location is not available, the updated location of the mobile master node may be determined based at least in part upon a determined position from an inertial navigation unit deployed on the autonomous vehicle transport. Thus, an embodiment provides the capability to navigate within a facility and indoors when GPS signals may be lost.

Those skilled in the art will appreciate that method 6800 as disclosed and explained above in various embodiments may be implemented on a mobile master node (such as exemplary master node 110a as illustrated in FIG. 4, and master node 6725 in FIGS. 67A-67D), running one or more parts of a control and management code (such as code 425) to implement any of the above described functionality. Such code may be stored on a non-transitory computer-readable medium (such as memory storage 415 in an exemplary mobile master node). Thus, when executing such code, a processing unit of the master node (such as unit 400) may be operative to perform the various steps as disclosed above.

Furthermore, another embodiment includes a node-enabled transport vehicle. The transport vehicle comprises an autonomous vehicle operative to move from an initial location to a shipping location in response to control input. The shipping location may be, for example, a delivery point, a drop-off point, a pickup point, a waypoint in an anticipated route for the autonomous vehicle, or a first waypoint of a plurality of waypoints on an anticipated route as the vehicle approaches a transit destination for a package transaction.

The transport vehicle further comprises a control system disposed on the autonomous vehicle. The control system (e.g., control system 6705 shown in FIGS. 67A-67D) has an output coupled to the control input of the autonomous vehicle (such as the input to propulsion systems 6710 and steering system 6715). The control system further has at least one input for receiving an instruction on a desired movement for the autonomous vehicle and producing a control signal on the output responsive to the instruction received.

The transport vehicle further comprises a mobile master node associated with it. The mobile master node is one of a plurality of nodes in a wireless node network that can communicate directly with a server in the network. As described above, the mobile master node may, in one embodiment, be integrated into one of the processor-based electronic systems onboard the autonomous vehicle. But in another embodiment, the mobile master node may be a standalone unit attached or otherwise physically associated with the vehicle. The mobile master node provides a directional output signal as an instruction to the input of the control system.

In more detail, the mobile master node comprises a node processing unit, node memory, and a short-range and longer range communication interfaces. The node memory is coupled to the node processing unit and at least maintains code for execution by the node processing unit, as well as data generated during operation of the mobile master node. The short-range communication interface is coupled to the processing unit and can communicate with an ID node associated with the shipping location. The ID node is another of the plurality of nodes and can communicate directly with the mobile master node over the short-range communication interface but is unable to communicate directly with the server in the network. The longer range communication interface is coupled to the node processing unit and provides the means to communicate directly with the server.

The node processing unit of the mobile master node, when executing the code maintained on the node memory, is operative to perform steps and operations as described and set forth above with respect to FIG. 68 and method 6800. In more detail, the node processing unit is operative, as such, to detect, over the short-range communication interface, a signal broadcast from the ID node associated with the shipping location. The node processing unit is operative to transmit an instruction over the short-range communication interface to the ID node, where the instruction causes the ID node to lower a power level of the signal broadcast from the ID node. An example of this is illustrated in FIGS. 67A and 67B where the power levels are initially at a higher level 6745*a* but are changed to a lower level 6745*b*.

The node processing unit is then operative to identify the signal broadcast from the ID node with the lowered power level, determine a direction from the mobile master node to the ID node based upon the detected signal with the lowered power level, and provide the determined direction as the instruction to the input of the control system.

In a further embodiment of the node-enable transport vehicle, the node processing unit may be further operative to determine the direction to the ID node and provide the determined direction as the directional output signal as the power level of the detected signal broadcast from the ID node is incrementally decreased over time and as the mobile master node approaches the shipping location.

In yet another embodiment, the node processing unit may be further operative to receive an ID node identification from the server over the longer range communication interface. Here, the ID node identification is related to the ID node associated with the shipping location and the node processing unit may be further operative to detect the ID node identification of the ID node associated with the shipping location from the signal broadcast from the ID node associated with the shipping location.

In another embodiment, the node processing unit may be further operative to instruct the control system based upon the directional input to cause the autonomous vehicle transport to stop moving when a current location of the mobile master node is within a predetermined range of the ID node associated with the shipping location. In that embodiment, the node processing unit may be further operative to transmit an update to the server reflecting that the current location of the mobile master node is within the predetermined range of the ID node. Thus, the server is updated with current location and status information so as to be ready to respond to requests for such information.

In still another embodiment, context data may be used with a node-enabled transport vehicle to provide enhanced navigation abilities. In particular, an embodiment may have the node memory maintaining context data with the node processing unit being further operative to access a part of the context data that relates to an operating environment (more specifically, an anticipated operating environment) of the ID node. The node processing unit may be further operative to determine the direction to the ID node with reference to the accessed context data as the power level of the signal is incrementally decreased over time and as the mobile master node approaches the ID node.

In another embodiment of the node-enabled transport vehicle, the autonomous vehicle may further comprises at least one sensor disposed on the autonomous vehicle and coupled at least to the node processing unit of the mobile master node (or, alternatively, coupled to the control system on the autonomous vehicle). In this embodiment, which also leverages the use of context data, the node processing unit may be further operative to access a part of the context data that relates to an anticipated operating environment of the ID node, gather proximity data from the at least one sensor, and determine the direction to the ID node with reference to the accessed context data and the proximity sensor data as the power level of the signal is incrementally decreased over time and as the mobile master node approaches the ID node. Thus, the autonomous vehicle may be navigating with the advantage of referring to the sensed proximity of the vehicle, an anticipated operative environment of the ID node where they are and are headed, and with a direction determined based on the changing ID node broadcast power levels detected. Further, the operating environment of the ID node may be within a shipping facility, such as a package sorting facility.

In a further embodiment, the node-enabled transport vehicle (more specifically, the mobile master node within the vehicle) may be able to provide location information for the vehicle to the server. In one embodiment, the mobile master node may include onboard location circuitry (such as a GPS chipset and antenna) coupled to the node processing unit such that the unit may be further operative to obtain an updated location of the mobile master node from the onboard location circuitry, and transmit the updated location over the longer range communication interface to the server as the mobile master node approaches the shipping location.

In another embodiment, the vehicle may also include an inertial navigation unit deployed on the autonomous vehicle that generates a determined position for the location of the autonomous vehicle. For example, an exemplary inertial navigation unit may use accelerometers, gyroscopes, magnetometers, and/or pressure sensors as part of determining a position based upon such sensors. In this embodiment, the node processing unit may be further operative to determine an updated location of the mobile master node at least in part on the determined position obtained from the inertial navigation unit, and transmit the updated location over the longer range communication interface to the server.

In an embodiment having both onboard location circuitry in the mobile master node and the inertial navigation unit, the node processing unit may be further operative to determine if an updated location of the mobile master node from the onboard location circuitry is available. If so, it can transmit to the server over the longer range communication interface the updated location obtained from the onboard location circuitry. However, it can transmit to the server over the longer range communication interface the determined position obtained from the inertial navigation unit if the updated location is not available. Thus, a more robust ability to operate in outdoor and indoor environments is provided.

In still another embodiment where there are a number of waypoints (each of which are associated with an ID node), the node processing unit may be further operative to detect, over the short-range communication interface, a signal broadcast from the another ID node associated with a next of the waypoints. The node processing unit may be then operative to transmit an instruction over the short-range communication interface to the other ID node, where the instruction causes the other ID node to lower a power level of the signal broadcast from the another ID node. The node processing unit may then be operative to identify the signal broadcast from the other ID node with the lowered power level, determine a further direction on the anticipated route from the mobile master node to the other ID node based upon the detected signal with the lowered power level broadcast from the other ID node, and provide the determined direction on the anticipated route as the instruction to the input of the control system.

Autonomous Vehicle Package Transactions with Nodes

Figure 69A:
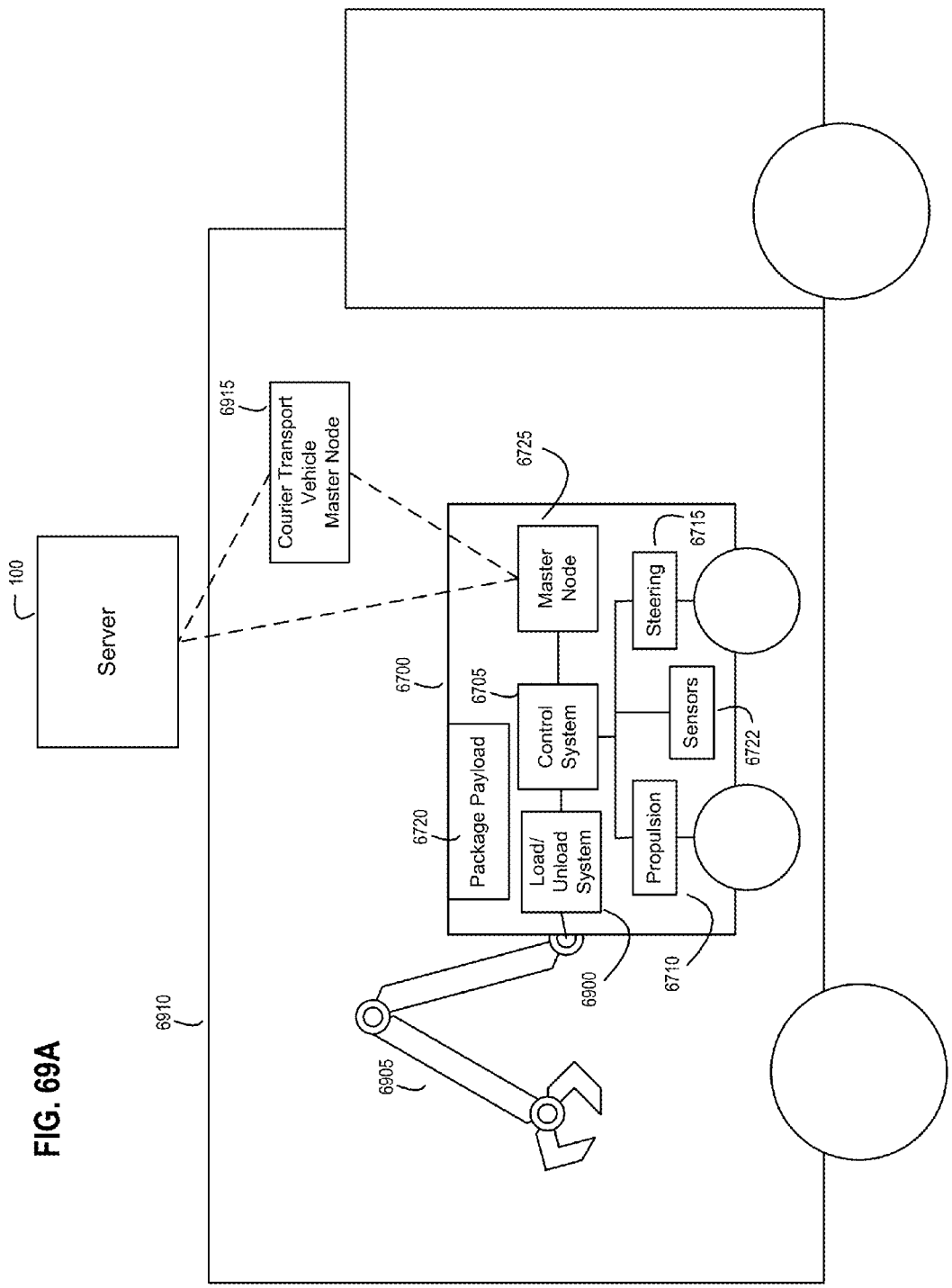
FIG. 69A is a diagram illustrating an exemplary courier transport vehicle having an exemplary node-enabled autonomous vehicle in accordance with an embodiment of the invention.

The use of an autonomous vehicle for package pickup and delivery (e.g., types of logistics transactions for a package) may be further enhanced using nodes in a wireless node network. FIG. 69A is a diagram illustrated an exemplary courier transport vehicle having an exemplary node-enabled autonomous vehicle in accordance with an embodiment of the invention. Referring now to FIG. 69A, exemplary node-enabled autonomous vehicle 6700 is shown within a courier transport vehicle 6910 that may be used to transport one or more packages (not shown) within vehicle 6910 for delivery at various locations or for simply ferrying such packages between locations. The advantageous use of a node-enabled autonomous vehicle, such as vehicle 6700, to assist with loading/unloading of vehicle 6910 as well as carrying out logistics transactions, such as picking up a package from a designated address or delivering a package to such an address may allow for a more efficient logistics system in an embodiment.

Exemplary node-enabled autonomous vehicle 6700 is shown in this illustrated embodiment more particularly includes an exemplary package articulation system having an electronic module 6900, which is connected to and controls an articulating system 6905 movable to place and remove a package from within the package payload storage 6720 of vehicle 6700. In one embodiment, the module and system may be implemented with a robotic arm having multiple degrees of freedom so as to provide greater flexibility in loading and unloading packages proximate to the vehicle 6700. However, those skilled in the art will appreciate that other embodiments of a package articulation system may be implemented using, for example, loading conveyors, multiple grasping extensions or arms from vehicle 6700, a loading platform that articulates down to an adequate level to help capture a package, and the like. Likewise, the end of articulating system 6905 is illustrated as having articulating contact points that can grasp a package, but other embodiments may use different types of structure to articulate and maintain a grasp and control of a package as it is placed in or removed from the package payload 6720.

In one embodiment, courier transit vehicle 6910 has a courier transit vehicle mobile master node 6915, such as that illustrated in FIG. 69A Such a master node 6915 on board the vehicle 6910 allows master node 6915 to more efficiently manage and report on packages picked up and delivered as well as deliver shipment information to the node-enabled. However, other embodiments may have master node 6725 in autonomous vehicle 6700 be responsible for downloading shipping information on packages that are subject to logistics transactions, such as picking them up or dropping them off.

Autonomous vehicle 6700 may be deployed from the courier transport vehicle 6910 and travel to and from a transaction location (e.g., a pickup location, address, designated area for dropping off packages, and the like) where the vehicle 6700 may pick up or drop off a package. Depending on how the exemplary autonomous vehicle 6700 and the exemplary courier transport vehicle 6910 are configured and the particular application details (e.g., how big and how many packages may be transported by each, etc.), deploying the autonomous vehicle 6700 may be accomplished by, for example, simply opening a back or side door of courier transport vehicle 6910. In another embodiment, autonomous vehicle 6700 may be quickly deployed from a dedicated launch bay (not shown) of courier transport vehicle 6910 where vehicle 6910 may include dedicated hardware to assist gather packages that have been brought to the vehicle 6910 during a pickup logistics transaction or to asset loading on or more packages from a storage area on vehicle 6910.

Figure 69B:
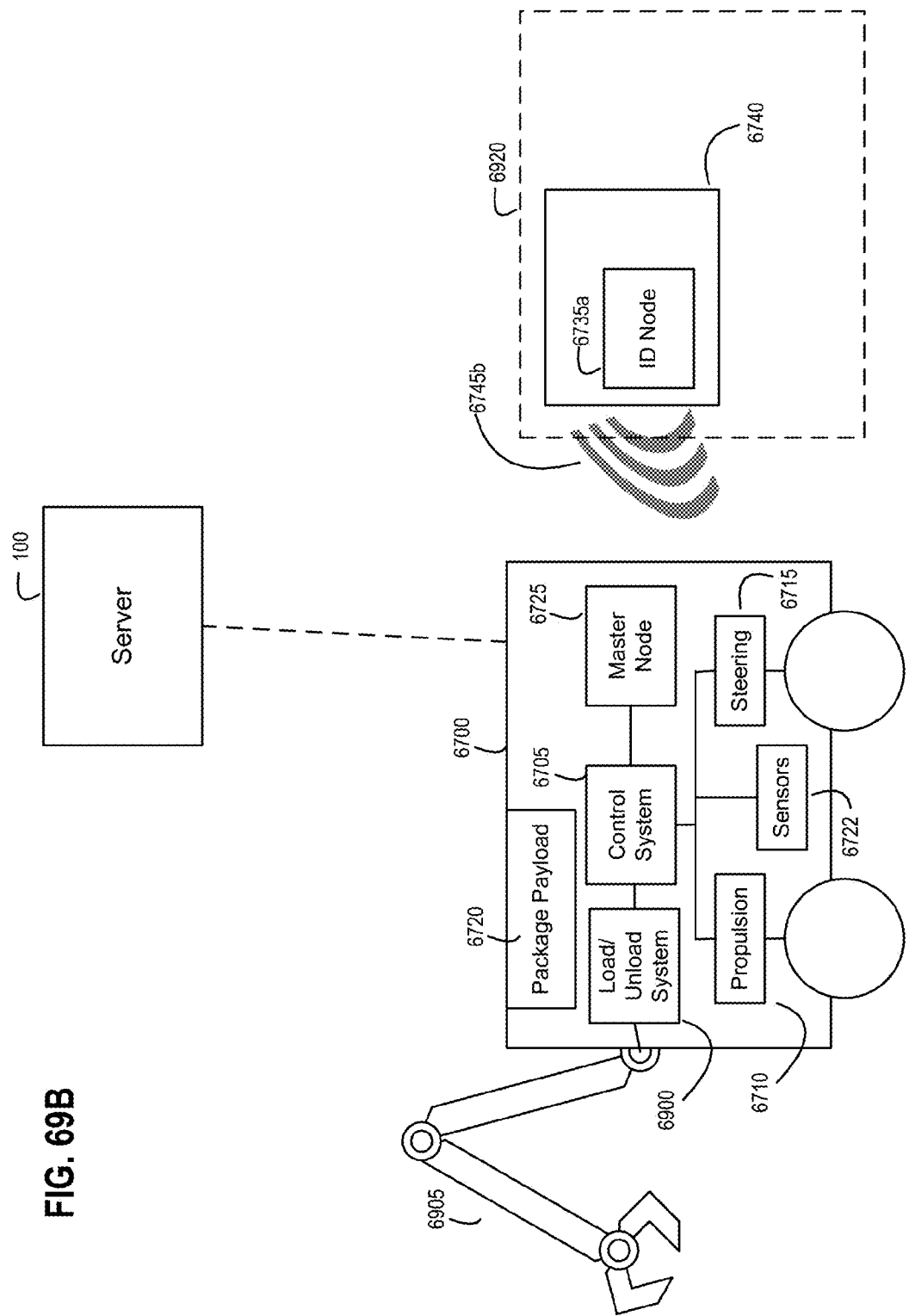
FIG. 69B is a diagram illustrating the exemplary node-enabled autonomous vehicle as it approaches a package and related ID node for an exemplary logistics transaction at a transaction location in accordance with an embodiment of the invention.

FIG. 69B is a diagram illustrated the exemplary node-enabled autonomous vehicle as it approaches a package and related ID node for an exemplary logistics transaction at a transaction location in accordance with an embodiment of the invention. Referring now to FIG. 69B, the autonomous vehicle 6700 has been deployed and approaches package 6740 having ID node 6735a within it. The package 6740 is located at a location or address, generally referred to as a transaction location 6920 for the package. In this example, the package 6740 is awaiting pickup and a shipping customer may have entered a shipment order where shipping information related to the order is maintained on the server 100. The autonomous vehicle 6700 would receive such shipping information so that it knows what package to pick up, where the pickup logistics transaction should take place, and an identification of any ID node associated with the package. Armed with that information, the mobile master node 6725 within autonomous vehicle 6700 is then operative to control how the autonomous vehicle 6700 automatically conducts the logistics transaction.

In another example, those skilled in the art will appreciate a similar type of operation takes place when the autonomous vehicle 6700 is deployed to conduct a drop off logistics transaction where the package is ferried by the vehicle 6700 to the transaction location 6920 and then removing the package from the package payload 6720 and placing the package at the location 6920 to deliver the package.

Figure 70:
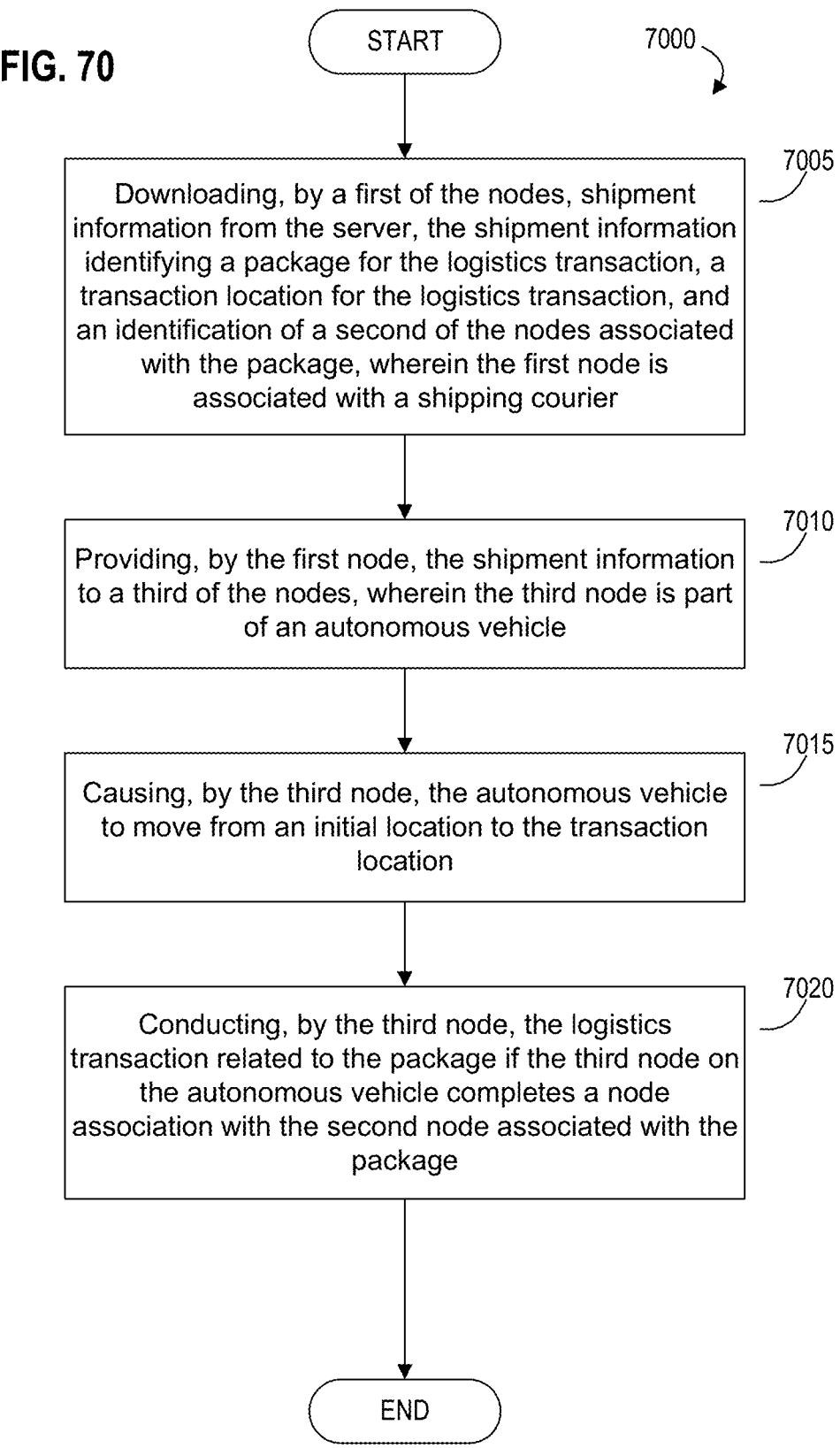
FIG. 70 is a flow diagram illustrating an exemplary method for automating a logistics transaction using a plurality of nodes and a server in a wireless node network in accordance with an embodiment of the invention.

FIG. 70 is a flow diagram illustrating an exemplary method for automating a logistics transaction using a plurality of nodes and a server in a wireless node network in accordance with an embodiment of the invention. Referring now to FIG. 70, method 7000 begins at step 7005 where a first of the nodes (a node associated with a shipping courier) downloads shipment information from the server. The shipment information identifies a package for the logistics transaction, a transaction location for the logistics transaction, and an identification of a second of the nodes associated with the package.

At step 7010, the first node provides the shipment information to a third of the nodes, wherein the third node is part of an autonomous vehicle. For example, as shown in FIG. 69A, courier transport vehicle master node 6915 may receive and download shipping formation on a package to be picked up (if the logistics transaction is a pick up operation for autonomous vehicle 6700) from server 100, and then provide that shipping information to mobile master node 6725 in vehicle 6700. In another embodiment, the embedded mobile master node 6725 may directly download the shipping information from server 100.

At step 7015, the third node causes the autonomous vehicle to move from an initial location (more generally referred a first location) to the transaction location. For example, as shown in FIG. 69B, mobile master node 6725 in autonomous vehicle 6700 may operate as the third node and causes vehicle 6700 to move from an initial deployment location outside of courier transport vehicle 6910 to a transaction location 6920 identified in the shipping information. This may be done with instructions and signals provided from node 6725 to control system 6705, which then manages operations of the propulsion system 6710 and steering system 6715.

At step 7020, method 7000 concludes when the third node conducts the logistics transaction related to the package if the third node on the autonomous vehicle completes a node association with the second node associated with the package. As explained above, generally a logistics transaction is a type of operation involving any logistics stage of shipping, such as picking up the package of interest, ferrying the package of interest between locations, dropping off the package of interest, moving the package of interest, etc.

In one embodiment where the logistics transaction comprises picking up the package at the transaction location after the third node associates with the second node, conducting the logistics transaction may be done when the third node detects a signal from the second node (associated with the package) as the autonomous vehicle approaches the transaction location. Thereafter, the conducting step may continue when the third node and the second node are associated, the package is picked up at the transaction location, and then placed into a package payload storage of the autonomous vehicle.

In this embodiment, method 7000 may also comprise returning, by the autonomous vehicle, to the courier transport vehicle to unload the package and the second node from the package payload storage of the autonomous vehicle, and then transmit a verification message to the server. The verification message confirms that the package was picked up and is on the courier transport vehicle.

In another embodiment where the logistics transaction comprises dropping off the package at the transaction location after the third node associates with the second node, conducting the logistics transaction may be done when the third node detects a signal from the second node as the autonomous vehicle approaches the transaction location. Thereafter, the conducting step may continue when the third node and the second node are associated, the package is removed from a package payload storage of the autonomous vehicle; and the autonomous vehicle is controlled to drop off the package at the transaction location.

In this embodiment, method 7000 may have deployed the autonomous vehicle from a courier transport vehicle at the initial location, and had the package loaded into a package payload storage of the autonomous vehicle prior to causing the autonomous vehicle to move from the initial location to the transaction location.

And still in this embodiment, method 7000 may also cause the autonomous vehicle to return to the courier transport vehicle; and transmit a verification message to the server, where the verification message confirms that the package was dropped off at the transaction location and is no longer on the courier transport vehicle.

In a more detailed embodiment, the first node and the third node may each be a mobile master node (such as master node 6915 in courier transport vehicle 6910 and master node 6725 embedded in or integrated as part of autonomous vehicle 6700. Each of the mobile master nodes is one of the plurality of nodes and is operative to communicate directly with the server in the wireless node network over a first communication path. In contrast, the second node may be an ID node, where the ID node is another of the plurality of nodes and is operative to communicate with each of the master nodes over a shorter range communication path but is unable to communicate directly with the server.

In another embodiment, an exemplary system is described for automating a logistics transaction related to a package. The system generally comprises three nodes—a first node associated with a courier transport vehicle, a second node associated with the package, and a third node integrated as part of an autonomous vehicle related to the courier transport vehicle. Examples of such nodes in an illustrated embodiment appear as master node 6915 associated with a courier transport vehicle 6910, ID node 6735a associated with the package 6740, and mobile master node 6725 integrated as part of an autonomous vehicle 6700 related to the courier transport vehicle 6910 as shown in FIGS. 69A and 69B.

In the system, the first node is operative to download shipment information from the server. The shipment information identifies the package for the logistics transaction, a transaction location for the logistics transaction related to the package, and an identification of the second node associated with the package. The first node also provides the shipment information to the third node.

And in the system, the third node is operative to cause the autonomous vehicle to move from a first location proximate the courier transport vehicle to the transaction location, and conduct the logistics transaction related to the package if the third node successfully associates with the second node associated with the package.

In an embodiment where the logistics transaction comprises picking up the package at the transaction location after the third node successfully associates with the second node, the ability of the third node to conduct the logistics transaction may be explained in more detail as detecting a signal from the second node associated with the package as the autonomous vehicle approaches the transaction location, associating the third node and the second node, instructing a package articulation system on the autonomous vehicle to pick up the package at the transaction location, and instructing the package articulation system to place the package in a package payload storage of the autonomous vehicle. Those skilled in the art will appreciate that having the third node instruct the package articulation system to perform a function generally involves providing a control signal to a system controlling the package articulation system (such as control system 6705 that controls the load/unload system 6900 and articulating arms 6905 of the package articulation system shown in FIGS. 69A and 69B).

In still a further embodiment, the third node may be further operative to cause the autonomous vehicle to return to the courier transport vehicle, instruct the package articulation system to unload the package and the second node associated with the package from the package payload storage of the autonomous vehicle into a storage area of the courier transport vehicle, and transmit a verification message to the server, wherein the verification message confirming that the package was picked up and is on the courier transport vehicle.

In another embodiment where the logistics transaction comprises dropping off the package at the transaction location after the third node successfully associates with the second node, the third node may be further operative to conduct the logistics transaction by being further operative to perform several more detailed operations. Specifically, the third node may be operative to detect a signal from the second node associated with the package as the autonomous vehicle approaches the transaction location, associate the third node and the second node, instruct a package articulation system on the autonomous vehicle to remove the package from a package payload storage of the autonomous vehicle, and instruct the package articulation system to drop off the package at the transaction location. Thereafter, the third node may be further operative to transmit a verification message to the server, where the verification message confirms that the package was dropped off at the transaction location.

In a more detailed embodiment of the system, the first node and the third node may each be implemented as a mobile master node, where each of the mobile master nodes is one of the plurality of nodes and is operative to communicate directly with the server in the wireless node network over a first communication path. And in more detail in this embodiment, the second node may be an ID node, where the ID node is another node of the plurality of nodes and is operative to communicate with each of the master nodes over a shorter range communication path but is unable to directly communicate with the server.

While an exemplary system in an embodiment is described above, another embodiment involves just a node-enabled autonomous vehicle that conducts a logistics transaction related to a package. In this embodiment, the node-enabled autonomous vehicle comprises an autonomous vehicle and a mobile master node integrated as part of the autonomous vehicle. The autonomous vehicle is operative to move, in response to control input, from an initial location to a transaction location related to the logistics transaction. The mobile master node is one of a plurality of nodes in a wireless node network and further comprises a node processing unit, a node memory, a short-range communication interface and a longer range communication interface. The node memory, short-range communication interface and longer range communication interface are each coupled to the node processing unit (such as shown in FIG. 4 for exemplary master node 110a). The short-range communication interface is operative to communicate with the nodes in the wireless node network, while the longer range communication interface is operative to communicate directly with a server in the wireless network.

The node processing unit of the mobile master node, when executing the code maintained on the node memory, is operative to perform several functions. In particular, the node processing unit is first operative to receive shipment information generated by the server. The shipment information identifies the package for the logistics transaction, the transaction location for the logistics transaction related to the package, and an identification of the second node associated with the package. The node processing unit is then operative to provide a control signal to control input of the autonomous vehicle causing the autonomous vehicle to move from the initial location to the transaction location, and automatically conduct the logistics transaction related to the package if the third node successfully associates with the second node associated with the package.

In one embodiment where the logistics transaction may comprise picking up the package at the transaction location after the third node successfully associates with the second node, the autonomous vehicle may further comprise a package payload storage and a package articulation system that may be operative to place the package within the package payload storage and remove the package from within the package payload storage. In the example shown in FIGS. 69A and 69B, such a payload storage appears as package payload 6720. While shown small in scale relate to other components in autonomous vehicle 6700, those skilled in the art will appreciate that the relative size shown in the figures is not limiting and that the size for such storage may be dictated by the size of packages anticipated to be transported, the propulsion capacity for the autonomous vehicle, etc. Likewise, the illustrated package articulation system shown in FIGS. 69A and 69B may take a variety of controllable machinery, such as lift gates, robotic arms, articulating scoops, and the like to capture a package and transport the package safely between locations.

In this embodiment here the logistics transaction is picking up the package, the third node may be further operative to automatically conduct the logistics transaction by being operative to detect a signal from the second node associated with the package as the autonomous vehicle approaches the transaction location, associate the third node and the second node, and provide a pickup control signal to the control input of the autonomous vehicle to cause the package articulation system on the autonomous vehicle to pick up the package at the transaction location and place the package in the package payload storage of the autonomous vehicle.

In a further embodiment, the third node may also be operative to cause the autonomous vehicle to return to the courier transport vehicle. This may be accomplished with a movement-related control signal. The third node may also be operative to provide an unload control signal to the control input of the autonomous vehicle to cause the package articulation system to unload the package and the second node associated with the package from the package payload storage of the autonomous vehicle, and then transmit a verification message to the server over the longer range communication interface, where the verification message confirming that the package was picked up.

In another embodiment where the logistics may comprise dropping off the package at the transaction location after the third node successfully associates with the second node, the autonomous vehicle may further comprise a package payload storage and a package articulation system operative to place the package within the package payload storage and remove the package from within the package payload storage.

In this embodiment, the third node may be further operative to conduct the logistics transaction by detecting a signal (e.g., a broadcast advertising signal) from the second node as the autonomous vehicle approaches the transaction location, associating the third node and the second node, and providing a drop off control signal to the control input of the autonomous vehicle. The drop off control signal causes the package articulation system on the autonomous vehicle to remove the package from within the package payload storage and place the package at the transaction location.

In another embodiment, the third node may be further operative to transmit a verification message to the server over the longer range communication interface, where the verification message confirms that the package was dropped off at the transaction location.

And in a more detailed embodiment, the second node associated with the package may be an ID node (another node of the plurality of nodes) and is operative to communicate with the mobile master node over the short-range communication interface but is unable to directly communicate with the server.

Equipment Monitoring Applications

Embodiments of a wireless hierarchical node network may be further applied to equipment monitoring situations where enhanced tracking and visibility may be desired. In more detail, exemplary ID nodes, exemplary master nodes, and an exemplary server operating in a hierarchy as a wireless node network provide the capacity for improved tracking and enhanced visibility to the location of items associated with such nodes (e.g., whether inside or outside of structures and containers). And when leveraging the sensing capabilities of some of such exemplary nodes, it provides the capacity to know what is going on with items to which the exemplary nodes are associated. For example, when a piece of equipment is being monitored using such a hierarchical node network, the monitoring system is able to leverage this enhanced tracking and visibility into what is going on and where to identify an actionable event so that a responsive action may be taken at the appropriate time and with the appropriate scope of action.

In a general embodiment, a piece of equipment may be any type of machine or apparatus where operation of the equipment is desired to be monitored. For example, such equipment may include, but is not limited to, medical equipment, office equipment, industrial equipment, manufacturing equipment, construction equipment, transportation equipment, laboratory equipment, sporting equipment, automotive equipment, farm equipment, marine equipment, mining equipment, and the like. While these examples are expressly noted here, those skilled in the art will appreciate that principles of an embodiment may be equally applicable to other types of equipment where monitoring the location and operation of that type of equipment may be desired.

Figure 71:
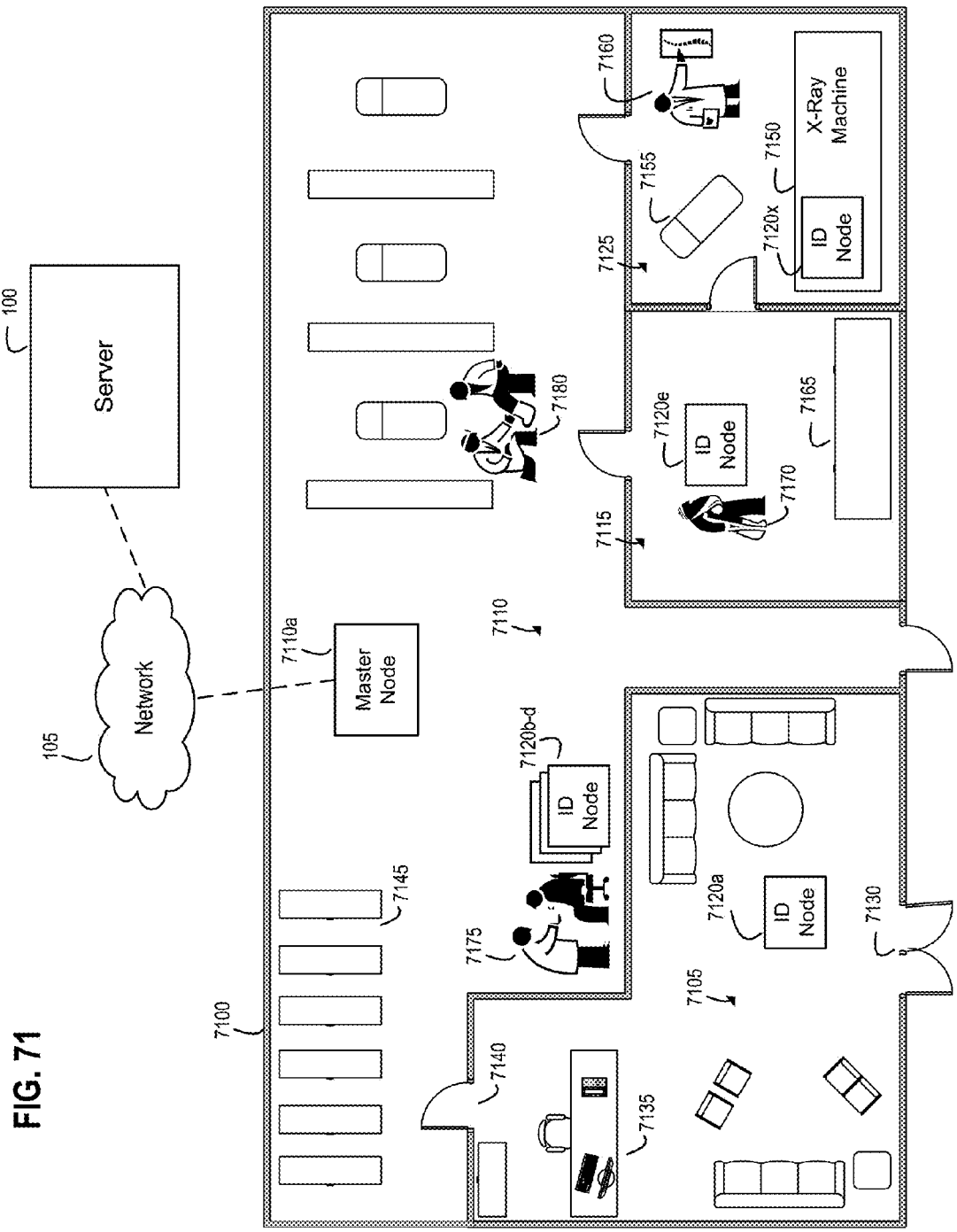
FIG. 71 is a diagram illustrating an exemplary hierarchical node network for monitoring a piece of equipment within an exemplary healthcare facility in accordance with an embodiment of the invention.

FIG. 71 is a diagram illustrating an exemplary hierarchical node network for monitoring a piece of equipment within an exemplary healthcare facility in accordance with an embodiment of the invention. The example environment illustrated in FIG. 71 is that of an exemplary healthcare facility 7100, such as an urgent care facility where medical patients may arrive, seek urgent treatment by medical personnel, have treatment using medical equipment within the facility, and may leave to return home to their residence after receiving treatment.

Referring now to FIG. 71, exemplary healthcare facility 7100 is shown having several areas, such as a patient lobby 7105, an examination area 7110, a confidential records room 7115, and a diagnostic testing room 7125. A person, who may be considered a medical patient in a healthcare facility or under treatment or medical care at their residence, may enter facility 7100 through an entrance 7130. Once in the patient lobby 7105, the patient may check in at the front desk area 7135, where they may sign in and register, provide relevant information (e.g., name, billing information, contact information, and the like) and receive a healthcare identification card.

In this example, the healthcare identification card may incorporate an ID node 7120a within it. However, in other examples, those skilled in the art will appreciate that other items associated with the patient may incorporate or otherwise include an ID node, such as clothing worn by the patient, a medical identification bracelet or wristband provided by healthcare facility personnel upon registering at desk area 7135, a clipboard type of device provided by the facility with relevant documents to be reviewed and used during the patient's visit to the facility 7100, or an electronic user access device (such as a smartphone with an app that enables operation of the smartphone to be that of an ID node; or a tablet type device provided by the patient or facility with a similar app running to enable operation as an ID node associated with the patient).

Once the patient has checked in and after a wait in the patient lobby 7105, the patient may be called back to the examination area 7100 (or notified of this via the ID node's user interface, such as a light, sound, or simple alphanumeric display). The patient may enter examination area 7105 through door 7140 for an initial examination or triage examination by a medical technician 7175 using various medical equipment, such as blood pressure monitor, a cardiac monitor, and a pulse oximeter (each of which are associated with their own ID nodes 7120b-d). While not shown in FIG. 71, facility 7100 may also include a storage area where an inventory of different medical equipment may be stored (each piece of equipment having an ID node associated with it).

After having the preliminary testing done by medical technician 7175, the patient may move over to another part of the examination area 7100 (which may be open or in closed off distinct examination rooms) for further examination by another healthcare provider 7180 (e.g., a physician or nurse). If during the examination by the healthcare provider 7180, it is determined that diagnostic testing may also be needed to further diagnose the patient's symptoms and treat the patient, the patient may be directed to enter diagnostic testing room 7125. Once in diagnostic testing room 7125, the patient may be instructed to lay down on testing table 7155 while another healthcare provider (e.g., a radiologist or x-ray technician) activates x-ray machine 7150 (which has an ID node 7120x associated with it). After the test, the patient may be directed back to the examination area 7110 or back to the patient lobby 7105. However, if the patient's treatment is complete, the patient may check out and leave the facility.

In some situations, the patient may not be familiar with the layout of the facility 7100 and wander into areas where the patient is not anticipated to be, such as the confidential records room 7115. For example, a patient 7170 may have an ID node 7120e integrated into her medical identification bracelet or wristband. The patient 7170 may have been in an automobile accident and had an x-ray on x-ray machine 7150 operated by technician 7160. Given the x-ray testing confirmed a broken ankle and arm; a physician 7180 may have put her leg and arm in casts as part of the treatment. The patient 7170 may be confused and, while attempting to leave the examination area 7110, may have entered confidential records room 7115 where she is not anticipated nor permitted to be. As will be explained in more detail, the use of ID node 7120e here may proactively warn the patient as well as others that she is located in an area where she is not anticipated to be.

More generally, in such an exemplary medical environment, the ID nodes may be associated with a person or a piece of equipment and be operative to monitor an activity of the person or an operation of the piece of equipment. Additionally, those skilled in the art will appreciate based on the prior discussion of exemplary ID nodes, master nodes, and servers, such ID nodes in this medical environment are operative to communicate directly with master node 7110a but are unable to directly communicate with server 100. However, the master node 7110a is operative to directly communicate with the server 100 and separately communicate with the ID nodes shown in FIG. 71. Those skilled in the art will further appreciate the while only one master node 7110a is shown in FIG. 71 for facility 7100, this is done for simplicity of explanation and that other embodiments may deploy one or more other master nodes that are also operative to communicate directly with server 100 and each other, as well as ID nodes that broadcast advertising signals within the reception range of the respective master nodes.

FIG. 72 is a flow diagram illustrating an exemplary method for monitoring a piece of equipment (e.g., a blood pressure monitor, a pulse oximeter, an x-ray machine, etc.) using a hierarchical node network having at least an ID node, a master node, and a server in accordance with an embodiment of the invention. Referring now to FIG. 72, method 7200 begins at step 7205 with the master node associating with the ID node when the master node detects a signal broadcast from the ID node. The ID node is associated with the piece of equipment, such as medical equipment, office equipment, industrial equipment, manufacturing equipment, construction equipment, transportation equipment, laboratory equipment, sporting equipment, automotive equipment, marine equipment, and mining equipment. These are examples of equipment where operations may be monitored. The ID node (such as ID node 7120x shown in FIG. 71 or exemplary ID node 120a shown in FIG. 3) is operative to monitor an operation of the piece of equipment and to communicate directly with the master node but is unable to directly communicate with the server. However, the master node is operative to directly communicate with the server and separately communicate with the ID node.

For example, as shown in FIG. 71, ID node 7120x can monitor an operation of the x-ray machine 7150 (e.g., when it was activated, what operation was performed, gather information from the machine on which operator or technician activated it, how long it was operated, and patient information related to the test performed during the operation of the machine, etc.). In doing so, ID node 7120x may be implemented as a type of sensor node having sensors or other interfacing circuitry onboard (and as explained with reference to exemplary ID node 120a in FIG. 3) to gather information from x-ray machine 7150 and monitor desired operations of the machine 7150. ID node 7120x can communicate directly with the master node 7110a but is unable to directly communicate with the server 100 where master node 7110a can directly communicate with the server 100 over a longer-range communication path (e.g., WIFI) and separately communicate with the ID node 7110a over, for example, a shorter-range communication path (e.g., a Bluetooth® enabled communication path between Bluetooth® enabled devices).

In one embodiment, the associating step of method 7100 may further comprise establishing a passive association between the master node and the ID node without requiring without requiring a prior authority granted by the server. However, in another embodiment, the associating step of method 7100 may further comprise establishing an active association between the master node and the ID node. The active association, in contrast to the passive association, reflects an authorized connection between the master node and the ID node based upon an authority granted by the server. In one example, the master node sends an association request to the server prior to associating the master node and ID node associated with the piece of equipment. However, in other examples, such a request is made unnecessary if the server preauthorizes such an association. This avoids the need for the master node to request the authority from the server after detecting the signal broadcast from the ID node.

At step 7210, method 7200 continues with the server determining a location of the ID node. The location of the ID node associated with the piece of equipment may factor into what an actionable event is, which may require a responsive action to be taken. In more detail, the step of determining the location of the ID node may further comprise tracking the location of the ID node over time. And in even more detail, the step of determining the location of the ID node may further comprise tracking the location of the ID node over time and refining the location of the ID node based upon context data related to an operating environment of the piece of equipment and the ID node At step 7215, method 7200 continues with the ID node detecting an actionable event related to the operation of the piece of equipment. In one embodiment, the ID node alone may detect the actionable event. In another embodiment, the ID node may detect a condition for the actionable event related to the equipment's operation and report that condition to the master node, which may either use that condition information along with location information on the ID node to detect the actionable event or pass that condition information to the server where the actionable event may be detected using that condition information and other information (such as location data or context data related to the ID node or its operating environment).

In one or more detailed embodiments, method 7200 may detect an actionable event by detecting a movement status, an activation status, or a usage status related to the operation of the piece of equipment. An exemplary movement status may be whether the ID node (and the piece of equipment associated with it) was just moved, is not moving, or is moving relative to a path or anticipated point(s). An exemplary activation status may be a detected power up of the equipment in general or activation of a particular part of or feature used on the equipment. Those skilled in the art will appreciate that the level of granularity on such a detected activation will depend on the sophistication in the interfacing circuitry on the ID node and the ability to receive or monitor signals or environmental conditions related to the piece of equipment itself.

At step 7220, method 7200 continues with the ID node transmitting a message to the master node reporting the actionable event. At step 7225, method 7200 continues by notifying the server by the master node about the actionable event. However, in embodiments where detection of the actionable event occurs at the master node level or the server level (based at least in part on the condition information), those skilled in the art will appreciate there may be no need to transmit such a message to the master node or notify the server if the master node about the actionable event. Instead, such embodiments may transmit a message to the master node reporting the condition information, and the master node may then notify the server with that information.

At step 7230, method 7200 concludes with the server initiating a responsive action based upon the notification. In one embodiment, the step of initiating the responsive action step may comprise updating a billing attribute related to the operation of the piece of equipment. For example, the server may implement a billing system relating to use of the particular piece of equipment (such as a billing computer system for healthcare facility 7100) or the server may provide input to a separate billing computer system. Such a billing attribute may, for example, be in the form of an identification of the piece of equipment and a cost to be billed for use of the equipment monitored by the ID node.

In another embodiment, the step of initiating the responsive action step may comprise updating an inventory attribute related to the operation of the piece of equipment. Generally, the piece of equipment may be part of a managed inventory of equipment where it is desired to track or monitor different aspects of the inventory, such as what is in the inventory, where the inventory is collectively located, and how the inventory is used and may be aging. An exemplary inventor attribute may include information related to monitored aspects of the inventory (such as use of this piece of the equipment inventory, a location of this piece of the equipment inventory, and the like).

In still another embodiment, the step of initiating the responsive action step may comprise updating a maintenance attribute related to the operation of the piece of equipment. For example, the piece of equipment may have a maintenance schedule that is setup for that particular piece. An exemplary maintenance attribute may include operational time as it relates to such a maintenance schedule. Furthermore and more generally, an exemplary maintenance attribute to be updated may include information related to any service, repairs, refurbishment, parts replacement, or other maintenance done on the equipment.

In yet another embodiment, the step of initiating the responsive action step may generally comprise updating a usage attribute related to the operation of the piece of equipment. For example, this may generally be tracking time of operation (more generally usage time) for the piece of equipment. In another example, this may be monitored in more detail as to how modes of operation are enabled and used and for how long. Thus, an exemplary usage attribute may be a simple activation count but may be a snapshot of operations and all operational data generated when the piece of equipment is used. Those skilled in the art will appreciate that different embodiments may advantageously take advantage of the more complex implementations, despite the higher costs to do so and complexities at interfacing and storing such information sensed from the equipment by the ID node.

In a further embodiment, the step of initiating the responsive action step may comprise updating a quality assurance attribute related to the operation of the piece of equipment. Many pieces of equipment are used where the user is concerned about quality and the users employ quality assurance programs to monitor and make sure operations are accurate and have a high standard of quality. An exemplary quality assurance attribute related to the operation of the piece of equipment may involve tracking and monitoring the output of the equipment to ensure that the equipment is running at an acceptable level (not providing erroneous results, is operating in calibration, etc.).

In another embodiment of method 7200, the master node may avoid the need to immediately notify the server regarding the actionable event and may be able to initiate a responsive action (such as that described above) prior to informing the server of the actionable event. Such an embodiment places more computational responsibility at the level of the master node, but may provide a timing advantage by not requiring notification of the server as a precondition for initiating the responsive action.

Another embodiment includes a hierarchical node network for monitoring a piece of equipment. In this embodiment, the hierarchical node network comprises a server, a master node, and an ID node associated with a piece of equipment. The ID node is operative to monitor an operation of the piece of equipment, and can wirelessly communicate directly with the master node over a shorter range communication path but is unable to directly communicate with the server. The ID node is also operative to detect an actionable event related to the operation of the piece of equipment, and transmit a message to the master node reporting the actionable event.

The master node in the hierarchical node network is operative to directly wirelessly communicate with the server over a longer range communication path, associate with the ID node upon detection of a signal broadcast from the ID node, and notify the server about the actionable event reported in the message received from the ID node. The server is then operative, as part of the hierarchical node network here, to determine a location of the ID node, receive the notification from the master node regarding the actionable event, and initiate a responsive action based upon the notification. Thus, this embodiment and similar embodiments of the hierarchical node network for monitoring a piece of equipment may operate similar to that described above with respect to the various embodiments and operations of method 7200.

Again, while embodiments of the method for monitoring a piece of equipment and a hierarchical node network for monitoring a piece of equipment are largely describe above with respect to medical equipment in a medical or healthcare environment, such as that shown in FIG. 71, those skilled in the art will appreciate that the same principles may be applied to different kinds of equipment, such as office equipment (e.g., wirelessly monitoring use of toner in printers), industrial equipment (e.g., wirelessly monitoring the usage time for a turbine in a power plant), manufacturing equipment (e.g., wirelessly monitoring operator time on a welding machine), construction equipment (e.g., wirelessly logging the use of transmission oil consumption in a dozer), transportation equipment (e.g., wirelessly monitoring tire pressures on an automated airport bus), laboratory equipment (e.g., wirelessly monitoring use of a high energy output mode for a transmitter test rack), sporting equipment (e.g., wirelessly monitoring a number of impacts by an ID node embedded within an enhanced football helmet), automotive equipment (e.g., wirelessly monitoring use of a trailer hitch), farm equipment (e.g., wirelessly monitoring operator time on a combine harvester machine and where the combine harvester machine has been gathering crops), marine equipment (e.g., wirelessly monitoring energy expended by communications equipment onboard a marine vessel), and mining equipment (e.g., wirelessly monitoring use of fuel by a fleet of front-end loaders).

Personnel Monitoring Applications

Similar to embodiments related to equipment monitoring, embodiments of a wireless hierarchical node network may be further applied to monitoring people (such as medical patients) as they move and for, in some instances, quantifiable health characteristics of a person (such as heart rate, heart rhythm, blood pressure, blood sugar, respiration, blood gasses, and the like). Again, as noted above, exemplary ID nodes, exemplary master nodes, and an exemplary server may operate in a hierarchy as a wireless node network, which provides the capacity for improved tracking and enhanced visibility to where people associated with such nodes are (whether inside or outside of facilities) and what may be going on with or to such people. And when leveraging the sensing capabilities of some of such exemplary nodes (e.g., sensor nodes where an ID node or master node also includes one or more sensors), it provides the capacity to know what is going on with a person to which the exemplary nodes are associated. When a person is being monitored using such a hierarchical node network, the monitoring system is able to leverage this enhanced tracking and visibility into what is going on where and identify appropriate actionable events so that similarly appropriate responsive actions may be taken at the appropriate time for the person.

Referring back to the example healthcare facility illustrated in FIG. 71, server 100 is connected via network 105 to facility master node 7110a. Some of the ID nodes shown in FIG. 71 may be associated with a person as they approach and enter the facility, and receive treatment there. In one example, a patient is associated with an ID node typically upon entry to the facility. In more detail, a patient may have registered at desk 7135 and was given a healthcare identification bracelet, wrist band, or card with an integrated ID node 7120a in it. In this example, the healthcare personnel operating desk 7135 may activate the ID node 7120a and initially have it associated with the patient. In another embodiment, the patient may be able to use their smartphone (a type of user access device) running a particular app as they approach and enter facility 7100 so that the smartphone operates as the ID node 7120a associated with the person.

As shown in FIG. 71, that patient is currently located in the lobby area 7105 of healthcare facility 7100 and has not yet been treated. However, another patient 7170 (associated with a healthcare identification bracelet (or wristband) having integrated ID node 7120e) has already been treated. Specifically, patient 7170 was registered, received the bracelet with integrated ID node 7120e, was helped back to the examination area 7110, examined by physician 7180, and had x-ray images taken of her leg and arm in the diagnostic testing room. Patient 7170 then was treated in the examination area 7110 where her arm and leg were put in casts given the x-ray imaging revealed broken bones in those areas. However, patient 7170 may be confused and, while attempting to leave the examination area 7110, may have entered confidential records room 7115 where she is not anticipated to be. Indeed, by having a personal ID node (i.e., an ID node associated with the person), the patient's location may be monitored both indoors and outside by virtue of locating techniques and methods as applied using the wireless node network disclosed herein.

While FIG. 71 illustrates a medical environment of a healthcare facility (such as a hospital, doctor's office, urgent care facility, or dental office), those skilled in the art will quickly appreciate that the principles and advantages of monitoring a person using an exemplary wireless node network are also available in environments such as a residential environment. For example, the same principles and advantage of monitoring a person in a healthcare facility using an exemplary wireless node network may be applied when the person is at a residence or other type of building or area (e.g., in an office building, a manufacturing or industrial facility, a school, a camp, a shopping center or mall, a park, a restaurant, a stadium, a hotel, and the like) where components of the exemplary wireless network may be deployed in one or more embodiments.

FIG. 73 is a flow diagram illustrating an exemplary method for monitoring a person's activity using a hierarchical node network having at least an ID node, a master node, and a server in accordance with an embodiment of the invention. Referring now to FIG. 73, method 7300 begins at step 7305 with the master node associating with the ID node when the master node detects a signal broadcast from the ID node. The ID node, in method 7300, is associated with a person and operative to monitor the activity of the person and to communicate directly with the master node but is unable to directly communicate with the server. The master node, on the other hand, is operative to directly communicate with the server and separately communicate with the ID node. For example, facility master node 7110a can directly communicate with the server 100 over network 105 and can separately communicate with ID nodes within its communication range.

In one embodiment, method 7300 may have these nodes associating by establishing a passive association between the master node and the ID node without requiring without requiring a prior authority granted by the server. However, in another embodiment, method 7300 may have the nodes associating by establishing an active association between the master node and the ID node. The active association reflects an authorized connection between the master node and the ID node based upon an authority granted by the server. In a more detailed example, the authorized connection between the master node and the ID node may be preauthorized by the server to avoid the need for the master node to request the authority from the server after detecting the signal broadcast from the ID node.

At step 7310, method 7300 continues with the server determining a location of the ID node. As discussed above in detail in various ways, the server (or master node in another embodiment) may determine the location of the ID node associated with the person. In more detail, the step of determining the location of the ID node may further be accomplished by tracking the location of the ID node over time and refining the location of the ID node based upon context data related to an operating environment of the person and the ID node. For example, in the illustrated healthcare facility environment shown in FIG. 71, such exemplary context data may include dimensional and layout information on the facility 7100, anticipated regions of the facility 7100 where a patient may be anticipated to be located and regions where the patient is not anticipated to be located (e.g., confidential records room 7115), where particular equipment may be located (e.g., the location of x-ray machine 7150 associated with ID node 7120x), and signal degradation information on how a similar type of ID node may operate in a similar environment (e.g., taking account anticipated RF shielding effects or interference effects from known other broadcasting nodes in the area).

At step 7315, method 7300 continues with the ID node detecting an actionable event related to the activity of the person based upon the location of the ID node. As similarly noted with respect to step 7215 when monitoring a piece of equipment, the ID node alone may detect the actionable event at step 7315. In another embodiment, the ID node may detect a condition for the actionable event related to the person's activity (e.g., a health related condition or activity level condition) and report that condition to the master node, which may either use that condition information along with location information on the personal ID node to detect the actionable event or pass that condition information to the server where the actionable event may be detected using that condition information and other information (such as location data or context data related to the ID node or its operating environment).

In a detailed embodiment, method 7300 may detect an actionable event by detecting a movement status as the actionable event related to the activity of the person based upon the location of the ID node.

In another embodiment, the person is a medical patient. In further embodiments, those skilled in the art will understand that the person may be an office worker that works in and around an office building, a worker on a manufacturing line or within an industrial facility, a faculty or student working at or attending a school, a camp staff member or camper at a camp, a shopper at a mall or other retail facility, a diner or staff at a restaurant, the staff or an event attendee at a stadium, or a staff member or hotel guest at a hotel.

When the person associated with the ID node is a medical patient, another embodiment of method 7300 may have the patient located in a healthcare facility and the ID node having been integrated into a healthcare facility identification (such as a bracelet, wristband, ID card, or clip-on tag to wear on the person). The ID node, in other embodiments, may be incorporated into other items used by or carried by the patient, such as a clipboard, carrying bag, hospital clothing, or the like.

In this embodiment with the medical patient at the healthcare facility, method 7300 may detect the movement status, which may indicate the medical patient has left the healthcare facility based upon the location of the ID node. While in some cases, leaving the healthcare facility is normally anticipated after treatment, detection that the patient has left the facility may be unexpected in other cases where the patient has, for example, registered to stay in the facility and has not been checked out or otherwise authorized to leave the facility (e.g., the patient may not remember where they are or wake up with some confusion and mistakenly leave the facility).

In another example, the movement status may indicate the medical patient has entered a certain part of the healthcare facility based upon the location of the ID node. That part of the healthcare facility may be a location where the medical patient is not anticipated to be within the healthcare facility, such as a restricted area. For example, as shown in FIG. 71, patient 7170 has mistakenly wandered into the confidential records area 7115, which is an area that the patient 7170 is not anticipated to be located and an event calling for some responsive action.

Another embodiment may have the personal ID node implemented as a type of mobile sensor node associated with the patient. Implementing the node as a possible sensor node may allow the node to sense a quantifiable health characteristic related to the health of the medical patient. In more detail, method 7300 may implement step 7315 as detecting the actionable event as including sensing the quantifiable health characteristic using the mobile sensor node, and then detecting the actionable event when the sensed quantifiable health characteristic meets a predetermined condition. For example, if the ID node can sense blood pressure, the actionable event to detect may be when the ID node senses that the patient's blood pressure is greater than a threshold (as the predetermined condition). In another example, if the ID node can sense the patient's blood sugar level, the actionable even to detect may be when the ID node senses that the patient's blood sugar level either exceeds an upper threshold or goes below a lower threshold (as a more complex type of predetermined condition). The use of such a mobile sensor node to sense quantifiable health characteristics is not limited to use within a healthcare facility—those skilled in the art will appreciate that deploying such a node with a person as they go about a variety of daily activities with work, exercise, play, and rest may provide an extremely unobtrusive way to monitor the health of the patient outside the confines of a healthcare facility yet have prompt access to very current information and location data in case something goes wrong (as defined by the predetermined condition).

At step 7320, method 7300 continues by transmitting, by the ID node to the master node, a message reporting the actionable event. At step 7325, method 7300 continues by notifying the server by the master node about the actionable event. However, in embodiments where detection of the actionable event may occur at the master node level or the server level (based at least in part on the condition information), those skilled in the art will appreciate there may be no need to transmit such a message to the master node or notify the server if the master node about the actionable event. Instead, such embodiments may transmit a message to the master node reporting the condition information, and the master node may then notify the server with that information.

At step 7330, method 7300 concludes by initiating, by the server, a responsive action based upon the notification. In one embodiment, the step of initiating the responsive action may be accomplished with the server notifying one or more user access devices associated with a relative of the medical patient and/or a healthcare provider affiliated with the healthcare facility. For example, server 100 may have information on whom to contact in case of an actionable event, and be able to issue a call, text, or other warning or notification to the identified smartphone of a relative or the patient's physician.

In another embodiment of method 7300, the master node may avoid the need to immediately notify the server at step 7325 regarding the actionable event and may be able to initiate a responsive action (such as that described above) by the master node itself (to accomplish step 7330) prior to informing the server of the actionable event. Such an embodiment places more computational responsibility at the level of the master node, but may provide a timing advantage by not requiring notification of the server as a precondition for initiating the responsive action.

In still another more detailed embodiment of method 7300, the server may initiate a responsive action by tracking the movements of the medical patient to determine a pattern of movement; correlating the determined pattern of movement to a recorded change in patient behavior; and notifying a user access device associated with a healthcare provider affiliated with the healthcare facility, where the notification indicates the relationship between the determined pattern of movement and the recorded change in patient behavior. For example, tracking the movements of a patient to determine and unobtrusively establish patterns of movement may help a healthcare facility identify that the patient may be in the beginning or later phases of dementia or may help identify the extent of physical impairment being suffered by the patient.

As noted above, embodiments of method 7300 are applicable when the person may an office worker that works in and around an office building, a worker on a manufacturing line or within an industrial facility, a faculty or student working at or attending a school, a camp staff member or camper at a camp, a shopper at a mall or other retail facility, a diner or staff at a restaurant, the staff or an event attendee at a stadium, or a staff member or hotel guest at a hotel.

In one embodiment where the person is a medical patient located at a residence, rather than a healthcare facility, the actionable event detected may be a detected movement status in step 7315 where the movement status indicates the medical patient has left the residence based upon the location of the ID node. In another example, the movement status may indicate the medical patient is not moving at all over a period of time, or may be moving with a pattern of movement indicative of a medical condition (e.g., some type of physical impairment (such as a broken leg, a wheelchair that is not completely functional, etc.) or some type of mental impairment (such as dementia, Alzheimer's Disease, etc.)).

And in the embodiment where the person is a medical patient located at a residence, initiating the responsive action in step 7330 may involve having the server (or master node in some situations) notify a user access device associated with a relative of the medical patient and/or a particular healthcare provider.

In addition to the various embodiments of method 7300, another embodiment describes the hierarchical node network for monitoring an activity of a person. In this embodiment, the hierarchical node network comprises a server, a master node, and an ID node associated with a person (also referred to here as a personal ID node and explained above as a sensor node in some embodiments). The ID node is operative to wirelessly communicate directly with the master node over a shorter range communication path but is unable to directly communicate with the server.

The ID node is also operative to monitor the activity of the person, such as the person's location, a quantifiable characteristic of the person (e.g., blood pressure via blood pressure sensors, respiration via a respiration sensor coupled to the ID node, pulse via a pulse oximetry sensor, orientation of limbs or the head via accelerometer sensors on the ID node, other physiological characteristics via one or more biosensors coupled to or integrated into the ID node, etc.). As such, the ID node can detect an actionable event related to the activity of the person, and transmit a message to the master node reporting the actionable event.

The master node is operative to associate with the ID node upon detection of a signal broadcast from the ID node (such as an advertising packet message broadcast at a particular power level setting), and notify the server about the actionable event reported in the message received from the ID node. The server is operative to determine a location of the ID node, receive the notification from the master node regarding the actionable event, and initiate a responsive action based upon the notification. Thus, this embodiment and similar embodiments of the hierarchical node network for monitoring an activity of a person may operate similar to that described above with respect to the various embodiments and operations of method 7300.

Medical Treatment Application

Additional embodiments may use a hierarchical node network to enhance how a healthcare facility may operate as it provides medical treatment to patients. In particular, such embodiments may enhance the treatment process for a patient as they arrive and move throughout the facility by helping to initiate pre-staged preparations related to the medical treatment through the use of elements in a hierarchical node network.

In one example, referring back again to the healthcare facility 7100 shown in FIG. 71, a patient may arrive with a user access device (such as a smartphone or tablet) executing an app that has the device operating as a node (e.g., an app having functionality similar to code 325 as explained herein so that the device may operate as a type of ID node; or an app having functionality similar to code 425 as explained herein so that the device may operate as a type of master node that can directly communicate with the server and separately communicate with the ID node over a different communication path). The patient may have previously used the same or different user access device (e.g., their home computer) to locate a nearest health care facility associated with the network, and is prompted to provide status information related to the patient's upcoming visit.

Exemplary medical status information may include condition information related to a current medical problem with which the patient needs help and treatment at the facility. The exemplary condition information provided may include specifics on a symptom indication related to the health condition of the person. In other embodiments, exemplary status information may include but is not limited to initial or updated insurance information related to the patient or a relative of the patient, address information, information on reasons for the visit, the type of physician to be seen (e.g., a general physician, an ER physician, a specialist physician, such as an endocrinologist, etc.).

Such information may then be sent through the network to the server (e.g., through a direct connection from the user access device that is operating as an ID node to the server, or through an indirect connection to the server where the user access device connects and uploads the condition information to one or more intermediate devices first). Thus, as the patient approaches the facility 7100, the patient's own ID node, such as a user access device operating as, for example, an ID node in an embodiment may associate with the facility's master node 7110a. This user access device may not necessarily be the same device used by the patient to provide and upload the medical status information (such as the patient's condition information).

By facilitating the early provision and relevant consideration of this medical status information from a patient, an embodiment of the hierarchical node network may be able to track the location of the patient as it initiates one or more appropriate pre-staged preparations for the patient's impending visit to the facility and treatment once within the appropriate part of the facility. And the hierarchical node network's ability to track the patient's location as the patient moves (outside or indoors) also allows for adjustments to the pre-staged preparations, including adjustments made to better locate the patient based on context data about, for example, the facility. Furthermore, embodiments may provide for a proactive and interactive engagement with the patient prior to the patient's arrival at the healthcare facility, during the arrival and initial patient registration, and while the patient moves about within the facility.

In more detail, once the patient arrives and moves towards a registration desk, the patient's smartphone or other user access device operating as an ID node may pre-store relevant insurance information to be shared, as well as help facilitate an efficient co-pay payment transaction using node association (see, e.g., FIG. 36 and the accompanying description of embodiments for conducting a payment transaction using node association). For example, a patient's medical flex account system may stage credits on the patient's user access device operating as an ID node to use as currency for such a co-pay transaction.

FIG. 74 is a flow diagram illustrating an exemplary method for initiating a pre-staged preparation related to medical treatment to be provided to a patient at a healthcare facility using a hierarchical node network in accordance with an embodiment of the invention. Referring now to FIG. 74, method 7400 is described beginning at step 7405 where the master node associates with the ID node when the master node detects a signal broadcast from the ID node as the patient approaches the healthcare facility. Here, the ID node is associated with the patient seeking the medical treatment. For example, the ID node may be the patient's smartphone (a type of user access device) or a tablet running a particular app. The ID node can communicate directly with the master node, which is operative to directly communicate with the server and separately communicate with the ID node.

In another embodiment, the master node may receive an authorization from the server so that the master node may actively associate with the ID node. The authorization may, for example, permit the master node and the ID node to actively associate with each other prior to detecting the signal broadcast from the ID node. Thus, a type of pre-authorized association may be setup by the server. For example, if the patient seeking treatment at healthcare facility 7100 has uploaded their relevant condition information to server 100, server 100 may provide facility master node 7110a with an authorization to associate with the ID node associated with the patient as the server 100 may have registration information related to the patient that links the patient with the ID node (e.g., the patient's smartphone or tablet device running an app so that the patient's device operates as an ID node).

In a different embodiment, the master node may associate with the ID node by establishing an active association between the master node and the ID node when the master node detects the signal broadcast from the ID node as the patient approaches the healthcare facility. In more detail, the active association may reflect an authorized connection between the master node and the ID node based upon the authorization. This authorized connection then provides a secure communication path between the master node and the ID node for privately sharing data between the master node and the ID node.

At step 7410, method 7400 continues with the master node receiving medical status information securely transmitted by the ID node related to the patient. In more detail, the medical status information may comprise condition information securely transmitted by the ID node related to a health condition of the patient. In more detail, the condition information received may include at least a symptom indication related to the health condition of the patient. For example, when the patient arrives at facility 7100 and is approaching entrance 7130, the facility master node 7110a may receive condition information about the patient that includes symptom information that the patient's left ankle is bruised, swollen, and tender. Other types of medical status information may comprises at least one of new or updated insurance information on the patient or a relative of the patient, address information on the patient or relative of the patient, information related to a reason for the patient visiting the healthcare facility (e.g., scheduled appointment, ER visit, lab work visit, symptom information, etc.), and information related to a type of physician anticipated to be seen by the patient while visiting the healthcare facility (e.g., an internist, an endocrinologist, etc.)

At step 7415, method 7400 continues when the master node transmits the medical status information to the server. Transmitting the medical status information received from the ID node may be accomplished in a variety of manners, such as, for example, by sending the exact medical status information the master node received or, alternatively, sending a summary of the status information the master node received. By transmitting the medical status information to the server, the server is then aware of what symptoms and/or other information describe the patient's status or characterize the health condition of the patient prior to the visit.

At step 7420, method 7400 continues by determining, by the server, the location of the ID node. As discussed above in detail in various ways, the server (or master node in some embodiments of method 7400) may determine the location of the ID node associated with the patient. In more detail, the step of determining the location of the ID node may further be accomplished by tracking the location of the ID node over time and refining the location of the ID node based upon context data related to an operating environment of the patient and the ID node. For example, in the illustrated healthcare facility environment shown in FIG. 71, such exemplary context data may include dimensional and layout information on the facility 7100, anticipated regions of the facility 7100 where a patient may be anticipated to be located and regions where the patient is not anticipated to be located (e.g., confidential records room 7115), where particular equipment may be located (e.g., the location of x-ray machine 7150 associated with ID node 7120*x*), and signal degradation information on how a similar type of ID node may operate in a similar environment (e.g., taking account anticipated RF shielding effects or interference effects from known other broadcasting nodes in the area).

In particular, another embodiment of method 7400 may have the step of locating the ID node relying upon a changing power characteristic of the user access device operating as the ID node. Specifically, locating the ID node may comprise providing, by the server to the master node, an instruction to change a power characteristic (such as the RF output power level of the advertising signal broadcast from the ID node) of the user access device operating as the ID node, and having the master node send the instruction to the user access device operating as the ID node.

In a more detailed example, providing the instruction may be accomplished by refining a level of the power characteristic to a refined value based upon context data related to an anticipated operating environment of the user access device operating as the ID node. Then, the master node would provide the instruction to change the power characteristic of the user access device operating as the ID node to the refined value. For example, the output power level of the ID node may be refined to a lower adjusted value based upon information that may indicate there are a large number of ID nodes anticipated to be operating around the ID node as it is anticipated to move within the facility.

Another example may have the ID node instructed to change its RF output power level to a refined level to account for anticipated signal degradation that may occur within particular parts of the facility through which the ID node is predicted to move. More specifically, the step of refining may be accomplished by refining the level of the power characteristic to the refined value based upon the context data related to the anticipated operating environment of the user access device operating as the ID node as the user access device is anticipated to move to a predicted location (such as a busy examination area 7110) within the healthcare facility when the predicted location is related to the medical status information (e.g., condition information). For example, for the condition of a broken ankle or leg, the system may anticipate that the ID node associated with the patient will be moving to the examination area 7110 and move to the x-ray testing room 7125. Thus, the master node 7110*a* may refine the RF output level for ID node 7120*e* to a lower level as it moves through a crowded examination area 7110, but then refine it to a higher level as the ID node 7120*e* moves into a predicted area, such as the x-ray testing room 7125, where significant signal degradation by shielding may be anticipated. As such, embodiments may take advantage of one or more of the enhanced locating techniques as disclosed herein.

At step 7425, method 7400 concludes with the server (or in some embodiments, the master node) initiating a pre-staged preparation related to the patient visiting the healthcare facility for medical treatment based upon the determined location of the ID node and the medical status information. In a more detailed embodiment, the initiating step in method 7400 may be accomplished by providing a direction message from the server to the master node. The direction message may include a set of directions for the patient to a predicted location within the healthcare facility based upon the determined location of the ID node and the medical status information. For example, with the broken ankle patient discussed above, server 100 may coordinate with master node 7110*a* to provide a message to the patient's smartphone (operating as an ID node, such as ID node 7120*e*) to apprise the patient of where to go and what to bring. Those skilled in the art will appreciate that other relevant information may be provided as part of the direction message for display on a user interface of the smartphone.

In another more detailed embodiment, the initiating step in method 7400 may be implemented with the server accessing a record in a record database. While FIG. 5 illustrates exemplary server 100 as accessing one type of database (e.g., a context data database), those skilled in the art will appreciate that other such databases (e.g., medical record databases) may be available and accessible to server 100 or to other dedicated database server systems that access such a record at the direction and instruction of server 100. In this embodiment, the record (such as a medical record prepared and maintained by the healthcare facility 7100, a health record prepared by the patient themselves, etc.) is related to the patient and found as being based upon the determined location of the user access device operating as the ID node (e.g., the location of the ID node is near the x-ray diagnostic testing room 7125) and the medical status information (e.g., condition information on the tenderness and swelling of the patient's leg) so relevant imaging records related to the patient and, more specifically, the patient's leg may be accessed.

The accessed record may then be transmitted by the server to a user access device associated with a part of the healthcare facility related to the medical status information to pre-stage the accessed record before the user access device operating as the ID node is located at the part of the healthcare facility related to the medical status information. Thus, back in example of the patient with the broken ankle, server 100 may transmit the accessed relevant imaging records to an office computer (not shown) or tablet device (not shown) operated by the x-ray technician 7160 in room 7125.

Furthermore, method 7400 may also include the step of adjusting the pre-staged preparation based upon an updated location of the patient. For example, as the patient moves through the examination area 7110 and 7125 to receive treatment, the patient may have an updated location of moving back towards the examination area 7110. In this exemplary embodiment, any pre-staged relevant prior imaging records may be sent to a computer or tablet (not shown) operated by physician 7180 in the examination area. Thus, such a hierarchical node network may operate to provide context-driven treatment of a patient.

In a further embodiment, a more interactive, two-way exchange of information may be proactively employed as part of initiating such pre-staged preparations. For example, the step of initiating the pre-staged preparation may further comprise providing a context-driven inquiry from the server to the master node. The context driven inquiry may include one or more pre-screening prompts for additional information from the patient based upon the medical status information. With the context-driven inquiry from the server, the master node may then send one or more pre-screening prompts to the user access device operating as the ID node for display on a user interface of the user access device. Such pre-screening prompts allow for multiple exchanges of information to facilitate a more active user or patient engagement. Such prompts may, in one embodiment, ask pre-screening questions such as address information, insurance information or updates, co-pay information, symptom information, or other additional status information that may be refined from the medical status information originally provided.

In this further embodiment of method 7400, the master node may then receive feedback from the user access device operating as the ID node, where the feedback provides enhanced medical status information (e.g., more detailed condition information, updates to address and insurance information, and the like). The master node may then transmit the feedback to the server for use in refining the pre-staged preparation related to the patient visiting the healthcare facility for the medical treatment.

In addition to the various embodiments of method 7400, another embodiment describes the hierarchical node network for initiating one or more pre-staged preparations related to medical treatment for a patient at a healthcare facility. In this embodiment, the hierarchical node network comprises a server, a master node, and an ID node associated with a person (also referred to here as a personal ID node and explained above as a user access device (such as a smartphone) operating as the ID node). The ID node is operative to wirelessly communicate directly with the master node over a shorter range communication path. More specifically and under control of software (such as an app that implements code 325), ID node is operative to broadcast a signal as the patient approaches the healthcare facility, and securely transmit medical status information (related to a health condition of the patient) to the master node after associating with the master node.

The master node in the exemplary network is operative to detect the signal broadcast from the ID node as the patient approaches the healthcare facility, associate with the ID node upon detection of the signal broadcast from the ID node, receive the medical status information securely transmitted by the ID node, and notify the server with a message about the received medical status information.

The server in the exemplary network is operative to determine a location of the ID node, receive the message from the master node regarding the received medical status information, and initiate one or more pre-staged preparations related to the patient visiting the healthcare facility for the medical treatment based upon the determined location of the ID node and the received medical status information. Thus, this embodiment and similar embodiments of the hierarchical node network for initiating a pre-staged preparation related to medical treatment to be provided to a patient at a healthcare facility may operate similar to that described above with respect to the various embodiments and operations of method 7400.

Further Particular Embodiments

What follows below is a listing of exemplary sets of particular embodiments focusing on one or more aspects of the different embodiments described above. Each of the different sets of particular embodiments respectively effect improvements to the technology of asset identification and monitoring, location services, logistics operations & infrastructure, and node operation and management using an adaptive, context-aware wireless node network. As such, within each further embodiment heading are numbered aspects describing a specific technological application of one or more nodes in such a wireless node network that improve or otherwise enhance these technical fields, as explained and supported by the disclosure above. Each numbered aspect appearing below a heading may make reference to other numbered aspects that appear below that heading.

Further Embodiment 1—Methods & Systems for Managing Shipment of an Item Using a Wireless Node Network 1. A method for managing a shipment of an item using a wireless node network having at least one ID node, a plurality of master nodes, and a server, the method comprising: transmitting shipping information to the server to register the ID node and the item to be shipped; associating the ID node to a first master node related to a predicted path for shipping the item; updating the server to reflect the association between the ID node and the first master node; associating the ID node and a second master node related to the predicted path as the ID node transits the predicted path; and updating the server to reflect the association between the ID node and the second master node as the ID node continues to transit the predicted path.

2. The method of embodiment 1, wherein the first master node is a user access device from a group comprising a laptop computer, a desktop computer, a tablet device, a personal area network device, a smartphone device, and a smart wearable device.

3. The method of embodiment 2, wherein the step of associating the ID node to the first master node is performed prior to a pick-up event in the predicted path.

4. The method of embodiment 1, further comprising disassociating the ID node and the first master node; and updating the server to reflect the disassociation between the ID node and the first master node.

5. The method of embodiment 4 further comprising associating the ID node to a third master node related to the predicted path at an end of the predicted path for shipping the item; and notifying the server to reflect the association between the ID node and the third master node.

6. The method of embodiment 1, further comprising disassociating the ID node and the second master node; and updating the server to reflect the disassociation between the ID node and the second master node.

7. The method of embodiment 5, wherein the third master node is a user access device from a group comprising a laptop computer, a desktop computer, a tablet device, a personal area network device, a smartphone device, and a smart wearable device.

8. The method of embodiment 7, wherein the step of associating the ID node to the third master node is performed after a drop-off event in the predicted path.

9. The method of embodiment 1 further comprising receiving context data related to the predicted path.

10. The method of embodiment 9 further comprising relying upon the received context data to adjust for an environmental aspect of the predicted path when associating the ID node to either the first or second master nodes.

11. The method of embodiment 1, wherein the step of associating the ID node to the first master node further comprises associating the ID node to the first master node upon capture of a scan event.

12. A method for managing a shipment of an item using a wireless node network having at least one ID node, a plurality of master nodes, and a server, the method comprising: receiving, by the server, shipping information to register the ID node and the item to be shipped; providing a first set of authentication credentials to a first master node to permit the ID node to associate with the first master node related to a predicted path for shipping the item; receiving, by the server, an update to reflect the association between the ID node and the first master node; providing a second set of authentication credentials to a second master node to permit the ID node to associate with the second master node as the ID node transits the predicted path; and receiving, by the server, an update to reflect the association between the ID node and the second master node as the ID node continues to transit the predicted path.

13. The method of embodiment 12 further comprising: providing a third set of authentication credentials to a third master node to permit the ID node to associate with the third master node as the ID node near an end of the predicted path for shipping the item; and receiving, by the server, a notification to reflect the association between the ID node and the third master node.

14. The method of embodiment 13, wherein the first master node is a user access device from a group comprising a laptop computer, a desktop computer, a tablet device, a personal area network device, a smartphone device, and a smart wearable device.

15. The method of embodiment 14, wherein the step of providing the first set of authentication credentials to the first master node is performed prior to a pick-up event in the predicted path.

16. The method of embodiment 13, wherein the third master node is a user access device from a group comprising a laptop computer, a desktop computer, a tablet device, a personal area network device, a smartphone device, and a smart wearable device.

17. The method of embodiment 13, wherein the step of providing the third set of authentication credentials to the third master node is performed after a drop-off event in the predicted path.

18. The method of embodiment 13 further comprising providing context data to at least one of the first, second, and third master nodes, wherein the context data relates to an environmental aspect of a part of the predicted path.

19. The method of embodiment 18 further comprising relying upon the received context data to adjust for an environmental aspect of the predicted path when associating the ID node to any of the first, second, or third master nodes.

20. The method of embodiment 13 further comprising determining a location of the ID node based upon association information received by the server and location information related to at least one of the first, second, or third master nodes.

21. The method of embodiment 12 further comprising predicting a transit route for the item from a first point to a second point along at least a portion of the predicted path for shipping the item.

22. The method of embodiment 21, wherein the first point is an origin point and the second point is a destination point, the origin point and the destination point being identified in the shipping information.

23. The method of embodiment 21 further comprising adjusting the predicted path based upon context data.

24. A non-transitory computer-readable medium containing instructions which when executed on a processor performs a method for managing a shipment of an item using a wireless node network having at least one ID node, a plurality of master nodes, and a server, the method comprising: receiving, by the server, shipping information to register the ID node and the item to be shipped; predicting a first portion of a transit route for the item from a first point to a second point; authorizing a first master node to associate with the ID node near the first point; receiving, by the server, an update to reflect the association between the ID node and the first master node; authorizing a second master node to associate with the ID node as management responsibility of the ID node is handed off from the first master node to the second master node near the second point on the predicted first portion of the transit route; and receiving, by the server, an update to reflect the association between the ID node and the second master node.

25. The non-transitory computer readable medium of embodiment 24 further comprising: predicting a second portion of the transit route for the item from the second point to a third point; authorizing a third master node to associate with the ID node as management responsibility of the ID node is handed off from the second master node to the third master node near a third point on the predicted second portion of the transit route; receiving, by the server, a notification to reflect the association between the ID node and the third master node.

26. The non-transitory computer readable medium of embodiment 25, wherein the method further comprises determining a location of the ID node based upon association information received by the server and location information related to at least one of the first, second, or third master nodes.

27. The non-transitory computer readable medium of embodiment 24, wherein the step of authorizing the first master node is performed prior to a pick-up event for the ID node and the item to be shipped.

28. The non-transitory computer readable medium of embodiment 25, wherein the step of authorizing the third master node is performed after a drop-off event for the ID node and the item to be shipped.

29. A system for managing a shipment of an item using a wireless node network, the system comprising: an ID node registered to the item being shipped; a plurality of master nodes, wherein each of the master nodes are predicted to be located at a different part of at least a portion of an anticipated transit route for the item as the item is shipped from first point to a second point of the anticipated transit route, each of the master nodes being operative to communicate with the ID node over a short-range communication path; a server for tracking and reporting a location of the ID node and a location of the master nodes, and for transferring management responsibility of the ID node between the master nodes as the ID node moves along the portion of the anticipated transit route; and wherein the master nodes further comprise at least: a first of the master nodes associated with the ID node near the first point and prior to a pick-up event for the ID node and item to be shipped, and a second of the master nodes associated with the ID node near the second point of the anticipated transit route.

30. The system of embodiment 29, wherein the master nodes further comprise a third of the master nodes associated with the ID node after a drop-off event.

31. The system of embodiment 30, wherein the master node is a user access device related to a recipient of the item to be shipped.

32. The system of embodiment 29, wherein each of the master nodes is operative to update the server upon completing a disassociation or association with the ID node.

33. The system of embodiment 31, wherein the server is operative to transmit a set of authorization credentials to one of the master nodes and the ID node to authorize a desired association.

34. The system of embodiment 29, wherein the server is operative to determine the location of the ID node based upon context data relating to an environmental aspect of a part of the anticipated transit path.

Further Embodiment 2—Methods & Systems for Managing Shipment of an Item Using a Wireless Node Network 1. A method for dynamically changing an operational mode of node operations in a wireless node network having at least a plurality of master nodes and a server, the method comprising: detecting, by a first of the master nodes, an environmental change related to the first of the master nodes; in response to the detected environmental change, changing an operational mode for the first of the master nodes to a temporary ID node mode where the first of the master nodes no longer can self-determine its location; notifying the server by the first of the master nodes that the first of the master nodes is operating in the temporary ID node mode; and associating the first of the master nodes operating in the temporary ID node mode with a second of the master nodes.

2. The method of embodiment 1, wherein the environmental change is an anticipated environmental change related to the first of the master nodes.

3. The method of embodiment 1, wherein the step of detecting the environmental change is when the first of the master nodes no longer receives a location signal.

4. The method of embodiment 3, wherein the detected environmental change further comprises placement of at least the first of the master nodes within a container that impedes reception of the location signal by the first of the master nodes.

5. The method of embodiment 1, wherein the temporary ID node mode allows the first of the master nodes to communicate with the server while no longer being able to self-determine its location.

6. The method of embodiment 1, wherein the step of associating the first of the master nodes operating in the temporary ID node mode with the second of the master nodes further comprises: advertising by the first of the master nodes to the second of the master nodes regarding a request to connect with the second of the master nodes; receiving a response from the second of the master nodes by the first of the master nodes operating in the temporary ID node mode; and sending a reply to the second of the master nodes with information requested by the second of the master nodes in the response.

7. The method of embodiment 1, wherein the changing step further comprises changing the operational mode for the first of the master nodes to the temporary ID node mode while the first of the master nodes remains in a communication relationship with at least one ID node.

8. The method of embodiment 7 further comprising the steps of receiving information by the first of the master nodes from the at least one ID node, and forwarding the information to the second of the master nodes by the first of the master nodes operating in the temporary ID node mode.

9. The method of embodiment 8, wherein the forwarded information is sensor data gathered by the at least one ID node.

10. The method of embodiment 1 further comprising changing the operational mode for the first of the master nodes to a normal operational mode upon detecting a second environmental change related to the first of the master nodes, the normal operational mode being where the first of the master nodes can self-determine its location again.

11. A method for managing a dynamically changing operational mode of node operations in a wireless node network having at least a plurality of master nodes and a server, the method comprising: receiving a notification by the server from a first of the master nodes reporting an environmental change related to the first of the master nodes; recording a logical change of the first of the master nodes to be operating in a temporary ID node mode as a result of the environmental change; and authorizing the first of the master nodes operating in the temporary ID node mode to associate with a second of the master nodes.

12. The method of embodiment 11, wherein the environmental change comprises an anticipated environmental change related to the first of the master nodes.

13. The method of embodiment 12, wherein the anticipated environmental change comprises an adverse RF environment anticipated to be exposed to the first of the master nodes.

14. The method of embodiment 11 further comprising the step of updating context data consistent with the environmental change.

15. The method of embodiment 11, wherein the temporary ID node mode allows the first of the master nodes to communicate with the server while no longer being able to self-determine its location.

16. The method of embodiment 15, wherein the environmental change results from movement of the first of the master nodes to be within a container that impedes reception of the location signal by the first of the master nodes.

17. The method of embodiment 11 further comprising the step of receiving information from the second of the master nodes as forwarded information from the first of the master nodes when operating in the temporary ID node mode.

18. The method of embodiment 17, wherein the forwarded information is sensor data.

19. The method of embodiment 11 further comprising recording another logical change of the first of the master nodes back to a normal operational mode as a result of a second environmental change related to the first of the master nodes, the normal operational mode being where the first of the master nodes can self-determine its location again.

20. A non-transitory computer-readable medium containing instructions which when executed on a processor performs a method for dynamically changing an operational mode of node operations in a wireless node network having at least a plurality of master nodes and a server, the method comprising: detecting, by a first of the master nodes, an environmental change related to the first of the master nodes; in response to the detected environmental change, changing an operational mode for the first of the master nodes to a temporary ID node mode where the first of the master nodes no longer can self-determine its location; notifying the server by the first of the master nodes that the first of the master nodes is operating in the temporary ID node mode; and associating the first of the master nodes operating in the temporary ID node mode with a second of the master nodes.

21. The non-transitory computer-readable medium of embodiment 20, wherein the step of detecting the environmental change is when the first of the master nodes no longer receives a location signal.

22. The non-transitory computer-readable medium of embodiment 21, wherein the detected environmental change further comprises placement of at least the first of the master nodes within a container that impedes reception of the location signal by the first of the master nodes.

23. The non-transitory computer-readable medium of embodiment 20, wherein the temporary ID node mode allows the first of the master nodes to communicate with the server while no longer being able to self-determine its location.

24. The non-transitory computer-readable medium of embodiment 20, wherein the step of associating the first of the master nodes operating in the temporary ID node mode with the second of the master nodes further comprises: advertising by the first of the master nodes to the second of the master nodes regarding a request to connect with the second of the master nodes; receiving a response from the second of the master nodes by the first of the master nodes operating in the temporary ID node mode; and sending a reply to the second of the master nodes with information requested by the second of the master nodes in the response.

25. The non-transitory computer-readable medium of embodiment 20, wherein the changing step further comprises changing the operational mode for the first of the master nodes to the temporary ID node mode while the first of the master nodes remains in a communication relationship with at least one ID node.

26. The non-transitory computer-readable medium of embodiment 25, wherein the method further comprises receiving information by the first of the master nodes from the at least one ID node, and forwarding the information to the second of the master nodes by the first of the master nodes operating in the temporary ID node mode.

27. The non-transitory computer-readable medium of embodiment 26, wherein the forwarded information is sensor data gathered by the at least one ID node.

28. The non-transitory computer-readable medium of embodiment 20, wherein the method further comprises changing the operational mode for the first of the master nodes to a normal operational mode upon detecting a second environmental change related to the first of the master nodes, the normal operational mode being where the first of the master nodes can self-determine its location again.

29. A dynamically configurable wireless node network, comprising: a plurality of master nodes comprising at least a first master node and a second master node, each of the master nodes having a normal operating mode where the respective master node is operative to determine its own position, and a temporary ID node mode where the respective master node is no longer operative to determine its own position; and a server in communication with the master nodes; and wherein the first master node is operative to detect an environmental change related to the first master node, temporarily alter a current operating mode of the first master node from the normal operating mode to the temporary ID node mode, and wherein the second master node, when operating in the normal operating mode, is operative to associate with the first master node when the first master node is operating in the temporary ID node mode.

30. The dynamically configurable wireless node network of embodiment 29, wherein the server is operative to: receive a notification from the first master node reporting the environmental change; record a logical change of the first master node to be operating in the temporary ID node mode; and authorize the second master node to associate with the first master node when the first master node is operating in the temporary ID node mode.

31. The dynamically configurable wireless node network of embodiment 29, wherein the environmental change comprises an inability of the first master node to sufficiently receive and determine a position based upon a location signal.

32. The dynamically configurable wireless node network of embodiment 31, wherein the environmental change further comprises the first master node being exposed to an adverse RF environment that impedes reception of the location signal by the first master node.

33. The dynamically configurable wireless node network of embodiment 32, wherein the adverse RF environment further comprises placement of the first master node near shielding material.

34. The dynamically configurable wireless node network of embodiment 29, wherein the first master node operating in the temporary ID node mode is further operative to return to functioning as the first master node in the normal operating mode upon detecting a second environmental change.

35. The dynamically configurable wireless node network of embodiment 34, wherein the second environmental change is when the first master node receives a location signal to allow the first master node to determine its own location and return to functioning as the first master node in the normal operating mode.

36. The dynamically configurable wireless node network of embodiment 34, wherein the first master node is operative, when operating in the temporary ID node mode, to receive sensor information and forward the sensor information to the second master node.

Further Embodiment 3—Association Management in a Wireless Node Network

1. A method for association management of a wireless node network having at least a plurality of nodes and a server, the method comprising: identifying a first of the nodes as a potential for associating with a second of the nodes; transmitting an association request to the server; receiving a permissive response from the server related to the association request; and associating the first node and the second node.

2. The method of embodiment 1, wherein the identifying step further comprises reviewing a message sent by the first node to determine status information related to the first node; and analyzing the status information to determine whether the first node should be associated with the second node.

3. The method of embodiment 2, wherein the status information comprises one of a plurality of status levels, wherein the different status levels indicate whether the first node is requesting a connection to the second node.

4. The method of embodiment 1, wherein the association request identifies the first node and the second node to be associated and requests transmission of an appropriate security credential that enables the first node and the second node to securely connect and share data as part of associating.

5. The method of embodiment 1, wherein the step of receiving the permissive response further comprises receiving an authorization credential from the server, the authorization credential being created by the server and provided to authorize connecting the first node and the second node and sharing information between the first node and the second node.

6. The method of embodiment 5 further comprising the step of storing the authorization credential as security data on the second node.

7. The method of embodiment 5, wherein the associating step further comprises establishing an authenticated connection from the second node to the first node based upon the authorization credential.

8. The method of embodiment 1 further comprising securely providing shared data between the first node and the second node according to a profile established by the server.

9. The method of embodiment 1 further comprising gaining, by the second node, responsibility for a task after the second node is associated with the first node when responsibility for the task was previously with the first node.

10. The method of embodiment C1-8, wherein the second node is powered by an external power source and the first node is powered by a battery.

11. A method for association management of a wireless node network having at least a plurality of nodes and a server, the method comprising: receiving, at the server, an association request from a second of the nodes, the association request asking for permission to associate a first of the nodes to the second node; determining a location of the first node and second node; determining if associating the first node to the second node is desired based at least upon the location of the first node and the location of the second node; recording new association data if it is desired to associate the first node with the second node; and transmitting a response from the server to the second node granting the permission to associate the first node to the second node.

12. The method of embodiment 11, wherein the step of determining a location further comprises receiving location data for the second node and determining a location of the first node using at least one of a plurality of location methods available to the server for locating the first node.

13. The method of embodiment 11, wherein the step of transmitting the response further comprises: generating a first authorization credential that authorize connecting the first node and the second node and sharing information between the first node and the second node; and transmitting the first authorization credential as the response.

14. The method of embodiment 11, wherein the step of transmitting the response further comprises pre-staging a second authorization credential related to the second node and a third node if the server anticipates the second node will disassociate with the first node and later request to associate with the third node.

15. The method of embodiment 11 further comprising receiving shared data by the server, the shared data being transmitted from the second node, and the shared data originating from the first node.

16 The method of embodiment 11 further comprising receiving shared data by the server, the shared data being transmitted from the second node, and the shared data having parts that originate from each of the first node and the second node.

17. The method of embodiment 11 further comprising instructing the second node to take over responsibility for a task previously performed by the first node after the second node is associated with the first node.

18. The method of embodiment 17, wherein the second node is powered by an external power source and the first node is powered by a battery.

19. The method of embodiment 11, wherein the step of determining if associating the first node to the second node is desired further comprises determining if associating the first node to the second node is anticipated based upon context data.

20. The method of embodiment 19, wherein the step of determining if associating the first node to the second node is desired further comprises: identifying a current mode of filtering that limits potential nodes to be associated; and granting the permission to associate the first node to the second node only if the current mode of filtering allows the first node to be associated with the second node.

21. The method of embodiment 20, wherein the step of granting the permission further comprising granting the permission only if the current mode of filtering defines that the second node is within a locational range of the first node consistent with the current mode of filtering.

22. The method of embodiment 21 further comprising altering the current mode of filtering to another mode of filtering that allows the first node to be associated with the second node.

23. A non-transitory computer-readable medium containing instructions which when executed on a processor performs a method for association management of a wireless node network having at least a plurality of nodes and a server, the method comprising: receiving an association request from a second of the nodes, the association request asking for permission to associate a first of the nodes to the second node; determining a location of the first node and second node; determining if associating the first node to the second node is desired based at least upon the location of the first node and the location of the second node; recording new association data if it is desired to associate the first node with the second node; and transmitting a response to the second node granting the permission to associate the first node to the second node.

24. The non-transitory computer-readable medium of embodiment 23, wherein the step of determining a location further comprises receiving location data for the second node and using at least one of a plurality of location methods available to the server for locating the first node.

25. The non-transitory computer-readable medium of embodiment 23, wherein the step of transmitting the response further comprises transmitting a set of authorization credentials generated by the server, the authorization credentials being used to securely permit connecting the first node and the second node and securely exchanging operational information between the first node and the second node.

26. The non-transitory computer-readable medium of embodiment 23, wherein the method further comprises receiving shared data from the second node, the shared data originating from the first node as a type of the operational information securely exchanged between the first node and the second node.

27. The non-transitory computer-readable medium of embodiment 23, wherein the method further comprises instructing the second node by the server to take over responsibility for a task previously performed by the first node after the second node is associated with the first node.

28. The non-transitory computer-readable medium of embodiment 27, wherein the second node is powered by an external power source and the first node is powered by a battery.

29. The non-transitory computer-readable medium of embodiment 23, wherein the step of determining if associating the first node to the second node is desired further comprises: identifying a current mode of filtering that limits potential nodes to be associated; and associating the first node to the second node if the current mode of filtering allows the first node to be associated with the second node.

30. The non-transitory computer-readable medium of embodiment 29, wherein the step of associating the first node to the second node if the current mode of filtering defines that the second node is within a locational range of the first node consistent with the current mode of filtering.

31. The non-transitory computer-readable medium of embodiment 29, wherein the method further comprises the step of altering the current mode of filtering to another mode of filtering that allows the first node to be associated with the second node.

32. The non-transitory computer-readable medium of embodiment 29, wherein the current mode of filtering is one of multiple modes of filtering that define different levels of restrictions on which nodes may associate and be managed by other nodes.

33. A system for association management of a wireless node network, comprising: a first node; a second node comprising a node processing unit, a node volatile memory coupled to the node processing unit, a first communication interface coupled to the node processing unit, and a second communication interface coupled to the node processing unit, wherein the first communication interface provides a short-range communication path between the first node and the second node; and a server comprising a server processing unit, a server volatile memory, and a third communication interface that provides a longer range communication path between the server and the second communication interface of the second node; wherein the node processing unit, when executing at least a first program code section resident in the node volatile memory, is operative to identify the first node as a potential for associating with the second node, transmit an association request over the second communication interface to the server, receive an association response over the second communication interface from the server, the association response comprising at least authorization information generated by the server, provide the authorization information to the first node, and associate the first node and the second node, and wherein the server processing unit, when executing at least a second program code section resident in the server volatile memory, is operative to determine a location of the first node and second node, determine if associating the first node to the second node is desired based at least upon the location of the first node and the location of the second node, store new association data in the server volatile memory if it is desired to associate the first node with the second node, the new association data reflecting the associated status of the first and the second node, and transmit the authorization response to the second node granting the permission to associate the first node to the second node.

34. The system of embodiment 33, wherein the node processing unit is further operative to review status information related to the first node to determine whether the first node desires association with the second node.

35. The system of embodiment 33, wherein the node processing unit is further operative to securely provide shared data between the first node and the second node after the first node and the second node are associated and in accordance with a sharing profile provided by the server.

36. The system of embodiment 33, wherein the second node takes over responsibility of a task after the second node is successfully associated with the first node when responsibility for the task was previously with the first node.

37. The system of embodiment 36, wherein the second node is powered by an external power source and the first node is powered by a battery.

38. The system of embodiment 33, wherein the server processing unit is further operative to: set a current mode of filtering that limits potential nodes to be associated; and grant the permission to associate the first node to the second node only if the current mode of filtering allows the first node to be associated with the second node.

39. The system of embodiment 38, wherein the server processing unit is further operative to alter the current mode of filtering to a different mode of filtering that allows the first node to be associated with the second node.

40. A method for association management of a wireless node network having at least a plurality of nodes and a server, the method comprising: receiving, by a second of the nodes, a message broadcast from a first of the nodes; capturing, by the second node, an address of the first node from the message; associating the first node and the second node by storing the captured address of the first node and an address of the second node as association data in a memory of the second node; and transmitting, by the second node, the association data to the server.

41. The method of embodiment 40 further comprising the steps of: determining a location, by the second node, of the first node; and updating the server with a current location of the second node and the determined location of the first node.

42. The method of embodiment 41 further comprising receiving location information from the server, the location information defining a refined location of the first node.

43. The method of embodiment 41 further comprising updating the server by the second node with an updated association data when the second node does not receive an additional message broadcast from the first node, the updated association data reflecting that the first node is disassociated from the second node.

44. A managing node in a wireless node network having at least another node and a server, the managing node comprising: a processing unit; a first communication interface coupled to the processing unit, the first communication interface providing a first communication path to the another node, the first communication interface being operative to receive a message broadcast from the another node and provide the message to the processing unit; a second communication interface coupled to the processing unit, the second communication interface providing a second communication path to the server; a volatile memory coupled to the processing unit; a memory storage coupled to the processing unit, the memory storage maintaining a node association manager module; and wherein the processing unit, when executing instructions of the node association manager module, is operative to receive the message from the first communication interface, capture an address of the another node from the message, store the captured address of the another node and an address of the managing node as part of association data in the memory storage, the association data reflecting an association between the managing node and the another node, and transmit the association data to the server through the second communication interface.

45. The managing node of embodiment 44, wherein the memory storage also maintains a location manager module; and wherein the processing unit, when executing instructions of the location manager manager module, is operative to: determine a location of the another node, determine a current location of the managing node, and update the server with the current location of the managing node and the determined location of the another node.

46. The managing node of embodiment 45, wherein the processing unit, when executing instructions of the node association manager module, is further operative to update the server with updated association data when the first communication interface does not receive an additional message broadcast from the another node, the updated association data reflecting that the another node is disassociated from the managing node.

Further Embodiment 4—Context Management of a Wireless Node Network

1. A method for context management of a wireless node network having at least a plurality of nodes and a server, the method comprising: identifying, by the server, at least one of the nodes; determining context data that relates to an operating environment of the identified node as the identified node moves within the operating environment; and performing a management task related to the identified node with an adjustment made to account for the determined context data.

2. The method of embodiment 1, wherein the determining step further comprises determining the context data that relates to an anticipated operating environment of the identified node as the identified node moves in a predicted path towards a location of another node.

3. The method of embodiment 1, wherein the context data comprises one or more from the group comprising scan data, historic data, shipment data, RF data, and layout data.

4. The method of embodiment 2, wherein the determining step further comprises determining the context data that relates to the anticipated operating environment of the identified node and an anticipated operating environment of the another node as the identified node moves in the predicted path towards the another node for an expected association with the another node.

5. The method of embodiment 1, wherein the step of performing the management task comprises instructing the identified node to alter its operation based upon the determined context data.

6. The method of embodiment 1, wherein the step of performing the management task comprises associating the identified node with the another node with the adjustment made to alter an associating parameter based upon the determined context data.

7. The method of embodiment 6, wherein the associating parameter comprises at least one altered timing interval related to associating the identified node with the another node.

8. The method of embodiment 1, wherein the step of performing the management task comprises locating the identified node with the adjustment made to a power setting based upon the determined context data.

9. The method of embodiment 8, wherein the power setting further comprises an output power level adjusted to account for an adverse condition in the operating environment of the identified node.

10. The method of embodiment 9, wherein the output power level is adjusted to account for a shielding condition in the operating environment of the identified node, wherein the shielding condition may be caused by one or more from a group comprising packaging, package contents, and physical infrastructure.

11. The method of embodiment 1, wherein the step of performing the management task comprises providing the location of the identified node in response to a request received by the server related to a status of the identified node.

12. The method of embodiment 1, wherein the operating environment of the identified node further comprises one or more from a group comprising an electronic communication environment, a physical environment of an anticipated path along which the identified node moves, a conveyance environment related to how the identified node moves, and a density environment related to the density of the nodes within an area near the identified node.

13. A non-transitory computer-readable medium containing instructions which when executed on a processor performs a method for context management of a wireless node network having a plurality of nodes and a server, the method comprising: identifying, by the server, at least one of the nodes; determining context data that relates to an operating environment of the identified node as the identified node moves within the operating environment; and performing a management task related to the identified node with an adjustment made to account for the determined context data.

14. The non-transitory computer-readable medium of embodiment 13, wherein the determining step of the method further comprises determining the context data that relates to an anticipated operating environment of the identified node as the identified node moves in a predicted path towards a location of another node.

15. The non-transitory computer-readable medium of embodiment 13, wherein the context data comprises one or more from the group comprising scan data, historic data, shipment data, and layout data.

16. The non-transitory computer-readable medium of embodiment 14, wherein the determining step of the method further comprises determining the context data that relates to the anticipated operating environment of the identified node and an anticipated operating environment of the another node as the identified node moves in the predicted path towards the another node for an expected association with the another node.

17. The non-transitory computer-readable medium of embodiment 13, wherein the step of performing the management task comprises instructing the identified node to alter its operation based upon the determined context data.

18. The non-transitory computer-readable medium of embodiment 13, wherein the step of performing the management task comprises associating the identified node with the another node with the adjustment made to alter an associating parameter based upon the determined context data.

19. The non-transitory computer-readable medium of embodiment 18, wherein the associating parameter comprises at least one altered timing interval related to associating the identified node with the another node.

20. The non-transitory computer-readable medium of embodiment 13, wherein the step of performing the management task comprises locating the identified node with the adjustment made to a power setting based upon the determined context data.

21. The non-transitory computer-readable medium of embodiment 20, wherein the power setting further comprises an output power level adjusted to account for an adverse condition in the operating environment of the identified node.

22. The non-transitory computer-readable medium of embodiment 21, wherein the output power level is adjusted to account for a shielding condition in the operating environment of the identified node, wherein the shielding condition may be caused by one or more from a group comprising packaging, package contents, and physical infrastructure.

23. The non-transitory computer-readable medium of embodiment 20, wherein the step of performing the management task comprises providing the location of the identified node in response to a request received by the server related to a status of the identified node.

24. The non-transitory computer-readable medium of embodiment 13, wherein the operating environment of the identified node further comprises one or more from a group comprising an electronic communication environment, a physical environment of an anticipated path along which the identified node moves, a conveyance environment related to how the identified node moves, and a density environment related to the density of the nodes within an area near the identified node.

25. An apparatus for context management of a plurality of nodes in a wireless node network, comprising: a server in communication with a first of the nodes, the server comprising a server processing unit, a server volatile memory coupled to the server processing unit, a server memory storage coupled to the server processing unit, the server memory storage maintaining at least a program code section and context data, and a communication interface that provides a communication path between the server and the first node; and wherein the server processing unit, when executing at least the program code section resident in the server volatile memory, is operative to identify the first node as the first node moves within an operating environment along a path, access the server memory storage to determine which of the context data maintained on the server memory storage relates to the operating environment of the first node, identify an adjustment to be made related to the first node based upon the determined context data, and perform a management task related to the first node with the adjustment made to account for the determined context data.

26. The system of embodiment 25, wherein the context data maintained on the server memory storage further comprises information relating to an anticipated operating environment of the first node for when the first node will move along the path towards a location of another node.

27. The system of embodiment 25, wherein the context data maintained on the server memory storage further comprises at least one or more from the group comprising scan data, historic data, shipment data, and layout data.

28. The system of embodiment 26, wherein the server processing unit is further operative to determine which of the context data relates to the anticipated operating environment of the first node and an anticipated operating environment of the another node as the first node moves towards the another node for an expected association with the another node.

29. The system of embodiment 25, wherein the server processing unit is further operative to perform the management task by instructing the first node to alter its operation based upon the determined context data.

30. The system of embodiment 25, wherein the server processing unit is further operative to perform the management task by associating the first node with the another node with the adjustment made to alter an associating parameter based upon the determined context data.

31. The system of embodiment 30, wherein the associating parameter comprises at least one altered timing interval related to associating the first node with the another node.

32. The system of embodiment 25, wherein the server processing unit is further operative to perform the management task by locating the first node with the adjustment made to a power setting based upon the determined context data.

33. The system of embodiment 32, wherein the power setting further comprises an output power level adjusted to account for an adverse condition in the operating environment of the first node.

34. The system of embodiment 33, wherein the power setting further comprises the output power level adjusted to account for a shielding condition in the operating environment of the first node, wherein the shielding condition may be caused by one or more from a group comprising packaging, package contents, proximate package, proximate package contents, and physical infrastructure.

35. The system of embodiment 32, wherein the server processing unit is further operative to perform the management task by providing the location of the first node in response to a request received by the server, the request being related to a status of the first node.

36. The system of embodiment 25, wherein the operating environment of the first node further comprises one or more from a group comprising an electronic communication environment, a physical environment of the path, a conveyance environment related to how the identified node moves on the path, and a density environment related to the density of the nodes within an area on the path near the first node.

Further Embodiment 5—Proximity Node Location Using a Wireless Node Network

1. A method for locating one of a plurality of nodes in a wireless node network having a server, the method comprising: instructing a first other of the nodes and a second other of the nodes to detect any message broadcast from the one node over a time period; receiving, by the server, a first indication from the first other node, the first indication related to a characteristic of all messages broadcast from the one node that are detected by the first other node during the time period; receiving, by the server, a second indication from the second other node, the second indication related to the characteristic of all messages broadcast from the one node that are detected by the second other node during the time period; and determining a location of the one node based upon a difference in the first indication and the second indication.

2. The method of embodiment 1, wherein the first indication is a first count of messages broadcast from the one node that are detected by the first other node during the time period, and wherein the second indication is a second count of all messages broadcast from the one node that are detected by the second other node during the time period.

3. The method of embodiment 2, wherein the determining step further comprises determining the location of the one node to be closer to the first other node than the second other node when the first count is greater than the second count.

4. The method of embodiment 2 further comprising determining a node movement direction for the one node based upon comparing the first count and the second count over a plurality of the time periods.

5. The method of embodiment 1, wherein the first indication is a first time factor of all messages broadcast from the one node that are detected by the first other node during the time period, and wherein the second indication is a second time factor of all messages broadcast from the one node that are detected by the second other node during the time period.

6. The method of embodiment 5 further comprising determining a node movement direction for the one node based upon comparing the first time factor and the second time factor.

7. The method of embodiment 5, wherein the first time factor is an average transit time for a message detected at the first other node to go from the one node to the first other node, and wherein the second time factor is an average transit time for a message detected at the second other node to go from the one node to the second other node.

8. The method of embodiment 7, wherein the determining step further comprises determining the location of the one node to be closer to the first other node than the second other node when the first time factor is less than the second time factor.

9. The method of embodiment 1, wherein the first indication is a first average signal strength of all messages broadcast from the one node that are detected by the first other node during the time period; wherein the second indication is a second average signal strength of all messages broadcast from the one node that are detected by the second other node during the time period; wherein the determining step further comprises determining the location of the one node to be closer to the first other node than the second other node when the first average signal strength is greater than the second average signal strength; and further comprising the steps of: observing a degree of change in the first average signal strength and a degree of change in the second average signal strength over repeated time periods, and determining a node movement direction for the one node based upon comparing the degree of change in the first average signal strength and the degree of change in the second average signal strength.

10. The method of embodiment 1 further comprising refining the location of the one node based upon at least one of a first updated location received from the first other node and a second updated location received from the second other node.

11. The method of embodiment 1 further comprising comparing the location of the one node to a predicted path of the one node to determine if the one node is located outside the predicted path.

12. The method of embodiment 11 further comprising generating a notification if the one node is outside the predicted path.

13. The method of embodiment 1 further comprising determining context data related to the one node, and refining the location of the one node based upon the context data.

14. The method of embodiment 1 further comprising determining context data related to the closer of the first other node and the second other node when compared to the location of the one node, and refining the location of the one node based upon the context data.

15. The method of embodiment 1, wherein the one node is part of a node-enabled package; and wherein the step of determining the location of the one node further comprises determining the location of the one node while the one node is within the node-enabled package and while the node-enabled package is within a vehicle.

16. The method of embodiment 15 further comprising: generating a location message regarding where the node-enabled package is located within the vehicle based upon the determined location of the one node; and transmitting the location message to another network device in the wireless node network for display on a user interface of the another network device.

17. The method of embodiment 15 further comprising: accessing shipping information related to the node-enabled package; generating a relocation message regarding where the node-enabled package is to be relocated within the vehicle based upon the determined location of the one node and the accessed shipping information; and transmitting the location message to another network device in the wireless node network for display on a user interface of the another network device.

18. The method of embodiment 17, wherein the shipping information comprises weight information on the node-enabled package.

19. The method of embodiment 18, wherein the location of the node-enabled package within the vehicle is according to a loading scheme.

20. The method of embodiment 19, wherein the loading scheme is related to an anticipated delivery schedule.

21. The method of embodiment 15, wherein the vehicle is one from a group consisting of a truck, a van, a trailer, an aircraft, and a marine vessel.

22. A non-transitory computer-readable medium containing instructions which when executed on a processor performs a method for locating one of a plurality of nodes in a wireless node network having a server, the method comprising: instructing a first other of the nodes and a second other of the nodes to detect any message broadcast from the one node over a time period; receiving, by the server, a first indication from the first other node, the first indication related to a characteristic of all messages broadcast from the one node that are detected by the first other node during the time period; receiving, by the server, a second indication from the second other node, the second indication related to the characteristic of all messages broadcast from the one node that are detected by the second other node during the time period; and determining a location of the one node based upon a difference in the first indication and the second indication.

23. The non-transitory computer-readable medium of embodiment 22, wherein the first indication is a first count of all messages broadcast from the one node that are detected by the first other node during the time period, and wherein the second indication is a second count of all messages broadcast from the one node that are detected by the second other node during the time period.

24. The non-transitory computer-readable medium of embodiment 23, wherein the determining step further comprises determining the location of the one node to be closer to the first other node than the second other node when the first count is greater than the second count.

25. The non-transitory computer-readable medium of embodiment 23, wherein the method further comprises determining a node movement direction for the one node based upon comparing the first count and the second count over a plurality of the time periods.

26. The non-transitory computer-readable medium of embodiment 22, wherein the first indication is a first time factor of all messages broadcast from the one node that are detected by the first other node during the time period, and wherein the second indication is a second time factor of all messages broadcast from the one node that are detected by the second other node during the time period.

27. The non-transitory computer-readable medium of embodiment 26, wherein the method further comprises determining a node movement direction for the one node based upon comparing the first time factor and the second time factor.

28. The non-transitory computer-readable medium of embodiment 26, wherein the first time factor is an average transit time for a message detected at the first other node to go from the one node to the first other node, and wherein the second time factor is an average transit time for a message detected at the second other node to go from the one node to the second other node.

29. The non-transitory computer-readable medium of embodiment 26, wherein the determining step further comprises determining the location of the one node to be closer to the first other node than the second other node when the first time factor is less than the second time factor.

30. The non-transitory computer-readable medium of embodiment 22, wherein the first indication is a first average signal strength of all messages broadcast from the one node that are detected by the first other node during the time period; wherein the second indication is a second average signal strength of messages broadcast from the one node that are detected by the second other node during the time period; wherein the determining step further comprises determining the location of the one node to be closer to the first other node than the second other node when the first average signal strength is greater than the second average signal strength; and wherein the method further comprising the steps of: observing a degree of change in the first average signal strength and a degree of change in the second average signal strength over repeated time periods, and determining a node movement direction for the one node based upon comparing the degree of change in the first average signal strength and the degree of change in the second average signal strength.

31. The non-transitory computer-readable medium of embodiment 22, wherein the method further comprises refining the location of the one node based upon at least one of a first updated location received from the first other node and a second updated location received from the second other node.

32. The non-transitory computer-readable medium of embodiment 22, wherein the method further comprises comparing the location of the one node to a predicted path of the one node to determine if the one node is located outside the predicted path.

33. The non-transitory computer-readable medium of embodiment 33, wherein the method further comprises generating a notification if the one node is outside the predicted path.

34. The non-transitory computer-readable medium of embodiment 22, wherein the method further comprises determining context data related to the one node, and refining the location of the one node based upon the context data.

35. The non-transitory computer-readable medium of embodiment 22, wherein the method further comprises determining context data related to the closer of the first other node and the second other node when compared to the location of the one node, and refining the location of the one node based upon the context data.

36. The non-transitory computer-readable medium of embodiment 22, wherein the one node is part of a node-enabled package; and wherein the step of determining the location of the one node further comprises determining the location of the one node while the one node is within the node-enabled package and while the node-enabled package is within a vehicle.

37. The non-transitory computer-readable medium of embodiment 36, wherein the method further comprises: generating a location message regarding where the node-enabled package is located within the vehicle based upon the determined location of the one node; and transmitting the location message to another network device in the wireless node network for display on a user interface of the another network device.

38. The non-transitory computer-readable medium of embodiment 36, wherein the method further comprises: accessing shipping information related to the node-enabled package; generating a relocation message regarding where the node-enabled package is to be relocated within the vehicle based upon the determined location of the one node and the accessed shipping information; and transmitting the location message to another network device in the wireless node network for display on a user interface of the another network device.

39. The non-transitory computer-readable medium of embodiment 38, wherein the shipping information comprises weight information on the node-enabled package.

40. The non-transitory computer-readable medium of embodiment 39, wherein the location of the node-enabled package within the vehicle is according to a loading scheme.

41. The non-transitory computer-readable medium of embodiment 40, wherein the loading scheme is related to an anticipated delivery schedule.

42. The non-transitory computer-readable medium of embodiment 36, wherein the vehicle is one from a group consisting of a truck, a van, a trailer, an aircraft, and a marine vessel.

43. An apparatus for locating one of a plurality of nodes in a wireless node network, comprising: a server in communication with at least a first other of the nodes and a second other of the nodes, the server further comprising a server processing unit, a server volatile memory coupled to the server processing unit, a server memory storage coupled to the server processing unit, the server memory storage maintaining at least a program code section and location data, and a communication interface that provides a communication path operatively coupling the server with the first other node and the second other node; and wherein the server processing unit, when executing at least the program code section resident in the server volatile memory, is operative to send an operation message to the first other node instructing the first other node to detect any message broadcast from the one node over a time period, send another operation message to the second other node instructing the second other node to detect any message broadcast from the one node over the time period, receive, from the communication interface, a first indication from the first other node, the first indication related to a characteristic of all messages broadcast from the one node that are detected by the first other node during the time period, receive, from the communication interface, a second indication from the second other node, the second indication related to the characteristic of all messages broadcast from the one node that are detected by the second other node during the time period, and determine a location of the one node based upon a difference in the first indication and the second indication.

44. The apparatus of embodiment 43, wherein the first indication is a first count of all messages broadcast from the one node that are detected by the first other node during the time period, and wherein the second indication is a second count of all messages broadcast from the one node that are detected by the second other node during the time period.

45. The apparatus of embodiment 44, wherein the server processing unit is further operative to determine the location of the one node to be closer to the first other node than the second other node when the first count is greater than the second count.

46. The apparatus of embodiment 44, wherein the server processing unit is further operative to determine a node movement direction for the one node based upon comparing the first count and the second count over a plurality of the time periods.

47. The apparatus of embodiment 43, wherein the first indication is a first time factor of all messages broadcast from the one node that are detected by the first other node during the time period, and wherein the second indication is a second time factor of all messages broadcast from the one node that are detected by the second other node during the time period.

48. The apparatus of embodiment 47, wherein the server processing unit is further operative to determine a node movement direction for the one node based upon comparing the first time factor and the second time factor.

49. The apparatus of embodiment 47, wherein the first time factor is an average transit time for a message detected at the first other node to go from the one node to the first other node, and wherein the second time factor is an average transit time for a message detected at the second other node to go from the one node to the second other node.

50. The apparatus of embodiment 49, wherein the server processing unit is further operative to determine the location of the one node to be closer to the first other node than the second other node when the first time factor is less than the second time factor.

51. The apparatus of embodiment 43, wherein the first indication is a first average signal strength of all messages broadcast from the one node that are detected by the first other node during the time period; wherein the second indication is a second average signal strength of all messages broadcast from the one node that are detected by the second other node during the time period; wherein the determining step further comprises determining the location of the one node to be closer to the first other node than the second other node when the first average signal strength is greater than the second average signal strength; and wherein the server processing unit is further operative to observe a degree of change in the first average signal strength and a degree of change in the second average signal strength over repeated time periods, and determine a node movement direction for the one node based upon comparing the degree of change in the first average signal strength and the degree of change in the second average signal strength.

52. The apparatus of embodiment 43, wherein the server processing unit is further operative to refine the location of the one node based upon at least one of a first updated location received from the first other node and a second updated location received from the second other node.

53. The apparatus of embodiment 43, wherein the server processing unit is further operative to compare the location of the one node to a predicted path of the one node to determine if the one node is located outside the predicted path.

54. The apparatus of embodiment 53, wherein the server processing unit is further operative to generate a notification if the one node is outside the predicted path.

55. The apparatus of embodiment 43, wherein the server processing unit is further operative to determine context data related to the one node, and refine the location of the one node based upon the context data.

56. The apparatus of embodiment 43, wherein the server processing unit is further operative to determine context data related to the closer of the first other node and the second other node when compared to the location of the one node, and refine the location of the one node based upon the context data.

57. The apparatus of embodiment 43, wherein the one node is part of a node-enabled package; and wherein the server processing unit is further operative to determine the location of the one node while the one node is within the node-enabled package and while the node-enabled package is within a vehicle.

58. The apparatus of embodiment 57, wherein the server processing unit is further operative to: generate a location message regarding where the node-enabled package is located within the vehicle based upon the determined location of the one node; and transmit the location message via the communication interface to another network device in the wireless node network for display on a user interface of the another network device.

59. The apparatus of embodiment 57, wherein the server processing unit is further operative to: access shipping information related to the node-enabled package; generate a relocation message regarding where the node-enabled package is to be relocated within the vehicle based upon the determined location of the one node and the accessed shipping information; and transmit the location message via the communication interface to another network device in the wireless node network.

60. The apparatus of embodiment 59, wherein the shipping information comprises weight information on the node-enabled package.

61. The apparatus of embodiment 60, wherein the location of the node-enabled package within the vehicle is according to a loading scheme.

62. The apparatus of embodiment 61, wherein the loading scheme is related to an anticipated delivery schedule.

63. The apparatus of embodiment 57, wherein the vehicle is one from a group consisting of a truck, a van, a trailer, an aircraft, and a marine vessel.

Further Embodiment 6—Determining Node Location Using a Variable Power Characteristic of a Node in a Wireless Node Network 1. A method for location determination by varying a power characteristic of nodes in a wireless node network, the method comprising: (a) instructing a first of the nodes to vary the power characteristic for one or more signals broadcast by the first node; (b) identifying a first group of other nodes in the wireless node network that are near the first node based upon those of the other nodes that received at least one of the one or more signals broadcast by the first node as the first node varies the power characteristic; (c) identifying a closest one or more of the other nodes as a smallest group of the other nodes that received at least one of the one or more signals broadcast by the first node as the first node varies the power characteristic; and (d) determining a location of the first node based upon the closest one or more of the other nodes.

2. The method of embodiment 1, wherein the instructing step further comprises instructing the first node to vary the power characteristic by instructing the first node to incrementally decrease the power characteristic from a first value to a second value.

3. The method of embodiment 1, wherein the instructing step further comprises instructing the first node to vary the power characteristic by instructing the first node to incrementally increase the power characteristic from a second value to a first value.

4. The method of embodiment 1, wherein the power characteristic is an output power level of the one or more broadcast signals.

5. The method of embodiment 4, wherein the variations in the output power level of the one or more broadcast signals in steps (a)-(c) are set according to context data.

6. The method of embodiment 4, wherein the step (b) further comprises incrementally identifying which of the first group of other nodes are receiving at least one of the broadcast signals as the first node incrementally varies the output power level of the one or more signals broadcast, the incrementally identified nodes being a set of increasingly close nodes to the first node.

7. The method of embodiment 6, wherein the step (d) further comprises determining the location of the first node based upon the closest one or more of the other nodes and the set of increasingly close nodes to the first node.

8. The method of embodiment 1 further comprising: repeating steps (a)-(d) where a second of the nodes is instructed to vary the power characteristic for one or more signals broadcast by the second node; and refining the location of the first node based upon a location of the second node.

9. The method of embodiment 6 further comprising: repeating steps (a)-(d) where a second of the nodes is instructed to vary the power characteristic for one or more signals broadcast by the second node; and refining the location of the first node based upon a location of the second node and a set of increasingly close nodes to the second node.

10. The method of embodiment 1 further comprising determining context data related to the first node, and refining the location of the first node based upon the context data.

11. The method of embodiment 1 further comprising determining context data related to a closest node to the first node, and refining the location of the first node based upon the context data.

12. The method of embodiment 6 further comprising determining context data related to the incrementally identified nodes in the set of increasingly close nodes to the first node, and refining the location of the first node based upon the context data.

13. The method of embodiment 1, wherein the first node is part of a node-enabled package; and wherein the step of determining the location of the first node further comprises determining the location of the first node while the first node is within the node-enabled package and while the node-enabled package is within a vehicle.

14. The method of embodiment 13 further comprising the steps of: generating a location message regarding where the node-enabled package is located within the vehicle based upon the determined location of the first node; and transmitting the location message to another network device in the wireless node network for display on a user interface of the another network device.

15. The method of embodiment 13 further comprising the steps of: accessing shipping information related to the node-enabled package; generating a relocation message regarding where the node-enabled package is to be relocated within the vehicle based upon the determined location of the first node and the accessed shipping information; and transmitting the location message to another network device in the wireless node network for display on a user interface of the another network device.

16. The method of embodiment 15, wherein the shipping information comprises weight information on the node-enabled package.

17. The method of embodiment 16, wherein the location of the node-enabled package within the vehicle is according to a loading scheme.

18. The method of embodiment 17, wherein the loading scheme is related to an anticipated delivery schedule.

19. The method of embodiment 13, wherein the vehicle is one from a group consisting of a truck, a van, a trailer, an aircraft, and a marine vessel.

20. A non-transitory computer-readable medium containing instructions which when executed on a processor performs a method for location determination by varying a power characteristic of nodes in a wireless node network, the method comprising: (a) instructing a first of the nodes to vary the power characteristic for one or more signals broadcast by the first node; (b) identifying a first group of other nodes in the wireless node network that are near the first node based upon those of the other nodes that received at least one of the one or more signals broadcast by the first node as the first node varies the power characteristic; (c) identifying a closest one or more of the other nodes as a smallest group of the other nodes that received at least one of the one or more signals broadcast by the first node as the first node varies the power characteristic; and (d) determining a location of the first node based upon the closest one or more of the other nodes.

21. The non-transitory computer-readable medium of embodiment 20, wherein the instructing step further comprises instructing the first node to vary the power characteristic by instructing the first node to incrementally decrease the power characteristic from a first value to a second value.

22. The non-transitory computer-readable medium of embodiment 20, wherein the instructing step further comprises instructing the first node to vary the power characteristic by instructing the first node to incrementally increase the power characteristic from a second value to a first value.

23. The non-transitory computer-readable medium of embodiment 20, wherein the power characteristic is an output power level of the one or more broadcast signals.

24. The non-transitory computer-readable medium of embodiment 23, wherein the variations in the output power level of the one or more broadcast signals in steps (a)-(c) are set according to context data.

25. The non-transitory computer-readable medium of embodiment 23, wherein the step (b) further comprises incrementally identifying which of the first group of other nodes are receiving at least one of the broadcast signals as the first node incrementally varies the output power level of the one or more signals broadcast, the incrementally identified nodes being a set of increasingly close nodes to the first node.

26. The non-transitory computer-readable medium of embodiment 25, wherein the step (d) further comprises determining the location of the first node based upon the closest one or more of the other nodes and the set of increasingly close nodes to the first node.

27. The non-transitory computer-readable medium of embodiment 20, wherein the method further comprises: repeating steps (a)-(d) where a second of the nodes is instructed to vary the power characteristic for one or more signals broadcast by the second node; and refining the location of the first node based upon a location of the second node.

28. The non-transitory computer-readable medium of embodiment 25, wherein the method further comprises: repeating steps (a)-(d) where a second of the nodes is instructed to vary the power characteristic for one or more signals broadcast by the second node; and refining the location of the first node based upon a location of the second node and a set of increasingly close nodes to the second node.

29. The non-transitory computer-readable medium of embodiment 20, wherein the method further comprises determining context data related to the first node, and refining the location of the first node based upon the context data.

30. The non-transitory computer-readable medium of embodiment 20, wherein the method further comprises determining context data related to a closest node to the first node, and refining the location of the first node based upon the context data.

31. The non-transitory computer-readable medium of embodiment 25, wherein the method further comprises determining context data related to the incrementally identified nodes in the set of increasingly close nodes to the first node, and refining the location of the first node based upon the context data.

32. The non-transitory computer-readable medium of embodiment 20, wherein the first node is part of a node-enabled package; and wherein the step of determining the location of the first node further comprises determining the location of the first node while the first node is within the node-enabled package and while the node-enabled package is within a vehicle.

33. The non-transitory computer-readable medium of embodiment 32, wherein the method further comprises the steps of: generating a location message regarding where the node-enabled package is located within the vehicle based upon the determined location of the first node; and transmitting the location message to another network device in the wireless node network for display on a user interface of the another network device.

34. The non-transitory computer-readable medium of embodiment 32, wherein the method further comprises the steps of: accessing shipping information related to the node-enabled package; generating a relocation message regarding where the node-enabled package is to be relocated within the vehicle based upon the determined location of the first node and the accessed shipping information; and transmitting the location message to another network device in the wireless node network for display on a user interface of the another network device.

35. The non-transitory computer-readable medium of embodiment 34, wherein the shipping information comprises weight information on the node-enabled package.

36. The non-transitory computer-readable medium of embodiment 35, wherein the location of the node-enabled package within the vehicle is according to a loading scheme.

37. The non-transitory computer-readable medium of embodiment 36, wherein the loading scheme is related to an anticipated delivery schedule.

38. The non-transitory computer-readable medium of embodiment 32, wherein the vehicle is one from a group consisting of a truck, a van, a trailer, an aircraft, and a marine vessel.

39. An apparatus for location determination by varying a power characteristic of nodes in a wireless node network, comprising: a server operative to communicate with a plurality of nodes, the server further comprising a server processing unit, a server volatile memory coupled to the server processing unit, a server memory storage coupled to the server processing unit, the server memory storage maintaining at least a program code section and location data related to a location of one or more of the nodes, and a communication interface coupled to the server processing unit and that provides a communication path operatively coupling the server with the nodes; and wherein the server processing unit, when executing at least the program code section resident in the server volatile memory, is operative to: (a) send an instruction over the communication interface to a first of the nodes to vary the power characteristic for one or more signals broadcast by the first node, (b) identify a first group of other nodes in the wireless node network that are near the first node based upon those of the other nodes that received at least one of the one or more signals broadcast by the first node as the first node varies the power characteristic, (c) identify a closest one or more of the other nodes as a smallest group of the other nodes that received at least one of the one or more signals broadcast by the first node as the first node varies the power characteristic, (d) determine a location of the first node based upon the closest one or more of the other nodes, and (e) store the location of the first node as part of the location data maintained on the server memory storage.

40. The apparatus of embodiment 39, wherein the server processing unit is further operative to send the instruction to the first node to vary the power characteristic by providing an instruction for the first node over the communication interface, the instructing causing the first node to incrementally decrease the power characteristic from a first value to a second value.

41. The apparatus of embodiment 39, wherein the server processing unit is further operative to send the instruction to the first node to vary the power characteristic by providing an instruction for the first node over the communication interface, the instructing causing the first node to incrementally increase the power characteristic from a second value to a first value.

42. The apparatus of embodiment 39, wherein the power characteristic is an output power level of the one or more broadcast signals.

43. The apparatus of embodiment 42, wherein the variations in the output power level of the one or more broadcast signals in steps (a)-(c) are set according to context data.

44. The apparatus of embodiment 42, wherein the server processing unit is further operative to perform (b) by being operative to incrementally identify which of the first group of other nodes are receiving at least one of the broadcast signals as the first node incrementally varies the output power level of the one or more signals broadcast, the incrementally identified nodes being a set of increasingly close nodes to the first node.

45. The apparatus of embodiment 44, wherein the server processing unit is further operative to perform (d) by being operative to determine the location of the first node based upon the closest one or more of the other nodes and the set of increasingly close nodes to the first node.

46. The apparatus of embodiment 39, wherein the server processing unit is further operative to: repeat operations (a)-(d) where a second of the nodes is instructed to vary the power characteristic for one or more signals broadcast by the second node; and refine the location of the first node based upon a location of the second node.

47. The apparatus of embodiment 44, wherein the server processing unit is further operative to: repeating operations (a)-(d) where a second of the nodes is instructed to vary the power characteristic for one or more signals broadcast by the second node; and refine the location of the first node based upon a location of the second node and a set of increasingly close nodes to the second node.

48. The apparatus of embodiment 39, wherein the server processing unit is further operative to determine context data related to the first node, and refining the location of the first node based upon the context data.

49. The apparatus of embodiment 39, wherein the server processing unit is further operative to determine context data related to a closest node to the first node, and refining the location of the first node based upon the context data.

50. The apparatus of embodiment 44, wherein the server processing unit is further operative to determine context data related to the incrementally identified nodes in the set of increasingly close nodes to the first node, and refining the location of the first node based upon the context data.

51. The apparatus of embodiment 39, wherein the first node is part of a node-enabled package; and wherein the server processing unit is further operative to determine the location of the first node while the first node is within the node-enabled package and while the node-enabled package is within a vehicle.

52. The apparatus of embodiment 51, wherein the server processing unit is further operative to: generate a location message regarding where the node-enabled package is located within the vehicle based upon the determined location of the first node; and transmit the location message via the communication interface to another network device in the wireless node network for display on a user interface of the another network device.

53. The apparatus of embodiment 51, wherein the server processing unit is further operative to: access shipping information related to the node-enabled package; generate a relocation message regarding where the node-enabled package is to be relocated within the vehicle based upon the determined location of the first node and the accessed shipping information; and transmit the location message via the communication interface to another network device in the wireless node network.

54. The apparatus of embodiment 53, wherein the shipping information comprises weight information on the node-enabled package.

55. The apparatus of embodiment 54, wherein the location of the node-enabled package within the vehicle is according to a loading scheme.

56. The apparatus of embodiment 55, wherein the loading scheme is related to an anticipated delivery schedule.

Further Embodiment 7—Determining Node Location Using a Master Node Association in a Wireless Node Network 1. A method for location determination using one or more associations of nodes in a wireless node network, the method comprising: broadcasting one or more first messages by a first of the nodes at a first anticipated range distance; identifying which of the nodes associated with the first node received at least one of the first messages; broadcasting one or more second messages by the first node at a second anticipated range distance, which is incrementally smaller than the first anticipated range distance; and determining a location of one or more of the identified associated nodes that did not receive any second messages but received at least one of the first messages, the location being between the first anticipated range distance from the first node and the second anticipated range distance from the first node.

2. The method of embodiment 1 further comprising the steps of: broadcasting one or more third messages by the first node at a third anticipated range distance, which is incrementally smaller range than the second anticipated range distance; and determining a location of one or more of the identified associated nodes that did not receive any of the third messages but received at least one of the second messages, the location being between the second anticipated range distance from the first node and the third anticipated range distance from the first node.

3. The method of embodiment 1, wherein the first anticipated range distance is an optimal broadcasting range for the first of the nodes.

4. The method of embodiment 3, wherein the first anticipated range distance is the optimal range for the first of the nodes adjusted based upon context data.

5. The method of embodiment 4, wherein the first anticipated range distance and the second anticipated range distance are adjusted based upon one or more types of context data related to how an RF output signal from the first node may be impeded.

6. The method of embodiment 1, wherein the identifying step further comprises reviewing association data as part of identifying which of the nodes associated with the first node received at least one of the first messages.

7. The method of embodiment 1, wherein the identifying step further comprises identifying at least those of the nodes that are passively associated with the first node as part of identifying which of the nodes associated with the first node received at least one of the first messages.

8. The method of embodiment 1, wherein the identifying step further comprises identifying at least those of the nodes that are actively associated with the first node as part of identifying which of the nodes associated with the first node received at least one of the first messages.

9. The method of embodiment 1 further comprising the step of refining the location of the one or more of the identified associated nodes that did not receive any of the second messages but received at least one of the first messages by updating a location of the first node.

10. The method of embodiment 9, wherein the refining step further comprises: determining a current mobile location of the first node; and refining the location of the one or more of the identified associated nodes that did not receive any of the second messages but received at least one of the first messages based upon the current mobile location of the first node.

11. The method of embodiment 9 further comprising the step of transmitting the refined location to a server in the network.

12. The method of embodiment 1, wherein at least one of the one or more of the identified associated nodes is part of a node-enabled package; and wherein the step of determining the location of the at least one node further comprises determining the location of the at least one node while the at least one node is within the node-enabled package and while the node-enabled package is within a vehicle.

13. The method of embodiment 12 further comprising the steps of: generating a location message regarding where the node-enabled package is located within the vehicle based upon the determined location of the at least one node; and transmitting the location message to another network device in the wireless node network for display on a user interface of the another network device.

14. The method of embodiment 12 further comprising the steps of: accessing shipping information related to the node-enabled package; generating a relocation message regarding where the node-enabled package is to be relocated within the vehicle based upon the determined location of the at least one node and the accessed shipping information; and transmitting the location message to another network device in the wireless node network for display on a user interface of the another network device.

15. The method of embodiment 14, wherein the shipping information comprises weight information on the node-enabled package.

16. The method of embodiment 15, wherein the location of the node-enabled package within the vehicle is according to a loading scheme.

17. The method of embodiment 16, wherein the loading scheme is related to an anticipated delivery schedule.

18. The method of embodiment 12, wherein the vehicle is one from a group consisting of a truck, a van, a trailer, an aircraft, and a marine vessel.

19. A non-transitory computer-readable medium containing instructions which when executed on a processor performs a method for location determination using one or more associations of nodes in a wireless node network, the method comprising: broadcasting one or more first messages by a first of the nodes at a first anticipated range distance; identifying which of the nodes associated with the first node received at least one of the first messages; broadcasting one or more second messages by the first node at a second anticipated range distance, which is incrementally smaller than the first anticipated range distance; and determining a location of one or more of the identified associated nodes that did not receive any second messages but received at least one of the first messages, the location being between the first anticipated range distance from the first node and the second anticipated range distance from the first node.

20. The non-transitory computer-readable medium of embodiment 19, wherein the method further comprises the steps of: broadcasting one or more third messages by the first node at a third anticipated range distance, which is incrementally smaller range than the second anticipated range distance; and determining a location of one or more of the identified associated nodes that did not receive any of the third messages but received at least one of the second messages, the location being between the second anticipated range distance from the first node and the third anticipated range distance from the first node.

21. The non-transitory computer-readable medium of embodiment 19, wherein the first anticipated range distance is an optimal broadcasting range for the first of the nodes.

22. The non-transitory computer-readable medium of embodiment 21, wherein the first anticipated range distance is the optimal range for the first of the nodes adjusted based upon context data.

23. The non-transitory computer-readable medium of embodiment 22, wherein the first anticipated range distance and the second anticipated range distance are adjusted based upon one or more types of context data related to how an RF output signal from the first node may be impeded.

24. The non-transitory computer-readable medium of embodiment 19, wherein the identifying step further comprises reviewing association data as part of identifying which of the nodes associated with the first node received at least one of the first messages.

25. The non-transitory computer-readable medium of embodiment 19, wherein the identifying step further comprises identifying at least those of the nodes that are passively associated with the first node as part of identifying which of the nodes associated with the first node received at least one of the first messages.

26. The non-transitory computer-readable medium of embodiment 19, wherein the identifying step further comprises identifying at least those of the nodes that are actively associated with the first node as part of identifying which of the nodes associated with the first node received at least one of the first messages.

27. The non-transitory computer-readable medium of embodiment 19, wherein the method further comprises the step of refining the location of the one or more of the identified associated nodes that did not receive any of the second messages but received at least one of the first messages by updating a location of the first node.

28. The non-transitory computer-readable medium of embodiment 27, wherein the refining step further comprises: determining a current mobile location of the first node; and refining the location of the one or more of the identified associated nodes that did not receive any of the second messages but received at least one of the first messages based upon the current mobile location of the first node.

29. The non-transitory computer-readable medium of embodiment 27, wherein the method further comprises the step of transmitting the refined location to a server in the network.

30. The non-transitory computer-readable medium of embodiment 19, wherein at least one of the one or more of the identified associated nodes is part of a node-enabled package; and wherein the step of determining the location of the at least one node further comprises determining the location of the at least one node while the at least one node is within the node-enabled package and while the node-enabled package is within a vehicle.

31. The non-transitory computer-readable medium of embodiment 30 further comprising the steps of: generating a location message regarding where the node-enabled package is located within the vehicle based upon the determined location of the at least one node; and transmitting the location message to another network device in the wireless node network for display on a user interface of the another network device.

32. The non-transitory computer-readable medium of embodiment 30 further comprising the steps of: accessing shipping information related to the node-enabled package; generating a relocation message regarding where the node-enabled package is to be relocated within the vehicle based upon the determined location of the at least one node and the accessed shipping information; and transmitting the location message to another network device in the wireless node network for display on a user interface of the another network device.

33. The non-transitory computer-readable medium of embodiment 32, wherein the shipping information comprises weight information on the node-enabled package.

34. The non-transitory computer-readable medium of embodiment 33, wherein the location of the node-enabled package within the vehicle is according to a loading scheme.

35. The non-transitory computer-readable medium of embodiment 34, wherein the loading scheme is related to an anticipated delivery schedule.

36. A node apparatus in a wireless node network that uses location determination by association, comprising: a node processing unit; a node volatile memory coupled to the processing unit; a node memory storage coupled to the node processing unit, the node memory storage maintaining at least a program code section, association data, and location data; and a first communication interface that provides a first communication path operatively coupling the node with a plurality of other nodes in the network; a second communication interface that provides a second communication path operatively coupling the node with a server in the network; and wherein the node processing unit, when executing at least the program code section resident in the server volatile memory, is operative to transmit one or more first messages via the first communication interface at a first anticipated range distance, identify which of the others nodes that are associated with the first node received at least one of the first messages, transmit one or more second messages via the first communication interface at a second anticipated range distance, which is incrementally smaller than the first anticipated range distance, and determine a location of one or more of the identified associated nodes that did not receive any of the second messages but received at least one of the first messages, the location being between the first anticipated range distance from a known location of the node and the second anticipated range distance from the known location of the node.

37. The node apparatus of embodiment 36, wherein the node processing unit is further operative to: transmit one or more third messages via the first communication interface at a third anticipated range distance, which is incrementally smaller range than the second anticipated range distance; determine a location of one or more of the identified associated nodes that did not receive any of the third messages but received at least one of the second messages, the location being between the second anticipated range distance from the known location of the node and the third anticipated range distance from the known location of the node.

38. The node apparatus of embodiment 36, wherein the first anticipated range distance is an optimal broadcasting range for the first communication interface.

39. The node apparatus of embodiment 38, wherein the first anticipated range distance is the optimal range for the first communication interface adjusted based upon context data.

40. The node apparatus of embodiment 39, wherein the first range distance and the second range distance are adjusted based upon one or more types of context data related to how an RF output signal transmit from the first communication interface may be impeded by an environment of the node.

41. The node apparatus of embodiment 36, wherein the node processing unit is further operative to access the association data in the node memory storage when identifying which of the nodes associated with the first node received at least one of the first messages.

42. The node apparatus of embodiment 36, wherein the node processing unit is further operative to identify at least those of the nodes that are passively associated with the first node as part of identifying which of the nodes associated with the first node received at least one of the first messages.

43. The node apparatus of embodiment 36, wherein the node processing unit is further operative to identify at least those of the nodes that are actively associated with the first node as part of identifying which of the nodes associated with the first node received at least one of the first messages.

44. The node apparatus of embodiment 36, wherein the node processing unit is further operative to refine the location of the one or more of the identified associated nodes that did not receive any of the second messages but received at least one of the first messages by updating a location of the first node.

45. The node apparatus of embodiment 44, wherein the node processing unit is further operative to: determine a current mobile location of the first node; and refine the location of the one or more of the identified associated nodes that did not receive any of the second messages but received at least one of the first messages based upon the current mobile location of the first node.

46. The node apparatus of embodiment 44, wherein the node processing unit is further operative to transmit the refined location to the server over the second communication interface.

47. The node apparatus of embodiment 36, wherein the node processing unit is further operative to store the determined location in the node memory storage as part of the location data.

48. The node apparatus of embodiment 36, wherein at least one of the one or more of the identified associated nodes is part of a node-enabled package; and wherein the node processing unit is further operative to determine the location of the at least one node by being operative to determine the location of the at least one node while the at least one node is within the node-enabled package and while the node-enabled package is within a vehicle.

49. The node apparatus of embodiment 48, wherein the node processing unit is further operative to: generate a location message regarding where the node-enabled package is located within the vehicle based upon the determined location of the at least one node; and transmit the location message to another network device in the wireless node network for display on a user interface of the another network device.

50. The node apparatus of embodiment 48, wherein the node processing unit is further operative to: access shipping information related to the node-enabled package from the node memory storage; generate a relocation message regarding where the node-enabled package is to be relocated within the vehicle based upon the determined location of the at least one node and the accessed shipping information; and transmit the location message via the communication interface to another network device in the wireless node network for display on a user interface of the another network device.

51. The node apparatus of embodiment 50, wherein the shipping information comprises weight information on the node-enabled package.

52. The node apparatus of embodiment 51, wherein the location of the node-enabled package within the vehicle is according to a loading scheme.

53. The node apparatus of embodiment 52, wherein the loading scheme is related to an anticipated delivery schedule.

Further Embodiment 8—Determining Node Location Using a Lower Level Node Association in a Wireless Node Network 1. A method for location determination using one or more associations of nodes in a wireless node network, the method comprising: instructing a first of the nodes to broadcast one or more first messages at a first power level, the first power level being related to a first anticipated range distance; identifying which of the nodes associated with the first node have known locations; determining which of the identified associated nodes received at least one of the first messages; instructing the first node to broadcast one or more second messages at a second power level, the second power level being related to a second anticipated range distance and incrementally smaller than the first power level; determining which of the identified associated nodes received at least one of the second messages; and determining a location of the first node to be at or between the first anticipated range distance and the second anticipated range distance from each of the identified associated nodes that did not receive at least one of the second messages but received at least one of the first messages.

2. The method of embodiment 1, wherein the step of instructing the first node to broadcast the one or more second messages within a time interval after instructing the first node to broadcast the one or more first messages.

3. The method of embodiment 2, wherein the time interval is dynamically set based upon context data related to the first node.

4. The method of embodiment 3, wherein the time interval is reduced from a prior value when the context data related to the first node indicates the first node is moving.

5. The method of embodiment 3, wherein the time value of the interval is increased from a prior value when the context data related to the first node indicates the first node is substantially stationary.

6. The method of embodiment 1 further comprising the steps of: instructing the first node to broadcast one or more third messages at a third power level, the third power level being related to a third anticipated range distance and incrementally smaller range than the second anticipated range distance; and determining the location of the first node to be at or between the second anticipated range distance and the third anticipated range distance from each of the identified associated nodes that did not receive any of the third messages but received at least one of the second messages.

7. The method of embodiment 1, wherein the first anticipated range distance is an optimal range for the first of the nodes.

8. The method of embodiment 7, wherein the first anticipated range distance is the optimal range for the first of the nodes adjusted based upon context data.

9. The method of embodiment 8, wherein the first anticipated range distance and the second anticipated range distance are adjusted based upon one or more types of context data related to how an RF output signal broadcast from the first node may be impeded.

10. The method of embodiment 1, wherein the identifying step further comprises: reviewing association data that indicates which of the nodes are associated with the first node; determining which of the nodes are associated with the first node based upon the reviewed association data; and identifying which of the nodes determined to be associated with the first node have known locations.

11. The method of embodiment 10, wherein the step of determining step which of the nodes are associated with the first node further comprises determining which of the nodes are passively associated with the first node based upon the reviewed association data.

12. The method of embodiment 10, wherein the step of determining step which of the nodes are associated with the first node further comprises determining which of the nodes are actively associated with the first node based upon the reviewed association data.

13. The method of embodiment 1 further comprising the step of refining the location of the first node with an updated location of one or more of the identified associated nodes that did not receive any of the second messages but received at least one of the first messages.

14. The method of embodiment 1, wherein the first node is not self-aware of the location of the first node.

15. The method of embodiment 1, wherein the first node was previously self-aware of the location of the first node but is no longer self-aware of the location of the first node prior to broadcasting the one or more first messages.

16. The method of embodiment 15, wherein the first node is no longer self-aware of the location of the first node prior to broadcasting the first message because of a change in the environment surrounding the first node.

17. The method of embodiment 16, wherein the change in the environment further comprises when the first node has moved inside a structure that blocks location signals from being received by the first node.

18. The method of embodiment 1, wherein the first node is part of a node-enabled package; and wherein the step of determining the location of the first node further comprises determining the location of the first node while the first node is within the node-enabled package and while the node-enabled package is within a vehicle.

19. The method of embodiment 18 further comprising the steps of: generating a location message regarding where the node-enabled package is located within the vehicle based upon the determined location of the first node; and transmitting the location message to another network device in the wireless node network for display on a user interface of the another network device.

20. The method of embodiment 18 further comprising the steps of: accessing shipping information related to the node-enabled package; generating a relocation message regarding where the node-enabled package is to be relocated within the vehicle based upon the determined location of the one node and the accessed shipping information; and transmitting the location message to another network device in the wireless node network for display on a user interface of the another network device.

21. The method of embodiment 20, wherein the shipping information comprises weight information on the node-enabled package.

22. The method of embodiment 21, wherein the location of the node-enabled package within the vehicle is according to a loading scheme.

23. The method of embodiment 22, wherein the loading scheme is related to an anticipated delivery schedule.

24. The method of embodiment 18, wherein the vehicle is one from a group consisting of a truck, a van, a trailer, an aircraft, and a marine vessel.

25. A non-transitory computer-readable medium containing instructions which when executed on a processor performs a method for location determination using one or more associations of nodes in a wireless node network, the method comprising: instructing a first of the nodes to broadcast one or more first messages at a first power level, the first power level being related to a first anticipated range distance; identifying which of the nodes associated with the first node have known locations; determining which of the identified associated nodes received at least one of the first messages; instructing the first node to broadcast one or more second messages at a second power level, the second power level being related to a second anticipated range distance and incrementally smaller than the first power level; determining which of the identified associated nodes received at least one of the second messages; and determining a location of the first node to be at or between the first anticipated range distance and the second anticipated range distance from each of the identified associated nodes that did not receive at least one of the second messages but received at least one of the first messages.

26. The non-transitory computer-readable medium of embodiment 25, wherein the step of instructing the first node to broadcast the one or more second messages within a time interval after instructing the first node to broadcast the one or more first messages.

27. The non-transitory computer-readable medium of embodiment 26, wherein the time interval is dynamically set based upon context data related to the first node.

28. The non-transitory computer-readable medium of embodiment 27, wherein the time interval is reduced from a prior value when the context data related to the first node indicates the first node is moving.

29. The non-transitory computer-readable medium of embodiment 27, wherein the time value of the interval is increased from a prior value when the context data related to the first node indicates the first node is substantially stationary.

30. The non-transitory computer-readable medium of embodiment 25, wherein the method further comprises the steps of: instructing the first node to broadcast one or more third messages at a third power level, the third power level being related to a third anticipated range distance and incrementally smaller range than the second anticipated range distance; and determining the location of the first node to be at or between the second anticipated range distance and the third anticipated range distance from each of the identified associated nodes that did not receive any of the third messages but received at least one of the second messages.

31. The non-transitory computer-readable medium of embodiment 25, wherein the first anticipated range distance is an optimal range for the first of the nodes.

32. The non-transitory computer-readable medium of embodiment 31, wherein the first anticipated range distance is the optimal range for the first of the nodes adjusted based upon context data.

33. The non-transitory computer-readable medium of embodiment 32, wherein the first anticipated range distance and the second anticipated range distance are adjusted based upon one or more types of context data related to how an RF output signal broadcast from the first node may be impeded.

34. The non-transitory computer-readable medium of embodiment 25, wherein the identifying step further comprises: reviewing association data that indicates which of the nodes are associated with the first node; determining which of the nodes are associated with the first node based upon the reviewed association data; and identifying which of the nodes determined to be associated with the first node have known locations.

35. The non-transitory computer-readable medium of embodiment 34, wherein the step of determining step which of the nodes are associated with the first node further comprises determining which of the nodes are passively associated with the first node based upon the reviewed association data.

36. The non-transitory computer-readable medium of embodiment 34, wherein the step of determining step which of the nodes are associated with the first node further comprises determining which of the nodes are actively associated with the first node based upon the reviewed association data.

37. The non-transitory computer-readable medium of embodiment 25, wherein the method further comprises the step of refining the location of the first node with an updated location of one or more of the identified associated nodes that did not receive any of the second messages but received at least one of the first messages.

38. The non-transitory computer-readable medium of embodiment 25, wherein the first node is not self-aware of the location of the first node.

39. The non-transitory computer-readable medium of embodiment 25, wherein the first node was previously self-aware of the location of the first node but is no longer self-aware of the location of the first node prior to broadcasting the one or more first messages.

40. The non-transitory computer-readable medium of embodiment 39, wherein the first node is no longer self-aware of the location of the first node prior to broadcasting the first message because of a change in the environment surrounding the first node.

41. The non-transitory computer-readable medium of embodiment 40, wherein the change in the environment further comprises when the first node has moved inside a structure that blocks location signals from being received by the first node.

42. The non-transitory computer-readable medium of embodiment 25, wherein the first node is part of a node-enabled package; and wherein the step of determining the location of the first node further comprises determining the location of the first node while the first node is within the node-enabled package and while the node-enabled package is within a vehicle.

43. The non-transitory computer-readable medium of embodiment 42, wherein the method further comprises the steps of: generating a location message regarding where the node-enabled package is located within the vehicle based upon the determined location of the first node; and transmitting the location message to another network device in the wireless node network for display on a user interface of the another network device.

44. The non-transitory computer-readable medium of embodiment 42, wherein the method further comprises the steps of: accessing shipping information related to the node-enabled package; generating a relocation message regarding where the node-enabled package is to be relocated within the vehicle based upon the determined location of the first node and the accessed shipping information; and transmitting the location message to another network device in the wireless node network for display on a user interface of the another network device.

45. The non-transitory computer-readable medium of embodiment 44, wherein the shipping information comprises weight information on the node-enabled package.

46. The non-transitory computer-readable medium of embodiment 45, wherein the location of the node-enabled package within the vehicle is according to a loading scheme.

47. The non-transitory computer-readable medium of embodiment 46, wherein the loading scheme is related to an anticipated delivery schedule.

48. The non-transitory computer-readable medium of embodiment 42, wherein the vehicle is one from a group consisting of a truck, a van, a trailer, an aircraft, and a marine vessel.

49. A node apparatus in a wireless node network that uses location determination by association, comprising: a node processing unit; a node volatile memory coupled to the processing unit; a node memory storage coupled to the node processing unit, the node memory storage maintaining at least a program code section, association data, and location data; and a first communication interface coupled to the processing unit and that provides access to a first communication path operatively coupling the node with a plurality of other nodes in the network; and wherein the node processing unit, when executing at least the program code section resident in the node volatile memory, is operative to communicate an instruction via the first communication interface to a first of the nodes to cause the first node to broadcast one or more first messages at a first power level, the first power level being related to a first anticipated range distance; identify which of the nodes associated with the first node have known locations; determine which of the identified associated nodes received at least one of the first messages; communicate another instruction via the first communication interface to the first node to cause the first node to broadcast one or more second messages at a second power level, the second power level being related to a second anticipated range distance and incrementally smaller than the first power level; determine which of the identified associated nodes received at least one of the second messages; and determine a location of the first node to be at or between the first anticipated range distance and the second anticipated range distance from each of the identified associated nodes that did not receive at least one of the second messages but received at least one of the first messages.

50. The node apparatus of embodiment 49, wherein the node processing unit is further operative to communicate the another instruction via the first communication interface to the first node to broadcast the one or more second messages within a time interval after instructing the first node to broadcast the one or more first messages.

51. The node apparatus of embodiment 50, wherein the time interval is dynamically set based upon context data related to the first node.

52. The node apparatus of embodiment 51, wherein the time interval is reduced from a prior value when the context data related to the first node indicates the first node is moving.

53. The node apparatus of 51, wherein the time value of the interval is increased from a prior value when the context data related to the first node indicates the first node is substantially stationary.

54. The node apparatus of embodiment 49, wherein the node processor is further operative to: communicate a third instruction via the first communication interface to the first node to cause the first node to broadcast one or more third messages at a third power level, the third power level being related to a third anticipated range distance and incrementally smaller range than the second anticipated range distance; and determine the location of the first node to be at or between the second anticipated range distance and the third anticipated range distance from each of the identified associated nodes that did not receive any of the third messages but received at least one of the second messages.

55. The node apparatus of embodiment 49, wherein the first anticipated range distance is an optimal range for the first of the nodes.

56. The node apparatus of embodiment 55, wherein the first anticipated range distance is the optimal range for the first of the nodes adjusted based upon context data.

57. The node apparatus of embodiment 56, wherein the first anticipated range distance and the second anticipated range distance are adjusted based upon one or more types of context data related to how an RF output signal broadcast from the first node may be impeded.

58. The node apparatus of embodiment 49, wherein node processing unit is further operative to identify which of the nodes associated with the first node have known locations by being operative to: access the association data on the node memory storage, the association data indicating which of the nodes are associated with the first node; determine which of the nodes are associated with the first node based upon the accessed association data; and identify which of the nodes determined to be associated with the first node have known locations.

59. The node apparatus of embodiment 58, wherein node processing unit is further operative to determine which of the nodes are associated with the first node by being operative to determine which of the nodes are passively associated with the first node based upon the accessed association data.

60. The node apparatus of embodiment 58, wherein node processing unit is further operative to determine which of the nodes are associated with the first node by being operative to determine which of the nodes are actively associated with the first node based upon the accessed association data.

61. The node apparatus of embodiment 49, wherein the node processing unit is further operative to refine the location of the first node with an updated location of one or more of the identified associated nodes that did not receive any of the second messages but received at least one of the first messages.

62. The node apparatus of embodiment 49, wherein the first node is not self-aware of the location of the first node.

63. The node apparatus of embodiment 49, wherein the first node was previously self-aware of the location of the first node but is no longer self-aware of the location of the first node prior to broadcasting the one or more first messages.

64. The node apparatus of embodiment 63, wherein the first node is no longer self-aware of the location of the first node prior to broadcasting the first message because of a change in the environment surrounding the first node.

65. The node apparatus of embodiment 64, wherein the change in the environment further comprises when the first node has moved inside a structure that blocks location signals from being received by the first node.

66. The node apparatus of embodiment 49, wherein the node processing unit is further operative to store the determined location in the node memory storage as part of the location data.

67. The node apparatus of embodiment 49, wherein the first node is part of a node-enabled package; and wherein the node processing unit is further operative to determine the location of the first node by being further operative to determine the location of the first node while the first node is within the node-enabled package and while the node-enabled package is within a vehicle.

68. The node apparatus of embodiment 67, wherein the node processing unit is further operative to: generate a location message regarding where the node-enabled package is located within the vehicle based upon the determined location of the first node; and cause the first communication interface to transmit the location message to another network device in the wireless node network for display on a user interface of the another network device.

69. The node apparatus of embodiment 67, wherein the node processing unit is further operative to: access shipping information related to the node-enabled package, the shipping information being maintained on the node memory storage; generate a relocation message regarding where the node-enabled package is to be relocated within the vehicle based upon the determined location of the first node and the accessed shipping information; and cause the first communication interface to transmit the location message to another network device in the wireless node network for display on a user interface of the another network device.

70. The node apparatus of embodiment 69, wherein the shipping information comprises weight information on the node-enabled package.

71. The node apparatus of embodiment 70, wherein the location of the node-enabled package within the vehicle is according to a loading scheme.

72. The node apparatus of embodiment 71, wherein the loading scheme is related to an anticipated delivery schedule.

73. The node apparatus of embodiment 67, wherein the vehicle is one from a group consisting of a truck, a van, a trailer, an aircraft, and a marine vessel.

74. A server apparatus in a wireless node network that uses location determination by association, comprising: a server processing unit; a server volatile memory coupled to the server processing unit; a server memory storage coupled to the server processing unit, the server memory storage maintaining at least a program code section, association data, and location data; and a communication interface coupled to the server processing unit, the communication interface providing access to a first communication path operatively coupling the server apparatus with at least a first node in the network; and wherein the server processing unit, when executing at least the program code section resident in the server volatile memory, is operative to communicate with the first node via the communication interface to cause a second node in the network to broadcast one or more first messages at a first power level at the request of the first node, the first power level being related to a first anticipated range distance; identify which of the remaining nodes in the network associated with the second node have known locations; determine which of the identified associated nodes received at least one of the first messages; communicate with the first node via the communication interface to cause the second node to broadcast one or more second messages at a second power level at the request of the first node, the second power level being related to a second anticipated range distance and incrementally smaller than the first power level; determine which of the identified associated nodes received at least one of the second messages; and determine a location of the second node to be at or between the first anticipated range distance and the second anticipated range distance from each of the identified associated nodes that did not receive any of the second messages but received at least one of the first messages.

75. The server apparatus of embodiment 74, wherein the server processing unit is further operative to communicate with the first node via the communication interface to cause the second node to broadcast the one or more second messages within a time interval after communicating with the first node to cause the second node to broadcast the one or more first messages.

76. The server apparatus of embodiment 75, wherein the time interval is dynamically set based upon context data related to the second node.

77. The server apparatus of embodiment 74, wherein the first anticipated range distance is an optimal range for the second node.

78. The server apparatus of embodiment 77, wherein the first anticipated range distance is the optimal range for the second node adjusted based upon context data.

79. The server apparatus of embodiment 74, wherein the server processing unit is further operative to store the determined location in the server memory storage as part of the location data.

80. The node apparatus of embodiment 74, wherein the second node is part of a node-enabled package; and wherein the server processing unit is further operative to determine the location of the second node by being operative to determine the location of the second node while the second node is within the node-enabled package and while the node-enabled package is within a vehicle.

Further Embodiment 9—Determining Node Location Based on Context Data in a Wireless Node Network 1. A method for determining a location of a first node in a wireless node network based on context data and by a network device deployed in the wireless node network, the method comprising: accessing, by the network device, a first type of the context data related to a proximate environment of the first node, wherein the first type of the context data comprises signal degradation information on how a second node would operate in a similar environment to the proximate environment of the first node when the second node is a similar type as the first node; adjusting, by the network device, an anticipated communication distance related to the first node based upon on the first type of the context data; and determining, by the network device, the location of the first node based upon the adjusted communication distance.

2. The method of embodiment 1 further comprising determining a location of the first node; and wherein the first type of the context data related to the proximate environment of the first node is based upon the determined location of the first node.

3. The method of embodiment 1, wherein the signal degradation information is based upon a degraded operation of the second node when the similar environment is an adverse communication environment.

4. The method of embodiment 3, wherein the signal degradation information is based upon a difference in how the second node communicates when exposed to the adverse communication environment compared to how the second node communicates when exposed to a nominal communication environment.

5. The method of embodiment 1, wherein the signal degradation information is related to at least one of shielding and interference.

6. The method of embodiment 1, wherein the signal degradation information relates to at least shipment data for one or more items being shipped and located in the proximate environment of the first node.

7. The method of embodiment 6, wherein the shipment data further comprises data for one or more items that are currently shipped or have been shipped in the past.

8. The method of embodiment 1, wherein the signal degradation information relates to at least layout data for one or more physical structures in the proximate environment of the first node.

9. The method of embodiment 8, wherein the signal degradation information further relates to the at least layout data for one or more physical structures in the proximate environment of the node near a predicted path for the first node.

10. The method of embodiment 1, wherein the signal degradation information relates to at least historic data on one or more analyzed prior operations of the second node.

11. The method of embodiment 1, wherein the adjusted communication distance comprises an anticipated reduced range distance for a transmission from the first node.

12. The method of embodiment 1, wherein the adjusted communication distance comprises an anticipated reduced receiver sensitivity distance for the first node.

13. The method of embodiment 1, wherein the step of adjusting the communication distance further comprises adaptively adjusting, by the network device, the communication distance based upon the signal degradation information and a second type of the context data.

14. The method of embodiment 13, wherein the second type of the context data comprises information related to at least one of (a) how the first node is being moved and (b) a density of other nodes near the first node.

15. The method of embodiment 1 further comprising updating the adjusted communication distance by the network device based upon movement of the first node, and refining the location of the first node with an updated adjusted communication distance.

16. The method of embodiment 15, wherein the movement of the first node comprises an anticipated movement of the first node along a predicted transit path for the first node.

17. The method of embodiment 1, wherein the first node is part of a node-enabled package; and wherein the step of determining the location of the first node further comprises determining the location of the first node while the first node is within the node-enabled package and while the node-enabled package is within a vehicle.

18. The method of embodiment 17 further comprising the steps of: generating a location message regarding where the node-enabled package is located within the vehicle based upon the determined location of the first node; and transmitting the location message to another network device in the wireless node network for display on a user interface of the another network device.

19. The method of embodiment 17 further comprising the steps of: accessing shipping information related to the node-enabled package; generating a relocation message regarding where the node-enabled package is to be relocated within the vehicle based upon the determined location of the first node and the accessed shipping information; and transmitting the location message to another network device in the wireless node network for display on a user interface of the another network device.

20. The method of embodiment 19, wherein the shipping information comprises weight information on the node-enabled package.

21. The method of embodiment 20, wherein the location of the node-enabled package within the vehicle is according to a loading scheme.

22. The method of embodiment 21, wherein the loading scheme is related to an anticipated delivery schedule.

23. The method of embodiment 17, wherein the vehicle is one from a group consisting of a truck, a van, a trailer, an aircraft, and a marine vessel.

24. A non-transitory computer-readable medium containing instructions which when executed on a processor performs a method for determining a location of a first node in a wireless node network based on context data and by a network device deployed in the wireless node network, the method comprising: accessing, by the network device, a first type of the context data related to a proximate environment of the first node, wherein the first type of the context data comprises signal degradation information on how a second node would operate in a similar environment to the proximate environment of the first node when the second node is a similar type as the first node; adjusting, by the network device, an anticipated communication distance related to the first node based upon on the first type of the context data; and determining, by the network device, the location of the first node based upon the adjusted communication distance.

25. The non-transitory computer-readable medium of embodiment 24, wherein the method further comprises determining a location of the first node; and wherein the first type of the context data related to the proximate environment of the first node is based upon the determined location of the first node.

26. The non-transitory computer-readable medium of embodiment 24, wherein the signal degradation information is based upon a degraded operation of the second node when the similar environment is an adverse communication environment.

27. The non-transitory computer-readable medium of embodiment 26, wherein the signal degradation information is based upon a difference in how the second node communicates when exposed to the adverse communication environment compared to how the second node communicates when exposed to a nominal communication environment.

28. The non-transitory computer-readable medium of embodiment 24, wherein the signal degradation information is related to at least one of shielding and interference.

29. The non-transitory computer-readable medium of embodiment 24, wherein the signal degradation information relates to at least shipment data for one or more items being shipped and located in the proximate environment of the first node.

30. The non-transitory computer-readable medium of embodiment 29, wherein the shipment data further comprises data for one or more items that are currently shipped or have been shipped in the past.

31. The non-transitory computer-readable medium of embodiment 24, wherein the signal degradation information relates to at least layout data for one or more physical structures in the proximate environment of the first node.

32. The non-transitory computer-readable medium of embodiment 31, wherein the signal degradation information further relates to the at least layout data for one or more physical structures in the proximate environment of the first node near a predicted path for the first node.

33. The non-transitory computer-readable medium of embodiment 24, wherein the signal degradation information relates to at least historic data on one or more analyzed prior operations of the second node.

34. The non-transitory computer-readable medium of embodiment 24, wherein the adjusted communication distance comprises an anticipated reduced range distance for a transmission from the first node.

35. The non-transitory computer-readable medium of embodiment 24, wherein the adjusted communication distance comprises an anticipated reduced receiver sensitivity distance for the first node.

36. The non-transitory computer-readable medium of embodiment 24, wherein the step of adjusting the communication distance further comprises adaptively adjusting, by the network device, the communication distance based upon the signal degradation information and a second type of the context data.

37. The non-transitory computer-readable medium of embodiment 36, wherein the second type of the context data comprises information related to at least one of (a) how the first node is being moved and (b) a density of other nodes near the first node.

38. The non-transitory computer-readable medium of embodiment 24, wherein the method further comprises updating the adjusted communication distance by the network device based upon movement of the first node, and refining the location of the first node with an updated adjusted communication distance.

39. The non-transitory computer-readable medium of embodiment 38, wherein the movement of the first node comprises an anticipated movement of the first node along a predicted transit path for the first node.

40. The non-transitory computer-readable medium of embodiment 24, wherein the first node is part of a node-enabled package; and wherein the step of determining the location of the first node further comprises determining the location of the first node while the first node is within the node-enabled package and while the node-enabled package is within a vehicle.

41. The non-transitory computer-readable medium of embodiment 40, wherein the method further comprises the steps of: generating a location message regarding where the node-enabled package is located within the vehicle based upon the determined location of the first node; and transmitting the location message to another network device in the wireless node network for display on a user interface of the another network device.

42. The non-transitory computer-readable medium of embodiment 40, wherein the method further comprises the steps of: accessing shipping information related to the node-enabled package; generating a relocation message regarding where the node-enabled package is to be relocated within the vehicle based upon the determined location of the first node and the accessed shipping information; and transmitting the location message to another network device in the wireless node network for display on a user interface of the another network device.

43. The non-transitory computer-readable medium of embodiment 42, wherein the shipping information comprises weight information on the node-enabled package.

44. The non-transitory computer-readable medium of embodiment 43, wherein the location of the node-enabled package within the vehicle is according to a loading scheme.

45. The non-transitory computer-readable medium of embodiment 44, wherein the loading scheme is related to an anticipated delivery schedule.

46. The non-transitory computer-readable medium of embodiment 40, wherein the vehicle is one from a group consisting of a truck, a van, a trailer, an aircraft, and a marine vessel.

47. A network device for determining a location of a first node in a wireless node network based on context data, comprising: a processing unit; a volatile memory coupled to the processing unit; a memory storage coupled to the processing unit, the memory storage maintaining at least a program code section and the context data, wherein the context data comprises at least signal degradation information on how a second node would operate in a similar environment to a proximate environment of the first node when the second node is a similar type as the first node; and a communication interface coupled to the processing unit, wherein the communication interface provides a communication path operatively coupling the network device with the first node in the network; and wherein the processing unit, when executing at least the program code section resident in the volatile memory, is operative to connect with the memory storage to access the signal degradation information, adjust an anticipated communication distance related to the first node based upon on the signal degradation information, determine the location of the first node based upon the adjusted communication distance, and store the determined location of the first node as location data on the memory storage.

48. The network device of embodiment 47 further comprising location circuitry coupled to the processing unit; and wherein the processing unit if further operative to: determine a location of the network device based upon an output signal from the location circuitry received by the processing unit, and determine the location of the first node based upon the adjusted communication distance and the location of the network device, and wherein the first type of the context data related to the proximate environment of the first node is based upon the determined location of the first node.

49. The network device of embodiment 47, wherein the signal degradation information is based upon a degraded operation of the second node when the similar environment is an adverse communication environment.

50. The network device of embodiment 49, wherein the signal degradation information is based upon a difference in how the second node communicates when exposed to the adverse communication environment compared to how the second node communicates when exposed to a nominal communication environment.

51. The network device of embodiment 47, wherein the signal degradation information is related to at least one of shielding and interference.

52. The network device of embodiment 47, wherein the signal degradation information relates to at least shipment data for one or more items being shipped and located in the proximate environment of the first node.

53. The network device of embodiment 52, wherein the shipment data further comprises data for one or more items that are currently shipped or have been shipped in the past.

54. The network device of embodiment 47, wherein the signal degradation information relates to at least layout data for one or more physical structures in the proximate environment of the first node.

55. The network device of embodiment 54, wherein the signal degradation information further relates to the at least layout data for one or more physical structures in the proximate environment of the first node near a predicted path for the first node.

56. The network device of embodiment 47, wherein the signal degradation information relates to at least historic data on one or more analyzed prior operations of the second node.

57. The network device of embodiment 47, wherein the adjusted communication distance comprises an anticipated reduced range distance for a transmission from the first node.

58. The network device of embodiment 47, wherein the adjusted communication distance comprises an anticipated reduced receiver sensitivity distance for the first node.

59. The network device of embodiment 47, wherein processing unit is further operative to adaptively adjust the communication distance based upon the signal degradation information and a second type of the context data.

60. The network device of embodiment 59, wherein the second type of the context data comprises information related to at least one of (a) how the first node is being moved and (b) a density of other nodes near the first node.

61. The network device of embodiment 47, wherein the processing unit is further operative to update the adjusted communication distance based upon movement of the first node, refine the location of the first node with an updated adjusted communication distance, and store the refined location of the first node as the location data on the memory storage.

62. The network device of embodiment 61, wherein the movement of the first node comprises an anticipated movement of the first node along a predicted transit path for the first node.

63. The network device of embodiment 47, wherein the first node is part of a node-enabled package; and wherein the processing unit is further operative to determine the location of the first node while the first node is within the node-enabled package and while the node-enabled package is within a vehicle.

64. The network device of embodiment 63, wherein the processing unit is further operative to: generate a location message regarding where the node-enabled package is located within the vehicle based upon the determined location of the first node; and transmit the location message via the communication interface to another network device in the wireless node network for display on a user interface of the another network device.

65. The network device of embodiment 63, wherein the server processing unit is further operative to: access shipping information related to the node-enabled package; generate a relocation message regarding where the node-enabled package is to be relocated within the vehicle based upon the determined location of the first node and the accessed shipping information; and transmit the location message via the communication interface to another network device in the wireless node network.

66. The network device of embodiment 65, wherein the shipping information comprises weight information on the node-enabled package.

67. The network device of embodiment 66, wherein the location of the node-enabled package within the vehicle is according to a loading scheme.

68. The network device of embodiment 67, wherein the loading scheme is related to an anticipated delivery schedule.

Further Embodiment 10—Determining Node Location Using Chaining Triangulation in a Wireless Node Network 1. A method for determining a location using chaining triangulation for one of a plurality of nodes in a wireless node network having a server, the method comprising: receiving, by a server from a first of the nodes, a location of the first node; receiving, by the server from a second of the nodes, a location of the second node; inferring, by the server, a location of a third of the nodes; and triangulating, by the server, the location of the one node based upon a determined distance of the one node to the location of the first node, a determined distance of the one node to the location of the second node, and a determined distance of the one node to the inferred location of the third node.

2. The method of embodiment 1, wherein the inferring step further comprises determining, by the server, a proximate-based location of the third node relative to another of the nodes having a known location, the proximate-based location operating as the inferred location of the third node.

3. The method of embodiment 1 further comprising the steps of: transmitting, by the server to the one node, an instruction to cause the one node to broadcast a plurality of advertising signals over a period of time; and wherein the determined distance of the one node to the location of the first node is based upon captured signals from the one node by the first node over the period of time and reported to the server by the first node.

4. The method of embodiment 3, wherein the determined distance of the one node to the location of the second node is based upon captured signals from the one node by the second node and reported to the server by the second node.

5. The method of embodiment 1 further comprising the steps of: transmitting, by the server to the one node, an instruction to cause the one node to broadcast a plurality of advertising signals at different power levels; and wherein the determined distance of the one node to the location of the first node is based upon captured signals from the one node by the first node and reported to the server by the first node.

6. The method of embodiment 5, wherein the determined distance of the one node to the location of the second node is based upon captured signals from the one node by the second node and reported to the server by the second node.

7. The method of embodiment 1, wherein the step of inferring the location of the third node further comprises determining, by the server, a relative location of the third node to the first node.

8. The method of embodiment 1, wherein the step of inferring the location of the third node further comprises determining, by the server, a relative location of the third node to the second node.

9. The method of embodiment 1 further comprising adjusting, by the server, the inferred location of the third node to determine a refined location of the third node based upon third node context data related to the inferred location of the third node.

10. The method of embodiment 9, wherein the triangulating step further comprises the steps of: accessing, by the server, first node context data related to a contextual environment near the first node and second node context data related a contextual environment near the second node; adjusting, by the server, the determined distance of the one node to the location of the first node based upon the first node context data to provide a refined distance of the one node to the location of the of the first node; and triangulating, by the server, the location of the one node based upon the adjusted determined distance of the one node to the location of the first node, the adjusted determined distance of the one node to the location of second node, and a determined distance of the one node to the refined location of the third node.

11. The method of embodiment 1 further comprising transmitting the location information by the server upon receipt of a request for a location of the one node.

12. The method of embodiment 1, wherein the one node is part of a node-enabled package; and wherein the step of triangulating the location of the one node further comprises determining the location of the one node while the one node is within the node-enabled package and while the node-enabled package is within a vehicle.

13. The method of embodiment 12 further comprising: generating a location message regarding where the node-abled package is located within the vehicle based upon the determined location of the one node; and transmitting the location message to another network device in the wireless node network for display on a user interface of the another network device.

14. The method of embodiment 12 further comprising: accessing shipping information related to the node-enabled package; generating a relocation message regarding where the node-abled package is to be relocated within the vehicle based upon the determined location of the one node and the accessed shipping information; and transmitting the location message to another network device in the wireless node network for display on a user interface of the another network device.

15. The method of embodiment 14, wherein the shipping information comprises weight information on the node-enabled package.

16. The method of embodiment 15, wherein the location of the node-enabled package within the vehicle is according to a loading scheme.

17. The method of embodiment 16, wherein the loading scheme is related to an anticipated delivery schedule.

18. The method of embodiment 12, wherein the vehicle is one from a group consisting of a truck, a van, a trailer, an aircraft, and a marine vessel.

19. A non-transitory computer-readable medium containing instructions which when executed on a processor performs a method for determining a location using chaining triangulation for one of a plurality of nodes in a wireless node network having a server, the method comprising: receiving, by a server from a first of the nodes, a location of the first node; receiving, by the server from a second of the nodes, a location of the second node; inferring, by the server, a location of a third of the nodes; and triangulating, by the server, the location of the one node based upon a determined distance of the one node to the location of the first node, a determined distance of the one node to the location of second node, and a determined distance of the one node to the inferred location of the third node.

20. The non-transitory computer-readable medium of embodiment 19, wherein the inferring step further comprises determining, by the server, a proximate-based location of the third node relative to another of the nodes having a known location, the proximate-based location operating as the inferred location of the third node.

21. The non-transitory computer-readable medium of embodiment 19, wherein the method further comprises the steps of: transmitting, by the server to the one node, an instruction to cause the one node to broadcast a plurality of advertising signals over a period of time; and wherein the determined distance of the one node to the location of the first node is based upon captured signals from the one node by the first node over the period of time and reported to the server by the first node.

22. The non-transitory computer-readable medium of embodiment 21, wherein the determined distance of the one node to the location of the second node is based upon captured signals from the one node by the second node and reported to the server by the second node.

23. The non-transitory computer-readable medium of embodiment 19, wherein the method further comprises the steps of: transmitting, by the server to the one node, an instruction to cause the one node to broadcast a plurality of advertising signals at different power levels; and wherein the determined distance of the one node to the location of the first node is based upon captured signals from the one node by the first node and reported to the server by the first node.

24. The non-transitory computer-readable medium of embodiment 23, wherein the determined distance of the one node to the location of the second node is based upon captured signals from the one node by the second node and reported to the server by the second node.

25. The non-transitory computer-readable medium of embodiment 19, wherein the step of inferring the location of the third node further comprises determining, by the server, a relative location of the third node to the first node.

26. The non-transitory computer-readable medium of embodiment 19, wherein the step of inferring the location of the third node further comprises determining, by the server, a relative location of the third node to the second node.

27. The non-transitory computer-readable medium of embodiment 19, wherein the method further comprises adjusting, by the server, the inferred location of the third node to determine a refined location of the third node based upon third node context data related to the inferred location of the third node.

28. The non-transitory computer-readable medium of embodiment 27, wherein the triangulating step further comprises the steps of: accessing, by the server, first node context data related to a contextual environment near the first node and second node context data related a contextual environment near the second node; adjusting, by the server, the determined distance of the one node to the location of the first node based upon the first node context data to provide a refined distance of the one node to the location of the of the first node; and triangulating, by the server, the location of the one node based upon the adjusted determined distance of the one node to the location of the first node, the adjusted determined distance of the one node to the location of second node, and a determined distance of the one node to the refined location of the third node.

29. The non-transitory computer-readable medium of embodiment 19, wherein the method further comprises transmitting the location information by the server upon receipt of a request for a location of the one node.

30. The non-transitory computer-readable medium of embodiment 19, wherein the one node is part of a node-enabled package; and wherein the step of triangulating the location of the one node further comprises triangulating the location within a vehicle of the node-enabled package having the one node based upon the determined distance of the one node to the location of the first node, the determined distance of the one node to the location of the second node, and the determined distance of the one node to the inferred location of the third node.

31. The non-transitory computer-readable medium of embodiment 30, wherein the method further comprises: generating a location message regarding where the node-abled package is located within the vehicle based upon the determined location of the one node; and transmitting the location message to another network device in the wireless node network for display on a user interface of the another network device.

32. The non-transitory computer-readable medium of embodiment 30 further comprising: accessing shipping information related to the node-enabled package; generating a relocation message regarding where the node-abled package is to be relocated within the vehicle based upon the determined location of the one node and the accessed shipping information; and transmitting the location message to another network device in the wireless node network for display on a user interface of the another network device.

33. The non-transitory computer-readable medium of embodiment 32, wherein the shipping information comprises weight information on the node-enabled package.

34. The non-transitory computer-readable medium of embodiment 33, wherein the location of the node-enabled package within the vehicle is according to a loading scheme.

35. The non-transitory computer-readable medium of embodiment 34, wherein the loading scheme is related to an anticipated delivery schedule.

36. The non-transitory computer-readable medium of embodiment 30, wherein the vehicle is one from a group consisting of a truck, a van, a trailer, an aircraft, and a marine vessel.

37. A server apparatus for determining a location using chaining triangulation for one of a plurality of nodes in a wireless node network, the server apparatus comprising: a server processing unit; a server volatile memory coupled to the server processing unit; a server memory storage coupled to the server processing unit, the server memory storage maintaining at least a program code section and location data; and a communication interface that provides a communication path operatively coupling the server with a first node of the plurality of nodes and a second node of the plurality of nodes; and wherein the server processing unit, when executing at least the program code section resident in the server volatile memory, is operative to receive a request over the communication interface for the location of the one node, receive, from a first of the nodes, a location of the first node, store the location of the first node in the server memory storage as part of the location data maintained on the server memory storage, receive, from a second of the nodes, a location of the second node, store the location of the second node in the server memory storage as part of the location data maintained on the server memory storage, infer a location of a third of the nodes, store the inferred location of the third node in the server memory storage as part of the location data maintained on the server memory storage, triangulate the location of the one node based upon a determined distance of the one node to the location of the first node, a determined distance of the one node to the location of second node, and a determined distance of the one node to the inferred location of the third node, and transmit the location information over the communication interface in response to the request.

38. The server apparatus of embodiment 37, wherein the server processing unit is further operative to infer the location of the third of the nodes by being operative to determine a proximate-based location of the third node relative to another of the nodes having a known location, the proximate-based location operating as the inferred location of the third node.

39. The server apparatus of embodiment 37, wherein the server processing unit is further operative to: transmit an instruction over the communication interface to cause the one node to broadcast a plurality of advertising signals over a period of time; and wherein the determined distance of the one node to the location of the first node is based upon captured signals from the one node by the first node over the period of time and reported to the server by the first node.

40. The server apparatus of embodiment 39, wherein the determined distance of the one node to the location of the second node is based upon captured signals from the one node by the second node and reported to the server by the second node.

41. The server apparatus of embodiment 37, wherein the server processing unit is further operative to: transmit an instruction over the communication interface to cause the one node to broadcast a plurality of advertising signals at different power levels; and wherein the determined distance of the one node to the location of the first node is based upon captured signals from the one node by the first node and reported to the server by the first node.

42. The server apparatus of embodiment 41, wherein the determined distance of the one node to the location of the second node is based upon captured signals from the one node by the second node and reported to the server by the second node.

43. The server apparatus of embodiment 37, wherein the server processing unit is further operative to infer the location of the third node by being operative to determine a relative location of the third node to the first node.

44. The server apparatus of embodiment 37, wherein the server processing unit is further operative to infer the location of the third node by being operative to determine a relative location of the third node to the second node.

45. The server apparatus of embodiment 37, wherein the server processing unit is further operative to adjust the inferred location of the third node to determine a refined location of the third node based upon third node context data related to the inferred location of the third node.

46. The server apparatus of embodiment 45, wherein the server memory storage further maintains context data; and wherein the server processing unit is further operative to triangulate by being operative to: access first node context data as part of the context data maintained on the server memory storage, the first node context data being related to a contextual environment near the first node, access second node context data as part of the context data maintained on the server memory storage, the second node context data being related a contextual environment near the second node, adjust the determined distance of the one node to the location of the first node based upon the first node context data to provide a refined distance of the one node to the location of the of the first node, and triangulate the location of the one node based upon the adjusted determined distance of the one node to the location of the first node, the adjusted determined distance of the one node to the location of second node, and a determined distance of the one node to the refined location of the third node.

47. The server apparatus of embodiment 37, wherein the one node is part of a node-enabled package; and wherein the server processing unit is further operative to triangulate the location of the one node while the one node is within the node-enabled package and while the node-enabled package is within a vehicle.

48. The server apparatus of embodiment 47 further comprising: generating a location message regarding where the node-abled package is located within the vehicle based upon the determined location of the one node; and transmitting the location message to another network device in the wireless node network for display on a user interface of the another network device.

49. The server apparatus of embodiment 47 further comprising: accessing shipping information related to the node-enabled package; generating a relocation message regarding where the node-abled package is to be relocated within the vehicle based upon the determined location of the one node and the accessed shipping information; and transmitting the location message to another network device in the wireless node network for display on a user interface of the another network device.

50. The server apparatus of embodiment 49, wherein the shipping information comprises weight information on the node-enabled package.

51. The server apparatus of embodiment 50, wherein the location of the node-enabled package within the vehicle is according to a loading scheme.

52. The server apparatus of embodiment 51, wherein the loading scheme is related to an anticipated delivery schedule.

53. The server apparatus of embodiment 47, wherein the vehicle is one from a group consisting of a truck, a van, a trailer, an aircraft, and a marine vessel.

Further Embodiment 11—Node-Enabled Generation of a Shipping Label Using Elements of a Wireless Node Network 1. A method for generating a shipping label for an item to be shipped using a wireless node network having at least a master node associated with a shipping facility, a node associated with the a shipping customer, and a server, the method comprising: receiving, by the master node, shipping information from the server, the shipping information being related to the node associated with the shipping customer; detecting, by the master node, a signal from the node associated with the shipping customer as the node associated with the shipping customer approaches the shipping facility; associating the master node and the node associated with the shipping customer; and causing, by the master node, generation of the shipping label for the item to be shipped when the master node determines the node associated with the shipping customer is within a predetermined range of a location within the shipping facility.

2. The method of embodiment 1, wherein the node associated with the shipping customer is one from a group comprising an ID node, a first master node, a node package, a first user access device operating as an ID node, a second user access device operating as a master node, and a second master node operating in a temporary ID node mode.

3. The method of embodiment 2, wherein the first master node transitions from being operative to communicate with the master node associated with the shipping facility over a longer range communication path to operate in the temporary ID node mode when the first master node can receive a signal from the master node associated with the shipping facility over a short range communication path.

4. The method of embodiment 1 further comprising the step of causing, by the master node, generation of one or more additional shipping labels when the master node determines the node associated with the shipping customer is within a predetermined range of a location within the shipping facility.

5. The method of embodiment 1, wherein the location is one from a group comprising a drop off location for the item to be shipped, a generation location for the shipping label, and a pickup location for the shipping label.

6. The method of embodiment 1, wherein the shipping label comprises a tracking number associated with the shipping information, an address associated with the shipping information, information about a user shipping the item, and a machine readable reference to attach to the item to be shipped.

7. The method of embodiment 1, wherein the associating step further comprises establishing a passive association between the master node and the node associated with the shipping customer without requiring a secure connection between the master node and the node associated with the shipping customer.

8. The method of embodiment 1, wherein the associating step further comprises establishing an active association between the master node and the node associated with the shipping customer, the active association reflecting a secure connection between the master node and the node associated with the shipping customer.

9. The method of embodiment 1 further comprising determining, by the master node, that the node associated with the shipping customer is within the predetermined range of the designated location by instructing the node associated with the shipping customer to alter an RF power characteristic as part of locating the node associated with the shipping customer.

10. The method of embodiment 9, wherein the RF power characteristic of the node associated with the shipping customer is an RF transmission power level.

11. The method of embodiment 1 further comprising updating the server when the master node is no longer associated with the node associated with the shipping customer.

12. The method of embodiment 1 further comprising updating the server with location metric information related to analytics on movement of the node associated with the shipping customer within the shipping facility.

13. The method of embodiment 1 further comprising the steps of: determining if the shipping customer is a priority customer based upon the shipping information; and generating a notification for shipping facility personnel by the master node prior to generating the shipping label, the notification indicating that the shipping customer is the priority customer.

14. The method of embodiment 1 further comprising providing, by the master node, a message to a user access device operated by shipping facility personnel, the message causing the user access device to display a prompt related to offering the shipping customer packaging material.

15. The method of embodiment 1 further comprising causing, by the master node, generation of a coupon for packaging material for the item to be shipped.

16. The method of embodiment 1 further comprising providing a message to the node associated with the shipping customer, the message causing the node associated with the shipping customer to display a prompt related to an offer for packaging material.

17. The method of embodiment 16, wherein the packaging material comprises one from the group comprising a package, separator material, cushioning material, and a node-enabled package.

18. The method of embodiment 1 further comprising providing a message to a user access device operated by shipping facility personnel, the message causing the user access device to display a prompt related to offering the shipping customer a specialized packaging material for the item to be shipped based upon the value of the item to be shipped identified as part of the shipping information.

19. The method of embodiment 1 further comprising providing a message to a user access device operated by shipping facility personnel, the message causing the user access device to display a prompt related to offering the shipping customer a specialized packaging material for the item to be shipped based upon an indication that the item to be shipped is fragile.

20. A non-transitory computer-readable medium containing instructions which when executed on a processor performs a method for generating a shipping label for an item to be shipped using a wireless node network having at least a master node associated with a shipping facility, an ID node associated with the item, and a server, the method comprising: receiving, by the master node, shipping information from the server, the shipping information being related to the node associated with the shipping customer; detecting, by the master node, a signal from the node associated with the shipping customer as the node associated with the shipping customer approaches the shipping facility; associating the master node and the node associated with the shipping customer; and causing, by the master node, generation of the shipping label for the item to be shipped when the master node determines the node associated with the shipping customer is within a predetermined range of a location within the shipping facility.

21. The non-transitory computer-readable medium of embodiment 20, wherein the node associated with the shipping customer is one from a group comprising an ID node, a first master node, a node package, a first user access device operating as an ID node, a second user access device operating as a master node, and a second master node operating in a temporary ID node mode.

22. The non-transitory computer-readable medium of embodiment 21, wherein the second master node transitions from being operative to communicate with the master node associated with the shipping facility over a longer range communication path to operate in the temporary ID node mode when the second master node can receive a signal from the master node associated with the shipping facility over a short range communication path.

23. The non-transitory computer-readable medium of embodiment 20, wherein the method further comprises the step of causing, by the master node, generation of one or more additional shipping labels when the master node determines the node associated with the shipping customer is within a predetermined range of a location within the shipping facility.

24. The non-transitory computer-readable medium of embodiment 20, wherein the location is one from a group comprising a drop off location for the item to be shipped, a generation location for the shipping label, and a pickup location for the shipping label.

25. The non-transitory computer-readable medium of embodiment 20, wherein the shipping label comprises a tracking number associated with the shipping information, an address associated with the shipping information, information about a user shipping the item, and a machine readable reference to attach to the item to be shipped.

26. The non-transitory computer-readable medium of embodiment 20, wherein the associating step further comprises establishing a passive association between the master node and the node associated with the shipping customer without requiring a secure connection between the master node and the node associated with the shipping customer.

27. The non-transitory computer-readable medium of embodiment 20, wherein the associating step further comprises establishing an active association between the master node and the node associated with the shipping customer, the active association reflecting a secure connection between the master node and the node associated with the shipping customer.

28. The non-transitory computer-readable medium of embodiment 20, wherein the method further comprises determining, by the master node, that the node associated with the shipping customer is within the predetermined range of the designated location by instructing the node associated with the shipping customer to alter an RF power characteristic as part of locating the node associated with the shipping customer.

29. The non-transitory computer-readable medium of embodiment 28, wherein the RF power characteristic of the node associated with the shipping customer is an RF transmission power level.

30. The non-transitory computer-readable medium of embodiment 20, wherein the method further comprises updating the server when the master node is no longer associated with the node associated with the shipping customer.

31. The non-transitory computer-readable medium of embodiment 20, wherein the method further comprises updating the server with location metric information related to analytics on movement of the node associated with the shipping customer within the shipping facility.

32. The non-transitory computer-readable medium of embodiment 20, wherein the method further comprises the steps of: determining if the shipping customer is a priority customer based upon the shipping information; and generating a notification for shipping facility personnel by the master node prior to generating the shipping label, the notification indicating that the shipping customer is the priority customer.

33. The non-transitory computer-readable medium of embodiment 20, wherein the method further comprises providing, by the master node, a message to a user access device operated by shipping facility personnel, the message causing the user access device to display a prompt related to offering the shipping customer packaging material.

34. The non-transitory computer-readable medium of embodiment 20, wherein the method further comprises causing, by the master node, generation of a coupon for packaging material for the item to be shipped.

35. The non-transitory computer-readable medium of embodiment 20, wherein the method further comprises providing a message to the node associated with the shipping customer, the message causing the node associated with the shipping customer to display a prompt related to an offer for packaging material.

36. The non-transitory computer-readable medium of embodiment 35, wherein the packaging material comprises one from the group comprising a package, separator material, cushioning material, and a node-enabled package.

37. The non-transitory computer-readable medium of embodiment 20, wherein the method further comprises providing a message to a user access device operated by shipping facility personnel, the message causing the user access device to display a prompt related to offering the shipping customer a specialized packaging material for the item to be shipped based upon the value of the item to be shipped identified as part of the shipping information.

38. The non-transitory computer-readable medium of embodiment 20, wherein the method further comprises providing a message to a user access device operated by shipping facility personnel, the message causing the user access device to display a prompt related to offering the shipping customer a specialized packaging material for the item to be shipped based upon an indication that the item to be shipped is fragile.

39. A system for generating a shipping label for an item to be shipped using a wireless node network, comprising: a server; a master node associated with a shipping facility, the master node being operative to communicate with the server; a printer in operative communication with at least the master node, the printer being responsive to instructions from the master node; and a node associated with a shipping customer;

wherein the master node is programmatically operative to receive shipping information from the server, the shipping information being related to the node associated with the shipping customer, detect a signal from the node associated with the shipping customer as the node associated with the shipping customer approaches the shipping facility, associate the master node and the node associated with the shipping customer, and instruct the printer to generate of the shipping label for the item to be shipped when the master node determines the node associated with the shipping customer is within a predetermined range of a location within the shipping facility.

40. The system of embodiment 39, wherein the node associated with the shipping customer is one from a group comprising an ID node, a first master node, a node package, a first user access device operating as an ID node, a second user access device operating as a master node, and a second master node operating in a temporary ID node mode.

41. The system of embodiment 40, wherein the second master node transitions from being operative to communicate with the master node associated with the shipping facility over a longer range communication path to operate in the temporary ID node mode when the second master node can receive a signal from the master node associated with the shipping facility over a short range communication path.

42. The system of embodiment 39, wherein the master node is further operative instruct the printer to generate one or more additional shipping labels when the master node determines the node associated with the shipping customer is within a predetermined range of a location within the shipping facility.

43. The system of embodiment 39, wherein the location is one from a group comprising a drop off location for the item to be shipped, a generation location for the shipping label, and a pickup location for the shipping label.

44. The system of embodiment 39, wherein the shipping label comprises a tracking number associated with the shipping information, an address associated with the shipping information, information about a user shipping the item, and a machine readable reference to attach to the item to be shipped.

45. The system of embodiment 39, wherein the master node is further operative to associate by being operative to establish a passive association between the master node and the node associated with the shipping customer without requiring a secure connection between the master node and the node associated with the shipping customer.

46. The system of embodiment 39, wherein the master node is further operative to associate by being operative to establish an active association between the master node and the node associated with the shipping customer, the active association reflecting a secure connection between the master node and the node associated with the shipping customer.

47. The system of embodiment 39, wherein the master node is further operative to determine that the node associated with the shipping customer is within the predetermined range of the designated location by instructing the node associated with the shipping customer to alter an RF power characteristic as part of locating the node associated with the shipping customer.

48. The system of embodiment 47, wherein the RF power characteristic of the node associated with the shipping customer is an RF transmission power level.

49. The system of embodiment 39, wherein the master node is further operative to update the server when the master node is no longer associated with the node associated with the shipping customer.

50. The system of embodiment 39, wherein the master node is further operative to update the server with location metric information related to analytics on movement of the node associated with the shipping customer within the shipping facility.

51. The system of embodiment 39, wherein the master node is further operative to: determine if the shipping customer is a priority customer based upon the shipping information; and generate a notification for shipping facility personnel by the master node prior to generating the shipping label, the notification indicating that the shipping customer is the priority customer.

52. The system of embodiment 39, wherein the master node is further operative to provide a message to a user access device operated by shipping facility personnel, the message causing the user access device to display a prompt related to offering the shipping customer packaging material.

53. The system of embodiment 39, wherein the master node is further operative to cause the printer to generate a coupon for packaging material for the item to be shipped.

54. The system of embodiment 39, wherein the master node is further operative to provide a message to the node associated with the shipping customer, the message causing the node associated with the shipping customer to display a prompt related to an offer for packaging material.

55. The system of embodiment 54, wherein the packaging material comprises one from the group comprising a package, separator material, cushioning material, and a node-enabled package.

56. The system of embodiment 39, wherein the master node is further operative to provide a message to a user access device operated by shipping facility personnel, the message causing the user access device to display a prompt related to offering the shipping customer a specialized packaging material for the item to be shipped based upon the value of the item to be shipped identified as part of the shipping information.

57. The system of embodiment 39, wherein the master node is further operative to provide a message to a user access device operated by shipping facility personnel, the message causing the user access device to display a prompt related to offering the shipping customer a specialized packaging material for the item to be shipped based upon an indication that the item to be shipped is fragile.

Further Embodiment 12—Node Association Payment Transactions Using Elements of a Wireless Node Network 1. A method for conducting a payment transaction using node association in a wireless node network, the method comprising: detecting, by the master node, a signal from the ID node as the ID node approaches the master node, the master node being related to a payment receiver and the ID node being related to a payment provider; determining, by the master node, if the ID node desires to associate with the master node for the payment transaction based upon a first part of information within the signal; associating the master node and the ID node when the ID node desires to associate with the master node for the payment transaction; and submitting, by the master node, payment transaction data to the server, the payment transaction data being based upon a second part of information within the signal.

2. The method of embodiment 1, wherein the first part of information within the signal comprises an identification of a particular consumable to be purchased in the payment transaction.

3. The method of embodiment 1, wherein the second part of information within the signal comprises an identification of a payment source for the payment transaction.

4. The method of embodiment 3, wherein the payment source is a non-currency program.

5. The method of embodiment 1, wherein the associating step further comprises establishing a passive association between the master node and the ID node without requiring an authorized connection between the master node and ID node.

6. The method of embodiment 1, wherein the associating step further comprises establishing an active association between the master node and the ID node, the active association reflecting an authorized connection between the master node and ID node.

7. The method of embodiment 6, wherein the authorized connection is based upon a preloaded security credential.

8. The method of embodiment 6, wherein establishing the active association further comprises establishing the active association with the ID node after receiving an acknowledgement from the ID node related to the payment transaction.

9. The method of embodiment 1, wherein the ID node is a mobile user access device.

10. The method of embodiment 9, wherein the signal from the mobile user access device is a short-range transmission to the master node.

11. The method of embodiment 10, wherein the associating step further comprises altering a broadcasting mode of the master node and instructing the ID node to alter its broadcasting mode to enable associating the master node and the ID node.

12. The method of embodiment 1, wherein the payment transaction data reflects an authorization to complete the payment transaction based upon the successful association of the master node and the ID node.

13. A non-transitory computer-readable medium containing instructions which when executed on a processor performs a method for conducting a payment transaction using node association in a wireless node network, the method comprising: detecting, by the master node, a signal from the ID node as the ID node approaches the master node, the master node being related to a payment receiver and the ID node being related to a payment provider; determining, by the master node, if the ID node desires to associate with the master node for the payment transaction based upon a first part of information within the signal; associating the master node and the ID node when the ID node desires to associate with the master node for the payment transaction; and submitting, by the master node, payment transaction data to the server, the payment transaction data being based upon a second part of information within the signal.

14. The non-transitory computer-readable medium of embodiment 13, wherein the first part of information within the signal comprises an identification of a particular consumable to be purchased in the payment transaction.

15. The non-transitory computer-readable medium of embodiment 13, wherein the second part of information within the signal comprises an identification of a payment source for the payment transaction.

16. The non-transitory computer-readable medium of embodiment 15, wherein the payment source is a non-currency program.

17. The non-transitory computer-readable medium of embodiment 13, wherein the associating step further comprises establishing a passive association between the master node and the ID node without requiring an authorized connection between the master node and ID node.

18. The non-transitory computer-readable medium of embodiment 13, wherein the associating step further comprises establishing an active association between the master node and the ID node, the active association reflecting an authorized connection between the master node and ID node.

19. The non-transitory computer-readable medium of embodiment 18, wherein the authorized connection is based upon a preloaded security credential.

20. The non-transitory computer-readable medium of embodiment 18, wherein establishing the active association further comprises establishing the active association with the ID node after receiving an acknowledgement from the ID node related to the payment transaction.

21. The non-transitory computer-readable medium of embodiment 13, wherein the ID node is a mobile user access device.

22. The non-transitory computer-readable medium of embodiment 21, wherein the signal from the mobile user access device is a short-range transmission to the master node.

23. The non-transitory computer-readable medium of embodiment 22, wherein the associating step further comprises altering a broadcasting mode of the master node and instructing the ID node to alter its broadcasting mode to enable associating the master node and the ID node.

24. The non-transitory computer-readable medium of embodiment 13, wherein the payment transaction data reflects an authorization to complete the payment transaction based upon the successful association of the master node and the ID node.

25. A system for conducting a payment transaction using node association in a wireless node network, comprising: a server associated with a payment receiver; and a master node associated with the payment receiver, the master node being in communication with the server; wherein the master node is operative to detect a signal broadcast from an ID node as the ID node approaches the master node, the ID node being related to a payment provider, determine if the ID node desires to associate with the master node for the payment transaction based upon a first part of information within the signal, associate the master node and the ID node when the ID node desires to associate with the master node for the payment transaction, and submit payment transaction data to the server, the payment transaction data being based upon a second part of information within the signal.

26. The system of embodiment 25, wherein the first part of information within the signal comprises an identification of a particular consumable to be purchased in the payment transaction.

27. The system of embodiment 25, wherein the second part of information within the signal comprises an identification of a payment source for the payment transaction.

28. The system of embodiment 27, wherein the payment source is a non-currency program.

29. The system of embodiment 25, wherein the master node is further operative to associate with the ID node by establishing a passive association between the master node and the ID node without requiring an authorized connection between the master node and ID node.

30. The system of embodiment 25, wherein the master node is further operative to associate with the ID node by establishing an active association between the master node and the ID node, the active association reflecting an authorized connection between the master node and ID node.

31. The system of embodiment 30, wherein the authorized connection is based upon a preloaded security credential.

32. The system of embodiment 30, wherein the master node is further operative to associate with the ID node by establishing the active association with the ID node after receiving an acknowledgement from the ID node related to the payment transaction.

33. The system of embodiment 25, wherein the ID node is a mobile user access device.

34. The system of embodiment 33, wherein the signal from the mobile user access device is a short-range transmission to the master node.

35. The system of embodiment 34, wherein the master node is further operative to associate with the ID node by altering a broadcasting mode of the master node and instructing the ID node to alter its broadcasting mode to enable associating the master node and the ID node.

36. The system of embodiment 25, wherein the payment transaction data reflects an authorization to complete the payment transaction based upon the successful association of the master node and the ID node.

Further Embodiment 13—Node-Enabled Shipping without a Shipping Label Using Elements of a Wireless Node Network 1. A method for preparing a node-enabled shipment of an item to be shipped using a wireless node network having at least a node and a server, the method comprising: capturing an identification of the node to be related to the item by a user access device; entering shipping information into the user access device, the shipping information being related to the item, and the shipping information being linked with the identification of the node; storing the shipping information on the node; and combining the item to be shipped and the node.

2. The method of embodiment 1, wherein the node comprises one from a group consisting of an ID node, a master node, and a sensor node.

3. The method of embodiment 1, wherein the node comprises a mobile master node having at least one sensor onboard the master node for gathering environmental information about an environment near the master node.

4. The method of embodiment 1, wherein the step of capturing the identification of the node further comprises detecting an electronic identification of the node.

5. The method of embodiment 1, wherein the step of capturing the identification of the node further comprises viewing a readable identifier of the node.

6. The method of embodiment 1, wherein the step of capturing the identification of the node further comprises scanning a machine-readable identifier of the node.

7. The method of embodiment 1, wherein the step of combining the item to be shipped and the node further comprises placing the node within an interior of a package for the item to be shipped.

8. The method of embodiment 1, wherein the step of combining the item to be shipped and the node further comprises securely fixing the node to an interior surface of a package for the item to be shipped.

9. The method of embodiment 1, wherein the step of combining the item to be shipped and the node further comprises embedding the node as part of a package for the item to be shipped.

10. The method of embodiment 1, wherein the step of combining the item to be shipped and the node further comprises securely fixing the node to an exterior surface of a package for the item to be shipped.

11. The method of embodiment 1 further comprising uploading the shipping information to the server.

12. The method of embodiment 11, wherein the uploading step further comprises transmitting the shipping information to the server to pre-associate the shipping information for the node with another node in the network related to a person that will handle a logistics transaction for the item to be shipped.

13. The method of embodiment 1 further comprising the step of fixing an external notification to a package for the item to be shipped, the external notification providing notice that the package is a node shipment.

14. A non-transitory computer-readable medium containing instructions which when executed on a processor performs a method for preparing a node-enabled shipment of an item to be shipped using a wireless node network having at least a node and a server, the method comprising: capturing an identification of the node to be related to the item by a user access device; receiving shipping information into the user access device, the shipping information being related to the item and the shipping information being linked with the identification of the node; storing the shipping information on the node; and issuing a message to combine the item to be shipped and the node.

15. The non-transitory computer-readable medium of embodiment 14, wherein the node comprises one from a group consisting of an ID node, a master node, and a sensor node.

16. The non-transitory computer-readable medium of embodiment 14, wherein the node comprises a mobile master node having at least one sensor onboard the master node for gathering environmental information about an environment near the master node.

17. The non-transitory computer-readable medium of embodiment 14, wherein the step of capturing the identification of the node further comprises detecting an electronic identification of the node.

18. The non-transitory computer-readable medium of embodiment 14, wherein the step of capturing the identification of the node further comprises viewing a readable identifier of the node.

19. The non-transitory computer-readable medium of embodiment 14, wherein the step of capturing the identification of the node further comprises scanning a machine-readable identifier of the node.

20. The non-transitory computer-readable medium of embodiment 14, wherein the method further comprises uploading the shipping information to the server.

21. The non-transitory computer-readable medium of embodiment 20, wherein the uploading step further comprises transmitting the shipping information to the server to pre-associate the shipping information for the node with another node in the network related to a person that will handle a logistics transaction for the item to be shipped.

22. A system for preparing a node-enabled shipment of an item to be shipped using a wireless node network, comprising: a node comprising a node processing unit, a node memory storage coupled to the node processing unit, the node memory storage maintaining code for execution by the node processing unit, and a communication interface coupled to the node processing unit and operative to communicate with a user access device; and a server is operative to communicate with the node via the communication interface; wherein the node processing unit, when executing the code maintained on the node memory storage, is operative to emit an identification of the node to be related to the item by a user access device, receive shipping information from a user access device, the shipping information being related to the item and the shipping information being linked with the identification of the node, and store the shipping information on the node when the node and the item to be shipped are combined for shipping.

23. The system of embodiment 22, wherein the node comprises one from a group consisting of an ID node, a master node, and a sensor node.

24. The system of embodiment 22, wherein the node comprises a mobile master node having at least one sensor onboard the master node for gathering environmental information about an environment near the master node.

25. The system of embodiment 22, wherein the identification of the node further comprises an electronic identification of the node emitted by a short-range transmission from the node.

26. The system of embodiment 22, wherein the node is further operative to upload the shipping information to the server.

27. The system of embodiment 26, wherein the uploading step further comprises transmitting the shipping information to the server to pre-associate the shipping information for the node with another node in the network related to a person that will handle a logistics transaction for the item to be shipped.

28. The system of embodiment 26, wherein the server is operative to receive the shipping information from the node.

29. The system of embodiment 22, wherein the server is operative to receive the shipping information from the user access device.

Further Embodiment 14—A Node-enabled Logistics Receptacle in a Wireless Node Network 1. A method for operating a node-enabled logistics receptacle in a wireless node network having at least a first node related to an item being shipped, the method comprising: detecting, by the node-enabled logistics receptacle, a signal broadcast by the first node; associating the node-enabled logistics receptacle with the first node; determining a location of the first node; and altering a current inventory of nodes related to the node-enabled logistics receptacle based upon the location of the first node.

2. The method of embodiment 1 further comprising detecting if the first node is left within a vicinity of the node-enabled logistics receptacle based on the location of the first node.

3. The method of embodiment 2, wherein the vicinity of the node-enabled logistics receptacle is an area sufficiently proximate to the node-enabled logistics receptacle to indicate an item and node within the vicinity intends to be shipped.

4. The method of embodiment 1 further comprising detecting if the first node is within the node-enabled logistics receptacle based on the location of the first node 5. The method of embodiment 2 further comprising detecting removal of the first node from the vicinity of the node-enabled logistics receptacle.

6. The method of embodiment 2 further comprising detecting removal of the first node from within the node-enabled logistics receptacle.

7. The method of embodiment 1, wherein the node-enabled logistics receptacle operates as a master node, and further comprising the step of directly updating a server by the node-enabled logistics receptacle when the current inventory of nodes changes.

8. The method of embodiment 1, wherein the node-enabled logistics receptacle operates as an ID node, and further comprising transferring to a master node one or more results collected by the node-enabled logistics receptacle listening to at least one other ID node.

9. The method of embodiment 1, wherein the node-enabled logistics receptacle operates as a sensor node, and further comprising the step of transmitting an environmental update on the interior condition of the node-enabled logistics receptacle to a master node in the network.

10. The method of embodiment 1 further comprising the steps of: tracking inventory metric information about when each of the nodes in the current inventory of nodes arrive and depart from within the node-enabled logistics receptacle; and causing the inventory metric information to be sent to the server.

11. The method of embodiment 1 further comprising instructing the first node by the node-enabled logistics receptacle to change an output power setting on the first node to a different power level when the location of the first node places the first node in a temporary custody of the node-enabled logistics receptacle.

12. The method of embodiment 11, wherein the step of instructing the first node by the node-enabled logistics receptacle to change the output power setting on the first node to the different power level comprises adjusting a broadcast setting of a broadcast profile for the first node.

13. The method of embodiment 1, wherein the node-enabled logistics receptacle is a secured access receptacle.

14. A non-transitory computer-readable medium containing instructions which when executed on a processor performs a method for operating a node-enabled logistics receptacle in a wireless node network having at least a first node related to an item being shipped, the method comprising: detecting, by the node-enabled logistics receptacle, a signal broadcast by the first node; associating the node-enabled logistics receptacle with the first node; determining a location of the first node; and altering a current inventory of nodes related to the node-enabled logistics receptacle based upon the location of the first node.

15. The non-transitory computer-readable medium of embodiment 14, wherein the method further comprises detecting if the first node is left within a vicinity of the node-enabled logistics receptacle based on the location of the first node.

16. The non-transitory computer-readable medium of embodiment 15, wherein the vicinity of the node-enabled logistics receptacle is an area sufficiently proximate to the node-enabled logistics receptacle to indicate an item and node within the vicinity intends to be shipped.

17. The non-transitory computer-readable medium of embodiment 14, wherein the method further comprises detecting if the first node is within the node-enabled logistics receptacle based on the location of the first node.

18. The non-transitory computer-readable medium of embodiment 15, wherein the method further comprises detecting removal of the first node from the vicinity of the node-enabled logistics receptacle.

19. The non-transitory computer-readable medium of embodiment 15, wherein the method further comprises detecting removal of the first node from within the node-enabled logistics receptacle.

20. The non-transitory computer-readable medium of embodiment 14, wherein the node-enabled logistics receptacle operates as a master node, and wherein the method further comprises the step of directly updating a server by the node-enabled logistics receptacle when the current inventory of nodes changes.

21. The non-transitory computer-readable medium of embodiment 14, wherein the node-enabled logistics receptacle operates as an ID node, and wherein the method further comprises transferring to a master node one or more results collected by the node-enabled logistics receptacle listening to at least one other ID node.

22. The non-transitory computer-readable medium of embodiment 14, wherein the node-enabled logistics receptacle operates as a sensor node, and wherein the method further comprises the step of transmitting an environmental update on the interior condition of the node-enabled logistics receptacle to a master node in the network.

23. The non-transitory computer-readable medium of embodiment 14, wherein the method further comprises the steps of: tracking inventory metric information about when each of the nodes in the current inventory of nodes arrive and depart from within the node-enabled logistics receptacle; and causing the inventory metric information to be sent to the server.

24. The non-transitory computer-readable medium of embodiment 14, wherein the further comprising instructing the first node by the node-enabled logistics receptacle to change an output power setting on the first node to a different power level when the location of the first node places the first node in a temporary custody of the node-enabled logistics receptacle.

25. The non-transitory computer-readable medium of embodiment 24, wherein the step of instructing the first node by the node-enabled logistics receptacle to change the output power setting on the first node to the different power level comprises adjusting a broadcast setting of a broadcast profile for the first node.

26. The non-transitory computer-readable medium of embodiment 14, wherein the node-enabled logistics receptacle is a secured access receptacle.

27. A node-enabled logistics receptacle assembly in a wireless node network, comprising: a receptacle having an entrance opening through which an item being shipped and a related node can pass and a storage area for maintaining the item being shipped and the related node; an embedded node assembled with the receptacle, the embedded node further comprising a node processing unit, a node memory storage coupled to the node processing unit, the node memory storage maintaining code for execution by the node processing unit and a current inventory of nodes related to the receptacle, and a communication interface coupled to the node processing unit and operative to communicate with a user access device; and wherein the node processing unit, when executing the code maintained on the node memory storage, is operative to detect a signal broadcast by the node related to the item being shipped, associate the node-enabled logistics receptacle with the node related to the item being shipped, determine a location of the node related to the item being shipped, and alter the current inventory of nodes in the node memory storage based upon the location of the node related to the item being shipped.

28. The node-enabled logistics receptacle assembly of embodiment 27, wherein the node processing unit is further operative to detect if the node related to the item being shipped is left within a vicinity of the receptacle based on the location of the node related to the item being shipped.

29. The node-enabled logistics receptacle assembly of embodiment 28, wherein the vicinity of the receptacle is an area sufficiently proximate to the receptacle to indicate the item being shipped intends to be dropped off and picked up from the receptacle as part of shipping.

30. The node-enabled logistics receptacle assembly of embodiment 27, wherein the node processing unit is further operative to detect if the node related to the item being shipped is within the receptacle based on the location of the node related to the item being shipped 31. The node-enabled logistics receptacle assembly of embodiment 28, wherein the node processing unit is further operative to detect removal of the node related to the item being shipped from the vicinity of the receptacle.

32. The node-enabled logistics receptacle assembly of embodiment 28, wherein the node processing unit is further operative to detect removal of the node related to the item being shipped from within the receptacle.

33. The node-enabled logistics receptacle assembly of embodiment 27, wherein the embedded node operates as a master node, and wherein the node processing unit is further operative to directly update a server when the current inventory of nodes changes.

34. The node-enabled logistics receptacle assembly of embodiment 27, wherein the embedded node operates as an ID node, and wherein the node processing unit is further operative to transfer one or more results to a master node, the results having been collected by the embedded node listening to at least one other ID node.

35. The node-enabled logistics receptacle assembly of embodiment 27, wherein the embedded node operates as a sensor node having one or more environmental sensors, and wherein the node processing unit is further operative to detect an interior condition of the receptacle using the one or more environmental sensors, and transmit an environmental update on the interior condition of the receptacle to a master node in the network.

36. The node-enabled logistics receptacle assembly of embodiment 27, wherein the node processing unit is further operative to: track inventory metric information about when each of the nodes in the current inventory of nodes arrive and depart from within the node-enabled logistics receptacle; and cause the inventory metric information to be sent to the server.

37. The node-enabled logistics receptacle assembly of embodiment 27, wherein the embedded node is integral to the receptacle.

38. The node-enabled logistics receptacle assembly of embodiment 27, wherein the embedded node is fixedly secured to the receptacle.

39. The node-enabled logistics receptacle assembly of embodiment 27, wherein the embedded node further comprises at least one sensor that monitors for a deposited package the custody of which is temporarily maintained by the node-enabled logistics receptacle assembly.

40. The node-enabled logistics receptacle assembly of embodiment 39, wherein the at least one sensor comprises at least one from a group comprising an internal sensor, an external sensor, and a door sensor.

41. The node-enabled logistics receptacle assembly of embodiment 27, wherein the node processing unit is further operative to instruct the first node to change an output power setting on the first node to a different power level when the location of the first node places the first node in a temporary custody of the node-enabled logistics receptacle.

42. The node-enabled logistics receptacle assembly of embodiment 41, wherein the node processing unit is further operative to instruct the first node to change the output power setting on the first node to the different power level by being operative to adjust a broadcast setting of a broadcast profile for the first node.

43. The node-enabled logistics receptacle assembly of embodiment 27, wherein the node-enabled logistics receptacle is a secured access receptacle.

Further Embodiment 15—Methods & Systems for Node-Enabled Shipment Merging for a Set of Items being Shipped 1. A method for shipment merging of a set of items being shipped using a wireless node network having a master node, a group of ID nodes, and a server, the method comprising: receiving, by the master node, ID node identification information from the server, the ID node identification information defining the group of ID nodes, each ID node from the group of ID nodes being related to a different item from the set of items being shipped; associating each of the ID nodes in the group of ID nodes with the master node when the master node detects a signal from each of the ID nodes in the group of ID nodes as each of the ID nodes in the group of ID nodes approaches the master node; transmitting a notification to the server by the master node when a last one of the ID nodes in the group of the ID nodes is detected to be approaching the master node; and receiving, by the master node, a shipment merge indication from the server.

2. The method of embodiment 1, wherein the received ID node identification information is part of shipping information related to the set of items being shipped.

3. The method of embodiment 1, wherein the master node is associated with a containment.

4. The method of embodiment 3, wherein the containment is a customs holding area.

5. The method of embodiment 3, wherein the shipment merge indication further comprises an authorization for the set of items to be released from the containment.

6. The method of embodiment 3 further comprising the steps of: generating an authorization prompt message by the master node, the authorization prompt requesting an authorization for the set of items to be released from the containment; transmitting the authorization prompt message by the master node to another network device in the wireless node network; and receiving the authorization in response to the authorization prompt message.

7. The method of embodiment 5, wherein the authorization for the set of items to be released from the containment comprises a customs clearance notification authorizing release of the set of items from the containment as a single merged shipment.

8. The method of embodiment 1, wherein the associating step further comprises establishing a passive association between the master node and each of the ID nodes in the group of ID nodes without requiring an authorized connection between the master node and each of the ID nodes in the group of ID nodes.

9. The method of embodiment 1, wherein the associating step further comprises establishing an active association between the master node and each of the ID nodes in the group of ID nodes, the active association reflecting an authorized connection between the master node and each of the ID nodes in the group of ID nodes.

10. The method of embodiment 3 further comprising the step of disassociating each of the ID nodes in the group of ID nodes from the master node after the master node determines a collective location of the group of ID nodes is outside a predetermined vicinity of the containment and after the master node receives the shipment merge indication.

11. The method of embodiment 3 further comprising the step of notifying the server when any of the ID nodes in the group of ID nodes are detected by the master node as being located outside of the containment after the master node receives the shipment merge indication.

12. The method of embodiment 1 further comprising instructing each of the ID nodes in the group of ID nodes to store customs information in a memory of the respective each of the ID nodes in the group of ID nodes.

13. The method of embodiment 7 further comprising instructing each of the ID nodes in the group of ID nodes to store the customs clearance notification in a memory of the respective each of the ID nodes in the group of ID nodes.

14. A non-transitory computer-readable medium containing instructions which when executed on a processor performs a method for shipment merging for a set of items being shipped using a wireless node network having at least a master node, a group of ID nodes, and a server, the method comprising: receiving, by the master node, ID node identification information from the server, the ID node identification information defining the group of ID nodes, each ID node from the group of ID nodes being related to a different item from the set of items being shipped; associating each of the ID nodes in the group of ID nodes with the master node when the master node detects a signal from each of the ID nodes in the group of ID nodes as each of the ID nodes in the group of ID nodes approaches the master node; transmitting a notification to the server by the master node when a last one of the ID nodes in the group of the ID nodes is detected to be approaching the master node; and receiving, by the master node, a shipment merge indication from the server.

15. The non-transitory computer-readable medium of embodiment 14, wherein the received ID node identification information is part of shipping information related to the set of items being shipped.

16. The non-transitory computer-readable medium of embodiment 14, wherein the master node is associated with a containment.

17. The non-transitory computer-readable medium of embodiment 16, wherein the containment is a customs holding area.

18. The non-transitory computer-readable medium of embodiment 16, wherein the shipment merge indication further comprises an authorization for the set of items to be released from the containment.

19. The non-transitory computer-readable medium of embodiment 16, wherein the method further comprises: generating an authorization prompt message by the master node, the authorization prompt requesting an authorization for the set of items to be released from the containment; transmitting the authorization prompt message by the master node to another network device in the wireless node network; and receiving the authorization in response to the authorization prompt message.

20. The non-transitory computer-readable medium of embodiment 18, wherein the authorization for the set of items to be released from the containment comprises a customs clearance notification authorizing release of the set of items from the containment as a single merged shipment.

21. The non-transitory computer-readable medium of embodiment 14, wherein the associating step further comprises establishing a passive association between the master node and each of the ID nodes in the group of ID nodes without requiring an authorized connection between the master node and each of the ID nodes in the group of ID nodes.

22. The non-transitory computer-readable medium of embodiment 14, wherein the associating step further comprises establishing an active association between the master node and each of the ID nodes in the group of ID nodes, the active association reflecting an authorized connection between the master node and each of the ID nodes in the group of ID nodes.

23. The non-transitory computer-readable medium of embodiment 16, wherein the method further comprises the step of disassociating each of the ID nodes in the group of ID nodes from the master node after the master node determines a collective location of the group of ID nodes is outside a predetermined vicinity of the containment and after the master node receives the shipment merge indication.

24. The non-transitory computer-readable medium of embodiment 16, wherein the method further comprises the step of notifying the server when any of the ID nodes in the group of ID nodes are detected by the master node as being located outside of the containment after the master node receives the shipment merge indication.

25. The non-transitory computer-readable medium of embodiment 14, wherein the method further comprises instructing each of the ID nodes in the group of ID nodes to store customs information in a memory of the respective each of the ID nodes in the group of ID nodes.

26. The non-transitory computer-readable medium of embodiment 20, wherein the method further comprises instructing each of the ID nodes in the group of ID nodes to store the customs clearance notification in a memory of the respective each of the ID nodes in the group of ID nodes.

27. A method for shipment merging for a set of items being shipped using a wireless node network having at least a master node, a group of ID nodes, and a server, the method comprising: receiving ID node identification information from the master node, the ID node identification information defining the group of ID nodes, each ID node from the group of ID nodes being related to a different item from the set of items being shipped; scanning, by one ID node of the group of ID nodes, for a neighboring node; detecting a signal from the neighboring node; determining if the detected neighboring node is part of the group of ID nodes based upon the signal broadcast from the neighboring node; as a last one of the ID nodes in the group of ID nodes is detected to be the neighboring node, notifying a master node to instruct the server that the last one of the ID nodes in the group of ID nodes is approaching the one ID node; and receiving a shipment merge indication from the master node.

28. The method of embodiment 27, wherein the received ID node identification information is part of shipping information related to the set of items being shipped.

29. The method of embodiment 27, wherein the master node is associated with a containment.

30. The method of embodiment 29, wherein the containment is a customs holding area.

31. The method of embodiment 29, wherein the shipment merge indication further comprises an authorization for the set of items to be released from the containment.

32. The method of embodiment 31, wherein the authorization for the set of items to be released from the containment comprises a customs clearance notification authorizing release of the set of items from the containment as a single merged shipment.

33. The method of embodiment 31 further comprising storing customs information in a memory of each of the ID nodes in the group of ID nodes.

34. A non-transitory computer-readable medium containing instructions which when executed on a processor performs a method for shipment merging for a set of items being shipped using a wireless node network having at least a master node, a group of ID nodes, and a server, the method comprising: receiving ID node identification information from the master node, the ID node identification information defining the group of ID nodes, each ID node from the group of ID nodes being related to a different item from the set of items being shipped; scanning, by one ID node of the group of ID nodes, for a neighboring node; detecting a signal from the neighboring node; determining if the detected neighboring node is part of the group of ID nodes based upon the signal broadcast from the neighboring node; as a last one of the ID nodes in the group of ID nodes is detected to be the neighboring node, notifying a master node to instruct the server that the last one of the ID nodes in the group of ID nodes is approaching the master node; and receiving a shipment merge indication from the master node.

35. The non-transitory computer-readable medium of embodiment 34, wherein the received ID node identification information is part of shipping information related to the set of items being shipped.

36. The non-transitory computer-readable medium of embodiment 34, wherein the master node is associated with a containment.

37. The non-transitory computer-readable medium of embodiment 36, wherein the containment is a customs holding area.

38. The non-transitory computer-readable medium of embodiment 36, wherein the shipment merge indication further comprises an authorization for the set of items to be released from the containment.

39. The non-transitory computer-readable medium of embodiment 38, wherein the authorization for the set of items to be released from the containment comprises a customs clearance notification authorizing release of the set of items from the containment as a single merged shipment.

40. The non-transitory computer-readable medium of embodiment 38, wherein the method further comprises storing customs information in a memory of each of the ID nodes in the group of ID nodes.

41. A system for shipment merging of a set of items being shipped using a wireless node network, comprising: a server; a master node operative to communicate with the server, the master node further comprising a node processing unit, a node memory storage coupled to the node processing unit, the node memory storage maintaining code for execution by the node processing unit and an identification of a group of ID nodes where each of the ID nodes in the group of ID nodes is related to a different item in the set of items being shipped, a first communication interface coupled to the node processing unit and operative to communicate with the group of ID nodes, a second communication interface coupled to the node processing unit and operative to communicate with the server; and wherein the node processing unit, when executing the code maintained on the node memory storage, is operative to receive ID node identification information from the server, the ID node identification information defining the group of ID nodes, each ID node from the group of ID nodes being related to a different item from the set of items being shipped, associate each of the ID nodes in the group of ID nodes with the master node when the master node detects a signal from each of the ID nodes in the group of ID nodes as each of the ID nodes in the group of ID nodes approaches the master node, cause the second communication interface to transmit a notification to the server when a last one of the ID nodes in the group of the ID nodes is detected to be approaching the master node, and receive a shipment merge indication from the server via the second communication interface.

42. The system of embodiment 41, wherein the received ID node identification information is part of shipping information related to the set of items being shipped.

43. The system of embodiment 41, wherein the master node is associated with a containment area.

44. The system of embodiment 43, wherein the containment area is a customs holding area.

45. The system of embodiment 43, wherein the shipment merge indication further comprises an authorization for the set of items to be released from the containment area.

46. The system of embodiment 43 wherein the node processing unit is further operative to: generate an authorization prompt message by the master node, the authorization prompt requesting an authorization for the set of items to be released from the containment; transmit the authorization prompt message by the master node to another network device in the wireless node network; and receive the authorization in response to the authorization prompt message.

47. The system of embodiment 45, wherein the authorization for the set of items to be released from the containment area comprises a customs clearance notification authorizing release of the set of items from the containment area as a single merged shipment.

48. The system of embodiment 41, wherein the node processing unit is further operative to establish a passive association between the master node and each of the ID nodes in the group of ID nodes without requiring an authorized connection between the master node and each of the ID nodes in the group of ID nodes.

49. The system of embodiment 41, wherein the node processing unit is further operative to establish an active association between the master node and each of the ID nodes in the group of ID nodes, the active association reflecting an authorized connection between the master node and each of the ID nodes in the group of ID nodes.

50. The system of embodiment 43, wherein the node processing unit is further operative to disassociate each of the ID nodes in the group of ID nodes from the master node after the master node determines a collective location of the group of ID nodes is outside a predetermined vicinity of the containment area and after the master node receives the shipment merge indication.

51. The system of embodiment 43, wherein the node processing unit is further operative to notify the server when any of the ID nodes in the group of ID nodes are detected by the master node as being located outside of the containment area after the master node receives the shipment merge indication.

52. The system of embodiment 41, wherein the node processing unit is further operative to instruct each of the ID nodes in the group of ID nodes to store customs information in a memory of the respective each of the ID nodes in the group of ID nodes.

53. The system of embodiment 47 further comprising instructing each of the ID nodes in the group of ID nodes to store the customs clearance notification in a memory of the respective each of the ID nodes in the group of ID nodes.

Further Embodiment 16—Node-Enabled Delivery Notification Using Elements of a Wireless Node Network 1. A method for delivery notification using a wireless node network having at least an ID node, a master node, and a server, the method comprising: detecting, by the master node, a signal from the ID node as the ID node approaches the master node located substantially near a delivery point, the ID node being related to an item being shipped; determining, by the master node, shipping information related to the ID node and an intended recipient of the item being shipped; and transmitting a notification from the master node to the identified recipient, the notification informing the intended recipient about the item being substantially near the delivery point.

2. The method of embodiment 1, wherein the ID node comprises another master node operating temporarily as an ID node.

3. The method of embodiment 1, wherein the delivery point comprises a designated package handling area.

4. The method of embodiment 1, wherein the delivery point comprises a logistics receptacle.

5. The method of embodiment 1 further comprising determining an identification of the ID node based upon the signal from the ID node, and wherein the step of determining the shipping information further comprises determining, by the master node, the shipping information based upon the identification of the ID node.

6. The method of embodiment 1, wherein the transmitting step further comprises: forwarding the notification to the server from the master node; and causing the server to send the notification to the intended recipient.

7. The method of embodiment 1, wherein the step of determining the shipping information further comprises: notifying the server that the master node and the ID node are associated; and receiving the shipping information by the master node from the server in response to notifying the server.

8. The method of embodiment 7, wherein the notifying step further comprises notifying the server that the master node has established a passive association with the ID node without requiring an authorized connection between the master node and ID node.

9. The method of embodiment 1, wherein the notifying step further comprises notifying the server that the master node has established an active association with the ID node reflecting an authorized connection between the master node and ID node.

10. The method of embodiment 1 further comprising determining, by the master node, that the ID node is within a predetermined range of the delivery point by instructing the ID node to alter an RF transmission power level as the ID node approaches the delivery point before transmitting the notification to the intended recipient.

11. A non-transitory computer-readable medium containing instructions which when executed on a processor performs a method for delivery notification using a wireless node network having at least an ID node, a master node, and a server, the method comprising: detecting, by the master node, a signal from the ID node as the ID node approaches the master node located substantially near a delivery point, the ID node being related to an item being shipped; determining, by the master node, shipping information related to the ID node and an intended recipient of the item being shipped; and transmitting a notification from the master node to the identified recipient, the notification informing the intended recipient about the item being substantially near the delivery point.

12. The non-transitory computer-readable medium of embodiment 11, wherein the ID node comprises another master node operating temporarily as an ID node.

13. The non-transitory computer-readable medium of embodiment 11, wherein the delivery point comprises a designated package handling area.

14. The non-transitory computer-readable medium of embodiment 11, wherein the delivery point comprises a logistics receptacle.

15. The non-transitory computer-readable medium of embodiment 11, wherein the method further comprises determining an identification of the ID node based upon the signal from the ID node, and wherein the step of determining the shipping information further comprises determining, by the master node, the shipping information based upon the identification of the ID node.

16. The non-transitory computer-readable medium of embodiment 11, wherein the transmitting step further comprises: forwarding the notification to the server from the master node; and causing the server to send the notification to the intended recipient.

17. The non-transitory computer-readable medium of embodiment 11, wherein the step of determining the shipping information further comprises: notifying the server that the master node and the ID node are associated; and receiving the shipping information by the master node from the server in response to notifying the server.

18. The non-transitory computer-readable medium of embodiment 17, wherein the notifying step further comprises notifying the server that the master node has established a passive association with the ID node without requiring a secure connection between the master node and ID node.

19. The non-transitory computer-readable medium of embodiment 11, wherein the notifying step further comprises notifying the server that the master node has established an active association with the ID node reflecting an authorized connection between the master node and ID node.

20. The non-transitory computer-readable medium of embodiment 11, wherein the method further comprises determining, by the master node, that the ID node is within a predetermined range of the delivery point by instructing the ID node to alter an RF transmission power level as the ID node approaches the delivery point before transmitting the notification to the intended recipient.

21. A master node for delivery notification using a wireless node network having at least an ID node and a server, comprising: a node processing unit, a node memory storage coupled to the node processing unit, the node memory storage maintaining code for execution by the node processing unit and shipping information related to the ID node and an item being shipped, and a first communication interface coupled to the node processing unit and operative to communicate with the ID node; a second communication interface coupled to the node processing unit and operative to communicate with the server; and wherein the node processing unit, when executing the code maintained on the node memory storage, is operative to: detect a signal from the ID node on the first communication interface as the ID node approaches the master node located substantially near a delivery point, the ID node being related to the item being shipped, access the node memory storage to determine the shipping information related to the ID node and an intended recipient of the item being shipped from the shipping information, and instruct the second communication interface to transmit a notification from the master node to the intended recipient, the notification informing the identified recipient about the item being substantially near the delivery point.

22. The master node of embodiment 21, wherein the ID node comprises another master node operating temporarily as an ID node.

23. The master node of embodiment 21, wherein the delivery point comprises a designated package handling area.

24. The master node of embodiment 21, wherein the delivery point comprises a logistics receptacle.

25. The master node of embodiment 21, wherein the node processing unit is further operative to determine an identification of the ID node based upon the signal from the ID node, and determine the shipping information based upon the identification of the ID node.

26. The master node of embodiment 21, wherein the node processing unit is further operative to: forward the notification to the server from the master node; and communicate an instruction to the server to cause the server to send the notification to the intended recipient.

27. The master node of embodiment 21, wherein the node processing unit is further operative to: notify the server that the master node and the ID node are associated; and receive the shipping information by the master node from the server in response to notifying the server.

28. The master node of embodiment 27, wherein the node processing unit is further operative to notify the server that the master node has established a passive association with the ID node without requiring an authorized connection between the master node and ID node.

29. The master node of embodiment 21, wherein the node processing unit is further operative to notify the server that the master node has established an active association with the ID node reflecting an authorized connection between the master node and ID node.

30. The master node of embodiment 21, wherein the node processing unit is further operative to determine that the ID node is within a predetermined range of the delivery point by instructing the ID node to alter an RF transmission power level as the ID node approaches the delivery point before transmitting the notification to the intended recipient.

31. The master node of embodiment 21, wherein the node processing unit is further operative to transmit the notification by being operative to instruct the second communication interface to transmit the notification from the master node to the server for forwarding to the intended receipt.

32. A method for delivery notification using a wireless node network having at least an ID node, a courier master node, a mobile delivery point master node, and a server, the method comprising: detecting, by the mobile delivery point master node, a signal from the ID node as the ID node approaches the mobile delivery point master node, the mobile delivery point master node being related to a mobile delivery point, the ID node being related to an item being shipped; determining, by the mobile delivery point master node, shipping information related to the ID node, an intended recipient of the item being shipped, and the courier master node currently associated with the ID node; transmitting location information by the mobile delivery point master node to the courier master node, wherein the location information comprises a current location of the mobile delivery point master node at the mobile delivery point; and transmitting a notification from the mobile delivery point master node to the identified recipient, the notification informing the intended recipient about the item being substantially near the mobile delivery point.

33. The method of embodiment 32 further comprising the steps of: associating the ID node and the mobile delivery point master node to acknowledge delivery of the item being shipped; and notifying the server by the mobile delivery point master node about the acknowledged delivery.

34. The method of embodiment 32 further comprising transmitting a subsequent notification from the mobile delivery point master node to the identified recipient, the subsequent notification informing the intended recipient that the item has been delivered to the mobile delivery point.

35. The method of embodiment 32, wherein the mobile delivery point comprises a vehicle, and wherein the transmitted location information further comprises context data related to the vehicle.

36. The method of embodiment 35, wherein the context data related to the vehicle comprises at least one of a vehicular identification, a vehicular color, a vehicular type, a vehicular model, a vehicular make, a parking level, and a parking space number.

37. The method of embodiment 35, wherein the vehicle is related to the intended recipient and is accessible by delivery personnel associated with the courier master node.

38. The method of embodiment 32 further comprising determining, by the mobile delivery point master node, an identification of the ID node based upon the detected signal from the ID node, and wherein the determining step further comprises determining the shipping information, the intended recipient, and the courier master node based upon the identification of the ID node.

39. The method of embodiment 32, wherein the step of transmitting the notification further comprises forwarding, by the mobile delivery point master node, the notification to the server to cause the server to send the notification to the intended recipient.

40. The method of embodiment 32, wherein the determining step further comprises: notifying the server that the mobile delivery point master node and the ID node are associated; and receiving, by the mobile delivery point master node, responsive information from the server about the shipping information, the intended recipient, and the courier master node currently associated with the ID node.

41. The method of embodiment 40, wherein the notifying step further comprises notifying the server that the mobile delivery point master node has established a passive association with the ID node without requiring an authorized connection between the mobile delivery point master node and ID node.

42. The method of embodiment 40, wherein the notifying step further comprises notifying the server that the mobile delivery point master node has established an active association with the ID node reflecting an authorized connection between the mobile delivery point master node and ID node.

43. The method of embodiment 32 further comprising determining, by the mobile delivery point master node, that the ID node is within a predetermined range of the mobile delivery point by instructing the ID node to alter an RF transmission power level as the ID node approaches the mobile delivery point before transmitting the notification to the intended recipient.

44. The method of embodiment 32 further comprising the step of transmitting updated location information by the mobile delivery point master node to the courier master node.

45. The method of embodiment 32 further comprising the step of transmitting a warning notification by the mobile delivery point master node to the courier master node if the ID node is determined, by the mobile delivery point master node, to be moving away from the mobile delivery point master node.

46. A non-transitory computer-readable medium containing instructions which when executed on a processor performs a method for delivery notification using a wireless node network having at least an ID node, a courier master node, a mobile delivery point master node, and a server, the method comprising: detecting, by the mobile delivery point master node, a signal from the ID node as the ID node approaches the mobile delivery point master node, the mobile delivery point master node being related to a mobile delivery point, the ID node being related to an item being shipped; determining, by the mobile delivery point master node, shipping information related to the ID node, an intended recipient of the item being shipped, and the courier master node currently associated with the ID node; transmitting location information by the mobile delivery point master node to the courier master node, wherein the location information comprises a current location of the mobile delivery point master node at the mobile delivery point; and transmitting a notification from the mobile delivery point master node to the identified recipient, the notification informing the intended recipient about the item being substantially near the mobile delivery point.

47. The non-transitory computer-readable medium of embodiment 46 further comprising the steps of: associating the ID node and the mobile delivery point master node to acknowledge delivery of the item being shipped; and notifying the server by the mobile delivery point master node about the acknowledged delivery.

48. The non-transitory computer-readable medium of embodiment 46 further comprising transmitting a subsequent notification from the mobile delivery point master node to the identified recipient, the subsequent notification informing the intended recipient that the item has been delivered to the mobile delivery point.

49. The non-transitory computer-readable medium of embodiment 46, wherein the mobile delivery point comprises a vehicle, and wherein the transmitted location information further comprises context data related to the vehicle.

50. The non-transitory computer-readable medium of embodiment 49, wherein the context data related to the vehicle comprises at least one of a vehicular identification, a vehicular color, a vehicular type, a vehicular model, a vehicular make, a parking level, and a parking space number.

51. The non-transitory computer-readable medium of embodiment 49, wherein the vehicle is related to the intended recipient and accessible by delivery personnel associated with the courier master node.

52. The non-transitory computer-readable medium of embodiment 46 further comprising determining, by the mobile delivery point master node, an identification of the ID node based upon the detected signal from the ID node, and wherein the determining step further comprises determining the shipping information, the intended recipient, and the courier master node based upon the identification of the ID node.

53. The non-transitory computer-readable medium of embodiment 46, wherein the step of transmitting the notification further comprises forwarding, by the mobile delivery point master node, the notification to the server to cause the server to send the notification to the intended recipient.

54. The non-transitory computer-readable medium of embodiment 46, wherein the determining step further comprises: notifying the server that the mobile delivery point master node and the ID node are associated; and receiving, by the mobile delivery point master node, responsive information from the server about the shipping information, the intended recipient, and the courier master node currently associated with the ID node.

55. The non-transitory computer-readable medium of embodiment 54, wherein the notifying step further comprises notifying the server that the mobile delivery point master node has established a passive association with the ID node without requiring an authorized connection between the mobile delivery point master node and ID node.

56. The non-transitory computer-readable medium of embodiment 54, wherein the notifying step further comprises notifying the server that the mobile delivery point master node has established an active association with the ID node reflecting an authorized connection between the mobile delivery point master node and ID node.

57. The non-transitory computer-readable medium of embodiment 45, wherein the method further comprises determining, by the mobile delivery point master node, that the ID node is within a predetermined range of the mobile delivery point by instructing the ID node to alter an RF transmission power level as the ID node approaches the mobile delivery point before transmitting the notification to the intended recipient.

58. The non-transitory computer-readable medium of embodiment 45, wherein the method further comprises the step of transmitting updated location information by the mobile delivery point master node to the courier master node.

59. The non-transitory computer-readable medium of embodiment 45, wherein the method further comprises the step of transmitting a warning notification by the mobile delivery point master node to the courier master node if the ID node is determined, by the mobile delivery point master node, to be moving away from the mobile delivery point master node.

60. A mobile delivery point master node for delivery notification using a wireless node network having at least an ID node, a courier master node, and a server, comprising: a node processing unit; a node memory storage coupled to the node processing unit, the node memory storage maintaining code for execution by the node processing unit, shipping information related to the ID node and an item being shipped, and identification information related to the courier master node currently associated with the ID node; a location circuitry coupled to the node processing unit and operative to generate location information related to the current location of the mobile delivery point master node; a first communication interface coupled to the node processing unit and operative to communicate with the ID node; a second communication interface coupled to the node processing unit and operative to communicate with the server; and wherein the node processing unit, when executing the code maintained on the node memory storage, is operative to: detect a signal from the ID node via the first communication interface as the ID node approaches the mobile delivery point master node, the mobile delivery point master node being related to a mobile delivery point, the ID node being related to an item being shipped, access the node memory storage to determine the shipping information related to the ID node, an intended recipient of the item being shipped, and the courier master node currently associated with the ID node, cause the location information to be transmitted to the courier master node, wherein the location information comprises a current location of the mobile delivery point master node at the mobile delivery point, and instruct the second communication interface to transmit a notification from the mobile delivery point master node to the identified recipient, the notification informing the intended recipient about the item being substantially near the mobile delivery point.

61. The mobile delivery point master node of embodiment 60, wherein the node processing unit is further operative to: associate the ID node and the mobile delivery point master node to acknowledge delivery of the item being shipped; and notify the server through the second communication interface about the acknowledged delivery.

62. The mobile delivery point master node of embodiment 60, wherein the node processing unit is further operative to instruct the second communication interface to transmit a subsequent notification to the identified recipient, the subsequent notification informing the intended recipient that the item has been delivered to the mobile delivery point.

63. The mobile delivery point master node of embodiment 60, wherein the mobile delivery point comprises a vehicle, and wherein the transmitted location information further comprises context data related to the vehicle.

64. The mobile delivery point master node of embodiment 63, wherein the context data related to the vehicle comprises at least one of a vehicular identification, a vehicular color, a vehicular type, a vehicular model, a vehicular make, a parking level, and a parking space number.

65. The mobile delivery point master node of embodiment 60, wherein the vehicle is related to the intended recipient and is accessible by delivery personnel associated with the courier master node.

66. The mobile delivery point master node of embodiment 60, wherein the node processing unit is further operative to: determine an identification of the ID node based upon the detected signal from the ID node; and determine the shipping information, the intended recipient, and the courier master node based upon the identification of the ID node.

67. The mobile delivery point master node of embodiment 60, wherein the node processing unit is further operative to cause the second communication interface to forward the notification to the server, which causes the server to send the notification to the intended recipient.

68. The mobile delivery point master node of embodiment 60, wherein the node processing unit is further operative to: cause the second communication interface to notify the server that the mobile delivery point master node and the ID node are associated; and receiving, via the second communication interface, responsive information from the server about the shipping information, the intended recipient, and the courier master node currently associated with the ID node.

69. The mobile delivery point master node of embodiment 68, wherein the node processing unit is further operative to cause the second communication interface to notify the server that the mobile delivery point master node has established a passive association with the ID node without requiring an authorized connection between the mobile delivery point master node and ID node.

70. The mobile delivery point master node of embodiment 68, wherein the node processing unit is further operative to cause the second communication interface to notify the server that the mobile delivery point master node has established an active association with the ID node reflecting an authorized connection between the mobile delivery point master node and ID node.

71. The mobile delivery point master node of embodiment 60, wherein the node processing unit is further operative to determine that the ID node is within a predetermined range of the mobile delivery point by transmitting a message over the first communication interface to the ID node, wherein the message causes the ID node to alter an RF transmission power level as the ID node approaches the mobile delivery point.

72. The mobile delivery point master node of embodiment 60, wherein the node processing unit is further operative to read updated location information from the location circuitry and to cause the first communication interface to transmit the updated location information to the courier master node.

73. The mobile delivery point master node of embodiment 60, wherein the node processing unit is further operative to cause a warning notification to be transmitted to the courier master node if the ID node is determined to be moving away from the mobile delivery point master node.

74. A method for delivery notification using a wireless node network having at least an ID node, a courier master node, a mobile delivery point master node, and a server, the method comprising: detecting, by the mobile delivery point master node, a signal from the ID node as the ID node approaches the mobile delivery point master node, the mobile delivery point master node being related to a mobile delivery point, the ID node being related to an item being shipped; determining, by the mobile delivery point master node, shipping information related to the ID node and the courier master node currently associated with the ID node; transmitting location information by the mobile delivery point master node to the courier master node, wherein the location information comprises a current location of the mobile delivery point master node at the mobile delivery point; and transmitting a notification from the mobile delivery point master node to an entity identified in the shipping information, the notification informing the identified entity about the item being substantially near the mobile delivery point.

75. The method of embodiment 74 further comprising transmitting a subsequent notification from the mobile delivery point master node to the identified entity, the subsequent notification informing the identified entity that the item has been delivered to the mobile delivery point.

76. The method of embodiment 74, wherein the mobile delivery point comprises a vehicle, and wherein the transmitted location information further comprises context data related to the vehicle.

77. The method of embodiment 76, wherein the context data related to the vehicle comprises at least one of a vehicular identification, a vehicular color, a vehicular type, a vehicular model, a vehicular make, a parking level, a parking area, and a parking space number.

78. The method of embodiment 74, wherein the identified entity comprises an entity related to the mobile delivery point.

79. The method of embodiment 78, wherein the identified entity related to the mobile delivery point further comprises at least one of a shipping entity for the item, a business entity related to the mobile delivery point, and an intended recipient of the item.

80. The method of embodiment 79, wherein the vehicle is unrelated to the intended recipient but is related to the business entity, and wherein the vehicle is accessible by delivery personnel associated with the courier master node.

81. The method of embodiment 79, wherein the vehicle is unrelated to the intended recipient at the time of delivery.

82. The method of embodiment 74, wherein the step of transmitting the notification further comprises forwarding, by the mobile delivery point master node, the notification to the server to cause the server to send the notification to the identified entity.

83. The method of embodiment 74, wherein the determining step further comprises: notifying the server that the mobile delivery point master node and the ID node are associated; and receiving, by the mobile delivery point master node, responsive information from the server about the shipping information and the courier master node currently associated with the ID node.

84. The method of embodiment 74 further comprising determining, by the mobile delivery point master node, that the ID node is within a predetermined range of the mobile delivery point by instructing the ID node to alter an RF transmission power level as the ID node approaches the mobile delivery point before transmitting the notification to the identified entity.

85. The method of embodiment 74 further comprising the step of transmitting updated location information by the mobile delivery point master node to the courier master node.

86. The method of embodiment 74 further comprising the step of transmitting a warning notification by the mobile delivery point master node to the courier master node if the ID node is determined, by the mobile delivery point master node, to be moving away from the mobile delivery point master node.

87. A non-transitory computer-readable medium containing instructions which when executed on a processor performs a method for delivery notification using a wireless node network having at least an ID node, a courier master node, a mobile delivery point master node, and a server, the method comprising: detecting, by the mobile delivery point master node, a signal from the ID node as the ID node approaches the mobile delivery point master node, the mobile delivery point master node being related to a mobile delivery point, the ID node being related to an item being shipped; determining, by the mobile delivery point master node, shipping information related to the ID node and the courier master node currently associated with the ID node; transmitting location information by the mobile delivery point master node to the courier master node, wherein the location information comprises a current location of the mobile delivery point master node at the mobile delivery point; and transmitting a notification from the mobile delivery point master node to an entity identified in the shipping information, the notification informing the identified entity about the item being substantially near the mobile delivery point.

88. The non-transitory computer-readable medium of embodiment 87 further comprising transmitting a subsequent notification from the mobile delivery point master node to the identified entity, the subsequent notification informing the identified entity that the item has been delivered to the mobile delivery point.

89. The non-transitory computer-readable medium of embodiment 87, wherein the mobile delivery point comprises a vehicle, and wherein the transmitted location information further comprises context data related to the vehicle.

90. The non-transitory computer-readable medium of embodiment 89, wherein the context data related to the vehicle comprises at least one of a vehicular identification, a vehicular color, a vehicular type, a vehicular model, a vehicular make, a parking level, a parking area, and a parking space number.

91. The non-transitory computer-readable medium of embodiment 87, wherein the identified entity comprises an entity related to the mobile delivery point.

92. The non-transitory computer-readable medium of embodiment 91, wherein the identified entity related to the mobile delivery point further comprises at least one of a shipping entity for the item, a business entity related to the mobile delivery point, and an intended recipient of the item.

93. The non-transitory computer-readable medium of embodiment 92, wherein the vehicle is unrelated to the intended recipient but is related to the business entity, and wherein the vehicle is accessible by delivery personnel associated with the courier master node.

94. The non-transitory computer-readable medium of embodiment 92, wherein the vehicle is unrelated to the intended recipient at the time of delivery.

95. The non-transitory computer-readable medium of embodiment 87, wherein the step of transmitting the notification further comprises forwarding, by the mobile delivery point master node, the notification to the server to cause the server to send the notification to the identified entity.

96. The non-transitory computer-readable medium of embodiment 87, wherein the determining step further comprises: notifying the server that the mobile delivery point master node and the ID node are associated; and receiving, by the mobile delivery point master node, responsive information from the server about the shipping information and the courier master node currently associated with the ID node.

97. The non-transitory computer-readable medium of embodiment 87 further comprising determining, by the mobile delivery point master node, that the ID node is within a predetermined range of the mobile delivery point by instructing the ID node to alter an RF transmission power level as the ID node approaches the mobile delivery point before transmitting the notification to the identified entity.

98. The non-transitory computer-readable medium of embodiment 87 further comprising the step of transmitting updated location information by the mobile delivery point master node to the courier master node.

99. The non-transitory computer-readable medium of embodiment 87 further comprising the step of transmitting a warning notification by the mobile delivery point master node to the courier master node if the ID node is determined, by the mobile delivery point master node, to be moving away from the mobile delivery point master node.

100. A mobile delivery point master node for delivery notification using a wireless node network having at least an ID node, a courier master node, and a server, comprising: a node processing unit; a node memory storage coupled to the node processing unit, the node memory storage maintaining code for execution by the node processing unit, shipping information related to the ID node and an item being shipped, and identification information related to the courier master node currently associated with the ID node; a location circuitry coupled to the node processing unit and operative to generate location information related to the current location of the mobile delivery point master node; a first communication interface coupled to the node processing unit and operative to communicate with the ID node; a second communication interface coupled to the node processing unit and operative to communicate with the server; and wherein the node processing unit, when executing the code maintained on the node memory storage, is operative to: detect a signal from the ID node via the first communication interface as the ID node approaches the mobile delivery point master node, the mobile delivery point master node being related to a mobile delivery point, the ID node being related to an item being shipped, access the node memory storage to determine the shipping information related to the ID node and the courier master node currently associated with the ID node, cause the location information to be transmitted to the courier master node, wherein the location information comprises a current location of the mobile delivery point master node at the mobile delivery point, and instruct the second communication interface to transmit a notification to an entity identified in the shipping information, the notification informing the identified entity about the item being substantially near the mobile delivery point.

101. The mobile delivery point master node of embodiment 100, wherein the node processing unit is further operative to instruct the second communication interface to transmit a subsequent notification to the identified entity, the subsequent notification informing the identified entity that the item has been delivered to the mobile delivery point.

102. The mobile delivery point master node of embodiment 100, wherein the mobile delivery point comprises a vehicle, and wherein the transmitted location information further comprises context data related to the vehicle.

103 The mobile delivery point master node of embodiment 102, wherein the context data related to the vehicle comprises at least one of a vehicular identification, a vehicular color, a vehicular type, a vehicular model, a vehicular make, a parking level, a parking area, and a parking space number.

104. The mobile delivery point master node of embodiment 100, wherein the identified entity comprises an entity related to the mobile delivery point.

105. The mobile delivery point master node of embodiment 104, wherein the identified entity related to the mobile delivery point further comprises at least one of a shipping entity for the item, a business entity related to the mobile delivery point, and an intended recipient of the item.

106. The mobile delivery point master node of embodiment 105, wherein the vehicle is unrelated to the intended recipient but is related to the business entity, and wherein the vehicle is accessible by delivery personnel associated with the courier master node.

107. The mobile delivery point master node of embodiment 105, wherein the vehicle is unrelated to the intended recipient at the time of delivery.

108. The mobile delivery point master node of embodiment 100, wherein the node processing unit is further operative to instruct the second communication interface to transmit the notification by causing the second communication interface to forward the notification to the server to cause the server to send the notification to the identified entity.

109. The mobile delivery point master node of embodiment 100, wherein the node processing unit is further operative to access the node memory storage to determine the shipping information related to the ID node and the courier master node currently associated with the ID node by being further operative to: cause the second communication interface to notify the server that the mobile delivery point master node and the ID node are associated; and receive responsive information through the second communication interface from the server about the shipping information and the courier master node currently associated with the ID node.

110. The mobile delivery point master node of embodiment 100, wherein the node processing unit is further operative to determine that the ID node is within a predetermined range of the mobile delivery point by sending an instruction to the ID node over the first communication interface before causing the second communication interface to transmit the notification to the identified entity, wherein the instruction causes the ID node to alter an RF transmission power level as the ID node approaches the mobile delivery point.

111. The mobile delivery point master node of embodiment 100, wherein the node processing unit is further operative to cause updated location information to be transmitted to the courier master node.

112. The mobile delivery point master node of embodiment 100, wherein the node processing unit is further operative to cause a warning notification to be transmitted to the courier master node if the node processing unit determines the ID node is moving away from the mobile delivery point master node.

Further Embodiment 17—Node-enabled Order pickup Using Elements of a Wireless Node Network 1. A method for pickup of an order using a wireless node network having at least a master node associated with a pickup point for the order, a mobile user access device operating as an advertising ID node, and a server, the method comprising: receiving, by the master node, order information from the server, the order information providing an identification of the order and an identification of the mobile user access device registered for the pickup of the order; detecting, by the master node, a signal broadcast from the mobile user access device identified by the order information when the mobile user access device is operating as an advertising ID node in the network and as the mobile user access device approaches the master node; associating the master node and the identified mobile user access device operating as the advertising ID node; and notifying, by the master node, an order management system responsible for the order, notification occurring when the master node determines a location of the identified mobile user access device operating as the advertising ID node to be within a predetermined range of the pickup point.

2. The method of embodiment 1, wherein the pickup point comprises a designated order fulfillment area in a facility.

3. The method of embodiment 1, wherein the identification of the mobile user access device appears in header information of the signal broadcast from the mobile user access device operating as the advertising ID node.

4. The method of embodiment 1, wherein the mobile user access device operating as the advertising ID node is one from a group comprising a laptop computer, a tablet device, a personal area network device, a smartphone device, and a smart wearable device.

5. The method of embodiment 1, wherein the associating step further comprises establishing a passive association between the master node and the identified mobile user access device operating as the advertising ID node without requiring an authorized connection between the master node and the identified mobile user access device operating as the advertising ID node.

6. The method of embodiment 1, wherein the associating step further comprises establishing an active association between the master node and the identified mobile user access device operating as the advertising ID node reflecting an authorized connection between the master node and the identified mobile user access device operating as the advertising ID node.

7. The method of embodiment 6, wherein the establishing step further comprises: determining, by the master node, when the identified mobile user access device operating as the advertising ID node is connectable; requesting, by the master node, authorization from the server to associate with the identified mobile user access device operating as the advertising ID node; and receiving, by the master node, the requested authorization from the server to allow the authorized connection between the master node and the identified mobile user access device operating as the advertising ID node.

8. The method of embodiment 1, wherein the notifying step further comprises transmitting a message from the master node to the server, wherein the message causes the server to notify the order management system that the identified mobile user device related to the order is approaching the pickup point to receive the order.

9. The method of embodiment 8 further comprising the steps of: receiving, by the master node, an order update message from the order management system, the order update message reflecting a status of the order; and transmitting, by the master node, a pickup status message to the identified mobile user access device operating as the advertising ID node, the pickup status message informing the identified mobile user access device of the status of the order.

10. The method of embodiment 9, wherein the step of transmitting the pickup status message further comprises transmitting, by the master node, the pickup status message to the identified mobile user access device operating as the advertising ID node, the pickup status message causing the identified mobile user access device operating as the advertising ID node to display a prompt on a user interface of the identified mobile user access device.

11. The method of embodiment 10, wherein the prompt is related to at least one from the group comprising picking up the order, validating that the order has been picked up, and paying for the order.

12. The method of embodiment 1, wherein the order is a print order.

13. The method of embodiment 12, wherein the print order is a 3D print order.

14. A non-transitory computer-readable medium containing instructions which when executed on a processor performs a method for pickup of an order using a wireless node network having at least a master node associated with a pickup point for the order, a mobile user access device operating as an advertising ID node, and a server, the method comprising: receiving, by the master node, order information from the server, the order information providing an identification of the order and an identification of the mobile user access device registered for the pickup of the order; detecting, by the master node, a signal broadcast from the mobile user access device identified by the order information when the mobile user access device is operating as an advertising ID node in the network and as the mobile user access device approaches the master node; associating the master node and the identified mobile user access device operating as the advertising ID node; and notifying, by the master node, an order management system responsible for the order, notification occurring when the master node determines a location of the identified mobile user access device operating as the advertising ID node to be within a predetermined range of the pickup point.

15. The non-transitory computer-readable medium of embodiment 14, wherein the pickup point comprises a designated order fulfillment area in a facility.

16. The non-transitory computer-readable medium of embodiment 14, wherein the identification of the mobile user access device appears in header information of the signal broadcast from the mobile user access device operating as the advertising ID node.

17. The non-transitory computer-readable medium of embodiment 14, wherein the mobile user access device operating as the advertising ID node is one from a group comprising a laptop computer, a tablet device, a personal area network device, a smartphone device, and a smart wearable device.

18. The non-transitory computer-readable medium of embodiment 14, wherein the associating step further comprises establishing a passive association between the master node and the identified mobile user access device operating as the advertising ID node without requiring an authorized connection between the master node and the identified mobile user access device operating as the advertising ID node.

19. The non-transitory computer-readable medium of embodiment 14, wherein the associating step further comprises establishing an active association between the master node and the identified mobile user access device operating as the advertising ID node reflecting an authorized connection between the master node and the identified mobile user access device operating as the advertising ID node.

20. The non-transitory computer-readable medium of embodiment 19, wherein the establishing step further comprises: determining, by the master node, when the identified mobile user access device operating as the advertising ID node is connectable; requesting, by the master node, authorization from the server to associate with the identified mobile user access device operating as the advertising ID node; and receiving, by the master node, the requested authorization from the server to allow the authorized connection between the master node and the identified mobile user access device operating as the advertising ID node.

21. The non-transitory computer-readable medium of embodiment 14, wherein the notifying step further comprises transmitting a message from the master node to the server, wherein the message causes the server to notify the order management system that the identified mobile user device related to the order is approaching the pickup point to receive the order.

22. The non-transitory computer-readable medium of embodiment 21, wherein the method further comprises the steps of: receiving, by the master node, an order update message from the order management system, the order update message reflecting a status of the order; and transmitting, by the master node, a pickup status message to the identified mobile user access device operating as the advertising ID node, the pickup status message informing the identified mobile user access device of the status of the order.

23. The non-transitory computer-readable medium of embodiment 22, wherein the step of transmitting the pickup status message further comprises transmitting, by the master node, the pickup status message to the identified mobile user access device operating as the advertising ID node, the pickup status message causing the identified mobile user access device operating as the advertising ID node to display a prompt on a user interface of the identified mobile user access device.

24. The non-transitory computer-readable medium of embodiment 23, wherein the prompt is related to at least one from the group comprising picking up the order, validating that the order has been picked up, and paying for the order.

25. The non-transitory computer-readable medium of embodiment 14, wherein the order is a print order.

26. The non-transitory computer-readable medium of embodiment 25, wherein the print order is a 3D print order.

27. A master node for pickup of an order at a pickup point using a wireless node network having at least a server and a mobile user access device operating as an advertising ID node, the master node comprising: a node processing unit; a node memory coupled to the node processing unit, the node memory storage maintaining code for execution by the node processing unit and order information having an identification of the order and an identification of the mobile user access device registered to pick up the order; a first communication interface coupled to the node processing unit and operative to communicate with the mobile user access device operating as an advertising ID node over a short-range communication path; a second communication interface coupled to the node processing unit and operative to communicate with the server over a longer-range communication path; and wherein the node processing unit, when executing the code maintained on the node memory, is operative to: receive the order information from the server and maintain the order information on the node memory, receive a signal detected by the first communication interface and broadcast from the mobile user access device when the mobile user access device is operating as an advertising ID node in the network, the signal being detected when the mobile user access device approaches the first communication interface, associate the master node and the identified mobile user access device operating as the advertising ID node, determine if a location of the identified mobile user access device operating as the advertising ID node is within a predetermined range of the pickup point, and transmit a message over the second communication interface to notify an order management system responsible for the order, the message being transmitted when the identified mobile user access device operating as the advertising ID node is determined to be within a predetermined range of the pickup point.

28. The master node of embodiment 27, wherein the master node is associated with a designated order fulfillment area as the pickup point for the order.

29. The master node of embodiment 27, wherein node processing unit is further operative to determine if the signal detected by the first communication interface is from the identified mobile user access device by analyzing header information of the signal broadcast from the mobile user access device operating as the advertising ID node.

30. The master node of embodiment 27, wherein the mobile user access device operating as the advertising ID node is one from a group comprising a laptop computer, a tablet device, a personal area network device, a smartphone device, and a smart wearable device.

31. The master node of embodiment 27, wherein node processing unit is further operative to associate the master node and the identified mobile user access device operating as the advertising ID node by being further operative to establish a passive association between the master node and the identified mobile user access device operating as the advertising ID node without requiring an authorized connection over the first communication interface between the master node and the identified mobile user access device operating as the advertising ID node.

32. The master node of embodiment 27, wherein node processing unit is further operative to associate the master node and the identified mobile user access device operating as the advertising ID node by being further operative to establish an active association between the master node and the identified mobile user access device operating as the advertising ID node reflecting an authorized connection over the first communication interface between the master node and the identified mobile user access device operating as the advertising ID node.

33. The master node of embodiment 32, wherein the node processing unit is further operative to establish the active association by being further operative to: determine when the identified mobile user access device operating as the advertising ID node is connectable; transmit an authorization request over the second communication interface to the server; and receive an authorization response from the server over the second communication interface to allow the authorized connection between the master node and the identified mobile user access device operating as the advertising ID node, the authorized connection using the first communication interface.

34. The master node of embodiment 27, wherein the node processing unit is further operative to transmit the message over the second communication interface to notify the order management system by being further operative to transmit an intermediate message to the server to cause the server to notify the order management system that the identified mobile user device related to the order is approaching the pickup point to receive the order.

35. The master node of embodiment 34, wherein the node processing unit is further operative to: receive an order update message from the order management system over the second communication interface, the order update message reflecting a status of the order; and transmit a pickup status message to the identified mobile user access device operating as the advertising ID node over the first communication interface, the pickup status message informing the identified mobile user access device of the status of the order.

36. The master node of embodiment 35, wherein the node processing unit is further operative to transmit the pickup status message by being operative to transmit the pickup status message to the identified mobile user access device operating as the advertising ID node, the pickup status message causing the identified mobile user access device operating as the advertising ID node to display a prompt on a user interface of the identified mobile user access device.

37. The master node of embodiment 36, wherein the prompt is related to at least one from the group comprising picking up the order, validating that the order has been picked up, and paying for the order.

38. The master node of embodiment 27, wherein the order is a print order.

39. The master node of embodiment 38, wherein the print order is a 3D print order.

Further Embodiment 18—Node-Enabled Management of Delivery of a Shipped Item Using Elements of a Wireless Node Network 1. A method for managing a delivery of an item being shipped using a wireless node network having at least an ID node related to the item being shipped, a mobile user access device operative to function as a master node, and a server, the method comprising: receiving, by the mobile user access device operative to function as the master node, shipping information from the server, the shipping information being related to the item being shipped and an identification of the ID node; detecting, by the mobile user access device operative to function as the master node, a signal broadcast from the ID node as the ID node comes within a communication range of the mobile user access device operative to function as the master node; associating the ID node and the mobile user access device operating as the master node to acknowledge the delivery of the item; and notifying the server by the mobile user access device operating as the master node, the notification being about the acknowledged delivery.

2. The method of embodiment 1, wherein the step of associating further comprises establishing a preauthorized connection between the ID node and the mobile user access device operating as the master node to acknowledge the delivery of the item.

3. The method of embodiment 2, wherein the establishing step further comprises establishing the preauthorized connection between the ID node and the mobile user access device operating as the master node to acknowledge the delivery of the item based upon a previously authorized acceptance condition that occurs automatically when the mobile user access device operating as the master node detects the signal broadcast as an advertising signal from the ID node.

4. The method of embodiment 2, wherein the establishing step further comprises establishing the preauthorized connection between the ID node and the mobile user access device operating as the master node to acknowledge the delivery of the item based upon a previously authorized acceptance condition that occurs automatically when the mobile user access device operating as the master node is located within a threshold distance from the ID node.

5. The method of embodiment 1, wherein the step of associating further comprises establishing a preauthorized connection between the ID node and the mobile user access device operating as the master node to acknowledge the delivery of the item for automatic payment on delivery purposes.

6. The method of embodiment 5 further comprising notifying the server by the mobile user access device operating as the master node, the notification indicating the successfully established preauthorized connection and instructing the server to complete a payment transaction related to the item being shipped at a rate charged lower than if an active prompted connection was established for payment on delivery purposes between the ID node and the mobile user access device operating as the master node.

7. The method of embodiment 1, wherein the step of associating further comprises establishing an active prompted connection between the ID node and the mobile user access device operating as the master node to acknowledge the delivery of the item after receiving a prompted acknowledgment of the delivery of the item.

8. The method of embodiment 1, wherein the step of associating further comprises establishing an active prompted connection for payment on delivery purposes between the ID node and the mobile user access device operating as the master node.

9. The method of embodiment 8 further comprising notifying the server by the mobile user access device operating as the master node, the notification indicating a successfully established active prompted connection for payment on delivery purposes and instructing the server to complete a payment transaction related to the item being shipped.

10. A non-transitory computer-readable medium containing instructions which when executed on a processor performs a method for managing a delivery of an item being shipped using a wireless node network having at least an ID node related to the item being shipped, a mobile user access device operative to function as a master node, and a server, the method comprising: receiving, by the mobile user access device operative to function as the master node, shipping information from the server, the shipping information being related to the item being shipped and an identification of the ID node; detecting, by the mobile user access device operative to function as the master node, a signal broadcast from the ID node as the ID node comes within a communication range of the mobile user access device operative to function as the master node; associating the ID node and the mobile user access device operating as the master node to acknowledge the delivery of the item; and notifying the server by the mobile user access device operating as the master node about the acknowledged delivery.

11. The non-transitory computer-readable medium of embodiment 10, wherein the step of associating further comprises establishing a preauthorized connection between the ID node and the mobile user access device operating as the master node to acknowledge the delivery of the item.

12. The non-transitory computer-readable medium of embodiment 11, wherein the establishing step further comprises establishing the preauthorized connection between the ID node and the mobile user access device operating as the master node to acknowledge the delivery of the item based upon a previously authorized acceptance condition that occurs automatically when the mobile user access device operating as the master node detects the signal broadcast as an advertising signal from the ID node.

13. The non-transitory computer-readable medium of embodiment 11, wherein the establishing step further comprises establishing the preauthorized connection between the ID node and the mobile user access device operating as the master node to acknowledge the delivery of the item based upon a previously authorized acceptance condition that occurs automatically when the mobile user access device operating as the master node is located within a threshold distance from the ID node.

14. The non-transitory computer-readable medium of embodiment 10, wherein the step of associating further comprises establishing a preauthorized connection between the ID node and the mobile user access device operating as the master node to acknowledge the delivery of the item for automatic payment on delivery purposes.

15. The non-transitory computer-readable medium of embodiment 14, wherein the method further comprises notifying the server by the mobile user access device operating as the master node, the notification indicating the successfully established preauthorized connection and instructing the server to complete a payment transaction related to the item being shipped at a rate charged lower than if an active prompted connection was established for payment on delivery purposes between the ID node and the mobile user access device operating as the master node.

16. The non-transitory computer-readable medium of embodiment 10, wherein the step of associating further comprises establishing an active prompted connection between the ID node and the mobile user access device operating as the master node to acknowledge the delivery of the item after receiving a prompted acknowledgment of the delivery of the item.

17. The non-transitory computer-readable medium of embodiment 10, wherein the step of associating further comprises establishing an active prompted connection for payment on delivery purposes between the ID node and the mobile user access device operating as the master node.

18. The non-transitory computer-readable medium of embodiment 17, wherein the method further comprises notifying the server by the master node, the notification indicating a successfully established active prompted connection for payment on delivery purposes and instructing the server to complete a payment transaction related to the item being shipped.

19. A system for managing a delivery of an item being shipped using a wireless node network, the system comprising: a server; and a master node in communication with the server, the master node further comprising: a node processing unit, a node memory coupled to the node processing unit, the node memory maintaining code for execution by the node processing unit and shipping information related to the item being shipped, the shipping information comprising an identification of an ID node related to the item being shipped, a first communication interface coupled to the node processing unit and operative to communicate with the ID node over a short-range communication path, and a second communication interface coupled to the node processing unit and operative to communicate with the server over a longer-range communication path; and wherein the node processing unit, when executing the code maintained on the node memory, is operative to: receive the shipping information from the server, receive a signal detected by the first communication interface and broadcast from the ID node, the signal being detected as the ID node comes within a communication range of the first communication interface, associate the ID node and the master node to acknowledge the delivery of the item, and transmit a message over the second communication interface to notify the server about the acknowledged delivery.

20. The system of embodiment 19, wherein the master node comprises a mobile user access device.

21. The system of embodiment 20, wherein the mobile user access device comprises one from the group comprising a laptop computer, a desktop computer, a tablet device, a personal area network device, a smartphone device, and a smart wearable device.

22. The system of embodiment 19, wherein the node processing unit is further operative to associate the ID node and the master node by being further operative to establish a preauthorized connection between the ID node and the master node to acknowledge the delivery of the item.

23. The system of embodiment 19, wherein the node processing unit is further operative to associate the ID node and the master node by being further operative to establish a preauthorized connection between the ID node and the master node to acknowledge the delivery of the item for automatic payment on delivery purposes.

24. The system of embodiment 19, wherein the node processing unit is further operative to associate the ID node and the master node by being further operative to establish an active prompted connection between the ID node and the master node to acknowledge the delivery of the item after the master node receives input from a user of the master node, the input being a prompted acknowledgment of the delivery of the item.

25. The system of embodiment 19, wherein the node processing unit is further operative to associate the ID node and the master node by being further operative to establish an active prompted connection for payment on delivery purposes between the ID node and the master node.

26. The system of embodiment 25, wherein the node processing unit is further operative to notify the server over the second communication interface, the notification indicating a successfully established active prompted connection for payment on delivery purposes and instructing the server to complete a payment transaction related to the item being shipped.

Further Embodiment 19—Contextual Based Adaptive Adjust of Node Power Level in a Wireless Node Network 1. A method for adaptive adjustment of node power level in a wireless node network having a plurality of nodes and a server, comprising: fixing, by the server, an output power setting on a first of the nodes to a first power level when the first node is located in a first area, the first power level corresponding to a density of the nodes operating within the first area; detecting, by the server, if the first node has moved to a second area; and adapting, by the server, the output power setting on the first node to a second power level when the first node is located in the second area, the second power level corresponding to a density of the nodes operating within the second area.

2. The method of embodiment 1, wherein the first power level corresponds to a density of those of the nodes operating within the first area that are scanning.

3. The method of embodiment 1 further comprising adapting, by a second of the nodes, an output power setting on the second node to the second power level based upon shared data received by the second node from the first node.

4. The method of embodiment 1, wherein the second power level is higher than the first power level when the density of the nodes operating within the second area is less than the density of the nodes operating within the first area.

5. The method of embodiment 1, wherein the second power level is lower than the first power level when the density of the nodes operating within the second area is greater than the density of the nodes operating within the first area.

6. The method of embodiment 1, wherein the detecting step further comprises tracking the location of the first node as the first node moves from within the first area to within the second area, and determining when the location of the first node has moved to within the second area.

7. The method of embodiment 1, wherein the detecting step comprises detecting, by the server, if the first node is anticipated to be moving from the first area to the second area.

8. The method of embodiment 7, wherein the detecting step further comprises detecting, by the server, if the first node is anticipated to be moving from the first area to the second area by accessing context data related to an expected transit path of the first node.

9. The method of embodiment 8 further comprising the step of predicting, by the server, at least a portion of a predicted path for the first node, wherein the portion of the predicted path comprises the expected transit path of the first node from the first area to the second area.

10. The method of embodiment 1, wherein the adapting step comprises adapting, by the server, the output power setting on the first node to the second power level when the first node is passing a point in the second area.

11. The method of embodiment 10 further comprising: accessing, by the server, context data related to the designated point in the second area to anticipate a density of the nodes expected to be operating within a proximate environment of the point; and updating, by the server, the output power setting on the first node to a third power level when the server detects the node is approaching the point in the second area, the third power level corresponding to the density of the nodes expected to be operating within the proximate environment of the point.

12. A non-transitory computer-readable medium containing instructions which when executed on a processor performs a method for adaptive adjustment of node power level in a wireless node network having a plurality of nodes and a server, the method comprising: fixing, by the server, an output power setting on a first of the nodes to a first power level when the first node is located in a first area, the first power level corresponding to a density of the nodes operating within the first area; detecting, by the server, if the first node has moved to a second area; and adapting, by the server, the output power setting on the first node to a second power level when the first node is located in the second area, the second power level corresponding to a density of the nodes operating within the second area 13. The non-transitory computer-readable medium of embodiment 12, wherein the first power level corresponds to a density of those of the nodes operating within the first area that are scanning.

14. The non-transitory computer-readable medium of embodiment 12, wherein the second power level is higher than the first power level when the density of the nodes operating within the second area is less than the density of the nodes operating within the first area.

15. The non-transitory computer-readable medium of embodiment 12, wherein the second power level is lower than the first power level when the density of the nodes operating within the second area is greater than the density of the nodes operating within the first area.

16. The non-transitory computer-readable medium of embodiment 12, wherein the detecting step further comprises tracking the location of the first node as the first node moves from within the first area to within the second area, and determining when the location of the first node has moved to within the second area.

17. The non-transitory computer-readable medium of embodiment 12, wherein the detecting step comprises detecting, by the server, if the first node is anticipated to be moving from the first area to the second area.

18. The non-transitory computer-readable medium of embodiment 17, wherein the detecting step further comprises detecting, by the server, if the first node is anticipated to be moving from the first area to the second area by accessing context data related to an expected transit path of the first node.

19. The non-transitory computer-readable medium of embodiment 18, wherein the method further comprises the step of predicting, by the server, at least a portion of a predicted path for the first node, wherein the portion of the predicted path comprises the expected transit path of the first node from the first area to the second area.

20. The non-transitory computer-readable medium of embodiment 12, wherein the adapting step comprises adapting, by the server, the output power setting on the first node to the second power level when the first node is passing a point in the second area.

21. The non-transitory computer-readable medium of embodiment 20, wherein the method further comprises: accessing, by the server, context data related to the designated point in the second area to anticipate a density of the nodes expected to be operating within a proximate environment of the point; and updating, by the server, the output power setting on the first node to a third power level when the server detects the node is approaching the point in the second area, the third power level corresponding to the density of the nodes expected to be operating within the proximate environment of the point.

22. An apparatus for adaptive adjustment of node power level in a wireless node network, the apparatus comprising: a processing unit; a memory coupled to the processing unit, the memory maintaining code for execution by the processing unit and operational node density information related to a first area and a second area; a communication interface coupled to the processing unit and operative to communicate with at least a first of a plurality of nodes in the network; and wherein the processing unit, when executing the code maintained on the memory, is operative to: fix an output power setting on a first of the nodes to a first power level when the first node is located in a first area, the first power level corresponding to a density of the nodes operating within the first area, detect if the first node has moved to a second area, adapt the output power setting to a second power level when the first node is located in the second area, the second power level corresponding to a density of the nodes operating within the second area, and transmit a message over the communication interface to the first node to update the output power setting on the first node to the second power level.

23. The apparatus of embodiment 22, wherein the first power level corresponds to a density of those of the nodes operating within the first area that are scanning.

24 The apparatus of embodiment 22, wherein the second power level is higher than the first power level when the density of the nodes operating within the second area is less than the density of the nodes operating within the first area.

25. The apparatus of embodiment 22, wherein the second power level is lower than the first power level when the density of the nodes operating within the second area is greater than the density of the nodes operating within the first area.

26. The apparatus of embodiment 22, wherein the processing unit is further operative to detect if the first node has moved to the second area by being operative to track the location of the first node as the first node moves from within the first area to within the second area, and determine when the location of the first node has moved to within the second area.

27. The apparatus of embodiment 22, wherein the processing unit is further operative to detect by being operative to detect if the first node is anticipated to be moving from the first area to the second area.

28. The apparatus of embodiment 27, wherein the memory further maintains context data related to an expected transit path of the first node; and wherein the processing unit is further operative to detect if the first node is anticipated to be moving from the first area to the second area by being operative to access the context data on the memory, and using the context data to determine if the first node is anticipated to be moving from the first area to the second area.

29. The apparatus of embodiment 28, wherein the processing unit is further operative to predict at least a portion of a predicted path for the first node, wherein the at least portion of the predicted path comprises the expected transit path of the first node from the first area to the second area.

30. The apparatus of embodiment 22, wherein the processing unit is operative to adapt by being further operative to adapt the output power setting on the first node to the second power level when the first node is passing a point in the second area.

31 The apparatus of embodiment 30, wherein the memory also maintains context data related to the designated point in the second area; and wherein the processing unit is further operative to: access the context data to anticipate a density of the nodes expected to be operating within a proximate environment of the point; and update the output power setting on the first node to a third power level when the server detects the node is approaching the point in the second area, the third power level corresponding to the density of the nodes expected to be operating within the proximate environment of the point.

32. A method for adaptive adjustment of node power level in a wireless node network having a plurality of nodes and a server, comprising: fixing, by a first of the nodes, an output power setting on the first of the nodes to a first power level when the first node is located in a first area, the first power level corresponding to a density of the nodes operating within the first area; detecting by the first node if the first node has moved to a second area; and adapting the output power setting on the first node by the first node to a second power level when the first node is located in the second area, the second power level corresponding to a density of the nodes operating within the second area.

33. The method of embodiment 32, wherein the first node is a mobile master node.

34. The method of embodiment 32, wherein the first power level corresponds to a density of those of the nodes operating within the first area that are scanning.

35. The method of embodiment 32 further comprising adapting, by a second of the nodes, an output power setting on the second node to the second power level based upon shared data received by the second node from the first node.

36. The method of embodiment 32, wherein the second power level is higher than the first power level when the density of the nodes operating within the second area is less than the density of the nodes operating within the first area.

37. The method of embodiment 32, wherein the second power level is lower than the first power level when the density of the nodes operating within the second area is greater than the density of the nodes operating within the first area.

38. The method of embodiment 32, wherein the detecting step further comprises tracking the location of the first node as the first node moves from within the first area to within the second area, and determining when the location of the first node has moved to within the second area.

39. The method of embodiment 32, wherein the detecting step comprises detecting, by the first node, if the first node is anticipated to be moving from the first area to the second area.

40. The method of embodiment 39, wherein the detecting step further comprises detecting, by the first node, if the first node is anticipated to be moving from the first area to the second area by accessing context data stored on the first node and related to an expected transit path of the first node.

Further Embodiment 20—Proximity Based Adaptive Adjustment of Node Power Level in a Wireless Node Network 1. A method for adaptive adjustment of node power level in a wireless node network having a plurality of nodes and a server, comprising: detecting, by the server, if a number of other nodes operating proximate a first of the nodes exceeds a threshold; and adapting, by the server, an output power setting on the first node from an original level to an adapted level when the number of other nodes operating proximate the first node exceeds the threshold.

2. The method of embodiment 1, wherein the number of other nodes operating proximate the first node comprises a number of other nodes operating within a first communication area around the first node.

3. The method of embodiment 2, wherein the first communication area around the first node is defined by a transmission range around the first node or by a reception range from the first node.

4. The method of embodiment 3, wherein the first communication area around the first node is defined by a first transmission range around the first node adjusted based upon context data related to an environment proximate the first node.

5. The method of embodiment 4, wherein the context data comprises information on anticipated signal degradation for a similar environment to the environment proximate the first node.

6. The method of embodiment 1, wherein the adapted level comprises an RF output signal level that is decreased relative to the original level based upon the extent the number of other nodes operating proximate the first node exceeds the threshold.

7. The method of embodiment 1 further comprising altering the output power setting to the original level when the server detects the number of other nodes operating proximate the first node no longer exceeds the threshold.

8. A non-transitory computer-readable medium containing instructions which when executed on a processor performs a method for adaptive adjustment of node power level in a wireless node network having a plurality of nodes and a server, the method comprising: detecting, by the server, if a number of other nodes operating proximate a first of the nodes exceeds a threshold; and adapting, by the server, an output power setting on the first node from an original level to an adapted level when the number of other nodes operating proximate the first node exceeds the threshold.

9. The non-transitory computer-readable medium of embodiment 8, wherein the number of other nodes operating proximate the first node comprises a number of other nodes operating within a first communication area around the first node.

10. The non-transitory computer-readable medium of embodiment 9, wherein the first communication area around the first node is defined by a transmission range around the first node or by a reception range from the first node.

11. The non-transitory computer-readable medium of embodiment 10, wherein the first communication area around the first node is defined by a first transmission range around the first node adjusted based upon context data related to an environment proximate the first node.

12. The non-transitory computer-readable medium of embodiment 11, wherein the context data comprises information on anticipated signal degradation for a similar environment to the environment proximate the first node.

13. The non-transitory computer-readable medium of embodiment 8, wherein the adapted level comprises an RF output signal level that is decreased relative to the original level based upon the extent the number of other nodes operating proximate the first node exceeds the threshold.

14. The non-transitory computer-readable medium of embodiment 8, wherein the method further comprises altering the output power setting to the original level when the server detects the number of other nodes operating proximate the first node no longer exceeds the threshold.

15. A server apparatus for adaptive adjustment of node power level in a wireless node network of a plurality of nodes, the apparatus comprising: a processing unit; a memory coupled to the processing unit, the memory maintaining code for execution by the processing unit and location data regarding the nodes; a communication interface coupled to the processing unit and operative to communicate with at least a first of the of nodes in the network; and wherein the processing unit, when executing the code maintained on the memory, is operative to: access the location data on the memory, identify how many of the nodes are operating proximate the first node based upon the location data, detect if the identified number of other nodes operating proximate the first node exceeds a threshold, and adapt an output power setting on the first node from an original level to an adapted level when the identified number of other nodes operating proximate the first node exceeds the threshold.

16. The apparatus of embodiment 15, wherein the number of nodes operating proximate the first node comprises a number of nodes operating within a first communication area around the first node.

17. The apparatus of embodiment 16, wherein the first communication area around the first node is defined by a transmission range around the first node or by a reception range from the first node.

18. The apparatus of embodiment 17, wherein the first communication area around the first node is defined by a first transmission range around the first node adjusted based upon context data related to an environment proximate the first node.

19. The apparatus of embodiment 18, wherein the context data comprises information on anticipated signal degradation for a similar environment to the environment proximate the first node.

20. The apparatus of embodiment 15, wherein the adapted level comprises an RF output signal level that is decreased relative to the original level based upon the extent the number of nodes operating proximate the first node exceeds the threshold.

21. The apparatus of embodiment 15, wherein the processing unit is further operative to transmit a message to the first node to alter the output power setting to the original level when the number of nodes operating proximate the first node no longer exceeds the threshold.

22. A master node apparatus for adaptive adjustment of node power level in a wireless node network of a plurality of other nodes and a server, the apparatus comprising: a master node processing unit; a master node memory coupled to the master node processing unit, the master node memory maintaining code for execution by the master node processing unit and location data regarding the other nodes; a first communication interface coupled to the master node processing unit and operative to communicate with at least a first of the of other nodes in the network; a second communication interface is operative to communicate with the server; and wherein the master node processing unit, when executing the code maintained on the memory, is operative to: receive a threshold setting from the server over the second communication interface, identify how many of the other nodes are operating proximate the first node, detect if the identified number of other nodes operating proximate the first node exceeds the received threshold setting, and adapt an output power setting on the first node from an original level to an adapted level when the identified number of other nodes operating proximate the first node exceeds the threshold.

23. The master node of embodiment 22, wherein the master node processing unit is further operative to access the location data on the master node memory, and identify how many of the other nodes are operating proximate the first node based upon the location data.

24. The master node of embodiment 22, wherein the number of other nodes operating proximate the first node comprises a number of other nodes operating within a first communication area around the first node.

25. The master node of embodiment 24, wherein the first communication area around the first node is defined by a transmission range around the first node or by a reception range from the first node.

26. The master node of embodiment 24, wherein the first communication area around the first node is defined by a first transmission range around the first node adjusted based upon context data related to an environment proximate the first node.

27. The master node of embodiment 25, wherein the context data comprises information on anticipated signal degradation for a similar environment to the environment proximate the first node.

28. The master node of embodiment 22, wherein the adapted level comprises an RF output signal level that is decreased relative to the original level based upon the extent the number of other nodes operating proximate the first node exceeds the threshold setting.

29. The master node of embodiment 22, wherein the master node processing unit is further operative to transmit a message to the first node over the first communication interface to alter the output power setting to the original level when the number of other nodes operating proximate the first node no longer exceeds the threshold setting.

30. A method for adaptive adjustment of node power level in a wireless node network having a plurality of nodes and a server, comprising: detecting, by the server, if a signal strength level near a first of the nodes exceeds a threshold; and adapting, by the server, an output power setting on the first node from an original level to an adapted level when the signal strength level near the first node exceeds the threshold.

31. The method of embodiment 30, wherein the adapted level comprises an RF output signal level that is decreased relative to the original level based upon the extent the detected signal strength exceeds the threshold.

32. The method of embodiment 30 further comprising altering the output power setting to the original level when the server detects the signal strength level no longer exceeds the threshold.

33. A method for adaptive adjustment of node power level in a wireless node network having a plurality of nodes and a server, comprising: detecting, by the server, if a first of the nodes is located in an RF restricted area; and adapting, by the server, an output power setting on the first node from an original level to an adapted level when the first node is located in the RF restricted area.

34. The method of embodiment 33 further comprising altering the output power setting to the original level when the server detects the first node is no longer located in the RF restricted area.

Further Embodiment 21—Magnetically Altered Operations of a Node in a Wireless Node Network 1. A method for magnetically altering an operation of a node in a wireless node network having a master node operative to communicate with a server, comprising: detecting, by the node, one or more magnetic field changes in a proximate environment of the node; altering, by the node, a management function of the node in response to the detected one or more magnetic field changes; and transmitting, by the node to the master node, information about the altered management function to be forwarded to the server.

2. The method of embodiment 1, wherein the one or more magnetic field changes comprises an increase in a magnetic field in the proximate environment to the node.

3. The method of embodiment 1, wherein the one or more magnetic field changes comprises a decrease in a magnetic field in the proximate environment to the node.

4. The method of embodiment 1, wherein the detecting step further comprises sensing an altered configuration of a magnetic switch integrated within the node.

5. The method of embodiment 1, wherein the altering step comprises changing, by the node, a power condition of the node in response to the detected one or more magnetic field changes.

6. The method of embodiment 5, wherein the step of changing the power condition of the node comprises selectively energizing the node from a power source by actuating a magnetic switch integrated into the node to enable powered operation of the node in response to the detected one or more magnetic field changes.

7. The method of embodiment 1, wherein the altered management function comprises overriding a power setting previously established in response to a server command.

8. The method of embodiment 1, wherein the altered management function comprises transmitting an alert.

9. The method of embodiment 8, wherein the step of transmitting the alert comprises transmitting, by the node to the master node, a movement alert and location information related to the node.

10. The method of embodiment 8, wherein the step of transmitting the alert further comprises transmitting the alert by the node to a predetermined set of nodes in the network defined by a filtering mode set by the server.

11. The method of embodiment 8, wherein the step of transmitting the alert further comprises transmitting the alert by the node to a predetermined set of nodes in the network that overrides a filtering mode set by the server.

12. The method of embodiment 1, wherein the altered management function comprises altering association data related to the node.

13. The method of embodiment 12, wherein the step of altering the association data related to the node comprises changing the association data to reflect a change in an inventory management aspect of an item related to the node.

14. The method of embodiment 13, wherein the step of changing the association data to reflect the change in the inventory management aspect of the item related to the node comprises changing the association data to indicate movement of the item related to the node.

15. The method of embodiment 1, wherein the altered management function comprises logging usage information for an item related to the node.

16. The method of embodiment 15, wherein the usage information comprises time-related data on when the item has been moved relative to a source of the magnetic field.

17. The method of embodiment 16, wherein the detecting step comprises detecting, by the node, the one or more magnetic field changes in the proximate environment to the node when the node has been separated from a placement support for the node, the placement support being the source of the magnetic field.

18. The method of embodiment 1, wherein the node is part of a placement support for a moveable object having a source of the magnetic field.

19. The method of embodiment 18, wherein the altered management function comprises logging usage information for the moveable object having the source of the magnetic field.

20. The method of embodiment 19, wherein the usage information comprises information related to time and location data.

21. The method of embodiment 1, wherein the detected one or more magnetic field changes in the proximate environment to the magnetically actuated node include a plurality of changes that collectively indicate the management function to alter.

22. The method of embodiment 21, wherein the plurality of changes further comprises a series of magnetic field changes over a period of time.

23. The method of embodiment 1, wherein the detected one or more magnetic field changes in the proximate environment to the magnetically actuated node include a detected pattern.

24. The method of embodiment 22, wherein the detecting step further comprises detecting, by a magnetic switch integrated within the magnetically actuated node, the series of magnetic field changes over the period of time.

25. A non-transitory computer-readable medium containing instructions which when executed on a processor performs a method for magnetically altering an operation of a node in a wireless node network having a master node operative to communicate with a server, the method comprising: detecting, by the node, one or more magnetic field changes in a proximate environment of the node; altering, by the node, a management function of the node in response to the detected one or more magnetic field changes; and transmitting, by the node to the master node, information about the altered management function to be forwarded to the server.

26. The non-transitory computer-readable medium of embodiment 25, wherein the one or more magnetic field changes comprises an increase in a magnetic field in the proximate environment to the node.

27. The non-transitory computer-readable medium of embodiment 25, wherein the one or more magnetic field changes comprises a decrease in a magnetic field in the proximate environment to the node.

28. The non-transitory computer-readable medium of embodiment 25, wherein the detecting step further comprises sensing an altered configuration of a magnetic switch integrated within the node.

29. The non-transitory computer-readable medium of embodiment 25, wherein the altering step comprises changing, by the node, a power condition of the node in response to the detected one or more magnetic field changes.

30. The non-transitory computer-readable medium of embodiment 29, wherein the step of changing the power condition of the node comprises selectively energizing the node from a power source by actuating a magnetic switch integrated into the node to enable powered operation of the node in response to the detected one or more magnetic field changes.

31. The non-transitory computer-readable medium of embodiment 25, wherein the altered management function comprises overriding a power setting previously established in response to a server command.

32. The non-transitory computer-readable medium of embodiment 25, wherein the altered management function comprises transmitting an alert.

33. The non-transitory computer-readable medium of embodiment 32, wherein the step of transmitting the alert comprises transmitting, by the node to the master node, a movement alert and location information related to the node.

34. The non-transitory computer-readable medium of embodiment 32, wherein the step of transmitting the alert further comprises transmitting the alert by the node to a predetermined set of nodes in the network defined by a filtering mode set by the server.

35. The non-transitory computer-readable medium of embodiment 32, wherein the step of transmitting the alert further comprises transmitting the alert by the node to a predetermined set of nodes in the network that overrides a filtering mode set by the server.

36. The non-transitory computer-readable medium of embodiment 25, wherein the altered management function comprises altering association data related to the node.

37. The non-transitory computer-readable medium of embodiment 36, wherein the step of altering the association data related to the node comprises changing the association data to reflect a change in an inventory management aspect of an item related to the node.

38. The non-transitory computer-readable medium of embodiment 37, wherein the step of changing the association data to reflect the change in the inventory management aspect of the item related to the node comprises changing the association data to indicate movement of the item related to the node.

39. The non-transitory computer-readable medium of embodiment 25, wherein the altered management function comprises logging usage information for an item related to the node.

40. The non-transitory computer-readable medium of embodiment 39, wherein the usage information comprises time-related data on when the item has been moved relative to a source of the magnetic field.

41. The non-transitory computer-readable medium of embodiment 40, wherein the detecting step comprises detecting, by the node, the one or more magnetic field changes in the proximate environment to the node when the node has been separated from a placement support for the node, the placement support being the source of the magnetic field.

42. The non-transitory computer-readable medium of embodiment 25, wherein the node is part of a placement support for a moveable object having a source of the magnetic field.

43. The non-transitory computer-readable medium of embodiment 42, wherein the altered management function comprises logging usage information for the moveable object having the source of the magnetic field.

44. The non-transitory computer-readable medium of embodiment 43, wherein the usage information comprises information related to time and location data.

45. The non-transitory computer-readable medium of embodiment 25, wherein the detected one or more magnetic field changes in the proximate environment to the magnetically actuated node include a plurality of changes that collectively indicate the management function to alter.

46. The non-transitory computer-readable medium of embodiment 45, wherein the plurality of changes further comprises a series of magnetic field changes over a period of time.

47. The non-transitory computer-readable medium of embodiment 46, wherein the detecting step further comprises detecting, by a magnetic switch integrated within the magnetically actuated node, the series of magnetic field changes over the period of time.

48. A magnetically actuated node in a wireless node network, the magnetically actuated node comprising: a node processing unit; a node memory coupled to the node processing unit, the node memory maintaining code for execution by the node processing unit; a first communication interface coupled to the node processing unit and operative to communicate over a first communication path with a master node in the network, the master node being in communication with a server in the network over a second communication path; a magnetic switch having an output coupled to the node processing unit, wherein control of the magnetic switch is responsive to one or more magnetic field changes in a proximate environment of the magnetically actuated node; a power source for selectively energizing the magnetically actuated node; and wherein the node processing unit, when executing the code maintained on the node memory, is operative to: alter a management function of the magnetically actuated node when the magnetically actuated switch responds to the one or more magnetic field changes and sends a response signal from the output of the magnetically actuated switch to the node processing unit, and transmit a message to the master node, the message comprising information about the altered management function to be forwarded to the server.

49. The magnetically actuated node of embodiment 48, wherein the one or more magnetic field changes comprises an increase in a magnetic field in the proximate environment to the magnetically actuated node.

50. The magnetically actuated node of embodiment 48, wherein the one or more magnetic field changes comprises a decrease in a magnetic field in the proximate environment to the magnetically actuated node.

51. The magnetically actuated node of embodiment 48, wherein the node processing unit is operative to alter the management function by being further operative to override a power setting previously established in response to a server command.

52. The magnetically actuated node of embodiment 48, wherein the node processing unit is operative to alter the management function by being further operative to transmit an alert to the master node.

53. The magnetically actuated node of embodiment 52, wherein the node processing unit is operative to transmit the alert by being further operative to transmit a node movement alert and node location information to the master node.

54. The magnetically actuated node of embodiment 52, wherein the node processing unit is operative to transmit the alert by being operative to transmit the alert to a predetermined set of other nodes in the network defined by a filtering mode set by the server.

55. The magnetically actuated node of embodiment 52, wherein the node processing unit is operative to transmit the alert by being operative to transmit the alert to a predetermined set of nodes in the network that overrides a filtering mode set by the server.

56. The magnetically actuated node of embodiment 48, wherein the node processing unit is operative to alter the management function by being further operative to alter association data related to the node and store the altered association data in the node memory.

57. The magnetically actuated node of embodiment 56, wherein the node processing unit is operative to alter the association data related to the node by being operative to change the association data to reflect a change in an inventory management aspect of an item related to the magnetically actuated node.

58. The magnetically actuated node of embodiment 57, wherein the node processing unit is operative to change the association data to reflect the change in the inventory management aspect of the item related to the node by being further operative to change the association data to indicate movement of the item related to the magnetically actuated node.

59. The magnetically actuated node of embodiment 48, wherein the node processing unit is operative to alter the management function by being further operative to record usage information in the node memory, the usage information being for an item related to the magnetically actuated node.

60. The magnetically actuated node of embodiment 59, wherein the usage information comprises time-related data on when the item has been moved relative to a source of the magnetic field.

61. The magnetically actuated node of embodiment 60, further comprising a placement support holder for the magnetically actuated node having the source of the magnetic field, wherein the one or more magnetic field changes in the proximate environment to the node occur when the node is separated from the placement support for the magnetically actuated node.

62. The magnetically actuated node of embodiment 48, wherein the magnetically actuated node is part of a placement support holder for a moveable object having a source of the magnetic field.

63. The magnetically actuated node of embodiment 62, wherein the node processing unit is operative to alter the management function by being further operative to record usage information in the node memory, the usage information being for the moveable object having the source of the magnetic field.

64. The magnetically actuated node of embodiment 63, wherein the usage information comprises information related to time-related and location-related data.

65. The magnetically actuated node of embodiment 48, wherein the node processing unit is operative to alter the management function by being further operative to identify a series of magnetic field changes as being related to the management function based upon assessing the output of the magnetic switch over a period of time.

66. The magnetically actuated node of embodiment 48, further comprising: a second communication interface coupled to the node processing unit and operative to communicate over the second communication path with the server; and location circuitry having an input coupled to an antenna and an output coupled to the node processing unit, the location circuitry being operative to receive one or more location signals in the input from the antenna and provide a determined location of the magnetically actuated node on the output to the node processing unit.

Further Embodiment 22—Methods and Apparatus for Adjusting a Broadcast Setting of a Node in a Wireless Node Network 1. A method for adjusting a broadcast setting of a node in a wireless node network having a master node and a server, comprising: detecting, by the master node, an advertising signal from the node; establishing, by the master node, an active association with the node; determining an updated value for the broadcast setting of the node; and adjusting, by the master node, the broadcast setting of the node from a current value to the updated value.

2. The method of embodiment 1, wherein the active association reflects a secure connection between the master node and node.

3. The method of embodiment 1, wherein the broadcast setting of the node comprises an RF transmission output power level setting.

4. The method of embodiment 1, wherein the broadcast setting of the node comprises a frequency setting.

5. The method of embodiment 1, wherein the broadcast setting of the node comprises a timing setting.

6. The method of embodiment 1, wherein the updated value comprises a predetermined value related to a structure, the structure being associated with the master node.

7. The method of embodiment 6, wherein the updated value further comprises a default broadcast value related to an interior of the structure, the structure being a shipping container associated with the master node.

8. The method of embodiment 1, wherein the node is an ID node capable of communicating directly with the master node but incapable of communicating directly with the server.

9. The method of embodiment 1, wherein the step of adjusting the broadcast setting of the node further comprises modifying a broadcast profile of the node, wherein the broadcast profile defines the broadcast setting used when the node communicates with the master node.

10. The method of embodiment 1, wherein the determining step comprises receiving the updated value from the server.

11. A non-transitory computer-readable medium containing instructions which when executed on a processor performs a method for adjusting a broadcast setting of a node in a wireless node network having a master node and a server, the method comprising: detecting, by the master node, an advertising signal from the node; establishing, by the master node, an active association with the node; determining an updated value for the broadcast setting of the node; and adjusting, by the master node, the broadcast setting of the node from a current value to the updated value.

12. The non-transitory computer-readable medium of embodiment 11, wherein the active association reflects a secure connection between the master node and node.

13. The non-transitory computer-readable medium of embodiment 11, wherein the broadcast setting of the node comprises an RF transmission output power level setting.

14. The non-transitory computer-readable medium of embodiment 11, wherein the broadcast setting of the node comprises a frequency setting.

15. The non-transitory computer-readable medium of embodiment 11, wherein the broadcast setting of the node comprises a timing setting.

16. The non-transitory computer-readable medium of embodiment 11, wherein the updated value comprises a predetermined value related to a structure, the structure being associated with the master node.

17. The non-transitory computer-readable medium of embodiment 16, wherein the updated value further comprises a default broadcast value related to an interior of the structure, the structure being a shipping container associated with the master node.

18. The non-transitory computer-readable medium of embodiment 11, wherein the node is an ID node capable of communicating directly with the master node but incapable of communicating directly with the server.

19. The non-transitory computer-readable medium of embodiment 11, wherein the step of adjusting the broadcast setting of the node further comprises modifying a broadcast profile of the node, wherein the broadcast profile defines the broadcast setting used when the node communicates with the master node.

20. The non-transitory computer-readable medium of embodiment 11, wherein the determining step comprises receiving the updated value from the server.

21. A master node for adjusting a broadcast setting of a node in a wireless node network, the master node comprising: a processing unit; a memory coupled to the processing unit, the memory maintaining code for execution by the processing unit and an updated value for the broadcast setting of the node; a first communication interface coupled to the processing unit and operative to communicate with the node in the network; a second communication interface coupled to the processing unit and operative to communicate with a server in the network; and wherein the processing unit, when executing the code maintained on the memory, is operative to: detect that the first communication interface receives an advertising signal from the node, establish an active association with the node and store association data on the memory to reflect the active association between the master node and the node, access the updated value from the memory, and transmit a message to the node over the first communication interface, the message instructing the node to adjust a current value of the broadcast setting of the node to the updated value.

22. The master node of embodiment 21, wherein the broadcast setting of the node comprises an RF transmission output power level setting.

23. The master node of embodiment 21, wherein the broadcast setting of the node comprises a frequency setting.

24. The master node of embodiment 21, wherein the broadcast setting of the node comprises a timing setting.

25. The master node of embodiment 21, wherein the updated value comprises a predetermined value related to a structure, the structure being associated with the master node.

26. The master node of embodiment 25, wherein the updated value further comprises a default broadcast value related to an interior of the structure, the structure being a shipping container associated with the master node.

27. The master node of embodiment 21, wherein the node is an ID node operative to communicate directly with the master node over the first communication interface but incapable of communicating directly with the server.

28. The master node of embodiment 21, wherein the processing unit is further operative to receive the updated value from the server over the second communication interface.

29. The master node of embodiment 21, wherein the processing unit is further operative to modify a broadcast profile of the node, wherein the broadcast profile defines the broadcast setting used when the node communicates with the master node; and wherein the processing unit is further operative to transmit the message by being operative to transmit information to the node over the first communication interface, wherein the transmitting information reflecting the modified broadcast profile.

Further Embodiment 23—Methods and Apparatus for Enhanced Power Notification in a Wireless Node Network 1. A method for enhanced power notification from an ID node in a wireless node network having a master node and a server, comprising: detecting, by the ID node, a current power status for the ID node, the ID node being capable of communicating directly with the master node but incapable of communicating directly with the server; determining a current location of the ID node; and broadcasting, by the ID node, an enhanced power alert notification when the current power status of the ID node is below a threshold, the enhanced power alert notification indicating that the current power status of the ID node is below the threshold and including the current location of the ID node.

2. The method of embodiment 1, wherein the enhanced power alert notification further comprises a request for a replacement power source for the ID node.

3. The method of embodiment 1, wherein the enhanced power alert notification further comprises a request to recharge an existing power source in the ID node.

4. The method of embodiment 1 further comprising the step of assigning an alert level based upon the current power status for the ID node, and wherein the broadcasting step comprises broadcasting, by the ID node, the enhanced power alert notification when the current power status of the ID node is below the threshold, the enhanced power alert notification indicating that the current power status of the ID node is below the threshold and including at least the current location of the ID node and the assigned alert level.

5. The method of embodiment 4, wherein the assigned alert level instructs the master node to take a responsive action when the master node receives the broadcasted enhanced power alert notification, wherein the responsive action depends on the assigned alert level.

6. The method of embodiment 5, wherein the assigned alert level instructs the master node to notify the server after the master node receives the broadcasted enhanced power alert notification.

7. The method of embodiment 6, wherein the assigned alert level instructs the master node to notify the server about the current location of the ID node and the assigned alert level after the master node receives the broadcasted enhanced power alert notification.

8. The method of embodiment 1 further comprising the step of receiving, by the ID node, an alert response from the master node, the alert response changing a broadcast setting for the ID node.

9. The method of embodiment 1 further comprising prioritizing one or more operations within the ID node to conserve power when the current power status of the ID node is below the threshold.

10. The method of embodiment 1, wherein the threshold comprises a value based upon context data related to the ID node.

11. The method of embodiment 10, wherein the threshold comprises a value based upon context data related to a shipment journey status for the node.

12. A non-transitory computer-readable medium containing instructions which when executed on a processor performs a method for enhanced power notification from an ID node in a wireless node network having a master node and a server, the method comprising: detecting, by the ID node, a current power status for the ID node, the ID node being capable of communicating directly with the master node but incapable of communicating directly with the server; determining a current location of the ID node; and broadcasting, by the ID node, an enhanced power alert notification when the current power status of the ID node is below a threshold, the enhanced power alert notification indicating that the current power status of the ID node is below the threshold and including the current location of the ID node.

13. The non-transitory computer-readable medium of embodiment 12, wherein the enhanced power alert notification further comprises a request for a replacement power source for the ID node.

14. The non-transitory computer-readable medium of embodiment 12, wherein the enhanced power alert notification further comprises a request to recharge an existing power source in the ID node.

15. The non-transitory computer-readable medium of embodiment 12, wherein the method further comprises the step of assigning an alert level based upon the current power status for the ID node, and wherein the broadcasting step comprises broadcasting, by the ID node, the enhanced power alert notification when the current power status of the ID node is below the threshold, the enhanced power alert notification indicating that the current power status of the ID node is below the threshold and including at least the current location of the ID node and the assigned alert level.

16. The non-transitory computer-readable medium of embodiment 15, wherein the assigned alert level instructs the master node to take a responsive action when the master node receives the broadcasted enhanced power alert notification, wherein the responsive action depends on the assigned alert level.

17. The non-transitory computer-readable medium of embodiment 16, wherein the assigned alert level instructs the master node to notify the server after the master node receives the broadcasted enhanced power alert notification.

18. The non-transitory computer-readable medium of embodiment 17, wherein the assigned alert level instructs the master node to notify the server about the current location of the ID node and the assigned alert level after the master node receives the broadcasted enhanced power alert notification.

19. The non-transitory computer-readable medium of embodiment 12, wherein the method further comprises the step of receiving, by the ID node, an alert response from the master node, the alert response changing a broadcast setting for the ID node.

20. The non-transitory computer-readable medium of embodiment 12, wherein the method further comprises prioritizing one or more operations within the ID node to conserve power when the current power status of the ID node is below the threshold.

21. The non-transitory computer-readable medium of embodiment 12, wherein the threshold comprises a value based upon context data related to the ID node.

22. The non-transitory computer-readable medium of embodiment 21, wherein the threshold comprises a value based upon context data related to a shipment journey status for the node.

23. A network device in a wireless node network, the node comprising: a processing unit; a memory coupled to the processing unit, the memory maintaining code for execution by the processing unit; a short-range communication interface coupled to the processing unit and operative to communicate with another network device in the network; a power source coupled to the processing unit and providing power for the network device; and wherein the processing unit, when executing the code maintained on the memory, is operative to: detect a current power status of the power source, determine a current location of the network device, and broadcast an enhanced power alert notification over the short-range communication interface when the current power status of the power source is below a threshold, the enhanced power alert notification indicating that the current power status of the power source is below the threshold and including the current location of the network device.

24. The network device of embodiment 23, wherein the processing unit is operative to communicate directly with a master node in the wireless node network over the short-range communication interface but unable to communicate directly with a server in the wireless node network.

25. The network device of embodiment 23 further comprising a longer-range communication interface coupled to the processing unit and be operative to communicate with a server in the wireless node network.

26. The network device of embodiment 25 further comprising location circuitry coupled to the processing unit and operative to receive at least one location signal and provide the current location of the network device to the processing unit as part of determining the current location of the network device.

27. The network device of embodiment 23, wherein the processing unit is operative to determine the current location of the network device by accessing data maintained on the memory, the data representing the current location of the network device.

28. The network device of embodiment 23, wherein the enhanced power alert notification further comprises a request for a replacement power source for the network device.

29. The network device of embodiment 23, wherein the enhanced power alert notification further comprises a request to recharge an existing power source in the network device.

30. The network device of embodiment 23, wherein the processing unit is further operative to assign an alert level based upon the detected current power status of the power source, and wherein the processing unit is further operative to broadcast the enhanced power alert notification when the current power status is below the threshold, wherein the enhanced power alert notification indicating that the current power status is below the threshold and including at least the current location of the network device and the assigned alert level.

31. The network device of embodiment 23, wherein the processing unit is further operative to receive an alert response from another network device over the short-range communication interface, the alert response changing a broadcast setting for the network device.

32. The network device of embodiment 23, wherein the processing unit is further operative to prioritizing one or more operations of the network device to conserve power consumption within the network device when the current power status is below the threshold.

33. The network device of embodiment 23, wherein the threshold comprises a value based upon context data related to the ID node.

34. The network device of embodiment 33, wherein the threshold comprises a value based upon context data related to a shipment journey status for the node.

Further Embodiment 24—Methods and Apparatus for Monitoring a Conveyance Coupling Connection Using Elements of a Wireless Node Network 1. A method for monitoring at least one signal passing through a coupling connection from a first conveyance to a second conveyance, the coupling connection having a network device that communicates on a wireless node network, comprising: monitoring, by the network device, the at least one signal line passing through the coupling connection from the first conveyance to the second conveyance; detecting, by the network device, data on the monitored signal line; recording, by the network device, the detected data; and transmitting, by the network device, the detected data to another entity in the wireless network.

2. The method of embodiment 1, wherein the network device is an ID node operative to communicate directly with a master node in the wireless network but not operative to communicate directly with a server in the wireless node network; and wherein the another entity is the server.

3. The method of embodiment 1, wherein the network device is a master node operative to communicate directly with a server in the wireless node network; and wherein the another entity is the server.

4. The method of embodiment 1, wherein the coupling connection comprises a mated set of connectors; and wherein the network device is integrated into one of the mated connectors from the coupling connection.

5. The method of embodiment 1, wherein the coupling connection comprises an adapter, the adapter being disposed between a mated set of coupling connectors, wherein the network device is integrated as part of the adapter.

6. The method of embodiment 1, wherein the first conveyance comprises a vehicle and the second conveyance comprises a trailer.

7. The method of embodiment 6, wherein the coupling connection comprises an adapter, the adapter being disposed between a mated set of anti-lock braking system connectors linking the vehicle to the trailer.

8. The method of embodiment 1, wherein the first conveyance comprises a first railway vehicle and the second conveyance comprises a second railway vehicle.

9. The method of embodiment 1, wherein the first conveyance comprises a maritime conveyance and the second conveyance comprises a maritime barge.

10. The method of embodiment 1 further comprising receiving power for the network device from a power line passing through the coupling connection.

11. The method of embodiment 1 further comprising detecting, by the network device, when the first conveyance and the second conveyance are disconnected based upon the monitored status of the at least one signal line.

12. The method of embodiment 11, wherein the step of transmitting further comprises providing, by the network device, a message to a server in the wireless network, the message comprising the recorded data and a notification that the first conveyance and the second conveyance are disconnected.

13. The method of embodiment 1, wherein the detecting step further comprises detecting, by the network device, a change in state for the coupling connection.

14. The method of embodiment 13, wherein the change in state for the coupling connection reflects a change in power flowing from the first conveyance to the second conveyance.

15. The method of embodiment 13, wherein the change in state for the coupling connection reflects a changed RF environment detected by the network device.

16. A non-transitory computer-readable medium containing instructions which when executed on a processor performs a method for monitoring at least one signal passing through a coupling connection from a first conveyance to a second conveyance, the coupling connection having a network device that communicates on a wireless node network, the method comprising: monitoring, by the network device, the at least one signal line passing through the coupling connection from the first conveyance to the second conveyance; detecting, by the network device, data on the monitored signal line; recording, by the network device, the detected data; and transmitting, by the network device, the detected data to another entity in the wireless network.

17. The non-transitory computer-readable medium of embodiment 16, wherein the network device is an ID node operative to communicate directly with a master node in the wireless network but not operative to communicate directly with a server in the wireless node network; and wherein the another entity is the server.

18. The non-transitory computer-readable medium of embodiment 16, wherein the network device is a master node operative to communicate directly with a server in the wireless node network; and wherein the another entity is the server.

19. The non-transitory computer-readable medium of embodiment 16, wherein the coupling connection comprises a mated set of connectors; and wherein the network device is integrated into one of the mated connectors from the coupling connection.

20. The non-transitory computer-readable medium of embodiment 16, wherein the coupling connection comprises an adapter, the adapter being disposed between a mated set of coupling connectors, wherein the network device is integrated as part of the adapter.

21. The non-transitory computer-readable medium of embodiment 16, wherein the first conveyance comprises a vehicle and the second conveyance comprises a trailer.

22. The non-transitory computer-readable medium of embodiment 21, wherein the coupling connection comprises an adapter, the adapter being disposed between a mated set of anti-lock braking system connectors linking the vehicle to the trailer.

23. The non-transitory computer-readable medium of embodiment 16, wherein the first conveyance comprises a first railway vehicle and the second conveyance comprises a second railway vehicle.

24. The non-transitory computer-readable medium of embodiment 16, wherein the first conveyance comprises a maritime conveyance and the second conveyance comprises a maritime barge.

25. The non-transitory computer-readable medium of embodiment 16, wherein the method further comprises receiving power for the network device from a power line passing through the coupling connection.

26. The non-transitory computer-readable medium of embodiment 16, wherein the method further comprises detecting, by the network device, when the first conveyance and the second conveyance are disconnected based upon the monitored status of the at least one signal line.

27. The non-transitory computer-readable medium of embodiment 26, wherein the step of transmitting further comprises providing, by the network device, a message to a server in the wireless network, the message comprising the recorded data and a notification that the first conveyance and the second conveyance are disconnected.

28. The non-transitory computer-readable medium of embodiment 16, wherein the detecting step further comprises detecting, by the network device, a change in state for the coupling connection.

29. The non-transitory computer-readable medium of embodiment 28, wherein the change in state for the coupling connection reflects a change in power flowing from the first conveyance to the second conveyance.

30. The non-transitory computer-readable medium of embodiment 28, wherein the change in state for the coupling connection reflects a changed RF environment detected by the network device.

31. An apparatus for monitoring at least one signal passing from a first conveyance to a second conveyance, the apparatus comprising: a coupling connection providing a communication path for the at least one signal passing between the first conveyance and the second conveyance; and a network device disposed within the coupling connection and in connection with the at least one signal, the network device further comprising, a processing unit, a memory coupled to the processing unit, the memory maintaining code for execution by the processing unit, a communication interface coupled to the processing unit and operative to communicate with another network device in a wireless node network, and a signal monitor circuit having an input and output, wherein the input is coupled to the at least one signal line passing through the coupling connection on the communication path between the first conveyance and the second conveyance, and the output provides detected data from the at least one signal line to the processing unit; and wherein the processing unit of the network device, when executing the code maintained on the memory, is operative to: monitor the detected data provided from the signal monitor circuit, record the detected data to the memory for sharing with the another network device in the wireless node network, and transmit the recorded data over the communication interface to the another network device in the wireless network.

32. The network device of embodiment 31, wherein the communication interface of the network device is a short-range communication interface; and wherein the processing unit of the network device is further operative to communicate directly with a master node as the another network device in the wireless node network over the short-range communication interface but unable to communicate directly with a server in the wireless node network.

33. The network device of embodiment 31, wherein the network device further comprises a longer-range communication interface coupled to the processing unit and being operative to communicate with a server as the another network device in the wireless node network.

34. The network device of embodiment 31, wherein the network device is integrated as part of the coupling connection.

35. The network device of embodiment 31, wherein the coupling connection comprises an adapter, the adapter being disposed between a mated set of coupling connectors, wherein the network device is integrated as part of the adapter.

36. The network device of embodiment 31, wherein the first conveyance comprises a vehicle and the second conveyance comprises a trailer.

37. The network device of embodiment 36, wherein the coupling connection further comprises an adapter, the adapter being disposed between a mated set of anti-lock braking system connectors linking the vehicle to the trailer.

38. The network device of embodiment 31, wherein the first conveyance comprises a first railway vehicle and the second conveyance comprises a second railway vehicle.

39. The network device of embodiment 31, wherein the first conveyance comprises a maritime conveyance and the second conveyance comprises a maritime barge.

40. The network device of embodiment 31, wherein the network device is connected to a power line passing through the coupling connection.

41. The network device of embodiment 31, wherein the processing unit is further operative to detect when the first conveyance and the second conveyance are disconnected based upon a monitored status of the at least one signal line from the signal monitor circuit.

42. The network device of embodiment 41, wherein processing unit is further operative to transmit by being operative to provide a message to a server in the wireless network over the communication interface, the message comprising the recorded data and a notification that the first conveyance and the second conveyance are disconnected.

43. The network device of embodiment 31, wherein the processing unit is further operative to detect a change in state for the coupling connection.

44. The network device of embodiment 43, wherein the change in state for the coupling connection reflects a change in power flowing from the first conveyance to the second conveyance.

45. The network device of embodiment 43, wherein the change in state for the coupling connection reflects a changed RF environment detected by the network device.

Further Embodiment 25—Node-Enabled Sharing of Shipment Condition Information in a Wireless Node Network 1. A method for sharing shipment condition information in a wireless node network having a plurality of network devices and a server, comprising: detecting, by a first node, an advertising signal broadcast from a second node, the first node being a first of the network devices and related to a first package, the second node being a second of the network devices and related to a second package; associating the first node and the second node; accessing, by the first node, the shipment condition information from a memory in the first node; and transmitting, by the first node, the shipment condition information to the second node if the first node is authorized to share the shipment condition information with the second node.

2. The method of embodiment 1 further comprising receiving, by the first node, the shipment condition information from another of the network devices in the network and storing the shipment condition information on the memory in the first node.

3. The method of embodiment 1 further comprising receiving, by the first node, the shipment condition information from the server, and storing the shipment condition information on the memory in the first node.

4. The method of embodiment 1 further comprising receiving, by the first node, the shipment condition information from a master node as the another of the network devices in the network, and storing the shipment condition information on the memory in the first node.

5. The method of embodiment 1 further comprising receiving, by the first node, the shipment condition information from a sensor, and storing the shipment condition information on the memory in the first node.

6. The method of embodiment 1, wherein the accessing step further comprises accessing, by the first node, the shipment condition information as pre-staged information stored in the memory in the first node.

7. The method of embodiment 1, wherein the shipment condition information comprises environmental information about a physically proximate environment to the first node.

8. The method of embodiment 1, wherein the shipment condition information comprises environmental information about an environment anticipated to be proximate the first node.

9. The method of embodiment 7, wherein the environmental information comprises at least one from a group consisting of light, temperature, humidity, pressure, altitude, magnetic field strength, acceleration, vibration, impact, and orientation.

10. The method of embodiment 1, wherein the shipment condition information comprises location information about the first node.

11. The method of embodiment 1, wherein the shipment condition information comprises updated system information.

12. The method of embodiment 1, wherein the transmitting step further comprises transmitting, by the first node, the shipment condition information to the second node if the first node was pre-authorized to share the shipment condition information with the second node.

13. The method of embodiment 1, wherein the transmitting step comprising transmitting, by the first node, the shipment condition information to the second node if the first node was pre-authorized to share a designated type of shipment condition information with the second node and the shipment condition information accessed is the designated type of shipment condition information.

14. The method of embodiment 1 further comprising setting, by the first node, a status flag to indicate the first node has shipment condition information to be shared.

15. The method of embodiment 14, wherein the status flag comprises information in an advertising signal broadcast by the first node.

16. The method of embodiment 15 further comprising receiving, by the first node, a request from the second node in response to the advertising signal broadcast by the first node, the request asking for the first node to directly share the shipment condition information with the second node without requesting the shipment condition information from the server.

17. A non-transitory computer-readable medium containing instructions which when executed on a processor performs a method for sharing shipment condition information in a wireless node network having a plurality of network devices and a server, the method comprising: detecting, by a first node, an advertising signal broadcast from a second node, the first node being a first of the network devices and related to a first package, the second node being a second of the network devices and related to a second package; associating the first node and the second node; accessing, by the first node, the shipment condition information from a memory in the first node; and transmitting, by the first node, the shipment condition information to the second node if the first node is authorized to share the shipment condition information with the second node.

18. The non-transitory computer-readable medium of embodiment 17, wherein the method further comprises receiving, by the first node, the shipment condition information from another of the network devices in the network and storing the shipment condition information on the memory in the first node.

19. The non-transitory computer-readable medium of embodiment 17, wherein the method further comprises receiving, by the first node, the shipment condition information from the server, and storing the shipment condition information on the memory in the first node.

20. The non-transitory computer-readable medium of embodiment 17, wherein the method further comprises receiving, by the first node, the shipment condition information from a master node as the another of the network devices in the network, and storing the shipment condition information on the memory in the first node.

21. The non-transitory computer-readable medium of embodiment 17, wherein the method further comprises receiving, by the first node, the shipment condition information from a sensor, and storing the shipment condition information on the memory in the first node.

22. The non-transitory computer-readable medium of embodiment 17, wherein the accessing step further comprises accessing, by the first node, the shipment condition information as pre-staged information stored in the memory in the first node.

23. The non-transitory computer-readable medium of embodiment 17, wherein the shipment condition information comprises environmental information about a physically proximate environment to the first node.

24. The non-transitory computer-readable medium of embodiment 17, wherein the shipment condition information comprises environmental information about an environment anticipated to be proximate the first node.

25. The non-transitory computer-readable medium of embodiment 23, wherein the environmental information comprises at least one from a group consisting of light, temperature, humidity, pressure, altitude, magnetic field strength, acceleration, vibration, impact, and orientation.

26. The non-transitory computer-readable medium of embodiment 17, wherein the shipment condition information comprises location information about the first node.

27. The non-transitory computer-readable medium of embodiment 17, wherein the shipment condition information comprises updated system information.

28. The non-transitory computer-readable medium of embodiment 17, wherein the transmitting step further comprises transmitting, by the first node, the shipment condition information to the second node if the first node was pre-authorized to share the shipment condition information with the second node.

29. The non-transitory computer-readable medium of embodiment 17, wherein the transmitting step comprising transmitting, by the first node, the shipment condition information to the second node if the first node was pre-authorized to share a designated type of shipment condition information with the second node and the shipment condition information accessed is the designated type of shipment condition information.

30. The non-transitory computer-readable medium of embodiment 17, wherein the method further comprises setting, by the first node, a status flag to indicate the first node has shipment condition information to be shared.

31. The non-transitory computer-readable medium of embodiment 30, wherein the status flag comprises information in an advertising signal broadcast by the first node.

32. The non-transitory computer-readable medium of embodiment 31, wherein the method further comprises receiving, by the first node, a request from the second node in response to the advertising signal broadcast by the first node, the request asking for the first node to directly share the shipment condition information with the second node without requesting the shipment condition information from the server.

33. A method for requesting shared shipment condition information in a wireless node network having a plurality of network devices and a server, comprising: detecting, by a second node, an advertising signal broadcast from a first node, the first node being a first of the network devices and related to a first package, the second node being a second of the network devices and related to a second package; determining, by the second node, that the first node has the shipment condition information to share based upon status information in the advertising signal broadcast from the first node; associating the first node and the second node; transmitting a request, by the second node, for the shipment condition information if the status information indicates the first node has the shipment condition information to share; and receiving, by the second node, the shipment condition information from the first node if the first node is authorized to share the shipment condition information with the second node.

34. The method of embodiment 33, wherein the shipment condition information was generated by the first node.

35. The method of embodiment 34, wherein the shipment condition information comprises sensor data generated by the first node.

36. The method of embodiment 33, wherein the shipment condition information was generated by the server and provided to the first node.

37. The method of embodiment 33, wherein the shipment condition information comprises pre-staged data stored on a memory of the first node.

38. The method of embodiment 33, wherein the shipment condition information comprises environmental information about a physically proximate environment to the first node.

39. The method of embodiment 33, wherein the shipment condition information comprises environmental information about an environment anticipated to be proximate the first node.

40. The method of embodiment 38, wherein the environmental information comprises at least one from a group consisting of light, temperature, humidity, pressure, altitude, magnetic field strength, acceleration, vibration, impact, and orientation.

41. The method of embodiment 33, wherein the shipment condition information comprises location information about the first node.

42. The method of embodiment 33, wherein the shipment condition information comprises updated system information.

43. The method of embodiment 33, wherein the receiving step further comprises receiving, by the second node, the shipment condition information from the first node if the first node was pre-authorized to share the shipment condition information with the second node.

44. The method of embodiment 33, wherein the receiving step further comprises receiving, by the second node, the shipment condition information from the first node if the first node was pre-authorized to share a designated type of shipment condition information with the second node and the shipment condition information requested is the designated type of shipment condition information.

45. A non-transitory computer-readable medium containing instructions which when executed on a processor performs a method for requesting shared shipment condition information in a wireless node network having a plurality of network devices and a server, the method comprising: detecting, by a second node, an advertising signal broadcast from a first node, the first node being a first of the network devices and related to a first package, the second node being a second of the network devices and related to a second package; determining, by the second node, that the first node has the shipment condition information to share based upon status information in the advertising signal broadcast from the first node; associating the first node and the second node; transmitting a request, by the second node, for the shipment condition information if the status information indicates the first node has the shipment condition information to share; and receiving, by the second node, the shipment condition information from the first node if the first node is authorized to share the shipment condition information with the second node.

46. The non-transitory computer-readable medium of embodiment 45, wherein the shipment condition information was generated by the first node.

47. The non-transitory computer-readable medium of embodiment 46, wherein the shipment condition information comprises sensor data generated by the first node.

48. The non-transitory computer-readable medium of embodiment 45, wherein the shipment condition information was generated by the server and provided to the first node.

49. The non-transitory computer-readable medium of embodiment 45, wherein the shipment condition information comprises pre-staged data stored on a memory of the first node.

50. The non-transitory computer-readable medium of embodiment 45, wherein the shipment condition information comprises environmental information about a physically proximate environment to the first node.

51. The non-transitory computer-readable medium of embodiment 45, wherein the shipment condition information comprises environmental information about an environment anticipated to be proximate the first node.

52. The non-transitory computer-readable medium of embodiment 50, wherein the environmental information comprises at least one from a group consisting of light, temperature, humidity, pressure, altitude, magnetic field strength, acceleration, vibration, impact, and orientation.

53. The non-transitory computer-readable medium of embodiment 45, wherein the shipment condition information comprises location information about the first node.

54. The non-transitory computer-readable medium of embodiment 45, wherein the shipment condition information comprises updated system information.

55. The non-transitory computer-readable medium of embodiment 45, wherein the receiving step further comprises receiving, by the second node, the shipment condition information from the first node if the first node was pre-authorized to share the shipment condition information with the second node.

56. The non-transitory computer-readable medium of embodiment 45, wherein the receiving step further comprises receiving, by the second node, the shipment condition information from the first node if the first node was pre-authorized to share a designated type of shipment condition information with the second node and the shipment condition information requested is the designated type of shipment condition information.

57. A system for sharing shipment condition information in a wireless node network, the system comprising: a first node in the wireless node network, the first node being related to a first package being shipped, the first node further comprising a first processing unit, a first memory coupled to the processing unit, the first memory maintaining first code for execution by the first processing unit and the shipment condition information, and a first communication interface coupled to the first processing unit; and a second node in the wireless node network, the second node being related to a second package being shipped, the second package further comprising a second processing unit, a second memory coupled to the second processing unit, the second memory maintaining second code for execution by the second processing unit, and a second communication interface coupled to the second processing unit and operative to communicate with the first node over the first communication interface; and wherein the first processing unit of the first node, when executing the first code maintained on the first memory, is operative to: access the shipment condition information on the first memory, broadcast an advertising signal over the first communication interface, the advertising signal including status information on whether the first node has the shipment condition information to share, receive a request from the second node over the first communication interface, the request asking for the shipment condition information, associate the first node and the second node, and transmit the shipment condition information to the second node over the first communication interface if the first node is authorized to share the shipment condition information with the second node; and wherein the second processing unit of the second node, when executing the second code maintained on the second memory, is operative to detect the advertising signal broadcast from the first node, determine that the first node has the shipment condition information to share based upon the status information in the advertising signal broadcast from the first node, transmit the request for the shipment condition information to the first node over the second communication interface if the status information indicates the first node has the shipment condition information to share, and receive the shipment condition information from the first node when the first node is authorized to share the shipment condition information with the second node.

58. The system of embodiment 57, wherein first node further comprises a sensor coupled to the first processing unit, the sensor generating sensor data as the shipment condition information maintained in the first memory.

59. The system of embodiment 58, wherein the shipment condition information comprises sensor data.

60. The system of embodiment 57, wherein first processing unit is further operative to receive the shipment condition information from a server in the wireless node network.

61. The system of embodiment 57, wherein the shipment condition information maintained on the first memory comprises pre-staged data.

62. The system of embodiment 57, wherein the shipment condition information comprises environmental information about a proximate environment to the first node.

63. The system of embodiment 62, wherein the environmental information comprises at least one from a group consisting of light, temperature, humidity, pressure, altitude, magnetic field strength, acceleration, vibration, impact, and orientation.

64. The system of embodiment 57, wherein the shipment condition information comprises environmental information about a physically proximate environment to the first node.

65. The system of embodiment 57, wherein the shipment condition information comprises environmental information about an environment anticipated to be proximate the first node.

66. The system of embodiment 57, wherein the shipment condition information comprises location information about the first node.

67. The system of embodiment 57, wherein the shipment condition information comprises updated system information.

68. The system of embodiment 57, wherein the first processing unit is further operative to receive an authorization from a server in the wireless node network, the authorization permitting the first node to share the shipment condition information with the second node.

69. The system of embodiment 57, wherein the first processing unit is further operative to transmit the shipment condition information to the second unit over the first communication interface if the first node was pre-authorized to share the shipment condition information with the second node.

70. The system of embodiment 57, wherein the first processing unit is further operative to transmit the shipment condition information to the second unit over the first communication interface if the first node was pre-authorized to share a designated type of shipment condition information with the second node and the shipment condition information accessed in the first memory is the designated type of shipment condition information.

Further Embodiment 26—Methods & Systems for Managing Shipment of an Item Using a Wireless Node Network 1. A method for creating a hierarchical sensor network for a grouped set of packages being shipped, the hierarchical sensor network using a wireless node network having a mobile master node, an ID node and a server, comprising: associating, by the server, the mobile master node with one of the packages in the grouped set of packages, wherein the mobile master node is operative to communicate directly with the server in the wireless node network over a first communication path; associating, by the server, the ID node with another of the packages in the grouped set of packages, wherein the ID node is operative to communicate directly with the mobile master node over a second communication path but not operative to communicate directly with the server over the first communication path; and creating the hierarchical sensor network for the grouped set of packages with the mobile master node and the ID node when the server associates the mobile master node with the ID node.

2. The method of embodiment 1 further comprising the steps of: associating, by the server, an additional ID node with each of the remaining ones of the packages; and updating the hierarchical sensor network to further comprise each of the associated additional ID nodes.

3. The method of embodiment 1, wherein the grouped set of packages comprise a palletized group of packages being shipped together.

4. The method of embodiment 1, wherein the grouped set of packages comprise a group of packages together within a shipping container.

5. The method of embodiment 1 further comprising sensing, by the ID node, shipping condition information related to the another of the packages.

6. The method of embodiment 5, wherein the shipping condition information comprises at least one of environmental information and location information.

7. The method of embodiment 5 further comprising sharing, by the ID node, the sensed shipping condition information with the mobile master node.

8. The method of embodiment 7 further comprising providing, by the master node to the server, the shared sensed shipping condition information.

9. The method of embodiment 1 further comprising managing, by the server, power consumption of the hierarchical sensor network by transmitting a power management instruction to the master node by the server, the power management instruction causing the mobile master node to alter at least one operation of the mobile master node and the ID node to change power consumption by at least one of the mobile master node and the ID node.

10. A non-transitory computer-readable medium containing instructions which when executed on a processor performs a method for creating a hierarchical sensor network for a grouped set of packages being shipped, the hierarchical sensor network using a wireless node network having a mobile master node, an ID node and a server, the method comprising: associating, by the server, the mobile master node with one of the packages in the grouped set of packages, wherein the mobile master node is operative to communicate directly with the server in the wireless node network over a first communication path; associating, by the server, the ID node with another of the packages in the grouped set of packages, wherein the ID node is operative to communicate directly with the mobile master node over a second communication path but not operative to communicate directly with the server over the first communication path; and creating the hierarchical sensor network for the grouped set of packages when the server associates the mobile master node with the ID node.

11. The non-transitory computer-readable medium of embodiment 10, wherein the method further comprises the steps of: associating, by the server, an additional ID node with each of the remaining ones of the packages; and updating the hierarchical sensor network to further comprise each of the associated additional ID nodes.

12. The non-transitory computer-readable medium of embodiment 10, wherein the grouped set of packages comprise a palletized group of packages being shipped together.

13. The non-transitory computer-readable medium of embodiment 10, wherein the grouped set of packages comprise a group of packages together within a shipping container.

14. The non-transitory computer-readable medium of embodiment 10, wherein the method further comprises sensing, by the ID node, shipping condition information related to the another of the packages.

15. The non-transitory computer-readable medium of embodiment 14, wherein the shipping condition information comprises at least one of environmental information and location information.

16. The non-transitory computer-readable medium of embodiment 14, wherein the method further comprises sharing, by the ID node, the sensed shipping condition information with the mobile master node.

17. The non-transitory computer-readable medium of embodiment 16, wherein the method further comprises providing, by the master node to the server, the shared sensed shipping condition information.

18. The non-transitory computer-readable medium of embodiment 10, wherein the method further comprises managing, by the server, power consumption of the hierarchical sensor network by transmitting a power management instruction to the master node by the server, the power management instruction causing the mobile master node to alter at least one operation of the mobile master node and the ID node to change power consumption by at least one of the mobile master node and the ID node.

19. A method for creating a hierarchical sensor network for a grouped set of packages being shipped, the hierarchical sensor network using a wireless node network having a mobile master node, an ID node and a server, comprising: placing the mobile master node within one of the packages in the grouped set of packages, wherein the mobile master node is operative to communicate directly with a server in the wireless node network over a first communication path; placing an ID node within another of the packages in the grouped set of packages, wherein the ID node is operative to communicate directly with the master node over a second communication path but not operative to communicate directly with a server over the first communication path; enabling the mobile master node and the ID node with power; and activating the hierarchical sensor network for the grouped set of packages by causing the server to associate the mobile master node with the ID node.

20. The method of embodiment 19 further comprising the steps of: placing an additional ID node within each of the remaining ones of the packages; and enabling each of the additional ID nodes placed within each of the remaining ones of the packages, wherein the enabled each of the additional ID nodes are powered and discoverable by the mobile master node and added to the hierarchical sensor network when the enabled each of the additional ID nodes are associated with the mobile master node.

21. The method of embodiment 19 further comprising the steps of: placing an additional ID node within a remaining one of the packages; and enabling the additional ID node placed within the remaining one of the packages, wherein the enabled additional ID node is powered and discoverable by the mobile master node and added to the hierarchical sensor network when the enabled additional ID node is associated with the mobile master node.

22. The method of embodiment 19, wherein the grouped set of packages comprise a palletized group of packages being shipped together.

23. The method of embodiment 19, wherein the grouped set of packages comprise a group of packages together within a shipping container.

24. The method of embodiment 19 further comprising selecting the packages in the grouped set of packages as a monitored group of packages to be shipped together for at least a portion of a shipping path from an origin to a destination.

25. A method for creating a hierarchical sensor network for a grouped set of packages being shipped, the hierarchical sensor network using a wireless node network having a mobile master node, an ID node and a server, comprising: associating, by the mobile master node, one of the packages in the grouped set of packages with the mobile master node, wherein the mobile master node is operative to communicate directly with the server over a longer range communication path and operative to communicate with the ID node over a short range communication path; detecting, by the mobile master node, a signal broadcast from the ID node over the short range communication path; the ID node being associated with another of the packages in the grouped set of packages, wherein the ID node is operative to communicate directly with the mobile master node over the short range communication path but not operative to communicate directly with the server; transmitting, by the mobile master node, an authorization request to associate the mobile master node and the ID node; receiving a response from the server to authorize associating the mobile master node and the ID node; and establishing the hierarchical sensor network for the grouped set of packages with the mobile master node and the ID node when the mobile master node associates with the ID node.

26. The method of embodiment 25 further comprising the step of associating, by the mobile master node, an additional ID node with each of the remaining ones of the packages, wherein the hierarchical sensor network further comprises each of the associated additional ID nodes.

27. The method of embodiment 25, wherein the grouped set of packages comprise a palletized group of packages being shipped together.

28. The method of embodiment 25, wherein the grouped set of packages comprise a group of packages together within a shipping container.

29. The method of embodiment 25 further comprising receiving, by the mobile master node, shipping condition information from the ID node.

30. The method of embodiment 29, wherein the shipping condition information comprises at least one of environmental information and location information related to the ID node.

31. The method of embodiment 29 further comprising providing, by the mobile master node to the server, the shared shipping condition information from the ID node.

32. The method of embodiment 25 further comprising the steps of: receiving, by the mobile master node from the server, a power management instruction; and implementing the power management instruction by the mobile master node to manage power consumed by the mobile master node and the ID node.

33. The method of embodiment 32, wherein the step of implementing the power management instruction by the mobile master node further comprises instructing the ID node to alter an operation of the ID node in order to change the power consumed by the ID node.

34. The method of embodiment 33, wherein the step of implementing the power management instruction by the mobile master node further comprises altering an operation of the mobile master node in order to change the power consumed by the mobile master node.

35. A non-transitory computer-readable medium containing instructions which when executed on a processor performs a method for creating a hierarchical sensor network for a grouped set of packages being shipped, the hierarchical sensor network using a wireless node network having a mobile master node, an ID node and a server, the method comprising: associating, by the mobile master node, one of the packages in the grouped set of packages with the mobile master node, wherein the mobile master node is operative to communicate directly with the server in the wireless node network over a longer range communication path and operative to communicate with the ID node over a short range communication path; detecting, by the mobile master node, a signal broadcast from the ID node over the short range communication path; the ID node being associated with another of the packages in the grouped set of packages, wherein the ID node is operative to communicate directly with the mobile master node over the short range communication path but not operative to communicate directly with the server; transmitting, by the mobile master node, an authorization request to associate the mobile master node and the ID node; receiving a response from the server to authorize associating the mobile master node and the ID node; and establishing the hierarchical sensor network for the grouped set of packages when the mobile master node associates with the ID node.

36. The non-transitory computer-readable medium of embodiment 35, wherein the method further comprises the step of associating, by the mobile master node, an additional ID node with each of the remaining ones of the packages, wherein the hierarchical sensor network further comprises each of the associated additional ID nodes.

37. The non-transitory computer-readable medium of embodiment 35, wherein the grouped set of packages comprise a palletized group of packages being shipped together.

38. The non-transitory computer-readable medium of embodiment 35, wherein the grouped set of packages comprise a group of packages together within a shipping container.

39. The non-transitory computer-readable medium of embodiment 35, wherein the method further comprises receiving, by the mobile master node, shipping condition information from the ID node.

40. The non-transitory computer-readable medium of embodiment 39, wherein the shipping condition information comprises at least one of environmental information and location information.

41. The non-transitory computer-readable medium of embodiment 39, wherein the method further comprises providing, by the mobile master node to the server, the shared shipping condition information from the ID node.

42. The non-transitory computer-readable medium of embodiment 35, wherein the method further comprises the steps of: receiving, by the mobile master node from the server, a power management instruction; and implementing the power management instruction by the mobile master node to manage power consumed by the mobile master node and the ID node.

43. The non-transitory computer-readable medium of embodiment 42, wherein the step of implementing the power management instruction by the mobile master node further comprises instructing the ID node to alter an operation of the ID node in order to change the power consumed by the ID node.

44. The non-transitory computer-readable medium of embodiment 43, wherein the step of implementing the power management instruction by the mobile master node further comprises altering an operation of the mobile master node in order to change the power consumed by the mobile master node.

45. A hierarchical sensor system for a set of packages being shipped, the hierarchical sensor system comprising: a mobile master node associated with one of the packages in the set of packages, the mobile master node being operative to communicate with a server over a longer range communication path; a plurality of ID nodes, wherein each of the ID nodes is associated with one of the remaining packages in the set of packages, and each of the plurality of ID nodes being operative to communicate with the mobile master node over a short range communication path but unable to directly communicate with the server; wherein one or more of the ID nodes further comprises a sensor that collects shipment condition information about its associated package; and wherein the mobile master node is further operative to receive the collected shipment condition information from the ID nodes over the short range communication path and update the server over the longer range communication path with summary shipment condition information related to each of the packages in the set of packages, the summary shipment condition information being based upon the collected shipment condition information from the ID nodes.

46. The hierarchical sensor system of embodiment 45, wherein the mobile master node further comprises a sensor that collects shipment condition information about the one of the packages in the set of packages.

47. The hierarchical sensor system of embodiment 45, wherein the set of packages comprise a group of packages identified by shipping information to be related and shipped together, the shipping information maintained on the server and defined by a shipping customer.

48. The hierarchical sensor system of embodiment 45, wherein the set of packages comprise a palletized group of packages being shipped together.

49. The hierarchical sensor system of embodiment 45, wherein the set of packages comprise a group of packages together within a shipping container.

Further Embodiment 27—Multi-Entity Management of a Node in a Wireless Node Network 1. A method for multi-entity management of an ID node in a wireless node network, comprising: associating the ID node with a first entity user access device, the first entity user access device operating as a master node in the network and is operative to communicate directly with a server in the network over a first communication path and separately communicate with the ID node over a second communication path, wherein the ID node is operative to communicate directly with the first entity user access device over the second communication path but is unable to directly communicate with the server; providing, by the ID node to the associated first entity user access device, access to data collected by the ID node if authorized by an initial privilege; associating the ID node with a shipping entity master node in the network; providing, by the ID node to the associated shipping entity master node, access to the data collected by the ID node based upon a transferred privilege, the transferred privileged provided by the server to the shipping entity master node; associating the ID node with a second entity user access device; and providing, by the ID node to the associated second entity user access device, access to the data collected by the ID node if authorized by a destination privilege provided by the server to the second entity user access device.

2. The method of embodiment 1, wherein the initial privilege was provided by the server to the first entity user access device.

3. The method of embodiment 1, wherein the initial privilege comprises a paid privilege to access the data collected by the ID node.

4. The method of embodiment 1, wherein the initial privilege comprises a paid privilege to be provided a location of the ID node.

5. The method of embodiment 1, wherein the initial privilege comprises a paid privilege to track an item associated with the ID node over time.

6. The method of embodiment 1, wherein the initial privilege comprises a privilege for the first entity user access device to manage where the data collected by the ID node is stored.

7. The method of embodiment 6, wherein the initial privilege comprises a paid privilege to have the data collected by the ID node uploaded to the first entity user access device over the second communication path.

8. The method of embodiment 6, wherein the initial privilege comprises a paid privilege to have the data collected by the ID node uploaded to the server from the first entity user access device over the first communication path.

9. The method of embodiment 1, wherein the destination privilege comprises a paid privilege to access any of the data collected by the ID node.

10. The method of embodiment 1, wherein the destination privilege comprises a paid privilege to access only a limited portion of the data connected by the ID node.

11. The method of embodiment 1 further comprising restricting, by the ID node, the first entity user access device from directly accessing the data collected by the ID node after the ID node is associated with the shipping entity master node.

12. The method of embodiment 1, wherein the data collected by the ID node while the ID node is associated with the shipping entity master remains owned by a shipping entity related to the shipping entity master node when the second entity user access device is not authorized by the destination privilege.

13. The method of embodiment 1 further comprising requesting system updates from the server by the ID node regardless of where the data collected by the ID node is stored.

14. A non-transitory computer-readable medium containing instructions which when executed on a processor performs a method for multi-entity management of a node in a wireless node network, the method comprising: associating the ID node with a first entity user access device, the first entity user access device operating as a master node in the network and is operative to communicate directly with a server in the network over a first communication path and separately communicate with the ID node over a second communication path, wherein the ID node is operative to communicate directly with the first entity user access device over the second communication path but is unable to directly communicate with the server; providing, by the ID node to the associated first entity user access device, access to data collected by the ID node if authorized by an initial privilege; associating the ID node with a shipping entity master node in the network; providing, by the ID node to the associated shipping entity master node, access to the data collected by the ID node based upon a transferred privilege, the transferred privileged provided by the server to the shipping entity master node; associating the ID node with a second entity user access device; and providing, by the ID node to the associated second entity user access device, access to the data collected by the ID node if authorized by a destination privilege provided by the server to the second entity user access device.

15. The non-transitory computer-readable medium of embodiment 14, wherein the initial privilege was provided by the server to the first entity user access device.

16. The non-transitory computer-readable medium of embodiment 14, wherein the initial privilege comprises a paid privilege to access the data collected by the ID node.

17. The non-transitory computer-readable medium of embodiment 14, wherein the initial privilege comprises a paid privilege to be provided a location of the ID node.

18. The non-transitory computer-readable medium of embodiment 14, wherein the initial privilege comprises a paid privilege to track an item associated with the ID node over time.

19. The non-transitory computer-readable medium of embodiment 14, wherein the initial privilege comprises a privilege for the first entity user access device to manage where the data collected by the ID node is stored.

20. The non-transitory computer-readable medium of embodiment 19, wherein the initial privilege comprises a paid privilege to have the data collected by the ID node uploaded to the first entity user access device over the second communication path.

21. The non-transitory computer-readable medium of embodiment 19, wherein the initial privilege comprises a privilege to have the data collected by the ID node uploaded to the server from the first entity user access device over the first communication path.

22. The non-transitory computer-readable medium of embodiment 14, wherein the destination privilege comprises a paid privilege to access any of the data collected by the ID node.

23. The non-transitory computer-readable medium of embodiment 14, wherein the destination privilege comprises a paid privilege to access only a limited portion of the data connected by the ID node.

24. The non-transitory computer-readable medium of embodiment 14, wherein the method further comprises restricting, by the ID node, the first entity user access device from directly accessing the data collected by the ID node after the ID node is associated with the shipping entity master node.

25. The non-transitory computer-readable medium of embodiment 14, wherein the data collected by the ID node while the ID node is associated with the shipping entity master remains owned by a shipping entity related to the shipping entity master node when the second entity user access device is not authorized by the destination privilege.

26. The non-transitory computer-readable medium of embodiment 14, wherein the method further comprises requesting system updates from the server by the ID node regardless of where the data collected by the ID node is stored.

27. A method for multi-entity management of an ID node in a wireless node network, comprising: executing a program module of code on a first entity user access device to enable operation of the first entity user access device as a master node that is operative to communicate directly with a server over a first communication path and separately communicate with the ID node over a second communication path, the ID node being operative to communicate directly with the first entity user access device over the second communication path but unable to directly communicate with the server; transmitting a request to the server from the first entity user access device, the request being for an authorization to associate with the ID node and an initial privilege related to data to be collected by the ID node; receiving the authorization and the initial privilege from the server; associating the first entity user access device with the ID node; receiving, by the first entity user access device, data collected by the ID node if authorized by the initial privilege; and managing the data collected by the ID node.

28. The method of embodiment 27, wherein the initial privilege comprises a paid privilege.

29. The method of embodiment 27, wherein the initial privilege comprises a paid privilege for access to the data collected by the ID node.

30. The method of embodiment 27 further comprising receiving, by the first entity user access device, a location of the ID node if authorized by the initial privilege.

31. The method of embodiment 27 further comprising receiving, by the first entity user access device, a tracking update on the ID node if authorized by the initial privilege.

32. The method of embodiment 27, wherein the managing step further comprises managing where the data collected by the ID node is maintained in accordance with the initial privilege.

33. The method of embodiment 32, wherein the initial privilege allows the data collected by the ID node to be uploaded by the first entity user access device to the server over the first communication path.

34. The method of embodiment 27, wherein the initial privilege no longer authorizes the first entity user access device to receive the data collected by the ID node once the ID node associates with a shipping entity master node.

35. A method for multi-entity management of an ID node in a wireless node network, comprising: executing a program module of code on a recipient entity user access device to enable operation of the recipient entity user access device as a master node that is operative to communicate directly with a server over a first communication path and separately communicate with the ID node over a second communication path, the ID node being operative to communicate directly with the recipient entity user access device over the second communication path but unable to directly communicate with the server; transmitting a request to the server from the recipient user access device, the request being for an authorization to associate with the ID node and a destination privilege related to data to be collected by the ID node; receiving the authorization and the destination privilege from the server; associating the recipient user access device with the ID node; and receiving, by the recipient user access device, data collected by the ID node if authorized by the destination privilege.

36. The method of embodiment 35, wherein the destination privilege comprises a paid privilege.

37. The method of embodiment 35, wherein the destination privilege comprises a paid privilege to access only a limited portion of the data connected by the ID node.

38. The method of embodiment 35, wherein the destination privilege allows the data collected by the ID node to be uploaded by the recipient user access device to the server over the first communication path.

39. The method of embodiment 35, wherein management of the data collected by the ID node is limited to the server if the data collected by the ID node is not authorized to be received by the recipient user access device under the destination privilege.

40. An ID node managed by multiple entities using a wireless node network, the ID node comprising: a node processing unit; a node memory coupled to the processing unit, the memory maintaining code for execution by the processing unit and data collected by the ID node during operations of the node; a short-range communication interface coupled to the processing unit and operative to directly communicate with a master node in the network over a short-range communication path but unable to directly communicate with a server in the network; and wherein the node processing unit, when executing the code maintained on the node memory, is operative to: associate the ID node with a first entity user access device, the first entity user access device operating as the master node and being operative to communicate directly with the server over a longer range communication path and separately communicate with the ID node over the short-range communication path, provide the first entity user access device with access to the data collected by the ID node if authorized by an initial privilege, the initial privilege having been provided by the server to the first entity user access device, associate the ID node with a shipping entity master node in the network, provide the associated shipping entity master node with access to the data collected by the ID node based upon a transferred privilege, the transferred privileged provided by the server to the shipping entity master node, associate the ID node with a second entity user access device, the second entity user access device operating as another master node and being operative to communicate directly with the server over the longer range communication path and separately communicate with the ID node over the short-range communication path, and provide the associated second entity user access device with access to the data collected by the ID node if authorized by a destination privilege provided by the server to the second entity user access device.

41. The ID node of embodiment 40, wherein the initial privilege comprises a paid privilege to access the data collected by the ID node.

42. The ID node of embodiment 40, wherein the initial privilege comprises a paid privilege to be provided a location of the ID node.

43. The ID node of embodiment 40, wherein the initial privilege comprises a paid privilege to track an item associated with the ID node over time.

44. The ID node of embodiment 40, wherein the initial privilege comprises a privilege for the first entity user access device to manage where the data collected by the ID node is stored.

45. The ID node of embodiment 44, wherein the initial privilege comprises a paid privilege to have the data collected by the ID node uploaded from the node memory to the first entity user access device over the short-range communication path via the short-range communication interface.

46. The ID node of embodiment 44, wherein the initial privilege comprises a privilege to have the data collected by the ID node uploaded to the server from the first entity user access device over the longer range communication path.

47. The ID node of embodiment 40, wherein the destination privilege comprises a paid privilege to access any of the data collected by the ID node.

48. The ID node of embodiment 40, wherein the destination privilege comprises a paid privilege to access only a limited portion of the data connected by the ID node.

49. The ID node of embodiment 40, wherein the node processing unit is further operative to restrict the first entity user access device from directly accessing the node memory for the data collected by the ID node after the ID node is associated with the shipping entity master node.

50. The ID node of embodiment 40, wherein the data collected by the ID node while the ID node is associated with the shipping entity master remains owned by a shipping entity related to the shipping entity master node when the second entity user access device is not authorized by the destination privilege.

51. The ID node of embodiment 40, wherein the node processing unit is further operative to request a system update regardless of where the data collected by the ID node is stored.

Further Embodiment 28—Autonomous Transport Navigation to a Shipping Location Using Elements of a Wireless Node Network 1. A method for navigating to a shipping location by an autonomous transport vehicle using a plurality of nodes in a wireless node network, comprising: detecting, by a mobile master node associated with the autonomous transport vehicle, a signal broadcast from an ID node associated with the shipping location, wherein the mobile master node is one of the plurality of nodes and is operative to communicate directly with a server in the wireless node network over a first communication path, and wherein the ID node is another of the plurality of nodes and is operative to communicate directly with the mobile master node over a second communication path but not operative to communicate directly with the server over the first communication path; instructing, by the mobile master node, the ID node to lower a power level of the signal broadcast from the ID node; identifying, by the mobile master node, the signal broadcast from the ID node with the lowered power level; determining, by the mobile master node, a direction of the ID node relative to the mobile master node based upon the detected signal with the lowered power level; and navigating, by the mobile master node, to the ID node associated with the shipping location based upon the determined direction.

2. The method of embodiment 1, wherein the step of navigating further comprises navigating, by the mobile master node, to the ID node as the power level of the signal is incrementally decreased over time as the mobile master node approaches the ID node.

3. The method of embodiment 1 further comprising receiving, by the mobile master node from the server, an identification of the ID node.

4. The method of embodiment 3, wherein the detecting step further comprises detecting the identification of the ID node from the signal broadcast from the ID node.

5. The method of embodiment 1, wherein the shipping location comprises one from a group consisting of a delivery point, a drop-off point, and a pickup point.

6. The method of embodiment 1, wherein the mobile master node is associated with a control system of an autonomous vehicle transport; and wherein the step of navigating further comprises providing, by the mobile master node, the determined direction to an input of the control system.

7. The method of embodiment 6 further comprising the step of causing, by the mobile master node, the autonomous vehicle transport to stop moving when a current location of the mobile master node is within a predetermined range of the ID node.

8. The method of embodiment 6, wherein the step of navigating further comprises: accessing context data that relates to an operating environment of the ID node; and navigating, by the mobile master node, to the ID node with reference to the accessed context data as the power level of the signal is incrementally decreased over time and as the mobile master node approaches the ID node.

9. The method of embodiment 6, wherein the step of navigating further comprises: accessing context data that relates to an anticipated operating environment of the ID node; gathering proximity sensor data from at least one sensor deployed on the autonomous vehicle transport; and navigating, by the mobile master node, to the ID node with reference to the accessed context data and the proximity sensor data as the power level of the signal is incrementally decreased over time and as the mobile master node approaches the ID node.

10. The method of embodiment 9, wherein the operating environment of the ID node is within a package sorting facility.

11. The method of embodiment 1 further comprising transmitting, by the mobile master node to the server, an updated location of the mobile master node as the mobile master node approaches the ID node.

12. The method of embodiment 11, wherein the updated location of the mobile master node is determined using location circuitry on the mobile master node.

13. The method of embodiment 11, wherein the mobile master node is associated with a control system of an autonomous vehicle transport; and wherein the updated location of the mobile master node is determined based at least in part upon a determined position from an inertial navigation unit deployed on the autonomous vehicle transport.

14. The method of embodiment 11, wherein the updated location of the mobile master node is determined based upon an onboard location provided by location circuitry on the mobile master node when available and, when the onboard location is not available, the updated location of the mobile master node is determined based at least in part upon a determined position from an inertial navigation unit deployed on the autonomous vehicle transport.

15. The method of embodiment 1, wherein the shipping location comprises a waypoint in an anticipated route.

16. The method of embodiment 1, wherein the shipping location comprises a first waypoint of a plurality of waypoints on an anticipated route as the mobile master node approaches a transit destination for a package transaction, wherein each of the plurality of waypoints is associated with a different ID node.

17. A method for navigating to a shipping location by an autonomous transport vehicle using a plurality of nodes in a wireless node network, comprising: detecting, by a node associated with the autonomous transport vehicle, a signal broadcast from an ID node associated with the shipping location; instructing, by the node associated with the autonomous transport vehicle, the ID node to lower a power level of the signal broadcast from the ID node; identifying, by the node associated with the autonomous transport vehicle, the signal broadcast from the ID node with the lowered power level; determining, by the node associated with the autonomous transport vehicle, a direction of the ID node relative to the mobile master node based upon the detected signal with the lowered power level; and navigating, by the node associated with the autonomous transport vehicle, to the ID node associated with the shipping location based upon the determined direction.

18. The method of embodiment 17, wherein the node associated with the autonomous transport vehicle is at least one of a master node and another ID node, wherein the master node is operative to communicate directly with a server in the wireless node network over a first communication path, and wherein the another ID node is operative to communicate with other nodes in the wireless node network but unable to directly communicate with the server.

19. The method of embodiment 17, wherein the node associated with the autonomous transport vehicle comprises a master node temporarily operating as an ID node.

20. A non-transitory computer-readable medium containing instructions which when executed on a processor performs a method for navigating to a shipping location by an autonomous transport vehicle using a plurality of nodes in a wireless node network, the method comprising: detecting, by a mobile master node associated with the autonomous transport vehicle, a signal broadcast from an ID node associated with the shipping location, wherein the mobile master node is one of the plurality of nodes and is operative to communicate directly with a server in the wireless node network over a first communication path, and wherein the ID node associated with the shipping location is another of the plurality of nodes and is operative to communicate directly with the mobile master node over a second communication path but not operative to communicate directly with the server over the first communication path; instructing, by the mobile master node, the ID node associated with the shipping location to lower a power level of the signal broadcast from the ID node associated with the shipping location; identifying, by the mobile master node, the signal broadcast from the ID node with the lowered power level; determining, by the mobile master node, a direction of the ID node associated with the shipping location relative to the mobile master node based upon the detected signal with the lowered power level; and navigating, by the mobile master node, to the ID node associated with the shipping location based upon the determined direction.

21. The non-transitory computer-readable medium of embodiment 20, wherein the step of navigating further comprises navigating, by the mobile master node, to the ID node associated with the shipping location as the power level of the signal is incrementally decreased over time as the mobile master node approaches the ID node associated with the shipping location.

22. The non-transitory computer-readable medium of embodiment 20, wherein the method further comprises receiving, by the mobile master node from the server, an identification of the ID node associated with the shipping location.

23. The non-transitory computer-readable medium of embodiment 22, wherein the detecting step further comprises detecting the identification of the ID node associated with the shipping location from the signal broadcast from the ID node associated with the shipping location.

24. The non-transitory computer-readable medium of embodiment 20, wherein the shipping location comprises one from a group consisting of a delivery point, a drop-off point, and a pickup point.

25. The non-transitory computer-readable medium of embodiment 20, wherein the mobile master node is associated with a control system of an autonomous vehicle transport; and wherein the step of navigating further comprises providing, by the mobile master node, the determined direction to an input of the control system.

26. The non-transitory computer-readable medium of embodiment 25, wherein the method further comprises causing, by the mobile master node, the autonomous vehicle transport to stop moving when a current location of the mobile master node is within a predetermined range of the ID node associated with the shipping location.

27. The non-transitory computer-readable medium of embodiment 25, wherein the step of navigating further comprises: accessing context data that relates to an operating environment of the ID node; and navigating, by the mobile master node, to the ID node with reference to the accessed context data as the power level of the signal is incrementally decreased over time and as the mobile master node approaches the ID node.

28. The non-transitory computer-readable medium of embodiment 25, wherein the step of navigating further comprises: accessing context data that relates to an anticipated operating environment of the ID node; gathering proximity sensor data from at least one sensor deployed on the autonomous vehicle transport; and navigating, by the mobile master node, to the ID node with reference to the accessed context data and the proximity sensor data as the power level of the signal is incrementally decreased over time and as the mobile master node approaches the ID node.

29. The non-transitory computer-readable medium of embodiment 28, wherein the operating environment of the ID node is within a package sorting facility.

30. The non-transitory computer-readable medium of embodiment 20, wherein the method further comprises transmitting, by the mobile master node to the server, an updated location of the mobile master node as the mobile master node approaches the ID node.

31. The non-transitory computer-readable medium of embodiment 30, wherein the updated location of the mobile master node is determined using location circuitry on the mobile master node.

32. The non-transitory computer-readable medium of embodiment 30, wherein the mobile master node is associated with a control system of an autonomous vehicle transport; and wherein the updated location of the mobile master node is determined based at least in part upon a determined position from an inertial navigation unit deployed on the autonomous vehicle transport.

33. The non-transitory computer-readable medium of embodiment 30, wherein the updated location of the mobile master node is determined based upon an onboard location provided by location circuitry on the mobile master node when available and, when the onboard location is not available, the updated location of the mobile master node is determined based at least in part upon a determined position from an inertial navigation unit deployed on the autonomous vehicle transport.

34. The non-transitory computer-readable medium of embodiment 20, wherein the shipping location comprises a waypoint in an anticipated route.

35. The non-transitory computer-readable medium of embodiment 20, wherein the shipping location comprises a first waypoint of a plurality of waypoints on an anticipated route as the mobile master node approaches a transit destination for a package transaction, wherein each of the plurality of waypoints is associated with a different ID node.

36. A node-enabled transport vehicle, comprising: an autonomous vehicle operative to move from an initial location to a shipping location in response to control input; a control system disposed on the autonomous vehicle, the control system having an output coupled to the control input of the autonomous vehicle, the control system further having at least one input for receiving an instruction on a desired movement for the autonomous vehicle and producing a control signal on the output responsive to the instruction received; a mobile master node associated with the autonomous vehicle, the mobile master node providing a directional output signal as the instruction to the input of the control system, wherein the mobile master node is one of a plurality of nodes in a wireless node network; and wherein the mobile master node further comprises a node processing unit, a node memory coupled to the node processing unit, the node memory maintaining code for execution by the node processing unit, a short-range communication interface coupled to the processing unit and operative to communicate with an ID node associated with the shipping location, wherein the ID node is another of the plurality of nodes and is operative to communicate directly with the mobile master node over the short-range communication interface but not operative to communicate directly with a server in the network, a longer range communication interface coupled to the node processing unit and operative to communicate directly with the server; wherein the node processing unit of the mobile master node, when executing the code maintained on the node memory, is operative to detect, over the short-range communication interface, a signal broadcast from the ID node associated with the shipping location, transmit an instruction over the short-range communication interface to the ID node, the instruction causing the ID node to lower a power level of the signal broadcast from the ID node, identify the signal broadcast from the ID node with the lowered power level, determine a direction from the mobile master node to the ID node based upon the detected signal with the lowered power level, and provide the determined direction as the instruction to the input of the control system.

37. The node-enabled transport vehicle of embodiment 36, wherein the node processing unit is further operative to determine the direction to the ID node and provide the determined direction as the directional output signal as the power level of the detected signal broadcast from the ID node is incrementally decreased over time and as the mobile master node approaches the shipping location.

38. The node-enabled transport vehicle of embodiment 36, wherein the node processing unit is further operative to receive an ID node identification from the server over the longer range communication interface, the ID node identification being related to the ID node associated with the shipping location.

39. The node-enabled transport vehicle of embodiment 38, the node processing unit is further operative to detect the ID node identification of the ID node associated with the shipping location from the signal broadcast from the ID node associated with the shipping location.

40. The node-enabled transport vehicle of embodiment 36, wherein the shipping location comprises one from a group consisting of a delivery point, a drop-off point, and a pickup point.

41. The node-enabled transport vehicle of embodiment 36, wherein the node processing unit is further operative to instruct the control system based upon the directional input to cause the autonomous vehicle transport to stop moving when a current location of the mobile master node is within a predetermined range of the ID node associated with the shipping location.

42. The node-enabled transport vehicle of embodiment 41, wherein the node processing unit is further operative to transmit an update to the server reflecting that the current location of the mobile master node is within the predetermined range of the ID node.

43. The node-enabled transport vehicle of embodiment 41, wherein the node memory further maintains context data; and wherein the node processing unit is further operative to: access a part of the context data that relates to an operating environment of the ID node; and determine the direction to the ID node with reference to the accessed context data as the power level of the signal is incrementally decreased over time and as the mobile master node approaches the ID node.

44. The node-enabled transport vehicle of embodiment 41 further comprising at least one sensor disposed on the autonomous vehicle and coupled at least to the node processing unit of the mobile master node; wherein the node memory further maintains context data; and wherein the node processing unit is further operative to: access a part of the context data that relates to an anticipated operating environment of the ID node, gather proximity data from the at least one sensor, and determine the direction to the ID node with reference to the accessed context data and the proximity sensor data as the power level of the signal is incrementally decreased over time and as the mobile master node approaches the ID node.

45. The node-enabled transport vehicle of embodiment 44, wherein the operating environment of the ID node is within a package sorting facility.

46. The node-enabled transport vehicle of embodiment 36, wherein the mobile master node further comprises onboard location circuitry coupled to the node processing unit; wherein the node processing unit is further operative to: obtain an updated location of the mobile master node from the onboard location circuitry, and transmit the updated location over the longer range communication interface to the server as the mobile master node approaches the shipping location.

47. The node-enabled transport vehicle of embodiment 36 further comprising an inertial navigation unit deployed on the autonomous vehicle and generating a determined position for the location of the autonomous vehicle; and wherein the node processing unit is further operative to determine an updated location of the mobile master node at least in part on the determined position obtained from the inertial navigation unit, and transmit the updated location over the longer range communication interface to the server.

48. The node-enabled transport vehicle of embodiment 36 further comprising an inertial navigation unit deployed on the autonomous vehicle and generating a determined position for the location of the autonomous vehicle; and wherein the mobile master node further comprises onboard location circuitry coupled to the node processing unit; and wherein the node processing unit is further operative to: determine if an updated location of the mobile master node from the onboard location circuitry is available, and transmit to the server over the longer range communication interface the updated location obtained from the onboard location circuitry if available, and transmit to the server over the longer range communication interface the determined position obtained from the inertial navigation unit if the updated location is not available.

49. The node-enabled transport vehicle of embodiment 36, wherein the shipping location comprises a waypoint in an anticipated route for the autonomous vehicle.

50. The node-enabled transport vehicle of embodiment 36, wherein the shipping location comprises a first waypoint of a plurality of waypoints on an anticipated route as the autonomous vehicle approaches a transit destination for a package transaction, wherein each of the plurality of waypoints is associated with another ID node in the plurality of nodes.

51. The node-enabled transport vehicle of embodiment 50, wherein the node processing unit is further operative to: detect, over the short-range communication interface, a signal broadcast from the another ID node associated with a next of the waypoints, transmit an instruction over the short-range communication interface to the another ID node, the instruction causing the another ID node to lower a power level of the signal broadcast from the another ID node, identify the signal broadcast from the another ID node with the lowered power level, determine a further direction on the anticipated route from the mobile master node to the another ID node based upon the detected signal with the lowered power level broadcast from the another ID node, and provide the determined direction on the anticipated route as the instruction to the input of the control system.

Further Embodiment 29—Methods and Systems for Automating a Logistics Transaction Using an Autonomous Vehicle and Elements of a Wireless Node Network 1. A method for automating a logistics transaction using a plurality of nodes and a server in a wireless node network, comprising: downloading, by a first of the nodes, shipment information from the server, the shipment information identifying a package for the logistics transaction, a transaction location for the logistics transaction, and an identification of a second of the nodes associated with the package, wherein the first node is associated with a shipping courier; providing, by the first node, the shipment information to a third of the nodes, wherein the third node is part of an autonomous vehicle; causing, by the third node, the autonomous vehicle to move from a first location to the transaction location; and conducting, by the third node, the logistics transaction related to the package if the third node on the autonomous vehicle completes a node association with the second node associated with the package.

2. The method of embodiment 1, wherein the logistics transaction comprises picking up the package at the transaction location after the third node associates with the second node.

3. The method of embodiment 2, wherein conducting the logistics transaction further comprises: detecting, by the third node, a signal from the second node associated with the package as the autonomous vehicle approaches the transaction location; associating the third node and the second node; picking up the package at the transaction location; and placing the package in a package payload storage of the autonomous vehicle.

4. The method of embodiment 3 further comprising deploying the autonomous vehicle from a courier transport vehicle at the first location.

5. The method of embodiment 4 further comprising: returning, by the autonomous vehicle, to the courier transport vehicle to unload the package and the second node associated with the package from the package payload storage of the autonomous vehicle; and transmitting, by the third node, a verification message to the server, wherein the verification message confirming that the package was picked up and is on the courier transport vehicle.

6. The method of embodiment 1, wherein the logistics transaction comprises dropping off the package at the transaction location after the third node associates with the second node.

7. The method of embodiment 6, wherein conducting the logistics transaction further comprises: detecting, by the third node, a signal from the second node associated with the package as the autonomous vehicle approaches the transaction location; associating the third node and the second node; removing the package from a package payload storage of the autonomous vehicle; and dropping off the package at the transaction location.

8. The method of embodiment 7 further comprising the steps of: deploying the autonomous vehicle from a courier transport vehicle at the first location; and loading the package into a package payload storage of the autonomous vehicle prior to causing the autonomous vehicle to move from the first location to the transaction location.

9. The method of embodiment 8 further comprising the steps of: returning, by the autonomous vehicle, to the courier transport vehicle; and transmitting, by the third node, a verification message to the server, wherein the verification message confirming that the package was dropped off at the transaction location and is no longer on the courier transport vehicle.

10. The method of embodiment 1, wherein the first node and the third node are each a mobile master node, wherein each of the mobile master nodes is one of the plurality of nodes and is operative to communicate directly with the server in the wireless node network over a first communication path.

11. The method of embodiment 10, wherein the second node is an ID node, wherein the ID node is another node of the plurality of nodes and is operative to communicate with each of the master nodes over a shorter range communication path but is unable to communicate directly with the server 12. A system for automating a logistics transaction related to a package, comprising: a first of a plurality of nodes in a wireless node network, the first node associated with a courier transport vehicle and operative to be in communication with a server in the wireless node network; a second of the nodes, the second node associated with the package; a third of the nodes, the third node integrated as part of an autonomous vehicle related to the courier transport vehicle; wherein, the first node is operative to download shipment information from the server, the shipment information identifying the package for the logistics transaction, a transaction location for the logistics transaction related to the package, and an identification of the second node associated with the package, and provide the shipment information to the third node; and wherein the third node is operative to cause the autonomous vehicle to move from a first location proximate the courier transport vehicle to the transaction location, and conduct the logistics transaction related to the package if the third node successfully associates with the second node associated with the package.

13. The system of embodiment 12, wherein the logistics transaction comprises picking up the package at the transaction location after the third node successfully associates with the second node.

14. The system of embodiment 13, wherein the third node is further operative to conduct the logistics transaction by being further operative to: detect a signal from the second node associated with the package as the autonomous vehicle approaches the transaction location; associate the third node and the second node; instruct a package articulation system on the autonomous vehicle to pick up the package at the transaction location; and instruct the package articulation system to place the package in a package payload storage of the autonomous vehicle.

15. The system of embodiment 14, wherein the third node is further operative to: cause the autonomous vehicle to return to the courier transport vehicle; instruct the package articulation system to unload the package and the second node associated with the package from the package payload storage of the autonomous vehicle into a storage area of the courier transport vehicle; and transmit a verification message to the server, wherein the verification message confirming that the package was picked up and is on the courier transport vehicle.

16. The system of embodiment 12, wherein the logistics transaction comprises dropping off the package at the transaction location after the third node successfully associates with the second node.

17. The system of embodiment 16, wherein the third node is further operative to conduct the logistics transaction by being further operative to: detect a signal from the second node associated with the package as the autonomous vehicle approaches the transaction location; associate the third node and the second node; instruct a package articulation system on the autonomous vehicle to remove the package from a package payload storage of the autonomous vehicle; and instruct the package articulation system to drop off the package at the transaction location.

18. The system of embodiment 17, wherein the third node is further operative to transmit a verification message to the server, wherein the verification message confirming that the package was dropped off at the transaction location.

19. The system of embodiment 12, wherein the first node and the third node are each a mobile master node, wherein each of the mobile master nodes is one of the plurality of nodes and is operative to communicate directly with the server in the wireless node network over a first communication path.

20. The system of embodiment 19, wherein the second node comprises an ID node, wherein the ID node is another node of the plurality of nodes and is operative to communicate with each of the master nodes over a shorter range communication path but is unable to directly communicate with the server.

21. A node-enabled autonomous vehicle that conducts a logistics transaction related to a package, comprising: an autonomous vehicle operative to move, in response to control input, from a first location to a transaction location related to the logistics transaction; a mobile master node integrated as part of the autonomous vehicle, the mobile master node being one of a plurality of nodes in a wireless node network, wherein the mobile master node further comprises: a node processing unit, a node memory coupled to the node processing unit, the node memory maintaining code for execution by the node processing unit, a short-range communication interface coupled to the node processing unit and being operative to communicate with the nodes in the wireless node network; a longer range communication interface coupled to the node processing unit and operative to communicate directly with a server in the wireless network; and wherein the node processing unit of the mobile master node, when executing the code maintained on the node memory, is operative to receive shipment information generated by the server, the shipment information identifying the package for the logistics transaction, the transaction location for the logistics transaction related to the package, and an identification of the second node associated with the package, provide a control signal to control input of the autonomous vehicle causing the autonomous vehicle to move from the first location to the transaction location, and automatically conduct the logistics transaction related to the package if the third node successfully associates with the second node associated with the package.

22. The node-enabled autonomous vehicle of embodiment 21, wherein the logistics transaction comprises picking up the package at the transaction location after the third node successfully associates with the second node.

23. The node-enabled autonomous vehicle of embodiment 22, wherein the autonomous vehicle further comprises a package payload storage and a package articulation system that is operative to place the package within the package payload storage and remove the package from within the package payload storage; and wherein the third node is further operative to automatically conduct the logistics transaction by being operative to: detect a signal from the second node associated with the package as the autonomous vehicle approaches the transaction location, associate the third node and the second node, and provide a pickup control signal to the control input of the autonomous vehicle to cause the package articulation system on the autonomous vehicle to pick up the package at the transaction location and place the package in the package payload storage of the autonomous vehicle.

24. The node-enabled autonomous vehicle of embodiment 23, wherein the third node is further operative to: cause the autonomous vehicle to return to the courier transport vehicle; provide an unload control signal to the control input of the autonomous vehicle to cause the package articulation system to unload the package and the second node associated with the package from the package payload storage of the autonomous vehicle; and transmit a verification message to the server over the longer range communication interface, wherein the verification message confirming that the package was picked up.

25. The node-enabled autonomous vehicle of embodiment 21, wherein the logistics transaction comprises dropping off the package at the transaction location after the third node successfully associates with the second node.

26. The node-enabled autonomous vehicle of embodiment 25, wherein the autonomous vehicle further comprises a package payload storage and a package articulation system that is operative to place the package within the package payload storage and remove the package from within the package payload storage; and wherein the third node is further operative to conduct the logistics transaction by being further operative to: detect a signal from the second node associated with the package as the autonomous vehicle approaches the transaction location; associate the third node and the second node; and provide a drop off control signal to the control input of the autonomous vehicle to cause the package articulation system on the autonomous vehicle to remove the package from within the package payload storage and place the package at the transaction location.

27. The node-enabled autonomous vehicle of embodiment 26, wherein the third node is further operative to transmit a verification message to the server over the longer range communication interface, wherein the verification message confirming that the package was dropped off at the transaction location.

28. The node-enabled autonomous vehicle of embodiment 21, wherein the second node is an ID node, wherein the ID node is another node of the plurality of nodes and is operative to communicate with the mobile master node over the short-range communication interface but is unable to directly communicate with the server.

Further Embodiment 30—Node-Enabled Monitoring of a Piece of Equipment Using a Hierarchical Wireless Node Network 1. A method for monitoring a piece of equipment using a hierarchical node network having at least an ID node, a master node, and a server, the method comprising: associating, by the master node, the master node and the ID node when the master node detects a signal broadcast from the ID node, wherein the ID node is associated with the piece of equipment and operative to monitor an operation of the piece of equipment and to communicate directly with the master node but is unable to directly communicate with the server, and wherein the master node is operative to directly communicate with the server and separately communicate with the ID node; determining, by the server, a location of the ID node; detecting, by the ID node, an actionable event related to the operation of the piece of equipment; transmitting, by the ID node to the master node, a message reporting the actionable event; notifying the server by the master node about the actionable event; and initiating, by the server, a responsive action based upon the notification.

2. The method of embodiment 1, wherein the associating step further comprises establishing a passive association between the master node and the ID node without requiring without requiring a prior authority granted by the server.

3. The method of embodiment 1, wherein the associating step further comprises establishing an active association between the master node and the ID node, the active association reflecting an authorized connection between the master node and the ID node based upon an authority granted by the server.

4. The method of embodiment 3, wherein the authorized connection between the master node and the ID node is pre-authorized by the server to avoid the need for the master node to request the authority from the server after detecting the signal broadcast from the ID node.

5. The method of embodiment 1, wherein the piece of equipment comprises one from a group comprising medical equipment, office equipment, industrial equipment, manufacturing equipment, construction equipment, transportation equipment, laboratory equipment, sporting equipment, automotive equipment, marine equipment, and mining equipment.

6. The method of embodiment 1, wherein the step of detecting further comprises detecting, by the ID node, a movement status related to the operation of the piece of equipment.

7. The method of embodiment 1, wherein the step of detecting further comprises detecting, by the ID node, an activation status related to the operation of the piece of equipment.

8. The method of embodiment 1, wherein the step of detecting further comprises detecting, by the ID node, a usage status related to the operation of the piece of equipment.

9. The method of embodiment 1, wherein the step of initiating the responsive action step further comprises updating a billing attribute related to the operation of the piece of equipment.

10. The method of embodiment 1, wherein the step of initiating the responsive action step further comprises updating an inventory attribute related to the operation of the piece of equipment.

11. The method of embodiment 1, wherein the step of initiating the responsive action step further comprises updating a maintenance attribute related to the operation of the piece of equipment.

12. The method of embodiment 1, wherein the step of initiating the responsive action step further comprises updating a usage attribute related to the operation of the piece of equipment.

13. The method of embodiment 12, wherein the usage attribute related to the operation of the piece of equipment further comprises a usage time associated with an operator of the piece of equipment.

14. The method of embodiment 1, wherein the step of initiating the responsive action step further comprises updating a quality assurance attribute related to the operation of the piece of equipment.

15. The method of embodiment 1, wherein the step of determining the location of the ID node further comprises tracking the location of the ID node over time.

16. The method of embodiment 1, wherein the step of determining the location of the ID node further comprises tracking the location of the ID node over time and refining the location of the ID node based upon context data related to an operating environment of the piece of equipment and the ID node.

17. A hierarchical node network for monitoring a piece of equipment, the hierarchical node network comprising: a server; a master node operative to directly communicate with the server over a longer range communication path; and an ID node associated with the piece of equipment and operative to monitor an operation of the piece of equipment, the ID node being further operative to wirelessly communicate directly with the master node over a shorter range communication path but is unable to directly communicate with the server; wherein the ID node is operative to detect an actionable event related to the operation of the piece of equipment, and transmit a message to the master node reporting the actionable event; wherein the master node is operative to associate with the ID node upon detection of a signal broadcast from the ID node, and notify the server about the actionable event reported in the message received from the ID node, and wherein the server is operative to determine a location of the ID node, receive the notification from the master node regarding the actionable event, and initiate a responsive action based upon the notification.

18. The hierarchical node network of embodiment 17, wherein the master node is further operative to associate with the ID node by being operative to establish a passive association between the master node and the ID node without requiring a prior authority granted by the server.

19. The hierarchical node network of embodiment 17, wherein the master node is further operative to associate with the ID node by being operative to establish an active association between the master node and the ID node, the active association reflecting an authorized connection between the master node and the ID node based upon an authority granted by the server.

20. The hierarchical node network of embodiment 19, wherein the authorized connection between the master node and the ID node is preauthorized by the server to avoid the need for the master node to request the authority from the server after detecting the signal broadcast from the ID node.

21. The hierarchical node network of embodiment 17, wherein the piece of equipment comprises one from a group comprising medical equipment, office equipment, industrial equipment, manufacturing equipment, construction equipment, transportation equipment, laboratory equipment, sporting equipment, automotive equipment, marine equipment, and mining equipment.

22. The hierarchical node network of embodiment 17, wherein the ID node is further operative to detect by being operative to detect a movement status related to the operation of the piece of equipment.

23. The hierarchical node network of embodiment 17, wherein the ID node is further operative to detect by being operative to detect an activation status related to the operation of the piece of equipment.

24. The hierarchical node network of embodiment 17, wherein the ID node is further operative to detect by being operative to detect a usage status related to the operation of the piece of equipment.

25. The hierarchical node network of embodiment 17, wherein the server is further operative to initiate the responsive action by being operative to update a billing attribute related to the operation of the piece of equipment.

26. The hierarchical node network of embodiment 17, wherein the server is further operative to initiate the responsive action by being operative to update an inventory attribute related to the operation of the piece of equipment.

27. The hierarchical node network of embodiment 17, wherein the server is further operative to initiate the responsive action by being operative to update a maintenance attribute related to the operation of the piece of equipment.

28. The hierarchical node network of embodiment 17, wherein the server is further operative to initiate the responsive action by being operative to update a usage attribute related to the operation of the piece of equipment.

29. The hierarchical node network of embodiment 28, wherein the usage attribute related to the operation of the piece of equipment further comprises a usage time associated with an operator of the piece of equipment.

30. The hierarchical node network of embodiment 17, wherein the server is further operative to initiate the responsive action by being operative to update a quality assurance attribute related to the operation of the piece of equipment.

31. The hierarchical node network of embodiment 17, wherein the server is further operative to determine the location of the ID node by being operative to track the location of the ID node over time.

32. The hierarchical node network of embodiment 17, wherein the server is further operative to determine the location of the ID node by being operative to track the location of the ID node over time and refine the location of the ID node based upon context data related to an operating environment of the piece of equipment and the ID node.

Further Embodiment 31—Node-Enabled Monitoring of Activity of a Person Using a Hierarchical Node Network 1. A method for monitoring an activity of a person using a hierarchical node network having at least an ID node, a master node, and a server, the method comprising: associating, by the master node, the master node and the ID node when the master node detects a signal broadcast from the ID node, wherein the ID node is associated with a person and operative to monitor the activity of the person and to communicate directly with the master node but is unable to directly communicate with the server, and wherein the master node is operative to directly communicate with the server and separately communicate with the ID node; determining, by the server, a location of the ID node; detecting, by the ID node, an actionable event related to the activity of the person based upon the location of the ID node; transmitting, by the ID node to the master node, a message reporting the actionable event; notifying the server by the master node about the actionable event; and initiating, by the server, a responsive action based upon the notification.

2. The method of embodiment 1, wherein the associating step further comprises establishing a passive association between the master node and the ID node without requiring without requiring a prior authority granted by the server.

3. The method of embodiment 1, wherein the associating step further comprises establishing an active association between the master node and the ID node, the active association reflecting an authorized connection between the master node and the ID node based upon an authority granted by the server.

4. The method of embodiment 3, wherein the authorized connection between the master node and the ID node is pre-authorized by the server to avoid the need for the master node to request the authority from the server after detecting the signal broadcast from the ID node.

5. The method of embodiment 1, wherein the step of detecting further comprises detecting, by the ID node, a movement status related to the activity of the person based upon the location of the ID node, the movement status being the actionable event.

6. The method of embodiment 5, wherein the person is a medical patient.

7. The method of embodiment 6, wherein the medical patient is located in a healthcare facility and wherein the ID node is integrated into a healthcare facility identification.

8. The method of embodiment 7, wherein the movement status indicates the medical patient has left the healthcare facility based upon the location of the ID node.

9. The method of embodiment 7, wherein the movement status indicates the medical patient has entered a part of the healthcare facility based upon the location of the ID node, the part of the healthcare facility being a location where the medical patient is not anticipated to be within the healthcare facility.

10. The method of embodiment 6, wherein the step of initiating the responsive action further comprises notifying, by the server, a user access device associated with a relative of the medical patient.

11. The method of embodiment 7, wherein the step of initiating the responsive action further comprises notifying, by the server, a user access device associated with a healthcare provider affiliated with the healthcare facility.

12. The method of embodiment 7, wherein the step of initiating the responsive action further comprises: tracking, by the server, the movements of the medical patient to determine a pattern of movement; correlating the determined pattern of movement to a recorded change in patient behavior; and notifying, by the server, a user access device associated with a healthcare provider affiliated with the healthcare facility, the notification indicating the relationship between the determined pattern of movement and the recorded change in patient behavior.

13. The method of embodiment 1, wherein the person is a medical patient; wherein the ID node comprises a mobile sensor node associated with the person, the mobile sensor node being operative to sense a quantifiable health characteristic related to the health of the medical patient; and wherein the step of detecting the actionable event further comprises: sensing the quantifiable health characteristic using the mobile sensor node, and detecting the actionable event when the sensed quantifiable health characteristic meets a predetermined condition.

14. The method of embodiment 1, wherein the person is a medical patient located at a residence.

15. The method of embodiment 14, wherein the movement status indicates the medical patient has left the residence based upon the location of the ID node.

16. The method of embodiment 14, wherein the movement status indicates the medical patient is not moving.

17. The method of embodiment 14, wherein the movement status indicates the medical patient is moving with a pattern of movement indicative of a medical condition.

18. The method of embodiment 14, wherein the step of initiating the responsive action further comprises notifying, by the server, a user access device associated with a relative of the medical patient.

19. The method of embodiment 14, wherein the step of initiating the responsive action further comprises notifying, by the server, a user access device associated with a healthcare provider.

20. The method of embodiment 1, wherein the step of determining the location of the ID node further comprises tracking the location of the ID node over time and refining the location of the ID node based upon context data related to an operating environment of the person and the ID node.

21. A hierarchical node network for monitoring an activity of a person, the hierarchical node network comprising: a server; a master node operative to directly communicate with the server over a longer range communication path; and an ID node associated with the person and operative to monitor the activity of the person, the ID node being further operative to wirelessly communicate directly with the master node over a shorter range communication path but is unable to directly communicate with the server; wherein ID node is operative to detect an actionable event related to the activity of the person, and transmit a message to the master node reporting the actionable event; wherein the master node is operative to associate with the ID node upon detection of a signal broadcast from the ID node, and notify the server about the actionable event reported in the message received from the ID node; and wherein the server is operative to: determine a location of the ID node, receive the notification from the master node regarding the actionable event, and initiate a responsive action based upon the notification.

22. The hierarchical node network of embodiment 21, wherein the master node is further operative to associate by being operative to establish a passive association between the master node and the ID node without requiring without requiring a prior authority granted by the server.

23. The hierarchical node network of embodiment 21, wherein the master node is further operative to associate by being operative to establish an active association between the master node and the ID node, the active association reflecting an authorized connection between the master node and the ID node based upon an authority granted by the server.

24. The hierarchical node network of embodiment 23, wherein the authorized connection between the master node and the ID node is preauthorized by the server to avoid the need for the master node to request the authority from the server after detecting the signal broadcast from the ID node.

25. The hierarchical node network of embodiment 21, wherein the ID node is further operative to detect the actionable event by being operative to detect a movement status related to the activity of the person based upon the location of the ID node, the movement status being the actionable event.

26. The hierarchical node network of embodiment 25, wherein the person is a medical patient.

27. The hierarchical node network of embodiment 26, wherein the medical patient is located in a healthcare facility and wherein the ID node is integrated into a healthcare facility identification.

28. The hierarchical node network of embodiment 27, wherein the movement status indicates the medical patient has left the healthcare facility based upon the location of the ID node.

29. The hierarchical node network of embodiment 27, wherein the movement status indicates the medical patient has entered a part of the healthcare facility based upon the location of the ID node, the part of the healthcare facility being a location where the medical patient is not anticipated to be within the healthcare facility.

30. The hierarchical node network of embodiment 26, wherein the server is further operative to initiate the responsive action by being operative to notify a user access device associated with a relative of the medical patient.

31. The hierarchical node network of embodiment 27, wherein the server is further operative to initiate the responsive action by being operative to notify a user access device associated with a healthcare provider affiliated with the healthcare facility.

32. The hierarchical node network of embodiment 27, wherein the server is further operative to initiate the responsive action by being operative to: track the movements of the medical patient to determine a pattern of movement; correlate the determined pattern of movement to a recorded change in patient behavior; and notify a user access device associated with a healthcare provider affiliated with the healthcare facility, the notification indicating the relationship between the determined pattern of movement and the recorded change in patient behavior.

33. The hierarchical node network of embodiment 21, wherein the person is a medical patient; wherein the ID node further comprises a sensor operative to sense a quantifiable health characteristic related to the health of the medical patient; and wherein the ID node is further operative to detect the actionable event by being operative to: sense the quantifiable health characteristic using the mobile sensor node, and detect the actionable event when the sensed quantifiable health characteristic meets a predetermined condition.

34. The hierarchical node network of embodiment 21, wherein the person is a medical patient located at a residence.

35. The hierarchical node network of embodiment 21, wherein the movement status indicates the medical patient has left the residence based upon the location of the ID node.

36. The hierarchical node network of embodiment 21, wherein the movement status indicates the medical patient is not moving.

37. The hierarchical node network of embodiment 21, wherein the movement status indicates the medical patient is moving with a pattern of movement indicative of a medical condition.

38. The hierarchical node network of embodiment 21, wherein the server is further operative to initiate the responsive action by being operative to notify a user access device associated with a relative of the medical patient.

39. The hierarchical node network of embodiment 21, wherein the server is further operative to initiate the responsive action by being operative to notify a user access device associated with a healthcare provider.

40. The hierarchical node network of embodiment 21, wherein the server is further operative to determine the location of the ID node by being operative to: track the location of the ID node over time; and refine the location of the ID node based upon context data related to an operating environment of the person and the ID node.

Further Embodiment 32—Node-Enabled Preparation Related to Medical Treatment for a Patient Using a Hierarchical Node Network 1. A method for initiating a pre-staged preparation related to a medical treatment to be provided to a patient at a healthcare facility using a hierarchical node network having an ID node, a master node, and a server, the method comprising: associating, by the master node, the master node and the ID node when the master node detects a signal broadcast from the ID node as the patient approaches the healthcare facility, wherein the ID node is associated with the patient seeking the medical treatment, the ID node being operative to communicate directly with the master node, and wherein the master node is operative to directly communicate with the server and separately communicate with the ID node; receiving, by the master node, medical status information securely transmitted by the ID node related to the patient; transmitting, by the master node to the server, the medical status information received from the ID node; determining, by the server, the location of the ID node; and initiating, by the server, a pre-staged preparation related to the patient visiting the healthcare facility for the medical treatment based upon the determined location of the ID node and the medical status information.

2. The method of embodiment 1 further comprising receiving, by the master node, an authorization from the server to actively associate with the ID node.

3. The method of embodiment 2, wherein the step of receiving the authorization further comprises receiving, by the master node, the authorization from the server to actively associate the master node and the ID node prior to detecting the signal broadcast from the ID node.

4. The method of embodiment 2, wherein the associating step further comprises establishing an active association between the master node and the ID node when the master node detects the signal broadcast from the ID node as the patient approaches the healthcare facility.

5. The method of embodiment 4, wherein the active association reflects an authorized connection between the master node and the ID node based upon the authorization, the authorized connection providing a secure communication path between the master node and the ID node for privately sharing data between the master node and the ID node.

6. The method of embodiment 1, wherein the ID node comprises a user access device operating as the ID node.

7. The method of embodiment 6, wherein the step of determining the location of the ID node further comprises the steps of: providing, by the server to the master node, an instruction to change a power characteristic of the user access device operating as the ID node; and sending, by the master node, the instruction to the user access device operating as the ID node.

8. The method of embodiment 7, wherein the step of providing the instruction to change the power characteristic further comprises the steps of: refining a level of the power characteristic to a refined value based upon context data related to an anticipated operating environment of the user access device operating as the ID node; and providing the instruction to change the power characteristic of the user access device operating as the ID node to the refined value.

9. The method of embodiment 7, wherein the step of refining further comprises refining the level of the power characteristic to the refined value based upon the context data related to the anticipated operating environment of the user access device operating as the ID node as the user access device is anticipated to move to a predicted location within the healthcare facility, wherein the predicted location is related to the medical status information.

10. The method of embodiment 1, wherein the medical status information comprises at least one from a group comprising insurance information, address information, information related to a reason for the patient visiting the healthcare facility, and information related to a type of physician anticipated to be seen by the patient while visiting the healthcare facility.

11. The method of embodiment 1, wherein the medical status information comprises condition information securely transmitted by the ID node related to a health condition of the patient.

12. The method of embodiment 11, wherein the condition information received comprises at least a symptom indication related to the health condition of the patient.

13. The method of embodiment 6, wherein the step of initiating the pre-staged preparation further comprises the steps of: providing a direction message from the server to the master node, the direction message comprising a set of directions for the patient to a predicted location within the healthcare facility based upon the determined location of the ID node and the medical status information; and sending, by the master node, the direction message to the user access device operating as the ID node for display on a user interface of the user access device.

14. The method of embodiment 6, wherein the step of initiating the pre-staged preparation further comprises the steps of: accessing, by the server, a record in a record database, wherein the record is related to the patient based upon the determined location of the user access device operating as the ID node and the medical status information; and transmitting, by the server, the accessed record to a user access device associated with a part of the healthcare facility related to the condition information to pre-stage the accessed record before the user access device operating as the ID node is located at the part of the healthcare facility related to the medical status information.

15. The method of embodiment 1 further comprising adjusting the pre-staged preparation based upon an updated location of the patient.

16. The method of embodiment 6, wherein the step of initiating the pre-staged preparation further comprises the steps of: providing a context-driven inquiry from the server to the master node, the context driven inquiry comprising one or more pre-screening prompts for additional information from the patient based upon the medical status information; sending, by the master node, one or more pre-screening prompts to the user access device operating as the ID node for display on a user interface of the user access device; receiving, by the master node, feedback from the user access device operating as the ID node, the feedback providing enhanced medical status information; and transmitting the feedback to the server for use in refining the pre-staged preparation related to the patient visiting the healthcare facility for the medical treatment.

17. A hierarchical node network for initiating a pre-staged preparation related to medical treatment to be provided to a patient at a healthcare facility, the hierarchical node network comprising: a server, a master node operative to wirelessly communicate directly with the server over a longer range communication path; an ID node associated with the person and operative to wirelessly communicate directly with the master node over a shorter range communication path; wherein ID node is operative to broadcast a signal as the patient approaches the healthcare facility, and securely transmit medical status information to the master node after associating with the master node, the medical status information being related to the patient; wherein the master node is operative to detect the signal broadcast from the ID node as the patient approaches the healthcare facility, associate with the ID node upon detection of the signal broadcast from the ID node, receive the medical status information securely transmitted by the ID node, and notify the server with a message about the received medical status information; wherein the server is operative to: determine a location of the ID node, receive the message from the master node regarding the received medical status information, and initiate a pre-staged preparation related to the patient visiting the healthcare facility for the medical treatment based upon the determined location of the ID node and the received medical status information.

18. The hierarchical node network of embodiment 17, wherein the master node is further operative to receive an authorization from the server to actively associate with the ID node.

19. The hierarchical node network of embodiment 18, wherein the master node is further operative to receive the authorization from the server to actively associate the master node and the ID node prior to detecting the signal broadcast from the ID node.

20. The hierarchical node network of embodiment 18, wherein the master node is further operative to receive the authorization from the server to establish an active association between the master node and the ID node when the master node detects the signal broadcast from the ID node as the patient approaches the healthcare facility 21. The hierarchical node network of embodiment 20, wherein the active association reflects an authorized connection between the master node and the ID node based upon the authorization from the server, the authorized connection providing a secure communication path between the master node and the ID node for privately sharing data between the master node and the ID node.

22. The hierarchical node network of embodiment 17, wherein the ID node comprises a user access device operating as the ID node.

23. The hierarchical node network of embodiment 22, wherein the server is operative to determine the location of the ID node by being further operative to provide a power message to the master node to cause the master node to send an instruction to the user access device operating as the ID node to change a power characteristic of the user access device operating as the ID node; and wherein the master node is further operative to receive the power message and transmit the instruction to the user access device operating as the ID node.

24. The hierarchical node network of embodiment 23, wherein the server is operative to provide the power message to change the power characteristic by being further operative to: refine a level of the power characteristic to a refined value based upon context data related to an anticipated operating environment of the user access device operating as the ID node; and provide the power message to the master node to change the power characteristic of the user access device operating as the ID node to the refined value.

25. The hierarchical node network of embodiment 23, wherein the server is operative to refine the level of the power characteristic by being further operative to refine the level of the power characteristic to the refined value based upon the context data related to the anticipated operating environment of the user access device operating as the ID node as the user access device is anticipated to move to a predicted location within the healthcare facility, wherein the predicted location is related to the medical status information.

26. The hierarchical node network of embodiment 17, wherein the medical status information comprises at least one from a group comprising insurance information, address information, information related to a reason for the patient visiting the healthcare facility, and information related to a type of physician anticipated to be seen by the patient while visiting the healthcare facility.

27. The hierarchical node network of embodiment 17, wherein the medical status information comprises condition information securely transmitted by the ID node related to a health condition of the patient.

28. The hierarchical node network of embodiment 27, wherein the condition information received comprises at least a symptom indication related to the health condition of the patient.

29. The hierarchical node network of embodiment 22, wherein the server is operative to initiate the pre-staged preparation by being further operative to provide a direction message from the server to the master node, wherein the direction message comprises a set of directions for the patient to a predicted location within the healthcare facility based upon the determined location of the ID node and the medical status information; and wherein the master node is further operative to send the direction message to the user access device operating as the ID node for display on a user interface of the user access device.

30. The hierarchical node network of embodiment 22, wherein the server is operative to initiate the pre-staged preparation by being further operative to: access a record database for a record related to the patient based upon the determined location of the user access device operating as the ID node and the medical status information; and transmit the accessed record to a user access device associated with a part of the healthcare facility related to the condition information to pre-stage the accessed record before the user access device operating as the ID node is located at the part of the healthcare facility related to the medical status information.

31. The hierarchical node network of embodiment 17, wherein the server is further operative to adjust the pre-staged preparation based upon an updated location of the patient.

32. The method of embodiment 22, wherein the server is further operative to provide a context-driven inquiry to the master node, the context driven inquiry comprising one or more pre-screening prompts for additional information from the patient based upon the medical status information; and wherein the master node is further operative to: send one or more pre-screening prompts to the user access device operating as the ID node for display on a user interface of the user access device, receive feedback from the user access device operating as the ID node, the feedback providing enhanced medical status information, and transmit the feedback to the server for use in refining the pre-staged preparation related to the patient visiting the healthcare facility for the medical treatment.

Further Embodiment 33—Node-Enabled Packaging Materials Used to Ship an Item

1. A method for using node-enabled packaging material as part of a container for an item to be shipped, comprising: forming at least a part of the container with the packaging material; activating an ID node integrated as part of the packaging material, wherein the ID node is operative to communicate directly with a master node in a wireless node network but is unable to directly communicate with a server in the wireless node network; and registering shipping information with the server via a user access device operated by a shipping customer, the shipping information being related to the container and the ID node integrated as part of the packaging material of the container.

2. The method of embodiment 1 further comprising the step of sealing the item within the container having the ID node integrated as part of the packaging material of the container.

3. The method of embodiment 1 further comprising the step of placing the container at a first hand-off point for shipping the container.

4. The method of embodiment 3, wherein the step of placing the container further comprises providing the container to a courier associated with the master node near the first hand-off point.

5. The method of embodiment 3, wherein the step of placing the container further comprises depositing the container in a node-enabled logistics receptacle serviced by a courier, the node-enabled logistics receptacle being at the first hand-off point.

6. The method of embodiment 1, wherein the packaging material comprises one from a group consisting of a fiberboard container sheet, a packaging separator sheet, and cushioning material sheet.

7. The method of embodiment 1, wherein the ID node integrated as part of the packaging material of the container maintains container content information describing the item to be shipped.

8. The method of embodiment 7, wherein the container content information further comprises customs information for a customs declaration on the item in the container.

9. The method of embodiment 1, wherein the step of activating the ID node further comprises causing a power source within the ID node to energize the ID node integrated as part of the packaging material of the container and to turn on a status light of the ID node.

10. The method of embodiment 1, wherein the step of activating the ID node further comprises causing the ID node to change from a standby mode to a fully functioning mode.

11. The method of embodiment 1, wherein the step of registering the shipping information further comprises: entering a destination address for the container into the user access device as a first part of the shipping information; entering a tracking number into the user access device as a second part of the shipping information, the tracking number being related to the container; entering a node identification into the user access device as a third part of the shipping information, the node identification being related to the ID node integrated as part of the packaging material of the container; and causing the user access device to transmit the shipping information to the server.

12. A method for using node-enabled packaging material as part of a container for an item to be shipped, comprising: forming at least a part of the container with the packaging material; activating a node integrated as part of the packaging material, wherein the node is operative to communicate one or more network devices in a wireless node network; and registering shipping information with a server in the wireless node network via a user access device operated by a shipping customer, the shipping information being related to the container and the ID node integrated as part of the packaging material of the container.

13. The method of embodiment 12, wherein the node integrated as part of the packaging material comprises an ID node operative to communicate directly with a master node in the wireless node network but is unable to directly communicate with the server.

14. The method of embodiment 12, wherein the node integrated as part of the packaging material comprises a master node operative to communicate directly with the server.

15. The method of embodiment 12, wherein the packaging material comprises one from a group consisting of a fiberboard container sheet, a packaging separator sheet, and cushioning material sheet.

16. The method of embodiment 12, wherein the node integrated as part of the packaging material of the container maintains container content information describing the item to be shipped.

17. A node-enabled apparatus for packaging an item to be shipped, comprising: packaging material used as part of a container that packages the item to be shipped; an ID node integrated as part of the packaging material, wherein the ID node is operative to communicate directly with a master node in a wireless node network but is unable to directly communicate with a server in the wireless node network, the ID node further comprising a processing unit, a communication interface coupled to the processing unit, the communication interface providing a communication path to the master node, the communication interface being operative to receive a message broadcast from the master node and provide the message to the processing unit, a volatile memory coupled to the processing unit, a memory storage coupled to the processing unit, the memory storage maintaining code for execution by the processing unit and shipping information related to the container and the ID node integrated as part of the packaging material, a power source for energizing the ID node; and wherein the processing unit, when executing the code, is operative to receive the shipping information from a first node in the wireless node network, cause an advertising signal to be broadcast over the communication interface to the master node, and share at least a part of the shipping information with the master node.

18. The node-enabled apparatus of embodiment 17, wherein the ID node integrated as part of the packaging material further comprises a status light indicative of an activated state of the ID node.

19. The node-enabled apparatus of embodiment 18, wherein the processing unit is further operative to cause the status light to blink in a designated pattern upon receiving the shipping information.

20. The node-enabled apparatus of embodiment 18, wherein the status light is disposed within the packaging material but viewable from outside the container.

21. The node-enabled apparatus of embodiment 20, wherein the packaging material includes an opening and wherein the status light is disposed in a configuration within the packaging material where the status light aligns with the opening.

22. The node-enabled apparatus of embodiment 18, wherein the status light is disposed in a recessed part of the packaging material.

23. The node-enabled apparatus of embodiment 18, wherein the status light is disposed in a translucent part of the packaging material.

24 The node-enabled apparatus of embodiment 18, wherein the status light indicates a sensed error.

25 The node-enabled apparatus of embodiment 18, wherein the status light indicates a status of the item.

26. The node-enabled apparatus of embodiment 17, wherein the ID node integrated as part of the packaging material further comprises a switch coupled to the power source for allowing the power source to energize the ID node.

27. The node-enabled apparatus of embodiment 26, wherein the switch is magnetically activated when the switch detects a set of magnetic field changes.

28. The node-enabled apparatus of embodiment 26, wherein the detected set of magnetic field changes detected by the switch further comprise a series of magnetic field changes over a period of time that define an activation pattern.

29. The node-enabled apparatus of embodiment 17, wherein the packaging material further comprises at least a sheet of packaging material; and wherein the ID node integrated as part of the packaging material is embedded within the sheet of packaging material.

30. The node-enabled apparatus of embodiment 17, wherein the packaging material comprises one from a group consisting of a fiberboard container sheet, a packaging separator sheet, and cushioning material sheet.

Further Embodiment 34—Node-Enabled Proactive Notification of a Shipping Customer Regarding an Alternative Shipping Solution 1. A method for proactively notifying a shipping customer using a wireless node network about an alternative shipping solution when shipping a package, comprising: detecting a signal broadcast by a user access device related to a shipping customer as the device approaches a master node related to a shipping facility, the shipping customer approaching the shipping facility with the package to be shipped, wherein the user access device is operating as a node in the network; associating the user access device with the shipping facility master node; and providing a proactive notification about an alternative shipping solution to the user access device based upon a shipping status for the shipping facility.

2. The method of embodiment 1 further comprising receiving, by the shipping facility master node from a server in the network, shipping information related to the package to be shipped; and wherein the providing step further comprises providing the proactive notification about the alternative shipping solution to the user access device based upon the shipping information and the shipping status for the shipping facility.

3. The method of embodiment 1, wherein the providing step further comprises providing the proactive notification as a prompt message to be displayed on the user access device.

4. The method of embodiment 3 further comprising the step of receiving a confirmation message originating from the user access device.

5. The method of embodiment 1, wherein the user access device is one from a group comprising a laptop computer, a tablet device, a personal area network device, a smartphone device, and a smart wearable device.

6. The method of embodiment 5, wherein the user access device is operating as an ID node in the network, wherein the ID node is operative to directly communicate with the master node related to the shipping facility but unable to directly communicate with the server in the network.

7. The method of embodiment 5, wherein the user access device is operating as another master node in the network, wherein the another master node is operative to directly communicate with the master node related to the shipping facility and able to directly communicate with the server in the network.

8. The method of embodiment 1, wherein the step of providing the proactive notification to the user access device is performed by one of the shipping facility master node and the server.

9. The method of embodiment 1, wherein the shipping status for the shipping facility further comprises whether the shipping facility is not currently open for business.

10. The method of embodiment 1, wherein the shipping status for the shipping facility further comprises whether the shipping facility is no longer scheduled for a pickup event by a desired shipping courier identified in the shipping information.

11. The method of embodiment 1, wherein the shipping status for the shipping facility further comprises whether the shipping facility is unable to accept any package for shipment.

12. The method of embodiment 1, wherein the shipping status for the shipping facility further comprises facility operational information maintained by the server on whether the shipping facility is unable to accept a category of shipment related to the package.

13. The method of embodiment 1, wherein the shipping status for the shipping facility further comprises whether the shipping facility is unable to accept a package for shipment by a desired shipping service identified in the shipping information.

14. The method of embodiment 1, wherein the proactive notification about the alternative shipping solution further comprises information about an alternative shipping facility that is able to accept the package for shipment as the alternative shipping solution.

15. The method of embodiment 1, wherein the proactive notification about the alternative shipping solution further comprises information about a node-enabled logistics receptacle that is able to accept the package for shipment as the alternative shipping solution.

16. The method of embodiment 15, wherein the information about the node-enabled logistics receptacle that is able to accept the package for shipment further comprises directions to the node-enabled logistics receptacle.

17. The method of embodiment 1, wherein the step of providing the proactive notification about the alternative shipping solution further comprises: determining, by the server, a location of the user access device; determining if the shipping information and the shipping status for the shipping facility indicate the shipping facility is unable to accept the package for shipment; identifying a node-enabled logistics receptacle near the shipping facility as the alternative shipping solution; and transmitting the proactive notification to the user access device, the proactive notification providing directions to the identified node-enabled logistics receptacle.

18. The method of embodiment 17, wherein the identifying step further comprises: determining one of a plurality of node-enabled logistics receptacles is a closest unit to the user access device with a capacity to accept the package for shipment; and identifying the determined one of the node-enabled logistics receptacles to be the alternative shipping solution comprising the node-enabled logistics receptacle near the shipping facility.

19. A system for proactively notifying a shipping customer about an alternative shipping solution when shipping a package, the system comprising: a server in a wireless node network; and a master node in the wireless node network, the master node being related to a shipping facility, the shipping facility master node further comprising: a processing unit, a memory coupled to the processing unit, the memory maintaining code for execution by the processing unit, a short-range communication interface coupled to the processing unit and operative to communicate with another network device in the network, and a longer-range communication interface coupled to the processing unit and operative to directly communicate with the server; and wherein the processing unit of the shipping facility master node, when executing the code maintained on the memory, is operative to detect a signal broadcast by a user access device related to a shipping customer as the device approaches the shipping facility master node, the shipping customer approaching the shipping facility with the package to be shipped, wherein the user access device is operating as the another network device in the network, associate the user access device with the shipping facility master node, receive shipping information from the server, the shipping information being related to the package to be shipped, generate a proactive notification about an alternative shipping solution based upon the shipping information and a shipping status for the shipping facility, and cause the short-range communication interface to transmit the proactive notification to the user access device as the user access device approaches the shipping facility.

20. The system of embodiment 19, wherein the user access device is one from a group comprising a laptop computer, a tablet device, a personal area network device, a smartphone device, and a smart wearable device.

21. The system of embodiment 20, wherein the user access device is operating as an ID node in the network, wherein the ID node is operative to directly communicate with the shipping facility master node but unable to directly communicate with the server in the network.

22. The system of embodiment 20, wherein the user access device is operating as another master node in the network, wherein the another master node is operative to directly communicate with the shipping facility master node and able to directly communicate with the server in the network.

23. The system of embodiment 19, wherein the server is further operative to provide the proactive notification to the user access device.

24. The system of embodiment 19, wherein the shipping status for the shipping facility further comprises facility operational information maintained by the server on whether the shipping facility is not currently open for business.

25. The system of embodiment 19, wherein the shipping status for the shipping facility further comprises facility operational information maintained by the server on whether the shipping facility is no longer scheduled for a pickup event by a desired shipping courier identified in the shipping information.

26. The system of embodiment 19, wherein the shipping status for the shipping facility further comprises facility operational information maintained by the server on whether the shipping facility is unable to accept any package for shipment.

27. The system of embodiment 19, wherein the shipping status for the shipping facility further comprises facility operational information maintained by the server on whether the shipping facility is unable to accept a category of shipment related to the package.

28. The system of embodiment 19, wherein the shipping status for the shipping facility further comprises facility operational information maintained by the server on whether the shipping facility is unable to accept a package for shipment by a desired shipping service identified in the shipping information.

29. The system of embodiment 19, wherein the proactive notification about the alternative shipping solution further comprises information about an alternative shipping facility that is able to accept the package for shipment as the alternative shipping solution.

30. The system of embodiment 19, wherein the proactive notification about the alternative shipping solution further comprises information about a node-enabled logistics receptacle that is able to accept the package for shipment as the alternative shipping solution.

31. The system of embodiment 30, wherein the information about the node-enabled logistics receptacle that is able to accept the package for shipment further comprises directions to the node-enabled logistics receptacle.

32. The system of embodiment 19, wherein processing unit is further operative to provide generate the proactive notification about the alternative shipping solution by being operative to: determine a location of the user access device; determine if the shipping information and the shipping status for the shipping facility indicate the shipping facility is unable to accept the package for shipment; and identify a node-enabled logistics receptacle near the shipping facility as the alternative shipping solution.

33. The system of embodiment 32, wherein the processing unit is further operative to identify the node-enabled logistics receptacle near the shipping facility as the alternative shipping solution by being operative to: determine one of a plurality of node-enabled logistics receptacles is a closest unit to the user access device with a capacity to accept the package for shipment; and identify the determined one of the node-enabled logistics receptacles to be the alternative shipping solution comprising the node-enabled logistics receptacle near the shipping facility.

Further Embodiment 35—Methods and Apparatus for Assessing a Current Location of a Node-Enabled Logistics Receptacle 1. A method for assessing a current location for a node-enabled logistics receptacle, the method comprising: detecting a level of wireless communication signal activity on a communication interface on the node-enabled logistics receptacle, wherein the node-enabled logistics receptacle also being able to receive and temporarily maintain custody of a package being shipped; recording the detected level of wireless communication signal activity over a predetermined period of time in a memory disposed in the node-enabled logistics receptacle; comparing, by the node-enabled logistics receptacle, the recorded level of wireless communication signal activity over the predetermined period of time to a user criteria level for the node-enabled logistics receptacle; and assessing the current location for the node-enabled logistics receptacle based upon the comparison of the recorded level and the user criteria level.

2. The method of embodiment 1, wherein the detecting step further comprises detecting the level of wireless communication signal activity as detecting a number of signals broadcast by at least one wireless user access device, the at least one wireless user access device being operative to allow a user to interact with one or more network devices of a wireless node network.

3. The method of embodiment 2, wherein the at least one wireless user access device is a network device from a group comprising a laptop computer, a tablet device, a personal area network device, a smartphone device, and a smart wearable device.

4. The method of embodiment 2, wherein the user criteria level comprises a threshold number of signals broadcast by the at least one wireless user access device and detected by the node-enabled logistics receptacle.

5. The method of embodiment 1, wherein the detected level wireless communication signal activity over a predetermined period of time further is based upon a number of detected signals broadcast by at least one wireless user access device and a strength of each of the detected signals broadcast by the at least one wireless user access device.

6. The method of embodiment 5, wherein the user criteria level comprises a threshold number of detected signals broadcast by the at least one wireless user access device.

7. The method of embodiment 5, wherein the user criteria level comprises a threshold number of detected signals broadcast by the at least one wireless user access device having at least a threshold strength.

8. The method of embodiment 5, wherein the user criteria level comprises a threshold number of detected signals broadcast by the at least one wireless user access device having a minimum relative received signal strength.

9. The method of embodiment 1 further comprising transmitting an alert message to another network device in the network when the node-enabled logistics receptacle assesses the current location does not meet the user criteria level.

10. The method of embodiment 9, wherein the alert message provides the recorded level of wireless communication signal activity over the predetermined period of time to at least one of a master node in the network or a server in the network.

11. A non-transitory computer-readable medium containing instructions which when executed on a processor performs a method for assessing a current location for a node-enabled logistics receptacle, the method comprising: detecting a level of wireless communication signal activity on a communication interface on the node-enabled logistics receptacle, wherein the node-enabled logistics receptacle also being able to receive and temporarily maintain a package being shipped; recording the detected level of wireless communication signal activity over a predetermined period of time in a memory disposed in the node-enabled logistics receptacle; comparing, by the node-enabled logistics receptacle, the recorded level of wireless communication signal activity over the predetermined period of time to a user criteria level for the node-enabled logistics receptacle; and assessing the current location for the node-enabled logistics receptacle based upon the comparison of the recorded level and the user criteria level.

12. The non-transitory computer-readable medium of embodiment 11, wherein the detecting step further comprises detecting the level of wireless communication signal activity as detecting a number of signals broadcast by at least one wireless user access device, the at least one wireless user access device being operative to allow a user to interact with one or more network devices of a wireless node network.

13. The non-transitory computer-readable medium of embodiment 12, wherein the at least one wireless user access device is a network device from a group comprising a laptop computer, a tablet device, a personal area network device, a smartphone device, and a smart wearable device.

14. The non-transitory computer-readable medium of embodiment 12, wherein the user criteria level comprises a threshold number of signals broadcast by the at least one wireless user access device and detected by the node-enabled logistics receptacle.

15. The non-transitory computer-readable medium of embodiment 11, wherein the detected level wireless communication signal activity over a predetermined period of time further is based upon a number of detected signals broadcast by at least one wireless user access device and a strength of each of the detected signals broadcast by the at least one wireless user access device.

16. The non-transitory computer-readable medium of embodiment 15, wherein the user criteria level comprises a threshold number of detected signals broadcast by the at least one wireless user access device.

17. The non-transitory computer-readable medium of embodiment 15, wherein the user criteria level comprises a threshold number of detected signals broadcast by the at least one wireless user access device having at least a threshold strength.

18. The non-transitory computer-readable medium of embodiment 15, wherein the user criteria level comprises a threshold number of detected signals broadcast by the at least one wireless user access device having a minimum relative received signal strength.

19. The non-transitory computer-readable medium of embodiment 11, wherein the method further comprises transmitting an alert message to another network device in the network when the node-enabled logistics receptacle assesses the current location does not meet the user criteria level.

20. The non-transitory computer-readable medium of embodiment 19, wherein the alert message provides the recorded level of wireless communication signal activity over the predetermined period of time to at least one of a master node in the network or a server in the network.

21. A node-enabled logistics receptacle apparatus in a wireless node network, comprising: a logistics receptacle for receiving and temporarily maintaining a package being shipped, the receptacle having an entrance opening through which the package is received and a temporary storage area where the package is temporarily and securely maintained until an authorized pickup; and a node assembled with the receptacle, the node further comprising a node processing unit, a node memory storage coupled to the node processing unit, the node memory storage maintaining code for execution by the node processing unit and a user criteria level related to wireless communication signal activity near the node assembled with the receptacle, and at least one communication interface coupled to the node processing unit, the at least one communication interface being collectively operative to detect a signal broadcast from a user access device and communicate with another network device in the wireless node network; wherein the node processing unit, when executing the code maintained on the node memory storage, is operative to detect a level of wireless communication signal activity on the at least one communication interface, record the detected level of wireless communication signal activity over a predetermined period of time in the node memory storage, compare the recorded level of wireless communication signal activity over the predetermined period of time to the user criteria level for the node-enabled logistics receptacle maintained in the node memory storage, assess the current location for the node-enabled logistics receptacle based upon the comparison of the recorded level and the user criteria level, and transmit an alert message to another network device in the network when the node processing unit assesses the current location does not meet the user criteria level.

22. The node-enabled logistics receptacle apparatus of embodiment 21, wherein the node processing unit is further operative to detect the level of wireless communication signal activity by being operative to detect a number of signals broadcast by at least one wireless user access device, the at least one wireless user access device being operative to allow a user to interact with one or more network devices of a wireless node network.

23. The node-enabled logistics receptacle apparatus of embodiment 22, wherein the at least one wireless user access device is a network device from a group comprising a laptop computer, a tablet device, a personal area network device, a smartphone device, and a smart wearable device.

24. The node-enabled logistics receptacle apparatus of embodiment 22, wherein the user criteria level comprises a threshold number of signals broadcast by the at least one wireless user access device and detected by the node-enabled logistics receptacle.

25. The node-enabled logistics receptacle apparatus of embodiment 21, wherein the detected level wireless communication signal activity over the predetermined period of time further is based upon a number of detected signals broadcast by at least one wireless user access device and a strength of each of the detected signals broadcast by the at least one wireless user access device.

26. The node-enabled logistics receptacle apparatus of embodiment 25, wherein the user criteria level comprises a threshold number of detected signals broadcast by the at least one wireless user access device.

27. The node-enabled logistics receptacle apparatus of embodiment 25, wherein the user criteria level comprises a threshold number of detected signals broadcast by the at least one wireless user access device having at least a threshold strength.

28. The node-enabled logistics receptacle apparatus of embodiment 25, wherein the user criteria level comprises a threshold number of detected signals broadcast by the at least one wireless user access device having a minimum relative received signal strength.

29. The node-enabled logistics receptacle apparatus of embodiment 21, wherein the alert message provides the recorded level of wireless communication signal activity over the predetermined period of time to at least one of a master node in the network or a server in the network.

Further Embodiment 36—Methods and Apparatus for Proactively Reporting a Content Status of a Node-Enabled Logistics Receptacle 1. A method for proactively reporting a content status of a node-enabled logistics receptacle in a wireless node network, the method comprising: updating the content status stored in memory onboard the node-enabled logistics receptacle based upon whether the node-enabled logistics receptacle has received a package and is temporarily maintaining custody of the package; and broadcasting status information related to the updated content status for the node-enabled logistics receptacle.

2. The method of embodiment 1 further comprising requesting, by the node-enabled logistics receptacle, shipping information related to the package received.

3. The method of embodiment 2 further comprising receiving, by the node-enabled logistics receptacle, the requested shipping information related to the package.

4. The method of embodiment 3 further comprising identifying a shipping courier for the package from the requested shipping information received.

5. The method of embodiment 2, wherein the status information comprises a request to pick up the package from the node-enabled logistics receptacle.

6. The method of embodiment 4, wherein the status information comprises a request for the identified shipping courier to pick up the package from the node-enabled logistics receptacle.

7. The method of embodiment 5, wherein the status information comprises a request to pick up at least one package from the node-enabled logistics receptacle when a number of packages in the temporary custody of the node-enabled logistics receptacle is more than a pickup threshold.

8. The method of embodiment 1 further comprising the step of updating the content status stored in the memory onboard the node-enabled logistics receptacle based upon whether the node-enabled logistics receptacle detects the package has been removed from within the node-enabled logistics receptacle.

9. The method of embodiment 1 further comprising the step of broadcasting updated status information, wherein the updated status information comprises a message indicating there is no need for a shipping courier to service the node-enabled logistics receptacle.

10. The method of embodiment 1, wherein the broadcasting step further comprises broadcasting the status information from a master node in the node-enabled logistics receptacle directly to a server in the wireless node network.

11. The method of embodiment 1, wherein the broadcasting step further comprises broadcasting the status information from an ID node in the node-enabled logistics receptacle directly to a master node in the wireless node network, the master node being operative to forward the status information to a server in the wireless node network.

12. The method of embodiment 1 further comprising the step of determining whether the node-enabled logistics receptacle has received the package and is temporarily maintaining custody of the package based upon a detection result from at least one sensor deployed as part of the node-enabled logistics receptacle.

13. The method of embodiment 12, wherein the at least one sensor comprises at least one from a group comprising an internal sensor, an external sensor, and a door sensor.

14. A non-transitory computer-readable medium containing instructions which when executed on a processor performs a method for proactively reporting a content status of a node-enabled logistics receptacle in a wireless node network, the method comprising: updating the content status stored in memory onboard the node-enabled logistics receptacle based upon whether the node-enabled logistics receptacle has received a package and is temporarily maintaining custody of the package; and broadcasting status information related to the updated content status for the node-enabled logistics receptacle.

15. The non-transitory computer-readable medium of embodiment 14, wherein the method further comprises requesting, by the node-enabled logistics receptacle, shipping information related to the package received.

16. The non-transitory computer-readable medium of embodiment 15, wherein the method further comprises receiving, by the node-enabled logistics receptacle, the requested shipping information related to the package.

17. The non-transitory computer-readable medium of embodiment 16, wherein the method further comprises identifying a shipping courier for the package from the requested shipping information received.

18. The non-transitory computer-readable medium of embodiment 14, wherein the status information comprises a request to pickup the package from the node-enabled logistics receptacle.

19. The non-transitory computer-readable medium of embodiment 17, wherein the status information comprises a request for the identified shipping courier to pickup the package from the node-enabled logistics receptacle.

20. The non-transitory computer-readable medium of embodiment 18, wherein the status information comprises a request to pick up at least one package from the node-enabled logistics receptacle when a number of packages in the temporary custody of the node-enabled logistics receptacle is more than a pickup threshold.

21. The non-transitory computer-readable medium of embodiment 14, wherein the method further comprises the step of updating the content status stored in the memory onboard the node-enabled logistics receptacle based upon whether the node-enabled logistics receptacle detects the package has been removed from within the node-enabled logistics receptacle.

22. The non-transitory computer-readable medium of embodiment 14, wherein the method further comprises the step of broadcasting updated status information, wherein the updated status information comprises a message indicating there is no need for a shipping courier to service the node-enabled logistics receptacle.

23. The non-transitory computer-readable medium of embodiment 14, wherein the broadcasting step further comprises broadcasting the status information from a master node in the node-enabled logistics receptacle directly to a server in the wireless node network.

24. The non-transitory computer-readable medium of embodiment 14, wherein the broadcasting step further comprises broadcasting the status information from an ID node in the node-enabled logistics receptacle directly to a master node in the wireless node network, the master node being operative to forward the status information to a server in the wireless node network.

25. The non-transitory computer-readable medium of embodiment 14, wherein the method further comprise the step of determining whether the node-enabled logistics receptacle has received the package and is temporarily maintaining custody of the package based upon a detection result from at least one sensor deployed as part of the node-enabled logistics receptacle.

26. The non-transitory computer-readable medium of embodiment 25, wherein the at least one sensor comprises at least one from a group comprising an internal sensor, an external sensor, and a door sensor.

27. A node-enabled logistics receptacle apparatus in a wireless node network, comprising: a logistics receptacle for receiving and temporarily maintaining a package being shipped, the receptacle having an entrance opening through which the package is received and a temporary storage area where the package is temporarily and securely maintained until an authorized pickup; a node assembled with the receptacle, the node further comprising a node processing unit, a node memory storage coupled to the node processing unit, the node memory storage maintaining code for execution by the node processing unit and a content status related to one or more packages currently maintained within the logistics receptacle, and at least one communication interface coupled to the node processing unit, the at least one communication interface being collectively operative to communicate with another network device in the wireless node network; and wherein the node processing unit, when executing the code maintained on the node memory storage, is operative to update the content status stored in the node memory storage based upon whether the logistics receptacle has received the package and is temporarily maintaining custody of the package; and broadcast status information over the at least one communication interface, the status information being related to the updated content status for the logistics receptacle.

28. The node-enabled logistics receptacle of embodiment 27, wherein the node processing unit is further operative to transmit a request for shipping information related to the package received over the at least one communication interface.

29. The node-enabled logistics receptacle of embodiment 28, wherein the node processing unit is further operative to receive the requested shipping information related to the package over the at least one communication interface.

30. The node-enabled logistics receptacle of embodiment 29, wherein the node processing unit is further operative to identify a shipping courier for the package from the requested shipping information received.

31. The node-enabled logistics receptacle of embodiment 27, wherein the status information comprises a request to pick up the package from the node-enabled logistics receptacle.

32. The node-enabled logistics receptacle of embodiment 30, wherein the status information comprises a request for the identified shipping courier to pick up the package from the node-enabled logistics receptacle.

33. The node-enabled logistics receptacle of embodiment 31, wherein the status information comprises a request to pick up at least one package from the node-enabled logistics receptacle when a number of packages in the temporary custody of the logistics receptacle is more than a pickup threshold.

34. The node-enabled logistics receptacle of embodiment 27, wherein the node processing unit is further operative to update the content status stored in the node memory storage based upon whether the node processing unit detects the package has been removed from within the logistics receptacle.

35. The node-enabled logistics receptacle of embodiment 27, wherein the node processing unit is further operative to broadcast updated status information over the at least one communication interface, wherein the updated status information comprises a message indicating there is no need for a shipping courier to service the node-enabled logistics receptacle.

36. The node-enabled logistics receptacle of embodiment 27, wherein the node assembled with the receptacle comprises a master node operative to communicate directly to a server in the wireless node network; and wherein the node processing unit is further operative to broadcasting the status information over the at least one communication interface directly to the server in the wireless node network.

37. The node-enabled logistics receptacle of embodiment 27, wherein the node assembled with the receptacle comprises an ID node operative to communicate directly to a master node in the wireless node network; and wherein the node processing unit is further operative to broadcast the status information over the at least one communication interface directly to the master node in the wireless node network, the master node being operative to forward the status information to a server in the wireless node network.

38. The node-enabled logistics receptacle of embodiment 27, wherein the node assembled with the receptacle further comprises a sensor coupled to the node processing unit.

39. The node-enabled logistics receptacle of embodiment JJ3, wherein the sensor comprises an internal sensor that detects the package as being within the temporary storage area.

40. The node-enabled logistics receptacle of embodiment 39, wherein the sensor comprises an external sensor that detects whether another package is within a designated area near the logistics receptacle.

41. The node-enabled logistics receptacle of embodiment 39, wherein the sensor comprises a door sensor that detects whether a door of the logistics receptacle covering the entrance opening as moved to an open position.

42. A method for proactively reporting a content status of a node-enabled logistics receptacle in a wireless node network, the method comprising: detecting, by a node assembled within the node-enabled logistics receptacle, a signal broadcast from a master node in the wireless node network; accessing the content status stored in memory onboard the node-enabled logistics receptacle, the content status indicating whether the node-enabled logistics receptacle has received a package and is temporarily maintaining custody of the package; and broadcasting, by the node assembled within the node-enabled logistics receptacle status information to the master node related to the content status for the node-enabled logistics receptacle.

43. The method of embodiment 42 further comprising requesting, from the master node by the node assembled within the node-enabled logistics receptacle, shipping information related to the package.

44. The method of embodiment 43 further comprising receiving, by the node assembled within the node-enabled logistics receptacle, the requested shipping information related to the package.

45. The method of embodiment 44 further comprising identifying a shipping courier for the package from the requested shipping information received.

46. The method of embodiment 42, wherein the status information comprises a request to pick up the package from the node-enabled logistics receptacle.

47. The method of embodiment 45, wherein the status information comprises a request for the identified shipping courier to pick up the package from the node-enabled logistics receptacle.

48. The method of embodiment 42 further comprising the step of determining whether the node-enabled logistics receptacle has received the package and is temporarily maintaining custody of the package based upon a detection result from at least one sensor deployed as part of the node-enabled logistics receptacle.

49. The method of embodiment 48, wherein the at least one sensor comprises at least one from a group comprising an internal sensor, an external sensor, and a door sensor.

50. A non-transitory computer-readable medium containing instructions which when executed on a processor performs a method for proactively reporting a content status of a node-enabled logistics receptacle in a wireless node network, the method comprising: detecting, by a node assembled within the node-enabled logistics receptacle, a signal broadcast from a master node in the wireless node network; accessing the content status stored in memory onboard the node-enabled logistics receptacle, the content status indicating whether the node-enabled logistics receptacle has received a package and is temporarily maintaining the package; and broadcasting, by the node assembled within the node-enabled logistics receptacle status information to the master node related to the content status for the node-enabled logistics receptacle.

51. The non-transitory computer-readable medium of embodiment 50, wherein the method further comprises requesting, from the master node by the node assembled within the node-enabled logistics receptacle, shipping information related to the package.

52. The non-transitory computer-readable medium of embodiment 51, wherein the method further comprises receiving, by the node assembled within the node-enabled logistics receptacle, the requested shipping information related to the package.

53. The non-transitory computer-readable medium of embodiment 52, wherein the method further comprises identifying a shipping courier for the package from the requested shipping information received.

54. The non-transitory computer-readable medium of embodiment 50, wherein the status information comprises a request to pick up the package from the node-enabled logistics receptacle.

55. The non-transitory computer-readable medium of embodiment 53, wherein the status information comprises a request for the identified shipping courier to pick up the package from the node-enabled logistics receptacle.

56. The non-transitory computer-readable medium of embodiment 50, wherein the method further comprises the step of determining whether the node-enabled logistics receptacle has received the package and is temporarily maintaining custody of the package based upon a detection result from at least one sensor deployed as part of the node-enabled logistics receptacle.

57. The method of embodiment 56, wherein the at least one sensor comprises at least one from a group comprising an internal sensor, an external sensor, and a door sensor.

58. A node-enabled logistics receptacle apparatus in a wireless node network, comprising: a logistics receptacle for receiving and temporarily maintaining a package being shipped, the receptacle having an entrance opening through which the package is received and a temporary storage area where the package is temporarily and securely maintained until an authorized pickup; a node assembled with the receptacle, the node further comprising a node processing unit, a node memory storage coupled to the node processing unit, the node memory storage maintaining code for execution by the node processing unit and a content status related to one or more packages currently maintained within the logistics receptacle, and at least one communication interface coupled to the node processing unit, the at least one communication interface being collectively operative to communicate with another network device in the wireless node network; and wherein the node processing unit, when executing the code maintained on the node memory storage, is operative to detect a signal via the at least one communication interface, the signal having been broadcast from a master node in the wireless node network, access the content status stored in the node memory storage the node-enabled logistics receptacle; and cause the at least one communication interface to broadcast status information to the master node related to the content status for the node-enabled logistics receptacle.

59. The node-enabled logistics receptacle of embodiment 58, wherein the node processing unit is further operative to request shipping information related to the package from the master node.

60. The node-enabled logistics receptacle of embodiment 59, wherein the node processing unit is further operative to receive the requested shipping information related to the package from the master node.

61. The node-enabled logistics receptacle of embodiment 60, wherein the node processing unit is further operative to identify a shipping courier for the package from the requested shipping information received.

62. The node-enabled logistics receptacle of embodiment 58, wherein the status information comprises a request to pick up the package from the node-enabled logistics receptacle.

63. The node-enabled logistics receptacle of embodiment 61, wherein the status information comprises a request for the identified shipping courier to pick up the package from the node-enabled logistics receptacle.

64. The node-enabled logistics receptacle of embodiment 58, wherein the node assembled with the receptacle further comprises a sensor coupled to the node processing unit.

65. The node-enabled logistics receptacle of embodiment 64, wherein the sensor comprises an internal sensor that detects the package as being within the temporary storage area.

66. The node-enabled logistics receptacle of embodiment 64, wherein the sensor comprises an external sensor that detects whether another package is within a designated area near the logistics receptacle.

67. The node-enabled logistics receptacle of embodiment 64, wherein the sensor comprises a door sensor that detects whether a door of the logistics receptacle covering the entrance opening as moved to an open position.

Further Embodiment 37—Detecting a Plurality of Package Types within a Node-Enabled Logistics Receptacle 1. A method for detecting a plurality of package types in the custody of a node-enabled logistics receptacle in a wireless node network, the method comprising: detecting a first type of package by receiving a signal broadcast from a node within a first package prior to sensing a deposit of the first package with the node-enabled logistics receptacle, wherein the first type of package is a node-enabled package; detecting a second type of package by sensing a deposit of a second package with the node-enabled logistics receptacle without receiving a signal broadcast from a node within the second package, wherein the second type of package is not a node-enabled package; logging the detections of the first type of package and the second type of package; and notifying another network device within the wireless node network about the logged detection of the first type of package and the second type of package.

2. The method of embodiment 1, wherein the step of detecting the first type of package further comprises receiving the signal broadcast from the node within the first package within a predetermined time interval prior to sensing the deposit of the first package within the node-enabled logistics receptacle.

3. The method of embodiment 2, wherein the step of receiving the signal broadcast from the node within the first package further comprises associating the node within the first package with the node assembled within the node-enabled logistics receptacle.

4. The method of embodiment 1, wherein the step of detecting the second type of package further comprises sensing the deposit of the second package with the node-enabled logistics receptacle using a sensor coupled to a node assembled within the node-enabled logistics receptacle.

5. The method of embodiment 4, wherein the sensor comprises at least one from a group comprising an internal sensor, an external sensor, and a door sensor.

6. The method of embodiment 4, wherein the sensor comprises a motion detector coupled to the node assembled within the node-enabled logistics receptacle, wherein the motion detector senses movement of the first package and the second package when deposited within the interior storage region of the node-enabled logistics receptacle and provides the sensor signal to the node processing unit related to the sensed movement.

7. The method of embodiment 4, wherein the sensor comprises an impact sensor coupled to the node assembled within the node-enabled logistics receptacle, wherein the impact sensor registers a change in pressure exerted against a bottom surface of the interior storage region in response to an object deposited within the interior storage region and provides the sensor signal to the node processing unit related to the sensed impact.

8. The method of embodiment 4, wherein the sensor comprises a measurement scale coupled to the node assembled within the node-enabled logistics receptacle, wherein the measurement scale measures a weight of an object deposited within the interior storage region and provides the sensor signal to the node processing unit related to the measured weight.

9. A non-transitory computer-readable medium containing instructions which when executed on a processor performs a method for detecting a plurality of package types in the custody of a node-enabled logistics receptacle in a wireless node network, the method comprising: detecting a first type of package by receiving a signal broadcast from a node within a first package prior to sensing a deposit of the first package with the node-enabled logistics receptacle, wherein the first type of package is a node-enabled package; detecting a second type of package by sensing a deposit of a second package with the node-enabled logistics receptacle without receiving a signal broadcast from a node within the second package, wherein the second type of package is not a node-enabled package; logging the detections of the first type of package and the second type of package; and notifying another network device within the wireless node network about the logged detection of the first type of package and the second type of package.

10. The non-transitory computer-readable medium of embodiment 9, wherein the step of detecting the first type of package further comprises receiving the signal broadcast from the node within the first package within a predetermined time interval prior to sensing the deposit of the first package within the node-enabled logistics receptacle.

11. The non-transitory computer-readable medium of embodiment 10, wherein the step of receiving the signal broadcast from the node within the first package further comprises associating the node within the first package with the node assembled within the node-enabled logistics receptacle.

12. The non-transitory computer-readable medium of embodiment 9, wherein the step of detecting the second type of package further comprises sensing the deposit of the second package within the node-enabled logistics receptacle using a sensor coupled to a node assembled within the node-enabled logistics receptacle.

13. The non-transitory computer-readable medium of embodiment 12, wherein the sensor comprises at least one from a group comprising an internal sensor, an external sensor, and a door sensor.

14. The non-transitory computer-readable medium of embodiment 12, wherein the sensor comprises a motion detector coupled to the node assembled within the node-enabled logistics receptacle, wherein the motion detector senses movement of the first package and the second package when deposited within the interior storage region of the node-enabled logistics receptacle and provides the sensor signal to the node processing unit related to the sensed movement.

15. The non-transitory computer-readable medium of embodiment 12, wherein the sensor comprises an impact sensor coupled to the node assembled within the node-enabled logistics receptacle, wherein the impact sensor registers a change in pressure exerted against a bottom surface of the interior storage region in response to an object deposited within the interior storage region and provides the sensor signal to the node processing unit related to the sensed impact.

16. The non-transitory computer-readable medium of embodiment 12, wherein the sensor comprises a measurement scale coupled to the node assembled within the node-enabled logistics receptacle, wherein the measurement scale measures a weight of an object deposited within the interior storage region and provides the sensor signal to the node processing unit related to the measured weight.

17. A node-enabled logistics receptacle apparatus in a wireless node network that detects a plurality of package types, comprising: a logistics receptacle for receiving and temporarily maintaining custody of a package being shipped, the receptacle having an entrance opening through which the package is received and an internal storage region where the package is temporarily and securely maintained until an authorized pickup; a node assembled with the receptacle, the node further comprising a node processing unit, a node memory storage coupled to the node processing unit, the node memory storage maintaining code for execution by the node processing unit and logged detection information about the plurality of package types, at least one communication interface coupled to the node processing unit, the at least one communication interface being collectively operative to communicate with another network device in the wireless node network; and wherein the node processing unit, when executing the code maintained on the node memory storage, is operative to detect a first type of package by receiving a signal broadcast from a node within a first package prior to sensing a deposit of the first package with the node-enabled logistics receptacle, wherein the first type of package is a node-enabled package, detect a second type of package by sensing a deposit of a second package with the node-enabled logistics receptacle without receiving a signal broadcast from a node within the second package, wherein the second type of package is not a node-enabled package, log the detections of the first type of package and the second type of package as the detection information stored on the node memory storage, and cause the at least one communication interface to transmit a notification to another network device within the wireless node network about the logged detection of the first type of package and the second type of package.

18. The node-enabled logistics receptacle apparatus of embodiment 17, wherein the node processing unit is further operative to detect the first type of package by being operative to receive, via the at least one communication interface, the signal broadcast from the node within the first package within a predetermined time interval prior to sensing the deposit of the first package within the node-enabled logistics receptacle.

19. The node-enabled logistics receptacle apparatus of embodiment 18, wherein the node processing unit is further operative to receive the signal broadcast from the node within the first package by being operative to associate the node within the first package with the node assembled with the receptacle.

20. The node-enabled logistics receptacle apparatus of embodiment 17, wherein the node assembled with the receptacle further comprises a sensor coupled to the node processing unit; and wherein the node processing unit is further operative to detect the second type of package by being operative to sense the deposit of the second package within the node-enabled logistics receptacle based upon a sensor signal provided by the sensor to the node processing unit.

21. The node-enabled logistics receptacle apparatus of embodiment 20, wherein the sensor comprises at least one from a group comprising an internal sensor disposed within the internal storage region, an external sensor that monitors an area outside but near the logistics receptacle, and a door sensor that monitors the entrance opening.

22. The node-enabled logistics receptacle apparatus of embodiment 20, wherein the sensor further comprises a motion detector coupled to the node assembled with the receptacle, wherein the motion detector senses movement of the first package and the second package as the packages are deposited within the interior storage region and provides the sensor signal to the node processing unit related to the sensed movement.

23. The node-enabled logistics receptacle apparatus of embodiment 20, wherein the sensor further comprises an impact sensor coupled to the node assembled with the receptacle, wherein the impact sensor registers a change in pressure exerted against a bottom surface of the interior storage region in response to an object deposited within the interior storage region and provides the sensor signal to the node processing unit related to the sensed impact.

24. The node-enabled logistics receptacle apparatus of embodiment 20, wherein the sensor further comprises a measurement scale coupled to the node assembled with the receptacle, wherein the measurement scale measures a weight of an object deposited within the interior storage region and provides the sensor signal to the node processing unit related to the measured weight.

Further Embodiment 38—Methods and Apparatus for Deploying a Plurality of Pickup Entities for a Node-Enabled Logistics Receptacle 1. A method for deploying a plurality of pickup entities to a node-enabled logistics receptacle in a wireless node network, the method comprising: receiving, by a server in the wireless node network, a message from a node-enabled logistics receptacle, the message identifying a plurality of packages currently maintained within the node-enabled logistics receptacle ready for pickup; accessing shipping information from a server memory storage, the shipping information being related to the identified plurality of packages currently maintained with the node-enabled logistics receptacle; and identifying which of the plurality of pickup entities need to be deployed to provide one or more pickup services at the node-enabled logistics receptacle based upon the shipping information.

2. The method of embodiment 1 further comprising transmitting a pickup request over a communication interface to the identified ones of the pickup entities regarding the one or more pickup services to be performed at the node-enabled logistics receptacle.

3. The method of embodiment 1 further comprising updating historic data for the node-enabled logistics receptacle related to the identified ones of the pickup entities.

4. The method of embodiment 3 further comprising predicting a future pickup schedule for the node-enabled logistics receptacle based upon the updated historic data.

5. The method of embodiment 4 further comprising transmitting the future pickup schedule to those of the pickup entities having a predicted pickup service in the future pickup schedule for the node-enabled logistics receptacle.

6. The method of embodiment 1 further comprising notifying a previously scheduled one of the pickup entities if the previously scheduled one of the pickup entities is not one of the identified ones of the pickup entities regarding the one or more pickup services to be performed at the node-enabled logistics receptacle.

7. The method of embodiment 2, wherein the transmitting step further comprises: accessing an existing pickup schedule maintained in the server memory storage, the existing pickup schedule comprising one or more existing scheduled pickup services at the node-enabled logistics receptacle; and notifying one of the pickup entities that is on the existing pickup schedule but that is not identified as one of the plurality of pickup entities that they do not need to provide one or more pickup services at the node-enabled logistics receptacle based upon the shipping information.

8. The method of embodiment 7 further comprising revising the existing pickup schedule based on the identified ones of the plurality of pickup entities that need to provide one or more pickup services at the node-enabled logistics receptacle based upon the shipping information.

9. A non-transitory computer-readable medium containing instructions which when executed on a processor performs a method for deploying a plurality of pickup services to a node-enabled logistics receptacle in a wireless node network, the method comprising: receiving, by a server in the wireless node network, a message from a node-enabled logistics receptacle, the message identifying a plurality of packages currently maintained within the node-enabled logistics receptacle ready for pickup; accessing shipping information from a server memory storage, the shipping information being related to the identified plurality of packages currently maintained with the node-enabled logistics receptacle; and identifying which of the plurality of pickup entities need to be deployed to provide one or more pickup services at the node-enabled logistics receptacle based upon the shipping information.

10. The non-transitory computer-readable medium of embodiment 9 further comprising transmitting a pickup request over a communication interface to the identified ones of the pickup entities regarding the one or more pickup services to be performed at the node-enabled logistics receptacle.

11. The non-transitory computer-readable medium of embodiment 9 further comprising updating historic data for the node-enabled logistics receptacle related to the identified ones of the pickup entities.

12. The non-transitory computer-readable medium of embodiment 11 further comprising predicting a future pickup schedule for the node-enabled logistics receptacle based upon the updated historic data.

13. The non-transitory computer-readable medium of embodiment 12 further comprising transmitting the future pickup schedule to those of the pickup entities having a predicted pickup service in the future pickup schedule for the node-enabled logistics receptacle.

14. The non-transitory computer-readable medium of embodiment 9 further comprising notifying a previously scheduled one of the pickup entities if the previously scheduled one of the pickup entities is not one of the identified ones of the pickup entities regarding the one or more pickup services to be performed at the node-enabled logistics receptacle.

15. The non-transitory computer-readable medium of embodiment 10, wherein the transmitting step further comprises: accessing an existing pickup schedule maintained in the server memory storage, the existing pickup schedule comprising one or more existing scheduled pickup services at the node-enabled logistics receptacle; and notifying one of the pickup entities that is on the existing pickup schedule but that is not identified as one of the plurality of pickup entities that they do not need to provide one or more pickup services at the node-enabled logistics receptacle based upon the shipping information.

16. The non-transitory computer-readable medium of embodiment 15 further comprising revising the existing pickup schedule based on the identified ones of the plurality of pickup entities that need to provide one or more pickup services at the node-enabled logistics receptacle based upon the shipping information.

17. A server apparatus in a wireless node network for deploying a plurality of pickup services to a node-enabled logistics receptacle, comprising: at least one server processing unit; at least one server memory storage coupled to the server processing unit, the server memory storage maintaining code for execution by the server processing unit and shipping information about a plurality of packages currently maintained within the node-enabled logistics receptacle ready for pickup; a communication interface coupled to the server processing unit, the communication interface being collectively operative to communicate with at least the node-enabled logistics receptacle in the wireless node network; and wherein the server processing unit, when executing the code maintained on the server memory storage, is operative to receive a message from the node-enabled logistics receptacle over the communication interface, the message identifying the plurality of packages currently maintained within the node-enabled logistics receptacle ready for pickup, access the server memory storage to obtain the shipping information related to the identified plurality of packages currently maintained with the node-enabled logistics receptacle, and identify which of the plurality of pickup entities need to be deployed to provide one or more pickup services at the node-enabled logistics receptacle based upon the shipping information.

18. The server apparatus of embodiment 17, wherein the server processing unit is further operative to cause the communication interface to transmit a pickup request to the identified ones of the pickup entities regarding the one or more pickup services to be performed at the node-enabled logistics receptacle.

19. The server apparatus of embodiment 17, wherein the server processing unit is further operative to: update historic data for the node-enabled logistics receptacle related to the identified ones of the pickup entities; and store the updated historic data in the server memory storage.

20. The server apparatus of embodiment 19, wherein the server processing unit is further operative to predict a future pickup schedule for the node-enabled logistics receptacle based upon the updated historic data.

21. The server apparatus of embodiment 20, wherein the server processing unit is further operative to cause the future pickup schedule to be transmitted over the communication interface to those of the pickup entities having a predicted pickup service in the future pickup schedule for the node-enabled logistics receptacle.

22. The server apparatus of embodiment 17, wherein the server processing unit is further operative to notify a previously scheduled one of the pickup entities over the communications interface if the previously scheduled one of the pickup entities is not one of the identified ones of the pickup entities regarding the one or more pickup services to be performed at the node-enabled logistics receptacle.

23. The server apparatus of embodiment 18, wherein the server processing unit is further operative to cause the communication interface to transmit the pickup request by being operative to: access an existing pickup schedule maintained in the server memory storage, the existing pickup schedule comprising one or more existing scheduled pickup services at the node-enabled logistics receptacle; and notify, over the communication interface, one of the pickup entities that is on the existing pickup schedule but that is not identified as one of the plurality of pickup entities that they do not need to provide one or more pickup services at the node-enabled logistics receptacle based upon the shipping information.

24. The server apparatus of embodiment 23, wherein the server processing unit is further operative to revise the existing pickup schedule based on the identified ones of the plurality of pickup entities that need to provide one or more pickup services at the node-enabled logistics receptacle based upon the shipping information.

Further Embodiment 39—Methods and Apparatus for Pseudo Master Node Mode Operations in a Hierarchical Wireless Network.

1. A method for node communication within a hierarchical wireless node network having a plurality of ID nodes on a first level, a master node on a second level, and a server at a third level, the method comprising: associating a first of the ID nodes with the master node, the first of the ID nodes being unable to self-determine its location while the master node is adapted to self-determine its location via location circuitry; capturing, by the first of the ID nodes, relevant node information; and transmitting, by the first of the ID nodes operating in a pseudo master node mode in the hierarchical wireless node network, the relevant node information to the server without using the master node as an intermediary to the server.

2. The method of embodiment 1, wherein the relevant node information further comprises at least one of profile data, security data, association data, shared data, and sensor data.

3. The method of embodiment 2, wherein the sensor data comprises data collected from one or more sensors in communication with the first of the ID nodes.

4. The method of embodiment 3, wherein the data collected from the one or more sensors relates to at least one condition of a package associated with the first of the ID nodes.

5. The method of embodiment 2, wherein the capturing step further comprises capturing, by the first of the ID nodes, the relevant node information from a broadcast from a second of the ID nodes associated with the first of the ID nodes.

6. The method of embodiment 5, wherein the sensor data comprises data collected from one or more sensors in communication with the second of the ID nodes.

7. The method of embodiment 6, wherein the data collected from the one or more sensors relates to at least one condition of a package associated with the second of the ID nodes.

8. The method of embodiment 1, wherein the step of transmitting further comprises: generating a message for the server, the message including the relevant node information and formatted for a longer range communication path when compared to a shorter range communication path used to communicate between the ID nodes; and broadcasting the message on the longer range communication path to the server while avoiding the need to first send the message to the master node during transit to the server.

9. The method of embodiment 1, wherein the step of transmitting further comprises: determining a desired communication path for a message including the relevant node information, the desired communication path comprising at least one of a first communication path and a second communication path, wherein the first communication path includes the master node operates as an intermediary to the server and the second communication path not including the master node operating as the intermediary to the server; formatting the message for the server, the message formatted for the desired communication path; and broadcasting the message on the desired communication path to the server while avoiding the need to first send the message to the master node during transit to the server when the desired communication path is the second communication path.

10. A non-transitory computer-readable medium containing instructions which when executed on a processor performs a method for node communication within a hierarchical wireless node network having a plurality of ID nodes on a first level, a master node on a second level, and a server at a third level, the method comprising: associating a first of the ID nodes with the master node, the first of the ID nodes being unable to self-determine its location while the master node is adapted to self-determine its location via location circuitry; capturing, by the first of the ID nodes, relevant node information; and transmitting, by the first of the ID nodes operating in a pseudo master node mode in the hierarchical wireless node network, the relevant node information to the server without using the master node as an intermediary to the server.

11. The non-transitory computer-readable medium of embodiment 10, wherein the relevant node information further comprises at least one of profile data, security data, association data, shared data, and sensor data.

12. The non-transitory computer-readable medium of embodiment 11, wherein the sensor data comprises data collected from one or more sensors in communication with the first of the ID nodes.

13. The non-transitory computer-readable medium of embodiment 12, wherein the data collected from the one or more sensors relates to at least one condition of a package associated with the first of the ID nodes.

14. The non-transitory computer-readable medium of embodiment 11, wherein the capturing step further comprises capturing, by the first of the ID nodes, the relevant node information from a broadcast from a second of the ID nodes associated with the first of the ID nodes.

15. The non-transitory computer-readable medium of embodiment 14, wherein the sensor data comprises data collected from one or more sensors in communication with the second of the ID nodes.

16. The non-transitory computer-readable medium of embodiment 15, wherein the data collected from the one or more sensors relates to at least one condition of a package associated with the second of the ID nodes.

17. The non-transitory computer-readable medium of embodiment 10, wherein the step of transmitting further comprises: generating a message for the server, the message including the relevant node information and formatted for a longer range communication path when compared to a shorter range communication path used to communicate between the ID nodes; and broadcasting the message on the longer range communication path to the server while avoiding the need to first send the message to the master node during transit to the server.

18. The non-transitory computer-readable medium of embodiment 10, wherein the step of transmitting further comprises: determining a desired communication path for a message including the relevant node information, the desired communication path comprising at least one of a first communication path and a second communication path, wherein the first communication path includes the master node operates as an intermediary to the server and the second communication path not including the master node operating as the intermediary to the server; formatting the message for the server, the message formatted for the desired communication path; and broadcasting the message on the desired communication path to the server while avoiding the need to first send the message to the master node during transit to the server when the desired communication path is the second communication path.

19. A hierarchical wireless node network, comprising: a plurality of ID nodes disposed on a first level of the network; a master node disposed on a second level of the network, the master node having location circuitry with which to self-determine its location, the master node being further adapted and operative to associate with at least a first of the ID nodes; a server disposed on a third level of the network; and wherein the first of the ID nodes being adapted and operative to associate the first of the ID nodes with the master node, the first of the ID nodes being unable to self-determine its location, capture relevant node information; and transmit, in a pseudo master node mode, the relevant node information to the server without using the master node as an intermediary to the server.

20. The hierarchical wireless node network of embodiment 19, wherein the relevant node information further comprises at least one of profile data, security data, association data, shared data, and sensor data.

21. The hierarchical wireless node network of embodiment 20, wherein the first of the ID nodes further comprises one or more sensors that generate the sensor data.

22. The hierarchical wireless node network of embodiment 21, wherein the sensor data relates to at least one condition of a package associated with the first of the ID nodes.

23. The hierarchical wireless node network of embodiment 20, wherein the first of the ID nodes is further adapted and operative to capture the relevant node information from a broadcast signal originating from a second of the ID nodes associated with the first of the ID nodes.

24. The hierarchical wireless node network of embodiment 23, wherein the second of the ID nodes further comprises one or more sensors that generate the sensor data.

25. The hierarchical wireless node network of embodiment 24, wherein the sensor data relates to at least one condition of a package associated with the second of the ID nodes.

26. The hierarchical wireless node network of embodiment 19, wherein the first of the ID nodes is further adapted and operative to transmit in the pseudo master node mode by being adapted and operative to: generate a message for the server, the message including the relevant node information and formatted for a longer range communication path when compared to a shorter range communication path used to communicate between the ID nodes; and broadcast the message on the longer range communication path to the server while avoiding the need to first send the message to the master node during transit to the server.

27. The hierarchical wireless node network of embodiment 19, wherein the first of the ID nodes is further adapted and operative to transmit in the pseudo master node mode by being adapted and operative to: determine a desired communication path for a message including the relevant node information, the desired communication path comprising at least one of a first communication path and a second communication path, wherein the first communication path includes the master node operates as an intermediary to the server and the second communication path not including the master node operating as the intermediary to the server; format the message for the server, the message formatted for the desired communication path; and broadcast the message on the desired communication path to the server while avoiding the need to first send the message to the master node during transit to the server when the desired communication path is the second communication path.

Further Embodiment 40—Methods and Node Apparatus for Adaptive Node Communication in a Wireless Node Network.

1. A method for adaptive node communication within a wireless node network having a plurality of nodes, the method comprising: generating, by a first of the nodes, an advertising message in a first format; broadcasting, by the first of the nodes, the advertising message in the first format when the first of the nodes is in a first state; detecting a state change for the first of the nodes, the state change being associated with a changed relative environment of the first of the nodes; and adapting to the detected state change by altering the first format of the advertising message to a shortened format comprising an identifier for the first of the nodes, wherein the identifier is derived from the changed relative environment of the first of the nodes.

2. The method of embodiment 1, wherein the step of detecting the state change further comprises: switching, by the first of the nodes, between broadcasting the advertising message in the first format and scanning for a node signature indicative of the changed relative environment of the first of the nodes; and detecting the node signature as the first of the nodes is scanning.

3. The method of embodiment 1, wherein the changed relative environment comprises a change in a node density near the first of the nodes.

4. The method of embodiment 1, wherein the changed relative environment comprises a change in a movement aspect of the first of the nodes.

5. The method of embodiment 4, wherein the change in the movement aspect of the first of the nodes reflects that the first of the nodes is substantially stationary relative to a proximate structure.

6. The method of embodiment 5, wherein the proximate structure is moving while being substantially stationary relative to the first of the nodes.

7. The method of embodiment 6, wherein the proximate structure comprises at least one of a package containing device for the first of the nodes or a conveyance device associated with the first of the nodes.

8. The method of embodiment 7, wherein the conveyance device comprises one of a conveyor belt, a truck, a trailer, an aircraft, a train, and a delivery vehicle.

9. The method of embodiment 7, wherein the package containing device comprises one of a facility, a room, a bin, a container, a pallet, and a unit load device (ULD) type of transportation storage.

10. The method of embodiment 1, wherein the adapting step further comprises: generating, by the first of the nodes, an abbreviated version of the advertising message according to the shortened format; and broadcasting, by the first of the nodes, the abbreviated version of the advertising message in response to detecting the state change associated with the changed relative environment of the first of the nodes.

11. The method of embodiment 1 further comprising dynamically altering a variable broadcast format of the advertising message when detecting at least one further state change of the first of the nodes.

12. A non-transitory computer-readable storage medium containing instructions which when executed on a processor performs a method for adaptive node communication within a wireless node network having a plurality of nodes, the method comprising: generating, by a first of the nodes, an advertising message in a first format; broadcasting, by the first of the nodes, the advertising message in the first format when the first of the nodes is in a first state; detecting a state change for the first of the nodes, the state change being associated with a changed relative environment of the first of the nodes; and adapting to the detected state change by altering the first format of the advertising message to a shortened format comprising an identifier of the first of the nodes and the node device's prior state.

13. The non-transitory computer-readable storage medium of embodiment 12, wherein the step of detecting the state change further comprises: switching, by the first of the nodes, between broadcasting the advertising message in the first format and scanning for a node signature indicative of the changed relative environment of the first of the nodes; and detecting the node signature as the first of the nodes is scanning.

14. The non-transitory computer-readable storage medium of embodiment 12, wherein the changed relative environment comprises a change in a node density near the first of the nodes.

15. The non-transitory computer-readable storage medium of embodiment 12, wherein the changed relative environment comprises a change in a movement aspect of the first of the nodes.

16. The non-transitory computer-readable storage medium of embodiment 15, wherein the change in the movement aspect of the first of the nodes reflects that first of the nodes is substantially stationary relative to a proximate structure.

17. The non-transitory computer-readable storage medium of embodiment 16, wherein the proximate structure is moving while being substantially stationary relative to the first of the nodes.

18. The non-transitory computer-readable storage medium of embodiment 17, wherein the proximate structure comprises at least one of a package containing device for the first of the nodes or a conveyance device associated with the first of the nodes.

19. The non-transitory computer-readable storage medium of embodiment 18, wherein the conveyance device comprises one of a conveyor belt, a truck, a trailer, an aircraft, a train, and a delivery vehicle.

20. The non-transitory computer-readable storage medium of embodiment 18, wherein the package containing device comprises one of a facility, a room, a bin, a container, a pallet, and a unit load device (ULD) type of transportation storage.

21. The non-transitory computer-readable storage medium of embodiment 12, wherein the adapting step further comprises: generating, by the first of the nodes, an abbreviated version of the advertising message according to the shortened format; and broadcasting, by the first of the nodes, the abbreviated version of the advertising message in response to detecting the state change associated with the changed relative environment of the first of the nodes.

22. The non-transitory computer-readable storage medium of embodiment 12 further comprising dynamically altering a variable broadcast format of the advertising message when detecting at least one further state change of the first of the nodes.

23. A node device in a wireless node network, comprising: a node processing unit; a node volatile memory coupled to the node processing unit; a node memory storage coupled to the node processing unit, the node memory storage maintaining an adaptive messaging program section; a communication interface coupled to the node processing unit and that provides access to other nodes in the wireless node network; wherein the node processing unit is adapted and operative to load the adaptive messaging program section into the node volatile memory and, when executing at least the adaptive messaging program section when resident in the node volatile memory, is further adapted and operative to: generate an advertising message in a first format; instruct the communication interface to broadcast the advertising message in the first format when the node device is in a first state; detect a state change associated with a changed relative environment of the node device; adapt to the detected state change by altering the first format of the advertising message to a shortened format comprising an identifier for node device, wherein the identifier is derived from the changed relative environment of the node device; and instruct the communication interface to broadcast the advertising message using the shortened format.

24. The node device of embodiment 23, wherein the node processing unit is adapted and operative to detect the state change by being further adapted and operative to: instruct the communication interface to switch between broadcasting the advertising message in the first format and scanning for a node signature indicative of the changed relative environment of the first of the nodes; and detect the node signature as the communication interface is scanning.

25. The node device of embodiment 23, wherein the changed relative environment comprises a change in a node density near the first of the nodes.

26. The node device of embodiment 23, wherein the changed relative environment comprises a change in a movement aspect of the node device.

27. The node device of embodiment 26, wherein the change in the movement aspect of the node device reflects that the node device is substantially stationary relative to a proximate structure.

28. The node device of embodiment 27, wherein the proximate structure is moving while being substantially stationary relative to the first of the nodes.

29. The node device of embodiment 28, wherein the proximate structure comprises at least one of a package containing device for the node device or a conveyance device associated with the node device.

30. The node device of embodiment 29, wherein the conveyance device comprises one of a conveyor belt, a truck, a trailer, an aircraft, a train, and a delivery vehicle.

31. The node device of embodiment 29, wherein the package containing device comprises one of a facility, a room, a bin, a container, a pallet, and a unit load device (ULD) type of transportation storage.

32. The node device of embodiment 23, wherein the node processing unit is adapted and operative to adapt to the detected state change by being further adapted and operative to: generate an abbreviated version of the advertising message according to the shortened format; and cause the communication interface to broadcast the abbreviated version of the advertising message in response to detecting the state change associated with the changed relative environment of the node device.

33. The node device of embodiment 23, wherein the node processing unit is further adapted and operative to dynamically alter a variable broadcast format of the advertising message when the node processing unit detects at least one further state change of the node device.

34. A method for controlling adaptive node communication within a wireless node network having a master node and an ID node, the method comprising: detecting, by the master node, an advertising message being broadcast by the ID node, wherein the advertising message having a first format; detecting, by the master node, a state change relative to the ID node, the state change being associated with a changed relative environment of the ID node; and instructing the ID node, by the master node, to alter the first format of the advertising message to a shortened format comprising an identifier for the ID node, wherein the identifier is derived from the changed relative environment of the ID node.

35. The method of embodiment 34, wherein the changed relative environment comprises a change in a node density near the ID node.

36. The method of embodiment 34, wherein the changed relative environment comprises a change in a movement aspect of the ID node.

37. The method of embodiment 36, wherein the change in the movement aspect of the ID node reflects that the ID node is substantially stationary relative to a proximate structure.

38. The method of embodiment 37, wherein the proximate structure is moving while being substantially stationary relative to the ID node.

39. The method of embodiment 38, wherein the proximate structure comprises at least one of a package containing device for the ID node or a conveyance device associated with the ID node.

40. The method of embodiment 39, wherein the conveyance device comprises one of a conveyor belt, a truck, a trailer, an aircraft, a train, and a delivery vehicle.

41. The method of embodiment 39, wherein the package containing device comprises one of a facility, a room, a bin, a container, a pallet, and a unit load device (ULD) type of transportation storage.

42. The method of embodiment 34, wherein the instructing step further comprises transmitting, by the master node, a control message to the ID node, wherein the control message causes the ID node to broadcast the advertising message according to a variable broadcast format as the shortened format.

43. The method of embodiment 42, wherein the variable broadcast format comprises at least one of a shortened global format, a shortened nested format, and a shortened local format.

44. The method of embodiment 43, wherein the shortened global format comprises a global identifier of the ID node derived from the master node detecting the state change.

45. The method of embodiment 44, wherein the global identifier of the ID node comprises a full identifier for the master node detecting the state change and a shortened reference to the ID node.

46. The method of embodiment 43, wherein the shortened nested format comprises a nested identifier of the ID node, wherein the nested identifier comprises a plurality of hierarchical references to higher level nodes associated with the ID node.

47. The method of embodiment 46, wherein the nested identifier indicates the ID node relationships with the higher level nodes.

48. The method of embodiment 46, wherein the nested identifier further comprises a shortened reference to the ID node.

49. The method of embodiment 43, wherein the shortened local format comprises a local identifier of the ID node derived from an abbreviated node reference for the master node detecting the state change.

50. The method of embodiment 49, wherein the abbreviated node reference for the master node detecting the state change comprises a collapsed reference to the master node and a shortened reference to the ID node.

51. The method of embodiment 34 further comprising the step of instructing, by the master node, the ID node to alter the shortened format of the advertising message back to the first format when the master node detects at least one further state change of the ID node.

52. A non-transitory computer-readable storage medium containing instructions which when executed on a processor performs a method for controlling adaptive node communication within a wireless node network having a master node and an ID node, the method comprising: detecting, by the master node, an advertising message being broadcast by the ID node, wherein the advertising message having a first format; detecting, by the master node, a state change relative to the ID node, the state change being associated with a changed relative environment of the ID node; and instructing the ID node, by the master node, to alter the first format of the advertising message to a shortened format comprising an identifier for the ID node, wherein the identifier is derived from the changed relative environment of the ID node.

53. The non-transitory computer-readable storage medium of embodiment 52, wherein the changed relative environment comprises a change in a node density near the ID node.

54. The non-transitory computer-readable storage medium of embodiment 52, wherein the changed relative environment comprises a change in a movement aspect of the ID node.

55. The non-transitory computer-readable storage medium of embodiment 54, wherein the change in the movement aspect of the ID node reflects that the ID node is substantially stationary relative to a proximate structure.

56. The non-transitory computer-readable storage medium of embodiment 55, wherein the proximate structure is moving while being substantially stationary relative to the ID node.

57. The non-transitory computer-readable storage medium of embodiment 56, wherein the proximate structure comprises at least one of a package containing device for the ID node or a conveyance device associated with the ID node.

58. The non-transitory computer-readable storage medium of embodiment 57, wherein the conveyance device comprises one of a conveyor belt, a truck, a trailer, an aircraft, a train, and a delivery vehicle.

59. The non-transitory computer-readable storage medium of embodiment 57, wherein the package containing device comprises one of a facility, a room, a bin, a container, a pallet, and a unit load device (ULD) type of transportation storage.

60. The non-transitory computer-readable storage medium of embodiment 52, wherein the instructing step further comprises transmitting, by the master node, a control message to the ID node, wherein the control message causes the ID node to broadcast the advertising message according to a variable broadcast format as the shortened format.

61. The non-transitory computer-readable storage medium of embodiment 60, wherein the variable broadcast format comprises at least one of a shortened global format, a shortened nested format, and a shortened local format.

62. The non-transitory computer-readable storage medium of embodiment 61, wherein the shortened global format comprises a global identifier of the ID node derived from the master node detecting the state change.

63. The non-transitory computer-readable storage medium of embodiment 62, wherein the global identifier of the ID node comprises a full identifier for the master node detecting the state change and a shortened reference to the ID node.

64. The non-transitory computer-readable storage medium of embodiment 61, wherein the shortened nested format comprises a nested identifier of the ID node, wherein the nested identifier comprises a plurality of hierarchical references to higher level nodes associated with the ID node.

65. The non-transitory computer-readable storage medium of embodiment 64, wherein the nested identifier indicates the ID node relationships with the higher level nodes.

66. The non-transitory computer-readable storage medium of embodiment 64, wherein the nested identifier further comprises a shortened reference to the ID node.

67. The non-transitory computer-readable storage medium of embodiment 61, wherein the shortened local format comprises a local identifier of the ID node derived from an abbreviated node reference for the master node detecting the state change.

68. The non-transitory computer-readable storage medium of embodiment 67, wherein the abbreviated node reference for the master node detecting the state change comprises a collapsed reference to the master node and a shortened reference to the ID node.

69. The non-transitory computer-readable storage medium of embodiment 52 further comprising the step of instructing, by the master node, the ID node to alter the shortened format of the advertising message back to the first format when the master node detects at least one further state change of the ID node.

70. A node device in a wireless node network having a plurality of nodes, comprising: a node processing unit; a node volatile memory coupled to the node processing unit; a node memory storage coupled to the node processing unit, the node memory storage maintaining an adaptive messaging program section; a communication interface coupled to the node processing unit and that provides access to others of the nodes in the wireless node network; wherein the node processing unit is adapted and operative to load the adaptive messaging program section into the node volatile memory and, when executing at least the adaptive messaging program section when resident in the node volatile memory, is further adapted and operative to: receive an indication from the communication interface, the indication reflecting that the communication interface detected an advertising message in a first format being broadcast by the ID node, detect a state change relative to one of the nodes, the state change being associated with a changed relative environment of the one of the nodes, and instruct the communication interface to broadcast a command to the one of the nodes, the command causing the one of the nodes to alter the first format of the advertising message to a shortened format comprising an identifier for the one of the nodes, wherein the identifier is derived from the changed relative environment of the one of the nodes.

71. The node device of embodiment 70, wherein the changed relative environment comprises a change in a node density near the one of the nodes.

72. The node device of embodiment 70, wherein the changed relative environment comprises a change in a movement aspect of the one of the nodes.

73. The node device of embodiment 72, wherein the change in the movement aspect of the one of the nodes reflects that the one of the nodes is substantially stationary relative to a proximate structure.

74. The node device of embodiment 73, wherein the proximate structure is moving while being substantially stationary relative to the one of the nodes.

75. The node device of embodiment 74, wherein the proximate structure comprises at least one of a package containing device for the one of the nodes or a conveyance device associated with the one of the nodes.

76. The node device of embodiment 75, wherein the conveyance device comprises one of a conveyor belt, a truck, a trailer, an aircraft, a train, and a delivery vehicle.

77. The node device of embodiment 75, wherein the package containing device comprises one of a facility, a room, a bin, a container, a pallet, and a unit load device (ULD) type of transportation storage.

78. The node device of embodiment 70, wherein the command causes the one of the nodes to broadcast the advertising message according to a variable broadcast format as the shortened format.

79. The node device of embodiment 78, wherein the variable broadcast format comprises at least one of a shortened global format, a shortened nested format, and a shortened local format.

80. The node device of embodiment 79, wherein the shortened global format comprises a global identifier of the one of the nodes derived from the node device that detects the state change.

81. The node device of embodiment 80, wherein the global identifier of the one of the nodes comprises a full identifier for the node device detecting the state change and a shortened reference to the one of the nodes.

82. The node device of embodiment 79, wherein the shortened nested format comprises a nested identifier of the one of the nodes, wherein the nested identifier comprises a plurality of hierarchical references to higher level others of the nodes associated with the one of the nodes.

83. The node device of embodiment 82, wherein the nested identifier indicates the one of the nodes relationships with the higher level others of the nodes.

84. The node device of embodiment 82, wherein the nested identifier further comprises a shortened reference to the one of the nodes.

85. The node device of embodiment 79, wherein the shortened local format comprises a local identifier of the one of the nodes derived from an abbreviated node reference for the node device detecting the state change.

86. The node device of embodiment 85, wherein the abbreviated node reference for the node device detecting the state change comprises a collapsed reference to the node device and a shortened reference to the one of the nodes.

87. The node device of embodiment 70, wherein the node processing unit is further adapted and operative to instruct the one of the nodes to alter the shortened format of the advertising message back to the first format when detecting at least one further state change of the one of the nodes.

In summary, it should be emphasized that the sequence of operations to perform any of the methods and variations of the methods described in the embodiments herein are merely exemplary, and that a variety of sequences of operations may be followed while still being true and in accordance with the principles of the present invention.

At least some portions of exemplary embodiments outlined above may be used in association with portions of other exemplary embodiments to better manage and locate nodes in a wireless node network or use such nodes and network elements as part of a hierarchical node network. Moreover, at least some of the exemplary embodiments disclosed herein may be used independently from one another and/or in combination with one another and may have applications to devices and methods not disclosed herein. However, those skilled in the art will appreciate that the exemplary nodes described above as operating within an embodiment of a wireless node network may be considered a system of different network elements, such as nodes, network devices operating as nodes, and a server.

Those skilled in the art will appreciate that embodiments may provide one or more advantages, and not all embodiments necessarily provide all or more than one particular advantage as set forth here. Additionally, it will be apparent to those skilled in the art that various modifications and variations can be made to the structures and methodologies described herein. Thus, it should be understood that the invention is not limited to the subject matter discussed in the description. Rather, the present invention, as recited in the claims below, is intended to cover modifications and variations.

What is claimed:

1. A non-transitory computer-readable medium containing instructions which when executed on a processor performs a method for association management of a wireless node network having at least a plurality of nodes and a server, the method comprising:
   receiving an association request from a second of the nodes, the association request asking for permission to associate a first of the nodes to the second node;
   determining a location of the first node and second node;
   determining if associating the first node to the second node is desired based at least upon the location of the first node and the location of the second node;
   recording new association data if it is desired to associate the first node with the second node; and
   transmitting a response to the second node granting the permission to associate the first node to the second node.

2. The non-transitory computer-readable medium of claim 1, wherein the step of determining a location further comprises receiving location data for the second node and using at least one of a plurality of location methods available to the server for locating the first node.

3. The non-transitory computer-readable medium of claim 1, wherein the step of transmitting the response further comprises transmitting a set of authorization credentials generated by the server, the authorization credentials being used to securely permit connecting the first node and the second node and securely exchanging operational information between the first node and the second node.

4. The non-transitory computer-readable medium of claim 1, wherein the method further comprises receiving shared data from the second node, the shared data originating from the first node as a type of the operational information securely exchanged between the first node and the second node.

5. The non-transitory computer-readable medium of claim 1, wherein the method further comprises instructing the second node by the server to take over responsibility for a task previously performed by the first node after the second node is associated with the first node.

6. The non-transitory computer-readable medium of claim 5, wherein the second node is powered by an external power source and the first node is powered by a battery.

7. The non-transitory computer-readable medium of claim 1, wherein the step of determining if associating the first node to the second node is desired further comprises:
   identifying a current mode of filtering that limits potential nodes to be associated; and
   associating the first node to the second node if the current mode of filtering allows the first node to be associated with the second node.

8. The non-transitory computer-readable medium of claim 7, wherein the step of associating the first node to the second node if the current mode of filtering defines that the second node is within a locational range of the first node consistent with the current mode of filtering.

9. The non-transitory computer-readable medium of claim 7, wherein the method further comprises the step of altering the current mode of filtering to another mode of filtering that allows the first node to be associated with the second node.

10. The non-transitory computer-readable medium of claim 7, wherein the current mode of filtering is one of multiple modes of filtering that define different levels of restrictions on which nodes may associate and be managed by other nodes.

11. A method for association management of a wireless node network having at least a plurality of nodes and a server, the method comprising:
  receiving, by a second of the nodes, a message broadcast from a first of the nodes;
  capturing, by the second node, an address of the first node from the message;
  associating the first node and the second node by storing the captured address of the first node and an address of the second node as association data in a memory of the second node;
  transmitting, by the second node, the association data to the server;
  determining a location, by the second node, of the first node; and
  updating the server with a current location of the second node and the determined location of the first node.

12. The method of claim 11 further comprising receiving location information from the server, the location information defining a refined location of the first node.

13. The method of claim 11 further comprising updating the server by the second node with an updated association data when the second node does not receive an additional message broadcast from the first node, the updated association data reflecting that the first node is disassociated from the second node.

14. A managing node in a wireless node network having at least another node and a server, the managing node comprising:
  a processing unit;
  a first communication interface coupled to the processing unit, the first communication interface providing a first communication path to the another node, the first communication interface being operative to receive a message broadcast from the another node and provide the message to the processing unit;
  a second communication interface coupled to the processing unit, the second communication interface providing a second communication path to the server;
  a volatile memory coupled to the processing unit;
  a memory storage coupled to the processing unit, the memory storage maintaining a node association manager module; and
  wherein the processing unit, when executing instructions of the node association manager module, is operative to
    receive the message from the first communication interface,
    capture an address of the another node from the message,
    store the captured address of the another node and an address of the managing node as part of association data in the memory storage, the association data reflecting an association between the managing node and the another node, and
    transmit the association data to the server through the second communication interface.

15. The managing node of claim 14, wherein the memory storage also maintains a location manager module; and
  wherein the processing unit, when executing instructions of the location manager manager module, is operative to:
    determine a location of the another node,
    determine a current location of the managing node, and
    update the server with the current location of the managing node and the determined location of the another node.

16. The managing node of claim 15, wherein the processing unit, when executing instructions of the node association manager module, is further operative to update the server with updated association data when the first communication interface does not receive an additional message broadcast from the another node, the updated association data reflecting that the another node is disassociated from the managing node.

17. The managing node of claim 14 further comprising location circuitry coupled to the processing unit, wherein the location circuity being operative to generate one or more coordinates that reflect the current location of the managing node;
  wherein the processing unit is further operative to determine the current location of the managing node based upon the one or more generated coordinates.

18. The managing node of claim 14, wherein the first communication interface is further operative to receive shared data from the another node;
  wherein the processing unit of the managing node is further operative to
    receive the shared data from the first communication interface, and
    cause the second communication interface to transmit the shared data to the server.

19. The managing node of claim 18, wherein the shared data comprises information originated by a separate node in the wireless network and provided to the another node by the separate node.

20. The managing node of claim 14, wherein the managing node is a mobile type of node in the wireless node network.

* * * * *